United States Patent
Wilson et al.

(10) Patent No.: US 12,416,016 B2
(45) Date of Patent: Sep. 16, 2025

(54) ADENO-ASSOCIATED VIRUS (AAV) VECTORS, AAV VECTORS HAVING REDUCED CAPSID DEAMIDATION AND USES THEREFOR

(71) Applicant: The Trustees of the University of Pennsylvania, Philadelphia, PA (US)

(72) Inventors: James M. Wilson, Philadelphia, PA (US); April Tepe, Columbia, MD (US); Kevin Turner, Newtown Square, PA (US); Joshua Joyner Sims, Philadelphia, PA (US); Qiang Wang, Philadelphia, PA (US)

(*) Notice: Subject to any disclaimer, the term of this patent is extended or adjusted under 35 U.S.C. 154(b) by 1151 days.

(21) Appl. No.: 16/975,545

(22) PCT Filed: Feb. 27, 2019

(86) PCT No.: PCT/US2019/019861
§ 371 (c)(1),
(2) Date: Aug. 25, 2020

(87) PCT Pub. No.: WO2019/169004
PCT Pub. Date: Sep. 6, 2019

(65) Prior Publication Data
US 2021/0123073 A1    Apr. 29, 2021

Related U.S. Application Data

(60) Provisional application No. 62/722,382, filed on Aug. 24, 2018, provisional application No. 62/722,388, filed on Aug. 24, 2018, provisional application No. 62/703,673, filed on Jul. 26, 2018, provisional application No. 62/703,670, filed on Jul. 26, 2018, provisional application No. 62/677,474, filed on May 29, 2018, provisional application No. 62/667,585, filed on May 29, 2018, provisional application No. 62/677,471, filed on May 29, 2018, provisional application No. 62/667,881, filed on May 7, 2018, provisional application No. 62/667,888, filed on May 7, 2018, provisional application No. 62/667,587, filed on May 6, 2018, provisional application No. 62/663,797, filed on Apr. 27, 2018, provisional application No. 62/663,788, filed on Apr. 27, 2018, provisional application No. 62/635,968, filed on Feb. 27, 2018, provisional application No. 62/635,964, filed on Feb. 27, 2018.

(51) Int. Cl.
*C12N 15/86* (2006.01)
*C07K 14/005* (2006.01)

(52) U.S. Cl.
CPC ............ *C12N 15/86* (2013.01); *C07K 14/005* (2013.01); *C12N 2750/14121* (2013.01); *C12N 2750/14122* (2013.01); *C12N 2750/14143* (2013.01)

(58) Field of Classification Search
None
See application file for complete search history.

(56) References Cited

U.S. PATENT DOCUMENTS

| | | |
|---|---|---|
| 5,139,941 A | 8/1992 | Muzyczka et al. |
| 6,057,152 A | 5/2000 | Samulski et al. |
| 6,200,560 B1 | 3/2001 | Couto et al. |
| 6,204,059 B1 | 3/2001 | Samulski et al. |
| 6,221,349 B1 | 4/2001 | Couto et al. |
| 6,268,213 B1 | 7/2001 | Samulski et al. |
| 6,491,907 B1 | 12/2002 | Rabinowitz |
| 6,660,514 B1 | 12/2003 | Zolotukhin et al. |
| 6,951,753 B2 | 10/2005 | Shenk et al. |
| 7,094,604 B2 | 8/2006 | Snyder et al. |
| 7,125,717 B2 | 10/2006 | Carter |
| 7,172,893 B2 | 2/2007 | Rabinowitz |
| 7,201,898 B2 | 4/2007 | Monahan et al. |
| 7,229,823 B2 | 6/2007 | Samulski et al. |
| 7,439,065 B2 | 10/2008 | Ferrari et al. |
| 7,442,373 B2 | 10/2008 | Morrow et al. |
| 7,456,683 B2 | 11/2008 | Takano et al. |
| 7,588,772 B2 | 9/2009 | Kay et al. |
| 2006/0136184 A1 | 6/2006 | Gustafsson et al. |

(Continued)

FOREIGN PATENT DOCUMENTS

| | | |
|---|---|---|
| JP | 2007-507223 | 3/2007 |
| JP | 2008-538286 | 10/2008 |

(Continued)

OTHER PUBLICATIONS

Yang et al., Mass Spectrometric Analysis of Asparagine Deamidation and Aspartate Isomerization in Polypeptides. Electrophoresis, 2010. 31:1764.*

(Continued)

*Primary Examiner* — Christopher M Babic
*Assistant Examiner* — Kimberly A Aron
(74) *Attorney, Agent, or Firm* — Howson & Howson LLP; Cathy A Kodroff

(57) ABSTRACT

A recombinant adeno-associated virus (rAAV) vector comprising an AAV capsid having a heterogeneous population of vp1 proteins, a heterogeneous population of vp2 protein and a heterogeneous population of vp3 proteins. The capsid contains modified amino acids as compared to the encoded VP1 amino acid sequence, the capsid containing highly deamidated asparagine residues at asparagine-glycine pair, and further comprising multiple other, less deamidated asparagine and optionally glutamine residues.

25 Claims, 63 Drawing Sheets
Specification includes a Sequence Listing.

(56) References Cited

U.S. PATENT DOCUMENTS

| | | |
|---|---|---|
| 2007/0036760 A1 | 2/2007 | Wilson et al. |
| 2009/0197338 A1 | 8/2009 | Vandenberghe et al. |
| 2011/0294218 A1 | 12/2011 | Chatterjee et al. |
| 2013/0045186 A1 | 2/2013 | Gao et al. |
| 2014/0032186 A1 | 1/2014 | Gustafsson et al. |
| 2015/0315612 A1 | 11/2015 | Wilson et al. |
| 2017/0159027 A1 | 6/2017 | Wilson et al. |

FOREIGN PATENT DOCUMENTS

| | | |
|---|---|---|
| WO | WO-2003/042397 | 5/2003 |
| WO | WO 2005/033321 | 4/2005 |
| WO | WO 2006/110689 | 10/2006 |
| WO | WO-2011/126808 | 10/2011 |
| WO | WO-2017/075119 | 5/2017 |
| WO | WO-2017/100674 | 6/2017 |
| WO | WO-2017/100676 | 6/2017 |
| WO | WO-2017/160360 | 9/2017 |
| WO | WO-2017/180854 | 10/2017 |
| WO | WO-2017/181113 | 10/2017 |
| WO | WO-2018/035059 | 2/2018 |
| WO | WO-2018/160582 | 9/2018 |
| WO | WO 2018/160585 A2 | 9/2018 |

OTHER PUBLICATIONS

Wakankar et al., Formulation Considerations for Proteins Susceptible to Asparagine Deamidation and Aspartate Isomerization. Journal of Pharmaceutical Sciences, 2006. 95(11):2321-2336.*
Li et al., Effects of Acidic N+1 Residues on Asparagine Deamidation Rates in Solution and in the Solid State. Journal of Pharmaceutical Sciences, 2006. 94(3):666-675.*
Pierson et al. Resolving Adeno-Associated Viral Particle Diversity With Charge Detection Mass Spectrometry. Analytical Chemistry, 2016. 88: 6718-6725.*
Adachi et al., Drawing a high-resolution functional map of adeno-associated virus capsid by massively parallel sequencing, Nature Communications, vol. 5(3075), 2014.
Aydemir et al., Mutants at the 2-Fold Interface of Adeno-associated Virus Type 2 (AAV2) Structural Proteins Suggest a Role in Viral Transcription for AAV Capsids, Journal Virology, vol. 90(16):7196-7204, Aug. 2016.
Bish et al., Adeno-associated virus (AAV) serotype 9 provides global cardiac gene transfer superior to AAV1, AAV6, AAV7, and AAV8 in the mouse and rat, Human Gene Therapy, vol. 19(12): 1359-68, Dec. 2008.
Calcedo et al., Worldwide epidemiology of neutralizing antibodies to adeno- associated viruses, The Journal of Infectious Diseases, vol. 199(3):381-90, Feb. 2009.
Calcedo R., Wilson JM., AAV Natural Infection Induces Broad Cross-Neutralizing Antibody Responses to Multiple AAV Serotypes in Chimpanzees, Human Gene Therapy, vol. 27(2):79-82, May 2016.
Carrillo-Tripp et al., VIPERdb2: an enhanced and web API enabled relational database for structural virology, Nucleic Acids Reaserch, vol. 37:D436-42, Jan. 2009.
Chen et al., Biodistribution of AAV8 vectors expressing human low-density lipoprotein receptor in a mouse model of homozygous familial hypercholesterolemia, Human Gene Therapy Clinical Development, vol. 24(4):154-60, Dec. 2013.
Chicoine et al., Plasmapheresis eliminates the negative impact of AAV antibodies on microdystrophin gene expression following vascular delivery, Molecular Therapy, vol. 22(2):338-47, Feb. 2014.
Delano et al., PyMOL: An Open-Source Molecular Graphics Tool, vol. 40:82-92, 2002.
Ellis et al., A survey of ex vivo/in vitro transduction efficiency of mammalian primary cells and cell lines with Nine natural adeno-associated virus (AAV1-9) and one engineered adeno-associated virus serotype, Virology Journal, vol. 10:74, Mar. 2013.

Falese et al., Strategy to detect pre-existing immunity to AAV gene therapy, Gene Therapy, vol. 24(12):768-778, Dec. 2017.
Fisher et al., Transduction with recombinant adeno-associated virus for gene therapy is limited by leading-strand synthesis., Journal of Virology, vol. 70:520-532, Jan. 1996.
Flatmark et al., Deamidations in recombinant human phenylalanine hydroxylase. Identification of labile asparagine residues and functional characterization of Asn --> Asp mutant forms, The Journal of biological chemistry, vol. 278(17):15142-1515, Apr. 2003.
Flotte et al., Phase 2 clinical trial of a recombinant adeno-associated viral vector expressing al-antitrypsin: interim results, Human Gene Therapy, vol. 22(10):1239-47, Oct. 2011.
Foust et al., Intravascular AAV9 preferentially targets neonatal neurons and adult astrocytes, Nature Biotechnology, vol. 27(1):59-65, Jan. 2009.
Gao et al., Adeno-associated viruses undergo substantial evolution in primates during natural infections, Proc. Natl. Acad. Sci. U.S.A, vol. 100 (10):6081-6086, May 2003.
Gao et al., Novel adeno-associated viruses from rhesus monkeys as vectors for human gene therapy, Proc Natl Acad Sci USA, vol. 99(18):11854-9, Sep. 2002.
Geiger T., Clarke S., Deamidation, isomerization, and racemization at asparaginyl and aspartyl residues in peptides. Succinimide-linked reactions that contribute to protein degradation, Journal of Biological Chemistry, vol. 262(2):785-94, Jan. 1987.
George et al., Spk-8011: Preliminary Results from a Phase ½ Dose Escalation Trial of an Investigational AAV-Mediated Gene Therapy for Hemophilia a, Blood, vol. 130(Suppl 1):604, Dec. 2017.
Giles et al., Deamidation of Amino Acids on the Surface of Adeno-Associated Virus Capsids Leads to Charge Heterogeneity and Altered Vector Function, Molecular Theory, vol. 26:2848-2862, Oct. 2019.
Gonzalez-Quintela et al., Serum levels of immunoglobulins (IgG, IgA, IgM) in a general adult population and their relationship with alcohol consumption, smoking and common metabolic abnormalities, Clinical and Experimental Immunology, vol. 151(1):42-50, Jan. 2008.
Govindasamy et al., Structural Insights into Adeno-Associated Virus Serotype 5, Journal Virology, vol. 87(20):11187-99, Oct. 2013.
Greig et al., Non-Clinical Study Examining AAV8.TBG.hLDLR Vector-Associated Toxicity in Chow-Fed Wild-Type and LDLR+/− Rhesus Macaques, Human Gene Therapy Clinical Development, vol. 28(1):39-50, Mar. 2017.
Grieger & Samulski, Adeno-associated virus as a gene therapy vector: Vector development, production and clinical applications, Advances in Biochemical Engineering/Biotechnology, vol. 99:119-145, Oct. 2005.
Grimm et al., Titration of AAV-2 particles via a novel capsid ELISA: packaging of genomes can limit production of recombinant AAV-2, Gene Therapy, vol. 6:1322-1330, Aug. 1999.
Gurda et al., Capsid Antibodies to Different Adeno-Associated Virus Serotypes Bind Common Regions Journal Virology, vol. 87(16):9111-24, Aug. 2013.
Gurda et al., Mapping a neutralizing epitope onto the capsid of adeno-associated virus serotype 8, Journal Virology, vol. 86(15):7739-51, Aug. 2012.
Harrington et al., Neutralizing Antibodies Against Adeno-Associated Viral Capsids in Patients with mut Methylmalonic Acidemia, Human Gene Therapy, vol. 27(5):345-53, May 2016.
Henderson et al., Primary structure of human carbonic anhydrase C, The Journal of Biological Chemistry, vol. 251:5457-5463, Sep. 1976.
Houde et al., Post-translational Modifications Differentially Affect IgG1 Conformation and Receptor Binding, Molecular Cell Proteomics, vol. 9.8:1716-1728, Aug. 2010.
Huang et al., Characterization of the Adeno-Associated Virus 1 and 6 Sialic Acid Binding Site, Journal of Virology, vol. 90(11):5219-30, Jun. 2016.
Huttner et al., Genetic modifications of the adeno-associated virus type 2 capsid reduce the affinity and the neutralizing effects of human serum antibodies, Gene Therapy, vol. 10(26):2139-47, Nov. 2003.

(56) References Cited

OTHER PUBLICATIONS

Kleywegt, G., Crystallographic refinement of ligand complexes, Acta Crystallogr D Biol Crystallogr, vol. 63(Pt 1):94-100, Jan. 2007.

Kornegay et al., Widespread Muscle Expression of an AAV9 Human Mini-dystrophin Vector After Intravenous Injection in Neonatal Dystrophin-deficient Dogs, Molecular Therapy, vol. 18(8): 1501-8, Aug. 2010.

Leem et al., ABodyBuilder: Automated antibody structure prediction with data-driven accuracy estimation, Mabs, vol. 8(7):1259-1268, Oct. 2016.

Lock et al., Absolute determination of single-stranded and self-complementary adeno-associated viral vector genome titers by droplet digital PCR, Human Gene Therapy Methods, vol. 25(2):115-25, Apr. 2014.

Lock et al., Rapid, simple, and versatile manufacturing of recombinant adeno-associated viral vectors at scale, *Human Gene Therapy, vol.* 21(10):1259-71, Oct. 2010.

McCarty et al., Self-complementary recombinant adeno-associated virus (scAAV) vectors promote efficient transduction independently of DNA synthesis, Gene Therapy, vol. 8(16):1248-1254, Aug. 2001.

Mendell et al., Single-Dose Gene-Replacement Therapy for Spinal Muscular Atrophy, New England Journal of Medicine, vol. 377(18):1713-22, Nov. 2017.

Murray et al., Characterization of the capsid protein glycosylation of adeno-associated virus type 2 by high-resolution mass spectrometry, Journal of Virology, vol. 80(12):6171-6, Jun. 2006.

Nam et al., Structure of adeno-associated virus serotype 8, a gene therapy vector, Journal of Virology, vol. 81(22):12260-71, Nov. 2007.

Nebija et al., Quality Control and Stability Studies with the Monoclonal Antibody, Trastuzumab: Application of 1D- vs. 2D-Gel Electrophoresis, International Journal of Medical Studies, vol. 15(4):6399-411, Apr. 2014.

Parthasarathy, S., Murthy, MR., Analysis of temperature factor distribution in high-resolution protein structures, Protein Science : a Publication of the Protein Society, vol. 6:2561-7, Dec. 1997.

Rao et al., Specificity and affinity of natural product cyclopentapeptide inhibitors against A. fumigatus, human, and bacterial chitinases, Chemistry & Biology, vol. 12(1):65-76, Jan. 2005.

Raupp et al., The Threefold Protrusions of Adeno-Associated Virus Type 8 Are Involved in Cell Surface Targeting as Well as Postattachment Processing, *Journal of Virology, vol.* 86(17):9396-408, Sep. 2012.

Robinson, Ne., Robinson, AB., Molecular clocks, *Proc Natl Acad Sci USA, vol.* 98(3):944-949, Jan. 2001.

Rohou, A., Grigorieff, N., CTFFIND4: Fast and accurate defocus estimation from electron micrographs, Structural Biology, vol. 192(2):216-21, Nov. 2015.

Rose et al., Structural proteins of adenovirus-associated viruses, Journal of Virology, vol. 8(5):766-70, Nov. 1971.

Sawada-Hirai et al., Human anti-anthrax protective antigen neutralizing monoclonal antibodies derived from donors vaccinated with anthrax vaccine adsorbed, Journal of Immune Based Therapy Vaccines, vol. 2(1):5, May 2004.

Sommer et al., Quantification of adeno-associated virus particles and empty capsids by optical density measurement, Molecular Therapy, vol. 7:122-128, Jan. 2003.

Tse et al., Structure-guided evolution of antigenically distinct adeno-associated virus variants for immune evasion, Proc Natl Acad Sci USA, vol. 114(24):E4812-21, Jun. 2017.

Tseng et al., Adeno-Associated Virus Serotype 1 (AAV1)- and AAV5-Antibody Complex Structures Reveal Evolutionary Commonalities in Parvovirus Antigenic Reactivity, Journal of Virology, vol. 89(3):1794-808, Feb. 2015.

Tseng, Y., and Agbandje-McKenna, M., Mapping the AAV Capsid Host Antibody Response toward the Development of Second Generation Gene Delivery Vectors, Frontiers in Immunology, vol. 5:9, Jan. 2014.

Verma et al., Mechanistic Analysis of the Effect of Deamidation on the Immunogenicity of Anthrax Protective Antigen, Clinical and Vaccine Immunology, vol. 23(5):396-402, May 2016.

Wang et al., Impact of Pre-Existing Immunity on Gene Transfer to Nonhuman Primate Liver with Adeno-Associated Virus 8 Vectors, Human Gene Therapy, vol. 22(11):1389-1401, Nov. 2011.

Wobus et al., Monoclonal Antibodies against the Adeno-Associated Virus Type 2 (AAV-2) Capsid: Epitope Mapping and Identification of Capsid Domains Involved in AAV-2-Cell Interaction and Neutralization of AAV-2 Infection, Journal of Virology, vol. 74:9281-9293, Oct. 2000.

Xiao, C. and Rossmann, MG., Interpretation of electron density with stereographic roadmap projections, Journal of Structural Biology, vol. 158(2):182-7, 2007.

Xie et al., The atomic structure of adeno-associated virus (AAV-2), a vector for human gene therapy, Proc Natl Acad Sci USA, vol. 99(16):10405-10, Aug. 2002.

Yan et al., AUTO3DEM—an automated and high throughput program for image reconstruction of icosahedral particles, Journal of Structural Biology, vol. 157(1):73-82, Jan. 2007.

Yan, BX. and Sun, YQ., Glycine residues provide flexibility for enzyme active sites, The Journal of Biological Chemistry, vol. 272(6):3190-4, Feb. 1997.

Yang, H. and Zubarev, R., Mass spectrometric analysis of asparagine deamidation and aspartate isomerization in polypeptides, Electrophoresis, vol. 31(11):1764-72, Jun. 2010.

Zanta-Boussif et al., Validation of a mutated PRE sequence allowing high and sustained transgene expression while abrogating WHV-X protein synthesis: application to the gene therapy of WAS, Gene Therapy, vol. 16:605-619, Mar. 2009.

Zhao et al., A Viral Deamidase Targets the Helicase Domain of RIG-I to Block RNA-induced Activation, Cell Host Microbe, vol. 20(6):770-84, Dec. 2016.

Zhao et al., Emerging Roles of Protein Deamidation in Innate Immune Signaling, Journal of Virology, vol. 90(9):4262-8, May 2016.

Zhong et al., Tyrosine-phosphorylation of AAV2 vectors and its consequences on viral intracellular trafficking and transgene expression Virology, vol. 381(2):194-202, Nov. 2008.

International Search Report and Written Opinion issued in International Patent Application No. PCT/US2019/019804, dated Jun. 20, 2019.

International Search Report and Written Opinion issued in International Patent Application No. PCT/US2019/019861, dated Jun. 14, 20219.

International Preliminary Report on Patentability issued in International Patent Application No. PCT/US2019/019804, dated Aug. 27, 2020.

International Preliminary Report on Patentability issued in International Patent Application No. PCT/US2019/019861, dated Sep. 3, 2020.

International Patent Application No. PCT/US2016/065970, filed Dec. 9, 2016.

International Patent Application No. PCT/US2016/065976, filed Dec. 9, 2016.

International Patent Application No. PCT/US16/66013, filed Dec. 9, 2016.

International Patent Application No. PCT/US2016/065974, filed Dec. 9, 2016.

U.S. Appl. No. 62/322,071, filed Apr. 13, 2016.
U.S. Appl. No. 62/226,357, filed Dec. 11, 2015.
U.S. Appl. No. 62/322,098, filed Apr. 13, 2016.
U.S. Appl. No. 62/266,341, filed Dec. 11, 2015.
U.S. Appl. No. 62/322,055, filed Apr. 13, 2016.
U.S. Appl. No. 62/266,347, filed Dec. 11, 2015.
U.S. Appl. No. 62/322,083, filed Apr. 13, 2016.
US Patent Application No. 62/26,351, filed Dec. 11, 2015.
Giles et al., The Biological and Functional Effects of Spontaneous Deamidation of the AAV Capsid on Gene Therapy Vectors, Molecular Therapy, vol. 22(1):S85, Abstract, May 2014.

(56) References Cited

OTHER PUBLICATIONS

Giles et al., Immunological and Biochemical Evaluation of the AAV Capsid to Advance Next-Generation Gene Therapy Vector Design, University of Pennsylvania ScholarlyCommons, p. 1-173, Jan. 2018.
Extended European Search Report dated Mar. 3, 2022 issued in corresponding European Patent Application No. 19760152.9.
Office Action dated Mar. 16, 2022 issued in corresponding Chilean Patent Application No. 2020-2201, with unofficial English translation provided by local agent.
Official Action dated Nov. 10, 2022 issued in corresponding Eurasian Patent Application No. 202092015, with unofficial English translation provided by local agent.
Office Action dated Feb. 22, 2023 issued in corresponding Japanese Patent Application No. 2020-545159, with unofficial English translation provided by local agent.
Office Action dated Sep. 20, 2023 issued in corresponding Japanese Patent Application No. 2020-545159, with unofficial English translation provided by local agent.
Office Action dated Dec. 14, 2023 issued in corresponding Canadian Patent Application No. 3,091,795.
Office Action dated Jul. 29, 2023 issued in corresponding Chinese Patent. Application No. 201980029022. 1, with unofficial English translation provided by local agent.
Substantive Examination Report dated Feb. 1, 2023 issued in related Chilean. Patent Application No. 202002201, with unofficial English translation provided by local agent.
Memorandum Opinion and Order, *Regenxbio Inc. and The Trustees of the University of Pennsylvania v. Sarepta Therapeutics, Inc. and Sarepta Therapeutics Three, LLC*, U.S. District Court for the District of Delaware, No. 1:20-cv-01226, (D. Del., Jan. 5, 2024).
Official Action dated Mar. 12, 2024 issued in corresponding Eurasian Patent Application No. 202092015, with unofficial English translation provided by local agent.
Office Action dated Jun. 20, 2024, issued in corresponding Chinese Patent Application No. 201980029022. 1, with unofficial English translation provided by local agent.
Notice to Grant Patent Right dated Nov. 8, 2024, issued in corresponding Chinese Patent Application No. 201980029022. 1, with unofficial English translation provided by local agent.
Notification of Readiness to Grant Patent dated Dec. 12, 2024, issued in corresponding Eurasian Patent Application No. 202092015, with unofficial English translation provided by local agent.
Examination Report dated Aug. 30, 2024, issued in corresponding Australian Patent Application No. 2019228504.
Substantive Examination Report dated Jul. 4, 2024, issued in corresponding Chilean Patent Application No. 202202498, with unofficial English translation provided by local agent.
Preliminary Rejection dated Jun. 26, 2024, issued in corresponding Korean Patent Application No. 10-2020-7027462, with unofficial English translation provided by local agent.
Office Action dated Aug. 30, 2024, issued in corresponding Mexican Patent Application No. MX/a/2020/008932, with unofficial English translation provided by local agent.

* cited by examiner

FIG. 1A
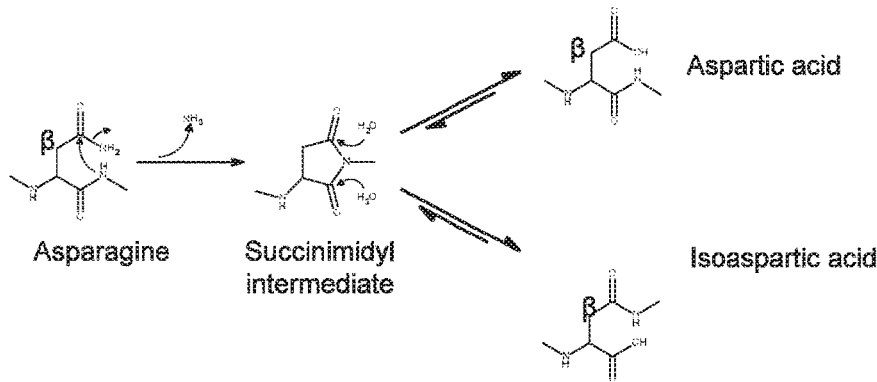
FIG. 1B
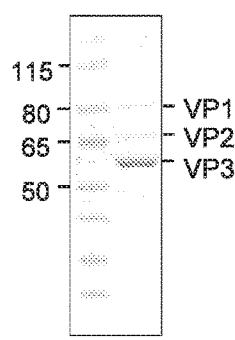
VP1
VP2
VP3
FIG. 1C
| Spot | pI | Spot | pI |
|---|---|---|---|
| 1 | 7.30 | 11 | 5.70 |
| 2 | 7.11 | 12 | 5.63 |
| 3 | 6.97 | 13 | 5.54 |
| 4 | 6.75 | 14 | 5.46 |
| 5 | 6.61 | 15 | 5.37 |
| 6 | 6.45 | 16 | 5.27 |
| 7 | 6.27 | 17 | 5.20 |
| 8 | 6.11 | 18 | 5.14 |
| 9 | 6.01 | 19 | 5.08 |
| 10 | 5.86 | 20 | 4.99 |
FIG. 1D
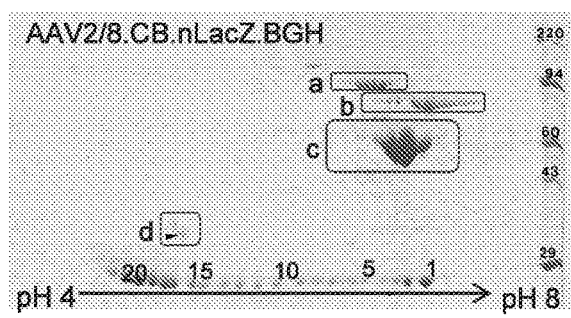
FIG. 1E    FIG. 1F    FIG. 1G
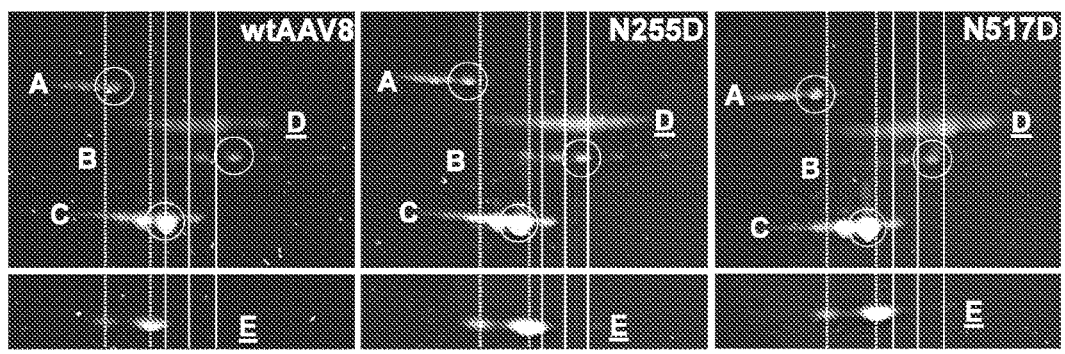
A-AAV8 VP1: 87kDa     B-AAV8 VP2: 73kDa     C-AAV8 VP3: 61kDa
D-Conalbumin: 76kDa   E-Turbonuclease: 27kDa Observed mass: 1619.8213 Da
Theoretical mass: 1619.8096 Da FIG. 3A
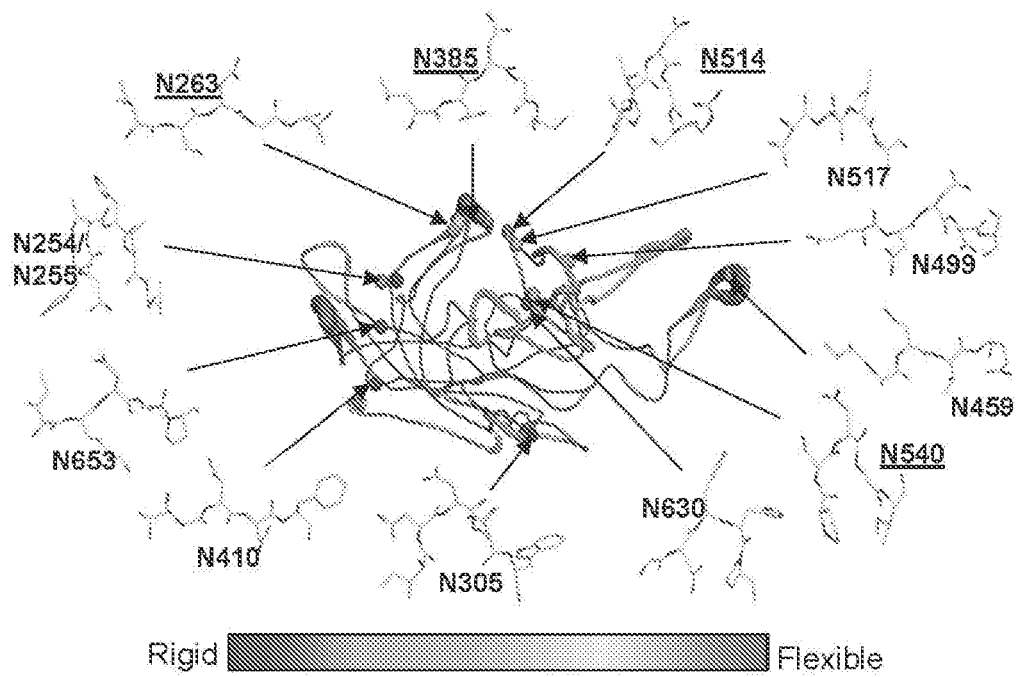
FIG. 3B  FIG. 3C
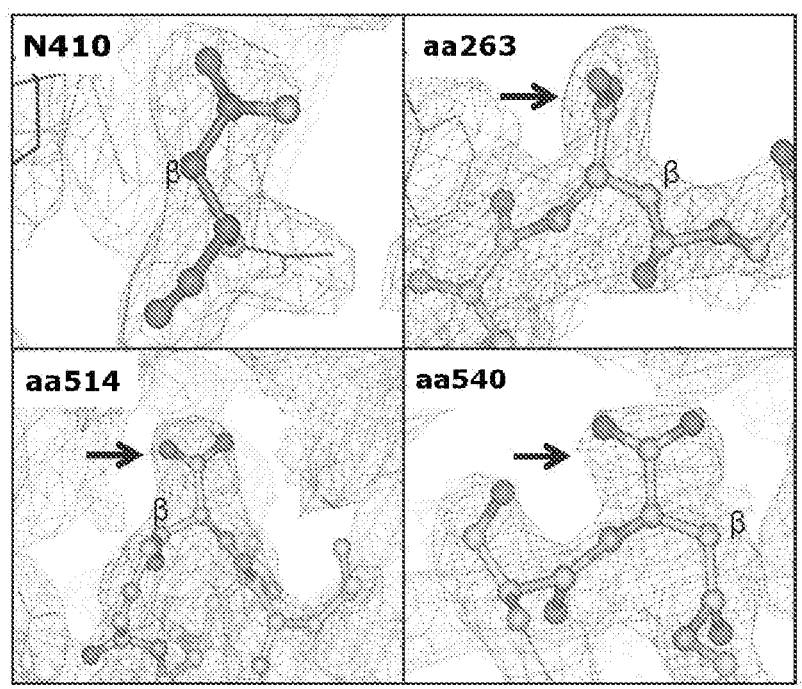
FIG. 3D  FIG. 3E

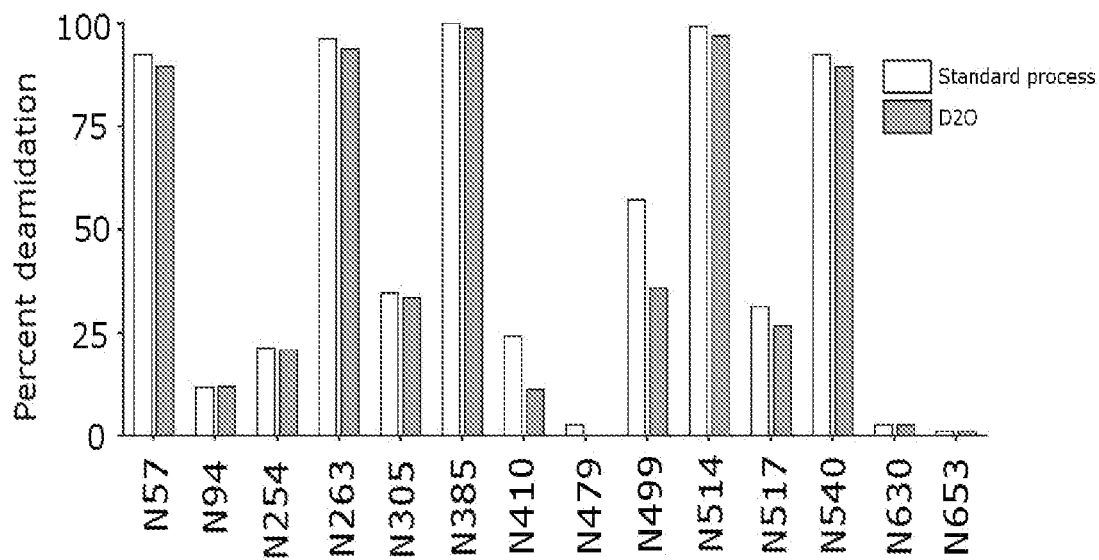

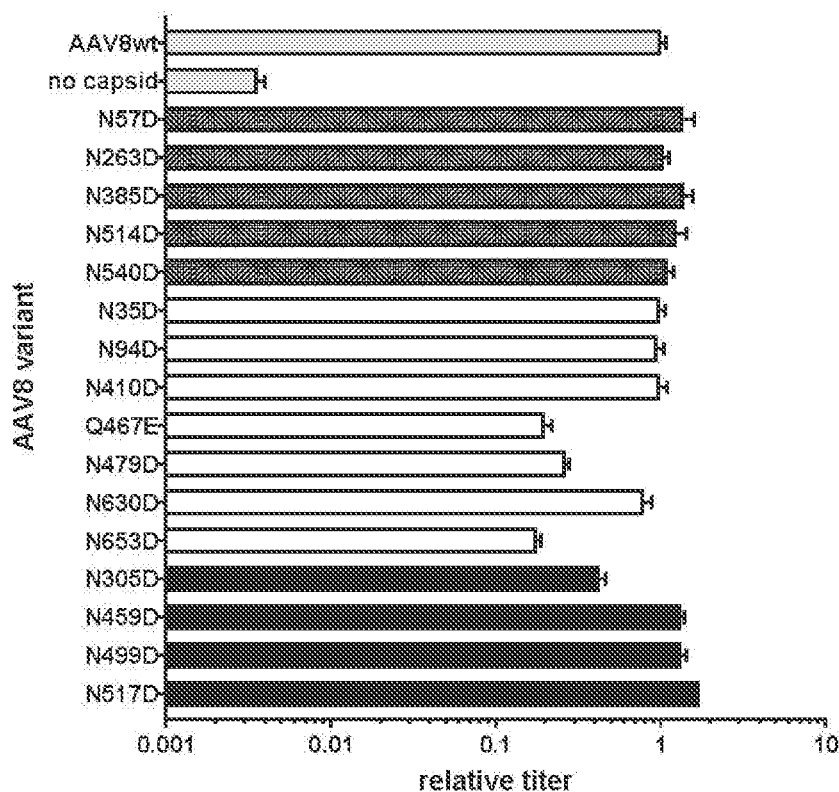
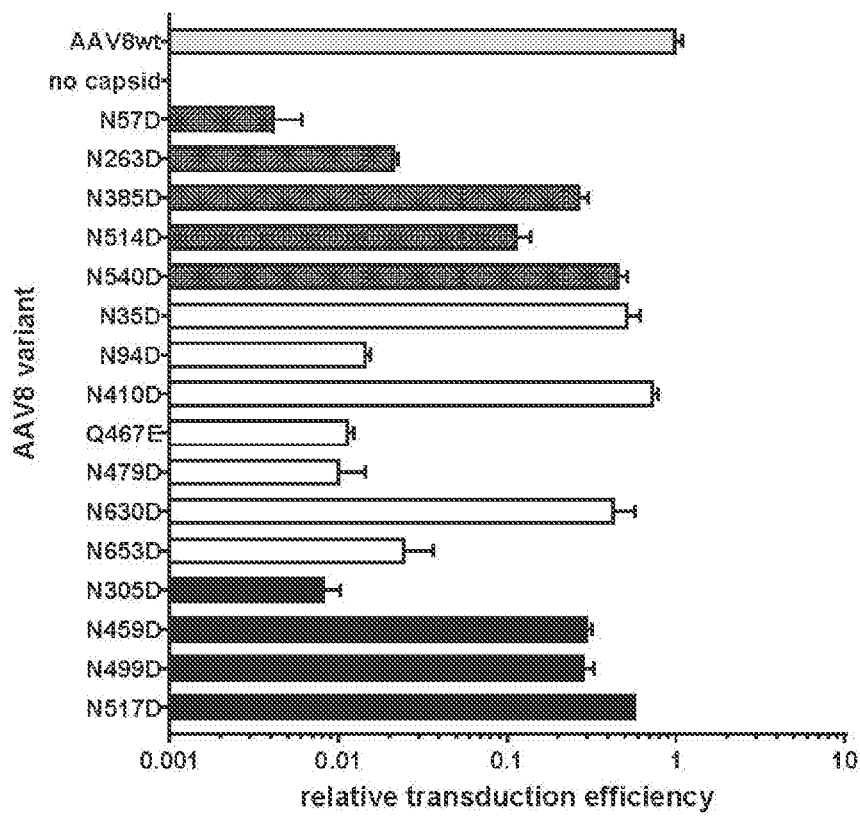

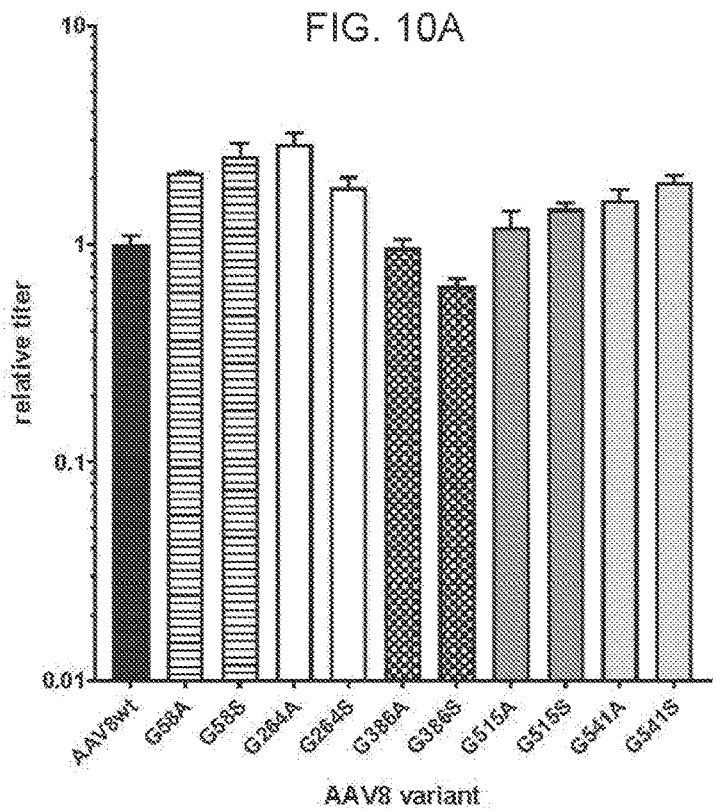
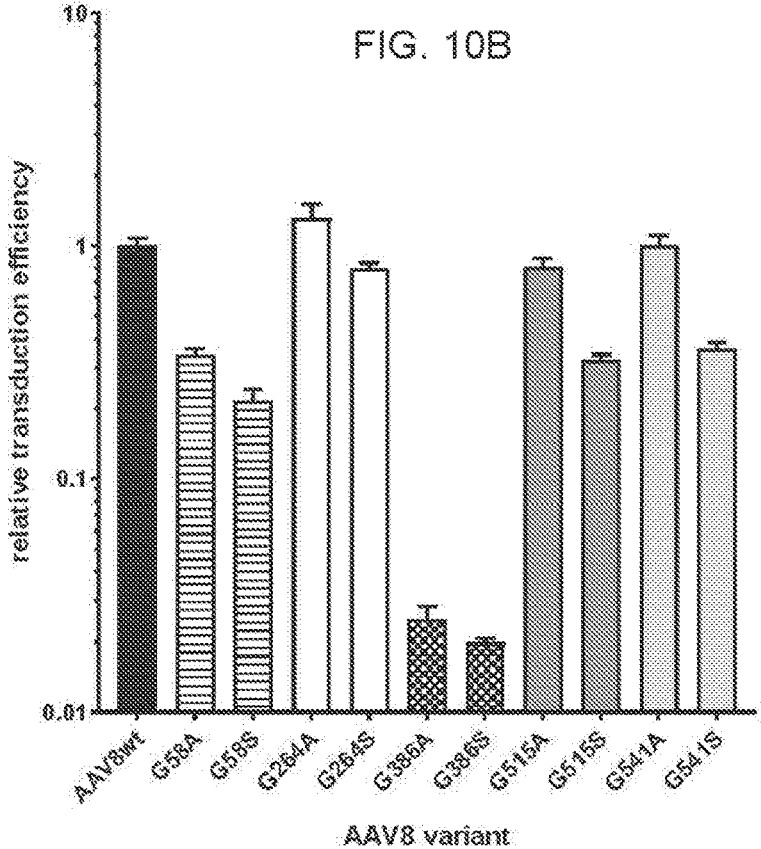

FIG. 11A
FIG. 11C
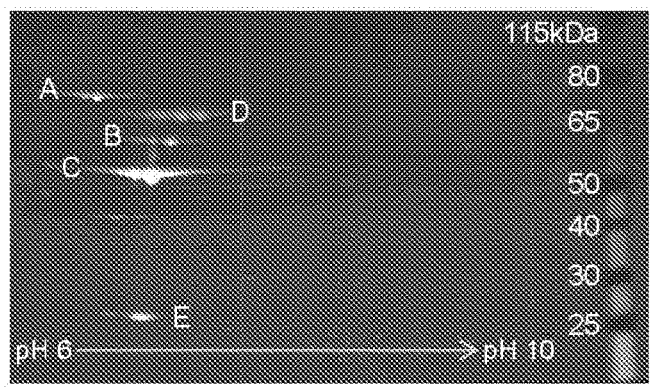
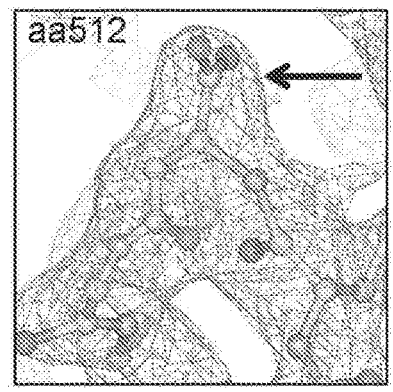
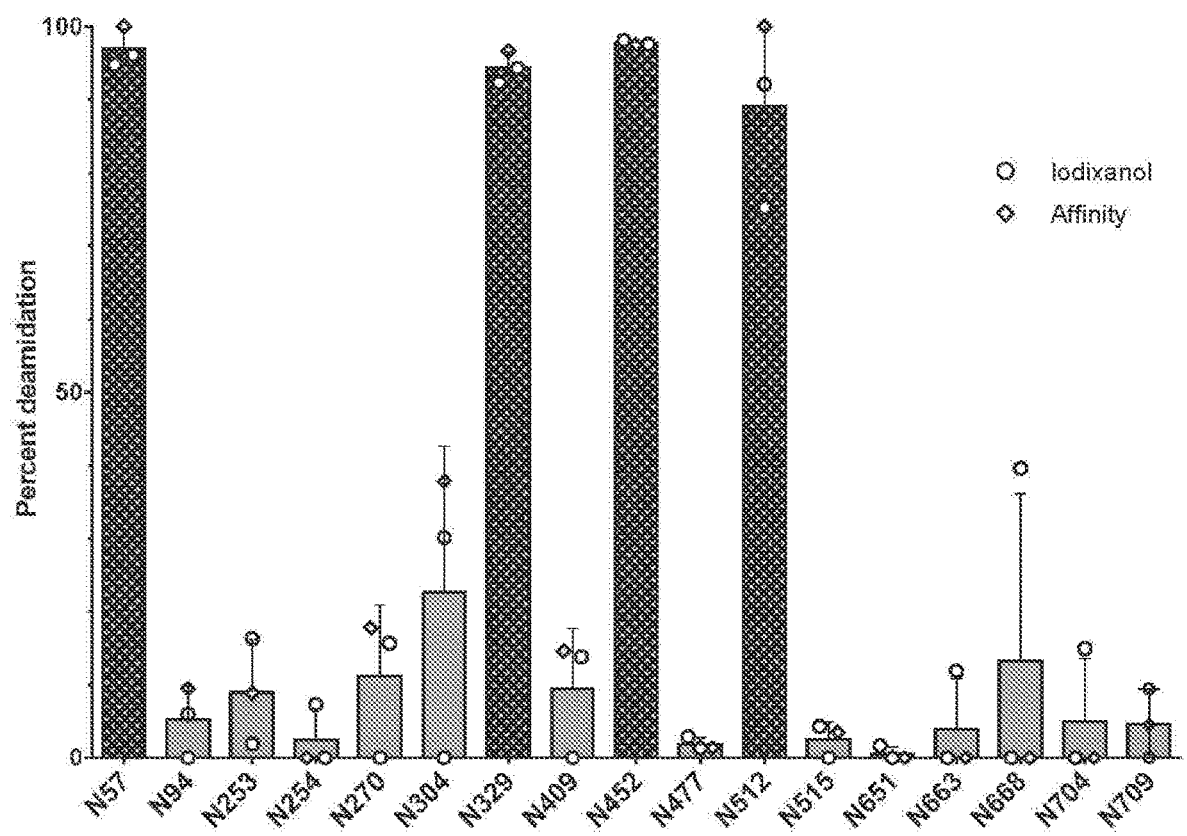
FIG. 11B

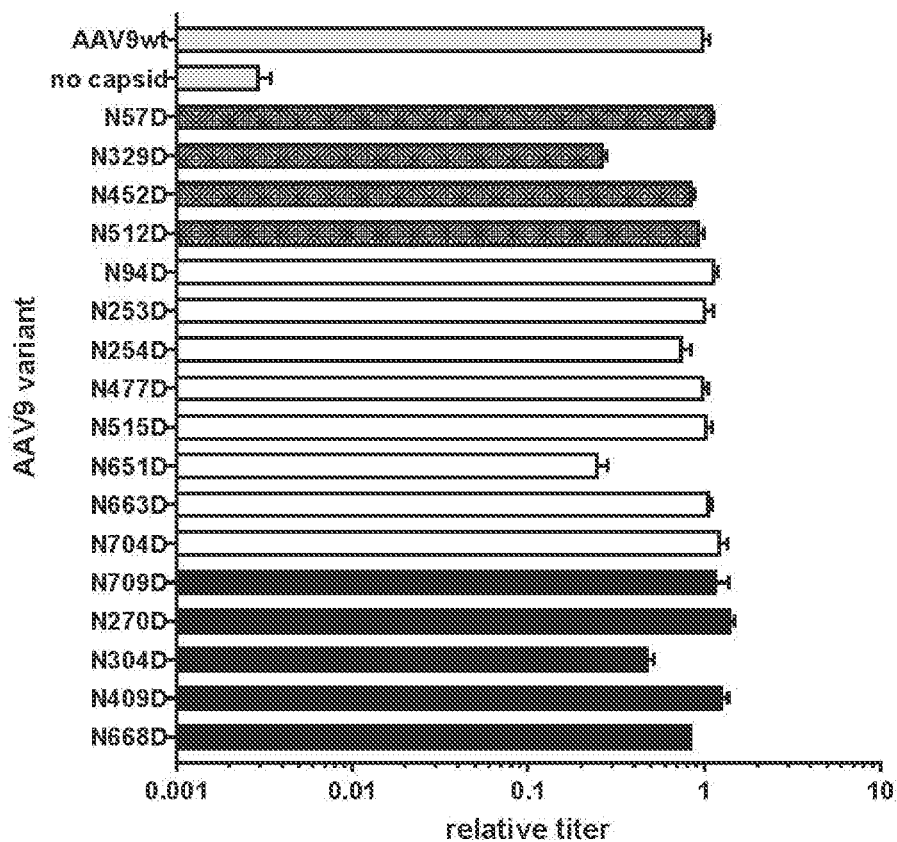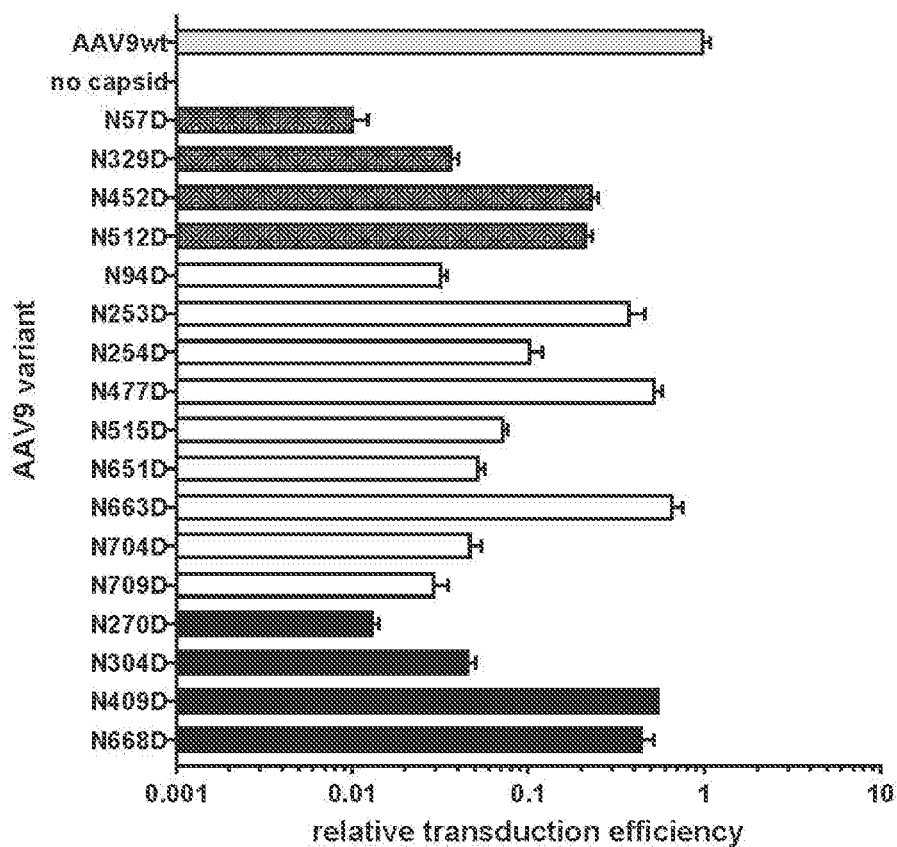

FIG. 12A (Clade F aa)

```
         |vp1 start
AAVG5   1 MSFVDHPPDWLEE-VGEGLREFLGLEAGPPKPNQQHQDQARGLVLPGYNYLGPNGLDRGEPVNRADEVAREHDISYNEQLEAGDNPYLKYNHADAEF
AAV9    1 MAADGYLPDWLEDNLSEGIREWWALKPGAPQPKANQQHQDNARGLVLPGYKYLGPGNGLDKGEPVNAADAAALEHDKAYDQQLKAGDNPYLKYNHADAEF
PHP.B   1 MAADGYLPDWLEDNLSEGIREWWALKPGAPQPKANQQHQDNARGLVLPGYKYLGPGNGLDKGEPVNEADAAALEHDKAYDQQLKAGDNPYLKYNHADAEF
                                                              |vp2 start
AAVG5 101 QEKLADDTSFGGNLGKAVFQAKKRVLEPFGLVEEGAKTAPTGKRIDDHFPKRKKARTEED---SKPS-------TSSDAEAGPSGSQQLQIPAQPASSLG
AAV9  101 QERLKEDTSFGGNLGRAVFQAKKRLLEPLGLVEEAAKTAPGKKRPVEQSPQEPDSSAGIGKSGAQPAKKRLNFGQTGDTES-VPDPQPIGEPPAAPSGVG
PHP.B 101 QERLKEDTSFGGNLGRAVFQAKKRLLEPLGLVEEAAKTAPGKKRPVEQSPQEPDSSVGIGKSGAQPAKKRLNFGQTGDTES-VPDPQPIGEPPAAPSGVG
           |vp3 start
AAVG5 201 ADTMASGGGAPVADNNEGADGVGSSSGNWHCDSQWLGDRVITTSTRTWALPTYNNHLYKQISNSTSGGSSNDAYFGYSTPWGYFDFNRFHCHFSPRDWQ
AAV9  201 SLTMASGGAPVADNNEGADGVGSSSGNWHCDSQWLGDRVITTSTRTWALPTYNNHLYKQISNSTSGGSSNDAYFGYSTPWGYFDFNRFHCHFSPRDWQ
PHP.B 201 SLTMASGGAPVADNNEGADGVGSSSGNWHCDSQWLGDRVITTSTRTWALPTYNNHLYKQISNSTSGGSSNDAYFGYSTPWGYFDFNRFHCHFSPRDWQ
AAVG5 301 RLINNNWGFRPKRLNFKLFNIQVKEVTDNNGVKTIANNLTSTVQVFTDSDYQLPYVLGSAHEGCLPPFPADVFMIPQYGYLTLNDGSQAVGRSSFYCLEY
AAV9  301 RLINNNWGFRPKRLNFKLFNIQVKEVTDNNGVKTIANNLTSTVQVFTDSDYQLPYVLGSAHEGCLPPFPADVFMIPQYGYLTLNDGSQAVGRSSFYCLEY
PHP.B 301 RLINNNWGFRPKRLNFKLFNIQVKEVTDNNGVKTIANNLTSTVQVFTDSDYQLPYVLGSAHEGCLPPFPADVFMIPQYGYLTLNDGSQAVGRSSFYCLEY
AAVG5 401 FPSQMLRTGNNFQFSYEFENVPFHSSYAHSQSLDRLMNPLIDQYLYYLSKTINGSGQNQQTLKFSVAGPSNMAVQGRNYIPGPSYRQQRVSTTVTQNNNS
AAV9  401 FPSQMLRTGNNFQFSYEFENVPFHSSYAHSQSLDRLMNPLIDQYLYYLSKTINGSGQNQQTLKFSVAGPSNMAVQGRNYIPGPSYRQQRVSTTVTQNNNS
PHP.B 401 FPSQMLRTGNNFQFSYEFENVPFHSSYAHSQSLDRLMNPLIDQYLYYLSKTINGSGQNQQTLKFSVAGPSNMAVQGRNYIPGPSYRQQRVSTTVTQNNNS
AAVG5 501 EFAWPGASSWALNGRNSLMNPGPAMASHKEGEDRFFPLSGSLIFGKQGTGRDNVDADKVMITNEEEIKTTNPVATESYGQVATNHQSAQ------AQAQ
AAV9  501 EFAWPGASSWALNGRNSLMNPGPAMASHKEGEDRFFPLSGSLIFGKQGTGRDNVDADKVMITNEEEIKTTNPVATESYGQVATNHQSAQ------AQAQ
PHP.B 501 EFAWPGASSWALNGRNSLMNPGPAMASHKEGEDRFFPLSGSLIFGKQGTGRDNVDADKVMITNEEEIKTTNPVATESYGQVATNHQSAQ------AQAQ
AAVG5 601 TGWVQNQGILPGMVWQDRDVYLQGPIWAKIPHTDGNFHPSPLMGGFGMKHPPPQILIKNTPVPADPPTAFNKDKLNSFITQYSTGQVSVEIEWELQKENS
AAV9  601 TGWVQNQGILPGMVWQDRDVYLQGPIWAKIPHTDGNFHPSPLMGGFGMKHPPPQILIKNTPVPADPPTAFNKDKLNSFITQYSTGQVSVEIEWELQKENS
PHP.B 601 TGWVQNQGILPGMVWQDRDVYLQGPIWAKIPHTDGNFHPSPLMGGFGMKHPPPQILIKNTPVPADPPTAFNKDKLNSFITQYSTGQVSVEIEWELQKENS
AAVG5 701 KRWNPEIQYTSNYYKSNNVEFAVNTEGVYSEPRPIGTRYLTRNL
AAV9  701 KRWNPEIQYTSNYYKSNNVEFAVNTEGVYSEPRPIGTRYLTRNL
PHP.B 701 KRWNPEIQYTSNYYKSNNVEFAVNTEGVYSEPRPIGTRYLTRNLMAADGYLPDWLEDNLSEGIREWWALKPGAPQPKANQQHQDNARGLVLPGYKYLGPG
```

FIG. 12B (Clade F nt)

```
AAVG5   1  atgtctttttgttgatcaccctccagattgg---ttggaagaagttggtgaaggtcttcgcgagttttgggcccttgaagcgggccaccgaaaccaaaac
PHP.B   1  atggctgccgatggttatcttccagattggctgttgtctccgaggacaaccttagtgaaggaattcgcgagtgtggtgggcttgaaacctgaagcccctcaaccaagg
AAV9    1  atggctgccgatggttatcttccagattggctgttgtctccgaggacaaccttagtgaaggaattcgcgagtgtggtgggcttgaaacctgaagcccctcaaccaagg
hu68    1  atggctgccgatggttatcttccagattggctgttgtctccgaggacaaccttagtgaaggaattcgcgagtgtggtgggcttgaaacctgaagcccctcaaccaagg AAVG5  101  ccaatcagcagcatcaagatcaagccgtgtcttgtgcctggttataactatctcggaccggaaacgtctcgatcgaggagcctgtcaacag
PHP.B  101  caaatcaacaacatcaagacaacgctcgagttcttgtgcttccggttacaaatacctggaccggacgactcgacaagggggagccggtcaacgc
AAV9   101  caaatcaacaacatcaagacaacgctcgagttcttgtgcttccggttacaaatacctggaccggacgactcgacaagggggagccggtcaacgc
hu68   101  caaatcaacaacatcaagacaacgctcgagttcttgtgcttccggttacaaatacctggaccggacgactcgacaagggggagccggtcaacgc AAVG5  201  ggcagacgaggtcgcgcgagagcacgacacatctcgtacaacggagcagcttgaggcgggagacaaccctacctcaagtacaaccacgcgacgcgagttt
PHP.B  201  agcagacgcggcggcgccctcgagcagcagcaagccagcagcagcagccgcaaggcgagcagtcttcaggccgagcagtctttcgaacctttggcctgttgaag
AAV9   201  agcagacgcggcggcgccctcgagcagcagcaagccagcagcagcagccgcaaggcgagcagtcttcaggccgagcagtctttcgaacctttggcctgttgaag
hu68   201  agcagacgcggcggcgccctcgagcagcagcaagccagcagcagcagccgcaaggcgagcagtcttcaggccgagcagtctttcgaacctttggcctgttgaag AAVG5  301  caggagaagctcgcgacgacacatcctcttcgggaaacctcggaaaggcagtctttcaggccaagaaaaagagagcttcttgaacctcttgtctgttgagg
PHP.B  301  agcagcggctcaaagaagataccgtcttgagcagcctgtagagacggctgtagagcagcagtcctgtagagcagcagtcctgtagagcagcagtcctgtagag
AAV9   301  agcagcggctcaaagaagataccgtcttgagcagcctgtagagacggctgtagagcagcagtcctgtagagcagcagtcctgtagagcagcagtcctgtagag
hu68   301  agcagcggctcaaagaagataccgtcttgagcagcctgtagagacggctgtagagcagcagtcctgtagagcagcagtcctgtagagcagcagtcctgtagag AAVG5  401  agggtgctaagacggcccctaccggaaagcggatagacggacctgtagagcggctgtagagcggcagtcctgaaaaagaaggcccggaccgaagaggactcca-------a------
PHP.B  401  aagcggctaagacggctcctcctgaaagaagaagaagaaaggccgactcctccgcgggtattggcaaatcggttgcacagcccgc
AAV9   401  aagcggctaagacggctcctcctgaaagaagaagaagaaaggccgactcctccgcgggtattggcaaatcggttgcacagcccgc
hu68   401  aagcggctaagacggctcctcctgaaagaagaagaagaaaggccgactcctccgcgggtattggcaaatcggttgcacagcccgc AAVG5  501  -------gccttccacctcgtcagacgccgaagctggacgcggatcccagcagctgcaaatcggagacccctcaaccaatcggagaacctccgcagccccctcaaccaatcggagaacctggatct
PHP.B  501  taaaaagagactcaatttcggttcagactggcgacacagagtcagtcgcagacagagtcagtcagtgcgacacagagtcagtcagtgcgacacagagtcagtcagtgcgacacagagtcagtcagt
AAV9   501  taaaaagagactcaatttcggttcagactggcgacacagagtcagtcgcagacagagtcagtcagtgcgacacagagtcagtcagtgcgacacagagtcagtcagtgcgacacagagtcagtcagt
hu68   501  taaaaagagactcaatttcggttcagactggcgacacagagtcagtcgcagacagagtcagtcagtgcgacacagagtcagtcagtgcgacacagagtcagtcagtgcgacacagagtcagtcagt
```

FIG. 12C (Clade F nt - cont'd)

```
AAVG5   601  gatacaatggcttcaggtggtggcgcaccagtggcagacaataacgaaggtgccgatggagtggtagttcctcggaaattggcattgcgattcccaat
PHP.B   601  cttacaatggcttcaggtggtggcgcaccagtggcagacaataacgaaggtgccgatggagtggtagttcctcggaaattggcattgcgattcccaat
AAV9    601  cttacaatggcttcaggtggtggcgcaccagtggcagacaataacgaaggtgccgatggagtggtagttcctcggaaattggcattgcgattcccaat
hu68    601  cttacaatggcttcaggtggtggcgcaccagtggcagacaataacgaaggtgccgatggagtggtagttcctcggaaattggcattgcgattcccaat AAVG5   701  ggctggggacagagtcatcaccaccagcacccaccagcacccaccagcacccaccagcacccaccagcacccgaacctgggccctgccccactacaacctacacctctacaagcaaatctccaacagcacatctggagg
PHP.B   701  ggctggggacagagtcatcaccaccagcacccaccagcacccaccagcacccaccagcacccaccagcacccgaacctgggccctgccccactacaacctacacctctacaagcaaatctccaacagcacatctggagg
AAV9    701  ggctggggacagagtcatcaccaccagcacccaccagcacccaccagcacccaccagcacccaccagcacccgaacctgggccctgccccactacaacctacacctctacaagcaaatctccaacagcacatctggagg
hu68    701  ggctggggacagagtcatcaccaccagcacccaccagcacccaccagcacccaccagcacccaccagcacccgaacctgggccctgccccactacaacctacacctctacaagcaaatctccaacagcacatctggagg AAVG5   801  atctttcaaatgacaacgcctacttcggctacagcacctcggctacagcacctcggctacagcacctcggctacagcacctcggctacagcacctcggctacagcacctacttctcggctacagcacctactcggctacagcacctactgggggtatttttgacttcaacagattccactgccacttctcaccacgtgactgactgactgactgactgactgactgactgactgactgactgactgactgactgactgactgactgactgactgactgactggcagcga
PHP.B   801  atctttcaaatgacaacgcctacttcggctacagcacctacttgacttcaacagattccactgccacttctcaccacgtgactgactgactgactgactgactgactgactgactgactgactgactgactgactgactgactgactgactgactgactgactgactgactgactggcagcga
AAV9    801  atctttcaaatgacaacgcctacttcggctacagcacctacttgacttcaacagattccactgccacttctcaccacgtgactgactgactgactgactgactgactgactgactgactgactgactgactgactgactgactgactgactgactgactgactgactgactgactggcagcga
hu68    801  atctttcaaatgacaacgcctacttcggctacagcacctacttgacttcaacagattccactgccacttctcaccacgtgactgactgactgactgactgactgactgactgactgactgactgactgactgactgactgactgactgactgactgactgactgactgactgactggcagcga AAVG5   901  ctcatcaacaacaactgggattccggcctaagcgactcaacttcaagctcttcaacattcaggtcaaagaggttacggacaacaatggagtcaagaccaagagaccaagagaccaagagaccaagagaccaagagaccaagagaccaagagaccaagagaccaagagaccaagagaccaagagaccaagagaccaagagaccaagaga
PHP.B   901  ctcatcaacaacaactgggattccggcctaagcgactcaacttcaagctcttcaacattcaggtcaaagaggttacggacaacaatggagtcaagacca
AAV9    901  ctcatcaacaacaactgggattccggcctaagcgactcaacttcaagctcttcaacattcaggtcaaagaggttacggacaacaatggagtcaagacca
hu68    901  ctcatcaacaacaactgggattccggcctaagcgactcaacttcaagctcttcaacattcaggtcaaagaggttacggacaacaatggagtcaagacca AAVG5  1001  tcgccaataaccttaccagcacgacgtcttcacggactcagactcagctcccgtacgtgctcggtcgtgctgcgggctgcctccgccgtt
PHP.B  1001  tcgccaataaccttaccagcacgacgtcttcacggactcagactcagctcccgtacgtgctcggtcgtgctgcgggctgcctccgccgtt
AAV9   1001  tcgccaataaccttaccagcacgacgtcttcacggactcagactcagctcccgtacgtgctcggtcgtgctgcgggctgcctccgccgtt
hu68   1001  tcgccaataaccttaccagcacgacgtcttcacggactcagactcagctcccgtacgtgctcggtcgtgctgcgggctgcctccgccgtt AAVG5  1101  cccagcggacgtttttcatgattcctcagtatctgacgttaatgatgaagccaggccgttcgttcgtccttttactgcctgctgaatatttc
PHP.B  1101  cccagcggacgtttttcatgattcctcagtatctgacgttaatgatgaagccaggccgttcgttcgtccttttactgcctgctgaatatttc
AAV9   1101  cccagcggacgtttttcatgattcctcagtatctgacgttaatgatgaagccaggccgttcgttcgtccttttactgcctgctgaatatttc
hu68   1101  cccagcggacgtttttcatgattcctcagtatctgacgttaatgatgaagccaggccgttcgttcgtccttttactgcctgctgaatatttc AAVG5  1201  ccgtcgcaaatgctaagaacgggtaacaacttccagttcagtacgagtttgagaacgtacctttccatagcagctcacagccaaagcctggacc
PHP.B  1201  ccgtcgcaaatgctaagaacgggtaacaacttccagttcagtacgagtttgagaacgtacctttccatagcagctcacagccaaagcctggacc
AAV9   1201  ccgtcgcaaatgctaagaacgggtaacaacttccagttcagtacgagtttgagaacgtacctttccatagcagctcacagccaaagcctggacc
hu68   1201  ccgtcgcaaatgctaagaacgggtaacaacttccagttcagtacgagtttgagaacgtacctttccatagcagctatgcagccacagcaaaaccctgacc
```

FIG. 12D (Clade F - cont'd)

```
AAVG5  1301  gactaatgaatccactcatcgaccaatacttgtactatctctcaaagactattaacggttctggacagaatcaacaaacgctaaaattcagtgtggccgg
PHP.B  1301  gactaatgaatccactcatcgaccaatacttgtactatctctcctagaactattaacggttctggacagaatcaacaaacgctaaaattcagtgtggccgg
AAV9   1301  gactaatgaatccactcatcgaccaatacttgtactatctctcaaagactattaacggttctggacagaatcaacaaacgctaaaattcagtgtggccgg
hu68   1301  gactcatgaatccactcatcgaccaatacttgtactatctctcaaagactattaacggttctggacagaatcaacaaacgctaaaattcagtgtggccgg AAVG5  1401  acccagcaacatggctgtgtccagggaagaaactacatacctggaccagcaccactgtgtctcaaccactgactcaaaacaacaacagcgaa
PHP.B  1401  acccagcaacatggctgtgtccagggaagaaactacatacctggaccagcaccactgtgtctcaaccactgactcaaaacaacaacagcgaa
AAV9   1401  acccagcaacatggctgtgtccagggaagaaactacatacctggaccagcaccactgtgtctcaaccactgactcaaaacaacaacagcgaa
hu68   1401  acccagcaacatggctgtgtccagggaagaaactacatacctggaccagcaccactgtgtctcaaccactgactcaaaacaacaacagcgaa AAVG5  1501  tttgcttgcctggagctcttcttggctctcaatgacgtaatagcttgatgaatcctggacctgctatggccagccacaaagaaggaggaggaccgtt
PHP.B  1501  tttgcttgcctggagctcttcttggctctcaatgacgtaatagcttgatgaatcctggacctgctatggccagccacaaagaaggaggaggaccgtt
AAV9   1501  tttgcttgcctggagctcttcttggctctcaatgacgtaatagcttgatgaatcctggacctgctatggccagccacaaagaaggaggaggaccgtt
hu68   1501  tttgcttgcctggagctcttcttggctctcaatgacgtaatagcttgatgaatcctggacctgctatggccagccacaaagaaggaggaggaccgtt AAVG5  1601  tctttcctttgtctgatctttaattttggcaaacaaggaactgaagagacaacaagtcatgataaccaacgaagaagaagaaattaa
PHP.B  1601  tctttcctttgtctgatctttaattttggcaaacaaggaactgaagagacaacaagtcatgataaccaacgaagaagaagaaattaa
AAV9   1601  tctttcctttgtctgatctttaattttggcaaacaaggaactgaagagacaacaagtcatgataaccaacgaagaagaagaaattaa
hu68   1601  tctttcctttgtctgatctttaattttggcaaacaaggaactgaagagacaacaagtcatgataaccaacgaagaagaagaaattaa AAVG5  1701  aactactaaccggtagcaacggagtcctatggacaagtggccacaaaccaccagagtgcccaag------------cacaggcgcagacc
PHP.B  1701  aactactaaccggtagcaacggagtcctatggacaagtggccacaaaccaccagagtgcccaaactttggcggtgccttaaggcacaggcgcagacc
AAV9   1701  aactactaaccggtagcaacggagtcctatggacaagtggccacaaaccaccagagtgcccaag------------cacaggcgcagacc
hu68   1701  aactaccaaccagtcaacggagtcctatggacaagtggccacaaaccaccagagtgcccaag------------cacaggcgcagacc AAVG5  1801  ggctgggttcaaaaccaaggaatacttccgggtatggttggcaggacagagatgtgtacctgcaaggaccatttggccaaaattcctcacacggacg
PHP.B  1801  ggttgggttcaaaaccaaggaatacttccgggtatggttggcaggacagagatgtgtacctgcaaggaccatttggccaaaattcctcacacggacg
AAV9   1801  ggctgggttcaaaaccaaggaatacttccgggtatggttggcaggacagagatgtgtacctgcaaggaccatttggccaaaattcctcacacggacg
hu68   1801  ggctgggttcaaaaccaaggaatacttccgggtatggttggcaggacagagatgtgtacctgcaaggaccatttggccaaaattcctcacacggacg
```

FIG. 12E (Clade F – cont'd)

```
AAVG5   1901  gcaactttcacccttctccgctgatgggagggtttggaatgaagcaccgcctcctcctcagatcctcatcaaaaacacacctgtacctgcggatcctccaac
PHP.B   1901  gcaactttcacccttctccgctgatgggagggtttggaatgaagcaccgcctcctcctcagatcctcatcaaaaacacacctgtacctgcggatcctccaac
AAV9    1901  gcaactttcacccttctccgctgatgggagggtttggaatgaagcaccgcctcctcctcagatcctcatcaaaaacacacctgtacctgcggatcctccaac
hu68    1901  gcaactttcacccttctccgctgatgggagggtttggaatgaagcaccgcctcctcctcagatcctcatcaaaaacacacctgtacctgcggatcctccaac AAVG5   2001  ggcccttcaacaaggacaagctgaactctttcatcacccagtattctactggccaagtcagcgtggagatcgagtgggagctgcagaaggaaaacagcaag
PHP.B   2001  ggcccttcaacaaggacaagctgaactctttcatcacccagtattctactggccaagtcagcgagatcgagtgggagctgcagaaggaaaacagcaag
AAV9    2001  ggccttcaacaaggacaagctgaactctttcatcacccagtattctactggccaagtcagcgagatcgagtgggagctgcagaaggaaaacagcaag
hu68    2001  ggcttcaacaaggacaagctgaactctttcatcacccagtattctactggccaagtcagcgagattgagtgggagctgcagaaggaaaacagcaag AAVG5   2101  cgctggaacccggagatccagtacacttccaactattacaagtctaataatgttgaatttgcttgttaatactgaaggtgtatatagtgaaccccgccca
PHP.B   2101  cgctggaacccggagatccagtacacttccaactattacaagtctaataatgttgaatttgcttgttaatactgaaggtgtatatagtgaaccccgccca
AAV9    2101  cgctggaacccggagatccagtacacttccaactattacaagtctaataatgttgaatttgcttgttaatactgaaggtgtatatagtgaaccccgccca
hu68    2101  cgctggaacccggagatccagtacacttccaactattacaagtctaataatgttgaatttgcttgttaatactgaaggtgtttattctgaaccccgccca AAVG5   2201  ttggcaccagatacctgactcgtaatctg
PHP.B   2201  ttggcaccagatacctgactcgtaatctg
AAV9    2201  ttggcaccagatacctgactcgtaatctg
hu68    2201  ttggcaccagatacctgactcgtaatctg
```

FIG. 13A (AAV8)

|vp1 start
AAV8T   1  MAADGYLPDWLEDNLSEGIREWWALKPGAPKPKANQQKQDDGRGLVLPGYKYLGPFNGLDKGEPVNAADAAALEHDKAYDQQLQAGDNPYLRYNHADAEF
AAVG3   1  MAADGYLPDWLEDNLSEGIREWWALKPGAPKPKANQQKQDDGRGLVLPGYKYLGPFNGLDKGEPVNAADAAALEHDKAYDQQLQAGDNPYLRYNHADAEF
AAV8    1  MAADGYLPDWLEDNLSEGIREWWALKPGAPKPKANQQKQDDGRGLVLPGYKYLGPFNGLDKGEPVNAADAAALEHDKAYDQQLQAGDNPYLRYNHADAEF
                                                                      |vp2 start
AAV8T 101  QERLQEDTSFGGNLGRAVFQAKKRVLEPLGLVEEGAKTAPGKKRPVEPSPQRSPDSSTGIGKKGQQPARKRLNFGQTGDSESVPDPQPLGEPPAAPSGVG
AAVG3 101  QERLQEDTSFGGNLGRAVFQAKKRVLEPLGLVEEGAKTAPGKKRPVEPSPQRSPDSSTGIGKKGQQPARKRLNFGQTGDSESVPDPQPLGEPPAAPSGVG
AAV8  101  QERLQEDTSFGGNLGRAVFQAKKRVLEPLGLVEEGAKTAPGKKRPVEPSPQRSPDSSTGIGKKGQQPARKRLNFGQTGDSESVPDPQPLGEPPAAPSGVG
           |vp3 start
AAV8T 201  PNTMAAGGAPMADNNEGADGVGSSSGNWHCDSTWLGDRVITTSTRTWALPTYNNHLYKQISSGTH=GATNDNTYFGYSTPWGYFDFNRFHCHFSPRDWQ
AAVG3 201  PNTMAAGGAPMADNNEGADGVGSSSGNWHCDSTWLGDRVITTSTRTWALPTYNNHLYKQISNGTSGGATNDNTYFGYSTPWGYFDFNRFHCHFSPRDWQ
AAV8  201  PNTMAAGGAPMADNNEGADGVGSSSGNWHCDSTWLGDRVITTSTRTWALPTYNNHLYKQISNGTSGGATNDNTYFGYSTPWGYFDFNRFHCHFSPRDWQ AAV8T 301  RLINNNWGFRPKRLSFKLFNIQVKEVTQNEGTKTIANNLTSTIQVFTDSEYQLPYVLGSAHQGCLPPFPADVFMIPQYGYLTLNNGSQAVGRSSFYCLEY
AAVG3 301  RLINNNWGFRPKRLSFKLFNIQVKEVTQNEGTKTIANNLTSTIQVFTDSEYQLPYVLGSAHQGCLPPFPADVFMIPQYGYLTLNNGSQAVGRSSFYCLEY
AAV8  301  RLINNNWGFRPKRLSFKLFNIQVKEVTQNEGTKTIANNLTSTIQVFTDSEYQLPYVLGSAHQGCLPPFPADVFMIPQYGYLTLNNGSQAVGRSSFYCLEY AAV8T 401  FPSQMLRTGNNFQFTYTFEDVPFHSSYAHSQSLDRLMNPLIDQYLYYLSRTQTTGGSRPTQTLGFSQGGPNTMANQAKNWLPGPCYRQQRVSTTTGQNNN
AAVG3 401  FPSQMLRTGNNFQFTYTFEDVPFHSSYAHSQSLDRLMNPLIDQYLYYLSRTQTTGGTANTQTLGFSQGGPNTMANQAKNWLPGPCYRQQRVSTTTGQNNN
AAV8  401  FPSQMLRTGNNFQFTYTFEDVPFHSSYAHSQSLDRLMNPLIDQYLYYLSRTQTTGGTANTQTLGFSQGGPNTMANQAKNWLPGPCYRQQRVSTTTGQNNN AAV8T 501  SNFAWTAGTKYHLNGRNSLANPGIAMATHKDDEERFFPSNGILIFGKQNAARDNADYSDVMLTSEEEIKTTNPVATEEYGIVGDNLQLYNTAPGSVFVNS
AAVG3 501  SNFAWTAGTKYHLNGRNSLANPGIAMATHKDDEERFFPSNGILIFGKQNAARDNADYSDVMLTSEEEIKTTNPVATEEYGIVCDNLQSRNTAPREEIVNS
AAV8  501  SNFAWTAGTKYHLNGRNSLANPGIAMATHKDDEERFFPSNGILIFGKQNAARDNADYSDVMLTSEEEIKTTNPVATEEYGIVADNLQQONTAPQIGTVNS AAV8T 601  QGALPGMVWQNRDVYLQGPIWAKIPHTDGNFHPSPLMGGFGLKHPPPQILIKNTPVPADPPTTFNQSKLNSFITQYSTGQVSVEIEWELQKENSKRWNPE
AAVG3 601  QGALPGMVWQNRDVYLQGPIWAKIPHTDGNFHPSPLMGGFGLKHPPPQILIKNTPVPADPPTTFNQSKLNSFITQYSTGQVSVEIEWELQKENSKRWNPE
AAV8  601  QGALPGMVWQNRDVYLQGPIWAKIPHTDGNFHPSPLMGGFGLKHPPPQILIKNTPVPADPPTTFNQSKLNSFITQYSTGQVSVEIEWELQKENSKRWNPE AAV8T 701  IQYTSNYYKSTSVDFAVNTEGVYSEPRPIGTRYLTRNL
AAVG3 701  IQYTSNYYKSTSVDFAVNTEGVYSEPRPIGTRYLTRNL
AAV8  701  IQYTSNYYKSTSVDFAVNTEGVYSEPRPIGTRYLTRNL

FIG. 13B (AAV8)

```
        |vp1 start
AAV8T   1  atggctgccgatggttatcttccagattggctctcgaggacaacctctctgagggcattcgcgagtggtgggcgctgaacctgaaacctggagcccgaagcccaaag
AAVG3   1  atggctgccgatggttatcttccagattggctctcgaggacaacctctctgagggcattcgcgagtggtgggcgctgaacctgaaacctggagcccgaagcccaaag
AAV8    1  atggctgccgatggttatcttccagattggctctcgaggacaacctctctgagggcattcgcgagtggtgggcgctgaacctgaaacctggagcccgaagcccaaag AAV8T 101  ccaaccagcaaaagcaggacgacggacggcggggtctgtgctcctggtgcttcctgctacaagtacctcggaccttcaacgactcgacaagggagccccgtcaacgc
AAVG3 101  ccaaccagcaaaagcaggacgacggacggcggggtctgtgctcctggtgcttcctgctacaagtacctcggaccttcaacgactcgacaagggagccccgtcaacgc
AAV8  101  ccaaccagcaaaagcaggacgacggacggcggggtctgtgctcctggtgcttcctgctacaagtacctcggaccttcaacgactcgacaagggagccccgtcaacgc AAV8T 201  ggcggacgcagcggcgccctcgagcacgacaaggcctacgaccagcagctgcaggcgggtgacaatcgtacctgcggtataaccacgccgacgccgagttt
AAVG3 201  ggcggacgcagcggcgccctcgagcacgacaaggcctacgaccagcagctgcaggcgggtgacaatcgtacctgcggtataaccacgccgacgccgagttt
AAV8  201  ggcggacgcagcggcgccctcgagcacgacaaggcctacgaccagcagctgcaggcgggtgacaatcgtacctgcggtataaccacgccgacgccgagttt AAV8T 301  caggagcgtctgcaagaagatacgtcttttgggggcaacctcgggcgagcagtcttccaggccagtcttcctgaacctctcggtctgttgagg
AAVG3 301  caggagcgtctgcaagaagatacgtcttttgggggcaacctcgggcgagcagtcttccaggccagtcttcctgaacctctcggtctgttgagg
AAV8  301  caggagcgtctgcaagaagatacgtcttttgggggcaacctcgggcgagcagtcttccaggccagtcttcctgaacctctcggtctgttgagg AAV8T 401  aaggcgctaagacggctcctggaaagaagaagaagaccggtagagcacggacctcctcctcctcagacgttctccagagcgttctcccagcagccatcaccccagcgttctcctcctcagtttctcgggcatcggcaagaaaggccaacagcc
AAVG3 401  aaggcgctaagacggctcctggaaagaagaagaagaccggtagagcacggacctcctcctcctcagacgttctccagagcgttctcccagcagccatcaccccagcgttctcctcctcagtttctcgggcatcggcaagaaaggccaacagcc
AAV8  401  aaggcgctaagacggctcctggaaagaagaagaagaccggtagagcacggacctcctcctcctcagacgttctccagagcgttctcccagcagccatcaccccagcgttctcctcctcagtttctcgggcatcggcaagaaaggccaacagcc
                                                         |vp2 start
AAV8T 501  cgccagaaaaagactcaattttggtcagactggcctcagatgcgactcagttcctcagatcagtcagtaacaatgcagacaataacgaaggcgccgacgaagccgccgacgccacctacctaagaccttcaaacctcaacctcaacctcaacctcaacctccagagtggggtagttcctggaaattgcattgcgattcca
AAVG3 501  cgccagaaaaagactcaattttggtcagactggcctcagatgcgactcagttcctcagatcagtcagtaacaatgcagacaataacgaaggcgccgacgaagccgccgacgccacctacctaagaccttcaaacctcaacctcaacctcaacctcaacctccagagtggggtagttcctggaaattgcattgcgattcca
AAV8  501  cgccagaaaaagactcaattttggtcagactggcctcagatgcgactcagttcctcagatcagtcagtaacaatgcagacaataacgaaggcgccgacgaagccgccgacgccacctacctaagaccttcaaacctcaacctcaacctcaacctcaacctccagagtggggtagttcctggaaattgcattgcgattcca
                |vp3 start
AAV8T 601  cctaatacaatgctggcgcaggcggtggcgcaccaatgcagacaacacccagccgaacctggcccctgccaacctggccctgcccaccacctacaacagcctacaacaactctacaagcaaatctcctctctggtactca
AAVG3 601  cctaatacaatgctggcgcaggcggtggcgcaccaatgcagacaacacccagccgaacctggcccctgccaacctggccctgcccaccacctacaacagcctacaacaactctacaagcaaatctcctctctggtactca
AAV8  601  cctaatacaatgctggcgcaggcggtggcgcaccaatgcagacaacacccagccgaacctggcccctgccaacctggccctgcccaccacctacaacagcctacaacaactctacaagcaaatctcctctctggtactca AAV8T 701  catggctgggcggacagagtcatcaccaccaccaccaccacctggccgcccctgcccctgccaacctggcctgccaacctggcccctgccccctggggggtatttttgactttaacagattccactttcaccactgactggcag---
AAVG3 701  catggctgggcggacagagtcatcaccaccaccaccaccacctggccgcccctgcccctgccaacctggcctgccaacctggcccctgccccctggggggtatttttgactttaacagattccactttcaccactgactggcag---
AAV8  701  catggctgggcggacagagtcatcaccaccaccaccaccacctggccgcccctgcccctgccaacctggcctgccaacctggcccctgccccctggggggtatttttgactttaacagattccactttcaccactgactggcag---

AAV8T 801  tggagccaccaacaacgacaacacacacctacttcggctacgcccggggggtatttttgactttaacagattccactttcaccactgactggcag
AAVG3 801  aggagccaccaacaacgacaacacacacctacttcggctacgcccggggggtatttttgactttaacagattccactttcaccactgactggcag
AAV8  801  aggagccaccaacaacgacaacacacacctacttcggctacgcccggggggtatttttgactttaacagattccactttcaccactgactggcag
```

FIG. 13C (AAV8 - cont'd)

```
AAV8T  901  cgactcatcatcaacaacaactggggattccggcccaagagagactcagctcttcaagctcttcaacatccaggtcaaggaggtcacgcagaatgaaggcaccaaga
AAVG3  901  cgactcatcatcaacaacaactggggattccggcccaagagagactcagctcttcaagctcttcaacatccaggtcaaggaggtcacgcagaatgaaggcaccaaga
AAV8   901  cgactcatcatcaacaacaactggggattccggcccaagagagactcagctcttcaagctcttcaacatccaggtcaaggaggtcacgcagaatgaaggcaccaaga AAV8T 1001  ccatcgccaataaacctcaccagcaccatccagttgtttacggactcggagtaccagtcgccgtctctcggcttctcggctgcctcctgcccaccaggggctgcctcc
AAVG3 1001  ccatcgccaataaacctcaccagcaccatccagttgtttacggactcggagtaccagtcgccgtctctcggcttctcggctgcctcctgcccaccaggggctgcctcc
AAV8  1001  ccatcgccaataaacctcaccagcaccatccagttgtttacggactcggagtaccagtcgccgtctctcggcttctcggctgcctcctgcccaccaggggctgcctcc AAV8T 1101  gttcccggcgacgtgttcatgattcccagtagtacggctacctaacactcaacaacgtagtcaggccgtgggacgtcctcctcctactgcctgaatac
AAVG3 1101  gttcccggcgacgtgttcatgattcccagtagtacggctacctaacactcaacaacgtagtcaggccgtgggacgtcctcctcctactgcctgaatac
AAV8  1101  gttcccggcgacgtgttcatgattcccagtagtacggctacctaacactcaacaacgtagtcaggccgtgggacgtcctcctcctactgcctgaatac AAV8T 1201  tttccttcgcagatgctgagaacggcaacaacttccagtttacttactacacacctcgaggacgtgccttccacagcagctacgcccacagccagagcttgg
AAVG3 1201  tttccttcgcagatgctgagaacggcaacaacttccagtttacttactacacacctcgaggacgtgccttccacagcagctacgcccacagccagagcttgg
AAV8  1201  tttccttcgcagatgctgagaacggcaacaacttccagtttacttactacacacctcgaggacgtgccttccacagcagctacgcccacagccagagcttgg AAV8T 1301  accggctgatgaatcctctgattgaccagtacctgtatctccggactcaaacaacaggtgggagtaggcctacgcagactctgggcttcagcca
AAVG3 1301  accggctgatgaatcctctgattgaccagtacctgtatctccggactcaaacaacaggtgggagtaggcctacgcagactctgggcttcagcca
AAV8  1301  accggctgatgaatcctctgattgaccagtacctgtatctccggactcaaacaacaggtgggagtaggcctacgcagactctgggcttcagcca AAV8T 1401  aggtgggcctaatacaatggccaatcaggcagaactggctgccaagaacgtctcaacgacaacggcaaacaacaat
AAVG3 1401  aggtgggcctaatacaatggccaatcaggcagaactggctgccaagaacgtctcaacgacaacggcaaacaacaat
AAV8  1401  aggtgggcctaatacaatggccaatcaggcagaactggctgccaagaacgtctcaacgacaacggcaaacaacaat AAV8T 1501  agcaactttgcctggactgctgggaccaaatacccattggaagaaattcattggctatgcatcgctaatcctgctgcaacacacaaagacgacgagg
AAVG3 1501  agcaactttgcctggactgctgggaccaaatacccattggaagaaattcattggctatgcatcgctaatcctgctgcaacacacaaagacgacgagg
AAV8  1501  agcaactttgcctggactgctgggaccaaatacccattggaagaaattcattggctatgcatcgctaatcctgctgcaacacacaaagacgacgagg AAV8T 1601  agcgttttttcccagtaacgggatcctgattttttgcaaacaaaatgctgccagagacaatgcggattacagcgatgtcatgctcaccagcagcgaggaaga
AAVG3 1601  agcgttttttcccagtaacgggatcctgattttttgcaaacaaaatgctgccagagacaatgcggattacagcgatgtcatgctcaccagcagcgaggaaga
AAV8  1601  agcgttttttcccagtaacgggatcctgattttttgcaaacaaaatgctgccagagacaatgcggattacagcgatgtcatgctcaccagcagcgaggaaga
```

FIG. 13D (AAV8 - cont'd)

```
AAV8T  1701  aatcaaaaccactaaccctgtgtgctacagaggaatacggtatcgtgggtgataacttgcagttgtataacacggctcctggttcggtgttgtcaacagc
AAVG3  1701  aatcaaaaccactaaccctgtgtgctacagaggaatacggtatcgtgggtgataacttgcagttgtataacacggctcctggttcggtgttgtcaacagc
AAV8   1701  aatcaaaaccactaaccctgtgtgctacagaggaatacggtatcgtgggtgataacttgcagttgtataacacggctcctggttcggtgttgtcaacagc AAV8T  1801  caggggccttaccccgtatggtctgcagaaccggacgtgtacctgcaggtcccatctggcgcagcagataacacggctcctcaaattgaactgtcaacagc
AAVG3  1801  caggggccttaccccgtatggtctgcagaaccggacgtgtacctgcaggtcccatctggcgcagcagataacacggctcctcaaattgaactgtcaacagc
AAV8   1801  caggggccttaccccgtatggtctgcagaaccggacgtgtacctgcaggtcccatctggcgcagcagataacacggctcctcaaattgaactgtcaacagc AAV8T  1901  ctccgctgatgggcggctttggcctgaaacatcctccgctccagatcctgatcaagaacacgcctgtacctgcggatcctccgacaccttcaaccagtc
AAVG3  1901  ctccgctgatgggcggctttggcctgaaacatcctccgctccagatcctgatcaagaacacgcctgtacctgcggatcctccgacaccttcaaccagtc
AAV8   1901  ctccgctgatgggcggctttggcctgaaacatcctccgctccagatcctgatcaagaacacgcctgtacctgcggatcctccgacaccttcaaccagtc AAV8T  2001  aaagctgaactctttcatcacgcaatacagcagcagcggacaggtcagcgtggacaggtcagcgtggaaattgaatgggagctgcagaaggaaaacagcaagcgctgaaccccgag
AAVG3  2001  aaagctgaactctttcatcacgcaatacagcagcagcggacaggtcagcgtggacaggtcagcgtggaaattgaatgggagctgcagaaggaaaacagcaagcgctgaaccccgag
AAV8   2001  aaagctgaactctttcatcacgcaatacagcagcagcggacaggtcagcgtggacaggtcagcgtggaaattgaatgggagctgcagaaggaaaacagcaagcgctgaaccccgag AAV8T  2101  atccagtacacctccaactactacaaatctacaagtgtggactttgctgttaatacagaaggcgtgtactctgaaccccgcccattgcaccgttacc
AAVG3  2101  atccagtacacctccaactactacaaatctacaagtgtggactttgctgttaatacagaaggcgtgtactctgaaccccgcccattgcaccgttacc
AAV8   2101  atccagtacacctccaactactacaaatctacaagtgtggactttgctgttaatacagaaggcgtgtactctgaaccccgcccattgcaccgttacc AAV8T  2201  tcacccgtaatctg
AAVG3  2201  tcacccgtaatctg
AAV8   2201  tcacccgtaatctg
```

FIG. 14A (AAVrh10)

```
         |vp1 start
AAVG2  1   MAADGYLPDWLEDNLSEGIREWWDLKPGAPKPKANQKQDDGRGLVLPGYKYLGPFNGLDKGEPVNEADAAALEHDKAYDQQLKAGDNPYLRYNHADAEF
rh10   1   MAADGYLPDWLEDNLSEGIREWWDLKPGAPKPKANQKQDDGRGLVLPGYKYLGPFNGLDKGEPVNAADAAALEHDKAYDQQLKAGDNPYLRYNHADAEF
hu37   1   MAADGYLPDWLEDNLSEGIREWWDLKPGAPKPKANQKQDDGRGLVLPGYKYLGPFNGLDKGEPVNAADAAALEHDKAYDQQLKAGDNPYLRYNHADAEF

|vp2 start
AAVG2  101 QERLQEDTSFGGNLGRAVFQAKKRVLEPLGLVEEAAKTAPGKKRPVEPSPQRSPDSSTGIGKKGQQPARKRLNFGQTGDSESVPDPQPIGEPPAGPSGLG
rh10   101 QERLQEDTSFGGNLGRAVFQAKKRVLEPLGLVEEGAKTAPGKKRPVEPSPQRSPDSSTGIGKKGQQPAKKRLNFGQTGDSESVPDPQPIGEPPAGPSGLG
hu37   101 QERLQEDTSFGGNLGRAVFQAKKRVLEPLGLVEEAAKTAPGKKRPVEPSPQRSPDSSTGIGKKGQQPAKKRLNFGQTGDSESVPDPQPIGEPPAGPSGLG

|vp3 start
AAVG2  201 SGTMAAGGAPMADNNEGADGVGSSSGNWHCDSTWLGDRVITTSTRTWALPTYNNHLYKQISNGTSGGSTNDNTYFGYSTPWGYFDFNRFHCHFSPRDWQ
rh10   201 SGTMAAGGAPMADNNEGADGVGSSSGNWHCDSTWLGDRVITTSTRTWALPTYNNHLYKQISNGTSGGSTNDNTYFGYSTPWGYFDFNRFHCHFSPRDWQ
hu37   201 SGTMAAGGAPMADNNEGADGVGSSSGNWHCDSTWLGDRVITTSTRTWALPTYNNHLYKQISNGTSGGSTNDNTYFGYSTPWGYFDFNRFHCHFSPRDWQ AAVG2  301 RLINNNWGFRPKRLSFKLFNIQVKEVTQNEGTKTIANNLTSTIQVFTDSEYQLPYVLGSAHQGCLPPFPADVFMIPQYGYLTLNNGSQAVGRSSFYCLEY
rh10   301 RLINNNWGFRPKRLNFKLFNIQVKEVTQNEGTKTIANNLTSTIQVFTDSEYQLPYVLGSAHQGCLPPFPADVFMIPQYGYLTLNNGSQAVGRSSFYCLEY
hu37   301 RLINNNWGFRPKRLSFKLFNIQVKEVTQNEGTKTIANNLTSTIQVFTDSEYQLPYVLGSAHQGCLPPFPADVFMIPQYGYLTLNNGSQAVGRSSFYCLEY AAVG2  401 FPSQMLRTGNNFEFSYTFEDVPFHSSYAHSQSLLDRLMNPLIDQYLYYLSRTQSTGGTQGTQQLLFSQAGPANMSAQAKNWLPGPCYRQQRVSTTLSQNNN
rh10   401 FPSQMLRTGNNFEFSYQFEDVPFHSSYAHSQSLLDRLMNPLIDQYLYYLSRTQSTGGTAGTQQLLFSQAGPNNMSAQAKNWLPGPCYRQQRVSTTLSQNNN
hu37   401 FPSQMLRTGNNFEFSYTFEDVPFHSSYAHSQSLLDRLMNPLIDQYLYYLSRTQSTGGTQGTQQLLFSQAGPANMSAQAKNWLPGPCYRQQRVSTTLSQNNN AAVG2  501 SNFAWTGATKYHLNGRDSLVNPGVAMATHKDDEERFFPSSGVLMFGKQGAGRDNVDYSSVMLTSEEEIKTTNPVATEQYGVVADNLQQTNTGPIVGNVNS
rh10   501 SNFAWTGATKYHLNGRDSLVNPGVAMATHKDDEERFFPSSGVLMFGKQGAGKDNVDYSSVMLTSEEEIKTTNPVATEQYGVVADNLQQNAAPIVGAVNS
hu37   501 SNFAWTGATKYHLNGRDSLVNPGVAMATHKDDEERFFPSSGVLMFGKQGAGRDNVDYSSVMLTSEEEIKTTNPVATEQYGVVADNLQQTNTGPIVGNVNS AAVG2  601 QGALPGMVWQNRDVYLQGPIWAKIPHTDGNFHPSPLMGGFGLKHPPPQILIKNTPVPADPPTTFSQAKLASFITQYSTGQVSVEIEWELQKENSKRWNPE
rh10   601 QGALPGMVWQNRDVYLQGPIWAKIPHTDGNFHPSPLMGGFGLKHPPPQILIKNTPVPADPPTTFSQAKLASFITQYSTGQVSVEIEWELQKENSKRWNPE
hu37   601 QGALPGMVWQNRDVYLQGPIWAKIPHTDGNFHPSPLMGGFGLKHPPPQILIKNTPVPADPPTTFSQAKLASFITQYSTGQVSVEIEWELQKENSKRWNPE AAVG2  701 IQYTSNYYKSTNVDFAVNTEGTYSEPRPIGTRYLTRNL
rh10   701 IQYTSNYYKSTNVDFAVNTDGTYSEPRPIGTRYLTRNL
hu37   701 IQYTSNYYKSTNVDFAVNTEGTYSEPRPIGTRYLTRNL
```

FIG. 14B (AAVrh10)

| vp1 start

```
AAVG2      1   atggctgctgacggttatcttccagattggctctcgaggacaacctctctgagggcattcgcgagtggtgggacctgaaacctgaaacctggagccccaaggccccaagg
AAVhu37    1   atggctgctgacggttatcttccagattggctctcgaggacaacctctctgagggcattcgcgagtggtgggacctgaaacctgaaacctggagccccaaggccccaagg
AAVrh10    1   atggctgccgatggtgttatcttccagattggctctcgaggacaacctctctgagggcattcgcgagtggtgggacttgaaacctgaaacctggagcccgaaacccaaag AAVG2    101   ccaaccagcagaagcaggacgacggccggggtctggtgcttcctggctacaagtacctcgacactcggaccctcaacggactcgacaaggggggagcccgtcaacga
AAVhu37  101   ccaaccagcagaagcaggacgacggccggggtctggtgcttcctggctacaagtacctcgacactcggaccctcaacggactcgacaaggggggagcccgtcaacgc
AAVrh10  101   ccaaccagcaaaagcaggacgacggccggggtctggtgcttcctggctacaagtacctcgacactcggaccctcaacggactcgacaaggggggagcccgtcaacgc AAVG2    201   ggcggacgcgcggccctcgagcacgacaagcctacgacaagctcaaatccgtacctcgtgataaccacgcgcgacgccgagttt
AAVhu37  201   ggcggacgcgcagccctcgagcacgacaagcctacgacaagctcaaatccgtacctcgtgataaccacgcgcgacgccgagttt
AAVrh10  201   ggcggacgcgcagccctcgagcacgacaagcctacgacaagctcaaatccgtacctcgtgataaccacgcgcgacgccgagttt AAVG2    301   caggagcgtctgcaagagatacgtctttttgggggcaacctcggcgagcagtcttccaggccaagaagcgggttctcgaacctctcggtctgttgagg
AAVhu37  301   caggagcgtctgcaagagatacgtctttttgggggcaacctcggcgagcagtcttccaggccaagaagcgggttctcgaacctctcggtctgttgagg
AAVrh10  301   caggagcgtctgcaagagatacgtctttttgggggcaacctcggcgagcagtcttccaggccaagaagcgggttctcgaacctctcggtctgttgagg

| vp2 start
AAVG2    401   aagctgctaagacggctcctgaaagaagagaagaagaccgtagaaccgtcacctcagcgatcctccgactcctcccgactcggcaaaaaaggccagcagcc
AAVhu37  401   aagctgctaagacggctcctgaaagaagagaagaagaccgtagaaccgtcacctcagcgatcctccgactcctcccgactcggcatcggcaaggcagcagcc
AAVrh10  401   aagcgctaagacggctcctgaaagaagagaagaagaccgtagaaccgtccatcacccagcgttctccagcgcgttctccagcgcgttctccagcgcgttctccagcg

| vp3 start
AAVG2    501   cgcgagaaagagactgaactttgggcagactggcgactcagagtcagtccccgaccctcaaccaatcggagaaccaccagcagcccctctggtctggga
AAVhu37  501   cgctaaaaagagactgaactttgttcagactggcgactcagagtcagtccccgaccctcaaccaatcggagaaccaccagcagcccctctggtctggga
AAVrh10  501   cgcgaaaagagactcaactttgggcagactggcgactcagagtcagtccccgaccctcaaccaatcggagaaccaccagcagcccctctggtctggga AAVG2    601   tctggtacaatggctgcaggcgtggcgctccaatggcagacaataacggcgccgagtgggtagttcctcaggaaattggcattgcgattcca
AAVhu37  601   tctggtacaatggctgcaggcgtggcgctccaatggcagacaataacggcgccgagtgggtagttcctcaggaaattggcattgcgattcca
AAVrh10  601   tctggtacaatggctgcaggcgtggcgctccaatggcagacaataacggcgccgagtgggtagttcctcaggaaattggcattgcgattcca AAVG2    701   catggctgggcgacagagtcatcaccaccgcaggcccctgccccaccacccgaacctgggccctcccaccacccgaacctgggccctacaagcaaatccaacacggactggggg
AAVhu37  701   catggctgggcgacagagtcatcaccaccgcaggcccctgccccaccacccgaacctgggccctcccaccacccgaacctgggccctacaagcaaatatccaacacggactggggg
AAVrh10  701   catggctgggcgacagagtcatcaccaccgcaggcccctgccccaccacccgaacctgggccctcccaccacccgaacctgggccctacaagcaaatccaacacggactggggg
```

FIG. 14C (AAVrh10)

```
AAVG2    801   aggaagcaccaacgacaacacctacttcggctacagcacccctgggtattttgacttcaacagattccactgtcacttctcaccacgtgactggcag
AAVhu37  801   aggaagcaccaacgacaacacctacttcggctacagcacccctgggtattttgacttcaacagattccactgtcacttctcaccacgtgactggcag
AAVrh10  801   aggaagcaccaacgacaacacctacttcggctacagcacccctggggggtatttttgacttaacagattccactgccacttctcaccacgtgactggcag AAVG2    901   agactcatcaacaacaactgggattccggcccaagagactcagtcttcaacatccaggttaaggaggtcacgcagaatgaaggcaccaaga
AAVhu37  901   cgactcatcaacaacaactgggattccggcccaaaaagactcagtcttcaacatccaggtcaacatccaggtcaagaggtcacgcagaatgaaggcaccaaga
AAVrh10  901   cgactcatcaacaacaactgggattccggcccaagagactcagtcttcaacatccaggtcaacatccaggtcaagaggtcacgcagaatgaaggcaccaaga AAVG2    1001  ccatcgccaataaccttaccagcgattcagttgcacgtatttacgactcggaataccagctgccgtcctcggctcgcaccagggctgcctgcctcc
AAVhu37  1001  ccatcgccaataaccttaccagcgattcagttgcacgtatttacgactcggaatatacgactcggaataccagctgccgtcctcggctcgcaccagggctgcctgcctcc
AAVrh10  1001  ccatcgccaataaccttaccagcgattcagttgcacgcacgtatttacgactcggaataccagctgccgtcctcggctcgcaccagggctgcctgcctcc AAVG2    1101  gttccggcggatgtcttcatgattcccagtacgctacctgacactgacaacgaagtcaagccgtagccggaagtcaagccgtgctcatttcattctactgctgaatat
AAVhu37  1101  gttccggcggacgtcttcatgattcccagtacgctacctgacactgacaacaatgacaacaatgacaacgaagtcaagccgtagccgtggccgtggccttcctcctctactgctgaatat
AAVrh10  1101  gttccggcggacgtcttcatgattcccagtacgctacctgacactgacaacaatgacaacaatgacaacgaagtcaagccgtagccgtggccgtgctcatttcattctactgctgagtac AAVG2    1201  tttccatctcaaatgctgcggactggaaacaactttgaatttagctacaacttgaattttgagttgctacacctttgaggacgtgcctccacagcagctacgcacacagagcctgg
AAVhu37  1201  tttccatctcaaatgctgcggaactggaaacaactttgaatttagctcagctcagctagctacacctttgaggacgtgcctccacagcagctacgcacacagagcttgg
AAVrh10  1201  ttccttctcaaatgctgcggaacggggcaacaacagtcagtcgagtttgagttcagtcagttcagttcagtctacacctttgaggacgtgcctccacagcagctacgcacacagagcctgg AAVG2    1301  accggctgatgaaccctctcatcgaccagtacctgtattaccgtacctgacctattccagaactcagtcgaactcagtcgaactcagtcgaactcagtcgaactcagtcggagatcagtcgaggaactcaaggtacacagcagcagcaattgttattttctca
AAVhu37  1301  accgactgatgaatcctctcatcgaccagtacctgtactgacctatctcaccaaggaggaactcaaggtacaccagcagcaattgttattttctca
AAVrh10  1301  accggctgatgaaccctctcatcgaccagtacctgtactgacctattccagaactcagtcgtctcggactcggactcgcggagaactcaaggtaccaggaactcagcagtgtctattttctca AAVG2    1401  agcggcctgcaaatatgtcggctcaggcttcaagttccagaactggctgctgctctgctgctacgacacagcgtacgacacagcgtcgcacacacgcgacacacgcaaaacaacaac
AAVhu37  1401  agtggcctgcaaacatgtcggctcaggctcaggctcaggctcagaactgctaagaactgctctcctctctctctctacgacacactgtacgacacactgtcgcacacactgtcgcacacactgcgacaaaacaacaac
AAVrh10  1401  ggcgggcctaataacatgtcggctcaggctcagacccaaaaaactgctcagcacaacgctcctgctcagcaacgctcctgctcagcaacgctcctgctcacgacacactgtcgcacacactgtcgcacacactgcgacaaataacaac AAVG2    1501  agcaactttgcttgactggtgccacgaaatatcatctgaacgggaagagactcttggtgaatcccggttgtatgcgttgttgctatggcaacgcataaggacgagg
AAVhu37  1501  agcaactttgcttgactggtgccacgaaatatcatctgaacgggaagagactcttggtgaatcccggttgtatgcgttgttgctatggcaacgcataaggacgacgagg
AAVrh10  1501  agcaactttgcctgactggtgccaccaagagtatcatcatcaccctgaacgggaacagagactcttggtgaatccccggtgaatcccggttgtatgcgttgttgctatggcaaccccaccaaggacgacgaag
```

FIG. 14D (AAVrh10)

```
AAVG2     1601  aacgtttcttttccatcgagcggagtcctgatgtttgaaagagacaatgtgctggaagagacaatgtgctgg...
AAVhu37   1601  aacgcttcttccgtcgagtggagtcctgatgtcgaaaaacaggtgctggaatgtgctgg...
AAVrh10   1601  agcgatttttccgtccagcggagtcttaatgttgggaaaagacaacgtgggaaagcagc...

AAVG2     1701  aatcaagaccactaaccctgtagccactgaacaataacggcgtgtggctgctgatcaact...
AAVhu37   1701  aattaaaaccactaaccccgtagccacaagaacaataacggtgtgtggctgctgatcaac...
AAVrh10   1701  aattaaaaccaccaaccagtggccacaagagtaacggcgtgtggctgctgatcaac...

AAVG2     1801  caaggagccttacctgtctggcatgtcttggcagaaccgagacgtgtacctgcaggtccc...
AAVhu37   1801  caaggagccttacctgtctggcatgtcttggcagaaccgagacgtgtacctgcaggtccc...
AAVrh10   1801  caaggagccttacctgtctggcatgtcttggcagaaccgggacgtgtacctgcaggtccc...

AAVG2     1901  ctcctctgatgggcggctttggactgaaacaccccgctctccctcaaatcctgatcaaga...
AAVhu37   1901  cacgctaatggaggattggactgaaacaccccgctccccctcctcctgatcctgatcctg...
AAVrh10   1901  cgccgctgatggaggcttggactgaaacaccccgctccccctcctcctgattaagaataa...

AAVG2     2001  gaaattggcttcctccttcatcacgcagtatagtcacgcagtacgcagcacccggacacc...
AAVhu37   2001  gaaattggcttcctccttcattacgcagtacgcagcacccggacacccggacaccggaca...
AAVrh10   2001  taagctggcgtcgttcatcacgcagtcagcagtcagcagtgatcgcagtcagcagtcagc...

AAVG2     2101  attcagtatacttccaactactacaaatctacaaatgtggactttgctgtcaatacccga...
AAVhu37   2101  attcagtacacttccaaatctacaaatctacaaatgtggactttgctgtcaatacagaga...
AAVrh10   2101  attcaatacacttccaactactacaaatctacaaatgtggactttgctgtgttaacaca...

AAVG2     2201  tcacccgtaatctg
AAVhu37   2201  tcacccgtaatctg
AAVrh10   2201  tcacccgtaatctg
```

Liver

Muscle

- In vivo testing, B6 mice
— AAV8.AR2.08, 2e12 gc/mouse, 2 weeks, i.v.

| Code | Amount per mouse (GC) |
|---|---|
| BC01 | 6.87E+09 |
| BC02 | 1.04E+10 |
| BC03 | 1.59E+10 |
| BC04 | 2.41E+10 |
| BC05 | 3.67E+10 |
| BC06 | 5.57E+10 |
| BC07 | 8.47E+10 |
| BC08 | 1.29E+11 |
| BC09 | 1.96E+11 |
| BC10 | 2.97E+11 |
| BC11 | 4.52E+11 |
| BC12 | 6.87E+11 |
| Total gc of the mix | 2.00E+12 |

FIG 18B

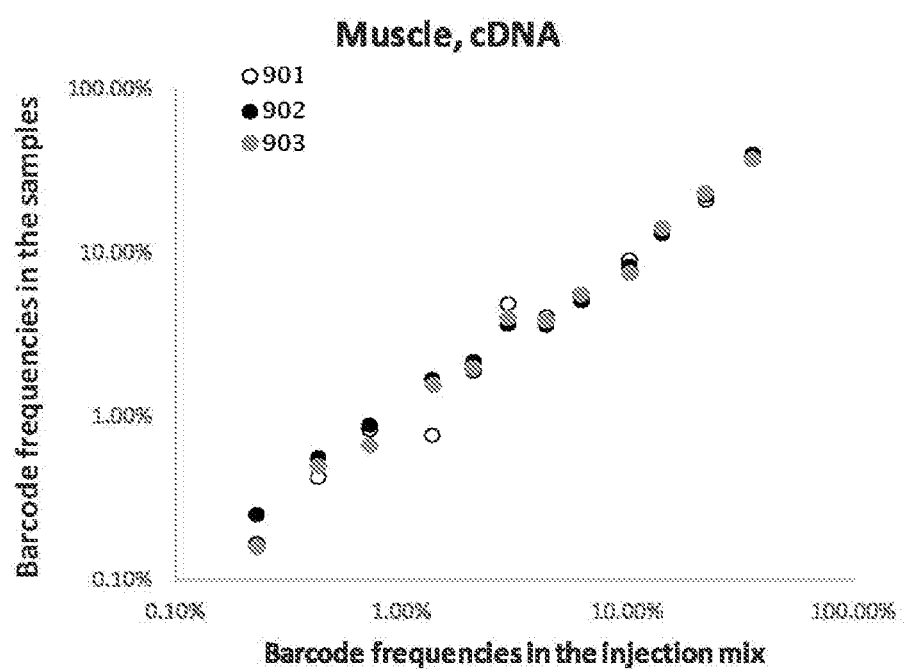

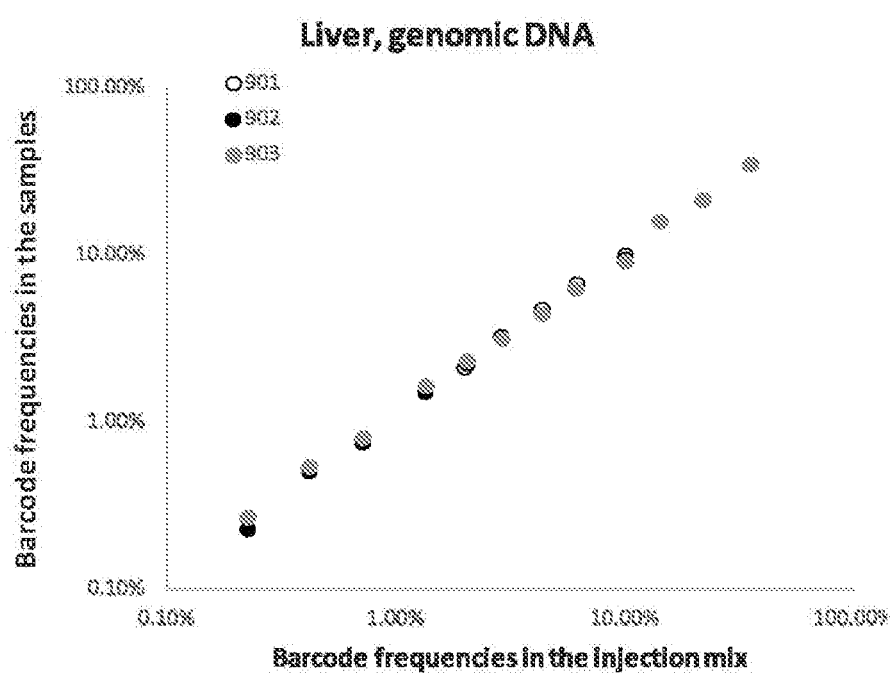

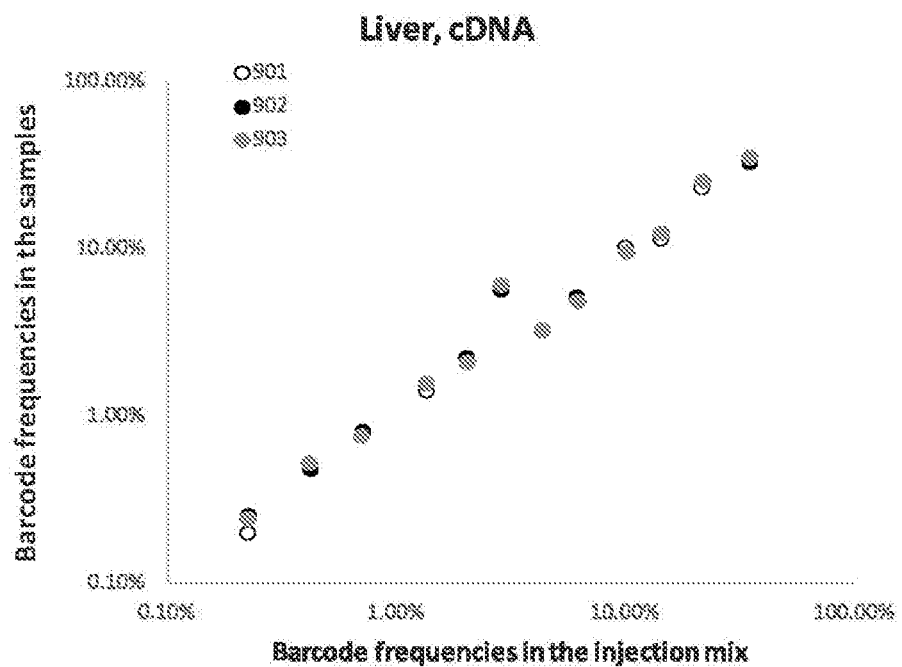

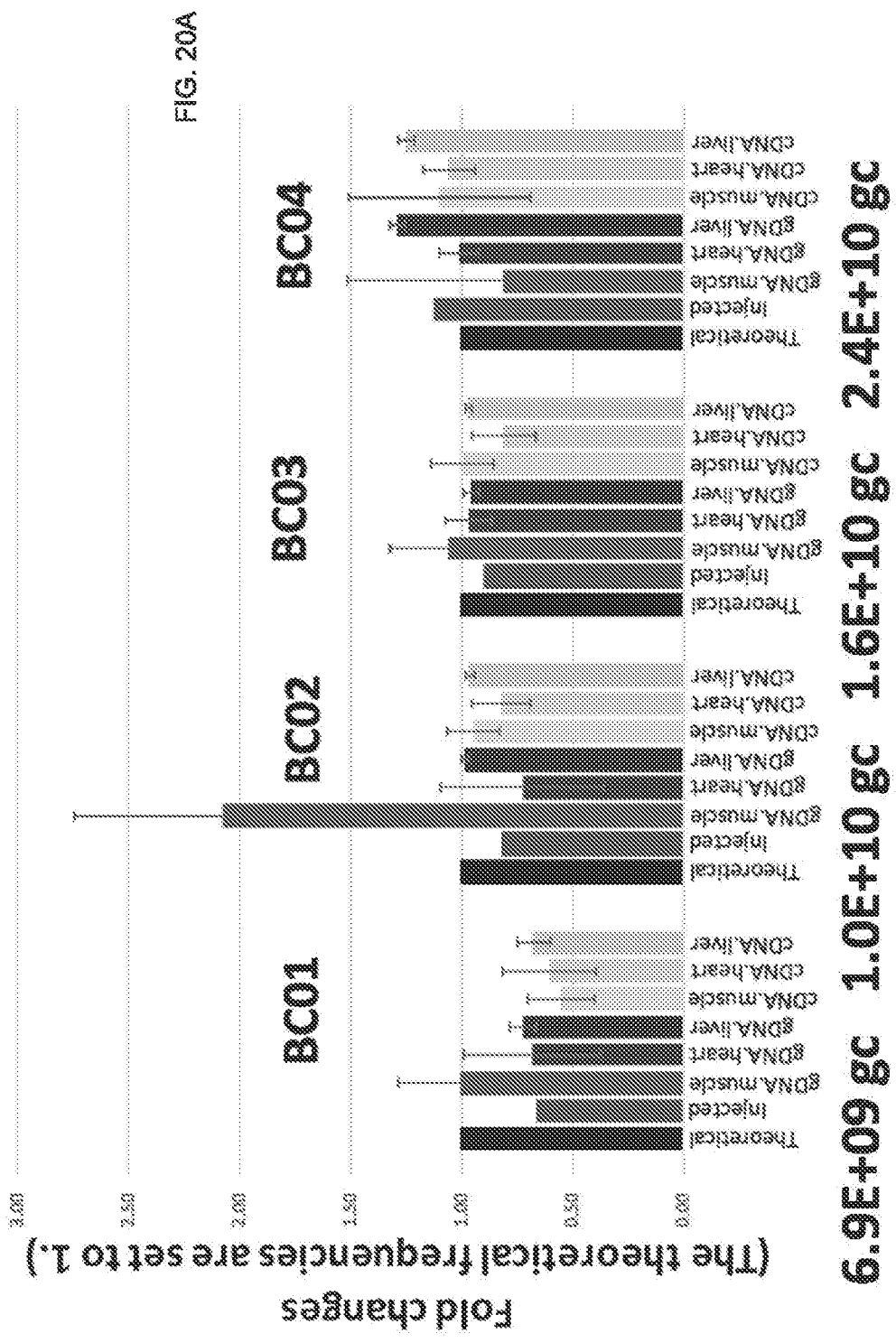
FIG. 20A The barcodes and their genome frequencies injection.

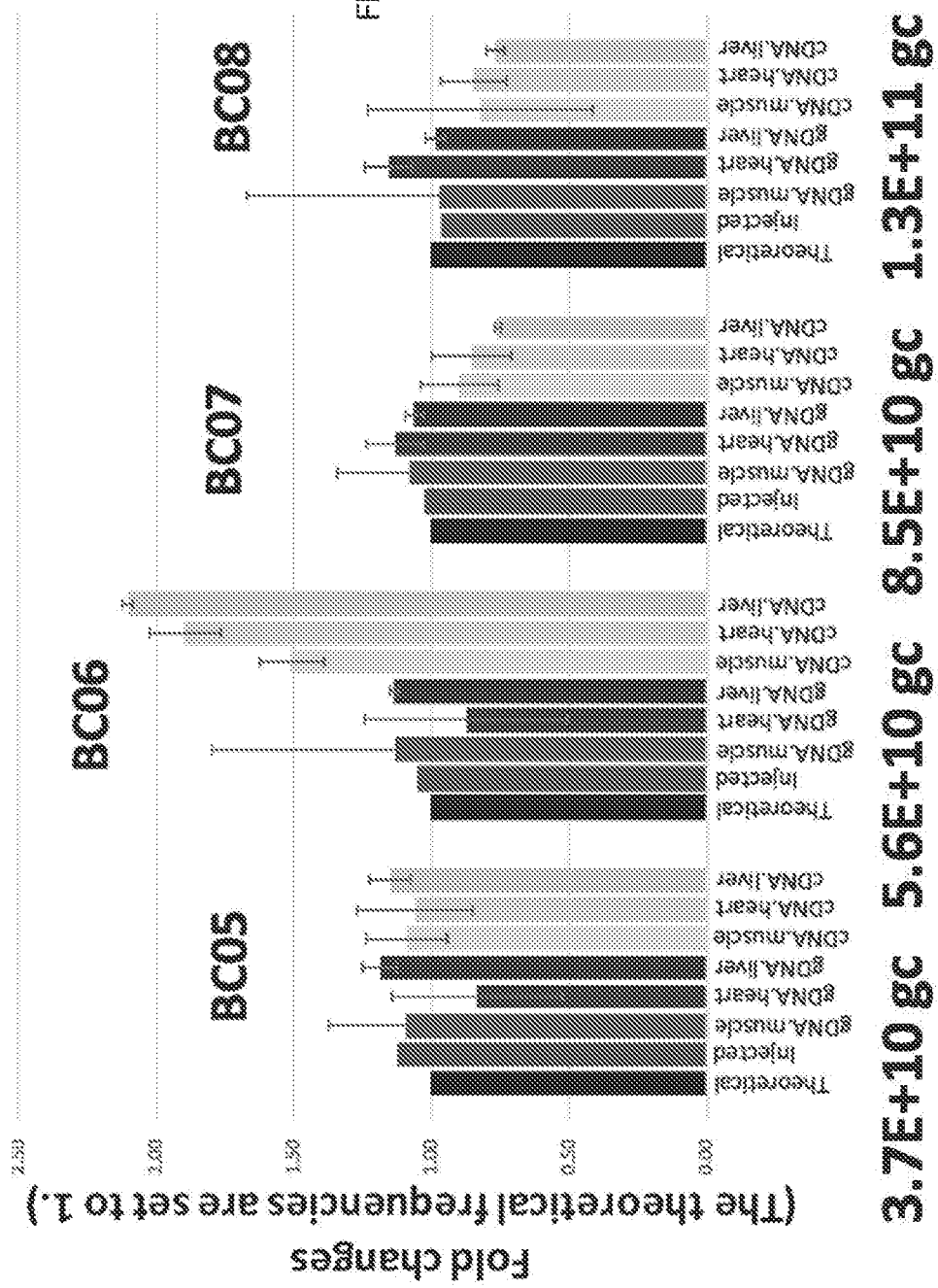

FIG. 23

| Lot # | Vector Name | Genome Titer ddPCR-GC/ml | ddPCR-Total Yield | Purity |
|---|---|---|---|---|
| WL184CS | AAVG3.TBG.PI.eGFP.WPRE.bGH(p0080:p0146) | 1.141e14 GC/ml | 6.104e14 GC | 100.000 |
| WL1549CS | AAV8.TBG.PI.eGFP.WPRE.bGH | 1.11e14 | 5.578e14 | 98.9 |
| WL1956CS | AAVrh79.TBG.PI.eGFP.WPRE.bGH(p3889:p0146) | 1.609e14 | 8.568e14 | |

FIG. 25

17-07: Liver Transduction by New Serotypes

AAV.TBG.EGFP.WPRE (1x10$^{13}$ ddGC/kg), day 7 necropsy

| Serotype | ID | Species | Sex | Weight (kg) |
|---|---|---|---|---|
| AAV8 | RA1475 | rhesus | F | 4.60 |
| AAVrh79 | RA2362 | cyno | F | 4.10 |
| AAV8.AR2.08 | 8292 | cyno | M | 8.55 |
| AAV8.AR2.08 | RQ9471 | rhesus | F | 9.26 |

ADENO-ASSOCIATED VIRUS (AAV) VECTORS, AAV VECTORS HAVING REDUCED CAPSID DEAMIDATION AND USES THEREFOR

CROSS-REFERENCE TO RELATED APPLICATIONS

This is a National Stage Entry under 35 U.S.C. 371 of International Patent Application No. PCT/US2019/019861, filed Feb. 27, 2019, which claims priority to U.S. Provisional Patent Application No. 62/635,964, filed Feb. 27, 2018, U.S. Provisional Patent Application No. 62/635,968, filed Feb. 27, 2018, U.S. Provisional Patent Application No. 62/663,788, filed Apr. 27, 2018, U.S. Provisional Patent Application No. 62/663,797, filed Apr. 27, 2018, U.S. Provisional Patent Application No. 62/667,587, filed May 6, 2018, U.S. Provisional Patent Application No. 62/667,888, filed May 7, 2018, U.S. Provisional Patent Application No. 62/667,881, filed May 7, 2018, U.S. Provisional Patent Application No. 62/677,471, filed May 29, 2018, U.S. Provisional Patent Application No. 62/677,474, filed May 29, 2018, U.S. Provisional Patent Application No. 62/667,585, filed May 29, 2018, U.S. Provisional Patent Application No. 62/703,670, filed Jul. 26, 2018, U.S. Provisional Patent Application No. 62/703,673, filed Jul. 26, 2018, U.S. Provisional Patent Application No. 62/722,382, filed Aug. 24, 2018, and U.S. Provisional Patent Application No. 62/722,388, filed Aug. 24, 2018. These applications are incorporated by reference herein.

STATEMENT OF FEDERALLY SPONSORED RESEARCH

This invention was made with government support under P01HL059407 awarded by the National Institutes of Health. The government has certain rights in the invention.

REFERENCE TO A SEQUENCE LISTING SUBMITTED VIA EFS-WEB

The content of the text filed of the sequence listing named "18-8592PCT_Sequence_Listing_ST25" which was created on Feb. 27, 2019 and electronically submitted via EFS-Web herewith the application is incorporated herein by reference in its entirety.

BACKGROUND OF THE INVENTION

The adeno-associated virus (AAV) capsid is icosahedral in structure and is comprised of 60 of viral protein (VP) monomers (VP1, VP2, and VP3) in a 1:1:10 ratio (Xie Q, et al. *Proc Natl Acad Sci USA.* 2002; 99 (16): 10405-10). The entirety of the VP3 protein sequence (~535aa) is contained within the C-terminus of both VP1 and VP2, and the shared VP3 sequences are primarily responsible for the overall capsid structure. Due to the structural flexibility of the VP1/VP2 unique regions and the low representation of VP1 and VP2 monomers relative to VP3 monomers in the assembled capsid, VP3 is the only capsid protein to be resolved via x-ray crystallography (Nam H J, et al. *J Virol.* 2007; 81 (22): 12260-71). VP3 contains nine hypervariable regions (HVRs) that are the primary source of sequence variation between AAV serotypes (Govindasamy L, et al. *J Virol.* 2013; 87 (20): 11187-99). Given their flexibility and location on the capsid surface, HVRs are largely responsible for interactions with target cells as well as with the immune system (Huang L Y, et al. *J Virol.* 2016: 90 (11): 5219-30; Raupp C, et al. *J Virol.* 2012; 86 (17): 9396-408). While the structures of a number of serotypes are published (Protein Data Bank (PDB) IDs 1LP3, 4RSO, 4V86, 3UX1. 3KIC, 2QA0, 2G8G from the Research Collaboratory for Structural Bioinformatics (RCSB) database) for the structure entries for AAV2, AAVrh.8, AAV6, AAV9, AAV3B, AAVS, and AAV4, respectively), there is very little information in the literature regarding modifications on the surface of these capsids. Research suggests that intracellular phosphorylation of the capsid occurs at specific tyrosine residues (Zhong L, et al. *Virology.* 2008; 381 (2): 194-202). Despite putative glycosylation sites in the primary VP3 sequence, no glycosylation events have been identified in AAV2 (Murray S, et al. *J Virol.* 2006; 80 (12): 6171-6; Jin X, et al. *Hum Gene Ther Methods.* 2017; 28 (5): 255-267); other AAV serotypes have not yet been evaluated for capsid glycosylation.

AAV gene therapy vectors have undergone less of the molecular-level scrutiny that typically accompanies the development and manufacturing of recombinant protein therapeutics. AAV capsid post-translational modifications (PTM) have largely been unexplored, so accordingly, little is known about their potential to impact function, or about strategies to control PTM levels in manufactured AAV therapies.

Variations in post-translational modifications of non-gene therapy protein therapeutics have complicated their development as drugs. Jenkins, N, Murphy, L, and Tyther, R (2008). Post-translational modifications of recombinant proteins: significance for biopharmaceuticals. Mol Biotechnol 39:113-118; Houde, D, Peng, Y, Berkowitz, S A, and Engen, JR (2010). Post-translational modifications differentially affect IgGI conformation and receptor binding. Mol Cell Proteomics 9:1716-1728. For example, deamidation of selected amino acids modulates the stability of and the immune response to the recombinant protective antigen-based anthrax vaccine. (Powell B S, et al. *Proteins.* 2007; 68 (2): 458-79; Verma A, et al. *Clin Vaccine Immunol.* 2016; 23 (5): 396-402). In some instances, this process is catalyzed by viral or bacterial deamidases to modulate host cell signaling pathways or innate immune responses (Zhao J, et al. *J Virol.* 2016; 90 (9): 4262-8; Zhao J, et al. *Cell Host Microbe.* 2016; 20 (6): 770-84). More commonly, endogenous deamidation is an enzyme-independent spontaneous process. Although the purpose of spontaneous deamidation has not been fully elucidated, previous studies have suggested that this event serves as a molecular clock to indicate the relative age of a protein and regulate its turnover (Robinson N E and Robinson A B. *Proc Natl Acad Sci USA.* 2001; 98 (3): 944-9).

Deamidation occurs when the amide group of asparagine or less frequently glutamine undergoes nucleophilic attack from an adjacent nitrogen atom and the amide group is lost. This process leads to a succinimidyl intermediate (Yang H and Zubarev R A. *Electrophoresis.* 2010; 31 (11): 1764-72) that, via hydrolysis, resolves into a mixture of aspartic acid and isoaspartic acid (or glutamic acid and isoglutamic acid) (Catak S, et al. *J Phys Chem A.* 2009; 113 (6): 1111-20). Studies of short, synthetic peptides estimate that this hydrolysis results in a 3:1 mixture of isoaspartic acid to aspartic acid (Geiger T. and Clarke S. *J Biol Chem.* 1987; 262 (2): 785-94.

There continues to be a need for compositions comprising AAV-based constructs for delivery of heterologous molecules which have stable receptor binding and/or stable capsids, avoid neutralizing antibodies and/or retain purity on storage.

SUMMARY OF THE INVENTION

In one embodiment, a composition is provided which includes a mixed population of recombinant adeno-associated virus (rAAV), each of said rAAV comprising: (a) an AAV capsid comprising about 60 capsid vp1 proteins, vp2 proteins and vp3 proteins, wherein the vp1, vp2 and vp3 proteins are: a heterogeneous population of vp1 proteins which are produced from a nucleic acid sequence encoding a selected AAV vp1 amino acid sequence, a heterogeneous population of vp2 proteins which are produced from a nucleic acid sequence encoding a selected AAV vp2 amino acid sequence, a heterogeneous population of vp3 proteins which produced from a nucleic acid sequence encoding a selected AAV vp3 amino acid sequence, wherein: the vp1, vp2 and vp3 proteins contain subpopulations with amino acid modifications comprising at least two highly deamidated asparagines (N) in asparagine-glycine pairs in the AAV capsid and optionally further comprising subpopulations comprising other deamidated amino acids, wherein the deamidation results in an amino acid change; and (b) a vector genome in the AAV capsid, the vector genome comprising a nucleic acid molecule comprising AAV inverted terminal repeat sequences and a non-AAV nucleic acid sequence encoding a product operably linked to sequences which direct expression of the product in a host cell.

In certain embodiments, the deamidated asparagines are deamidated to aspartic acid, isoaspartic acid, an interconverting aspartic acid/isoaspartic acid pair, or combinations thereof. In certain embodiments, the capsid further comprises deamidated glutamine(s) which are deamidated to ($\alpha$)-glutamic acid, $\gamma$-glutamic acid, an interconverting ($\alpha$)-glutamic acid/$\gamma$-glutamic acid pair, or combinations thereof.

In a further aspect, a recombinant adeno-associated virus (rAAV) is provided which comprises: (A) an AAVrh79 capsid comprising one or more of: (1) AAVrh79 capsid proteins comprising: a heterogeneous population of AAVrh79 vp1 proteins selected from: vp1 proteins produced by expression from a nucleic acid sequence which encodes the predicted amino acid sequence of 1 to 738 of SEQ ID NO:2, vp1 proteins produced from SEQ ID NO: 1, or vp1 proteins produced from a nucleic acid sequence at least 70% identical to SEQ ID NO: 1 which encodes the predicted amino acid sequence of 1 to 738 of SEQ ID NO:2, a heterogeneous population of AAVrh79 vp2 proteins selected from: vp2 proteins produced by expression from a nucleic acid sequence which encodes the predicted amino acid sequence of at least about amino acids 138 to 738 of SEQ ID NO:2, vp2 proteins produced from a sequence comprising at least nucleotides 412 to 2214 of SEQ ID NO:1, or vp2 proteins produced from a nucleic acid sequence at least 70% identical to at least nucleotides 412 to 2214 of SEQ ID NO:1 which encodes the predicted amino acid sequence of at least about amino acids 138 to 738 of SEQ ID NO:2, a heterogeneous population of AAVrh79 vp3 proteins selected from: vp3 proteins produced by expression from a nucleic acid sequence which encodes the predicted amino acid sequence of at least about amino acids 204 to 738 of SEQ ID NO:2, vp3 proteins produced from a sequence comprising at least nucleotides 610 to 2214 of SEQ ID NO:1, or vp3 proteins produced from a nucleic acid sequence at least 70% identical to at least nucleotides 610 to 2214 of SEQ ID NO:1 which encodes the predicted amino acid sequence of at least about amino acids 204 to 738 of SEQ ID NO:2; and/or (2) a heterogeneous population of vp1 proteins which are the product of a nucleic acid sequence encoding the amino acid sequence of SEQ ID NO: 2, a heterogeneous population of vp2 proteins which are the product of a nucleic acid sequence encoding the amino acid sequence of at least about amino acids 138 to 738 of SEQ ID NO: 2, and a heterogeneous population of vp3 proteins which are the product of a nucleic acid sequence encoding at least amino acids 204 to 738 of SEQ ID NO:2, wherein: the vp1, vp2 and vp3 proteins contain subpopulations with amino acid modifications comprising at least two highly deamidated asparagines (N) in asparagine-glycine pairs in SEQ ID NO: 2 and optionally further comprising subpopulations comprising other deamidated amino acids, wherein the deamidation results in an amino acid change; and (B) a vector genome in the AAVrh79 capsid, the vector genome comprising a nucleic acid molecule comprising AAV inverted terminal repeat sequences and a non-AAV nucleic acid sequence encoding a product operably linked to sequences which direct expression of the product in a host cell.

In another aspect, a method of transducing a target tissue is provided. In one embodiment, the method includes administering an AAV having an AAVrh79 capsid as described herein. In one embodiment, a method of transducing liver tissue is provided, comprising administering an AAV having the AAVrh79 capsid. In another embodiment, a method of transducing muscle tissue is provided, comprising administering an AAV having the AAVrh79 capsid.

In yet another aspect, a method of reducing deamidation of an AAVrh79 capsid is provided. In one embodiment, the method includes producing an AAVrh79 capsid from a nucleic acid sequence containing modified AAVrh79 VP codons, the nucleic acid sequence comprising independently modified glycine codons at one to four of the asparagine-glycine pairs located at position N57, N263, N385 and/or N514 in SEQ ID NO: 2, such that the modified codon encodes an amino acid other than glycine. In another embodiment, the method includes producing an AAVrh79 capsid from a nucleic acid sequence containing modified AAVrh79 vp codons, the nucleic acid sequence comprising independently modified glycine codons at one to four of the asparagine-glycine pairs located at position N94, N254, N305, N410, and/or N479 of SEQ ID NO: 2.

In a further embodiment, a rAAV8.AR2.08 is provided which comprises: (A) an AAV8.AR2.08 capsid comprising one or more of: (1) AAV8.2.08 capsid proteins comprising: a heterogeneous population of AAV8.AR2.08 vp1 proteins selected from: vp1 proteins produced by expression from a nucleic acid sequence which encodes the predicted amino acid sequence of 1 to 738 of SEQ ID NO: 18, vp1 proteins produced from SEQ ID NO: 17, or vp1 proteins produced from a nucleic acid sequence at least 70% identical to SEQ ID NO: 17 which encodes the predicted amino acid sequence of 1 to 738 of SEQ ID NO:18, a heterogeneous population of AAV8.AR2.08 vp2 proteins selected from: AAV8.AR2.08 vp2 proteins produced by expression from a nucleic acid sequence which encodes the predicted amino acid sequence of at least about amino acids 138 to 738 of SEQ ID NO:18, vp2 proteins produced from a sequence comprising at least nucleotides 412 to 2214 of SEQ ID NO: 17, or vp2 proteins produced from a nucleic acid sequence at least 70% identical to at least nucleotides 412 to 2214 of SEQ ID NO:17 which encodes the predicted amino acid sequence of at least about amino acids 138 to 738 of SEQ ID NO:18, a heterogeneous population of AAV8.AR2.08 vp3 proteins selected from: vp3 proteins produced by expression from a nucleic acid sequence which encodes the predicted amino acid sequence of at least about amino acids 204 to 738 of SEQ ID NO:18, vp3 proteins produced from a sequence comprising at least nucleotides 607 to 2214 of SEQ ID NO:17, or vp3 proteins produced from a nucleic acid sequence at least 70% identical to at least nucleotides 607 to 2214 of SEQ ID NO:17 which encodes the predicted amino acid sequence of at least about amino acids 204 to 738 of SEQ ID NO:18; and/or (2) a heterogeneous population of vp1 proteins which are the product of a nucleic acid sequence encoding the amino acid sequence of SEQ ID NO: 18, a heterogeneous population of vp2 proteins which are the product of a nucleic acid sequence encoding the amino acid sequence of at least about amino acids 138 to 738 of SEQ ID NO: 18, and a heterogeneous population of vp3 proteins which are the product of a nucleic acid sequence encoding at least amino acids 204 to 738 of SEQ ID NO: 18 wherein: the vp1, vp2 and vp3 proteins contain subpopulations with amino acid modifications comprising at least two highly deamidated asparagines (N) in asparagine-glycine pairs in SEQ ID NO: 18 and optionally further comprising subpopulations comprising other deamidated amino acids, wherein the deamidation results in an amino acid change; and (B) a vector genome in the AAV8.AR2.08 capsid, the vector genome comprising a nucleic acid molecule comprising AAV inverted terminal repeat sequences and a non-AAV nucleic acid sequence encoding a product operably linked to sequences which direct expression of the product in a host cell.

In another aspect, a method of transducing a target tissue is provided. In one embodiment, the method includes administering an AAV having an AAV8.AR2.08 capsid as described herein. In one embodiment, a method of transducing liver tissue is provided, comprising administering an AAV having the AAV8.AR2.08 capsid. In another embodiment, a method of transducing muscle tissue is provided, comprising administering an AAV having the AAV8.AR.2.08 capsid.

In yet another aspect, a method of reducing deamidation of an AAV8.AR2.08 capsid is provided. In one embodiment, the method includes producing an AAV8.AR2.08 capsid from a nucleic acid sequence containing modified AAV8.AR2.08 vp codons, the nucleic acid sequence comprising independently modified glycine codons at one to four of the asparagine—glycine pairs located at position N57, N263, N385, N514, and/or N540 in SEQ ID NO: 18, such that the modified codon encodes an amino acid other than glycine. In another embodiment, the method includes producing an AAV8.AR2.08 capsid from a nucleic acid sequence containing modified AAV8.AR2.08 vp codons, the nucleic acid sequence comprising independently modified glycine codons at one to four of the asparagine-glycine pairs located at position N94, N254, N305, N521, N590, Q601, N653, and/or N665 of SEQ ID NO: 18.

In certain embodiments, a rAAV5.5.9 is provided which comprises: (A) an AAV5.5.9 capsid comprising one or more of: (1) AAVG5 capsid proteins comprising: a heterogeneous population of AAV5.5.9 vp1 proteins selected from: vp1 proteins produced by expression from a nucleic acid sequence which encodes the predicted amino acid sequence of 1 to 726 of SEQ ID NO: 10, vp1 proteins produced from SEQ ID NO:9, or vp1 proteins produced from a nucleic acid sequence at least 70% identical to SEQ ID NO:9 which encodes the predicted amino acid sequence of 1 to 726 of SEQ ID NO:1, a heterogeneous population of AAV5.5.9 vp2 proteins selected from: AAVG5 vp2 proteins produced by expression from a nucleic acid sequence which encodes the predicted amino acid sequence of at least about amino acids 137 to 726 of SEQ ID NO: 10, vp2 proteins produced from a sequence comprising at least nucleotides 409 to 2178 of SEQ ID NO:9, or vp2 proteins produced from a nucleic acid sequence at least 70% identical to at least nucleotides 409 to 2178 of SEQ ID NO:9 which encodes the predicted amino acid sequence of at least about amino acids 137 to 726 of SEQ ID NO:10, a heterogeneous population of AAV5.5.9 vp3 proteins selected from: AAV5.5.9 vp3 proteins produced by expression from a nucleic acid sequence which encodes the predicted amino acid sequence of at least about amino acids 203 to 726 of SEQ ID NO:10, vp3 proteins produced from a sequence comprising at least nucleotides 607 to 2178 of SEQ ID NO:9, or vp3 proteins produced from a nucleic acid sequence at least 70% identical to at least nucleotides 607 to 2178 of SEQ ID NO: 9 which encodes the predicted amino acid sequence of at least about amino acids 203 to 726 of SEQ ID NO:10; and/or (2) a heterogeneous population of vp1 proteins which are the product of a nucleic acid sequence encoding the amino acid sequence of SEQ ID NO: 10, a heterogeneous population of vp2 proteins which are the product of a nucleic acid sequence encoding the amino acid sequence of at least about amino acids 137 to 726 of SEQ ID NO: 10, and a heterogeneous population of vp3 proteins which are the product of a nucleic acid sequence encoding at least amino acids 203 to 726 of SEQ ID NO:10 wherein: the vp1, vp2 and vp3 proteins contain subpopulations with amino acid modifications comprising at least two highly deamidated asparagines (N) in asparagine-glycine pairs in SEQ ID NO: 10 and optionally further comprising subpopulations comprising other deamidated amino acids, wherein the deamidation results in an amino acid change; and (B) a vector genome in the AAV5.5.9 capsid, the vector genome comprising a nucleic acid molecule comprising AAV inverted terminal repeat sequences and a non-AAV nucleic acid sequence encoding a product operably linked to sequences which direct expression of the product in a host cell.

In another aspect, a method of transducing a target tissue is provided. In one embodiment, the method includes administering an AAV having an AAV5.5.9 capsid as described herein. In one embodiment, a method of transducing liver tissue is provided, comprising administering an AAV having the AAV5.5.9 capsid. In another embodiment, a method of transducing muscle tissue is provided, comprising administering an AAV having the AAV5.5.9 capsid.

In yet another aspect, a method of reducing deamidation of an AAV5.5.9 capsid is provided. In one embodiment, the method includes producing an AAV5.5.9 capsid from a nucleic acid sequence containing modified AAV5.5.9 vp codons, the nucleic acid sequence comprising independently modified glycine codons at one to four of the asparagine-glycine pairs located at position N57, N319, N442, and/or N502 in SEQ ID NO: 10, such that the modified codon encodes an amino acid other than glycine. In another embodiment, the method includes producing an AAV5.5.9 capsid from a nucleic acid sequence containing modified AAV5.5.9 vp codons, the nucleic acid sequence comprising independently modified glycine codons at one to four of the asparagine-glycine pairs located at position N35, N113, N204, N217, N243, N249, N293/294, N304, N399/400, N505, Q589, N618, N641, N653, N658, and/or N699 of SEQ ID NO: 10.

In another aspect, a composition comprising a mixed population of recombinant AAVrh79, AAV8.AR2.08, or AAV5.5.9, as described herein, is provided.

In yet another aspect, a recombinant AAV (rAAV) as described herein is provided, for delivering a desired gene product to a subject in need thereof.

In another aspect, a rAAV production system useful for producing a rAAV as described herein is provided. In one embodiment, the system includes (a) an AAVrh79, AAV8.AR2.08, or AAV5.5.9 capsid nucleic acid sequence encoding the predicted amino acid sequence of SEQ ID NO: 2, 10, or 18; (b) a nucleic acid molecule suitable for packaging into the AAV capsid, said nucleic acid molecule comprising at least one AAV inverted terminal repeat (ITR) and a non-AAV nucleic acid sequence encoding a gene product operably linked to sequences which direct expression of the product in a host cell; and (c) sufficient AAV rep functions and helper functions to permit packaging of the nucleic acid molecule into the recombinant AAV capsid.

These and other aspects of the invention will be apparent from the following detailed description of the invention.

BRIEF DESCRIPTION OF THE DRAWINGS

FIG. 1A-FIG. 1G. Electrophoretic analysis of AAV8 VP isoforms. (FIG. 1A) Diagram illustrating the mechanism by which asparagine residues undergo nucleophilic attack by adjacent nitrogen atoms, forming a succinimidyl intermediate. This intermediate then undergoes hydrolysis, resolving into a mixture of aspartic acid and isoaspartic acid. The beta carbon is labeled as such. The diagram was generated in BIOVIA Draw 2018. (FIG. 1B) 1 µg of AAV8 vector was run on a denaturing one-dimensional SDS-PAGE. (FIG. 1C) Isoelectric points of carbonic anhydrase pI marker spots are shown. (FIG. 1D) 5 µg of AAV8 vector was analyzed by two-dimensional gel electrophoresis and stained with Coomassie Blue. Spots 1-20 are carbamylated carbonic anhydrase pI markers. Boxed regions are as follows: a=VP1, b=VP2, c=VP3, d=internal tropomyosin marker (arrow: tropomyosin spot of MW=33 kDa, pI=5.2). Isoelectric focusing was performed with a pI range of 4-8. FIG. 1E-FIG. 1G) Results of isoelectric focusing performed with a pI range of 4-8. 1e11 GC of wtAAV8 (FIG. 1E) or mutant (FIG. 1F and FIG. 1G) vector, which were analyzed by 2D gel electrophoresis and stained with Sypro Ruby. Protein labeling: A=VP1; B=VP2; C=VP3, D=chicken egg white conalbumin marker, E=turbonuclease marker. Isoelectric focusing was performed with a pI range of 6-10. Primary VP1/2/3 isoform spots are circled, and migration distance of major spots of markers are indicated by vertical lines (turbonuclease=dashed, conalbumin=solid).

(FIG. 2A-FIG. 2B) Electrospray ionization (ESI) mass spectrometry and theoretical and observed masses of the 3+ peptide (93-103) containing Asn-94 (FIG. 2A) and Asp-94 (FIG. 2B) are shown. (FIG. 2C-FIG. 2D) ESI mass spectrometry and theoretical and observed masses of the 3+ peptide (247-259) containing Asn-254 (FIG. 2C) and Asp-254 (FIG. 2D) are shown. The observed mass shifts for Asn-94 and Asn-254 were 0.982 Da and 0.986 Da, respectively, versus a theoretical mass shift of 0.984 Da. (FIG. 2E) Percent deamidation at specific asparagine and glutamine residues of interest are shown for AAV8 tryptic peptides purified by different methods. Bars indicating deamidation at asparagine residues with N+1 glycines are crosshatched. Residues determined to be at least 2% deamidated in at least one prep analyzed were included. Data are represented as mean±standard deviation.

FIG. 3A-FIG. 3E. Structural modeling of the AAV8 VP3 monomer and analysis of deamidated sites. (FIG. 3A) The AAV8 VP3 monomer (PDB identifier: 3RA8) is shown in a coil representation. The ribbon indicates the relative degree of flexibility. Spheres indicate residues of interest. Expanded diagrams are ball and stick representations of residues of interest and their surrounding residues to demonstrate local protein structure. Underlined residues are those in NG motifs. FIG. 3B-FIG. 3E: Isoaspartic models of deamidated asparagines with N+1 glycines are shown. The 2FoFc electron density map (1 sigma level) generated from refinement of the AAV8 crystal structure (PDB ID: 3RA8) with (FIG. 3B) an asparagine model of N410 in comparison with isoaspartic acid models of (FIG. 3C) N263, (FIG. 3D) N514, and (FIG. 3E) N540. Electron density map is shown. The beta carbon is labeled as such. Arrow indicates electron density corresponding to the R group of the residue of interest.

FIG. 4A-FIG. 4D. Determination of factors influencing AAV8 capsid deamidation. An AAV8 prep was (FIG. 4A) incubated at 70° C. for three or seven days, (FIG. 4B) exposed to pH 2 or pH 10 for seven days, or (FIG. 4C) prepared for mass spectrometry using $D_2O$ in place of $H_2O$ to determine possible sources of deamidation not intrinsic to AAV capsid formation. (FIG. 4D) A dot blot of vector treated as in FIG. 4A using the B1 antibody (reacts to denatured capsid) and an AAV8 conformation specific antibody (reacts to intact capsids) to assess capsid structural integrity.

(FIG. 7A) Titers of wtAAV8 and mutant vectors were produced by small-scale triple transfection in 293 cells, as measured by quantitative PCR (qPCR). Titers are reported relative to the wtAAV8 control. Transduction efficiencies were measured as described in FIG. 3B. Titers and transduction efficiencies are normalized to the value for the wtAAV8 control. (FIG. 7B) Representative luciferase images at day 14 post-injection are shown for mice receiving wtAAV8.CB7.ffluc and N499Q capsid mutant vector. (FIG. 7C) Luciferase expression on day 14 of the study periods from C57BL/6 mice injected intravenously with wtAAV8 or mutant vectors (n=3 or 4) was measured by luciferase imaging and reported in total flux units. All data are represented as mean+standard deviation.

FIG. 8A and FIG. 8B show the results of in vitro analysis of the impact of genetic deamidation on vector performance. (FIG. 8A) Titers of wtAAV8 and genetic deamidation mutant vectors produced by small-scale triple transfection in 293 cells, as measured by quantitative PCR (qPCR). Titers are reported relative to the wtAAV8 control. NG sites with high deamidation (patterned bars), sites with low deamidation (white bars) and highly variable sites (black bars) are presented with wtAAV8 and a negative control. (FIG. 8B) Transduction efficiency of mutant AAV8 vectors producing firefly luciferase reported relative to the wtAAV8 control. Transduction efficiency is measured in luminescence units generated per GC added to HUH17 cells, and is determined by performing transductions with crude vector at multiple dilutions. Transduction efficiency data are normalized to the wt reference. All data are represented as mean±standard deviation.

(FIG. 9A) Vector production (DNAseI resistant Genome Copies, GC) for a timecourse of triple-transfected HEK 293 cells producing AAV8 vector packaging a luciferase reporter gene. GC levels are normalized to the maximum observed value. (FIG. 9B) Purified timecourse vector was used to transduce Huh7 cells. Transduction efficiency (luminescence units per GC added to target cells) was measured as in FIG. 8B using multiple dilutions of purified timecourse vector samples. Error bars represent the standard deviation of at least 10 technical replicates for each sample time. Deamidation of AAV8 NG sites (FIG. 9C) and non-NG sites (FIG. 9D) for vector collected 1, 2 and 5 days post transfection.

FIG. 10A-FIG. 10D illustrates the impact of stabilizing asparagines on vector performance. FIG. 10A shows titers of wtAAV8 and +1 position mutant vectors produced by small-scale triple transfection in 293 cells, as measured by quantitative PCR (qPCR). Titers are reported relative to the wtAAV8 control. FIG. 10B shows the transduction efficiency of mutant AAV8 vectors producing firefly luciferase reported relative to the wtAAV8 control. Transduction efficiency was measured as in FIG. 8B using crude vector material. A two-sample t-test (*p<0.005) was run to determine significance between wtAAV8 and mutant transduction efficiency for G264A/G515A and G264A/G541A. FIG. 10C shows luciferase expression on day 14 of the study period in the liver region from C57BL/6 mice injected intravenously with wtAAV8 or mutant vectors (n=3 to 5) measured by luciferase imaging and reported in total flux units. FIG. 10D shows the titers and transduction efficiency of multi-site AAV8 mutant vectors producing firefly luciferase reported relative to the wtAAV8 control. All data are represented as mean±standard deviation.

FIG. 11A-FIG. 11C. Analysis of asparagine and glutamine deamidation in AAV9 capsid proteins. (FIG. 11A) 1e11 GCs of wtAAV9 were analyzed by 2D gel electrophoresis and stained with Sypro Ruby. Protein labeling: A=VP1; B=VP2; C=VP3, D=chicken egg white conalbumin marker, E=turbonuclease marker. Isoelectric focusing was performed with a pI range of 6-10. (FIG. 11B) Percent deamidation at specific asparagine and glutamine residues of interest are shown for AAV9 tryptic peptides purified by different methods. Bars indicating deamidation at asparagine residues with N+1 glycines are crosshatched. Residues determined to be at least 2% deamidated in at least one prep analyzed were included. Data are represented as mean±standard deviation. (FIG. 11C) Isoaspartic model of N512 is shown in the 2FoFc electron density map generated by non-biased refinement of the AAV9 crystal structure (PDB ID: 3UX1). Arrow indicates electron density corresponding to the R group of residue N512.

(FIG. 11D) Two AAV9 preps were incubated at 70° C. for three or seven days or (FIG. 11F) exposed to pH 2 or pH 10 for seven days to determine possible sources of deamidation not intrinsic to AAV capsid formation. Data are represented as mean±standard deviation. (FIG. 11F) A dot blot of vector treated as in FIG. 11D using the B1 antibody (reacts to denatured capsid) to assess capsid structural integrity.

FIG. 11G and FIG. 11H illustrate in vitro analysis of the impact of genetic deamidation on vector performance for AAV9. (FIG. 11G) Titers of wtAAV9 and genetic deamidation mutant vectors were produced by small-scale triple transfection in 293 cells, as measured by quantitative PCR (qPCR). Titers are reported relative to the wtAAV9 control. NG sites with high deamidation (patterned bars), sites with low deamidation (white bars) and highly variable sites (black bars) are presented with wtAAV8 and a negative control. (FIG. 11H) The transduction efficiency of mutant AAV9 vectors producing firefly luciferase are reported relative to the wtAAV9 control. All data are represented as mean±standard deviation.

(FIG. 11I) Vector production (DNAseI resistant Genome Copies, GC) for a timecourse of triple-transfected HEK 293 cells producing AAV9 vector packaging a luciferase reporter gene. GC levels are normalized to the maximum observed value. (FIG. 11J) Crude timecourse vector was used to transduce Huh7 cells. (FIG. 11K) Transduction efficiencies of vector collected 1 day post transfection vs 5 days post transfection are shown for crude and purified vector samples. Transduction efficiency is expressed as luciferase activity/GC, normalized to the value at day 1.

FIG. 12A provides an alignment of the amino acid sequences of AAV5.5.9 [SEQ ID NO: 10] (also sometimes called AAVG5), AAV9 [SEQ ID NO: 4], and AAVPHP.B [SEQ ID NO: 12], prepared using Clustal Omega 1.2.2 and its default parameters for alignment. FIGS. 12B-12E provide an alignment of the nucleotide sequences of AAV5.5.9 [SEQ ID NO: 9], PHP.B [SEQ ID NO: 11], AAV9 [SEQ ID NO: 3], and AAVhu68 [SEQ ID NO: 14].

FIG. 13A provides an alignment of the amino acid sequences of AAV8Triple mutant (AAV8T) [SEQ ID NO: 16], AAV8.AR2.08 [SEQ ID NO: 18] (also sometimes called AAVG3 or AR2 or AAV.AR2). and AAV8 [SEQ ID NO: 20], prepared using Clustal Omega 1.2.2 and its default parameters for alignment. FIGS. 13B-13D provide an alignment of the nucleotide sequences of AAV8 Triple Mutant [SEQ ID NO: 15], AAV8.AR2.08 [SEQ ID NO: 17], AAV8 [SEQ ID NO: 19].

FIG. 14A provides an alignment of the amino acid sequences of AAVrh79 [SEQ ID NO: 2] (also sometimes called AAVG2), AAVrh10 [SEQ ID NO: 24] and AAVhu37 [SEQ ID NO: 22], using Clustal Omega 1.2.2 and its default parameters for alignment. FIGS. 14B-14D provide an alignment of the nucleotide sequences of AAVrh79 [SEQ ID NO: 1], AAVrh10 [SEQ ID NO: 22] and AAVhu37 [SEQ ID NO: 21].

FIGS. 19A-FIG. 20C show the results of the barcode biodistribution experiments of Example 5. Individual tissue samples were analyzed for individual barcode frequency in the sample vs. injection mix for genomic and cDNA. Results are shown for muscle (FIG. 19A, 19B); heart (FIG. 19C and FIG. 19D) and liver (FIG. 19E and FIG. 19F). Fold changes as compared to theoretical frequencies are shown in FIG. 20A-FIG. 20C.

FIG. 23 compares AAV8 vs. AAV8.AR2.08 vs. AAVrh79 for titer and yield relating to manufacturability.

FIGS. 25-28 show results following administration of AAV vectors to non-human primates. FIG. 25 provides details for vectors and animals used for studies. FIG. 26 quantifies levels of GC and GFP detected in liver from animals that received AAV8, AAVrh79, or AAV8.AR2.08 vectors. FIG. 27 summarizes levels of GFP expression in HNP livers. FIG. 28 shows level of vector detected in tissue from HNP that were administered AAV8, AAVrh79, or AAV8.AR2.08 vectors.

DETAILED DESCRIPTION OF THE INVENTION

Figure 2A:
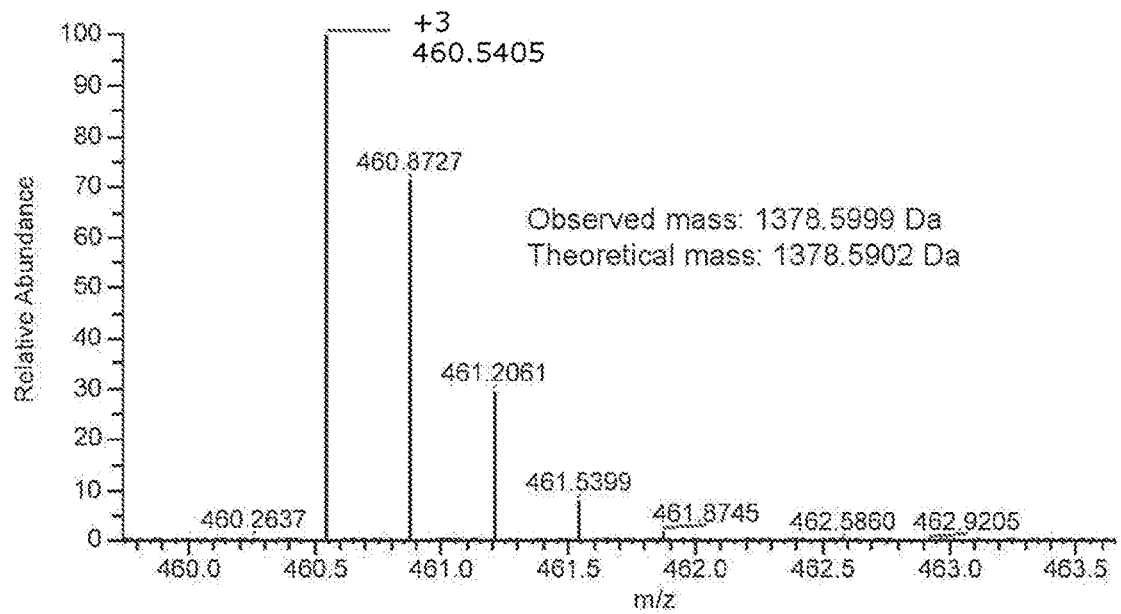
FIG. 2A-FIG. 2E. Analysis of asparagine and glutamine deamidation in AAV8 capsid proteins.
Figure 2B:
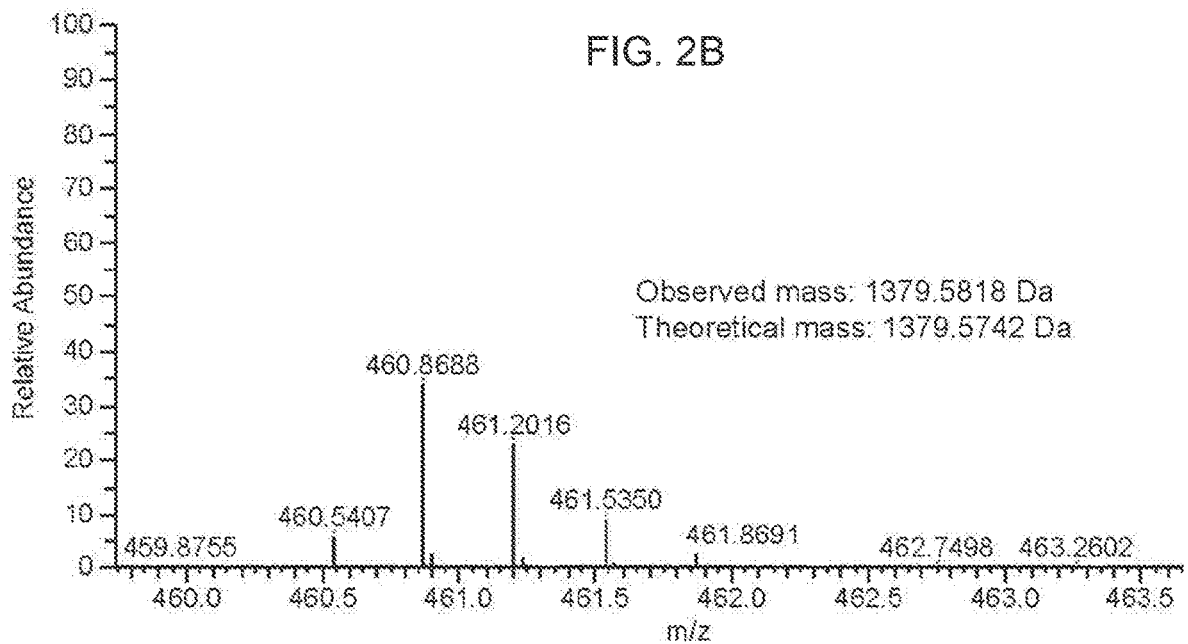
Figure 2C:
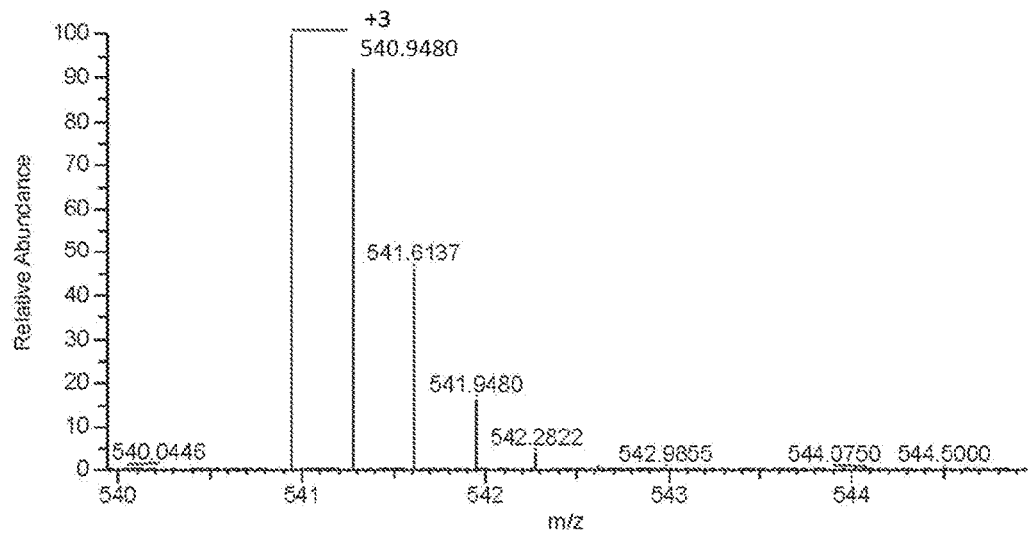
Figure 2D:
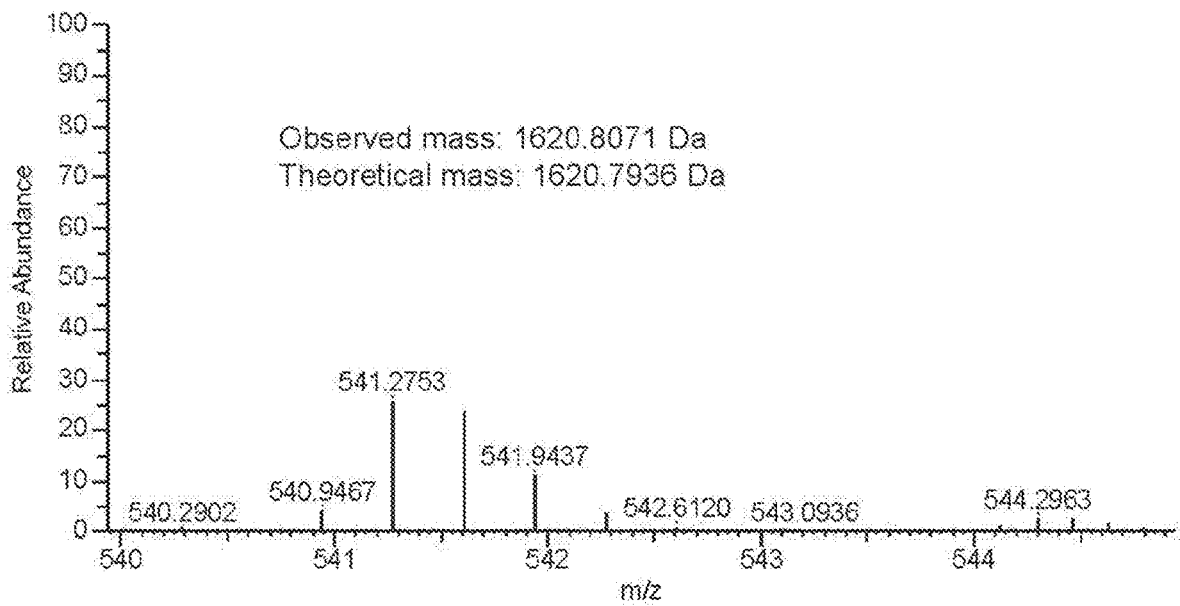

Provided herein are recombinant adeno-associated virus (rAAV) having sequence and charge heterogeneity in each of the three populations of capsid proteins VP1, VP2, and VP3 found within the capsid of a recombinant AAV and compositions containing same. Provided herein are novel rAAV, as well as methods for reducing the deamidation, and optionally other capsid monomer modifications. Further provided herein are modified rAAV having decreased modifications, which are useful for providing rAAV having capsids which retain greater stability, potency. and/or purity.

A "recombinant AAV" or "rAAV" is a DNAse-resistant viral particle containing two elements, an AAV capsid and a vector genome containing at least non-AAV coding sequences packaged within the AAV capsid. Unless otherwise specified, this term may be used interchangeably with the phrase "rAAV vector". The rAAV is a "replication-defective virus" or "viral vector", as it lacks any functional AAV rep gene or functional AAV cap gene and cannot generate progeny. In certain embodiments, the only AAV sequences are the AAV inverted terminal repeat sequences (ITRs), typically located at the extreme 5' and 3' ends of the vector genome in order to allow the gene and regulatory sequences located between the ITRs to be packaged within the AAV capsid.

As used herein, a "vector genome" refers to the nucleic acid sequence packaged inside the rAAV capsid which forms a viral particle. Such a nucleic acid sequence contains AAV inverted terminal repeat sequences (ITRs). In the examples herein, a vector genome contains, at a minimum, from 5' to 3', an AAV 5' ITR, coding sequence(s), and an AAV 3' ITR. ITRs from AAV2, a different source AAV than the capsid, or other than full-length ITRs may be selected. In certain embodiments, the ITRs are from the same AAV source as the AAV which provides the rep function during production or a transcomplementing AAV. Further, other ITRs may be used. Further, the vector genome contains regulatory sequences which direct expression of the gene products. Suitable components of a vector genome are discussed in more detail herein.

A rAAV is composed of an AAV capsid and a vector genome. An AAV capsid is an assembly of a heterogeneous population of vp1, a heterogeneous population of vp2, and a heterogeneous population of vp3 proteins. As used herein when used to refer to vp capsid proteins, the term "heterogeneous" or any grammatical variation thereof, refers to a population consisting of elements that are not the same, for example, having vp1, vp2 or vp3 monomers (proteins) with different modified amino acid sequences.

As used herein, the term "heterogeneous population" as used in connection with vp1, vp2 and vp3 proteins (alternatively termed isoforms), refers to differences in the amino acid sequence of the vp1, vp2 and vp3 proteins within a capsid. The AAV capsid contains subpopulations within the vp1 proteins, within the vp2 proteins and within the vp3 proteins which have modifications from the predicted amino acid residues. These subpopulations include, at a minimum, certain deamidated asparagine (N or Asn) residues. For example, certain subpopulations comprise at least one, two, three or four highly deamidated asparagines (N) positions in asparagine-glycine pairs and optionally further comprising other deamidated amino acids, wherein the deamidation results in an amino acid change and other optional modifications.

As used herein, a "subpopulation" of vp proteins refers to a group of vp proteins which has at least one defined characteristic in common and which consists of at least one group member to less than all members of the reference group, unless otherwise specified. For example, a "subpopulation" of vp1 proteins may be at least one (1) vp1 protein and less than all vp1 proteins in an assembled AAV capsid, unless otherwise specified. A "subpopulation" of vp3 proteins may be one (1) vp3 protein to less than all vp3 proteins in an assembled AAV capsid, unless otherwise specified. For example, vp1 proteins may be a subpopulation of vp proteins; vp2 proteins may be a separate subpopulation of vp proteins, and vp3 are yet a further subpopulation of vp proteins in an assembled AAV capsid. In another example, vp1, vp2 and vp3 proteins may contain subpopulations having different modifications, e.g., at least one, two, three or four highly deamidated asparagines, e.g., at asparagine-glycine pairs.

Unless otherwise specified, highly deamidated refers to at least 45% deamidated, at least 50% deamidated, at least 60% deamidated, at least 65% deamidated, at least 70%, at least 75%, at least 80%, at least 85%, at least 90%, at least 95%, at least 97%, at least 99%, or up to about 100% deamidated at a referenced amino acid position, as compared to the predicted amino acid sequence at the reference amino acid position (e.g., at least 80% of the asparagines at amino acid 57 of SEQ ID NO:2 may be deamidated based on the total vp1 proteins may be deamidated based on the total vp1, vp2 and vp3 proteins). Such percentages may be determined using 2D-gel, mass spectrometry techniques, or other suitable techniques.

Without wishing to be bound by theory, the deamidation of at least highly deamidated residues in the vp proteins in the AAV capsid is believed to be primarily non-enzymatic in nature, being caused by functional groups within the capsid protein which deamidate selected asparagines, and to a lesser extent, glutamine residues. Efficient capsid assembly of the majority of deamidation vp1 proteins indicates that either these events occur following capsid assembly or that deamidation in individual monomers (vp1, vp2 or vp3) is well-tolerated structurally and largely does not affect assembly dynamics. Extensive deamidation in the VP1-unique (VP1-u) region (~aa 1-137), generally considered to be located internally prior to cellular entry, suggests that VP deamidation may occur prior to capsid assembly.

Without wishing to be bound by theory, the deamidation of N may occur through its C-terminus residue's backbone nitrogen atom conducts a nucleophilic attack to the Asn's side chain amide group carbon atom. An intermediate ring-closed succinimide residue is believed to form. The succinimide residue then conducts fast hydrolysis to lead to the final product aspartic acid (Asp) or iso aspartic acid (IsoAsp). Therefore, in certain embodiments, the deamidation of asparagine (N or Asn) leads to an Asp or IsoAsp, which may interconvert through the succinimide intermediate e.g., as illustrated below.

As provided herein, each deamidated N in the VP1, VP2 or VP3 may independently be aspartic acid (Asp), isoaspartic acid (isoAsp), aspartate, and/or an interconverting blend of Asp and isoAsp, or combinations thereof. Any suitable ratio of α- and isoaspartic acid may be present. For example, in certain embodiments, the ratio may be from 10:1 to 1:10 aspartic to isoaspartic, about 50:50 aspartic: isoaspartic, or about 1:3 aspartic: isoaspartic, or another selected ratio.

In certain embodiments, one or more glutamine (Q) may deamidates to glutamic acid (Glu), i.e., α-glutamic acid, γ-glutamic acid (Glu), or a blend of α- and γ-glutamic acid, which may interconvert through a common glutarinimide intermediate. Any suitable ratio of α- and γ-glutamic acid may be present. For example, in certain embodiments, the ratio may be from 10:1 to 1:10 α to γ, about 50:50 α:γ, or about 1:3 α:γ, or another selected ratio.

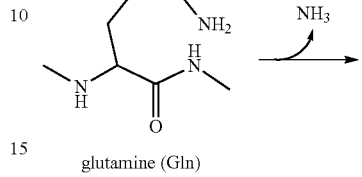

glutamine (Gln)

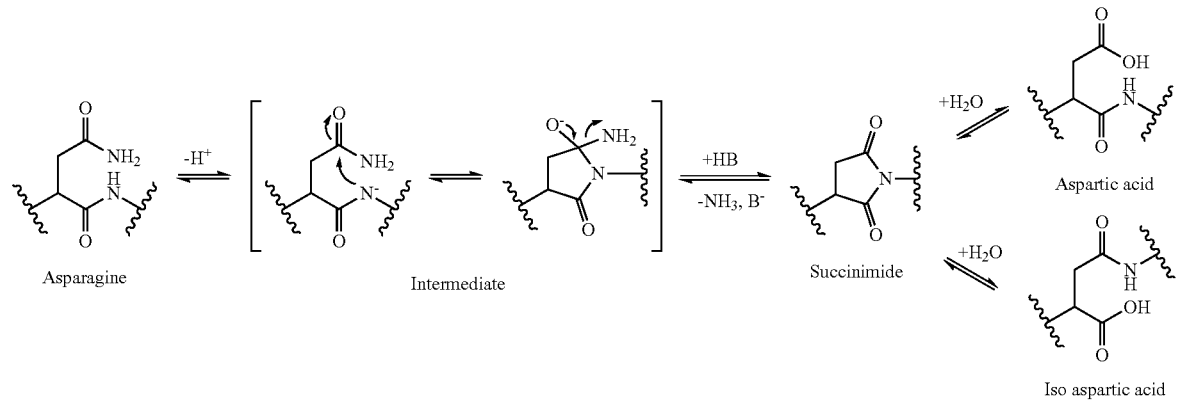

Asparagine    Intermediate    Succinimide    Aspartic acid

Iso aspartic acid

-continued

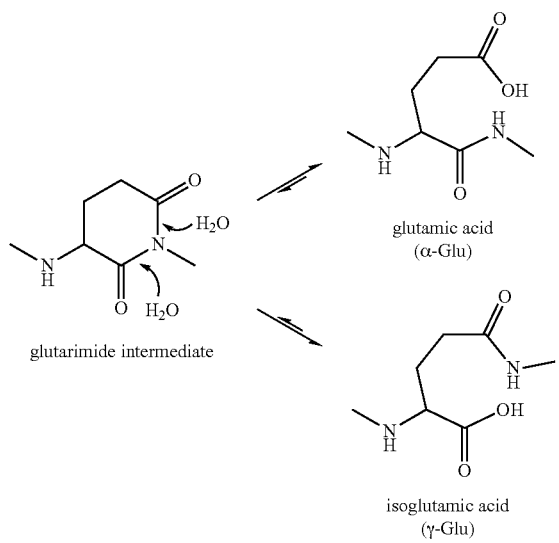

glutarimide intermediate glutamic acid (α-Glu)

isoglutamic acid (γ-Glu)

Thus, an rAAV includes subpopulations within the rAAV capsid of vp1, vp2 and/or vp3 proteins with deamidated amino acids, including at a minimum, at least one subpopulation comprising at least one highly deamidated asparagine.

In addition, other modifications may include isomerization, particularly at selected aspartic acid (D or Asp) residue positions. In still other embodiments, modifications may include an amidation at an Asp position.

In certain embodiments, an AAV capsid contains subpopulations of vp1, vp2 and vp3 having at least 1, at least 2, at least 3, at least 4, at least 5 to at least about 25 deamidated amino acid residue positions, of which at least 1 to 10%, at least 10 to 25%, at least 25 to 50%, at least 50 to 70%, at least 70 to 100%, at least 75 to 100%, at least 80-100% or at least 90-100% are deamidated as compared to the encoded amino acid sequence of the vp proteins. The majority of these may be N residues. However, Q residues may also be deamidated.

As used herein, "encoded amino acid sequence" refers to the amino acid which is predicted based on the translation of a known DNA codon of a referenced nucleic acid sequence being translated to an amino acid. The following table illustrates DNA codons and twenty common amino acids, showing both the single letter code (SLC) and three letter code (3LC).

| Amino Acid | SLC | 3LC | DNA codons |
|---|---|---|---|
| Isoleucine | I | Ile | ATT, ATC, ATA |
| Leucine | L | Leu | CTT, CTC, CTA, CTG, TTA, TTG |
| Valine | V | Val | GTT, GTC, GTA, GTG |
| Phenylalanine | F | Phe | TTT, TTC |
| Methionine | M | Met | ATG |
| Cysteine | C | Cys | TGT, TGC |
| Alanine | A | Ala | GCT, GCC, GCA, GCG |
| Glycine | G | Gly | GGT, GGC, GGA, GGG |
| Proline | P | Pro | CCT, CCC, CCA, CCG |
| Threonine | T | Thr | ACT, ACC, ACA, ACG |
| Serine | S | Ser | TCT, TCC, TCA, TCG, AGT, AGC |
| Tyrosine | Y | Tyr | TAT, TAC |
| Tryptophan | W | Trp | TGG |
| Glutamine | Q | Gln | CAA, CAG |
| Asparagine | N | Asn | AAT, AAC |
| Histidine | H | His | CAT, CAC |
| Glutamic acid | E | Glu | GAA, GAG |
| Aspartic acid | D | Asp | GAT, GAC |
| Lysine | K | Lys | AAA, AAG |
| Arginine | R | Arg | CGT, CGC, CGA, CGG, AGA, AGG |
| Stop codons | Stop | | TAA, TAG, TGA |

In certain embodiments, a rAAV has an AAV capsid having vp1, vp2 and vp3 proteins having subpopulations comprising combinations of two, three, four, five or more deamidated residues at the positions set forth in the tables provided herein and incorporated herein by reference.

Deamidation in the rAAV may be determined using 2D gel electrophoresis, and/or mass spectrometry, and/or protein modelling techniques. Online chromatography may be performed with an Acclaim PepMap column and a Thermo UltiMate 3000 RSLC system (Thermo Fisher Scientific) coupled to a Q Exactive HF with a NanoFlex source (Thermo Fisher Scientific). MS data is acquired using a data-dependent top-20 method for the Q Exactive HF, dynamically choosing the most abundant not-yet-sequenced precursor ions from the survey scans (200-2000 m/z). Sequencing is performed via higher energy collisional dissociation fragmentation with a target value of 1e5 ions determined with predictive automatic gain control and an isolation of precursors was performed with a window of 4 m/z. Survey scans were acquired at a resolution of 120,000 at m/z 200. Resolution for HCD spectra may be set to 30,000 at m/z200 with a maximum ion injection time of 50 ms and a normalized collision energy of 30. The S-lens RF level may be set at 50, to give optimal transmission of the m/z region occupied by the peptides from the digest. Precursor ions may be excluded with single, unassigned, or six and higher charge states from fragmentation selection. BioPharma Finder 1.0 software (Thermo Fischer Scientific) may be used for analysis of the data acquired. For peptide mapping, searches are performed using a single-entry protein FASTA database with carbamidomethylation set as a fixed modification; and oxidation, deamidation, and phosphorylation set as variable modifications, a 10-ppm mass accuracy, a high protease specificity, and a confidence level of 0.8 for MS/MS spectra. Examples of suitable proteases may include, e.g., trypsin or chymotrypsin. Mass spectrometric identification of deamidated peptides is relatively straightforward, as deamidation adds to the mass of intact molecule +0.984 Da (the mass difference between OH and —NH$_2$ groups). The percent deamidation of a particular peptide is determined by mass area of the deamidated peptide divided by the sum of the area of the deamidated and native peptides. Considering the number of possible deamidation sites, isobaric species which are deamidated at different sites may co-migrate in a single peak. Consequently, fragment ions originating from peptides with multiple potential deamidation sites can be used to locate or differentiate multiple sites of deamidation. In these cases, the relative intensities within the observed isotope patterns can be used to specifically determine the relative abundance of the different deamidated peptide isomers. This method assumes that the fragmentation efficiency for all isomeric species is the same and independent on the site of deamidation. It will be understood by one of skill in the art that a number of variations on these illustrative methods can be used. For example, suitable mass spectrometers may include, e.g. a quadrupole time of flight mass spectrometer (QTOF), such as a Waters Xevo or Agilent 6530 or an orbitrap instrument, such as the Orbitrap Fusion or Orbitrap Velos (Thermo Fisher). Suitably liquid chromatography systems include, e.g., Acquity UPLC system from Waters or Agilent systems (1100 or 1200 series). Suitable data analysis software may include, e.g., MassLynx (Waters), Pinpoint and Pepfinder (Thermo Fischer Scientific), Mascot (Matrix Science), Peaks DB (Bioinformatics Solutions). Still other techniques may be described, e.g., in X. Jin et al, Hu Gene Therapy Methods, Vol. 28, No. 5, pp. 255-267, published online Jun. 16, 2017.

In addition to deamidations, other modifications may occur do not result in conversion of one amino acid to a different amino acid residue. Such modifications may include acetylated residues, isomerizations, phosphorylations, or oxidations.

Modulation of Deamidation: In certain embodiments, the AAV is modified to change the glycine in an asparagine-glycine pair, to reduce deamidation. In other embodiments, the asparagine is altered to a different amino acid, e.g., a glutamine which deamidates at a slower rate; or to an amino acid which lacks amide groups (e.g., glutamine and asparagine contain amide groups); and/or to an amino acid which lacks amine groups (e.g., lysine, arginine and histidine contain a: nine groups). As used herein, amino acids lacking amide or amine side groups refer to, e.g., glycine, alanine, valine, leucine, isoleucine, serine, threonine, cystine, phenylalanine, tyrosine, or tryptophan, and/or proline. Modifications such as described may be in one, two, or three of the asparagine-glycine pairs found in the encoded AAV amino acid sequence. In certain embodiments, such modifications are not made in all four of the asparagine-glycine pairs. Thus, a method for reducing deamidation of AAV and/or engineered AAV variants having lower deamidation rates. Additionally, or alternatively one or more other amide amino acids may be changed to a non-amide amino acid to reduce deamidation of the AAV. In certain embodiments, a mutant AAV capsid as described herein contains a mutation in an asparagine-glycine pair, such that the glycine is changed to an alanine or a serine. A mutant AAV capsid may contain one, two or three mutants where the reference AAV natively contains four NG pairs. In certain embodiments, an AAV capsid may contain one, two, three or four such mutants where the reference AAV natively contains five NG pairs. In certain embodiments, a mutant AAV capsid contains only a single mutation in an NG pair. In certain embodiments, a mutant AAV capsid contains mutations in two different NG pairs. In certain embodiments, a mutant AAV capsid contains mutation is two different NG pairs which are located in structurally separate location in the AAV capsid. In certain embodiments, the mutation is not in the VP1-unique region. In certain embodiments, one of the mutations is in the VP1-unique region. Optionally, a mutant AAV capsid contains no modifications in the NG pairs, but contains mutations to minimize or eliminate deamidation in one or more asparagines, or a glutamine, located outside of an NG pair.

In certain embodiments, a method of increasing the potency of a rAAV vector is provided which comprises engineering an AAV capsid which eliminating one or more of the NGs in the wild-type AAV capsid. In certain embodiments, the coding sequence for the "G" of the "NG" is engineered to encode another amino acid. In certain examples below, an "S" or an "A" is substituted. However, other suitable amino acid coding sequences may be selected. See, e.g., the tables below in which based on the numbering of AAV8, the coding sequence for at least one of the following positions: N57+1, N263+1, N385+1, N514+1, N540+1, is modified, or as shown in the tables below. In certain embodiments, AAV8 mutants avoid changing the NG pairs at positions N57, N94, N263, N305, Q467, N479, and/or N653. In certain embodiments, other AAVs avoid mutation at corresponding N positions as determined based on an alignment with AAV8, using AAV8 numbering as a reference.

These amino acid modifications may be made by conventional genetic engineering techniques. For example, a nucleic acid sequence containing modified AAV vp codons may be generated in which one to three of the codons encoding glycine in arginine-glycine pairs are modified to encode an amino acid other than glycine. In certain embodiments, a nucleic acid sequence containing modified arginine codons may be engineered at one to three of the arginine-glycine pairs, such that the modified codon encodes an amino acid other than arginine. Each modified codon may encode a different amino acid. Alternatively, one or more of the altered codons may encode the same amino acid. In certain embodiments, these modified AAVrh79, AAV8.AR2.08 or AAV5.5.9 nucleic acid sequences may be used to generate a mutant rAAV having a capsid with lower deamidation than the native AAVrh79, AAV8.AR2.08 or AAV5.5.9 capsid. Such mutant rAAV may have reduced immunogenicity and/or increase stability on storage, particularly storage in suspension form.

Also provided herein are nucleic acid sequences encoding the AAV capsids having reduced deamidation. It is within the skill in the art to design nucleic acid sequences encoding this AAV capsid, including DNA (genomic or cDNA), or RNA (e.g., mRNA). Such nucleic acid sequences may be codon-optimized for expression in a selected system (i.e., cell type) can be designed by various methods. This optimization may be performed using methods which are available on-line (e.g., GeneArt), published methods, or a company which provides codon optimizing services, e.g., DNA2.0 (Menlo Park, CA). One codon optimizing method is described, e.g., in International Patent Publication No. WO 2015/012924, which is incorporated by reference herein in its entirety. See also, e.g., US Patent Publication No. 2014/0032186 and US Patent Publication No. 2006/0136184. Suitably, the entire length of the open reading frame (ORF) for the product is modified. However, in some embodiments, only a fragment of the ORF may be altered. By using one of these methods, one can apply the frequencies to any given polypeptide sequence and produce a nucleic acid fragment of a codon-optimized coding region which encodes the polypeptide. A number of options are available for performing the actual changes to the codons or for synthesizing the codon-optimized coding regions designed as described herein. Such modifications or synthesis can be performed using standard and routine molecular biological manipulations well known to those of ordinary skill in the art. In one approach, a series of complementary oligonucleotide pairs of 80-90 nucleotides each in length and spanning the length of the desired sequence are synthesized by standard methods. These oligonucleotide pairs are synthesized such that upon annealing, they form double stranded fragments of 80-90 base pairs, containing cohesive ends, e.g., each oligonucleotide in the pair is synthesized to extend 3, 4, 5, 6, 7, 8, 9, 10, or more bases beyond the region that is complementary to the other oligonucleotide in the pair. The single-stranded ends of each pair of oligonucleotides are designed to anneal with the single-stranded end of another pair of oligonucleotides. The oligonucleotide pairs are allowed to anneal, and approximately five to six of these double-stranded fragments are then allowed to anneal together via the cohesive single stranded ends, and then they ligated together and cloned into a standard bacterial cloning vector, for example, a TOPO® vector available from Invitrogen Corporation, Carlsbad, Calif. The construct is then sequenced by standard methods. Several of these constructs consisting of 5 to 6 fragments of 80 to 90 base pair fragments ligated together, i.e., fragments of about 500 base pairs, are prepared, such that the entire desired sequence is represented in a series of plasmid constructs. The inserts of these plasmids are then cut with appropriate restriction enzymes and ligated together to form the final construct. The final construct is then cloned into a standard bacterial cloning vector, and sequenced. Additional methods would be immediately apparent to the skilled artisan. In addition, gene synthesis is readily available commercially.

In certain embodiments, AAV capsids are provided which have a heterogeneous population of AAV capsid isoforms (i.e., VP1, VP2, VP3) which contain multiple highly deamidated "NG" positions. In certain embodiments, the highly deamidated positions are in the locations identified below, with reference to the predicted full-length VP1 amino acid sequence. In other embodiments, the capsid gene is modified such that the referenced "NG" is ablated and a mutant "NG" is engineered into another position.

In certain embodiments, the mixed population of rAAV results from a production system using a single AAV capsid nucleic acid sequence encoding a predicted AAV VP1 amino acid sequence of one AAV type. However, the production and manufacture process provides the heterogenous population of capsid proteins described above.

In certain embodiments, a novel isolated AAVrh79 capsid is provided. The nucleic acid sequence encoding the AAV is provided in SEQ ID NO:1 and the encoded amino acid sequence is provided in SEQ ID NO: 2.

In certain embodiments, a rAAV comprises a AAVrh79 capsid. An AAVrh79 capsid comprises a heterogeneous population of AAVrh79 vp1 proteins, AAVrh79 vp2 proteins, and AAVrh79 vp3 proteins. In one embodiment, the AAVrh79 capsid is produced by expression from a nucleic acid sequence which encodes the predicted amino acid sequence of 1 to 738 of SEQ ID NO:2. Optionally, sequences co-expressing the vp3 protein from a nucleic acid sequence excluding the vp1-unique region (about aa 1 to 137) or the vp2-unique region (about aa 1 to 203), vp1 proteins produced from SEQ ID NO:1, or vp1 proteins produced from a nucleic acid sequence at least 70% identical to SEQ ID NO:1 which encodes the predicted amino acid sequence of 1 to 738 of SEQ ID NO:2. In other embodiments, the AAVrh79 vp2 proteins produced by expression from a nucleic acid sequence which encodes the predicted amino acid sequence of at least about amino acids 138 to 738 of SEQ ID NO:2, vp2 proteins produced from a sequence comprising at least nucleotides 412 to 2214 of SEQ ID NO:1, or vp2 proteins produced from a nucleic acid sequence at least 70% identical to at least nucleotides 412 to 2214 of SEQ ID NO: 1 which encodes the predicted amino acid sequence of at least about amino acids 138 to 738 of SEQ ID NO: 2, AAVrh79 vp3 proteins produced by expression from a nucleic acid sequence which encodes the predicted amino acid sequence of at least about amino acids 204 to 738 of SEQ ID NO:2, vp3 proteins produced from a sequence comprising at least nucleotides 610 to 2214 of SEQ ID NO:1, or vp3 proteins produced from a nucleic acid sequence at least 70% identical to at least nucleotides 610 to 2214 of SEQ ID NO:1 which encodes the predicted amino acid sequence of at least about amino acids 204 to 738 of SEQ ID NO:2.

In certain embodiments, an AAVrh79 capsid comprises: a heterogeneous population of vp1 proteins which are the product of a nucleic acid sequence encoding the amino acid sequence of SEQ ID NO: 2, a heterogeneous population of vp2 proteins which are the product of a nucleic acid sequence encoding the amino acid sequence of at least about amino acids 138 to 738 of SEQ ID NO: 2, and a heterogeneous population of vp3 proteins which are the product of a nucleic acid sequence encoding at least amino acids 204 to 738 of SEQ ID NO: 2.

The AAVrh79 vp1, vp2 and vp3 proteins contain subpopulations with amino acid modifications comprising at least two highly deamidated asparagines (N) in asparagine-glycine pairs in SEQ ID NO: 2 and optionally further comprising subpopulations comprising other deamidated amino acids, wherein the deamidation results in an amino acid change. High levels of deamidation at N-G pairs N57, N263, N385 and/or N514 are observed, relative to the number of SEQ ID NO:2. Deamidation has been observed in other residues, as shown in the table below and in the examples. In certain embodiments, AAVrh79 may have other residues deamidated, e.g., typically at less than 10% and/or may have other modifications, including methylations (e.g., ~R487) (typically less than 5%, more typically less than 1% at a given residue), isomerization (e.g., at D97) (typically less than 5%, more typically less than 1% at a given residue, phosphorylation (e.g., where present, in the range of about 10 to about 60%, or about 10 to about 30%, or about 20 to about 60%) (e.g., at one or more of S149, ~S153, ~S474, ~T570, ~S665), or oxidation (e.g, at one or more of W248, W307, W307, M405, M437, M473, W480, W480, W505, M526, M544, M561, W621, M637, and/or W697). Optionally the W may oxidize to kynurenine.

TABLE A

AAVrh79 Deamidation

| AAVrh79 Deamidation based on VP1 numbering | % Deamidation |
|---|---|
| N57 + Deamidation | 65-90, 70-95, 80-95, 75-100, 80-100, or 90-100 |
| N94 + Deamidation | 5-15, about 10 |
| ~N254 + Deamidation | 10-20 |
| ~N263 + Deamidation | 75-100 |
| ~N305 + Deamidation | 1-5 |
| ~N385 + Deamidation | 65-90, 70-95, 80-95, 75-100, 80-100, or 90-100 |
| ~N410 + Deamidation | 1-25, |
| N479 + Deamidation | 1-5, 1-3 |
| ~N514 + Deamidation | 65-90, 70-95, 80-95, 75-100, 80-100, or 90-100 |
| ~Q601 + Deamidation | 0-1 |
| N653 + Deamidation | 0-2 |

In certain embodiments, an AAVrh79 capsid is modified in one or more of the positions identified in the preceding table, in the ranges provided below, as determined using mass spectrometry with a trypsin enzyme. In certain embodiments, one or more of the following positions, or the glycine following the N is modified as described herein. Residue numbers are based on the AAVrh79 sequence provided herein. See, SEQ ID NO: 2.

In certain embodiments, the nucleic acid sequence encoding the AAVrh79 vp1 capsid protein is provided in SEQ ID NO: 1. In other embodiments, a nucleic acid sequence of 70% to 99.9% identity to SHQ ID NO: 1 may be selected to express the AAVrh79 capsid proteins. In certain other embodiments, the nucleic acid sequence is at least about 75% identical, at least 80% identical, at least 85%, at least 90%, at least 95%, at least 97% identical, or at least 99% to 99.9% identical to SEQ ID NO: 1. However, other nucleic acid sequences which encode the amino acid sequence of SEQ ID NO: 2 may be selected for use in producing rAAV capsids. In certain embodiments, the nucleic acid sequence has the nucleic acid sequence of SEQ ID NO: 1 or a sequence at least 70% to 99% identical, at least 75%, at least 80%, at least 85%, at least 90%, at least 95%, at least 97%, at least 99%, identical to SEQ ID NO: 1 which encodes SEQ ID NO: 2. In certain embodiments, the nucleic acid sequence has the nucleic acid sequence of SEQ ID NO: 1 or a sequence at least 70% to 99. %, at least 75%, at least 80%, at least 85%, at least 90%, at least 95%, at least 97%, at least 99%, identical to about nt 412 to about nt 2214 of SEQ ID NO: 1 which encodes the vp2 capsid protein (about aa 138 to 738) of SEQ ID NO: 2. In certain embodiments, the nucleic acid sequence has the nucleic acid sequence of about nt 610 to about nt 2214 of SEQ ID NO:1 or a sequence at least 70% to 99. %, at least 75%, at least 80%, at least 85%, at least 90%, at least 95%, at least 97%, at least 99%, identical to nt SEQ ID NO: 1 which encodes the vp3 capsid protein (about aa 204 to 738) of SEQ ID NO: 2.

The invention also encompasses nucleic acid sequences encoding mutant AAVrh79, in which one or more residues has been altered in order to decrease deamidation, or other modifications which are identified herein. Such nucleic acid sequences can be used in production of mutant rAAVrh79 capsids.

In certain embodiments, a novel AAV8.AR2.08 capsid is provided. The nucleic acid sequence encoding the AAV is provided in SEQ ID NO: 17 and the encoded amino acid sequence is provided in SEQ ID NO:18. In one embodiment, a recombinant adeno-associated virus (rAAV) has an AAV8.AR2.08 capsid. An alignment of the amino acid sequences of AAV8T, AAV8.AR2.08 and AAV8 are provided in FIG. 13A. An alignment of the nucleic acid sequences of AAV8T, AAV8.AR2.08 and AAV8 are provided in FIG. 13B-13D.

In certain embodiments. an AAV8.AR2.08 capsid comprises AAV8.AR2.08 capsid proteins comprising: AAV8.AR2.08 vp1 proteins produced by expression from a nucleic acid sequence which encodes the predicted amino acid sequence of 1 to 738 of SEQ ID NO: 18, vp1 proteins produced from SEQ ID NO: 17, or vp1 proteins produced from a nucleic acid sequence at least 70% identical to SEQ ID NO: 17 which encodes the predicted amino acid sequence of 1 to 738 of SEQ ID NO:18, AAV8.AR2.08 vp2 proteins produced by expression from a nucleic acid sequence which encodes the predicted amino acid sequence of at least about amino acids 138 to 738 of SEQ ID NO:18, vp2 proteins produced from a sequence comprising at least nucleotides 412 to 2214 of SEQ ID NO:17, or vp2 proteins produced from a nucleic acid sequence at least 70% identical to at least nucleotides 412 to 2214 of SEQ ID NO:17 which encodes the predicted amino acid sequence of at least about amino acids 138 to 738 of SEQ ID NO:18, AAV8.AR2.08 vp3 proteins produced by expression from a nucleic acid sequence which encodes the predicted amino acid sequence of at least about amino acids 204 to 738 of SEQ ID NO:18, vp3 proteins produced from a sequence comprising at least nucleotides 610 to 2214 of SEQ ID NO:17, or vp3 proteins produced from a nucleic acid sequence at least 70% identical to at least nucleotides 610 to 2214 of SEQ ID NO:17 which encodes the predicted amino acid sequence of at least about amino acids 204 to 738 of SEQ ID NO:18.

Additionally, or alternatively an AAV8.AR2.08 capsid comprises: a heterogeneous population of vp1 proteins which are the product of a nucleic acid sequence encoding the amino acid sequence of SEQ ID) NO: 18, a heterogeneous population of vp2 proteins which are the product of a nucleic acid sequence encoding the amino acid sequence of at least about amino acids 138 to 738 of SEQ ID NO: 18, and a heterogeneous population of vp3 proteins which are the product of a nucleic acid sequence encoding at least amino acids 204 to 738 of SEQ ID NO:18 wherein: the vp1, vp2 and vp3 proteins contain subpopulations with amino acid modifications comprising at least two highly deamidated asparagines (N) in asparagine-glycine pairs in SEQ ID NO: 18 and optionally further comprising subpopulations comprising other deamidated amino acids, wherein the deamidation results in an amino acid change. AAV8.AR2.08 is characterized by having highly deamidated residues, e.g., at positions N57, N263, N385, N514 and N540 based on the numbering of the AAV8.AR2.08 VP1 [SEQ ID NO: 18]. Additionally, residues at the positions following table and the detailed table in the application show the deamidations which have been observed in the AAV8.AR2.08 capsid.

In certain embodiments, an AAV8.AR2.08 capsid is modified in one or more of the following positions, in the ranges provided below, as determined using mass spectrometry with a trypsin enzyme. In certain embodiments, one or more of the following positions, or the glycine following the N is modified as described herein. For example, in certain embodiments, a G may be modified to an S or an A, e.g., at position 58, 264, 386, 515, or 541. Significant reduction in deamidation is observed when NG57/58 is altered to NS 57/58 or NA57/58. However, in certain embodiments, an increase in deamidation is observed when NG is altered to NS or NA. In certain embodiments, an N of an NG pair is modified to a Q while retaining the G. In certain embodiments, both amino acids of an NG pair are modified. In certain embodiments, N385Q results in significant reduction of deamidation in that location. In certain embodiments, N499Q results in significant increase of deamidation in that location.

In addition to deamidation, other modifications may include isomerization (e.g, at one or more of D442 and/or D584) (1-15%), phosphorylations (e.g, at one or more of ~S149, ~T417, ~T454, ~T493, S600, and/or ~T663), and/or oxidations (e.g., at one or more of positions ~W22, ~M204, ~M212, W248, W307, M405, M437, M473, W480, W505, M526, M561, M607, ~W609, W621, M637, W697). Still other positions may have such these or other modifications (e.g., acetylation or further deamidations).

TABLE B

| AAV8.AR2.08 Deamidation | |
|---|---|
| AAV8.AR2.08 Deamidation based on VP1 numbering SEQ ID NO: 18 | % |
| N57 + Deamidation | 65-90, 70-95, 80-95, 75-100, 80-100, or 90-100 |
| N94 + Deamidation | 1-15 |
| ~N254 + Deamidation | 1-15 |
| ~N263 + Deamidation | 65-90, 70-95, 80-95, 75-100, 80-100, or 90-100 |
| ~N305 + Deamidation | 1-15 |
| ~N385 + Deamidation | 65-90, 70-95, 80-95, 75-100, 80-100, or 90-100 |
| ~N514 + Deamidation | 65-100 |
| ~N521 + Deamidation | 1-10 |
| ~N540 + Deamidation | 65-90, 70-95, 80-95, 75-100, 80-100, or 90-100 |
| N590 + Deamidation | 0-5 |
| Q601 + Deamidation | 0-5 |
| N653 + Deamidation | 0-5 |
| N665 + Deamidation | 0-5 |

In certain embodiments, the nucleic acid sequence encoding the AAV8.AR2.08 vp1 capsid protein is provided in SEQ ID NO: 17. In other embodiments, a nucleic acid sequence of 70% to 99.9% identity to SEQ ID NO: 17 may be selected to express the AAV8.AR2.08 capsid proteins. In certain other embodiments, the nucleic acid sequence is at least about 75% identical, at least 80% identical, at least 85%, at least 90%, at least 95%, at least 97% identical, or at least 99% to 99.9% identical to SEQ ID NO: 17. However, other nucleic acid sequences which encode the amino acid sequence of SEQ ID NO: 18 may be selected for use in producing rAAV8.AR2.08 capsids. In certain embodiments, the nucleic acid sequence has the nucleic acid sequence of SEQ ID NO: 17 or a sequence at least 70% to 99% identical, at least 75%, at least 80%, at least 85%, at least 90%, at least 95%, at least 97%, at least 99%, identical to SEQ ID NO: 17 which encodes SEQ ID NO: 18. In certain embodiments, the nucleic acid sequence has the nucleic acid sequence of SEQ ID NO: 17 or a sequence at least 70% to 99. %, at least 75%, at least 80%, at least 85%, at least 90%, at least 95%, at least 97%, at least 99%, identical to about nt 412 to about nt 2214 of SEQ ID NO: 17 which encodes the vp2 capsid protein (about aa 138 to 738) of SEQ ID NO: 18. In certain embodiments, the nucleic acid sequence has the nucleic acid sequence of about nt 607 to about nt 2214 of SEQ ID NO:

17 or a sequence at least 70% to 99. %, at least 75%, at least 80%, at least 85%, at least 90%, at least 95%, at least 97%, at least 99%, identical to nt SEQ ID NO: 17 which encodes the vp3 capsid protein (about aa 204 to 738) of SEQ ID NO:18.

The invention also encompasses nucleic acid sequences encoding mutant AAV8.2.08, in which one or more residues has been altered in order to decrease deamidation, or other modifications which are identified herein. Such nucleic acid sequences can be used in production of mutant rAAV8.2.08.

In certain embodiments, a novel AAV5.5.9 capsid is provided. The nucleic acid sequence encoding the AAV is provided in SEQ ID NO:9 and the encoded amino acid sequence is provided in SEQ ID NO: 10. An alignment of the amino acid sequences of AAV5.5.9, AAV9, and AAVPHP.B is shown in FIG. 12A. An alignment of the nucleic acid sequences of AAV5.5.9, AAV9, and AAVPHP.B is shown in FIG. 12B-12E. In one embodiment, a recombinant adeno-associated virus (rAAV) has an AAV5.5.9 capsid comprising: AAV5.5.9 capsid proteins comprising: a heterogeneous population of AAV5.5.9 vp1 proteins produced by expression from a nucleic acid sequence which encodes the predicted amino acid sequence of 1 to 726 of SEQ ID NO: 10, vp1 proteins produced from SEQ ID NO:9, or vp1 proteins produced from a nucleic acid sequence at least 70% identical to SEQ ID NO:9 which encodes the predicted amino acid sequence of 1 to 726 of SEQ ID NO: 10; a heterologous population of AAV5.5.9 vp2 proteins produced by expression from a nucleic acid sequence which encodes the predicted amino acid sequence of at least about amino acids 137 to 726 of SEQ ID NO:10, vp2 proteins produced from a sequence comprising at least nucleotides 409 to 2178 of SEQ ID NO:9, or vp2 proteins produced from a nucleic acid sequence at least 70% identical to at least nucleotides 577 to 2178 of SEQ ID NO: 9 which encodes the predicted amino acid sequence of at least about amino acids 137 to 726 of SEQ ID NO:10, and a heterologous population of AAV5.5.9 vp3 proteins produced by expression from a nucleic acid sequence which encodes the predicted amino acid sequence of at least about amino acids 193 to 726 of SEQ ID NO:10, vp3 proteins produced from a sequence comprising at least nucleotides 577 to 2178 of SEQ ID NO:9, or vp3 proteins produced from a nucleic acid sequence at least 70% identical to at least nucleotides 577 to 2178 of SEQ ID NO:9 which encodes the predicted amino acid sequence of at least about amino acids 193 to 726 of SEQ ID NO:10.

Additionally or alternatively, an AAV5.5.9 capsid comprises: a heterogeneous population of vp1 proteins which are the product of a nucleic acid sequence encoding the amino acid sequence of SEQ II) NO: 10, a heterogeneous population of vp2 proteins which are the product of a nucleic acid sequence encoding the amino acid sequence of at least about amino acids 137 to 726 of SEQ ID NO: 10, and a heterogeneous population of vp3 proteins which are the product of a nucleic acid sequence encoding at least amino acids 193 to 726 of SEQ ID NO:10 wherein: the vp1, vp2 and vp3 proteins contain subpopulations with amino acid modifications comprising at least two highly deamidated asparagines (N) in asparagine-glycine pairs in SEQ ID NO: 10 and optionally further comprising subpopulations comprising other deamidated amino acids, wherein the deamidation results in an amino acid change.

TABLE C

AAV5.5.9 Deamidation

AAV5.5.9
Deamidation based on VP1
numbering SEQ ID NO: 10

| | % |
|---|---|
| N35 + Deamidation | 0-15, 1-10 |
| ~N57 + Deamidation | 65-90, 70-95, 80-95, 75-100, 80-100, or 90-100 |
| N113 + Deamidation | 0-15 |
| ~N204 + Deamidation | 0-20, 1-20 |
| N217 + Deamidation | 0-5, 1-5 |
| ~N243 + Deamidation | 0-25, 1-25 |
| Q249 + Deamidation | 1-20 |
| N293/294 + Deamidation | 10-45, 15-40 |
| N304 + Deamidation | 1-10 |
| N309 + Deamidation | 1-2 |
| Q311 + Deamidation | 1-2 |
| ~N319 + Deamidation | 65-90, 70-95, 80-95, 75-100, 80-100, or 90-100 |
| N399/400 + Deamidation | 5-40, 10-40, 15-35 |
| ~N442 + Deamidation | 65-90, 70-95, 80-95, 75-100, 80-100, or 90-100 |
| N467 + Deamidation | 1-5 |
| N502 + Deamidation | 65-90, 70-95, 80-95, 75-100, 80-100, or 90-100 |
| N505 + Deamidation | 5-25, 10-25 |
| ~Q589 + Deamidation | 5-30, 10-30 |
| N618 + Deamidation | 1-15, 5-10 |
| ~N641 + Deamidation | 1-15, 5-10 |
| N653 + Deamidation | 1-15, 5-10 |
| ~N658 + Deamidation | 5-40, 10-30 |
| N694 + Deamidation | 0-5 |
| ~N699 + Deamidation | 1-10 |

In certain embodiments, the nucleic acid sequence encoding the AAV5.5.9 vp1 capsid protein is provided in SEQ ID NO: 9. In other embodiments, a nucleic acid sequence of 70% to 99.9% identity to SEQ ID NO: 9 may be selected to express the AAV5.5.9 capsid proteins. In certain other embodiments, the nucleic acid sequence is at least about 75% identical, at least 80% identical, at least 85%, at least 90%, at least 95%, at least 97% identical, or at least 99% to 99.9% identical to SEQ ID NO: 9. However, other nucleic acid sequences which encode the amino acid sequence of SEQ ID NO: 10 may be selected for use in producing rAAV5.5.9 capsids. In certain embodiments, the nucleic acid sequence has the nucleic acid sequence of SEQ ID NO: 10 or a sequence at least 70% to 99% identical, at least 75%, at least 80%, at least 85%, at least 90%, at least 95%, at least 97%, at least 99%, identical to SEQ ID NO: 9 which encodes SEQ ID NO: 10. In certain embodiments, the nucleic acid sequence has the nucleic acid sequence of SEQ ID NO: 9 or a sequence at least 70% to 99. %, at least 75%, at least 80%, at least 85%, at least 90%, at least 95%, at least 97%, at least 99%, identical to about nt 409 to about nt 2178 of SEQ ID NO: 9 which encodes the vp2 capsid protein (about aa 137 to 726) of SEQ ID NO: 10. In certain embodiments, the nucleic acid sequence has the nucleic acid sequence of about nt 577 to about nt 2178 of SEQ ID NO:9 or a sequence at least 70% to 99%, at least 75%, at least 80%, at least 85%, at least 90%, at least 95%, at least 97%, at least 99%, identical to nt 577 to 2178 SEQ ID NO: 9 which encodes the vp3 capsid protein (about aa 193 to 726) of SEQ ID NO: 10.

The invention also encompasses nucleic acid sequences encoding mutant AAV5.5.9, in which one or more residues has been altered in order to decrease deamidation, or other modifications which are identified herein. Such nucleic acid sequences can be used in production of mutant rAAV5.59.

I. rAAV Vectors

As indicated above, the novel AAV sequences and proteins are useful in production of rAAV and are also useful in recombinant AAV vectors which may be antisense delivery vectors, gene therapy vectors, or vaccine vectors. Additionally, the engineered AAV capsids described herein may be used to engineer rAAV vectors for delivery of a number of suitable nucleic acid molecules to target cells and tissues.

Genomic sequences which are packaged into an AAV capsid and delivered to a host cell are typically composed of, at a minimum, a transgene and its regulatory sequences, and AAV inverted terminal repeats (ITRs). Both single-stranded AAV and self-complementary (sc) AAV are encompassed with the rAAV. The transgene is a nucleic acid coding sequence, heterogeneous to the vector sequences, which encodes a polypeptide, protein, functional RNA molecule (e.g., miRNA, miRNA inhibitor) or other gene product, of interest. The nucleic acid coding sequence is operatively linked to regulatory components in a manner which permits transgene transcription, translation, and/or expression in a cell of a target tissue.

The AAV sequences of the vector typically comprise the cis-acting 5' and 3' inverted terminal repeat sequences (See, e.g., B. J. Carter, in "Handbook of Parvoviruses", ed., P. Tijsser, CRC Press, pp. 155 168 (1990)). The ITR sequences are about 145 bp in length. Preferably, substantially the entire sequences encoding the ITRs are used in the molecule, although some degree of minor modification of these sequences is permissible. The ability to modify these ITR sequences is within the skill of the art. (See, e.g., texts such as Sambrook et al, "Molecular Cloning. A Laboratory Manual", 2d ed., Cold Spring Harbor Laboratory, New York (1989); and K. Fisher et al., J. Virol., 70:520 532 (1996)). An example of such a molecule employed in the present invention is a "cis-acting" plasmid containing the transgene, in which the selected transgene sequence and associated regulatory elements are flanked by the 5' and 3' AAV ITR sequences. In one embodiment, the ITRs are from an AAV different than that supplying a capsid, resulting in a pseudotyped vector. In one embodiment, the ITR sequences from AAV2. A shortened version of the 5' ITR, termed AITR, has been described in which the D-sequence and terminal resolution site (trs) are deleted. In other embodiments, the full-length AAV 5' and 3' ITRs are used. However, ITRs from other AAV sources may be selected. Where the source of the ITRs is from AAV2 and the AAV capsid is from another AAV source, the resulting vector may be termed pseudotyped. However, other configurations of these elements may be suitable.

In addition to the major elements identified above for the recombinant AAV vector, the vector also includes conventional control elements necessary which are operably linked to the transgene in a manner which permits its transcription, translation and/or expression in a cell transfected with the plasmid vector or infected with the virus produced by the invention. As used herein, "operably linked" sequences include both expression control sequences that are contiguous with the gene of interest and expression control sequences that act in trans or at a distance to control the gene of interest.

The regulatory control elements typically contain a promoter sequence as part of the expression control sequences, e.g., located between the selected 5' ITR sequence and the coding sequence. Constitutive promoters, regulatable promoters [see, e.g., WO 2011/126808 and WO 2013/04943], tissue specific promoters, or a promoter responsive to physiologic cues may be used may be utilized in the vectors described herein. The promoter(s) can be selected from different sources. e.g., human cytomegalovirus (CMV) immediate-early enhancer/promoter, the SV40 early enhancer/promoter, the JC polyomavirus promoter, myelin basic protein (MBP) or glial fibrillary acidic protein (GFAP) promoters, herpes simplex virus (HSV-1) latency associated promoter (LAP), rouse sarcoma virus (RSV) long terminal repeat (LTR) promoter, neuron-specific promoter (NSE), platelet derived growth factor (PDGF) promoter, hSYN, melanin-concentrating hormone (MCH) promoter, CBA, matrix metalloprotein promoter (MPP), and the chicken beta-actin promoter. In one embodiment, the promoter is a liver specific promoter, such as that termed LSP exemplified herein.

In addition to a promoter a vector may contain one or more other appropriate transcription initiation, termination, enhancer sequences, efficient RNA processing signals such as splicing and polyadenylation (polyA) signals; sequences that stabilize cytoplasmic mRNA for example WPRE; sequences that enhance translation efficiency (i.e., Kozak consensus sequence); sequences that enhance protein stability; and when desired, sequences that enhance secretion of the encoded product. An example of a suitable enhancer is the CMV enhancer. Other suitable enhancers include those that are appropriate for desired target tissue indications. In one embodiment, the expression cassette comprises one or more expression enhancers. In one embodiment, the expression cassette contains two or more expression enhancers. These enhancers may be the same or may differ from one another. For example, an enhancer may include a CMV immediate early enhancer. This enhancer may be present in two copies which are located adjacent to one another. Alternatively, the dual copies of the enhancer may be separated by one or more sequences. In still another embodiment, the expression cassette further contains an intron, e.g, the chicken beta-actin intron. Other suitable introns include those known in the art, e.g., such as are described in WO 2011/126808. Examples of suitable polyA sequences include, e.g., SV40, SV50, bovine growth hormone (bGH), human growth hormone, and synthetic polyAs. Optionally, one or more sequences may be selected to stabilize mRNA. An example of such a sequence is a modified WPRE sequence, which may be engineered upstream of the polyA sequence and downstream of the coding sequence [see, e.g., MA Zanta-Boussif, et al, Gene Therapy (2009) 16:605-619.

These rAAVs are particularly well suited to gene delivery for therapeutic purposes and for immunization, including inducing protective immunity. Further, the compositions of the invention may also be used for production of a desired gene product in vitro. For in vitro production, a desired product (e.g., a protein) may be obtained from a desired culture following transfection of host cells with a rAAV containing the molecule encoding the desired product and culturing the cell culture under conditions which permit expression. The expressed product may then be purified and isolated, as desired. Suitable techniques for transfection, cell culturing, purification, and isolation are known to those of skill in the art.

Therapeutic Transgenes

Useful products encoded by the transgene include a variety of gene products which replace a defective or deficient gene, inactivate or "knock-out", or "knock-down" or reduce the expression of a gene which is expressing at an undesirably high level, or delivering a gene product which has a desired therapeutic effect. In most embodiments, the therapy will be "somatic gene therapy", i.e., transfer of genes to a cell of the body which does not produce sperm or eggs. In certain embodiments, the transgenes express proteins have the sequence of native human sequences. However, in other embodiments, synthetic proteins are expressed. Such proteins may be intended for treatment of humans, or in other embodiments, designed for treatment of animals, including companion animals such as canine or feline populations, or for treatment of livestock or other animals which come into contact with human populations.

Examples of suitable gene products may include those associated with familial hypercholesterolemia, muscular dystrophy, cystic fibrosis, and rare or orphan diseases. Examples of such rare disease may include spinal muscular atrophy (SMA), Huntingdon's Disease, Rett Syndrome (e.g., methyl-CpG-binding protein 2 (MeCP2); UniProtKB-P51608), Amyotrophic Lateral Sclerosis (ALS), Duchenne Type Muscular dystrophy, Friedrichs Ataxia (e.g., frataxin), progranulin (PRGN) (associated with non-Alzheimer's cerebral degenerations, including, frontotemporal dementia (FTD), progressive non-fluent aphasia (PNFA) and semantic «lemential), among others. See, e.g., www_orpha_net/consor/cgi-bin/Disease_Search_List_php; rarediseases_info_nih_gov/diseases.

Examples of suitable genes may include, e.g., hormones and growth and differentiation factors including, without limitation, insulin, glucagon, glucagon-like peptide-1 (GLP1), growth hormone (GH), parathyroid hormone (PTH), growth hormone releasing factor (GRF), follicle stimulating hormone (FSH), luteinizing hormone (LH), human chorionic gonadotropin (hCG), vascular endothelial growth factor (VEGF), angiopoietins, angiostatin, granulocyte colony stimulating factor (GCSF), erythropoietin (EPO) (including, e.g., human, canine or feline epo), connective tissue growth factor (CTGF), neutrophic factors including, e.g., basic fibroblast growth factor (bFGF), acidic fibroblast growth factor (aFGF), epidermal growth factor (EGF), platelet-derived growth factor (PDGF), insulin growth factors I and II (IGF-I and IGF-II), any one of the transforming growth factor α superfamily, including TGFα, activins, inhibins, or any of the bone morphogenic proteins (BMP) BMPs 1-15, any one of the heregluin/neuregulin/ARIA/neu differentiation factor (NDF) family of growth factors, nerve growth factor (NGF), brain-derived neurotrophic factor (BDNF), neurotrophins NT-3 and NT-4/5, ciliary neurotrophic factor (CNTF), glial cell line derived neurotrophic factor (GDNF), neurturin, agrin, any one of the family of semaphorins/collapsins, netrin-1 and netrin-2, hepatocyte growth factor (HGF), ephrins, noggin, sonic hedgehog and tyrosine hydroxylase.

Other useful transgene products include proteins that regulate the immune system including, without limitation, cytokines and lymphokines such as thrombopoietin (TPO), interleukins (IL) IL-1 through IL-36 (including, e.g., human interleukins IL-1, IL-1α, IL-1β, IL-2, IL-3, IL-4, IL-6, IL-8, IL-12, IL-11, IL-12, IL-13, IL-18, IL-31, IL-35), monocyte chemoattractant protein, leukemia inhibitory factor, granulocyte-macrophage colony stimulating factor, Fas ligand, tumor necrosis factors α and β, interferons α, β, and γ, stem cell factor, flk-2/flt3 ligand. Gene products produced by the immune system are also useful in the invention. These include, without limitations, immunoglobulins IgG, IgM, IgA, IgD and IgE, chimeric immunoglobulins, humanized antibodies, single chain antibodies, T cell receptors, chimeric T cell receptors, single chain T cell receptors, class I and class II MHC molecules, as well as engineered immunoglobulins and MHC molecules. For example, in certain embodiments, the rAAV antibodies may be designed to delivery canine or feline antibodies, e.g., such as anti-IgE, anti-IL31, anti-CD20, anti-NGF, anti-GnRH. Useful gene products also include complement regulatory proteins such as complement regulatory proteins, membrane cofactor protein (MCP), decay accelerating factor (DAF), CR1, CF2, CD59, and C1 esterase inhibitor (C1-INH).

Still other useful gene products include any one of the receptors for the hormones, growth factors, cytokines, lymphokines, regulatory proteins and immune system proteins. The invention encompasses receptors for cholesterol regulation and/or lipid modulation, including the low density lipoprotein (LDL) receptor, high density lipoprotein (HDL) receptor, the very low density lipoprotein (VLDL) receptor, and scavenger receptors. The invention also encompasses gene products such as members of the steroid hormone receptor superfamily including glucocorticoid receptors and estrogen receptors, Vitamin D receptors and other nuclear receptors. In addition, useful gene products include transcription factors such as jun, fos, max, mad, serum response factor (SRF), AP-1, AP2, myb, MyoD and myogenin, ETS-box containing proteins, TFE3, E2F, ATFI, ATF2, ATF3, ATF4, ZF5, NFAT, CREB, HNF-4, C/EBP, SP1, CCAAT-box binding proteins, interferon regulation factor (IRF-1), Wilms tumor protein, ETS-binding protein, STAT, GATA-box binding proteins, e.g., GATA-3, and the forkhead family of winged helix proteins.

Other useful gene products include, carbamoyl synthetase I, ornithine transcarbamylase (OTC), arginosuccinate synthetase, arginosuccinate lyase (ASL) for treatment of argunosuccinate lyase deficiency, arginase, fumarylacetate hydrolase, phenylalanine hydroxylase, alpha-1 antitrypsin, rhesus alpha-fetoprotein (AFP), rhesus chorionic gonadotrophin (CG), glucose-6-phosphatase, porphobilinogen deaminase, cystathione beta-synthase, branched chain ketoacid decarboxylase, albumin, isovaleryl-coA dehydrogenase, propionyl CoA carboxylase, methyl malonyl CoA mutase, glutaryl CoA dehydrogenase, insulin, beta-glucosidase, pyruvate carboxylate, hepatic phosphorylase, phosphorylase kinase, glycine decarboxylase, H-protein, T-protein, a cystic fibrosis transmembrane regulator (CFTR) sequence, and a dystrophin gene product [e.g., a mini- or micro-dystrophin]. Still other useful gene products include enzymes such as may be useful in enzyme replacement therapy, which is useful in a variety of conditions resulting from deficient activity of enzyme. For example, enzymes that contain mannose-6-phosphate may be utilized in therapies for lysosomal storage diseases (e.g., a suitable gene includes that encoding β-glucuronidase (GUSB)).

In certain embodiments, the rAAV may be used in gene editing systems, which system may involve one rAAV or co-administration of multiple rAAV stocks. For example, the rAAV may be engineered to deliver SpCas9, SaCas9, ARCUS, Cpf1, and other suitable gene editing constructs.

Still other useful gene products include those used for treatment of hemophilia, including hemophilia B (including Factor IX) and hemophilia A (including Factor VIII and its variants, such as the light chain and heavy chain of the heterodimer and the B-deleted domain; U.S. Pat. Nos. 6,200,560 and 6,221,349). In some embodiments, the minigene comprises first 57 base pairs of the Factor VIII heavy chain which encodes the 10 amino acid signal sequence, as well as the human growth hormone (hGH) polyadenylation sequence. In alternative embodiments, the minigene further comprises the A1 and A2 domains, as well as 5 amino acids from the N-terminus of the B domain, and/or 85 amino acids of the C-terminus of the B domain, as well as the A3, C1 and C2 domains. In yet other embodiments, the nucleic acids encoding Factor VIII heavy chain and light chain are provided in a single minigene separated by 42 nucleic acids coding for 14 amino acids of the B domain [U.S. Pat. No. 6,200,560].

Other useful gene products include non-naturally occurring polypeptides, such as chimeric or hybrid polypeptides having a non-naturally occurring amino acid sequence containing insertions, deletions or amino acid substitutions. For example, single-chain engineered immunoglobulins could be useful in certain immunocompromised patients. Other types of non-naturally occurring gene sequences include antisense molecules and catalytic nucleic acids, such as ribozymes, which could be used to reduce overexpression of a target.

Reduction and/or modulation of expression of a gene is particularly desirable for treatment of hyperproliferative conditions characterized by hyperproliferating cells, as are cancers and psoriasis. Target polypeptides include those polypeptides which are produced exclusively or at higher levels in hyperproliferative cells as compared to normal cells. Target antigens include polypeptides encoded by oncogenes such as myb, myc, fyn, and the translocation gene bcr/abl, ras, src, P53, neu, trk and EGRF. In addition to oncogene products as target antigens, target polypeptides for anti-cancer treatments and protective regimens include variable regions of antibodies made by B cell lymphomas and variable regions of T cell receptors of T cell lymphomas which, in some embodiments, are also used as target antigens for autoimmune disease. Other tumor-associated polypeptides can be used as target polypeptides such as polypeptides which are found at higher levels in tumor cells including the polypeptide recognized by monoclonal antibody 17-1A and folate binding polypeptides.

Other suitable therapeutic polypeptides and proteins include those which may be useful for treating individuals suffering from autoimmune diseases and disorders by conferring a broad based protective immune response against targets that are associated with autoimmunity including cell receptors and cells which produce "self"-directed antibodies. T cell mediated autoimmune diseases include Rheumatoid arthritis (RA), multiple sclerosis (MS), Sjögren's syndrome, sarcoidosis, insulin dependent diabetes mellitus (IDDM), autoimmune thyroiditis, reactive arthritis, ankylosing spondylitis, scleroderma, polymyositis, dermatomyositis, psoriasis, vasculitis, Wegener's granulomatosis, Crohn's disease and ulcerative colitis. Each of these diseases is characterized by T cell receptors (TCRs) that bind to endogenous antigens and initiate the inflammatory cascade associated with autoimmune diseases.

Further illustrative genes which may be delivered via the rAAV include, without limitation, glucose-6-phosphatase, associated with glycogen storage disease or deficiency type 1A (GSD1), phosphoenolpyruvate-carboxykinase (PEPCK), associated with PEPCK deficiency; cyclin-dependent kinase-like 5 (CDKL5), also known as serine/threonine kinase 9 (STK9) associated with seizures and severe neurodevelopmental impairment; galactose-1 phosphate uridyl transferase, associated with galactosemia; phenylalanine hydroxylase, associated with phenylketonuria (PKU); branched chain alpha-ketoacid dehydrogenase, associated with Maple syrup urine disease; fumarylacetoacetate hydrolase, associated with tyrosinemia type 1; methylmalonyl-CoA mutase, associated with methylmalonic acidemia; medium chain acyl CoA dehydrogenase, associated with medium chain acetyl CoA deficiency; ornithine transcarbamylase (OTC), associated with ornithine transcarbamylase deficiency; argininosuccinic acid synthetase (ASS1), associated with citrullinemia; lecithin-cholesterol acyltransferase (LCAT) deficiency; amethylmalonic acidemia (MMA); Niemann-Pick disease, type C1); propionic academia (PA); low density lipoprotein receptor (LDLR) protein, associated with familial hypercholesterolemia (FH); UDP-glucouronosyltransferase, associated with Crigler-Najjar disease; adenosine deaminase, associated with severe combined immunodeficiency disease; hypoxanthine guanine phosphoribosyl transferase, associated with Gout and Lesch-Nyan syndrome; biotimidase, associated with biotimidase deficiency; alpha-galactosidase A (a-Gal A) associated with Fabry disease); ATP7B associated with Wilson's Disease; beta-glucocerebrosidase, associated with Gaucher disease type 2 and 3; peroxisome membrane protein 70 kDa, associated with Zellweger syndrome; arylsulfatase A (ARSA) associated with metachromatic leukodystrophy, galactocerebrosidase (GALC) enzyme associated with Krabbe disease, alpha-glucosidase (GAA) associated with Pompe disease; sphingomyelinase (SMPD1) gene associated with Nieman Pick disease type A; argininosuccsinate synthase associated with adult onset type II citrullinemia (CTLN2); carbamoyl-phosphate synthase 1 (CPS1) associated with urea cycle disorders; survival motor neuron (SMN) protein, associated with spinal muscular atrophy; ceramidase associated with Farber lipogranulomatosis; b-hexosaminidase associated with GM2 gangliosidosis and Tay-Sachs and Sandhoff diseases; aspartylglucosaminidase associated with aspartylglucosaminuria; α-fucosidase associated with fucosidosis; α-mannosidase associated with alpha-mannosidosis; porphobilinogen deaminase, associated with acute intermittent porphyria (AIP); alpha-1 antitrypsin for treatment of alpha-1 antitrypsin deficiency (emphysema); erythropoietin for treatment of anemia due to thalassemia or to renal failure; vascular endothelial growth factor, angiopoietin-1, and fibroblast growth factor for the treatment of ischemic diseases; thrombomodulin and tissue factor pathway inhibitor for the treatment of occluded blood vessels as seen in, for example, atherosclerosis, thrombosis, or embolisms; aromatic amino acid decarboxylase (AADC), and tyrosine hydroxylase (TH) for the treatment of Parkinson's disease; the beta adrenergic receptor, anti-sense to, or a mutant form of, phospholamban, the sarco (endo) plasmic reticulum adenosine triphosphatase-2 (SERCA2), and the cardiac adenylyl cyclase for the treatment of congestive heart failure; a tumor suppressor gene such as p53 for the treatment of various cancers; a cytokine such as one of the various interleukins for the treatment of inflammatory and immune disorders and cancers; dystrophin or minidystrophin and utrophin or miniutrophin for the treatment of muscular dystrophies; and, insulin or GLP-1 for the treatment of diabetes.

Additional genes and diseases of interest include, e.g., dystonin gene related diseases such as Hereditary Sensory and Autonomic Neuropathy Type VI (the DST gene encodes dystonin; dual AAV vectors may be required due to the size of the protein (~7570 aa); SCN9A related diseases, in which loss of function mutants cause inability to feel pain and gain of function mutants cause pain conditions, such as erythromelagia. Another condition is Charcot-Marie-Tooth type 1F and 2E due to mutations in the NEFL gene (neurofilament light chain). characterized by a progressive peripheral motor and sensory neuropathy with variable clinical and electrophysiologic expression.

In certain embodiments, the rAAV described herein may be used in treatment of mucopolysaccharidoses (MPS) disorders. Such rAAV may contain carry a nucleic acid sequence encoding α-L-iduronidase (IDUA) for treating MPS I (Hurler, Hurler-Scheie and Scheie syndromes); a nucleic acid sequence encoding iduronate-2-sulfatase (IDS) for treating MPS II (Hunter syndrome); a nucleic acid sequence encoding sulfamidase (SGSH) for treating MPSIII A, B, C, and D (Sanfilippo syndrome); a nucleic acid sequence encoding N-acetylgalactosamine-6-sulfate sulfatase (GALNS) for treating MPS IV A and B (Morquio syndrome); a nucleic acid sequence encoding arylsulfatase B (ARSB) for treating MPS VI (Maroteaux-Lamy syndrome); a nucleic acid sequence encoding hyaluronidase for treating MPSI IX (hyaluronidase deficiency) and a nucleic acid sequence encoding beta-glucuronidase for treating MPS VII (Sly syndrome).

Immunogenic Transgenes

In some embodiments, an rAAV vector comprising a nucleic acid encoding a gene product associated with cancer (e.g., tumor suppressors) may be used to treat the cancer, by administering a rAAV harboring the rAAV vector to a subject having the cancer. In some embodiments, an rAAV vector comprising a nucleic acid encoding a small interfering nucleic acid (e.g., shRNAs, miRNAs) that inhibits the expression of a gene product associated with cancer (e.g., oncogenes) may be used to treat the cancer, by administering a rAAV harboring the rAAV vector to a subject having the cancer. In some embodiments, an rAAV vector comprising a nucleic acid encoding a gene product associated with cancer (or a functional RNA that inhibits the expression of a gene associated with cancer) may be used for research purposes, e.g., to study the cancer or to identify therapeutics that treat the cancer. The following is a non-limiting list of exemplary genes known to be associated with the development of cancer (e.g., oncogenes and tumor suppressors): AARS, ABCB1, ABCC4, ABI2, ABL1, ABL2, ACK1, ACP2, ACY1, ADSL, AK1, AKRIC2, AKT1, ALB, ANPEP, ANXA5, ANXA7, AP2M1, APC, ARHGAP5, ARHGEF5, ARID4A, ASNS, ATF4, ATM, ATP5B, ATP5O, AXL, BARD1, BAX, BCL2, BHLHB2, BLMH, BRAF, BRCA1, BRCA2, BTK, CANX, CAP1, CAPN1, CAPNS1, CAV1, CBFB, CBLB, CCL2, CCND1, CCND2, CCND3, CCNE1, CCT5, CCYR61, CD24, CD44, CD59, CDC20, CDC25, CDC25A, CDC25B, CDC2L5, CDK10, CDK4, CDK5, CDK9, CDKL1, CDKN1A, CDKN1B, CDKN1C, CDKN2A, CDKN2B, CDKN2D, CEBPG, CENPC1, CGRRF1, CHAF1A, CIB1, CKMT1, CLK1, CLK2, CLK3, CLNSIA, CLTC, COL1A1, COL6A3, COX6C, COX7A2, CRAT, CRHR1, CSF1R, CSK, CSNK1G2, CTNNA1, CTNNB1, CTPS, CTSC, CTSD, CUL1, CYR61, DCC, DCN, DDX10, DEK, DHCR7, DHRS2, DHX8, DLG3, DVL1, DVL3, E2F1, E2F3, E2F5, EGFR, EGR1, EIF5, EPHA2, ERBB2, ERBB3, ERBB4, ERCC3, ETV1, ETV3, ETV6, F2R, FASTK, FBN1, FBN2, FES, FGFR1, FGR, FKBP8, FN1, FOS, FOSL1, FOSL2, FOXGIA, FOXO1A, FRAP1, FRZB, FTL, FZD2, FZD5, FZD9, G22P1, GAS6, GCN5L2, GDF15, GNA13, GNAS, GNB2, GNB2L1, GPR39, GRB2, GSK3A, GSPT1, GTF21, HDAC1, HDGF, HMMR, HPRT1, HRB, HSPA4, HSPA5, HSPA8, HSPB1, HSPH1, HYAL1, HYOU1, ICAM1, ID1, ID2, IDUA, IER3, IFITM1, IGF1R, IGF2R, IGFBP3, IGFBP4, IGFBP5, IL1B, ILK, ING1, IRF3, ITGA3, ITGA6, ITGB4, JAK1, JARIDIA, JUN, JUNB, JUND, K-ALPHA-1, KIT, KITLG, KLK10, KPNA2, KRAS2, KRT18, KRT2A, KRT9, LAMB1, LAMP2, LCK, LCN2, LEP, LITAF, LRPAP1, LTF, LYN, LZTR1, MADH1, MAP2K2, MAP3K8, MAPK12, MAPK13, MAPKAPK3, MAPRE1, MARS, MAS1, MCC, MCM2, MCM4, MDM2, MDM4, MET, MGST1, MICB, MLLT3, MME, MMP1, MMP14, MMP17, MMP2, MNDA, MSH2, MSH6, MT3, MYB, MYBL1, MYBL2, MYC, MYCL1, MYCN, MYD88, MYL9, MYLK, NEO1, NF1, NF2, NFKB1, NFKB2, NFSF7, NID, NINE, NMBR, NME1, NME2, NME3, NOTCH1, NOTCH2, NOTCH4, NPM1, NQO1, NRID1, NR2F1, NR2F6, NRAS, NRG1, NSEP1, OSM, PA2G4, PABPC1, PCNA, PCTK1, PCTK2, PCTK3, PDGFA, PDGFB, PDGFRA, PDPK1, PEA15, PFDN4, PFDN5, PGAM1, PHB, PIK3CA, PIK3CB, PIK3CG, PIM1, PKM2, PKMYT1, PLK2, PPARD, PPARG, PPIH, PPPICA, PPP2R5A, PRDX2, PRDX4, PRKARIA, PRKCBP1, PRNP, PRSS15, PSMA1, PTCH, PTEN, PTGS1, PTMA, PTN, PTPRN, RABSA, RAC1, RAD50, RAF1, RALBP1, RAPIA, RARA, RARB, RASGRF1, RB1, RBBP4, RBI 2, REA, REL, RELA, RELB, RET, RFC2, RGS19, RHOA, RHOB, RHOC, RHOD, RIPK1, RPN2, RPS6 KB1, RRM1, SARS, SELENBP1, SEMA3C, SEMA4D, SEPP1, SERPINH1. SFN, SFPQ, SFRS7, SHB, SHH, SIAH2, SIVA, SIVA TP53, SKI, SKIL, SLC16A1, SLCIA4, SLC20A1, SMO, sphingomyelin phosphodiesterase 1 (SMPD1), SNAI2, SND1, SNRPB2, SOCS1, SOCS3, SOD1, SORT1, SPINT2, SPRY2, SRC, SRPX, STAT1, STAT2, STAT3, STAT5B, STC1, TAF1, TBL3, TBRG4, TCF1, TCF7L2, TFAP2C, TFDP1, TFDP2, TGFA, TGFB1, TGFB1, TGFBR2, TGFBR3, THBS1, TIE, TIMP1, TIMP3, TJP1, TK1, TLE1, TNF, TNFRSF10A, TNFRSF10B, TNFRSF1A, TNFRSF1B, TNFRSF6, TNFSF7, TNK1, TOB1, TP53, TP53BP2, TP5313, TP73, TPBG, TPT1, TRADD, TRAM1, TRRAP, TSG101, TUFM, TXNRD1, TYRO3, UBC, UBE2L6, UCHL1, USP7, VDAC1, VEGF, VHL, VIL2, WEE1, WNT1, WNT2, WNT2B, WNT3, WNT5A, WT1, XRCC1, YES1, YWHAB, YWHAZ, ZAP70, and ZNF9.

A rAAV vector may comprise as a transgene, a nucleic acid encoding a protein or functional RNA that modulates apoptosis. The following is a non-limiting list of genes associated with apoptosis and nucleic acids encoding the products of these genes and their homologues and encoding small interfering nucleic acids (e.g., shRNAs, miRNAs) that inhibit the expression of these genes and their homologues are useful as transgenes in certain embodiments of the invention: RPS27A, ABL1, AKT1, APAF1, BAD, BAGI, BAG3, BAG4, BAK1, BAX, BCL10, BCL2, BCL2A1, BCL2L1, BCL2L10, BCL2L11, BCL2L12, BCL2L13, BCL2L2, BCLAF1. BFAR, BID, BIK, NAIP, BIRC2, BIRC3, XIAP, BIRC5, BIRC6, BIRC7, BIRC8, BNIPI, BNIP2, BNIP3, BNIP3L, BOK, BRAF, CARD10, CARD11, NLRC4, CARD14, NOD2, NODI, CARD6, CARDS, CARDS, CASPI, CASP10, CASP14, CASP2, CASP3, CASP4, CASP5, CASP6, CASP7, CASP8, CASP9, CFLAR, CIDEA, CIDEB, CRADD, DAPK1, DAPK2, DFFA, DFFB, FADD, GADD45A, GDNF, HRK, IGFIR, LTA, LTBR, MCL1, NOL3, PYCARD, RIPKI, RIPK2, TNF, TNFRSF10A, TNFRSF10B, TNFRSF10C, TNFRSF10D, TNFRSF11B, TNFRSF12A, TNFRSF14, TNFRSF19, TNFRSF1A, TNFRSF1B, TNFRSF21, TNFRSF25, CD40, FAS, TNFRSF6B, CD27, TNFRSF9, TNFSF10, TNFSF14, TNFSF18, CD40LG, FASLG, CD70, TNFSF8, TNFSF9, TP53, TP53BP2, TP73, TP63, TRADD, TRAFI, TRAF2, TRAF3, TRAF4, and TRAF5.

Useful transgene products also include miRNAs. miRNAs and other small interfering nucleic acids regulate gene expression via target RNA transcript cleavage/degradation or translational repression of the target messenger RNA (mRNA). miRNAs are natively expressed, typically as final 19-25 non-translated RNA products. miRNAs exhibit their activity through sequence-specific interactions with the 3' untranslated regions (UTR) of target mRNAs. These endogenously expressed miRNAs form hairpin precursors which are subsequently processed into a miRNA duplex, and further into a "mature" single stranded miRNA molecule. This mature miRNA guides a multiprotein complex, miRISC, which identifies target site, e.g., in the 3' UTR regions, of target mRNAs based upon their complementarity to the mature miRNA.

The following non-limiting list of miRNA genes, and their homologues, are useful as transgenes or as targets for small interfering nucleic acids encoded by transgenes (e.g., miRNA sponges, antisense oligonucleotides, TuD RNAs) in certain embodiments of the methods: hsa-let-7a, hsa-let-7a*, hsa-let-7b, hsa-let-7b*, hsa-let-7c, hsa-let-7c*, hsa-let-7d, hsa-let-7d*, hsa-let-7e, hsa-let-7e*, hsa-let-7f, hsa-let-7f-1*, hsa-let-7f-2*, hsa-let-7g, hsa-let-7g*, hsa-let-71, hsa-let-71*. hsa-miR-1, hsa-miR-100, hsa-miR-100*, hsa-miR-101, hsa-miR-101*, hsa-miR-103, hsa-miR-105, hsa-miR-105*, hsa-miR-106a, hsa-miR-106a*, hsa-miR-106b, hsa-miR-106b*, hsa-miR-107, hsa-miR-10a, hsa-miR-10a*, hsa-miR-10b, hsa-miR-10b*, hsa-miR-1178, hsa-miR-1179, hsa-miR-1180, hsa-miR-1181, hsa-miR-1182, hsa-miR-1183, hsa-miR-1184, hsa-miR-1185, hsa-miR-1197, hsa-miR-1200, hsa-miR-1201, hsa-miR-1202, hsa-miR-1203, hsa-miR-1204, hsa-miR-1205, hsa-miR-1206, hsa-miR-1207-3p, hsa-miR-1207-5p, hsa-miR-1208, hsa-miR-122, hsa-miR-122*, hsa-miR-1224-3p, hsa-miR-1224-5p, hsa-miR-1225-3p, hsa-miR-1225-5p, hsa-miR-1226, hsa-miR-1226*, hsa-miR-1227, hsa-miR-1228, hsa-miR-1228*, hsa-miR-1229, hsa-miR-1231, hsa-miR-1233, hsa-miR-1234, hsa-miR-1236, hsa-miR-1237, hsa-miR-1238, hsa-miR-124, hsa-miR-124*, hsa-miR-1243, hsa-miR-1244, hsa-miR-1245, hsa-miR-1246, hsa-miR-1247, hsa-miR-1248, hsa-miR-1249, hsa-miR-1250, hsa-miR-1251, hsa-miR-1252, hsa-miR-1253, hsa-miR-1254, hsa-miR-1255a, hsa-miR-1255b, hsa-miR-1256, hsa-miR-1257, hsa-miR-1258, hsa-miR-1259, hsa-miR-125a-3p, hsa-miR-125a-5p, hsa-miR-125b, hsa-miR-125b-1*, hsa-miR-125b-2*, hsa-miR-126, hsa-miR-126*, hsa-miR-1260, hsa-miR-1261, hsa-miR-1262, hsa-miR-1263, hsa-miR-1264, hsa-miR-1265, hsa-miR-1266, hsa-miR-1267, hsa-miR-1268, hsa-miR-1269, hsa-miR-1270, hsa-miR-1271, hsa-miR-1272, hsa-miR-1273, hsa-miR-127-3p, hsa-miR-1274a, hsa-miR-1274b, hsa-miR-1275, hsa-miR-127-5p, hsa-miR-1276, hsa-miR-1277, hsa-miR-1278, hsa-miR-1279, hsa-miR-128, hsa-miR-1280, hsa-miR-1281, hsa-miR-1282, hsa-miR-1283, hsa-miR-1284, hsa-miR-1285, hsa-miR-1286, hsa-miR-1287, hsa-miR-1288, hsa-miR-1289, hsa-miR-129*, hsa-miR-1290, hsa-miR-1291, hsa-miR-1292, hsa-miR-1293, hsa-miR-129-3p, hsa-miR-1294, hsa-miR-1295, hsa-miR-129-5p, hsa-miR-1296, hsa-miR-1297, hsa-miR-1298, hsa-miR-1299, hsa-miR-1300, hsa-miR-1301, hsa-miR-1302, hsa-miR-1303, hsa-miR-1304, hsa-miR-1305, hsa-miR-1306, hsa-miR-1307, hsa-miR-1308, hsa-miR-130a, hsa-miR-130a*, hsa-miR-130b, hsa-miR-130b*, hsa-miR-132, hsa-miR-132*, hsa-miR-1321, hsa-miR-1322, hsa-miR-1323, hsa-miR-1324, hsa-miR-133a, hsa-miR-133b, hsa-miR-134, hsa-miR-135a, hsa-miR-135a*, hsa-miR-135b, hsa-miR-135b*, hsa-miR-136, hsa-miR-136*, hsa-miR-137, hsa-miR-138, hsa-miR-138-1*, hsa-miR-138-2*, hsa-miR-139-3p, hsa-miR-139-5p, hsa-miR-140-3p, hsa-miR-140-5p, hsa-miR-141, hsa-miR-141*, hsa-miR-142-3p, hsa-miR-142-5p, hsa-miR-143, hsa-miR-143*, hsa-miR-144, hsa-miR-144*, hsa-miR-145, hsa-miR-145*, hsa-miR-146a, hsa-miR-146a*, hsa-miR-146b-3p, hsa-miR-146b-5p, hsa-miR-147, hsa-miR-147b, hsa-miR-148a, hsa-miR-148a*, hsa-miR-148b, hsa-miR-148b*, hsa-miR-149, hsa-miR-149*, hsa-miR-150, hsa-miR-150*, hsa-miR-151-3p, hsa-miR-151-5p, hsa-miR-152, hsa-miR-153, hsa-miR-154, hsa-miR-154*, hsa-miR-155, hsa-miR-155*, hsa-miR-15a, hsa-miR-15a*, hsa-miR-15b, hsa-miR-15b*, hsa-miR-16, hsa-miR-16-1*, hsa-miR-16-2*, hsa-miR-17, hsa-miR-17*, hsa-miR-181a, hsa-miR-181a+, hsa-miR-181a-2*, hsa-miR-181b, hsa-miR-181c, hsa-miR-181c*, hsa-miR-181d, hsa-miR-182, hsa-miR-182*, hsa-miR-1825, hsa-miR-1826, hsa-miR-1827, hsa-miR-183, hsa-miR-183*, hsa-miR-184, hsa-miR-185, hsa-miR-185*, hsa-miR-186, hsa-miR-186*, hsa-miR-187, hsa-miR-187*, hsa-miR-188-3p, hsa-miR-188-5p, hsa-miR-18a, hsa-miR-18a*, hsa-miR-18b, hsa-miR-18b*, hsa-miR-190, hsa-miR-190b, hsa-miR-191, hsa-miR-191*, hsa-miR-192, hsa-miR-192*, hsa-miR-193a-3p, hsa-miR-193a-5p, hsa-miR-193b, hsa-miR-193b*, hsa-miR-194, hsa-miR-194*, hsa-miR-195, hsa-miR-195*, hsa-miR-196a, hsa-miR-196a*, hsa-miR-196b, hsa-miR-197, hsa-miR-198, hsa-miR-199a-3p, hsa-miR-199a-5p, hsa-miR-199b-5p, hsa-miR-19a, hsa-miR-19a*, hsa-miR-19b, hsa-miR-19b-1*, hsa-miR-19b-2*, hsa-miR-200a, hsa-miR-200a*, hsa-miR-200b, hsa-miR-200b*, hsa-miR-200c, hsa-miR-200c*, hsa-miR-202, hsa-miR-202*, hsa-miR-203, hsa-miR-204, hsa-miR-205, hsa-miR-206, hsa-miR-208a, hsa-miR-208b, hsa-miR-20a, hsa-miR-20a*, hsa-miR-20b, hsa-miR-20b*, hsa-miR-21, hsa-miR-21*, hsa-miR-210, hsa-miR-211, hsa-miR-212, hsa-miR-214, hsa-miR-214*, hsa-miR-215, hsa-miR-216a, hsa-miR-216b, hsa-miR-217, hsa-miR-218, hsa-miR-218-1*, hsa-miR-218-2*, hsa-miR-219-1-3p, hsa-miR-219-2-3p, hsa-miR-219-5p, hsa-miR-22, hsa-miR-22*, hsa-miR-220a, hsa-miR-220b, hsa-miR-220c, hsa-miR-221, hsa-miR-221*, hsa-miR-222, hsa-miR-222*, hsa-miR-223, hsa-miR-223*, hsa-miR-224, hsa-miR-23a, hsa-miR-23a*, hsa-miR-23b, hsa-miR-23b*, hsa-miR-24, hsa-miR-24-1*, hsa-miR-24-2*, hsa-miR-25, hsa-miR-25*, hsa-miR-26a, hsa-miR-26a-1*, hsa-miR-26a-2*, hsa-miR-26b, hsa-miR-26b*, hsa-miR-27a, hsa-miR-27a*, hsa-miR-27b, hsa-miR-27b*, hsa-miR-28-3p, hsa-miR-28-5p, hsa-miR-296-3p, hsa-miR-296-5p, hsa-miR-297, hsa-miR-298, hsa-miR-299-3p, hsa-miR-299-5p, hsa-miR-29a, hsa-miR-29a*, hsa-miR-29b, hsa-miR-296-1*, hsa-miR-296-2*, hsa-miR-29c, hsa-miR-29c*, hsa-miR-300, hsa-miR-301a, hsa-miR-301b, hsa-miR-302a, hsa-miR-302a*, hsa-miR-302b, hsa-miR-302b*, hsa-miR-302c, hsa-miR-302c*, hsa-miR-302d, hsa-miR-302d*, hsa-miR-302e, hsa-miR-302f, hsa-miR-30a, hsa-miR-30a*, hsa-miR-30b, hsa-miR-30b*, hsa-miR-30c, hsa-miR-30c-1*, hsa-miR-30c-2*, hsa-miR-30d, hsa-miR-30d*, hsa-miR-30e, hsa-miR-30) e*, hsa-miR-31, hsa-miR-31*, hsa-miR-32, hsa-miR-32*, hsa-miR-320a, hsa-miR-320b, hsa-miR-320c, hsa-miR-320d, hsa-miR-323-3p, hsa-miR-323-5p, hsa-miR-324-3p, hsa-miR-324-5p, hsa-miR-325, hsa-miR-326, hsa-miR-328, hsa-miR-329, hsa-miR-330-3p, hsa-miR-330-5p, hsa-miR-331-3p, hsa-miR-331-5p, hsa-miR-335, hsa-miR-335*, hsa-miR-337-3p, hsa-miR-337-5p, hsa-miR-338-3p, hsa-miR-338-5p, hsa-miR-339-3p, hsa-miR-339-5p, hsa-miR-33a, hsa-miR-33a*, hsa-miR-33b, hsa-miR-33b*, hsa-miR-340, hsa-miR-340*, hsa-miR-342-3p, hsa-miR-342-5p, hsa-miR-345, hsa-miR-346, hsa-miR-34a, hsa-miR-34a*, hsa-miR-34b, hsa-miR-34b*, hsa-miR-34c-3p, hsa-miR-34c-5p, hsa-miR-361-3p, hsa-miR-361-5p, hsa-miR-362-3p, hsa-miR-362-5p, hsa-miR-363, hsa-miR-363*, hsa-miR-365, hsa-miR-367, hsa-miR-367*, hsa-miR-369-3p, hsa-miR-369-5p, hsa-miR-370, hsa-miR-371-3p, hsa-miR-371-5p, hsa-miR-372, hsa-miR-373, hsa-miR-373*, hsa-miR-374a, hsa-miR-374a*, hsa-miR-374b, hsa-miR-374b*, hsa-miR-375, hsa-miR-376a, hsa-miR-376a*. hsa-miR-376b, hsa-miR-376c, hsa-miR-377, hsa-miR-377*, hsa-miR-378, hsa-miR-378*, hsa-miR-379, hsa-miR-379*, hsa-miR-380, hsa-miR-380*, hsa-miR-381, hsa-miR-382, hsa-miR-383, hsa-miR-384, hsa-miR-409-3p, hsa-miR-409-5p, hsa-miR-410, hsa-miR-411, hsamiR-411*, hsa-miR-412, hsa-miR-421, hsa-miR-422a, hsa-miR-423-3p, hsa-miR-423-5p, hsa-miR-424, hsa-miR-424*, hsa-miR-425, hsa-miR-425*, hsa-miR-429, hsa-miR-431, hsa-miR-431*, hsa-miR-432, hsa-miR-432*, hsa-miR-433, hsa-miR-448, hsa-miR-449a, hsa-miR-449b, hsa-miR-450a, hsa-miR-450b-3p, hsa-miR-450b-5p, hsa-miR-451, hsa-miR-452, hsa-miR-452*, hsa-miR-453, hsa-miR-454, hsa-miR-454*, hsa-miR-455-3p, hsa-miR-455-5p, hsa-miR-483-3p, hsa-miR-483-5p, hsa-miR-484, hsa-miR-485-3p, hsa-miR-485-5p, hsa-miR-486-3p, hsa-miR-486-5p, hsa-miR-487a, hsa-miR-487b, hsa-miR-488, hsa-miR-488*, hsa-miR-489, hsa-miR-490-3p, hsa-miR-490-5p, hsa-miR-491-3p, hsa-miR-491-5p, hsa-miR-492, hsa-miR-493, hsa-miR-493*, hsa-miR-494, hsa-miR-495, hsa-miR-496, hsa-miR-497, hsa-miR-497*, hsa-miR-498, hsa-miR-499-3p, hsa-miR-499-5p, hsa-miR-500, hsa-miR-500*, hsa-miR-501-3p, hsa-miR-501-5p, hsa-miR-502-3p, hsa-miR-502-5p, hsa-miR-503, hsa-miR-504, hsa-miR-505, hsa-miR-505*, hsa-miR-506, hsa-miR-507, hsa-miR-508-3p, hsa-miR-508-5p, hsa-miR-509-3-5p, hsa-miR-509-3p, hsa-miR-509-5p, hsa-miR-510, hsa-miR-511, hsa-miR-512-3p, hsa-miR-512-5p, hsa-miR-513a-3p, hsa-miR-513a-5p, hsa-miR-513b, hsa-miR-513c, hsa-miR-514, hsa-miR-515-3p, hsa-miR-515-5p, hsa-miR-516a-3p, hsa-miR-516a-5p, hsa-miR-516b, hsa-miR-517*, hsa-miR-517a, hsa-miR-517b, hsa-miR-517c, hsa-miR-518a-3p, hsa-miR-518a-5p, hsa-miR-518b, hsa-miR-518c, hsa-miR-518c*, hsa-miR-518d-3p, hsa-miR-518d-5p, hsa-miR-518e, hsa-miR-518e*, hsa-miR-518f, hsa-miR-518f*, hsa-miR-519a, hsa-miR-519b-3p, hsa-miR-519c-3p, hsa-miR-519d, hsa-miR-519e, hsa-miR-519e*, hsa-miR-520a-3p, hsa-miR-520a-5p, hsa-miR-520b, hsa-miR-520c-3p, hsa-miR-520d-3p, hsa-miR-520d-5p, hsa-miR-520e, hsa-miR-520f, hsa-miR-520g, hsa-miR-520h, hsa-miR-521, hsa-miR-522, hsa-miR-523, hsa-miR-524-3p, hsa-miR-524-5p, hsa-miR-525-3p, hsa-miR-525-5p, hsa-miR-526b, hsa-miR-526b*, hsa-miR-532-3p, hsa-miR-532-5p, hsa-miR-539, hsa-miR-541, hsa-miR-541*, hsa-miR-542-3p, hsa-miR-542-5p, hsa-miR-543, hsa-miR-544, hsa-miR-545, hsa-miR-545*, hsa-miR-548a-3p, hsa-miR-548a-5p, hsa-miR-548b-3p, hsa-miR-5486-5p, hsa-miR-548c-3p, hsa-miR-548c-5p, hsa-miR-548d-3p, hsa-miR-548d-5p, hsa-miR-548e, hsa-miR-548f, hsa-miR-548g, hsa-miR-548h, hsa-miR-548i, hsa-miR-548j, hsa-miR-548k, hsa-miR-5481, hsa-miR-548m, hsa-miR-548n, hsa-miR-5480, hsa-miR-548p, hsa-miR-549, hsa-miR-550, hsa-miR-550*, hsa-miR-551a, hsa-miR-551b, hsa-miR-551b*, hsa-miR-552, hsa-miR-553, hsa-miR-554, hsa-miR-555, hsa-miR-556-3p, hsa-miR-556-5p, hsa-miR-557, hsa-miR-558, hsa-miR-559, hsa-miR-561, hsa-miR-562, hsa-miR-563, hsa-miR-564, hsa-miR-566, hsa-miR-567, hsa-miR-568, hsa-miR-569, hsa-miR-570, hsa-miR-571, hsa-miR-572, hsa-miR-573, hsa-miR-574-3p, hsa-miR-574-5p, hsa-miR-575, hsa-miR-576-3p, hsa-miR-576-5p, hsa-miR-577, hsa-miR-578, hsa-miR-579, hsa-miR-580, hsa-miR-581, hsa-miR-582-3p, hsa-miR-582-5p, hsa-miR-583, hsa-miR-584, hsa-miR-585, hsa-miR-586, hsa-miR-587, hsa-miR-588, hsa-miR-589, hsa-miR-589*, hsa-miR-590-3p, hsa-miR-590-5p, hsa-miR-591, hsa-miR-592, hsa-miR-593, hsa-miR-593*, hsa-miR-595, hsa-miR-596, hsa-miR-597, hsa-miR-598, hsa-miR-599, hsa-miR-600, hsa-miR-601, hsa-miR-602, hsa-miR-603, hsa-miR-604, hsa-miR-605, hsa-miR-606, hsa-miR-607, hsa-miR-608, hsa-miR-609, hsa-miR-610, hsa-miR-611, hsa-miR-612, hsa-miR-613, hsa-miR-614, hsa-miR-615-3p, hsa-miR-615-5p, hsa-miR-616, hsa-miR-616*, hsa-miR-617, hsa-miR-618, hsa-miR-619, hsa-miR-620, hsa-miR-621, hsa-miR-622, hsa-miR-623, hsa-miR-624, hsa-miR-624*, hsa-miR-625, hsa-miR-625*, hsa-miR-626, hsa-miR-627, hsa-miR-628-3p, hsa-miR-628-5p, hsa-miR-629, hsa-miR-629*, hsa-miR-630, hsa-miR-631, hsa-miR-632, hsa-miR-633, hsa-miR-634, hsa-miR-635, hsa-miR-636, hsa-miR-637, hsa-miR-638, hsa-miR-639, hsa-miR-640, hsa-miR-641, hsa-miR-642, hsa-miR-643, hsa-miR-644, hsa-miR-645, hsa-miR-646, hsa-miR-647, hsa-miR-648, hsa-miR-649, hsa-miR-650, hsa-miR-651, hsa-miR-652, hsa-miR-653, hsa-miR-654-3p, hsa-miR-654-5p, hsa-miR-655, hsa-miR-656, hsa-miR-657, hsa-miR-658, hsa-miR-659, hsa-miR-660, hsa-miR-661, hsa-miR-662, hsa-miR-663, hsa-miR-663b, hsa-miR-664, hsa-miR-664*, hsa-miR-665, hsa-miR-668, hsa-miR-671-3p, hsa-miR-671-5p, hsa-miR-675, hsa-miR-7, hsa-miR-708, hsa-miR-708*, hsa-miR-7-1*, hsa-miR-7-2*, hsa-miR-720, hsa-miR-744, hsa-miR-744*, hsa-miR-758, hsa-miR-760, hsa-miR-765, hsa-miR-766, hsa-miR-767-3p, hsa-miR-767-5p, hsa-miR-768-3p, hsa-miR-768-5p, hsa-miR-769-3p, hsa-miR-769-5p, hsa-miR-770-5p, hsa-miR-802, hsa-miR-873, hsa-miR-874, hsa-miR-875-3p, hsa-miR-875-5p, hsa-miR-876-3p, hsa-miR-876-5p, hsa-miR-877, hsa-miR-877*, hsa-miR-885-3p, hsa-miR-885-5p, hsa-miR-886-3p, hsa-miR-886-5p, hsa-miR-887, hsa-miR-888, hsa-miR-888*, hsa-miR-889, hsa-miR-890, hsa-miR-891a, hsa-miR-891b, hsa-miR-892a, hsa-miR-892b, hsa-miR-9, hsa-miR-9*, hsa-miR-920, hsa-miR-921, hsa-miR-922, hsa-miR-923, hsa-miR-924, hsa-miR-92a, hsa-miR-92a-1*, hsa-miR-92a-2*, hsa-miR-92b, hsa-miR-92b*, hsa-miR-93, hsa-miR-93*, hsa-miR-933, hsa-miR-934, hsa-miR-935, hsa-miR-936, hsa-miR-937, hsa-miR-938, hsa-miR-939, hsa-miR-940, hsa-miR-941, hsa-miR-942, hsa-miR-943, hsa-miR-944, hsa-miR-95, hsa-miR-96, hsa-miR-96*, hsa-miR-98, hsa-miR-99a, hsa-miR-99a*, hsa-miR-99b, and hsa-miR-99b*. For example, miRNA targeting chromosome 8 open reading frame 72 (C9orf72) which expresses superoxide dismutase (SOD1), associated with amyotrophic lateral sclerosis (ALS) may be of interest.

A miRNA inhibits the function of the mRNAs it targets and, as a result, inhibits expression of the polypeptides encoded by the mRNAs. Thus, blocking (partially or totally) the activity of the miRNA (e.g., silencing the miRNA) can effectively induce, or restore, expression of a polypeptide whose expression is inhibited (derepress the polypeptide). In one embodiment, derepression of polypeptides encoded by mRNA targets of a miRNA is accomplished by inhibiting the miRNA activity in cells through any one of a variety of methods. For example, blocking the activity of a miRNA can be accomplished by hybridization with a small interfering nucleic acid (e.g., antisense oligonucleotide, miRNA sponge, TuD RNA) that is complementary, or substantially complementary to, the miRNA, thereby blocking interaction of the miRNA with its target mRNA. As used herein, a small interfering nucleic acid that is substantially complementary to a miRNA is one that is capable of hybridizing with a miRNA, and blocking the miRNA's activity. In some embodiments, a small interfering nucleic acid that is substantially complementary to a miRNA is a small interfering nucleic acid that is complementary with the miRNA at all but 1, 2, 3, 4, 5, 6, 7, 8, 9, 10, 11, 12, 13, 14, 15, 16, 17, or 18 bases. A "miRNA Inhibitor" is an agent that blocks miRNA function, expression and/or processing. For instance, these molecules include but are not limited to microRNA specific antisense, microRNA sponges, tough decoy RNAs (TuD RNAs) and microRNA oligonucleotides (double-stranded, hairpin, short oligonucleotides) that inhibit miRNA interaction with a Drosha complex.

Still other useful transgenes may include those encoding immunoglobulins which confer passive immunity to a pathogen. An "immunoglobulin molecule" is a protein containing the immunologically-active portions of an immunoglobulin heavy chain and immunoglobulin light chain covalently coupled together and capable of specifically combining with antigen. Immunoglobulin molecules are of any type (e.g., IgG, IgE, IgM, IgD, IgA and IgY), class (e.g., IgG1, IgG2, IgG3, IgG4, IgA1 and IgA2) or subclass. The terms "antibody" and "immunoglobulin" may be used interchangeably herein.

An "immunoglobulin heavy chain" is a polypeptide that contains at least a portion of the antigen binding domain of an immunoglobulin and at least a portion of a variable region of an immunoglobulin heavy chain or at least a portion of a constant region of an immunoglobulin heavy chain. Thus, the immunoglobulin derived heavy chain has significant regions of amino acid sequence homology with a member of the immunoglobulin gene superfamily. For example, the heavy chain in a Fab fragment is an immunoglobulin-derived heavy chain.

An "immunoglobulin light chain" is a polypeptide that contains at least a portion of the antigen binding domain of an immunoglobulin and at least a portion of the variable region or at least a portion of a constant region of an immunoglobulin light chain. Thus, the immunoglobulin-derived light chain has significant regions of amino acid homology with a member of the immunoglobulin gene superfamily.

An "immunoadhesin" is a chimeric, antibody-like molecule that combines the functional domain of a binding protein, usually a receptor, ligand, or cell-adhesion molecule, with immunoglobulin constant domains, usually including the hinge and Fc regions.

A "fragment antigen-binding" (Fab) fragment" is a region on an antibody that binds to antigens. It is composed of one constant and one variable domain of each of the heavy and the light chain.

The anti-pathogen construct is selected based on the causative agent (pathogen) for the disease against which protection is sought. These pathogens may be of viral, bacterial, or fungal origin, and may be used to prevent infection in humans against human disease, or in non-human mammals or other animals to prevent veterinary disease.

The rAAV may include genes encoding antibodies, and particularly neutralizing antibodies against a viral pathogen. Such anti-viral antibodies may include anti-influenza antibodies directed against one or more of Influenza A, Influenza B, and Influenza C. The type A viruses are the most virulent human pathogens. The serotypes of influenza A which have been associated with pandemics include, H1N1, which caused Spanish Flu in 1918, and Swine Flu in 2009; H2N2, which caused Asian Flu in 1957; H3N2, which caused Hong Kong Flu in 1968; H5N1, which caused Bird Flu in 2004; H7N7; H1N2; H9N2; H7N2; H7N3; and H10N7. Other target pathogenic viruses include, arenaviruses (including funin, machupo, and Lassa), filoviruses (including Marburg and Ebola), hantaviruses, picornoviridae (including rhinoviruses, echovirus), coronaviruses, paramyxovirus, morbillivirus, respiratory synctial virus, togavirus, coxsackievirus, JC virus, parvovirus B19, parainfluenza, adenoviruses, reoviruses, variola (Variola major (Smallpox)) and Vaccinia (Cowpox) from the poxvirus family, and varicella-zoster (pseudorabies). Viral hemorrhagic fevers are caused by members of the arenavirus family (Lassa fever) (which family is also associated with Lymphocytic choriomeningitis (LCM)), filovirus (ebola virus), and hantavirus (puremala). The members of picornavirus (a subfamily of rhinoviruses), are associated with the common cold in humans.

The coronavirus family, which includes a number of non-human viruses such as infectious bronchitis virus (poultry), porcine transmissible gastroenteric virus (pig), porcine hemagglutinatin encephalomyelitis virus (pig), feline infectious peritonitis virus (cat), feline enteric coronavirus (cat), canine coronavirus (dog). The human respiratory coronaviruses have been putatively associated with the common cold, non-A, B or C hepatitis, and sudden acute respiratory syndrome (SARS). The paramyxovirus family includes parainfluenza Virus Type 1, parainfluenza Virus Type 3, bovine parainfluenza Virus Type 3, rubulavirus (mumps virus, parainfluenza Virus Type 2, parainfluenza virus Type 4, Newcastle disease virus (chickens), rinderpest, morbillivirus, which includes measles and canine distemper, and pneumovirus, which includes respiratory syncytial virus (RSV). The parvovirus family includes feline parvovirus (feline enteritis), feline panleukopenia virus, canine parvovirus, and porcine parvovirus. The adenovirus family includes viruses (EX, AD7, ARD, O.B.) which cause respiratory disease. Thus, in certain embodiments, a rAAV vector as described herein may be engineered to express an anti-ebola antibody, e.g., 2G4, 4G7, 13C6, an anti-influenza antibody, e.g., FI6, CR8033, and anti-RSV antibody, e.g, palivizumab, motavizumab. A neutralizing antibody construct against a bacterial pathogen may also be selected for use in the present invention. In one embodiment, the neutralizing antibody construct is directed against the bacteria itself. In another embodiment, the neutralizing antibody construct is directed against a toxin produced by the bacteria. Examples of airborne bacterial pathogens include, e.g., *Neisseria meningitidis* (meningitis), *Klebsiella pneumonia* (pneumonia), *Pseudomonas aeruginosa* (pneumonia), *Pseudomonas pseudomallei* (pneumonia), *Pseudomonas mallei* (pneumonia), *Acinetobacter* (pneumonia), *Moraxella catarrhalis*, *Moraxella lacunata*, *Alkaligenes*, *Cardiobacterium*, *Haemophilus influenzae* (flu), *Haemophilus parainfluenzae*, *Bordetella pertussis* (whooping cough), *Francisella tularensis* (pneumonia/fever), *Legionella pneumonia* (Legionnaires disease), *Chlamydia psittaci* (pneumonia), *Chlamydia pneumoniae* (pneumonia), *Mycobacterium tuberculosis* (tuberculosis (TB)), *Mycobacterium kansasii* (TB), *Mycobacterium avium* (pneumonia), *Nocardia asteroides* (pneumonia), *Bacillus anthracis* (anthrax), *Staphylococcus aureus* (pneumonia), *Streptococcus pyogenes* (scarlet fever), *Streptococcus pneumoniae* (pneumonia), *Corynebacteria diphtheria* (diphtheria), *Mycoplasma pneumoniae* (pneumonia).

The rAAV may include genes encoding antibodies, and particularly neutralizing antibodies against a bacterial pathogen such as the causative agent of anthrax, a toxin produced by *Bacillius anthracis*. Neutralizing antibodies against protective agent (PA), one of the three peptides which form the toxoid, have been described. The other two polypeptides consist of lethal factor (LF) and edema factor (EF). Anti-PA neutralizing antibodies have been described as being effective in passively immunization against anthrax. See, e.g., U.S. Pat. No. 7,442,373; R. Sawada-Hirai et al, J Immune Based Ther Vaccines. 2004; 2:5. (on-line 2004 May 12). Still other anti-anthrax toxin neutralizing antibodies have been described and/or may be generated. Similarly, neutralizing antibodies against other bacteria and/or bacterial toxins may be used to generate an AAV-delivered anti-pathogen construct as described herein.

Antibodies against infectious diseases may be caused by parasites or by fungi, including, e.g., *Aspergillus* species, *Absidia corymbifera*, *Rhixpus stolonifer*, *Mucor plumbeaus*, *Cryptococcus neoformans*, *Histoplasm capsulatum*, *Blasto-*

*myces dermatitidis, Coccidioides immitis, Penicillium* species, *Micropolyspora faeni, Thermoactinomyces vulgaris, Alternaria alternate, Cladosporium species, Helminthosporium,* and *Stachybotrys* species.

The rAAV may include genes encoding antibodies, and particularly neutralizing antibodies, against pathogenic factors of diseases such as Alzheimer's disease (AD), Parkinson's disease (PD), GBA-associated-Parkinson's disease (GBA-PD), Rheumatoid arthritis (RA), Irritable bowel syndrome (IBS), chronic obstructive pulmonary disease (COPD), cancers, tumors, systemic sclerosis, asthma and other diseases. Such antibodies may be, without limitation, e.g., alpha-synuclein, anti-vascular endothelial growth factor (VEGF) (anti-VEGF), anti-VEGFA, anti-PD-1, anti-PDL1, anti-CTLA-4, anti-TNF-alpha, anti-IL-17, anti-IL-23, anti-IL-21, anti-IL-6, anti-IL-6 receptor, anti-IL-5, anti-IL-7, anti-Factor XII, anti-IL-2, anti-HIV, anti-IgE, anti-tumour necrosis factor receptor-1 (TNFR1), anti-notch 2/3, anti-notch 1, anti-OX40, anti-erb-b2 receptor tyrosine kinase 3 (ErbB3), anti-ErbB2, anti-beta cell maturation antigen, anti-B lymphocyte stimulator, anti-CD20, anti-HER2, anti-granulocyte macrophage colony-stimulating factor, anti-oncostatin M (OSM), anti-lymphocyte activation gene 3 (LAG3) protein, anti-CCL20, anti-serum amyloid P component (SAP), anti-prolyl hydroxylase inhibitor, anti-CD38, anti-glycoprotein IIb/IIIa, anti-CD52, anti-CD30, anti-IL-1beta, anti-epidermal growth factor receptor, anti-CD25, anti-RANK ligand, anti-complement system protein C5, anti-CD11a, anti-CD3 receptor, anti-alpha-4 ($\alpha$4) integrin, anti-RSV F protein, and anti-integrin $\alpha_4 \beta_7$. Still other pathogens and diseases will be apparent to one of skill in the art. Other suitable antibodies may include those useful for treating Alzheimer's Disease, such as, e.g., anti-beta-amyloid (e.g., crenezumab, solanezumab, aducanumab), anti-beta-amyloid fibril, anti-beta-amyloid plaques, anti-tau, a bapineuzamab, among others. Other suitable antibodies for treating a variety of indications include those described, e.g., in PCT/US2016/058968, filed 27 Oct. 2016, published as WO 2017/075119A1.

II. rAAV Vector Production

For use in producing an AAV viral vector (e.g., a recombinant (r) AAV), the expression cassettes can be carried on any suitable vector, e.g., a plasmid, which is delivered to a packaging host cell. The plasmids useful in this invention may be engineered such that they are suitable for replication and packaging in vitro in prokaryotic cells, insect cells, mammalian cells, among others. Suitable transfection techniques and packaging host cells are known and/or can be readily designed by one of skill in the art.

Methods for generating and isolating AAVs suitable for use as vectors are known in the art. See generally, e.g., Grieger & Samulski, 2005, "Adeno-associated virus as a gene therapy vector: Vector development, production and clinical applications," *Adv. Biochem. Engin/Biotechnol.* 99:119-145; Buning et al., 2008, "Recent developments in adeno-associated virus vector technology," *J. Gene Med.* 10:717-733; and the references cited below, each of which is incorporated herein by reference in its entirety. For packaging a transgene into virions, the ITRs are the only AAV components required in cis in the same construct as the nucleic acid molecule containing the expression cassettes. The cap and rep genes can be supplied in trans.

In one embodiment, the expression cassettes described herein are engineered into a genetic element (e.g., a shuttle plasmid) which transfers the transgene construct sequences carried thereon into a packaging host cell for production a viral vector. In one embodiment, the selected genetic element may be delivered to an AAV packaging cell by any suitable method, including transfection, electroporation, liposome delivery, membrane fusion techniques, high velocity DNA-coated pellets, viral infection and protoplast fusion. Stable AAV packaging cells can also be made. Alternatively, the expression cassettes may be used to generate a viral vector other than AAV. The methods used to make such constructs are known to those with skill in nucleic acid manipulation and include genetic engineering, recombinant engineering, and synthetic techniques. See, e.g., Molecular Cloning: A Laboratory Manual, cd. Green and Sambrook, Cold Spring Harbor Press, Cold Spring Harbor, NY (2012).

The term "AAV intermediate" or "AAV vector intermediate" refers to an assembled rAAV capsid which lacks the desired genomic sequences packaged therein. These may also be termed an "empty" capsid. Such a capsid may contain no detectable genomic sequences of an expression cassette, or only partially packaged genomic sequences which are insufficient to achieve expression of the gene product. These empty capsids are non-functional to transfer the gene of interest to a host cell.

The recombinant adeno-associated virus (AAV) described herein may be generated using techniques which are known. See, e.g., WO 2003/042397; WO 2005/033321, WO 2006/110689; U.S. Pat. No. 7,588,772 B2. Such a method involves culturing a host cell which contains a nucleic acid sequence encoding an AAV capsid protein; a functional rep gene; an expression cassette composed of, at a minimum, AAV inverted terminal repeats (ITRs) and a transgene; and sufficient helper functions to permit packaging of the expression cassette into the AAV capsid protein. Methods of generating the capsid, coding sequences therefor, and methods for production of rAAV viral vectors have been described. See, e.g., Gao, et al, Proc. Natl. Acad. Sci. U.S.A. 100 (10), 6081-6086 (2003) and US 2013/0045186A1.

In one embodiment, a production cell culture useful for producing a recombinant AAV is provided. Such a cell culture contains a nucleic acid which expresses the AAV capsid protein in the host cell; a nucleic acid molecule suitable for packaging into the AAV capsid, e.g., a vector genome which contains AAV ITRs and a non-AAV nucleic acid sequence encoding a gene product operably linked to sequences which direct expression of the product in a host cell; and sufficient AAV rep functions and adenovirus helper functions to permit packaging of the nucleic acid molecule into the recombinant AAV capsid. In one embodiment, the cell culture is composed of mammalian cells (e.g., human embryonic kidney 293 cells, among others) or insect cells (e.g., baculovirus).

Optionally the rep functions are provided by an AAV other than the AAV providing the capsid. For example the rep may be, but is not limited to, AAV1 rep protein, AAV2 rep protein, AAV3 rep protein, AAV4 rep protein, AAV5 rep protein, AAV6 rep protein, AAV7 rep protein, AAV8 rep protein; or rep 78, rep 68, rep 52, rep 40, rep68/78 and rep40/52; or a fragment thereof; or another source. Optionally, the rep and cap sequences are on the same genetic element in the cell culture. There may be a spacer between the rep sequence and cap gene. Any of these AAV or mutant AAV capsid sequences may be under the control of exogenous regulatory control sequences which direct expression thereof in a host cell.

In one embodiment, cells are manufactured in a suitable cell culture (e.g., HEK 293) cells. Methods for manufacturing the gene therapy vectors described herein include methods well known in the art such as generation of plasmid DNA used for production of the gene therapy vectors, generation of the vectors, and purification of the vectors. In some embodiments, the gene therapy vector is an AAV vector and the plasmids generated are an AAV cis-plasmid encoding the vector genome including the gene of interest, an AAV trans-plasmid containing AAV rep and cap genes, and an adenovirus helper plasmid. The vector generation process can include method steps such as initiation of cell culture, passage of cells, seeding of cells, transfection of cells with the plasmid DNA, post-transfection medium exchange to serum free medium, and the harvest of vector-containing cells and culture media. The harvested vector-containing cells and culture media are referred to herein as crude cell harvest. In yet another system, the gene therapy vectors are introduced into insect cells by infection with baculovirus-based vectors. For reviews on these production systems, see generally, e.g., Zhang et al., 2009, "Adenovirus-adeno-associated virus hybrid for large-scale recombinant adeno-associated virus production," Human Gene Therapy 20:922-929, the contents of each of which is incorporated herein by reference in its entirety. Methods of making and using these and other AAV production systems are also described in the following U.S. patents, the contents of each of which is incorporated herein by reference in its entirety: U.S. Pat. Nos. 5,139,941; 5,741,683; 6,057,152; 6,204,059; 6,268,213; 6,491,907; 6,660,514; 6,951,753; 7,094,604; 7,172,893; 7,201,898; 7,229,823; and 7,439,065.

The crude cell harvest may thereafter be subject method steps such as concentration of the vector harvest, diafiltration of the vector harvest, microfluidization of the vector harvest, nuclease digestion of the vector harvest, filtration of microfluidized intermediate, crude purification by chromatography, crude purification by ultracentrifugation, buffer exchange by tangential flow filtration, and/or formulation and filtration to prepare bulk vector.

A two-step affinity chromatography purification at high salt concentration followed anion exchange resin chromatography are used to purify the vector drug product and to remove empty capsids. These methods are described in more detail in International Patent Publication No. WO 2017/160360, which is incorporated by reference herein. Purification methods for AAV8 Publication No. WO2017/100676, and rh10, International Patent Publication No. WO 2017/100704 and for AAV1, International Patent Publication No. WO 2017/100674, are all incorporated by reference herein.

To calculate empty and full particle content, VP3 band volumes for a selected sample (e.g., in examples herein an iodixanol gradient-purified preparation where # of GC=# of particles) are plotted against GC particles loaded. The resulting linear equation (y=mx+c) is used to calculate the number of particles in the band volumes of the test article peaks. The number of particles (pt) per 20 µL loaded is then multiplied by 50 to give particles (pt)/mL. Pt/mL divided by GC/mL gives the ratio of particles to genome copies (pt/GC). Pt/mL-GC/mL gives empty pt/mL. Empty pt/mL divided by pt/mL and ×100 gives the percentage of empty particles.

Generally, methods for assaying for empty capsids and AAV vector particles with packaged genomes have been known in the art. See, e.g., Grimm et al., *Gene Therapy* (1999) 6:1322-1330; Sommer et al., Molec. Ther. (2003) 7:122-128. To test for denatured capsid, the methods include subjecting the treated AAV stock to SDS-polyacrylamide gel electrophoresis, consisting of any gel capable of separating the three capsid proteins, for example, a gradient gel containing 3-8% Tris-acetate in the buffer, then running the gel until sample material is separated, and blotting the gel onto nylon or nitrocellulose membranes, preferably nylon. Anti-AAV capsid antibodies are then used as the primary antibodies that bind to denatured capsid proteins, preferably an anti-AAV capsid monoclonal antibody, most preferably the B1 anti-AAV-2 monoclonal antibody (Wobus et al., *J. Virol.* (2000) 74:9281-9293). A secondary antibody is then used, one that binds to the primary antibody and contains a means for detecting binding with the primary antibody, more preferably an anti-IgG antibody containing a detection molecule covalently bound to it, most preferably a sheep anti-mouse IgG antibody covalently linked to horseradish peroxidase. A method for detecting binding is used to semi-quantitatively determine binding between the primary and secondary antibodies, preferably a detection method capable of detecting radioactive isotope emissions, electromagnetic radiation, or colorimetric changes, most preferably a chemiluminescence detection kit. For example, for SDS-PAGE, samples from column fractions can be taken and heated in SDS-PAGE loading buffer containing reducing agent (e.g., DTT), and capsid proteins were resolved on pre-cast gradient polyacrylamide gels (e.g., Novex). Silver staining may be performed using SilverXpress (Invitrogen, CA) according to the manufacturer's instructions or other suitable staining method, i.e. SYPRO ruby or coomassie stains. In one embodiment, the concentration of AAV vector genomes (vg) in column fractions can be measured by quantitative real time PCR (Q-PCR). Samples are diluted and digested with DNase I (or another suitable nuclease) to remove exogenous DNA. After inactivation of the nuclease, the samples are further diluted and amplified using primers and a TaqMan™ fluorogenic probe specific for the DNA sequence between the primers. The number of cycles required to reach a defined level of fluorescence (threshold cycle, Ct) is measured for each sample on an Applied Biosystems Prism 7700 Sequence Detection System. Plasmid DNA containing identical sequences to that contained in the AAV vector is employed to generate a standard curve in the Q-PCR reaction. The cycle threshold (Ct) values obtained from the samples are used to determine vector genome titer by normalizing it to the Ct value of the plasmid standard curve. End-point assays based on the digital PCR can also be used.

In one aspect, an optimized q-PCR method is used which utilizes a broad spectrum serine protease, e.g., proteinase K (such as is commercially available from Qiagen). More particularly, the optimized qPCR genome titer assay is similar to a standard assay, except that after the DNase I digestion, samples are diluted with proteinase K buffer and treated with proteinase K followed by heat inactivation. Suitably samples are diluted with proteinase K buffer in an amount equal to the sample size. The proteinase K buffer may be concentrated to 2 fold or higher. Typically, proteinase K treatment is about 0.2 mg/mL, but may be varied from 0.1 mg/mL to about 1 mg/mL. The treatment step is generally conducted at about 55° C. for about 15 minutes, but may be performed at a lower temperature (e.g., about 37° C. to about 50° C.) over a longer time period (e.g., about 20 minutes to about 30 minutes), or a higher temperature (e.g., up to about 60° C.) for a shorter time period (e.g., about 5 to 10 minutes). Similarly, heat inactivation is generally at about 95° C. for about 15 minutes, but the temperature may be lowered (e.g., about 70 to about 90° C.) and the time extended (e.g., about 20 minutes to about 30 minutes). Samples are then diluted (e.g., 1000 fold) and subjected to TaqMan analysis as described in the standard assay.

Additionally, or alternatively, droplet digital PCR (ddPCR) may be used. For example, methods for determining single-stranded and self-complementary AAV vector genome titers by ddPCR have been described. See, e.g., M.

Lock et al, Hum Gene Ther Methods. 2014 April; 25 (2): 115-25. doi: 10.1089/hgtb.2013.131. Epub 2014 Feb. 14.

In brief, the method for separating rAAV particles having packaged genomic sequences from genome-deficient AAV intermediates involves subjecting a suspension comprising recombinant AAV viral particles and AAV capsid intermediates to fast performance liquid chromatography, wherein the AAV viral particles and AAV intermediates are bound to a strong anion exchange resin equilibrated at a high pH, and subjected to a salt gradient while monitoring eluate for ultraviolet absorbance at about 260 and about 280. The pH may be adjusted depending upon the AAV selected. See, e.g., WO2017/160360 (AAV9), WO2017/100704 (AAVrh10), WO 2017/100676 (e.g., AAV8), and WO 2017/100674 (AAV1)] which are incorporated by reference herein. In this method, the AAV full capsids are collected from a fraction which is eluted when the ratio of A260/A280 reaches an inflection point. In one example, for the Affinity Chromatography step, the diafiltered product may be applied to a Capture Select™ Poros-AAV2/9 affinity resin (Life Technologies) that efficiently captures the AAV2 serotype. Under these ionic conditions, a significant percentage of residual cellular DNA and proteins flow through the column, while AAV particles are efficiently captured.

III. Compositions and Uses

Provided herein are compositions containing at least one rAAV stock (e.g., an rAAV stock or a mutant rAAV stock) and an optional carrier, excipient and/or preservative. An rAAV stock refers to a plurality of rAAV vectors which are the same, e.g., such as in the amounts described below in the discussion of concentrations and dosage units.

As used herein, "carrier" includes any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Supplementary active ingredients can also be incorporated into the compositions. The phrase "pharmaceutically-acceptable" refers to molecular entities and compositions that do not produce an allergic or similar untoward reaction when administered to a host. Delivery vehicles such as liposomes, nanocapsules, microparticles, microspheres, lipid particles, vesicles, and the like, may be used for the introduction of the compositions of the present invention into suitable host cells. In particular, the rAAV vector delivered transgenes may be formulated for delivery either encapsulated in a lipid particle, a liposome, a vesicle, a nanosphere, or a nanoparticle or the like.

In one embodiment, a composition includes a final formulation suitable for delivery to a subject, e.g., is an aqueous liquid suspension buffered to a physiologically compatible pH and salt concentration. Optionally, one or more surfactants are present in the formulation. In another embodiment, the composition may be transported as a concentrate which is diluted for administration to a subject. In other embodiments, the composition may be lyophilized and reconstituted at the time of administration.

A suitable surfactant, or combination of surfactants, may be selected from among non-ionic surfactants that are non-toxic. In one embodiment, a difunctional block copolymer surfactant terminating in primary hydroxyl groups is selected, e.g., such as Pluronic® F68 [BASF], also known as Poloxamer 188, which has a neutral pH, has an average molecular weight of 8400. Other surfactants and other Poloxamers may be selected, i.e., nonionic triblock copolymers composed of a central hydrophobic chain of polyoxypropylene (poly(propylene oxide)) flanked by two hydrophilic chains of polyoxyethylene (poly(ethylene oxide)), SOLUTOL HS 15 (Macrogol-15 Hydroxystearate), LABRASOL (Polyoxy capryllic glyceride), polyoxy 10 oleyl ether, TWEEN (polyoxyethylene sorbitan fatty acid esters), ethanol and polyethylene glycol. In one embodiment, the formulation contains a poloxamer. These copolymers are commonly named with the letter "P" (for poloxamer) followed by three digits: the first two digits×100 give the approximate molecular mass of the polyoxypropylene core, and the last digit×10 gives the percentage polyoxyethylene content. In one embodiment Poloxamer 188 is selected. The surfactant may be present in an amount up to about 0.0005% to about 0.001% of the suspension.

The vectors are administered in sufficient amounts to transfect the cells and to provide sufficient levels of gene transfer and expression to provide a therapeutic benefit without undue adverse effects, or with medically acceptable physiological effects, which can be determined by those skilled in the medical arts. Conventional and pharmaceutically acceptable routes of administration include, but are not limited to, direct delivery to a desired organ (e.g., the liver (optionally via the hepatic artery), lung, heart, eye, kidney), oral, inhalation, intranasal, intrathecal, intratracheal, intraarterial, direct delivery to the eye (optionally via ocular delivery, subretinal injection, intra-retinal injection, intravitreal, topical), intravenous, intramuscular, subcutaneous, intradermal, and other parental routes of administration. In one embodiment, the route of administration is subretinal or intravitreal injection. Routes of administration may be combined, if desired.

Dosages of the viral vector will depend primarily on factors such as the condition being treated, the age, weight and health of the patient, and may thus vary among patients. For example, a therapeutically effective human dosage of the viral vector is generally in the range of from about 25 to about 1000 microliters to about 100 mL of solution containing concentrations of from about $1 \times 10^9$ to $1 \times 10^{16}$ genomes virus vector. The dosage will be adjusted to balance the therapeutic benefit against any side effects and such dosages may vary depending upon the therapeutic application for which the recombinant vector is employed. The levels of expression of the transgene can be monitored to determine the frequency of dosage resulting in viral vectors, preferably AAV vectors containing the minigene. Optionally, dosage regimens similar to those described for therapeutic purposes may be utilized for immunization using the compositions of the invention.

The replication-defective virus compositions can be formulated in dosage units to contain an amount of replication-defective virus that is in the range of about $1.0 \times 10^9$ GC to about $1.0 \times 10^{16}$ GC (to treat an average subject of 70 kg in body weight) including all integers or fractional amounts within the range, and preferably $1.0 \times 10^{12}$ GC to $1.0 \times 10^{14}$ GC for a human patient. In one embodiment, the compositions are formulated to contain at least $1 \times 10^9$, $2 \times 10^9$, $3 \times 10^9$, $4 \times 10^9$, $5 \times 10^9$, $6 \times 10^9$, $7 \times 10^9$, $8 \times 10^9$, or $9 \times 10^9$ GC per dose including all integers or fractional amounts within the range. In another embodiment, the compositions are formulated to contain at least $1 \times 10^{10}$, $2 \times 10^{10}$, $3 \times 10^{10}$, $4 \times 10^{10}$, $5 \times 10^{10}$, $6 \times 10^{10}$, $7 \times 10^{10}$, $8 \times 10^{10}$, or $9 \times 10^{10}$ GC per dose including all integers or fractional amounts within the range. In another embodiment, the compositions are formulated to contain at least $1 \times 10^{11}$, $2 \times 10^{11}$, $3 \times 10^{11}$, $4 \times 10^{11}$, $5 \times 10^{11}$, $6 \times 10^{11}$, $7 \times 10^{11}$, $8 \times 10^{11}$, or $9 \times 10^{11}$ GC per dose including all integers or fractional amounts within the range. In another embodiment, the compositions are formulated to contain at least $1 \times 10^{12}$, $2 \times 10^{12}$, $3 \times 10^{12}$, $4 \times 10^{12}$, $5 \times 10^{12}$, $6 \times 10^{12}$, $7 \times 10^{12}$, $8 \times 10^{12}$, or $9 \times 10^{12}$ GC per dose including all integers or fractional amounts within the range. In another embodiment, the compositions are formulated to contain at least $1 \times 10^{13}$, $2 \times 10^{13}$, $3 \times 10^{13}$, $4 \times 10^{13}$, $5 \times 10^{13}$, $6 \times 10^{13}$, $7 \times 10^{13}$, $8 \times 10^{13}$, or $9 \times 10^{13}$ GC per dose including all integers or fractional amounts within the range. In another embodiment, the compositions are formulated to contain at least $1 \times 10^{14}$, $2 \times 10^{14}$, $3 \times 10^{14}$, $4 \times 10^{14}$, $5 \times 10^{14}$, $6 \times 10^{14}$, $7 \times 10^{14}$, $8 \times 10^{14}$, or $9 \times 10^{14}$ GC per dose including all integers or fractional amounts within the range. In another embodiment, the compositions are formulated to contain at least $1 \times 10^{15}$, $2 \times 10^{15}$, $3 \times 10^{15}$, $4 \times 10^{15}$, $5 \times 10^{15}$, $6 \times 10^{15}$, $7 \times 10^{15}$, $8 \times 10^{15}$, or $9 \times 10^{15}$ GC per dose including all integers or fractional amounts within the range. In one embodiment, for human application the dose can range from $1 \times 10^{10}$ to about $1 \times 10^{12}$ GC per dose including all integers or fractional amounts within the range.

These above doses may be administered in a variety of volumes of carrier, excipient or buffer formulation, ranging from about 25 to about 1000 microliters, or higher volumes, including all numbers within the range, depending on the size of the area to be treated, the viral titer used, the route of administration, and the desired effect of the method. In one embodiment, the volume of carrier, excipient or buffer is at least about 25 µL. In one embodiment, the volume is about 50 µL. In another embodiment, the volume is about 75 µL. In another embodiment, the volume is about 100 µL. In another embodiment, the volume is about 125 µL. In another embodiment, the volume is about 150 µL. In another embodiment, the volume is about 175 µL. In yet another embodiment, the volume is about 200 µL. In another embodiment, the volume is about 225 µL. In yet another embodiment, the volume is about 250 µL. In yet another embodiment, the volume is about 275 µL. In yet another embodiment, the volume is about 300 µL. In yet another embodiment, the volume is about 325 µL. In another embodiment, the volume is about 350 µL. In another embodiment, the volume is about 375 µL. In another embodiment, the volume is about 400 µL. In another embodiment, the volume is about 450 µL. In another embodiment, the volume is about 500 µL. In another embodiment, the volume is about 550 µL. In another embodiment, the volume is about 600 µL. In another embodiment, the volume is about 650 µL. In another embodiment, the volume is about 700 µL. In another embodiment, the volume is between about 700 and 1000 µL.

In certain embodiments, the dose may be in the range of about $1 \times 10^9$ GC/g brain mass to about $1 \times 10^{12}$ GC/g brain mass. In certain embodiments, the dose may be in the range of about $3 \times 10^{10}$ GC/g brain mass to about $3 \times 10^{11}$ GC/g brain mass. In certain embodiments, the dose may be in the range of about $5 \times 10^{10}$ GC/g brain mass to about $1.85 \times 10^{11}$ GC/g brain mass.

In another aspect, an aqueous suspension suitable for administration to a subject is provided. In one embodiment, the suspension includes an aqueous suspending liquid and about $1 \times 10^9$ viral particles to about $1 \times 10^{13}$ GC or viral particles per eye of a recombinant adeno-associated virus (rAAV) as described herein useful as a therapeutic for the treatment or prevention of ocular diseases. In one embodiment, the suspension is suitable for subretinal or intravitreal injection.

In one embodiment, the viral constructs may be delivered in doses of from at least about least $1 \times 10^9$ GCs to about $1 \times 10^{15}$ GC, or about $1 \times 10^{11}$ GC to $5 \times 10^{13}$ GC. Suitable volumes for delivery of these doses and concentrations may be determined by one of skill in the art. For example, volumes of about 1 µL to 150 mL may be selected, with the higher volumes being selected for adults. Typically, for newborn infants a suitable volume is about 0.5 mL to about 10 mL, for older infants, about 0.5 mL to about 15 mL may be selected. For toddlers, a volume of about 0.5 mL to about 20 mL may be selected. For children, volumes of up to about 30 mL may be selected. For pre-teens and teens, volumes up to about 50 mL may be selected. In still other embodiments, a patient may receive an intrathecal administration in a volume of about 5 mL to about 15 mL are selected, or about 7.5 mL to about 10 mL. Other suitable volumes and dosages may be determined. The dosage will be adjusted to balance the therapeutic benefit against any side effects and such dosages may vary depending upon the therapeutic application for which the recombinant vector is employed.

The above-described recombinant vectors may be delivered to host cells according to published methods. The rAAV, preferably suspended in a physiologically compatible carrier, may be administered to a human or non-human mammalian patient. In certain embodiments, for administration to a human patient, the rAAV is suitably suspended in an aqueous solution containing saline, a surfactant, and a physiologically compatible salt or mixture of salts. Suitably, the formulation is adjusted to a physiologically acceptable pH, e.g., in the range of pH 6 to 9, or pH 6.5 to 7.5, pH 7.0 to 7.7, or pH 7.2 to 7.8. As the pH of the cerebrospinal fluid is about 7.28 to about 7.32, for intrathecal delivery, a pH within this range may be desired; whereas for intravenous, subretinal or intravitreal delivery, a pH of about 6.8 to about 7.2 may be desired. However, other pHs within the broadest ranges and these subranges may be selected for other route of delivery.

In another embodiment, the composition includes a carrier, diluent, excipient and/or adjuvant. Suitable carriers may be readily selected by one of skill in the art in view of the indication for which the transfer virus is directed. For example, one suitable carrier includes saline, which may be formulated with a variety of buffering solutions (e.g., phosphate buffered saline). Other exemplary carriers include sterile saline, lactose, sucrose, calcium phosphate, gelatin, dextran, agar, pectin, peanut oil, sesame oil, and water. The buffer/carrier should include a component that prevents the rAAV from sticking to the infusion tubing but does not interfere with the rAAV binding activity in vivo. A suitable surfactant, or combination of surfactants, may be selected from among non-ionic surfactants that are nontoxic. In one embodiment, a difunctional block copolymer surfactant terminating in primary hydroxyl groups is selected, e.g., such as Pluronic® F68 [BASF], also known as Poloxamer 188, which has a neutral pH, has an average molecular weight of 8400. Other surfactants and other Poloxamers may be selected, i.e., nonionic triblock copolymers composed of a central hydrophobic chain of polyoxypropylene (poly(propylene oxide)) flanked by two hydrophilic chains of polyoxyethylene (poly(ethylene oxide)), SOLUTOL HS 15 (Macrogol-15 Hydroxystearate), LABRASOL (Polyoxy capryllic glyceride), polyoxy-oleyl ether, TWEEN (polyoxyethylene sorbitan fatty acid esters), ethanol and polyethylene glycol. In one embodiment, the formulation contains a poloxamer. These copolymers are commonly named with the letter "P" (for poloxamer) followed by three digits: the first two digits×100 give the approximate molecular mass of the polyoxypropylene core, and the last digit×10 gives the percentage polyoxyethylene content. In one embodiment Poloxamer 188 is selected. The surfactant may be present in an amount up to about 0.0005% to about 0.001% of the suspension. In one example, the formulation may contain, e.g., buffered saline solution comprising one or more of sodium chloride, sodium bicarbonate, dextrose, magnesium sulfate (e.g., magnesium sulfate·7H$_2$O), potassium chloride, calcium chloride (e.g., calcium chloride·2H$_2$O), dibasic sodium phosphate, and mixtures thereof, in water. Suitably, for intrathecal delivery, the osmolarity is within a range compatible with cerebrospinal fluid (e.g., about 275 to about 290); see, e.g., emedicine_medscape_com/article/2093316-overview. Optionally, for intrathecal delivery, a commercially available diluent may be used as a suspending agent, or in combination with another suspending agent and other optional excipients. See, e.g., Elliotts B® solution [Lukare Medical]. In other embodiments, the formulation may contain one or more permeation enhancers. Examples of suitable permeation enhancers may include, e.g., mannitol, sodium glycocholate, sodium taurocholate, sodium deoxycholate, sodium salicylate, sodium caprylate, sodium caprate, sodium lauryl sulfate, polyoxyethylene-9-laurel ether, or EDTA.

Optionally, the compositions of the invention may contain, in addition to the rAAV and carrier(s), other conventional pharmaceutical ingredients, such as preservatives, or chemical stabilizers. Suitable exemplary preservatives include chlorobutanol, potassium sorbate, sorbic acid, sulfur dioxide, propyl gallate, the parabens, ethyl vanillin, glycerin, phenol, and parachlorophenol. Suitable chemical stabilizers include gelatin and albumin.

The compositions according to the present invention may comprise a pharmaceutically acceptable carrier, such as defined above. Suitably, the compositions described herein comprise an effective amount of one or more AAV suspended in a pharmaceutically suitable carrier and/or admixed with suitable excipients designed for delivery to the subject via injection, osmotic pump, intrathecal catheter, or for delivery by another device or route. In one example, the composition is formulated for intrathecal delivery.

As used herein, the terms "intrathecal delivery" or "intrathecal administration" refer to a route of administration for drugs via an injection into the spinal canal, more specifically into the subarachnoid space so that it reaches the cerebrospinal fluid (CSF). Intrathecal delivery may include lumbar puncture, intraventricular (including intracerebroventricular (ICV)), suboccipital/intracisternal, and/or C1-2 puncture. For example, material may be introduced for diffusion throughout the subarachnoid space by means of lumbar puncture. In another example, injection may be into the cisterna *magna*.

As used herein, the terms "intracisternal delivery" or "intracisternal administration" refer to a route of administration for drugs directly into the cerebrospinal fluid of the cisterna *magna* cerebellomedularis, more specifically via a suboccipital puncture or by direct injection into the cisterna *magna* or via permanently positioned tube.

In one aspect, the vectors provided herein may be administered intrathecally via the method and/or the device. See, e.g., WO 2017/181113, which is incorporated by reference herein. Alternatively, other devices and methods may be selected. The method comprises the steps of advancing a spinal needle into the cisterna *magna* of a patient, connecting a length of flexible tubing to a proximal hub of the spinal needle and an output port of a valve to a proximal end of the flexible tubing, and after said advancing and connecting steps and after permitting the tubing to be self-primed with the patient's cerebrospinal fluid, connecting a first vessel containing an amount of isotonic solution to a flush inlet port of the valve and thereafter connecting a second vessel containing an amount of a pharmaceutical composition to a vector inlet port of the valve. After connecting the first and second vessels to the valve, a path for fluid flow is opened between the vector inlet port and the outlet port of the valve and the pharmaceutical composition is injected into the patient through the spinal needle, and after injecting the pharmaceutical composition, a path for fluid flow is opened through the flush inlet port and the outlet port of the valve and the isotonic solution is injected into the spinal needle to flush the pharmaceutical composition into the patient.

This method and this device may each optionally be used for intrathecal delivery of the compositions provided herein. Alternatively, other methods and devices may be used for such intrathecal delivery.

It is to be noted that the term "a" or "an" refers to one or more. As such, the terms "a" (or "an"), "one or more," and "at least one" are used interchangeably herein.

The words "comprise", "comprises", and "comprising" are to be interpreted inclusively rather than exclusively. The words "consist", "consisting", and its variants, are to be interpreted exclusively, rather than inclusively. While various embodiments in the specification are presented using "comprising" language, under other circumstances, a related embodiment is also intended to be interpreted and described using "consisting of" or "consisting essentially of" language.

As used herein, the term "about" means a variability of 10% (+10%) from the reference given, unless otherwise specified.

As used herein, "disease", "disorder" and "condition" are used interchangeably, to indicate an abnormal state in a subject.

Unless defined otherwise in this specification, technical and scientific terms used herein have the same meaning as commonly understood by one of ordinary skill in the art and by reference to published texts, which provide one skilled in the art with a general guide to many of the terms used in the present application.

The term "expression" is used herein in its broadest meaning and comprises the production of RNA or of RNA and protein. With respect to RNA, the term "expression" or "translation" relates in particular to the production of peptides or proteins. Expression may be transient or may be stable.

As used herein, the term "NAb titer" a measurement of how much neutralizing antibody (e.g., anti-AAV Nab) is produced which neutralizes the physiologic effect of its targeted epitope (e.g., an AAV). Anti-AAV NAb titers may be measured as described in, e.g., Calcedo, R., et al., Worldwide Epidemiology of Neutralizing Antibodies to Adeno-Associated Viruses. Journal of Infectious Diseases, 2009. 199 (3): p. 381-390, which is incorporated by reference herein.

As used herein, an "expression cassette" refers to a nucleic acid molecule which comprises a coding sequence, promoter, and may include other regulatory sequences therefor, which cassette may be delivered via a genetic element (e.g., a plasmid) to a packaging host cell and packaged into the capsid of a viral vector (e.g., a viral particle). Typically, such an expression cassette for generating a viral vector contains the coding sequence for the gene product described herein flanked by packaging signals of the viral genome and other expression control sequences such as those described herein.

The abbreviation "sc" refers to self-complementary. "Self-complementary AAV" refers a construct in which a coding region carried by a recombinant AAV nucleic acid sequence has been designed to form an intra-molecular double-stranded DNA template. Upon infection, rather than waiting for cell mediated synthesis of the second strand, the two complementary halves of scAAV will associate to form one double stranded DNA (dsDNA) unit that is ready for immediate replication and transcription. See, e.g., D M McCarty et al, "Self-complementary recombinant adeno-associated virus (scAAV) vectors promote efficient transduction independently of DNA synthesis", Gene Therapy, (August 2001), Vol 8, Number 16, Pages 1248-1254. Self-complementary AAVs are described in, e.g., U.S. Pat. Nos. 6,596,535; 7,125,717; and 7,456,683, each of which is incorporated herein by reference in its entirety.

As used herein, the term "operably linked" refers to both expression control sequences that are contiguous with the gene of interest and expression control sequences that act in trans or at a distance to control the gene of interest.

The term "heterologous" when used with reference to a protein or a nucleic acid indicates that the protein or the nucleic acid comprises two or more sequences or subsequences which are not found in the same relationship to each other in nature. For instance, the nucleic acid is typically recombinantly produced, having two or more sequences from unrelated genes arranged to make a new functional nucleic acid. For example, in one embodiment, the nucleic acid has a promoter from one gene arranged to direct the expression of a coding sequence from a different gene. Thus, with reference to the coding sequence, the promoter is heterologous.

A "replication-defective virus" or "viral vector" refers to a synthetic or artificial viral particle in which an expression cassette containing a gene of interest is packaged in a viral capsid or envelope, where any viral genomic sequences also packaged within the viral capsid or envelope are replication-deficient; i.e., they cannot generate progeny virions but retain the ability to infect target cells. In one embodiment, the genome of the viral vector does not include genes encoding the enzymes required to replicate (the genome can be engineered to be "gutless"-containing only the transgene of interest flanked by the signals required for amplification and packaging of the artificial genome), but these genes may be supplied during production. Therefore, it is deemed safe for use in gene therapy since replication and infection by progeny virions cannot occur except in the presence of the viral enzyme required for replication.

In many instances, rAAV particles are referred to as DNase resistant. However, in addition to this endonuclease (DNase), other endo- and exo-nucleases may also be used in the purification steps described herein, to remove contaminating nucleic acids. Such nucleases may be selected to degrade single stranded DNA and/or double-stranded DNA, and RNA. Such steps may contain a single nuclease, or mixtures of nucleases directed to different targets, and may be endonucleases or exonucleases.

The term "nuclease-resistant" indicates that the AAV capsid has fully assembled around the expression cassette which is designed to deliver a transgene to a host cell and protects these packaged genomic sequences from degradation (digestion) during nuclease incubation steps designed to remove contaminating nucleic acids which may be present from the production process.

The term "translation" in the context of the present invention relates to a process at the ribosome, wherein an mRNA strand controls the assembly of an amino acid sequence to generate a protein or a peptide.

As used throughout this specification and the claims, the terms "comprising" and "including" are inclusive of other components, elements, integers, steps and the like. Conversely, the term "consisting" and its variants are exclusive of other components, elements, integers, steps and the like.

As described above, the term "about" when used to modify a numerical value means a variation of ±10%, unless otherwise specified.

The following examples are illustrative only and are not intended to limit the present invention.

EXAMPLES

The following examples report the extensive deamidation of AAV8 and additional diverse AAV serotypes, with supporting evidence from structural, biochemical, and mass spectrometry approaches. The extent of deamidation at each site was dependent on the age of the vector and multiple primary-sequence and 3D-structural factors, but was largely independent of the conditions of vector recovery and purification. We demonstrate the potential for deamidation to impact vector transduction activity, and correlate an early timepoint loss in vector activity to rapidly progressing, spontaneous deamidation at several AAV8 asparagines. We explore mutational strategies that stabilize side-chain amides, improving vector transduction and reducing the lot-to-lot molecular variability that is a key concern in biologics manufacturing. This study illustrates a previously unknown aspect of AAV capsid heterogeneity and highlights its importance in the development of these vectors for gene therapy.

In Example 1 the characterization of post-translational modifications to the AAV8 vector capsid by one- and two-dimensional gel electrophoresis, mass spectrometry, and de novo structural modeling. Following the identification of a number of putative deamidation sites on the capsid surface, we evaluate their impact on capsid structure and function both in vitro and in vivo. Example 1 further extends this analysis to AAV9 to determine if this phenomenon applies to serotypes other than AAV8, confirming that deamidation of the AAV capsid is not serotype specific. Examples 2-5 show deamidation in distinct AAVs.

Example 1: Deamidation of Amino Acids on the Surface of Adeno-Associated Virus Capsids A. Materials and Methods
1. 1D and 2D Gel Electrophoresis For ID SDS polyacrylamide gel electrophoresis (SDS-PAGE) analysis, we first denatured AAV vectors at 80° C. for 20 minutes in the presence of lithium dodecyl sulfate and reducing agent. Then, we ran them on a 4-12% Bis-Tris gel for 90 minutes at 200V and stained with Coomassie blue. For the data in FIG. 1A-FIG. 1D, Kendrick Laboratories, Inc. (Madison, WI) performed the 2D gel electrophoresis. For subsequent experiments, we performed 2D SDS-PAGE in-house. For this, we combined $3 \times 10^{11}$ GCs of AAV vector with 500U turbonuclease marker (Accelagen, San Diego, CA) in 150 μL phosphate buffered saline (PBS) with 35 mM NaCl and 1 mM MgCl2 and incubated at 37° C. for ten minutes. We next added nine volumes of absolute ethanol, vortexed the samples, and incubated them at −80° C. for at least two hours followed by incubation on ice for five minutes and centrifugation at maximum speed for 30 minutes at 15° C. We decanted the supernatant and air-dried the pellet, which we then resuspended in resuspension buffer #1 [0.15% SDS, 50 mM dithiothreitol (DTT), 10 mM Tris pH 7.5, and 1 μL pH6-9 ampholytes, ThermoFisher ZM0023, added day-of, in ddH$_2$O] and incubated undisturbed at room temperature. After 30 minutes, we flicked the sample tubes to mix them, added 1µg chicken conalbumin marker (Sigma Aldrich, St. Louis, MO), and incubated the samples at 37° C. for 30 minutes, flicking to mix at 15 minutes. Samples were then transferred to 50° C. for 15-20 minutes, vortexed, incubated at 95° C. for 2.5 minutes, and allowed to cool before being centrifuged at maximum speed for one minute and briefly vortexed. We then mixed 10 µL of each sample with 140 µL resuspension buffer #2 (9.7M urea, 2% CHAPS, 0.002% bromophenol blue, and 0.05% ampholytes, described above, added day-of, in $ddH_2O$) and incubated at room temperature for ten minutes. We then applied the mixtures to pH 6-10 immobilized pH gradient (IPG) strips (ThermoFisher Waltham, MA) and ran them on the ZOOM IPGRunner system according to manufacturer's instructions. We used the following isoelectric focusing parameters: 100-1,000V for 120 minutes, 1,000-2,000V for 120 minutes, 2,000V for 120 minutes, limits of 0.1W and 0.05 mA per strip run. IPG strips were then reduced and loaded in a single-well 4-12% Bis-Tris gel and run in 1D as described above. We determined the relative migration of AAV VPs by comparison to internal control proteins turbonuclease (Accelagen, 27 kDa) and chicken egg white conalbumin (Sigma Aldrich, 76 kDa, pI 6.0-6.6).

2. Vector Production

The University of Pennsylvania Vector Core produced recombinant AAV vectors for 1D and 2D gel electrophoresis and mass spectrometry experiments and purified them by cesium chloride or iodixanol gradients as previously described. (Lock M, et al. *Hum Gene Ther* 2010; 21 (10): 1259-71; Gao G P, et al. *Proc Natl Acad Sci USA*. 2002; 99 (18): 11854-9). We produced the affinity purified vectors as follows: We grew HEK293 cells in ten 36-layer hyperstack vessels (Corning), co-transfected them with a mixture of vector genome plasmid (pAAV-LSP-IVS2.hFIXco-WPRE-bGH), trans plasmid containing AAV2 rep and AAV8 cap genes, and adenovirus helper plasmid. We used PEIpro (PolyPlus) as the transfection reagent. Five days post transfection, the supernatant was harvested, clarified through Sartoguard PES Midicap filters (Sartorious Stedim), and treated with benzonase (Millipore), after which we added salt to bring it to 0.6M. The clarified bulk harvest material was concentrated ten-fold by tangential flow filtration (TFF) and then diafiltered against four volumes of affinity column loading buffer. We captured vectors on a POROS CaptureSelect (ThermoFisher) affinity column and eluted the vector peak at low pH directly into neutralization buffer. We diluted the neutralized eluate into a high-pH binding buffer and loaded it onto an anion exchange polishing column (Cimultus QA-8; Bia Separations), where the preparation was enriched for genome-containing (full) particles. The full vector particles were eluted with a shallow salt elution gradient and neutralized immediately. Finally, we subjected the vector to a second round of TFF for final concentration and buffer exchange into formulation buffer (PBS+0.001% pluronic F-68).

We produced mutant vectors for in vitro assays by small-scale triple transfection of HEK293 cells in six-well plates. We mixed 5.6 µL of a 1 mg/ml polyethylenimine solution in 90 µL serum-free media with plasmid DNA (0.091 µg cis plasmid, 0.91 µg trans plasmid, 1.82 µg deltaF6 Ad-helper plasmid, in 90 µL serum-free media), incubated it at room temperature for 15 minutes, and added it to cells in and additional 0.8 mL of fresh serum-free media. The next day, we replaced 0.5 mL of the top media with full serum media. We harvested vector three days post-transfection by three freeze/thaw cycles followed by centrifugation to remove cell debris and supernatant harvest. Cis plasmid contained a transgene cassette encoding the firefly luciferase transgene under the control of the chicken-beta actin (CB7) promoter with the Promega chimeric intron and rabbit beta-globin (RBG) polyadenylation signal. Trans plasmid encoded the wtAAV8 cap gene; to generate mutant AAV8 cap variants, we used the Quikchange Lightning Mutagenesis kit (Agilent Technologies, Wilmington, DE). Vector was titered as previously described. (Lock M, et al. *Hum Gene Ther* 2010; 21 (10): 1259-71).

For timecourse vector production experiments, we generated vector by medium-scale triple transfection of HEK293 cells in 15 cm tissue culture dishes. Per plate, we mixed 36 µL of a 1 mg/mL polyethylenimine solution in 2 mL serum-free media with plasmid DNA (0.6 µg cis plasmid, 5.8 µg trans plasmid, 11.6 µg deltaF6 Ad-helper plasmid), incubated it at room temperature for 15 minutes, and added it to cells at approximately 60% confluency on plates refreshed with 14 ml of serum-free media. The following day, we replaced 8 ml of the top media with fresh, full serum media. We harvested vector by collecting all top media, scraping cells from the dish and freezing this at −80° C. We recovered crude vector from the supernatant/cell mixture by applying 3 freeze/thaw cycles, and clarifying the lysate by centrifugation. We purified and concentrated the vector for mass spectrometry analysis by adding benzonase, 1M Tris pH7.5, and 5M NaCl to the clarified lysate to final concentrations of 20 mM Tris and 360 mM NaCl. We captured vectors on a 1 ml POROS CaptureSelect affinity column and eluted the vector peak at low pH directly into neutralization buffer. Fractions were analysed by absorbance at 280 nm, and the most concentrated fraction was subjected to mass spectrometry analysis.

For in vivo experiments, we produced vectors as previously described with a wtAAV8 capsid or with one of the 6 deamidation mutants; the transgene cassette included a CB7 promoter, PI intron, firefly luciferase transgene, and RBG polyadenylation signal (Lock M, et al. *Hum Gene Ther* 2010; 21 (10): 1259-71).

3. Mass Spec Run/Digest/Analysis

Materials: We purchased ammonium bicarbonate, DTT, iodoacetamide (IAM), and 18O-enriched water (97.1% purity) from Sigma (St. Louis, MO); and acetonitrile, formic acid, trifluoroacetic acid (TFA), 8M guanidine hydrochloride (GndHCl), and trypsin from Thermo Fischer Scientific (Rockford, IL).

Trypsin digestion: We prepared stock solutions of 1M DTT and 1.0M iodoacetamide. Capsid proteins were denatured and reduced at 90° C. for ten minutes in the presence of 10 mM DTT and 2M GndHCl. We allowed the samples to cool to room temperature and then alkylated them with 30 mM IAM at room temperature for 30 minutes in the dark. We quenched the alkylation reaction with the addition of 1 mL DTT. We added 20 mM ammonium bicarbonate (pH 7.5-8) to the denatured protein solution at a volume that diluted the final GndHCl concentration to 200 mM. We added trypsin solution for a 1:20 trypsin to protein ratio and incubated at 37° C. overnight. After digestion, we added TFA to a final concentration of 0.5% to quench the digestion reaction.

For 18O-water experiments, the capsid sample was first buffer exchanged into 100 mM ammonium bicarbonate prepared in 18O-water using Zeba spin desalting columns (Thermo Scientific, Rockford, IL). To ensure a complete removal of the water in the sample, we performed the buffer exchange twice. We prepared stock solutions of 1M DTT and 1M IAM in 18O-water. We followed the same denaturation, alkylation, and digestion steps as above with 18O-water reagents and buffers.

Liquid chromatography tandem-mass spectrometry: We performed online chromatography with an Acclaim PepMap column (15 cm long, 300 µm inner diameter) and a Thermo UltiMate 3000 RSLC system (Thermo Fisher Scientific) coupled to a Q Exactive HF with a NanoFlex source (Thermo Fisher Scientific). During online analysis, the column temperature was maintained at a temperature of 35° C. We separated peptides with a gradient of mobile phase A (MilliQ water with 0.1% formic acid) and mobile phase B (acetonitrile with 0.1% formic acid). We ran the gradient from 4% B to 6% B over 15 minutes, to 10% B for 25 minutes (40 minutes total), and then to 30% B for 46 minutes (86 minutes total). We loaded the samples directly to the column. The column size was 75 cm×15 um I.D. and was packed with 2 micron C18 media (Acclaim PepMap). Due to the loading, lead-in, and washing steps, the total time for each liquid chromatography tandem-mass spectrometry run was about two hours.

We acquired mass spectrometry data using a data-dependent top-20 method on the Q Exactive HF mass spectrometer, dynamically choosing the most abundant not-yet-sequenced precursor ions from the survey scans (200-2000 m/z). We performed sequencing via higher energy collisional dissociation fragmentation with a target value of 1e5 ions determined with predictive automatic gain control; we performed isolation of precursors with a window of 4m/z. We acquired survey scans at a resolution of 120,000 at 200m/z. We set the resolution for HCD spectra to 30,000 at m/z200 with a maximum ion injection time of 50 ms and a normalized collision energy of 30. We set the S-lens RF level to 50, which gave optimal transmission of the m/z region occupied by the peptides from our digest. We excluded precursor ions with single, unassigned, or six and higher charge states from fragmentation selection.

Data processing: We used BioPharma Finder 1.0 software (Thermo Fischer Scientific) to analyze all data acquired. For peptide mapping, we performed searches using a single-entry protein FASTA database with carbamidomethylation set as a fixed modification, and oxidation, deamidation, and phosphorylation set as variable modifications. We used a 10 ppm mass accuracy, a high protease specificity, and a confidence level of 0.8 for tandem-mass spectrometry spectra. Mass spectrometric identification of deamidated peptides is relatively straightforward, as deamidation adds to the mass of intact molecule +0.984 Da (the mass difference between —OH and —NH2 groups). We determined the percent deamidation of a particular peptide by dividing the mass area of the deamidated peptide by the sum of the area of the deamidated and native peptides. Considering the number of possible deamidation sites, isobaric species that are deamidated at different sites may co-migrate at a single peak. Consequently, fragment ions originating from peptides with multiple potential deamidation sites can be used to locate or differentiate multiple sites of deamidation. In these cases, the relative intensities within the observed isotope patterns can be used to specifically determine the relative abundance of the different deamidated peptide isomers. This method assumes that the fragmentation efficiency for all isomeric species is the same and independent of the site of deamidation. This approach allows the definition of the specific sites involved in deamidation and the potential combinations involved in deamidation.

Secondary data processing: Secondary analysis of raw mass spectrometry was performed at the University of Maryland, Baltimore County using the following method. Peaks Studio v5.3 software (Bioinformatics Solutions Inc.) was used for all mass spectrometry analysis. Data refinement of the raw data files was performed with the following parameters: a precursor m/z tolerance of ≤10 ppm, and precursor charge state with a minimum of 2, maximum of 4. De novo sequencing of the input spectrum was performed using the Peaks algorithm with a precursor ion error tolerance of 10 ppm and product ion error tolerances of 0.1 Da. The digestion enzyme was set as trypsin, the variable modifications were oxidation, phosphorylation, and deamidation, and the fixed modification was carbamidomethylation of cysteine.

4. Structural Analysis of the AAV Capsid

We obtained the AAV8 atomic coordinates, structural factors, and associated capsid model from the RCSB Protein Data Bank (PDB ID: 3RA8). We performed structure refinement and generated an electron density independent of the primary amino acid sequence of AAV8 VP3 for use in three-dimensional (3D)) structural analysis of the capsid. We performed this analysis in order to observe the isoaspartic acid electron density in the AAV8 capsid that was not biased by the expected primary sequence of AAV8 VP3. Using the resulting structure, we modeled the four asparagines in the AAV8 VP3 primary sequence with N+1 glycines as isoaspartic acids and then refined the AAV8 capsid structure using Crystallography and NMR System (CNS) software by strictly imposing the icosahedral non-crystallographic matrices using the standard refinement protocol (Brunger A T, et al. *Acta Crystallogr D Biol Crystallogr* 1998; 54 (Pt 5): 905-21). We obtained a structural model of isoaspartic acid from the HIC-UP database, followed by generation of a molecular dictionary in PRODRG for structure refinement (Kleywegt G J *Acta Crystallogr D Biol Crystallogr* 2007; 63 (Pt 1): 94-100). We then calculated the average electron density map of the AAV8 capsid (also in CNS) and visualized it using COOT software, followed by minor adjustments of the resulting model to fit the modeled isoaspartic acid residues into the electron density map (Emsley P and Cowtan K *Acta Crystallogr D Biol Crystallogr* 2004; 60 (Pt 12 Pt 1): 2126-32). We repeated this protocol to additionally model N512 in the AAV9 VP3 primary sequence with N+1 glycines (PDB ID: 3UX1). We generated all figures using COOT, PyMol, and UCSF Chimera (Emsley P and Cowtan K *Acta Crystallogr D Biol Crystallogr* 2004; 60 (Pt 12 Pt 1): 2126-32; DeLano W L *PyMOL: An Open-Source Molecular Graphics Tool* Vol. 40, 2002:82-92; Pettersen E F, et al. *J Comput Chem* 2004; 25 (13): 1605-12). We obtained a number of structures of previously identified deamidated proteins (PDB IDs: 1DY5, 4E7G, 1RTU, 1W9V, 4E7D, and 1C9D) for comparison of their electron density map for deamidated isoaspartic acid residues with our modeled isoaspartic acid residues from AAV8 and AAV9 (Rao F V, et al. *Chem Biol* 2005; 12 (1): 65-76; Noguchi S, et al. *Biochemistry* 1995; 34 (47): 15583-91; Esposito L, et al. *J Mol Biol* 2000; 297 (3): 713-32).

We determined temperature factors for deamidated residues by averaging the temperature factors for each atom of each asparagine residue reported in the AAV8 or AAV9 crystal structure atomic coordinates (PDB ID: 3RA8, 3UX1).

5. Animal Studies

The Institutional Animal Care and Use Committee of the University of Pennsylvania approved all animal procedures. To evaluate vector performance, we injected eight-week-old C57BL/6 mice intravenously via tail vein injection with 3e10 GCs of wtAAV8 or capsid mutant vector in a volume of 100 μL. All mice were sacrificed at day 14. For in vivo evaluation of luciferase expression, mice (~20g) were anesthetized and injected intraperitoneally with 200 μL or 15 mg/mL luciferin substrate (Perkin Elmer, Waltham, MA). Mice were imaged five minutes after luciferin administration and imaged via an IVIS Xenogen In Vivo Imaging System. We used Living Image 3.0 software to quantify signal in the described regions of interest. We took measurements at days 7 and 14.

6. Evaluation of Mutant Vector Titer and In Vitro Transduction Efficiency

We determined vector titers by qPCR of the DNAseI-resistant genomes. The qPCR primers anneal to the polyadenylation sequence of the packaged transgene. For in vitro evaluation of vector transduction efficiency by luciferase expression, we seeded 0.9e5 Huh7 cells/well in a black-walled 96-well plate in complete DMEM (10% fetal bovine serum, 1% penicillin/streptomycin). The next day, we removed the media and replaced it with 50 μL crude or purified vector diluted in complete media. We tested 4 dilutions in a 3 fold dilution series for each crude vector sample. After 48 hours, we prepared luciferin (Promega, Madison, WI) in complete media at 0.3 μg/uL and added it to transduced cells in a volume of 50 μL. Results were read on a Biotek Clarity luminometer. We find that luciferase activity/GC added to target cells is constant over a wide range of GCs, but can become saturated at high MOIs. Thus we inspect the dilution series data (luminescent units vs GC) for linearity, exclude the highest point if saturation is evident, and calculate an average Luciferase/GC for values in the linear range of each assay for each variant. This yields a transduction efficiency value. The data are normalized to simplify comparison by setting the wt control to a value of 1.

7. Biodistribution

We extracted DNA from liver samples using the QIAamp DNA Mini Kit (Qiagen, Hilden, Germany), and then analyzed the DNA for vector GC by real-time PCR as described previously with a primer/probe set designed against the RBG polyadenylation signal of the transgene cassette (Chen S J, et al. *Hum Gene Ther Clin Dev* 2013; 24 (4): 154-60).

Primer Sequences for AAV8 Mutants

| | Sequence | Description |
|---|---|---|
| SED ID NO: 56 | CGACAACCGGGCAAAACcagAATAGCAACTTTGCCTGG | QC mutagenic primers to change AAV8 N499 to Q |
| SED ID NO: 57 | CCAGGCAAAGTTGCTATTCTGGTTTTGCCCGGTTGTCG | QC mutagenic primers to change AAV8 N499 to Q |
| SED ID NO: 58 | GACAACCGGGCAAAACgacAATAGCAACTTTGCCTG | QC mutagenic primers to change AAV8 N499 to D |
| SED ID NO: 59 | CAGGCAAAGTTGCTATTGTCGTTTTGCCCGGTTGTC | QC mutagenic primers to change AAV8 N499 to D |
| SED ID NO: 60 | GGAGGCACGGCAcagACGCAGACTCTGGG | qc mutagenic primers to change AAV8 N459 to Q |
| SED ID NO: 61 | CCCAGAGTCTGCGTCTGTGCCGTGCCTCC | qc mutagenic primers to change AAV8 N459 to Q |
| SED ID NO: 62 | CAGGAGGCACGGCAgatACGCAGACTCTGG | qc mutagenic primers to change AAV8 N459 to D |
| SED ID NO: 63 | CCAGAGTCTGCGTATCTGCCGTGCCTCCTG | qc mutagenic primers to change AAV8 N459 to D |
| SED ID NO: 64 | ctcctcccgatgtcgcgttggagatttgc | AAV8 NA263 F |
| SED ID NO: 65 | gcaaatctccaacgcgacatcgggaggag | AAV8 NA263 R |
| SED ID NO: 66 | cccacgcctgactagcgttgttgagtgtta | AAV8 NA385 F |
| SED ID NO: 67 | taacactcaacaacgctagtcaggccgtggg | AAV8 NA385 R |
| SED ID NO: 68 | ggattagccaatgaatttcttgcattcagatggtatttggtcc | AAV8 NA514 F |
| SED ID NO: 69 | ggaccaaataccatctgaatgcaagaaattcattggctaatcc | AAV8 NA514 R |
| SED ID NO: 70 | tttgccaaaaatcaggatcgcgttactgggaaaaaaacg | AAV8 NA540 F |
| SED ID NO: 71 | cgttttttcccagtaacgcgatcctgattttttggcaaa | AAV8 NA540 R |
| SED ID NO: 72 | ggacccttcaacgcactcgacaagggg | AAV8 NA57 F |
| SED ID NO: 73 | cccccttgtcgagtgcgttgaagggtcc | AAV8 NA57 R |
| SED ID NO: 74 | tggctcctcccgatgtgctgttggagatttgcttg | AAV8 N5263 F |
| SED ID NO: 75 | caagcaaatctccaacagcacatcgggaggagcca | AAV8 NS263 R |
| SED ID NO: 76 | cccacgcctgactactgttgttgagtgttagg | AAV8 NS385 F |
| SED ID NO: 77 | cctaacactcaacaacagtagtcaggccgtggg | AAV8 NS385 R |

-continued

| | Sequence | Description |
|---|---|---|
| SED ID NO: 78 | ttagccaatgaatttctgctattcagatggtatttggtcccagcag | AAV8 NS514 F |
| SED ID NO: 79 | ctgctgggaccaaataccatctgaatagcagaaattcattggctaa | AAV8 NS514 R |
| SED ID NO: 80 | ttgtttgccaaaaatcaggatgctgttactgggaaaaaaacgctc | AAV8 NS540 F |
| SED ID NO: 81 | gagcgttttttttcccagtaacagcatcctgattttttggcaaacaa | AAV8 NS540 R |
| SED ID NO: 82 | ctccccccttgtcgaggctgttgaagggtccgag | AAV8 NS57 F |
| SED ID NO: 83 | ctcggacccttcaacagcctcgacaaggggag | AAV8 NS57 R |
| SED ID NO: 84 | cagcgactcatcaacGACaactggggattccg | QC primer for AAV8 N305D |
| SED ID NO: 85 | ggaggcacggcaGATacgcagactctgg | QC primer for AAV8 N459D |
| SED ID NO: 86 | gacaaccgggcaaaaacGACaatagcaactttgcctg | QC primer for AAV8 N499D |
| SED ID NO: 87 | ccatctgaatggaagaGATtcattggctaatcctggcatc | QC primer for AAV8 N517D |
| SED ID NO: 88 | cgaagcccaaagccGACcagcaaaagcagg | QC primer for AAV8 N35D |
| SED ID NO: 89 | gtacctgcggtatGACcacgccgacgcc | QC primer for AAV8 N94D |
| SED ID NO: 90 | gatgctgagaaccggcGACaacttccagtttacttac | QC primer for AAV8 N410D |
| SED ID NO: 91 | cagactctgggcttcagcGATggtgggcctaatacaatg | QC primer for AAV8 Q467D |
| SED ID NO: 92 | ccaatcaggcaaagGACtggctgccaggac | QC primer for AAV8 N479D |
| SED ID NO: 93 | cacggacggcGACttccacccgtctc | QC primer for AAV8 N630D |
| SED ID NO: 94 | gatcctgatcaagGACacgcctgtacctgcg | QC primer for AAV8 N653D |
| SED ID NO: 95 | gtacctcggacccttcCAGggactcgacaaggg | QC primer for AAV8 N57Q |
| SED ID NO: 96 | ctacaagcaaatctccCAGgggacatcgggaggagc | QC primer for AAV8 N263Q |
| SED ID NO: 97 | gctacctaacactcaacCAGggtagtcaggccgtgg | QC primer for AAV8 N385Q |
| SED ID NO: 98 | gctgggaccaaataccatctgCAGggaagaaattcattggc | QC primer for AAV8 N514Q |
| SED ID NO: 99 | ggagcgttttttttcccagtCAGgggatcctgattttttggc | QC primer for AAV8 N540Q |
| SED ID NO: 100 | cggaatccccagttgtcgttgatgagtcgctg | QC primer for AAV8 N305D |
| SED ID NO: 101 | ccagagtctgcgtatctgccgtgcctcc | QC primer for AAV8 N459D |
| SED ID NO: 102 | caggcaaagttgctattgtcgttttgccggttgtc | QC primer for AAV8 N499D |
| SED ID NO: 103 | gatgccaggattagccaatgaatctcttccattcagatgg | QC primer for AAV8 N517D |
| SED ID NO: 104 | cctgcttttgctggtcggctttgggcttcg | QC primer for AAV8 N35D |
| SED ID NO: 105 | ggcgtcggcgtggtcataccgcaggtac | QC primer for AAV8 N94D |
| SED ID NO: 106 | gtaagtaaactggaagttgtcgccggttctcagcatc | QC primer for AAV8 N410D |
| SED ID NO: 107 | cattgtattaggcccaccatcgctgaagcccagagtctg | QC primer for AAV8 Q467D |
| SED ID NO: 108 | gtcctggcagccagtcctttgcctgattgg | QC primer for AAV8 N479D |
| SED ID NO: 109 | gagacgggtggaagtcgccgtccgtg | QC primer for AAV8 N630D |
| SED ID NO: 110 | cgcaggtacaggcgtgtccttgatcaggatc | QC primer for AAV8 N653D |
| SED ID NO: 111 | gcagcgactcatcaacGACaactggggattccggc | alternative longer primer to make AAV8 N305D by qc mutagenesis |
| SED ID NO: 112 | GCCGGAATCCCCAGTTGTCGTTGATGAGTCGCTGC | alternative longer primer to make AAV8 N305D by qc mutagenesis |
| SED ID NO: 113 | cagcgactcatcaacGACaactggggattccggc | alternative longer primer to make AAV8 N305D by qc mutagenesis |

-continued

| Sequence | | Description |
|---|---|---|
| SED ID NO: 114 | GCCGGAATCCCCAGTTGTCGTTGATGAGTCGCTG | alternative longer primer to make AAV8 N305D by qc mutagenesis |
| SED ID NO: 115 | gcgactcatcaacGACaactggggattccg | alternative shorter primer to make AAV8 N305D by qc mutagenesis |
| SED ID NO: 116 | CGGAATCCCCAGTTGTCGTTGATGAGTCGC | alternative shorter primer to make AAV8 N305D by qc mutagenesis |
| SED ID NO: 117 | ctctgggcttcagcGAAggtgggcctaatac | mutagenic QC primer to make AAV8 Q467E |
| SED ID NO: 118 | GTATTAGGCCCACCTTCGCTGAAGCCCAGAG | mutagenic QC primer to make AAV8 Q467E |
| SED ID NO: 119 | cctcggaccttcGACggactcgacaagg | QC primer for AAV8 N57D |
| SED ID NO: 120 | tacaagcaaatctccGACgggacatcgggaggag | QC primer for AAV8 N263D |
| SED ID NO: 121 | ctacctaacactcaacGACggtagtcaggccgtg | QC primer for AAV8 N385D |
| SED ID NO: 122 | ctgggaccaaataccatctgGATggaagaaattcattggctaatc | QC primer for AAV8 N514D |
| SED ID NO: 123 | gagcgttttttcccagtGACgggatcctgattttttggc | QC primer for AAV8 N540D |
| SED ID NO: 124 | ccttgtcgagtccgtcgaagggtccgagg | QC primer for AAV8 N57D |
| SED ID NO: 125 | ctcctcccgatgtcccgtcggagatttgcttgta | QC primer for AAV8 N263D |
| SED ID NO: 126 | cacggcctgactaccgtcgttgagtgttaggtag | QC primer for AAV8 N385D |
| SED ID NO: 127 | gattagccaatgaatttcttccatccagatggtatttggtcccag | QC primer for AAV8 N514D |
| SED ID NO: 128 | gccaaaaatcaggatcccgtcactgggaaaaaaacgctc | QC primer for AAV8 N540D |

B. Results

AAV8 Shows Substantial Charge Heterogeneity in its Capsid Proteins

To qualitatively assess the presence of post-translational modifications on the AAV8 vector capsid that could affect vector performance, we analyzed AAV8 total capsid protein purified by iodixanol gradient both by 1D and 2D gel electrophoresis. In a 1D reducing sodium dodecyl sulfate SDS gel, VP1, VP2, and VP3 resolved as single bands at the appropriate molecular weights (FIG. 1B) (Rose J A, et al. *J Virol* 1971; 8 (5): 766-70). When further evaluated by 2D gel electrophoresis, which separates proteins based on charge (FIG. 1C), each of the capsid proteins additionally resolved as a series of distinct spots with different isoelectric points (pIs) ranging from pH 6.3 to >7.0 dependent on the VP isoform (FIG. 1D). Individual spots on each VP were separated by discrete intervals of 0.1 pI units as measured as migration relative to the carbonic anhydrase isoform internal isoelectric point standards, suggesting a single residue charge change. The presence of these isoforms suggests that each VP has the potential to undergo many modifications, thereby causing them to migrate differently under isoelectric focusing.

Deamidation, in which a fraction of (typically asparagine) side-chain amide groups are converted to carboxylic acid (FIG. 1A), is a common source of charge heterogeneity in protein preparations. To determine if deamidation could be responsible for the distinct population of VP charge isoforms, we mutated two AAV8 asparagine residues individually to aspartate. These capsid mutations should shift the charge by an amount equivalent to the complete deamidation of a single additional asparagine residue. 2D gel analysis of the mutants indicates the major spots for VP1, VP2, and VP3 shifted one spot location more acidic (0.1 pH units) than the equivalent spots in wild-type (wt) AAV8 (FIG. 1E-FIG. 1G). The magnitude of this shift is equivalent to the observed spacing between the wt VP charge isoforms. Thus, the 2D gel patterning of AAV capsid proteins is consistent with multi-site deamidation.

Spontaneous Deamidation Occurs on the AAV8 Vector Capsid

To identify modifications responsible for the discrete spotting pattern for each capsid protein, we analyzed a panel of AAV8 vectors by mass spectrometry. Coverage of the AAV8 capsid protein averaged >95% of the total VP1 sequence (data not shown). We detected extensive deamidation of a subset of asparagine and glutamine residues by mass spectroscopy, which showed an increase of ~1 Da in the observed mass of the individual peptides as compared to predicted values based on the sequence encoded by the DNA; we observed this pattern of deamidation in all preparations of AAV8 vectors (FIG. 2A-FIG. 2D).

To evaluate the global heterogeneity of deamidation between commonly used purification methods and to examine deamidation in the VP1 and VP2 unique regions, we selected nine lots of AAV8 produced by triple transfection in 293 cells and purified them by either cesium chloride gradient, iodixanol gradient, or affinity chromatography. Vectors also varied with respect to promoters and transgene cassettes. To determine if the presence of the vector genome had an impact on deamidation, we also evaluated an AAV8 prep produced by triple transfection in 293 cells in the absence of cis plasmid (producing empty capsids only) and purified by iodixanol gradient.

Figure 2E:
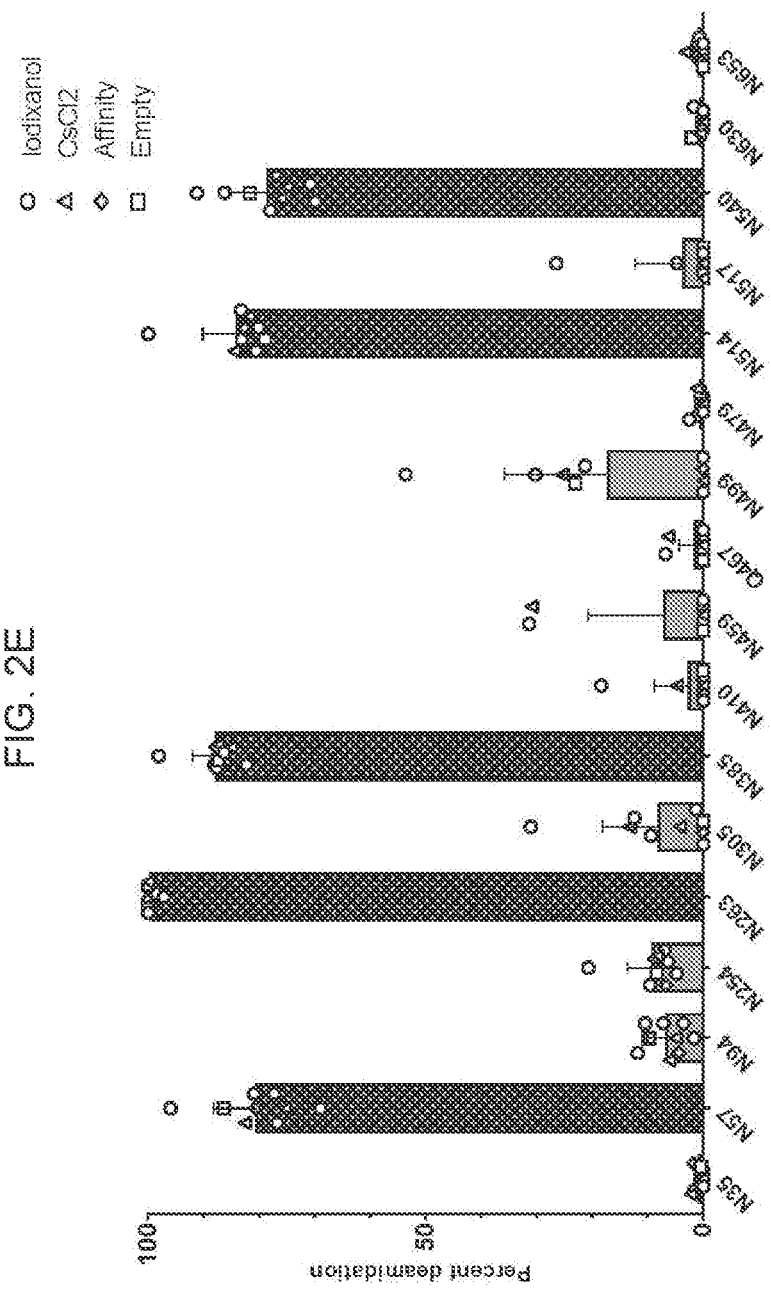

A wide range of deamidation was present across asparagine and glutamine residues of the AAV8 capsid, ranging from undetectable to over 99% of individual amino acids being deamidated (FIG. 2E). The highest levels of deamidation (>75%) occurred at asparagine residues where the N+1 residue was glycine (i.e., NG pairs) (Table 1). We detected lower levels of deamidation (i.e., up to 17%) at additional asparagine residues where the N+1 was not glycine. The average deamidation for asparagines was largely consistent between preps. We also detected deamidation at glutamine residues but at a lower frequency than at asparagines; the highest percent we observed was <2% at Q467 (FIG. 7). This observation was inconsistent across preparations (data not shown). We observed the greatest preparation-to-preparation differences at residue N499 (N+1 residue is asparagine), with values ranging from <1% to over 50% deamidation. Regardless, the variations we observed in deamidation between preparations of vector did not appear to be related to purification method, transgene identity, or the presence of vector genome, suggesting that these factors do not impact deamidation rates.

TABLE 1

Characteristics of AAV8 deamidated residues of interest.

| | N + 1 residue | Structural topology | Structural motif | Average % deamidation | Temperature factor ($Å^2$) |
|---|---|---|---|---|---|
| N35 | Q | N/A | N/A | 1 | N/A |
| N57 | G | N/A | N/A | 80 | N/A |
| N94 | H | N/A | N/A | 7 | N/A |
| N254* | N | Surface exposed | Not assigned | 9 | 35 |
| N255* | H | Surface exposed | Not assigned | N/A | 42 |
| N263 | G | Surface exposed | HVR I | 99 | 51 |
| N305 | N | Buried | Alpha helix | 8 | 33 |
| N385 | G | Surface exposed | HVR III | 88 | 41 |
| N410 | N | Buried | Not assigned | 3 | 33 |
| N459 | T | Surface exposed | HVR IV | 7 | 65 |
| N499 | N | Surface exposed | HVR V | 17 | 45 |
| N514* | G | Surface exposed | HVR V | 84 | 36 |
| N517* | S | Surface exposed | HVR V | 4 | 40 |
| N540* | G | Buried | HVR VII | 79 | 40 |
| N630* | F | Buried | Not assigned | 1 | 32 |
| N653 | T | Surface exposed | HI loop | 1 | 35 |

Asterisks represent residues selected for further analysis.

Figure 4A:
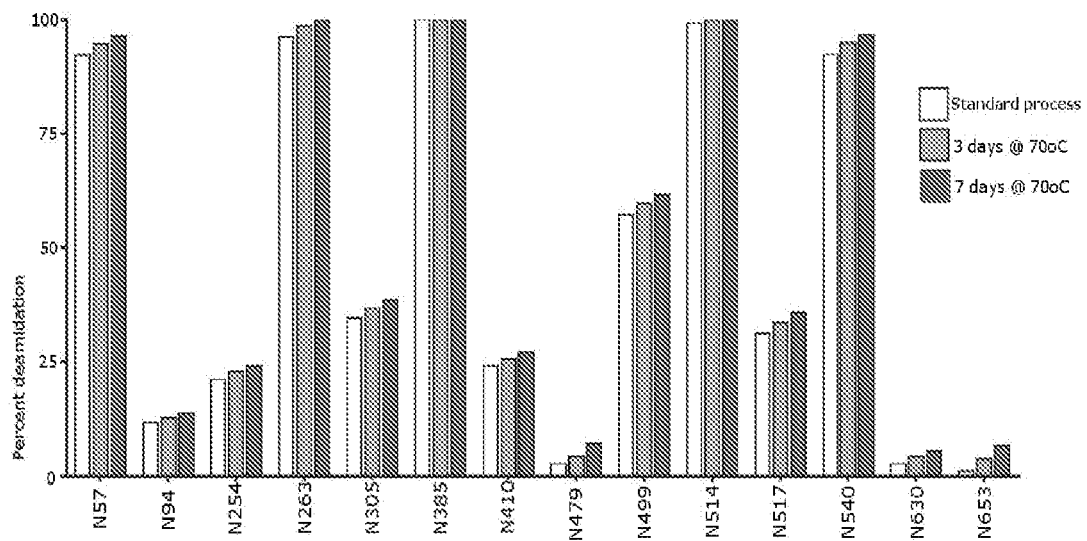
Figure 4B:
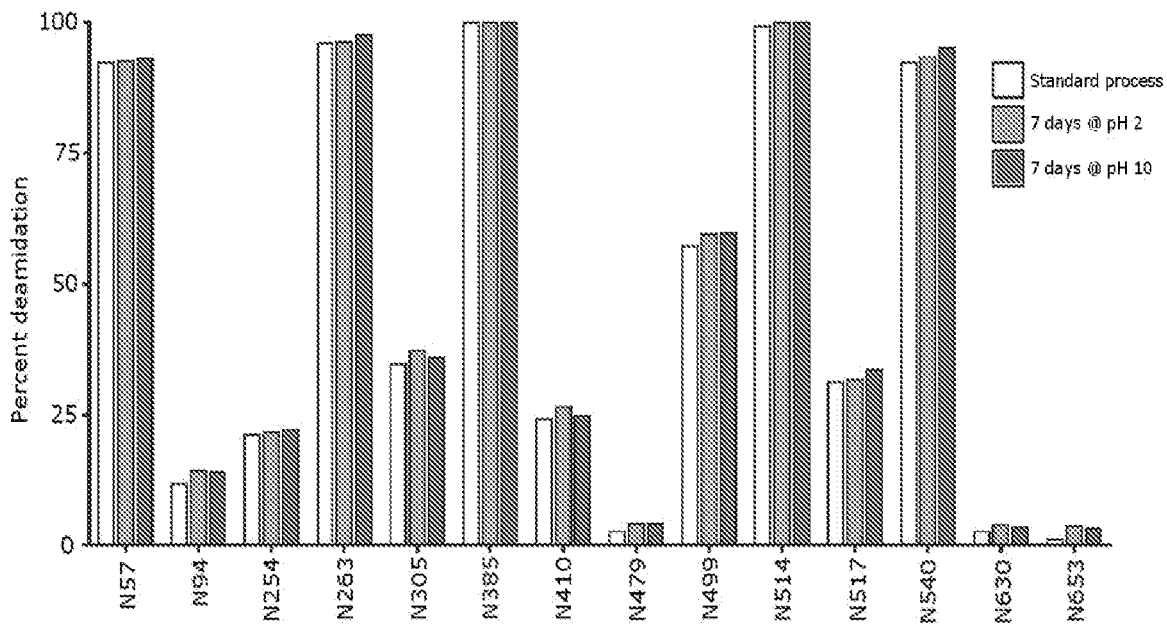

Next, we ran a series of experiments to determine if sample handling contributed to the observed levels of deamidation in AAV8. Extreme temperature (70° C. for 7 days) or pH (pH 2 or pH 10 for 7 days) did not significantly induce additional deamidation in the AAV8 capsid (FIG. 4A and FIG. 4B). Given this resistance, we reason that it was unlikely that the deamidation observed occurred only in the purification phase, which was shorter and relatively mild in comparison. We attempted to perform mass spectrometry analysis on unpurified vector to determine the extent of deamidation before and after purification, but were unsuccessful. Likewise, heavy water controls indicate that processing specific to our mass spectrometry workflow do not contribute additional deamidation events (FIG. 4C).

Figure 5A:
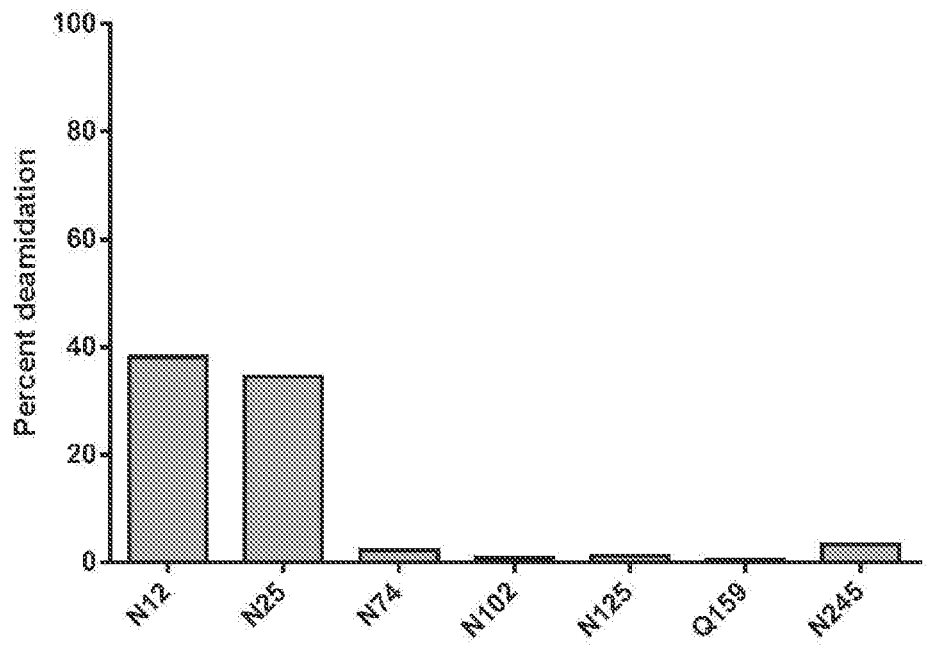
FIG. 5A-FIG. 5B. Deamidation frequencies in non-AAV proteins. Deamidation percentages are shown for two non-AAV recombinant proteins containing NG motifs likely to be deamidated, human carbonic anhydrase (FIG. 5A) and rat phenylalanine-hydroxylase (FIG. 5B), for comparison with AAV deamidation percentages.
Figure 5B:
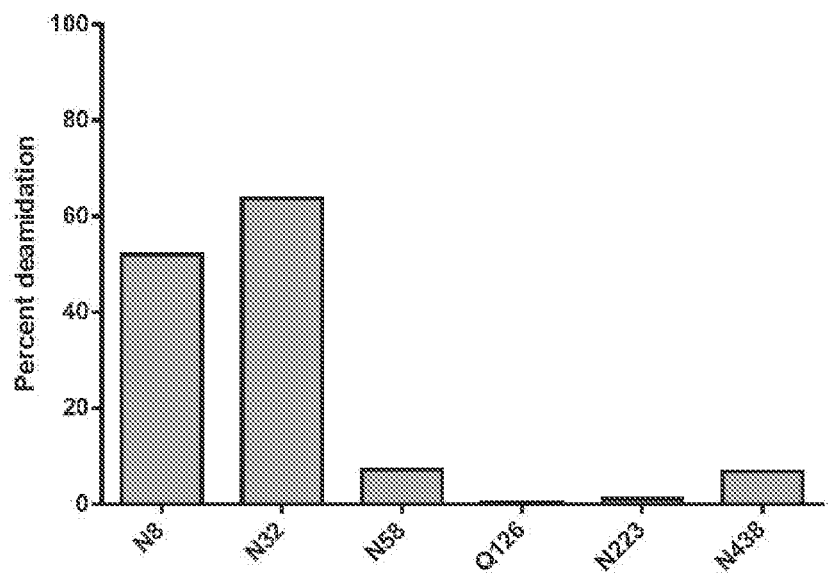
Figure 6:
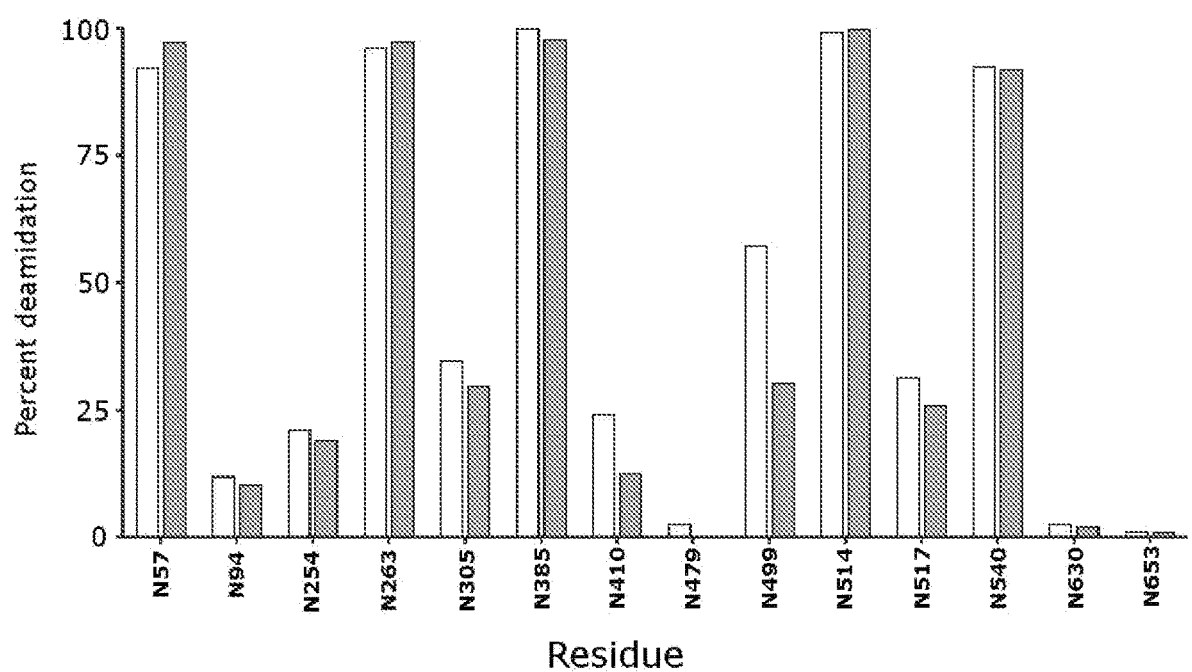
FIG. 6. Comparison of AAV8 percent deamidation calculated using data analysis pipelines from two institutions. Percent deamidation at specific asparagine and glutamine residues of interest are shown for AAV8 tryptic peptides evaluated at two different institutions.

To validate our mass spectrometry workflow, we examined two recombinant proteins that have been evaluated previously for deamidation; our findings (FIG. 5A and FIG. 5B) agree with the published results [Henderson, LE, Henriksson, D, and Nyman, PO (1976). Primary structure of human carbonic anhydrase C. *The Journal of biological chemistry* 251:5457-5463 and Carvalho, RN, Solstad, T, Bjorgo, E, Barroso, J F, and Flatmark, T (2003). Deamidations in recombinant human phenylalanine hydroxylase. Identification of labile asparagine residues and functional characterization of Asn→Asp mutant forms. *The Journal of biological chemistry* 278:15142-1515]. Additionally, we engaged a secondary institution to evaluate our raw data from AAV8. This independent analysis identified the same sites as deamidated, with minimal variation in the extent of modification at each site attributable to software-to-software variations in peak detection and area calculation (FIG. 6).

Figure 7A:
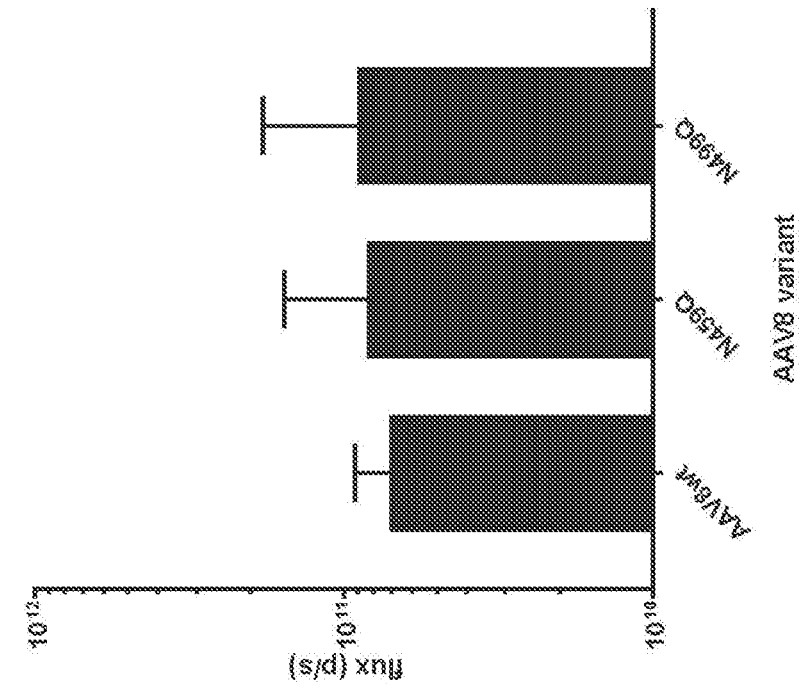
FIG. 7A-FIG. 7C illustrate functional asparagine substitutions at non-NG sites with high variability between lots.

Structural Topology, Temperature Factor, and the Identity of the N+1 Amino Acid Contribute to Deamidation Frequency As the structure of AAV8 has been solved and published (PDB identifier: 2QA0) (Nam H J, et al. *J Virol* 2011; 85 (22): 11791-99), we next examined the AAV8 capsid structure for evidence of favorable conditions for non-enzymatic deamidation and to correlate percent deamidation with established structural features (Nam H J, et al. *J Virol* 2007; 81 (22): 12260-71). We focused on asparagine residues exclusively, as the factors influencing asparagine deamidation are better characterized in the literature and asparagine deamidation events are far more common than glutamine deamidation events (Robinson, NE, and Robinson, AB (2001). Molecular clocks. *Proc Natl Acad Sci USA* 98:944-949). We also determined the temperature (or B) factor for each of these residues from the AAV8 crystal structure; temperature factor is a measure of the displacement of an atom from its mean position, with higher values indicating a larger displacement, higher thermal vibration, and therefore increased flexibility (Parthasarathy S and Murphy M R. *Protein Science: A Publication of the Protein Society* 1997; 6:2561-7). The majority of asparagines of interest were located in or near the surface-exposed HVRs (Table 1), which are structurally favorable for deamidation and provide a solvent-exposed environment (Govindasamy L, et al. *J Virol* 2013; 87 (20): 11187-99). We found that residues located in these flexible loop regions were, on average, more frequently deamidated than residues in less flexible regions such as beta strands and alpha helices. For example, the NG residue at position N263 is part of HVR I, has a high temperature factor, and was >98% deamidated on average (FIG. 7A and FIG. 6, Table 1). N514, which was deamidated ~85% of the time (FIG. 3 and FIG. 6, Table 1), is also in an HVR (HVR V) with an N+1 glycine; however, the local temperature factor is relatively low in comparison to that of N263 due to its interaction with residues on other VP monomers at the three-fold axis. Less-favorable+1 residues and lower local temperature factors correlated with lower deamidation, even for HVR residues. For example, N517 was on average only 4% deamidated (Table 1); this residue has an equivalent temperature factor to the highly deamidated N514, but its N+1 residue is a serine, decreasing the likelihood of deamidation events due to steric hindrance. This demonstrates that a number of factors cumulatively determine the extent of deamidation at a given capsid position, although the identity of the +1 residue is apparently the most influential factor.

To test the role of the +1 residue in asparagine deamidation, we generated mutant vectors in which AAV8 NG sites were individually mutated at the +1 position to either alanine or serine. Model peptide studies indicate that NG peptides deamidate with a half-life as short as 1 day, whereas NA or NS peptides typically deamidate 25- or 16-fold more slowly, respectively (Robinson N E and Robinson A B. *Proc Natl Acad Sci USA*. 2001; 98 (8): 4367-72). Mass spectrometry analysis of the vector mutants confirmed the central role of the +1 site in determining the extent of vector deamidation. NG sites in this set (>80% deamidation in wt) showed selective stabilization of the adjacent asparagine when the +1 site was changed to alanine (<5% deamidation) or serine (<14% deamidation) (Table 2).

TABLE 2

Extent of deamidation (%) at
five AAV8 NG sites in wt and six +1 site mutants

| position\variant | WT (average) | G58S | G58A | G264A | G386S | G386A | G515A |
| --- | --- | --- | --- | --- | --- | --- | --- |
| N57 | 81.8 | 8.4 | 1.9 | 89.7 | 89.7 | 91.6 | 93.6 |
| N263 | 99.3 | 98.2 | 98.9 | 4.8 | 100.0 | 94.5 | 97.2 |
| N385 | 89.1 | 96.3 | 94.8 | 97.1 | 13.5 | 2.5 | 97.0 |
| N514 | 85.2 | 100.0 | 98.0 | 98.8 | 100.0 | 100.0 | 2.2 |
| N540 | 84.5 | 95.0 | 92.6 | 97.9 | 96.9 | 86.1 | 89.5 |

Residues that were at least partially buried and not readily exposed to solvent and/or were located in regions of low local flexibility in the intact, fully assembled AAV8 capsid had a lower frequency of deamidation compared to those located in a more favorable environment Table 1). Despite this, a few of the residues in unfavorable conditions were deamidated. For example, N630 is at least partially buried but still had a detectable degree of deamidation. For this residue, the presence of phenylalanine as the N+1 residue suggests that this region could be a novel site of non-enzymatic autoproteolytic cleavage within the AAV8 VP3 protein.

Structural Modeling of AAV8 VP3 Confirms Deamidation Events

To provide direct evidence of deamidation in the context of an assembled capsid, we evaluated the crystal structure of AAV8 (Nam H-J, et al. *J Virol* 2011; 85 (22): 11791-9). The resolution of the available crystal structure (i.e., 2.7 Å) of this serotype is not high enough to identify the terminal atoms in the R groups and, therefore, is insufficient to directly distinguish between asparagine, aspartic and isoaspartic acid residues. Other aspects of the structure of the isomer of aspartic acid that forms under these conditions provided us an opportunity to determine deamidation from the 2.7 Å structure. This analysis was based on two assumptions: 1) The predominant product of spontaneous deamidation of an asparagine is isoaspartic rather than aspartic acid, which is generated at a 3:1 ratio (Geiger T and Clarke S. *J Biol Chem* 1987; 262 (2): 785-94), and 2) an asparagine or aspartic acid can be differentiated from an isoaspartic acid because the electron density map corresponding to the R group of isoaspartic acid is shorter in length. This shorter R group is created when the beta carbon from the R group of isoaspartic acid is lost when incorporated into the main chain of the AAV8 VP3 capsid protein backbone following resolution of the succinimidyl intermediate during the deamidation reaction.

We first refined the AAV8 structure itself, generating an AAV8 capsid electron density that was not biased by the known AAV8 VP3 sequence. We then examined the refined AAV8 crystal structure for evidence of deamidation based on the presence of a shorter R group associated with isoaspartic acid (FIG. 3A-FIG. 3E). The electron density map confirmed a shorter R group for the highly deamidated N+1 glycine residues at positions 263 (FIG. 3C), 385 (not shown), 514 (FIG. 3D), and 540 (FIG. 3E) when compared to the asparagine at 410 that had no deamidation detected by mass spectrometry (FIG. 3B). The deamidation indicated by the electron density map is therefore consistent with the data generated by mass spectrometry at these sites with >75% deamidation. The resulting isoaspartic acid models were comparable to isoaspartic acid residues observed in the crystal structures of other known deamidated proteins, supporting the validity of our analysis of AAV8 (Rao F V, et al. *Chem Biol*. 2005; 12 (1): 65-76; Noguchi S, et al. *Biochemistry* 1995; 34 (47): 15583-91; Esposito L, et al. *J Mol Biol* 2000; 297 (3): 713-32). This structural analysis serves as an independent confirmation of the deamidation phenomena observed when analyzing the AAV8 capsid via mass spectrometry.

Deamidation of the AAV Capsid is not Serotype Specific

Figure 11D:
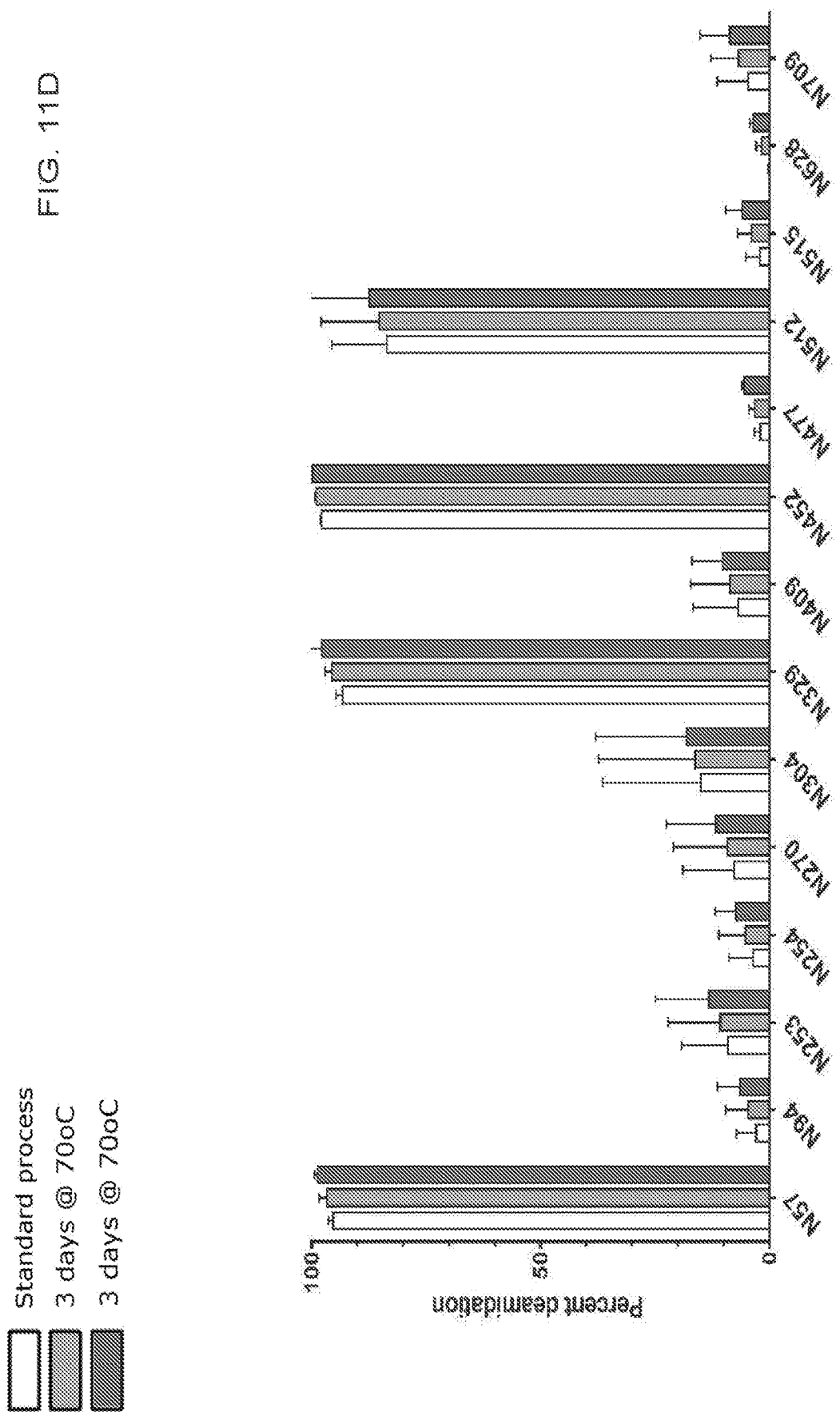
FIG. 11D-FIG. 11F. Determination of factors influencing AAV9 capsid deamidation.
Figure 11E:
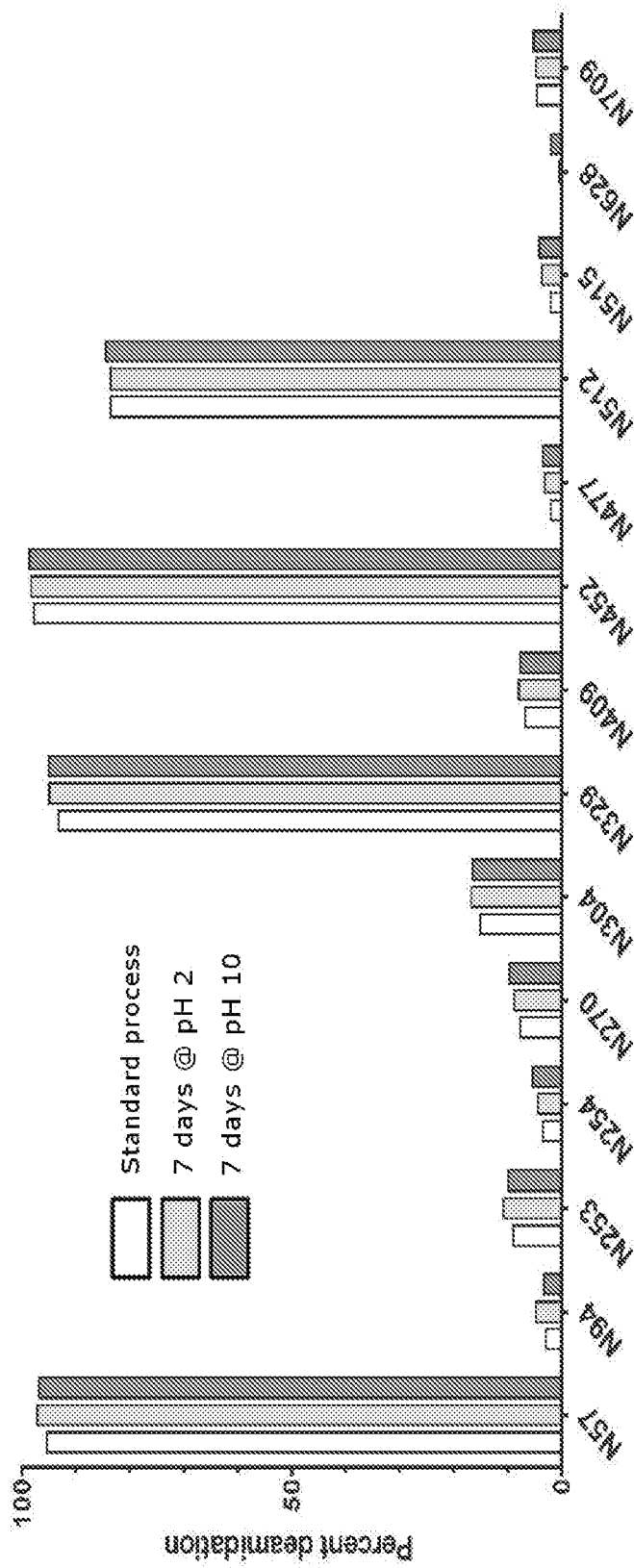
Figure 11F:
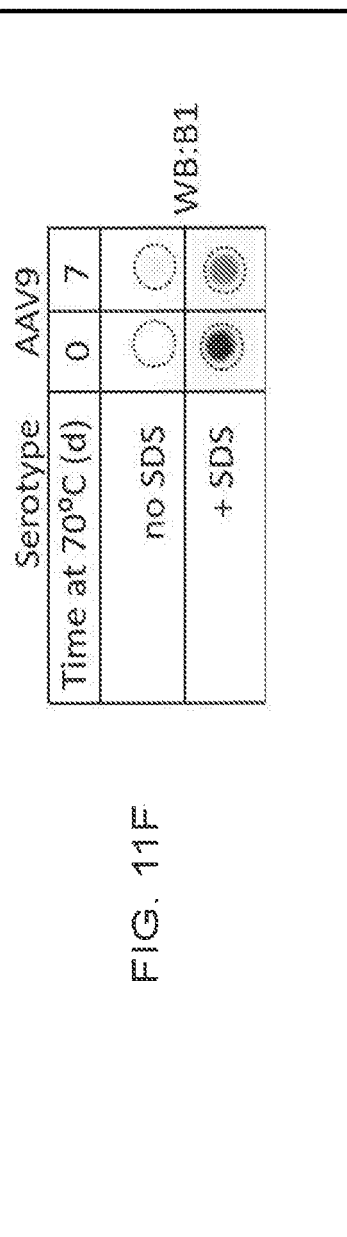

We investigated serotypes beyond AAV8 for evidence of capsid deamidation. We examined AAV9 vector preparations using 2D gel electrophoresis (FIG. 11A) and mass spectrometry (FIG. 11B), including controls for potential vector-processing effects (FIG. 11D-FIG. 11F). The pattern and extent of AAV9 deamidation was similar to that of AAV8. All four AAV9 NG sites were >85% deamidated; 13 non-NG sites were deamidated to lesser extent, with a few sites showing high lot-to-lot variability in % deamidation. Next, we applied our structural analysis workflow and refit existing AAV9 crystallographic data (FIG. 11C, Table 3). As with AAV8, isoaspartic acid fit better into the electron density of several NG sites in the AAV9 crystal structure. We extended our 2D gel analysis (data not shown) and mass spectrometry (summarized in Table 4) to five additional evolutionarily diverse serotypes (rh32.33, AAV7, AAV5, AAV4, AAV3B and AAV1). All of the capsids examined contain a similar pattern and extent of deamidation, indicating that this modification is widespread in clinically relevant AAV vectors, and is determined by similar underlying primary-sequence and structural factors.

TABLE 3

Characteristics of AAV9 deamidated residues of interest.

| | N + 1 residue | Structural topology | Structural motif | Average % deamidation | Temperature factor (Å^2) |
| --- | --- | --- | --- | --- | --- |
| N57 | G | N/A | N/A | 97 | N/A |
| N94 | H | N/A | N/A | 5 | N/A |
| N253 | N | Surface exposed | Not assigned | 9 | 41 |
| N254 | H | Surface exposed | Not assigned | 2 | 50 |
| N270 | D | Surface exposed | HVR I | 11 | 65 |
| N304 | N | Buried | Alpha helix | 23 | 35 |
| N329 | G | Surface exposed | HVR II | 94 | 89 |
| N409 | N | Buried | Not assigned | 9 | 36 |
| N452 | G | Surface exposed | HVR IV | 98 | 64 |
| N477 | Y | Buried | Not assigned | 2 | 33 |

TABLE 3-continued

Characteristics of AAV9 deamidated residues of interest.

| | N + 1 residue | Structural topology | Structural motif | Average % deamidation | Temperature factor (Å^2) |
|---|---|---|---|---|---|
| *N512* | G | Surface exposed | HVR V | 89 | 48 |
| *N515* | S | Surface exposed | HVR V | 3 | 47 |
| *N651* | T | Buried | HI loop | 1 | 38 |
| N663 | K | Surface exposed | HI loop | 4 | 49 |
| *N668* | S | Surface exposed | HI loop | 13 | 52 |
| *N704* | Y | Surface exposed | HVR IX | 5 | 68 |
| N709 | N | Surface exposed | HVR IX | 5 | 55 |

Conserved asparagine residues with homologous N + 1 residues (in comparison to AAV8) are denoted in italics (determined by alignment of the full-length amino acid sequences of AAV8 and AAV9 VP1).

TABLE 4

Extent of deamidation observed for diverse serotypes

| serotype | vector preps analyzed | Average % sequence Coverage by MS | # of NGs | average NG % deamidation | # of non NG sites observed deamidated | average non-NG % deamidation |
|---|---|---|---|---|---|---|
| AAV1 | 3 | 91.4 | 4 | 95.6 | 19 | 12.9 |
| AAV3B | 1 | 89.8 | 4 | 97.0 | 9 | 9.4 |
| AAV4 | 3 | 84.7 | 4 | 96.2 | 15 | 15.3 |
| AAV5 | 1 | 88.7 | 3 | 88.7 | 11 | 15.3 |
| AAV7 | 1 | 90.9 | 4 | 92.1 | 9 | 13 |
| AAV8 | 21 | 93.4 | 5 | 90.5 | 37 | 7.4 |
| AAV9 | 7 | 90.2 | 4 | 95.5 | 26 | 5.3 |
| rh32.33 | 1 | 100 | 3 | 97.4 | 14 | 16.2 |

Deamidation Events can Affect Capsid Assembly and Transduction Efficiency

One approach to testing the functional impact of deamidation is by substituting asparagine with aspartate by genetic mutation. We generated an aspartate mutant vector encoding a luciferase reporter for each deamidated AAV8 asparagine by small-scale triple transfection of 293 cells, and titered the vectors by qPCR of DNAseI resistant genome copies (FIG. 8A). The mutations rarely affected capsid assembly relative to wtAAV8, and effects were limited to mostly buried, non-NG sites with low overall deamidation in the wt vector. Next, we assessed the mutation panel for in vitro transduction efficiency of human liver-derived Huh7 cells (FIG. 8B). Several mutants showed impaired transduction efficiency, with positions N57, N94, N263, N305, Q467, N479, and N653 exhibiting >10-fold transduction loss. We observed a similar number of sensitive sites for AAV9 (FIG. 11G and FIG. 11H). As typically only a fraction of residues at a given position are deamidated endogenously, this approach has the potential to overestimate functional loss for proteins such as capsids where the functional unit is a homomeric assembly; endogenous modification at one capsid site may be compensated for by a neighboring subunit with an intact residue. Nonetheless, we reasoned that the method could help prioritize deamidated residues for future monitoring during manufacturing or mutational stabilization. Functional data from populations of endogenously deamidating vectors will be required to place this loss-of-function mutagenesis data in the proper context.

Vector Activity Loss Through Time is Correlated with Progressive Deamidation

Figure 9A:
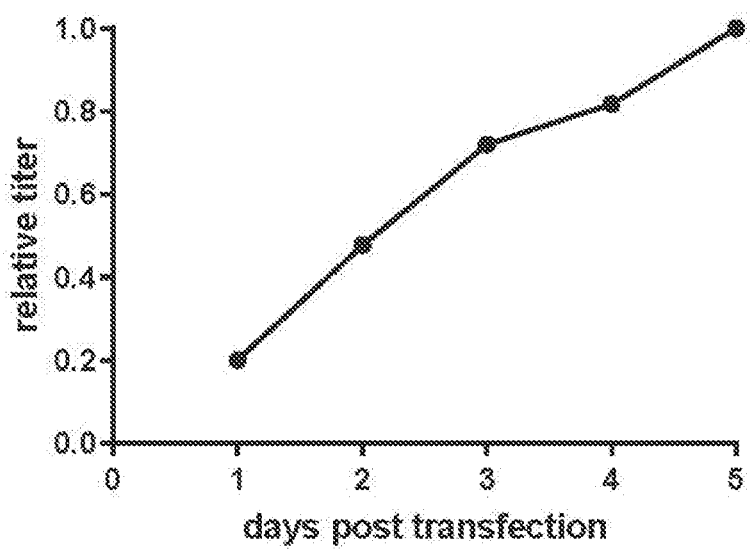
FIG. 9A-FIG. 9D) illustrate that vector activity loss through time is correlated to progressive deamidation.
Figure 9B:
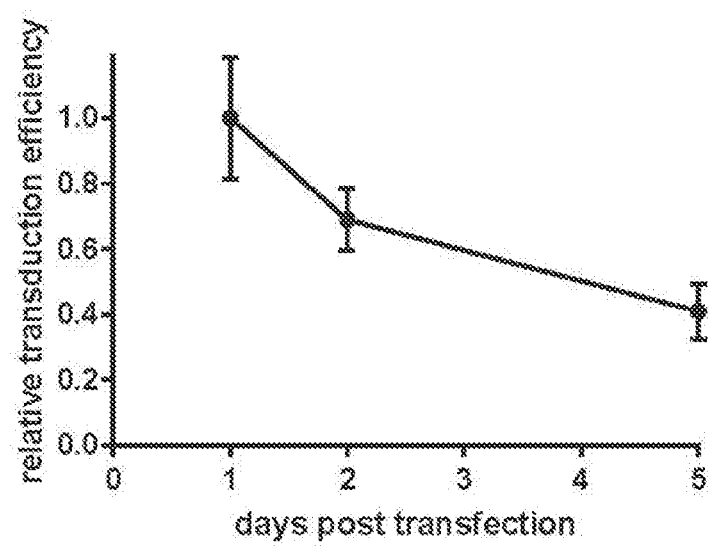
Figure 11I:
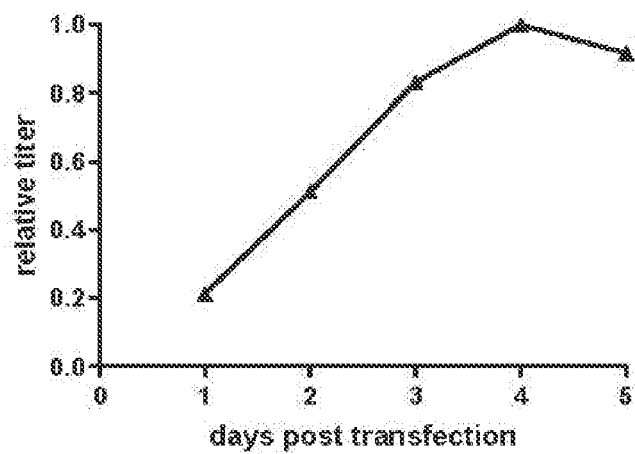
FIG. 11I-FIG. 11K show AAV9 vector in vitro potency through time.
Figure 11J:
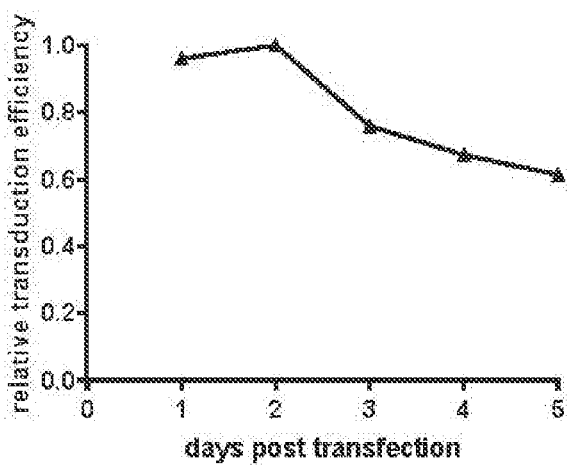
Figure 11K:
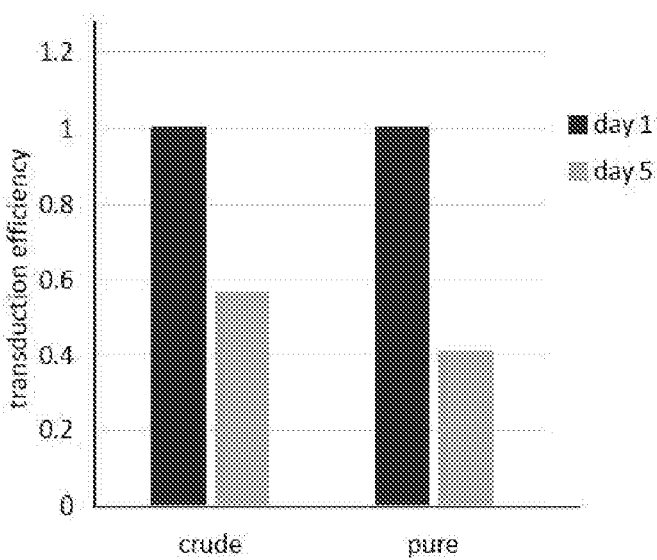

Given the apparently short half-life of NG deamidation, we reasoned that vector samples differing in age by as little as 1 day could show distinct deamidation profiles, thus providing an opportunity to correlate endogenous deamidation to function. Our large-scale vector preparation protocol calls for triple transfection of 293 cells followed by 5 days of incubation for vector production and 1-2 days for vector purification. To approximate this process, we prepared medium scale triple transfections (10×15 cm cell culture dishes each) of 293 cells with wt AAV8. We collected vector (2×15 cm cell culture dishes/day) at 1 day intervals for 5 days, preserving the timepoints until the end of the 5 day period by freezing vector at −80 C. Next, we assessed crude vector titer and in vitro transduction efficiency as described above. As expected, the number of assembled, DNAseI-resistant genome copies increased over time (FIG. 9A). We then quickly processed crude vector for early (day 1 and 2) and late (day 5) timepoints by affinity purification and measured in vitro transduction efficiency of huh7 cells. Relative transduction efficiency of the vector dropped progressively over time (FIG. 9B). In terms of transgene expression per GC added to target cells, day 5 vector was only 40% as efficient as day 1 material. This activity drop was observed for crude material as well, indicating a change in molecular composition before purification (FIG.). We observed a similar trend in activity loss for AAV9 over 5 days, with approximately 40% reduction in vector potency (FIG. 11I-FIG. 11K).

Figure 9C:
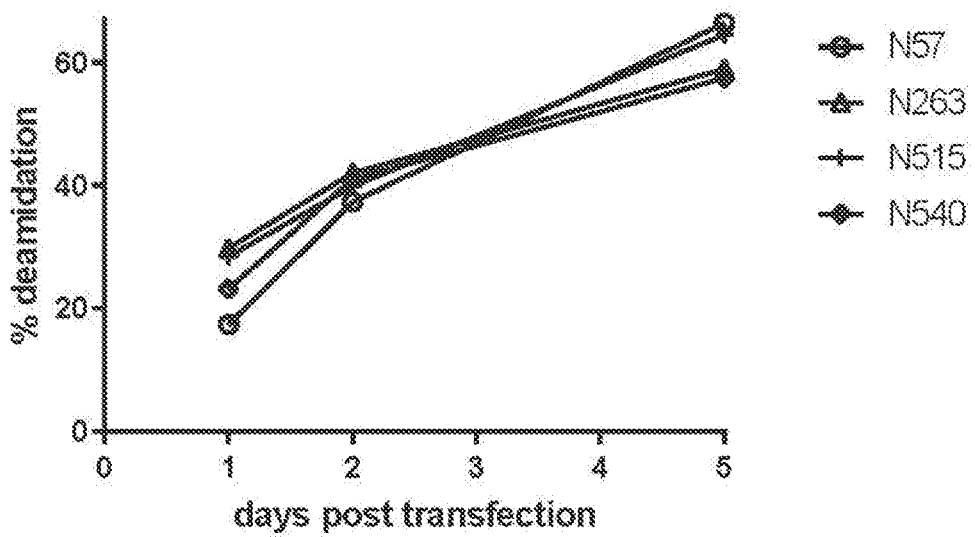
Figure 9D:
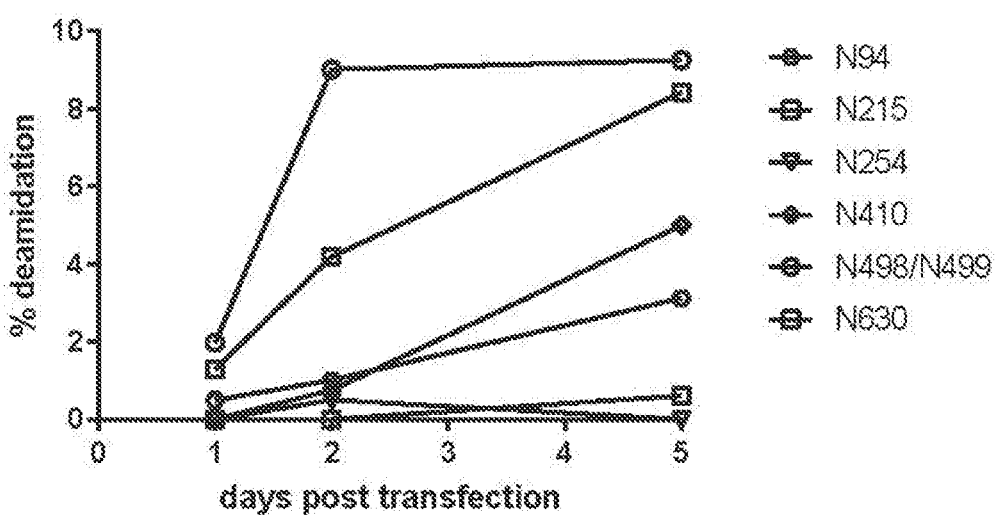

Next we measured deamidation of the time course samples by mass spectrometry. NG site deamidation progressed substantially over every interval, with an average of 25% deamidation at day 1, and >60% of sites converted by day 5 (FIG. 9C). Non-NG site deamidation generally progressed over 5 days, although at much lower levels and with less consistency between days 2 and 5 (FIG. 9D). The data correlates endogenous vector deamidation to an early timepoint decay in specific activity, and highlights a potential opportunity to capture more active vector by shortening the production cycle or finding capsid mutations that stabilize asparagines.

We note that the material used for mass spectrometry analysis in FIG. 2A-FIG. 2E was at least 7 days post-transfection, due to an additional 2 days for purification. The higher NG site deamidation in these samples (>80%) indicates that deamidation likely continues after the period of expression and during the recovery and purification processes at approximately the same rates until NG sites are completely deamidated or the vector sample is frozen. Thus deamidation is largely determined by the age of the vector and is not a process that is exclusive to or caused by the recovery and purification process. The much lower deamidation values in the day 1 material vs the day 5 material (both affinity purified) underscore this point.

Stabilizing NG Asparagines can Improve Vector Performance

Figure 10C:
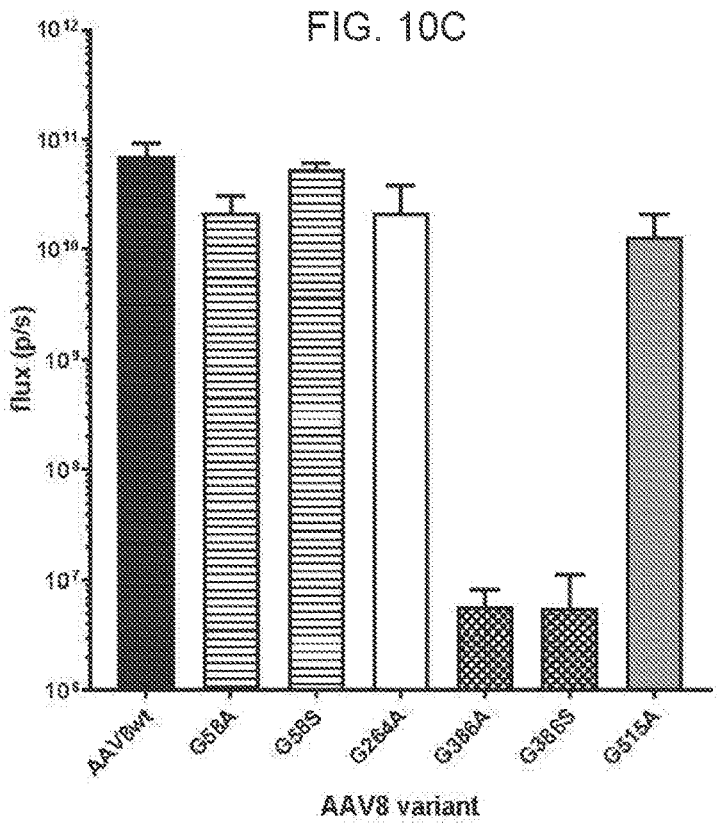

Given the correlation between vector NG deamidation and transduction efficiency loss, we reasoned that stabilizing NG amides by +1 site mutagenesis may improve vector function. We produced vector in small scale for AAV8 NG site mutants in which each +1 residue was individually converted to alanine or serine. Single+1 mutants were well tolerated in terms of vector assembly (FIG. 10A) and transduction efficiency (FIG. 10B). G386 substitutions, located near a previously defined "dead zone" on the capsid surface (Aydemir F, et al. *J Virol* July 2016; 90 (16): 7196-204), were defective for in vitro transduction. The loss of function for G386 mutants could indicate a preference for a deamidated asparagine at N385. Alternatively, the additional sidechain bulk at the +1 position may have a negative impact on function that is independent of amide-group stabilization. No single-site mutants significantly improved in vitro transduction, in spite of dramatic stabilization of their neighboring asparagines (Table 2). Because in vitro and in vivo transduction activities can be discordant, we tested a subset of the single-site+1 mutants for liver transduction in C57BL/6 mice. We performed intravenous tail vein injection (n=3 to 5) and examined luciferase expression by imaging weekly for 2 weeks (FIG. 10C). In vivo and in vitro transduction data were in agreement to within the associated errors of each assay (i.e., within the error range). G386 substitutions were defective for transduction, while+1 site mutations at other positions were largely tolerated, transducing liver at levels equivalent to but not exceeding wtAAV8.

Figure 10D:
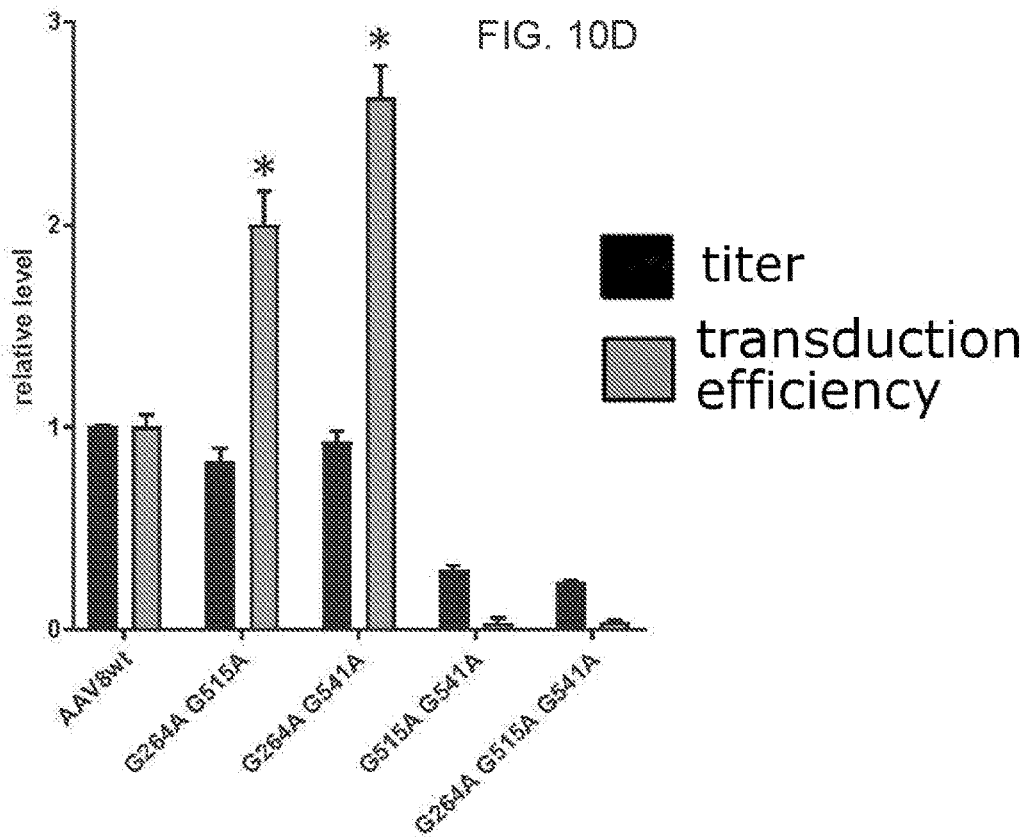

Because stabilizing the amide at any one NG site may be necessary but not sufficient for functional restoration, we next evaluated vector variants with combinations of +1 site alanine substitutions. We recombined all 3 AAV8 NG sites for which the +1 alanine was highly functional (N263, N514, and N540). Some combinations, including the triple mutant G264A/G515A/G541A, assembled poorly and were dysfunctional for transduction. However, both pairwise combinations involving N263 (G246A/G515A and G264A/G541A) improved in vitro transduction efficiency (2.0- and 2.6-fold over wtAAV8, respectively) with no loss of titer (FIG. 10D). Because these mutations introduce at least two changes (N-amide stabilization and a +1 residue side chain substitution) these data do not conclusively link NG deamidation to functional loss. However, the data are consistent with the model established in the timecourse study in which NG site deamidation can impact in vitro transduction efficiency.

Functional Asparagine Substitutions Improve Lot-to-Lot Reproducibility in Vector Manufacturing Another potentially problematic aspect of the vector deamidation profiles we report is the high lot-to-lot variability in deamidation at some positions. For wtAAV8, this variability is most pronounced for N459 (observed deamidation ranging from 0% to 31%) and N499 (observed deamidation ranging from 0% to 53%). Variability in post-translational modifications is typically de facto avoided during biologics development, either by avoiding clones altogether that exhibit this variability, carefully monitoring and controlling production strains and conditions, or by protein engineering of the affected candidate.

Figure 7B:
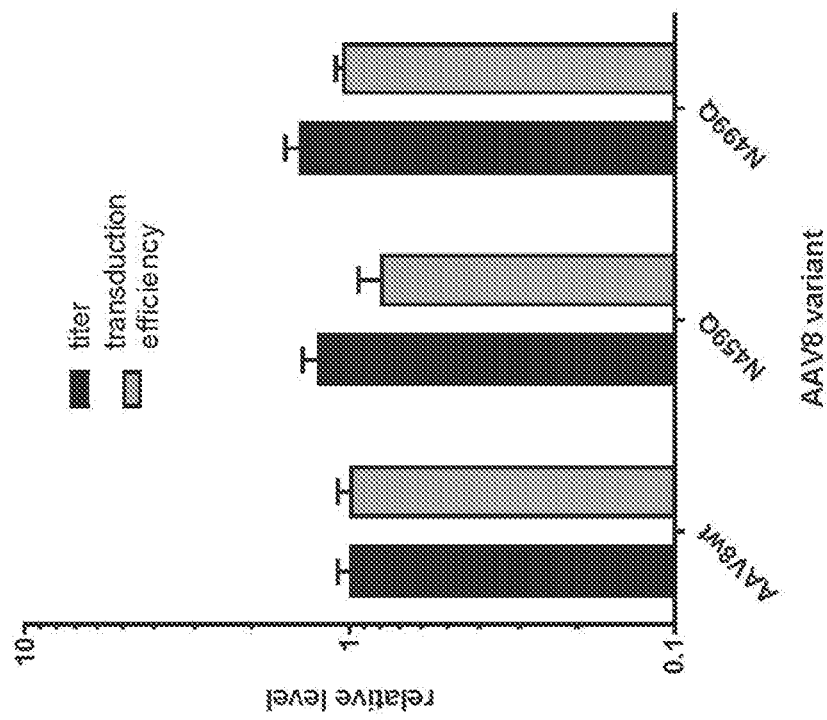
Figure 7C:
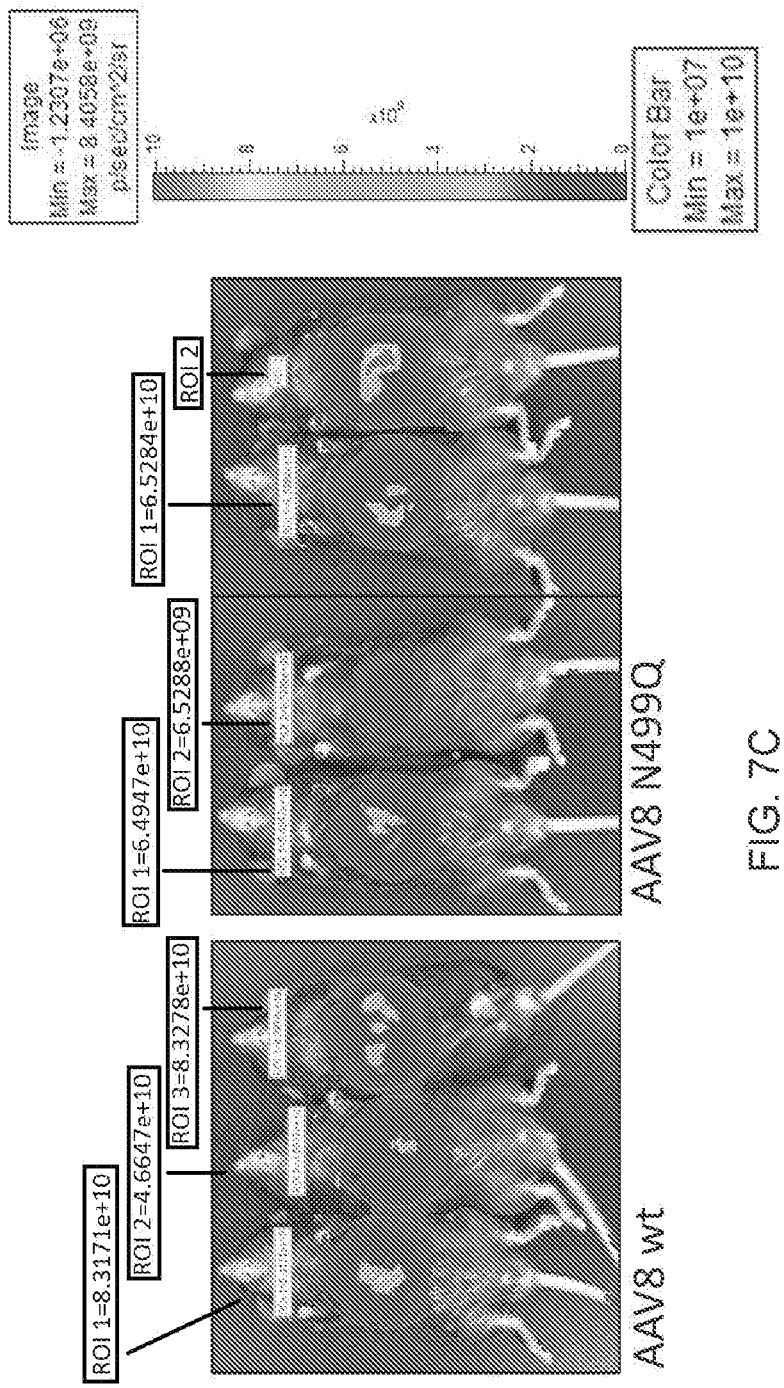

As we were unable to determine the production or processing factors contributing to N459 and N499 deamidation variability (FIG. 2E), we sought functional amino acid substitutions at these positions. We first evaluated small scale vector preparations for conservative substitutions to glutamine at each position individually. Both N459Q and N499Q were assembled efficiently into vector, and were equivalent to the wtAAV8 reference for in vitro transduction efficiency (FIG. 7A). Next, we produced the mutants in large scale and performed mass spectrometry. Consistent with our observations of extremely rare glutamine deamidation, we observed selective and complete stabilization of the glutamine amides at positions 459 or 499 in these mutants (data not shown). We evaluated these mutant lots in vivo as above for liver transduction after tail vein injection in C57BL/6 mice (FIG. 7B and FIG. 7C). The wtAAV8 vector lot used as a control in this experiment was deamidated 16.8% at N499, but no deamidation was detected at N459 (data not shown). Liver transduction at day 14 for both mutants was equivalent to wtAAV8. This data demonstrates the potential for a protein engineering approach to address the molecular variability associated with deamidation in manufactured AAV vectors.

C. Discussion

We identified and evaluated non-enzymatic deamidation of asparagine and glutamine residues on the AAV8 capsid independently by 2D gel electrophoresis, mass spectrometry, de novo protein modeling, and functional studies both in vitro and in vivo. Deamidation has been shown to occur in a wide variety of proteins and to significantly impact the activity of biologics, including antibody-based therapeutics (Nebija D et al. *Int J Mol Sci* 2014; 15 (4): 6399-411) and peptide-based vaccines (Verma A et al. *Clin Vaccine Immunol*. 2016; 23 (5): 396-402). Other viral proteins, such as the VP6 protein of rotavirus, have been shown by mass spectrometry to undergo deamidation events (Emslie K R et al. *Funct Integr Genomics* 2000; 1 (1): 12-24).

The context in which these deamidations occurred in AAV8 suggested that they are the result of spontaneous non-enzymatic events. Asparagine residues are known to be more extensively deamidated than glutamine residues; the amino acid downstream of the asparagine substantially influences the rate of deamidation with an N+1 of glycine (i.e., NG) being the most efficiently deamidated. We observed remarkable confirmation of the role of the N+1 amino acid in deamidation of AAV capsids in that every NG present in VPI was deamidated at levels >75% while deamidation was never consistently >20% in any of the other asparagines or glutamines in the capsid. Virtually all NG motifs in the AAV8 and AAV9 capsids (i.e., 7/9) were also present on the surface of the capsid contained in HVR regions that are associated with high rates of conformational flexibility and thermal vibration. This is consistent with previous reports of NG motifs of other proteins that are located in regions where flexibility may be required for proper protein function and not in more ordered structures, such as alpha helices or beta sheets (Yan B X and Sun Y Q *J Biol Chem* 1997; 272 (6): 3190-4). The preference of NG motifs in surface exposed HVRs further enhances the rate of deamidation by providing solvent accessibility and conformational flexibility, thereby facilitating the formation of the succinimidyl intermediate. As predicted, less favorable environments lead to much lower rates of deamidation.

An important question regarding the biology of AAV and its use as a vector is the functional consequences of these deamidations. Mutagenesis of the capsid DNA to convert an asparagine to an aspartic acid allows for an evaluation of capsids in which all amino acids at a particular site are represented as aspartic acids. However, no easy strategy exists to use mutagenesis to prevent deamidations other than potentially mutating the N+1 residue, which is confounded by direct consequences of the second site mutation. We studied a limited number of variants in which the asparagine residue was converted to an aspartic acid by mutagenesis. Functional analysis included capsid assembly and in vitro and in vivo transduction. The most substantial effects of mutagenesis on vector function were those involving asparagines that were incompletely deamidated at baseline and were not surface exposed. What was surprising, however, was that mutagenesis of the highly deamidated asparagine at 514 to an aspartic acid did have some effect on function. This result suggests that the presence of residual amounts of the corresponding amide may influence function. This could be due in part to the presence of hydrogen bond interactions between N514 and D531 of another three-fold related VP3 monomer (identified in the wtAAV8 crystal structure) that are lost upon conversion of this residue to aspartic acid following deamidation.

A better understanding of the factors that influence the extent of deamidation in AAV vectors is important when assessing the impact of these deamidations on the development of novel therapeutics. Incubation of vectors under extreme conditions, known to markedly accelerate deamidation kinetics, had little effect. Coupled with our isotope incorporation studies, this result suggests that deamidation occurs during capsid assembly and is not an artifact of vector processing or mass spectrometry analysis. Deamidations at NG sites are unlikely to have substantive impact on vector performance, as the reaction was virtually complete in every sample that we evaluated. However, our initial functional studies suggest that residual amounts of non-deamidated asparagines can contribute to function. We are more concerned about sites where deamidation was less complete, which in most cases was also associated with sample-to-sample variation. An example is the asparagine at position 499 that showed deamidation ranging from 0% to 53% with a mean of 17%. It is possible that subtle differences in the conditions of vector production could contribute to this heterogeneity. The striking similarity in deamidation in AAV8 and AAV9 suggests this is a property of this entire family of viruses.

In summary, we discovered substantial heterogeneity in the primary amino acid structure of AAV8 and AAV9 capsid proteins. These studies potentially impact the development of AAV as vectors in several ways. First, the actual amino acid sequences of the VP proteins are not what are predicted by the corresponding DNA sequences. Second, aspects of the production method could lead to variations in deamidation and corresponding changes in vector function. Until we have a handle on the factors that influence deamidation rates at non-NG sites and a better understanding of their functional consequences it may be necessary to include deamidation in the characterization of clinical-grade AAV vectors. 2D gel electrophoresis can provide an overall assessment of net deamidation, although mass spectrometry will be necessary to assess deamidation at specific residues.

Example 2: Deamidation AAV5.5.9

The novel sequences of AAV5.5.9 are provided in SEQ ID NO: 9 and 10, respectively. AAV5.5.9 vectors were assessed for deamidation as described in Example 1 for AAV9. Highly deamidated residues are seen at N57, N319, N442, N502.

| Modification SEQ ID NO: 10 | WL2019CS |
|---|---|
| Enzyme | Trypsin |
| % Coverage | 97.4 |
| N35 + Deamidation | 7.8 |
| ~N57 + Deamidation | 99.7 |
| N113 + Deamidation | 3.6 |
| ~N204 + Deamidation | 13.9 |
| N217 + Deamidation | 2.2 |
| ~N243 + Deamidation | 19.0 |
| Q249 + Deamidation | 11.4 |
| N293/294 + Deamidation | 37.3 |
| N304 + Deamidation | 6.2 |
| N309 + Deamidation | 0.7 |
| Q311 + Deamidation | 0.3 |
| ~N319 + Deamidation | 83.9 |
| N399/400 + Deamidation | 30.8 |
| ~N442 + Deamidation | 97.7 |
| N467 + Deamidation | 2.6 |
| N502 + Deamidation | 100.0 |
| N505 + Deamidation | 18.6 |
| ~Q589 + Deamidation | 21.1 |
| N618 + Deamidation | 6.6 |
| ~N641 + Deamidation | 8.1 |
| N653 + Deamidation | 8.3 |
| ~N658 + Deamidation | 21.7 |
| N694 + Deamidation | 0.6 |
| ~N699 + Deamidation | 8.6 |

Example 3: Deamidation AAVrh79 (Clade E)

AAVrh79 was isolated from DNA extracted from small bowel tissue of rhesus macaque. It has been characterized phylogenetically as being within Clade E (FIG. 14A-14D). Its sequences are provided herein, with the nucleotide sequences being in SEQ ID NO: 1 and the amino acid sequence being in SEQ ID NO:2. An alignment of the amino acid sequences of AAVrh79, AAVrh.10 and AAVhu.37 are provided in FIG. 14A. An alignment of the nucleic acid sequences of AAVrh79, AAVrh.10 and AAVhu.37 are provided in FIG. 14B-14D.

AAVrh79 has three amino acid differences in its primary sequence. Whereas AAVhu37 has an Ala located at position 67 and a Lys at position 169 of its primary VP1 sequence, AAVrh79 has a glutamic acid (E) at position 67 and an Arg at position 169. Differences in the DNA sequences of VP1 among rh.79, hu.37, and hu.40 are shown in FIG. 11B. Vectors expressing eGFP based on the various clade E variants were prepared and evaluated for their relative infectivity of Huh7 cells (FIG. 11C). C57BL/6 mice were injected with two dosage levels ($3\times10^{10}$ and $3\times10^{11}$ GC/mouse) of eGFP-expressing AAV8 or AAVrh.79 vectors and infectivity was assessed by fluorescence microscopy (Data not shown).

Figure 15A:
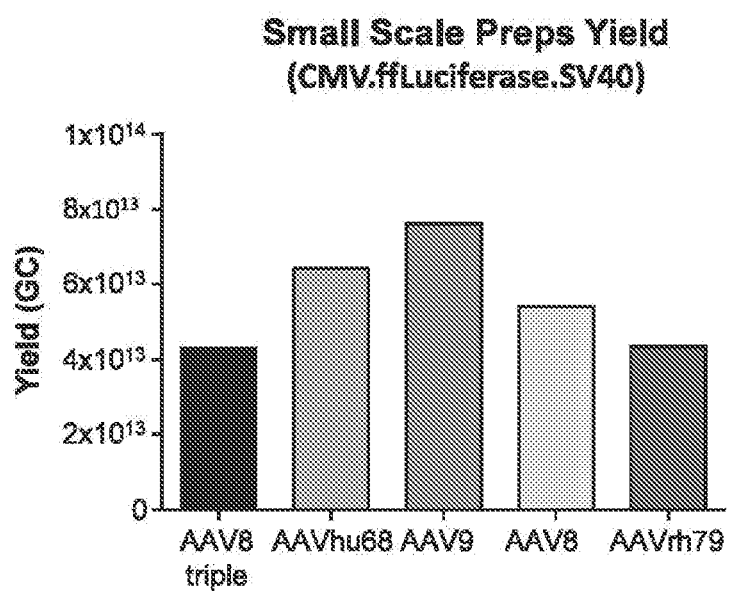
FIGS. 15A and 15B illustrate the production yield for AAV8triple, AAVhu68, AAV9, AAV9 and AAVrh79 in small scale or mega scale preps of the referenced vector.
Figure 15B:
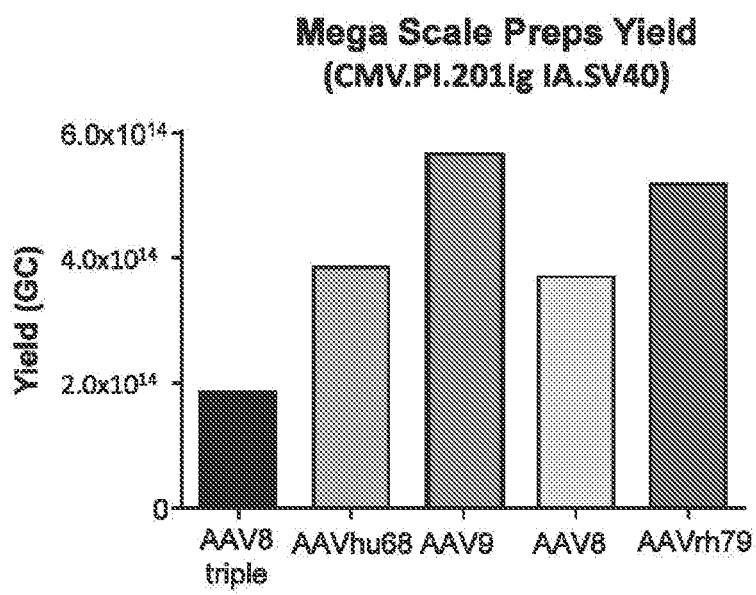
Figure 16:
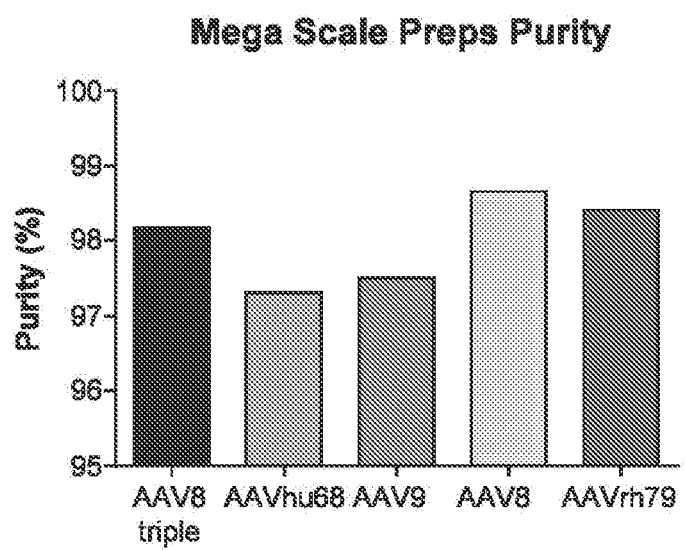
FIG. 16 provides the production purity of the mega scale preps of FIG. 15B.

Vectors based on AAVrh79 were prepared using known production techniques using the AAVrh79 nucleotide sequence for production of the cap, such as previously described for AAV8 vectors. The results of the production yield and production purity assessments are provided in FIGS. 15A-15B and FIG. 16, respectively.

To assess expression levels using AAVrh79 containing a marker gene (firefly luciferase), male RAG KO mice at 6-8 weeks of age were injected intramuscularly with $3\times10^{11}$ GC/mouse of vector performed using a Hamilton syringe. ffLuc expression was visualized by whole-body bioluminescence imaging as previously described [Greig J A, Peng H, Ohlstein J, Medina-Jaszek C A, Ahonkhai O, Mentzinger A, et al. (2014) *Intramuscular* Injection of AAV8 in Mice and Macaques Is Associated with Substantial Hepatic Targeting and Transgene Expression. PLOS ONE 9 (11): el12268_doi_org/-10_1371/journal_pone_-0112268.] The results are provided in FIGS. 17A-17D.

Figure 17A:
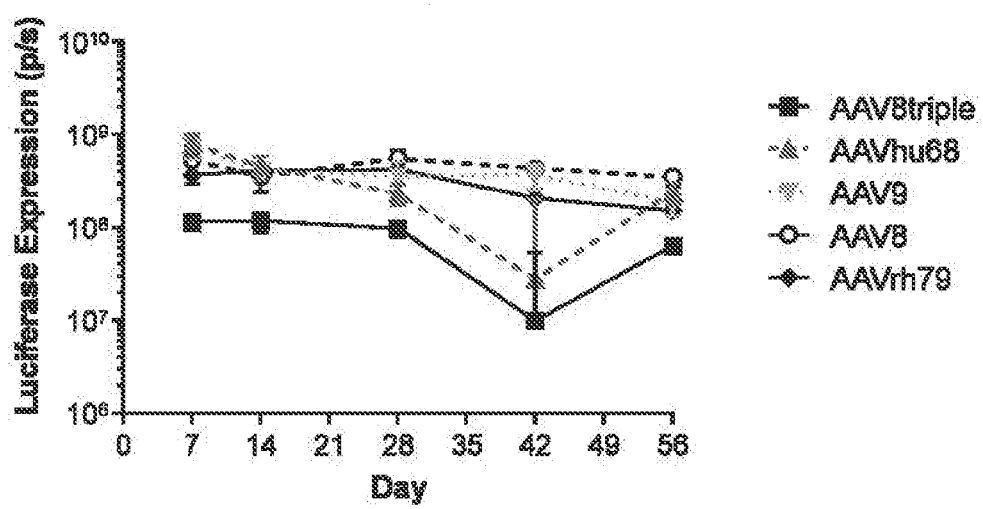
FIGS. 17A to 17D show expression of luciferase in liver and muscle tissue following intramuscular (IM) administration of $3 \times 10^{11}$ GC/mouse into the gastrocnemius muscle of male C57BL/6 mice (n=5/group) using vectors expressing firefly luciferase. Expression of AVV8triple, AAVhu68, AAV9, AAV8, and AAVrh79 vectors was compared following intramuscular administration of $10^{13}$ GC/kg AAVrh79 into male and female cynomolgus macaques (FIG. 17E). Vectors expressing a secreted transgene (201Ig IA) were administrated intramuscularly into the gastrocnemius muscle of male RAG KO mice (n=5/group) ($3 \times 10^{10}$ or $3 \times 10^{11}$ GC/mouse) (FIG. 17F). The results indicated that AAV8triple expresses better following IM injection and at the lower dose tested the difference in expression from AAV8triple was substantial. At higher the higher dose, AVVrh79 expressed at levels at comparable to the other vectors tested.
Figure 17B:
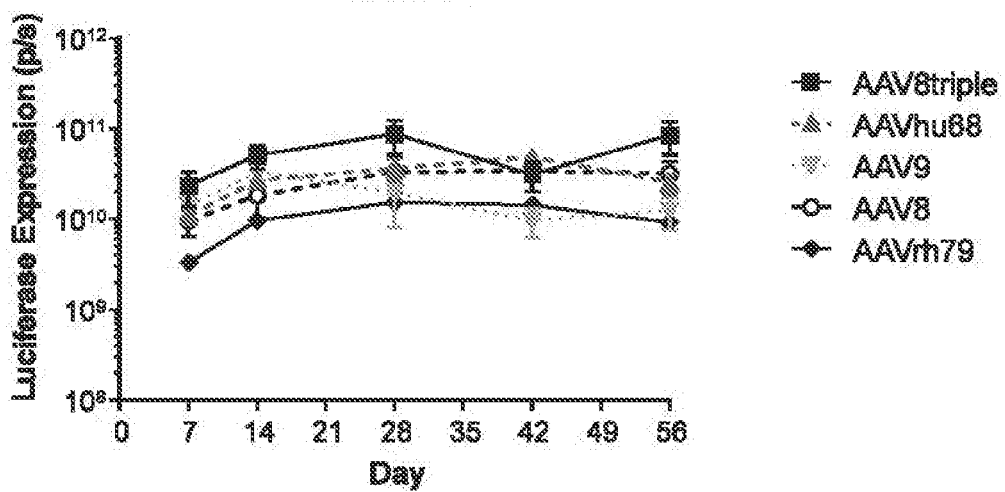
Figure 17C:
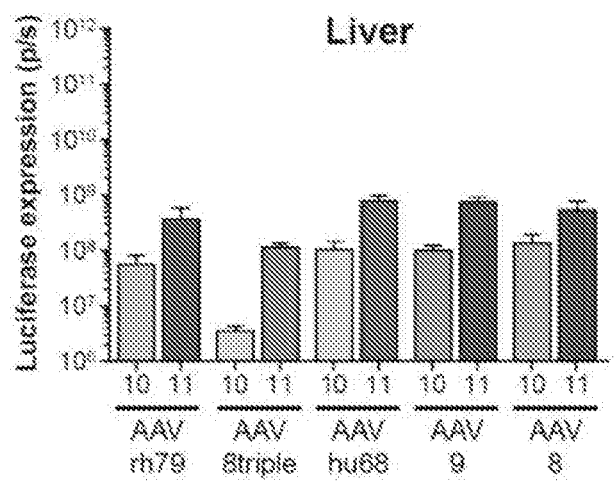
Figure 17D:
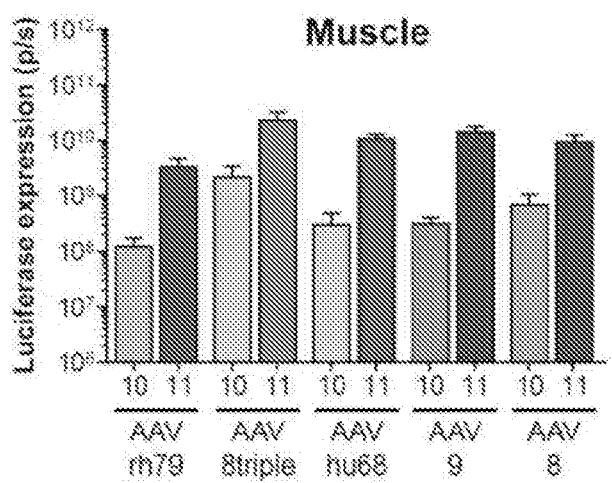
Figure 17E:
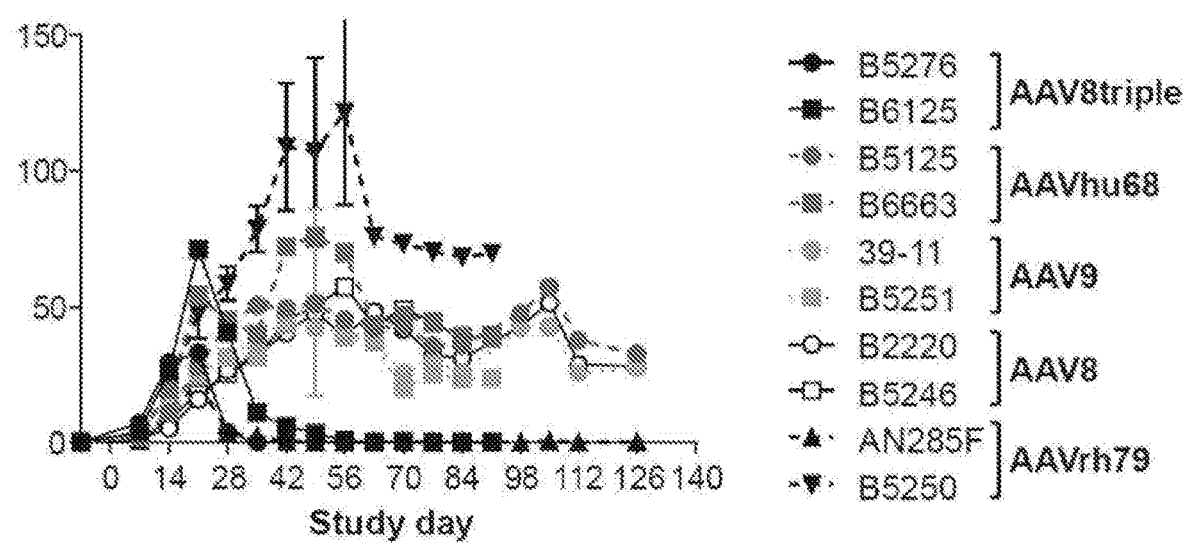

Expression of AVV8triple, AAVhu68, AAV9, AAV8, and AAVrh79 vectors was compared following intramuscular administration of $10^{13}$ GC/kg AAVrh79 into male and female cynomolgus macaques (FIG. 17E).

Figure 17F:
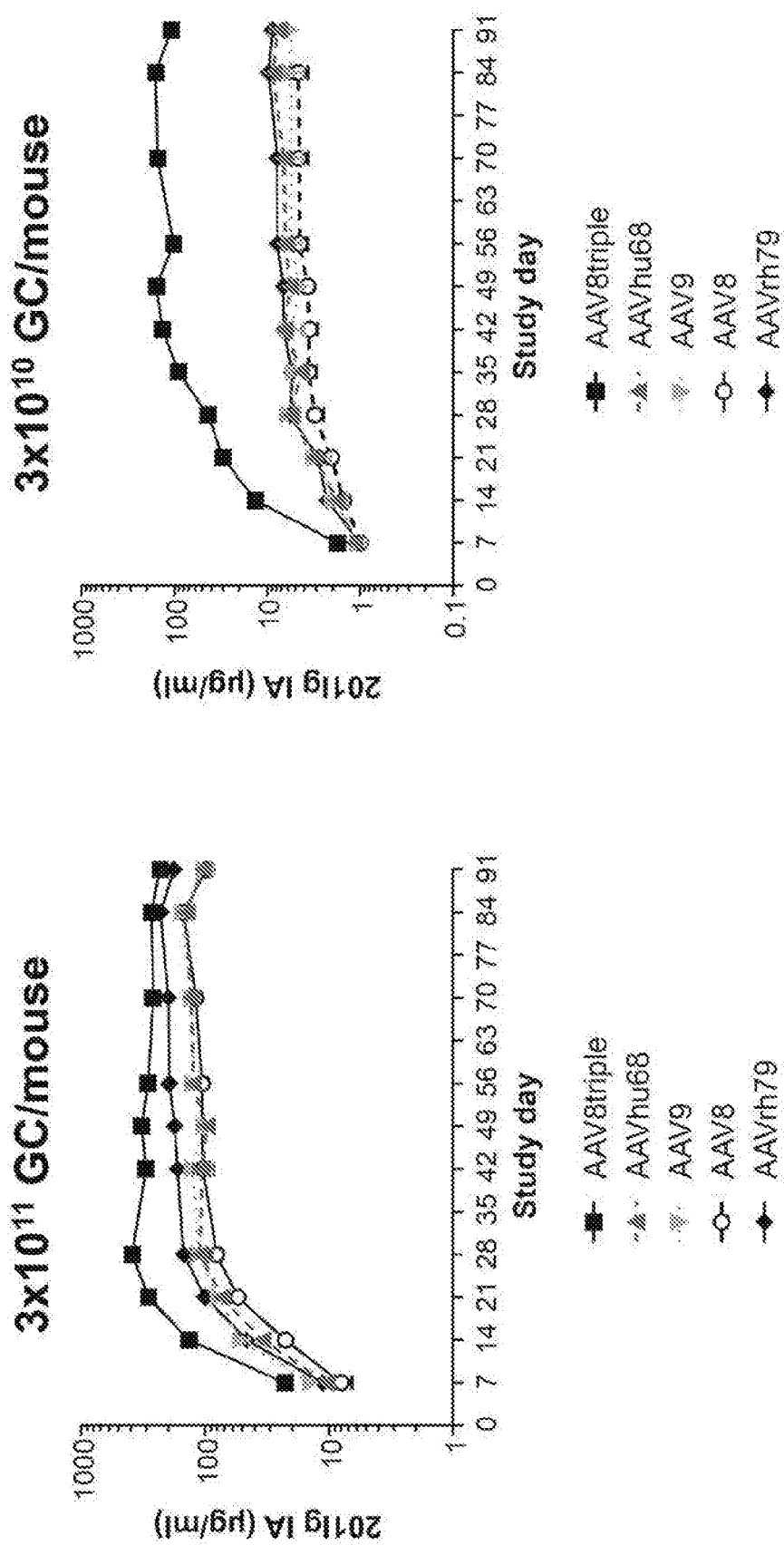

Vectors expressing a secreted transgene (201Ig IA) were administrated intramuscularly into the gastrocnemius muscle of male RAG KO mice (n=5/group) ($3\times10^{10}$ or $3\times10^{11}$ GC/mouse). The results indicated that AAV8triple expresses better following IM injection and at the lower dose tested the difference in expression from AAV8triple was substantial. At higher the higher dose, AVVrh79 expressed at levels at comparable to the other vectors tested (FIG. 17F).

Figure 18A:
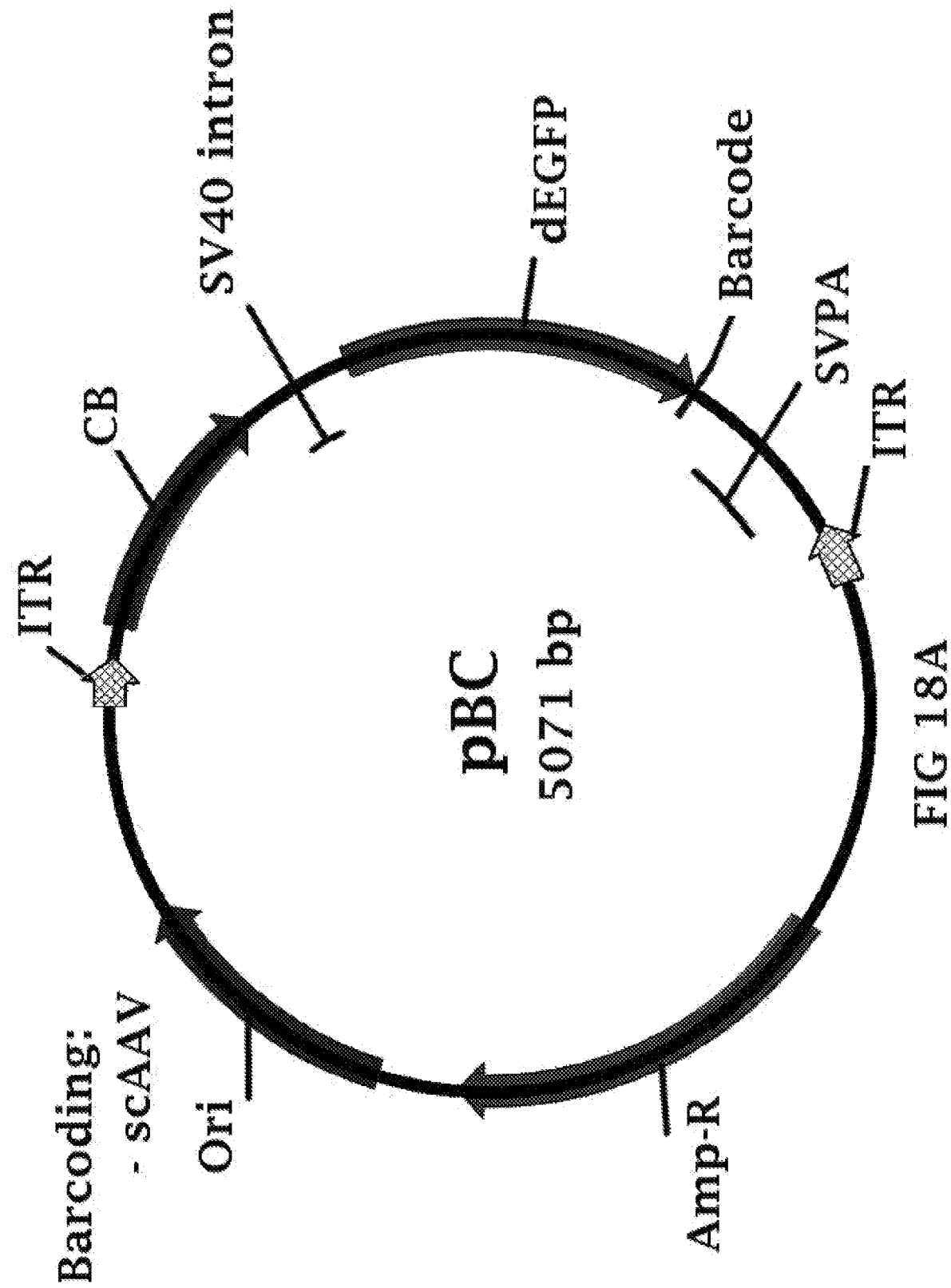
FIG. 18A shows the plasmid used for the barcode experiments in Example 5.
Figure 18C:
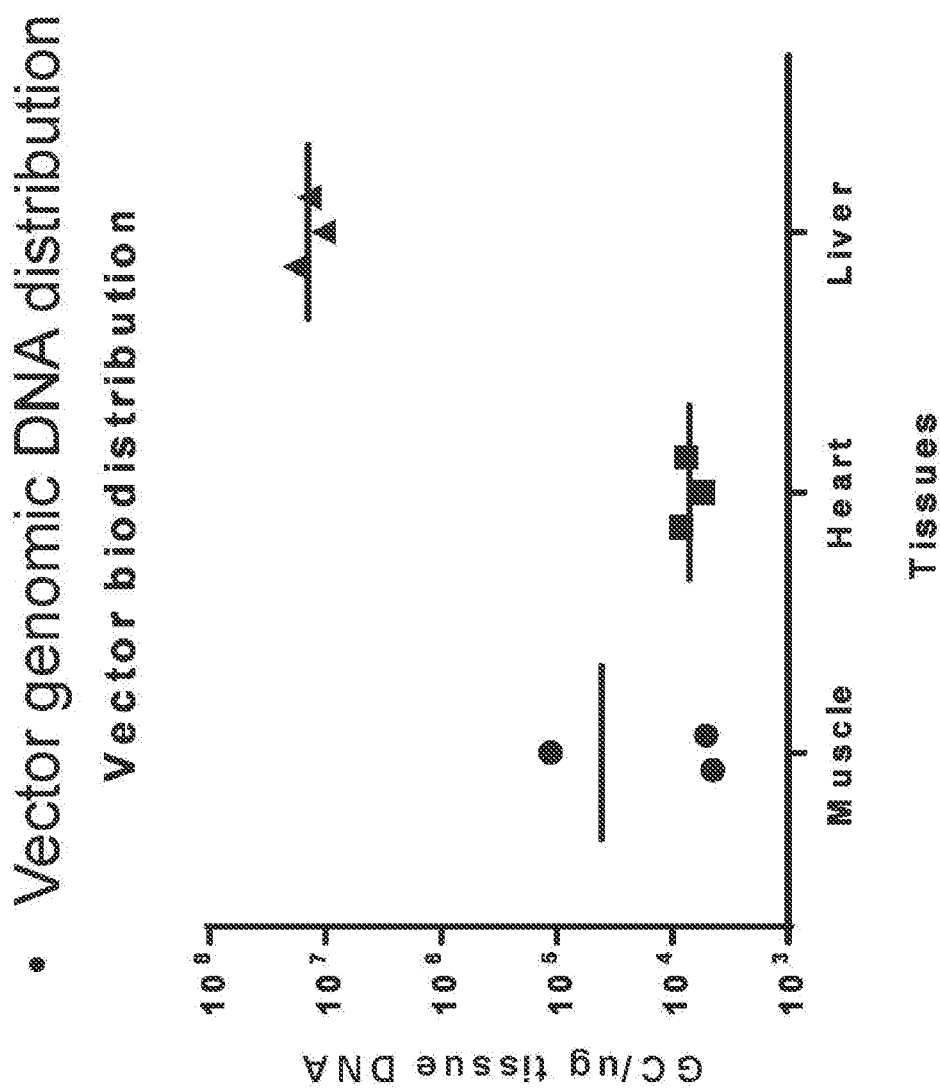
FIG. 18B shows the amounts of each AAV barcode variant injected into black 6 mice. The animals were sacrificed, tissue samples harvested, and DNA isolated from each of them. Total vector distribution for the three animals is shown in FIG. 18C. Actual vs. theoretical frequency of injected vector mix is shown in FIG. 18D.
Figure 18D:
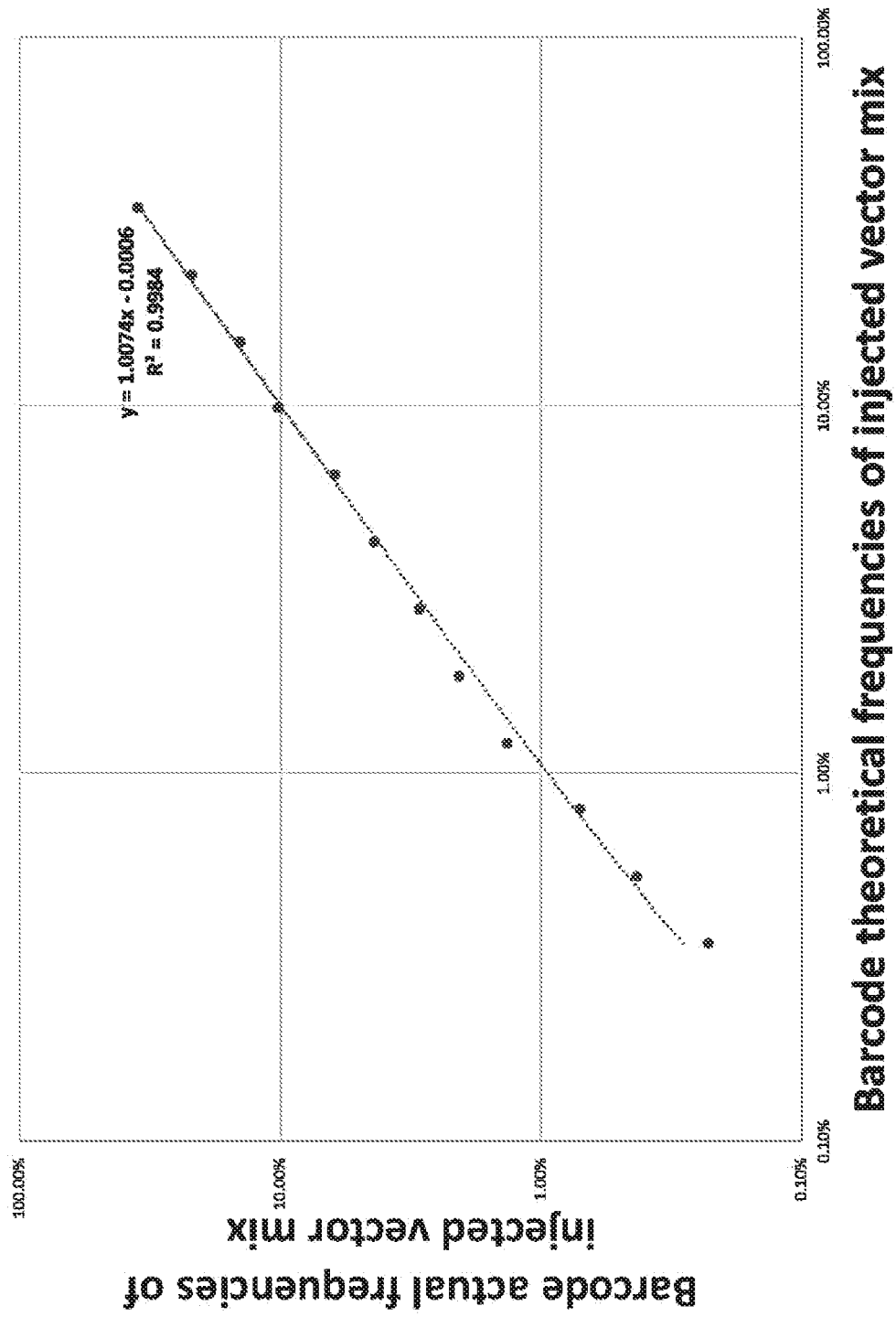

A female cynomolgus macaque (RA2362) was pre-screened for NAbs (FIG. 18A) and injected with AAVG2.TBG.eGFP.WPRE.bGH ($1\times10^{13}$ ddGC/kg, intravenously). The animal was euthanatized 7 days following treatment, and a necropsy was performed to isolate the liver and other tissues for analysis. GFP expression in the liver and spleen was evaluated on day 7 (FIGS. 18B and 18C). Levels of vector detected in various tissues are shown in FIG. 18D. Levels of GFP expression were evaluated in the livers animals that received AAVG2 (RA2362) or AAV8 and AAVG3 vectors (FIG. 18E-FIG. 1J). FIG. 18K shows levels of vector detected in various tissues from these animals.

Various AAV8 and AAVrh79 vectors were generated and, in some instances, multiple lots were produced. The yields of these AAV9 and AAVrh79 vector lots were compared (FIG. 19).

AAVrh79 vectors were assessed for deamidation as described in Example 1 for AAV8 and AAV9. The results show that the vectors contain four amino acids which are highly deamidated (N57, N263, N385, N514), which correspond to asparagines in asparagine-glycine pairs, based on the numbering of AAVrh79 (SEQ ID NO: 1). Lower deamidation percentages are consistently observed in residues N94, N254, N410.

| Modification AAVrh79 SEQ ID NO: 2 | WL1781S | WL1784S | WL1785S | WL1781S | WL1784S | WL1785S |
|---|---|---|---|---|---|---|
| Enzyme | Trypsin | Trypsin | Trypsin | Chymotrypsin | Chymotrypsin | Chymotrypsin |
| % Coverage | 89.6 | 93.9 | 92.4 | 91.3 | 88.7 | 89.9 |
| N57 + Deamidation | 99.3 | 80.9 | 82.9 | 99.6 | 80.1 | 86.4 |
| N94 + Deamidation | 10.4 | 9.6 | 9.9 | 10.5 | 9.4 | 10.0 |
| ~N254 + Deamidation | 16.0 | 15.8 | 16.4 | 15.3 | 16.3 | 16.7 |
| ~N263 + Deamidation | 84.3 | 93.5 | 95.3 | 82.9 | 89.5 | 90.6 |
| ~N305 + Deamidation | 3.2 | 2.5 | 2.4 | 3.2 | 2.6 | 2.3 |
| ~N385 + Deamidation | 79.1 | 100.0 | 100.0 | 76.9 | 96.6 | 92.9 |
| ~N410 + Deamidation | 2.0 | 17.8 | 23.9 | 2.0 | 17.6 | 23.0 |
| N479 + Deamidation | 2.0 | 2.0 | 1.9 | 2.0 | 2.0 | 2.0 |
| ~N514 + Deamidation | 100.0 | 97.2 | 97.0 | 97.4 | 94.6 | 98.1 |
| ~Q601 + Deamidation | 0.1 | | | | | |
| N653 + Deamidation | 1.3 | 1.1 | 1.4 | 1.3 | 1.1 | 1.5 |
| ~R487 + Methylation | 0.1 | 0.2 | 0.1 | 0.1 | 0.2 | 0.1 |
| D97 + Isomerization | 1.3 | | | 1.2 | | |
| S149 + Phosphorylation | 51.9 | 49.0 | 53.2 | 49.6 | 46.6 | 55.8 |
| ~S153 + Phosphorylation | 59.7 | 54.3 | 51.0 | 59.8 | 51.7 | 48.5 |
| ~S474 + Phosphorylation | | 7.3 | 4.5 | | 7.0 | 4.3 |
| ~T570 + Phosphorylation | 46.3 | 36.4 | 21.6 | 45.9 | 35.9 | 21.4 |
| ~S665 + Phosphorylation | 0.5 | 0.3 | 0.4 | 0.4 | 0.3 | 0.4 |
| W248 + Oxidation | | | 0.9 | | | |
| W307 + Oxidation | 1.7 | 1.2 | 1.5 | 1.8 | 1.3 | 1.5 |
| W307 + Oxidation to kynurenine | 0.3 | | 0.4 | | | |
| M405 + Oxidation | 5.8 | | | 6.0 | | |
| M437 + Oxidation | 15.0 | 5.2 | 95.4 | 15.1 | 5.3 | 12.0 |

-continued

| Modification AAVrh79 SEQ ID NO: 2 | WL1781S | WL1784S | WL1785S | WL1781S | WL1784S | WL1785S |
|---|---|---|---|---|---|---|
| M473 + Oxidation | 16.7 | 7.4 | 7.9 | 16.0 | 7.6 | 7.6 |
| W480 + Oxidation | 4.6 | 0.4 | 4.6 | 4.7 | 0.4 | 4.6 |
| W480 + Oxidation to kynurenine | | | 0.1 | | | |
| W505 + Oxidation | 2.4 | 2.2 | 1.3 | 2.5 | 2.1 | 1.3 |
| M526 + Oxidation | 19.0 | | | 18.6 | | |
| M544 + Oxidation | 30.9 | 20.7 | | 31.4 | 20.3 | |
| M561 + Oxidation | 15.6 | 7.7 | | 16.0 | 7.5 | |
| W621 + Oxidation to kynurenine | | | 0.0 | | | |
| M637 + Oxidation | 6.9 | 12.5 | 4.5 | 6.9 | 12.6 | 4.7 |
| W697 + Oxidation | | 0.5 | 0.6 | | 0.5 | 0.6 |

Example 4: Preparation of AAV8.2.08

As discussed in WO 2017/180854 (incorporated herein by reference), several AAV8 mutants were generated c41, c42, c46, g110, g113, g115 and g117 with mutations in the HVR.VIII region. As discussed in Gurda et al, the major ADK8 epitope lies in the HVR. VIII region (amino acids 586 to 591 using AAV8 vp1 numbering). Those mutants were tested in vitro for ADK8 resistance and some of them were tested in vivo for ADK8 resistance. See, e.g., Lochrie 2006 cited above.

Figure 24:
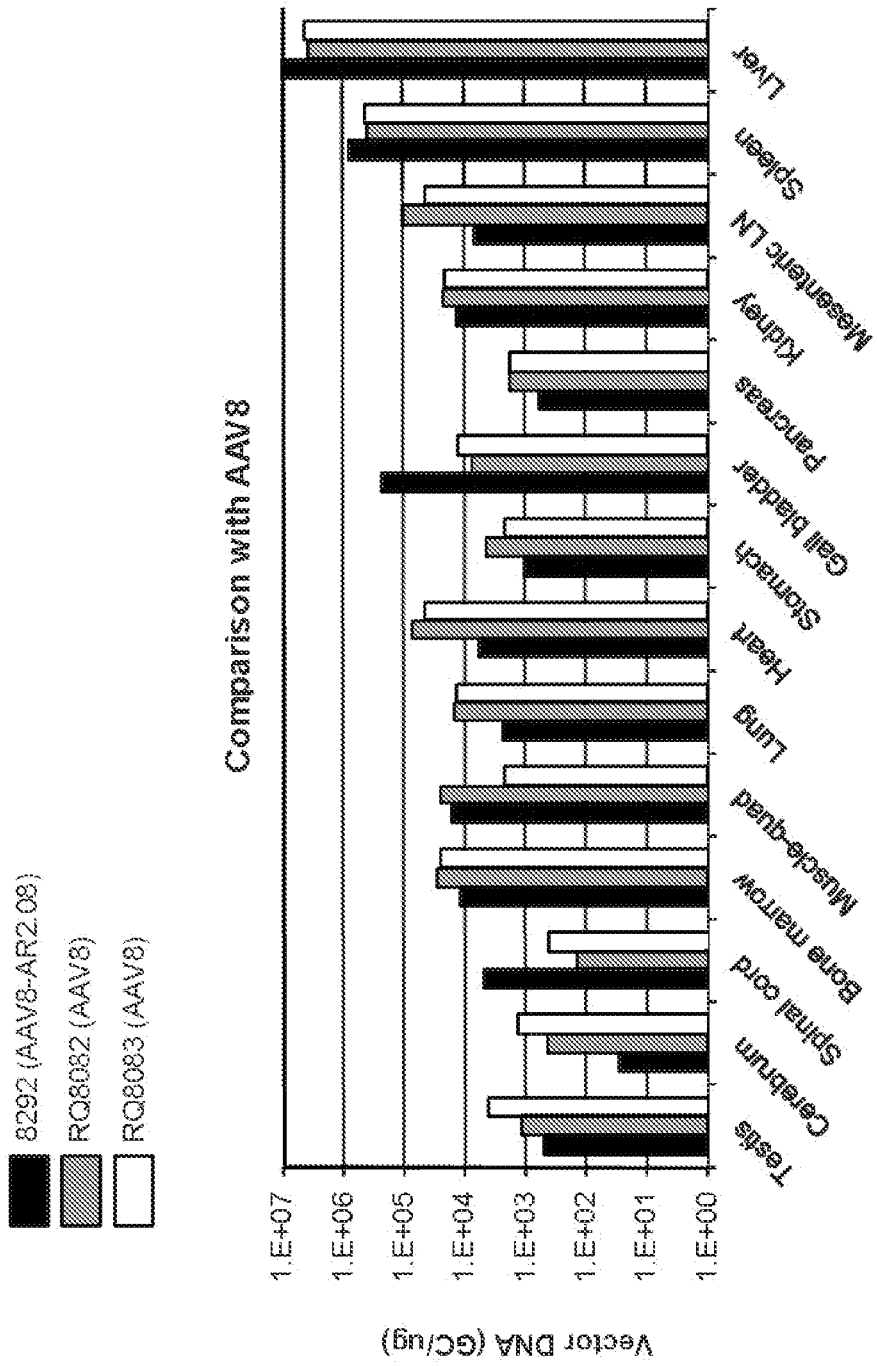
FIG. 24 shows AAV8.AR2.08 biodistribution in tissues (left most bar) compared with AAV8 (middle and right bars).
Figure 26A:
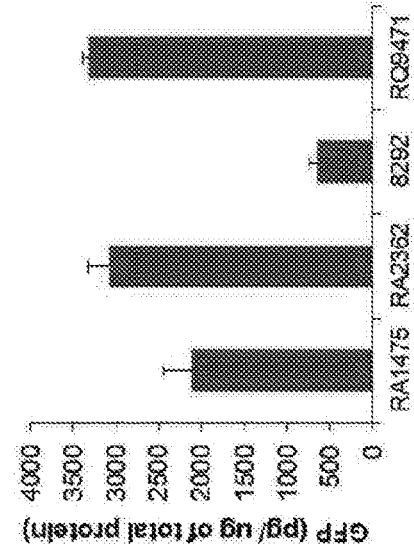
Figure 26B:
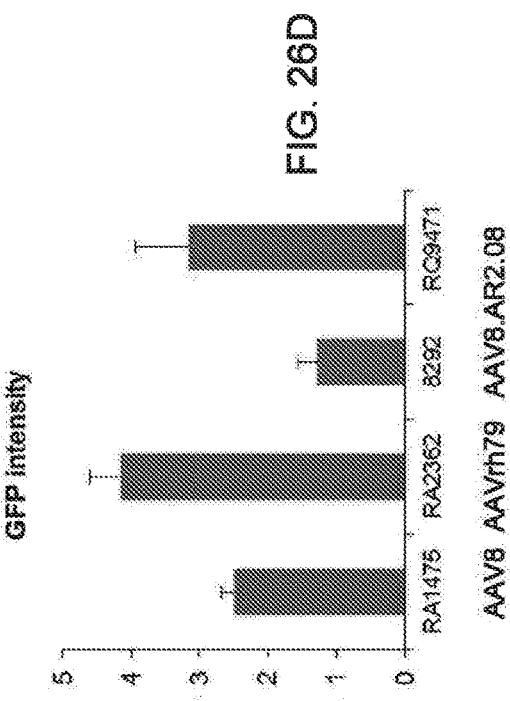
Figure 26C:
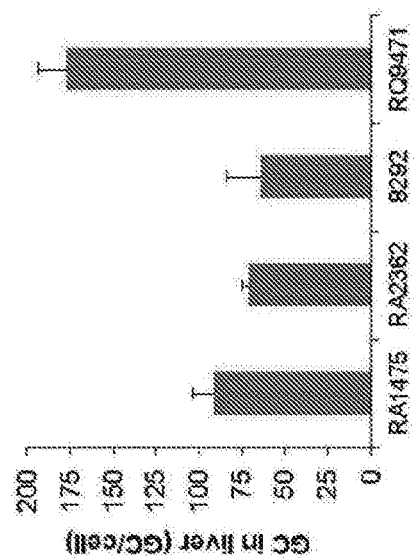
Figure 26D:
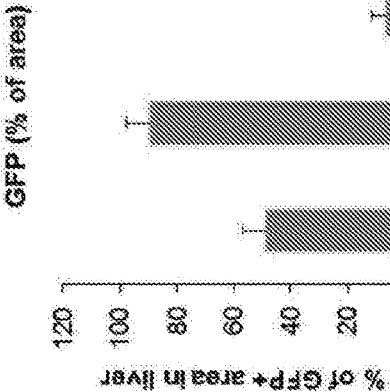
Figure 27A:
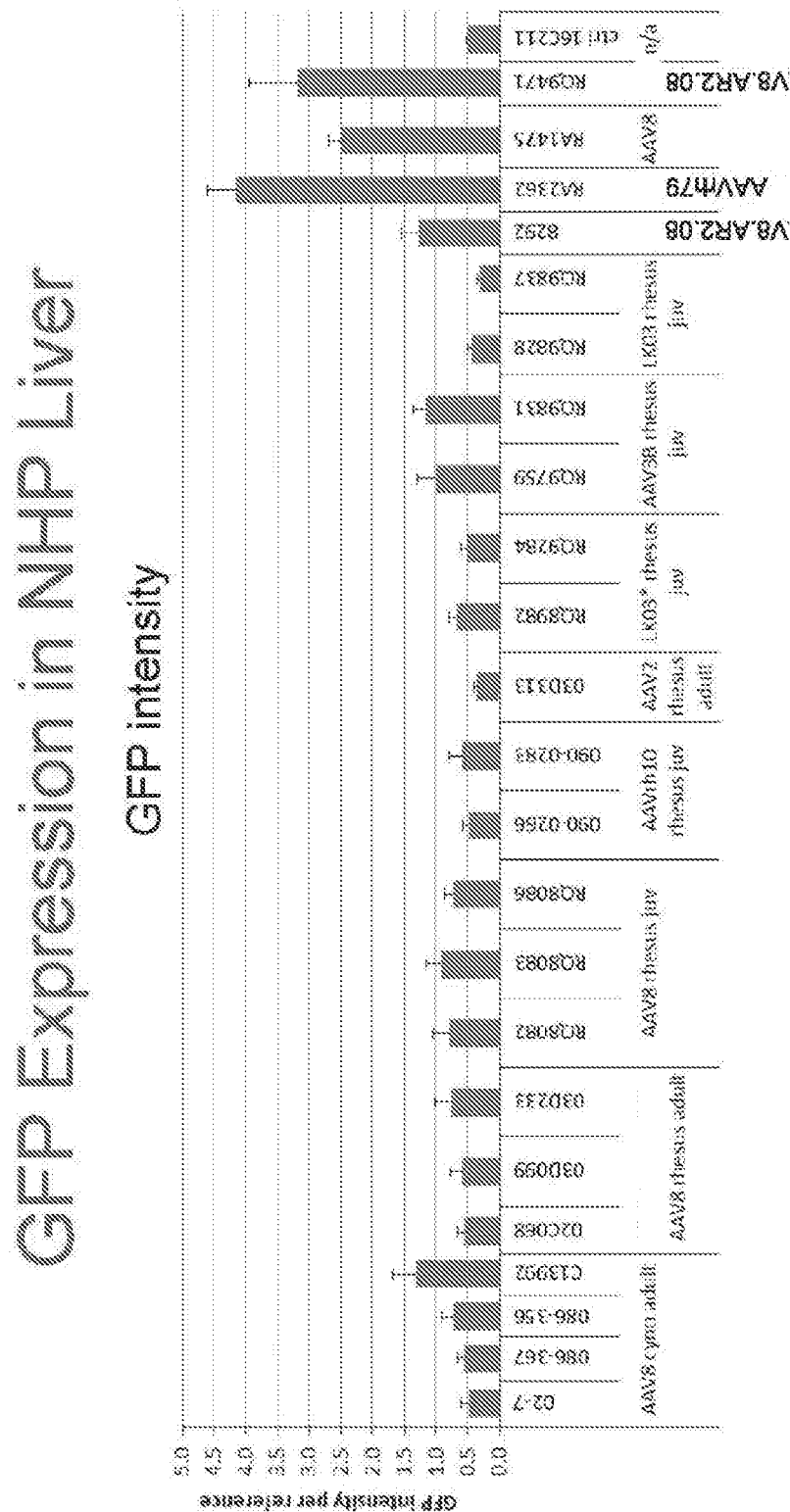
Figure 27B:
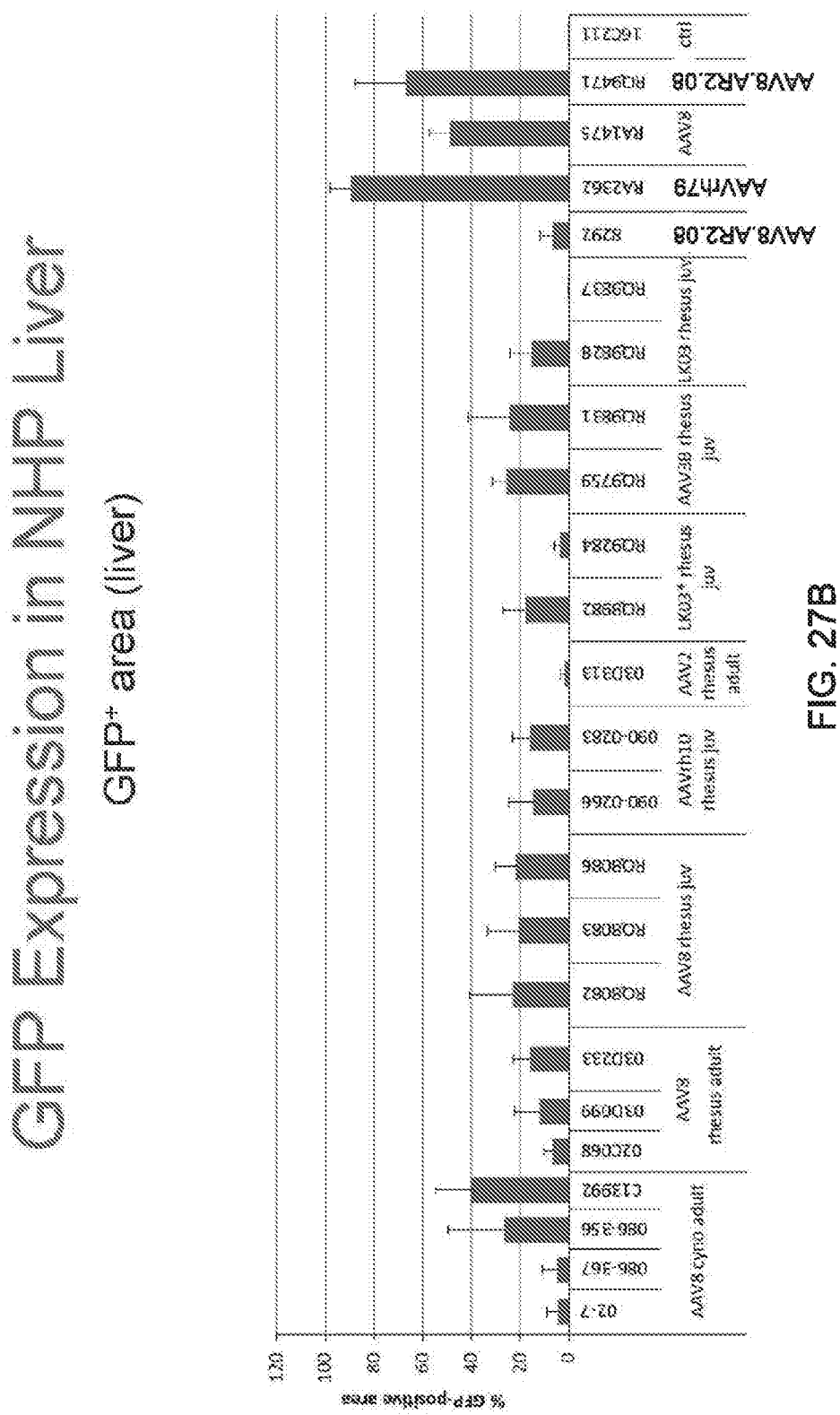

AR2.1-9 were randomly picked. AR2.25-61 were selected based on frequency. The randomly picked variants, as well as those higher-frequency ones, are alive, in terms of 6-well plate yield and Huh7 transduction. FIG. 24—shows expression in various tissues of AAV8.AR2.08 (left most set of bars).

Example 5: Deamidation of AAV8.AR2.08

The novel sequences of AAV8.AR2.08 are provided in SEQ ID NO: 17 and 18, respectively, which were designed as in Example 4.

A. Modifications AAV8.AR2.08 vectors were produced and assessed for modifications as described in Example 1 for AAV8. The results show that the vectors contain five amino acids which are highly deamidated (N57, N263, N385, N514, and N540), which correspond to asparagines in asparagine-glycine pairs, based on the numbering of AAV8.AR2.08 (SEQ ID NO: 18). Lower deamidation percentages are consistently observed in residues N94, N254, N410. In contrast to AAV8, deamidation is not observed at position N459 (average 7% in AAV8) or N499 (average 17% in AAV8).

| AAV8.AR2.08 Modification SEQ ID NO: 18 | WL1846CS | WL1846CS |
|---|---|---|
| Enzyme | Trypsin | Chymotrypsin |
| % Coverage | 97.4 | 92.3 |
| N57 + Deamidation | 90.7 | 89.5 |
| N94 + Deamidation | 9.0 | 9.3 |
| ~N254 + Deamidation | 11.8 | 11.7 |
| ~N263 + Deamidation | 88.6 | 86.3 |
| ~N305 + Deamidation | 5.8 | 5.5 |
| ~N385 + Deamidation | 86.1 | 83.3 |
| ~N514 + Deamidation | 100.0 | 99.6 |
| ~N521 + Deamidation | 2.0 | 2.1 |
| ~N540 + Deamidation | 78.6 | 80.5 |
| N590 + Deamidation | 0.4 | 0.4 |
| Q601 + Deamidation | 0.5 | 0.6 |
| N653 + Deamidation | 0.8 | 0.8 |
| N665 + Deamidation | 1.2 | 1.2 |
| D442 + Isomerization | 12.0 | |
| D584 + Isomerization | 1.0 | |
| ~S149 + Phosphorylation | 95.9 | 15.4 |
| ~T417 + Phosphorylation | 0.0 | |
| ~T454 + Phosphorylation | 0.1 | |
| ~T493 + Phosphorylation | 0.1 | |
| S600 + Phosphorylation | 1.1 | |
| ~T663 + Phosphorylation | 0.0 | |
| ~W22 + Oxidation | 1.0 | 1.0 |
| ~M204 + Oxidation | 0.1 | 0.1 |
| ~M212 + Oxidation | 2.9 | 2.9 |
| W248 + Oxidation | 0.7 | 0.7 |
| W307 + Oxidation | 0.6 | 0.6 |
| M405 + Oxidation | 0.3 | 0.3 |
| M437 + Oxidation | 70.3 | 21.0 |
| M473 + Oxidation | 1.7 | 1.7 |
| W480 + Oxidation | 0.3 | 0.3 |
| W505 + Oxidation | 0.6 | 0.6 |
| M526 + Oxidation | 1.0 | 1.0 |
| M561 + Oxidation | 1.0 | 1.0 |
| M607 + Oxidation | 2.4 | 2.5 |
| ~W609 + Oxidation | 0.1 | 0.1 |
| W621 + Oxidation | 0.8 | 0.8 |
| M637 + Oxidation | 2.9 | 3.0 |
| W697 + Oxidation | 0.2 | 0.2 |

B. Single cell RNA-seq reveals tissue localization and transcriptional signatures of transduced hepatocytes isolated from non-human primates following treatment with AAV8

Single cell RNA sequencing has proven to be a powerful technique to characterize the cellular transcriptome with unprecedented, single cell resolution. In our current work, we utilize single cell RNA-seq to study the transcriptional landscape of primary hepatocytes isolated from rhesus macaques following treatment with an AAV8 vector expressing GFP. Transcriptome analysis of FACS-sorted GFP+ and GFP-cells reveals tissue localization of transduced cells within the hepatic lobule as well as genes and regulatory pathways involved in hepatocyte transduction and the regulation of transgene expression.

For our study design, rhesus macaques were treated with either 1×1013 ddGC/kg AAV8.TBG.EGFP.WPRE (n=1) or 1×1013 ddGC/kg AAV8.2.08.TBG.EGFP.WPRE (AAV8 variant, n=1). Animals were euthanatized 7 days following treatment, and necropsies were performed to isolate the liver from both animals. Following treatment with collagenase and gradient centrifugation, isolated hepatocytes were FACS sorted by GFP transgene expression onto BD Precise™ 96 well plates. 192 single cells were isolated from each animal (96 GFP+ and 96 GFP−) and were subsequently used to prepare single cell RNA-seq libraries following the standard BD Precise™ protocol. Data were analyzed using the Seurat, Scran, and Scater packages in R in order to determine differentially expressed transcripts between GFP− and GFP+ sorted cells and to perform spatial reconstruction of isolated cells within the hepatic lobule using established transcriptional expression signatures.

AAV8.AR2.08 was found to have an increased liver tropism and exhibited a 1.5-fold increase in transduction efficiency as compared to AAV8. Single cell transcriptome analysis of sorted hepatocytes reveals transgene-expressing cells are evenly distributed across the hepatic lobule, showing a slight preference for the periportal region, which was also observed by histopathology. Interestingly, a subpopulation of sorted GFP− cells are found to express the transgene transcript at levels comparable to sorted GFP+ cells, suggesting that these cells are in fact transduced and express transgene mRNA, despite the absence of the detectable levels of translated protein. Comparing the transcriptional profiles of GFP− and GFP+ cells reveals differentially expressed transcripts involved in viral mRNA translation, elucidating possible pathways involved in the regulation of transgene protein expression in transduced cells.

Figure 28:
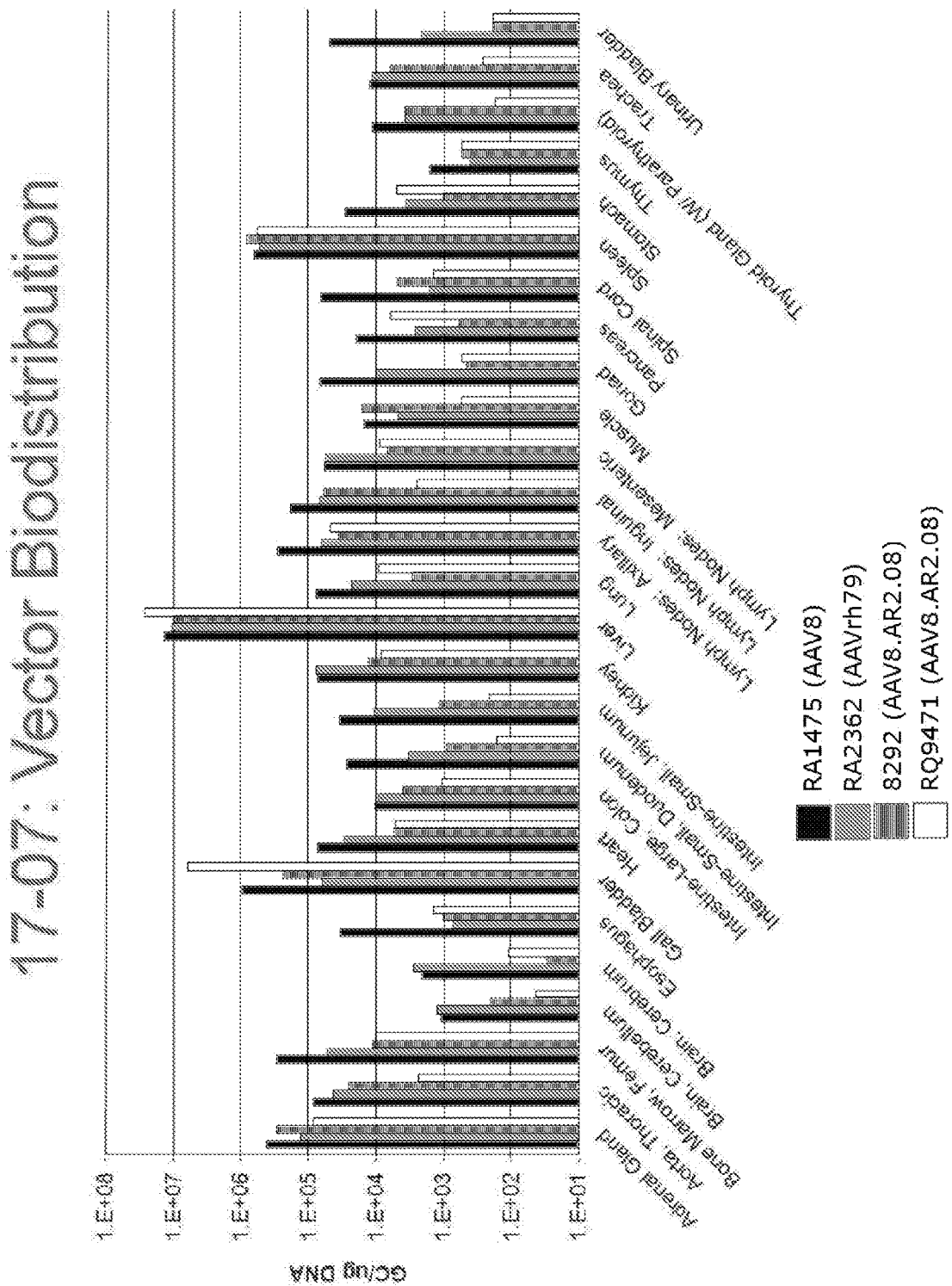
Figure 29:
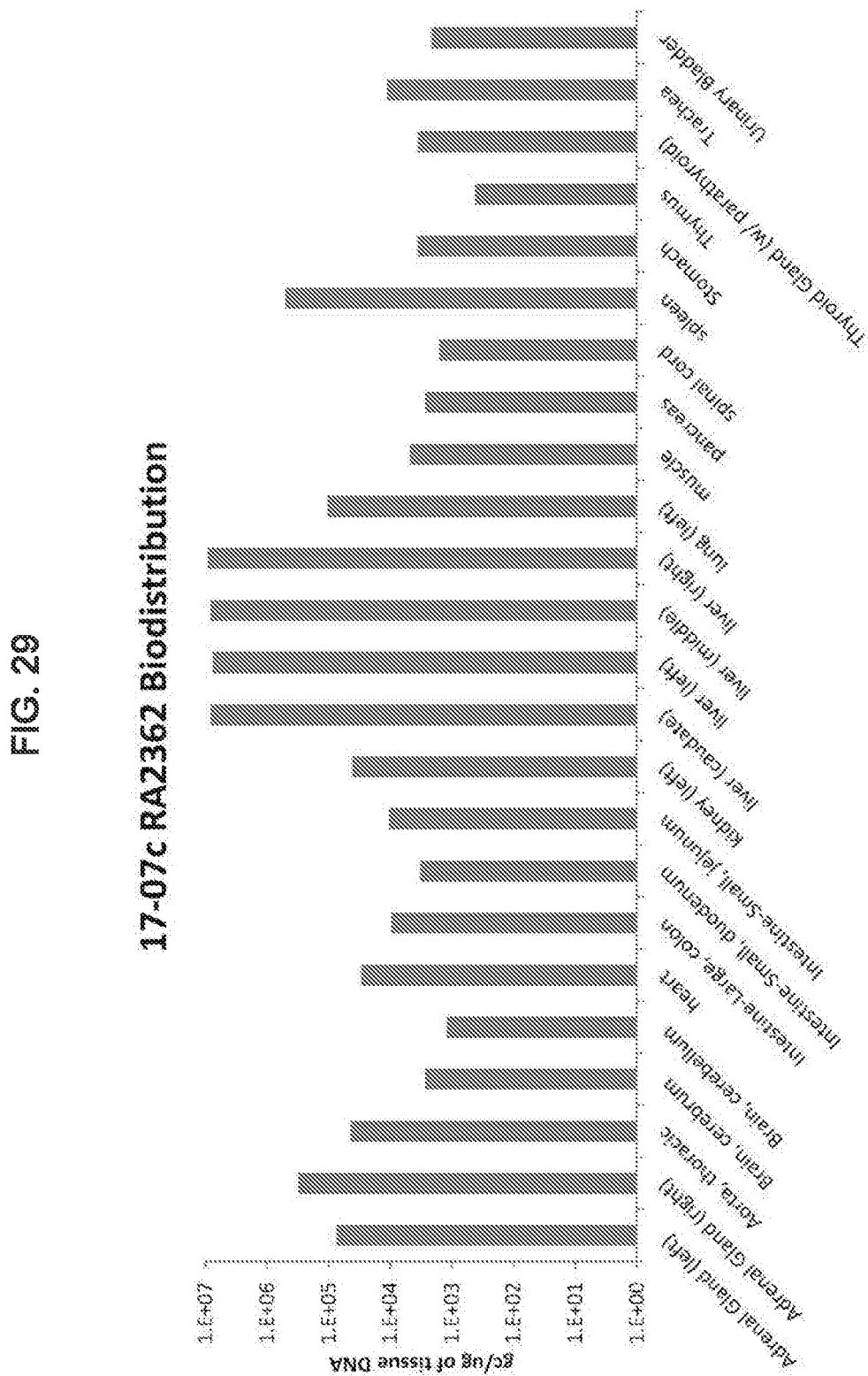
FIG. 29 shows biodistribution of AAVrh79 vector detected in various tissues.

C. Isolation of an adeno-associated virus 8 variant with better liver transduction and higher liver specificity in nonhuman primates with directed evolution through a human liver xenograft model To derive AAV variants with better transduction and higher specificity, we performed AAV-directed evolution, using saturation mutagenesis targeting surface exposed sites on the capsid of AAV8, the benchmark for liver gene therapy, followed by two rounds of in vivo enrichment in human liver xenograft mouse model, and isolated an AAV8 variant called AAV8.2.08. After intravenous injection into nonhuman primates at a dose of 1e13 genome copies (GC)/kg body weight, vector genome copies delivered by AAV8.AR2.08 in various organs (including lung, heart, stomach, pancreas, kidney, and mesenteric lymph nodes) decreased while the delivery increased in liver, compared to AAV8, implying better liver transduction and higher tissue specificity. Next generation sequencing indicated significant enrichment of AAV8.AR2.08 during the in vivo selections, demonstrating the potential of the approach for isolating capsids with new and improved tropisms. Other comparisons are shown in FIGS. 21 to 27). FIG. 28 shows biodistribution of AAV8.AR2.08 and AAV8.

D. Barcoding

Figure 19A:
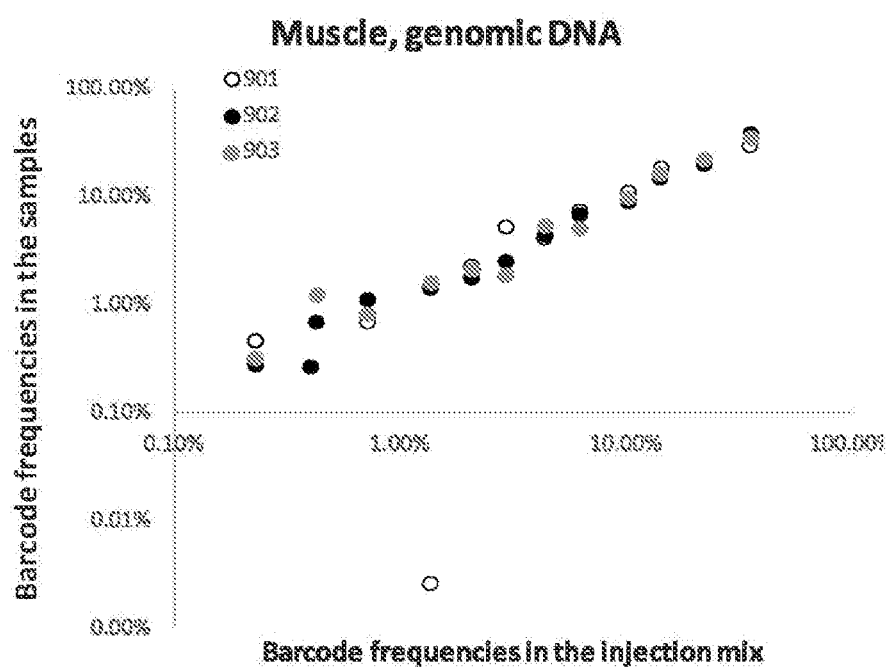
Figure 19C:
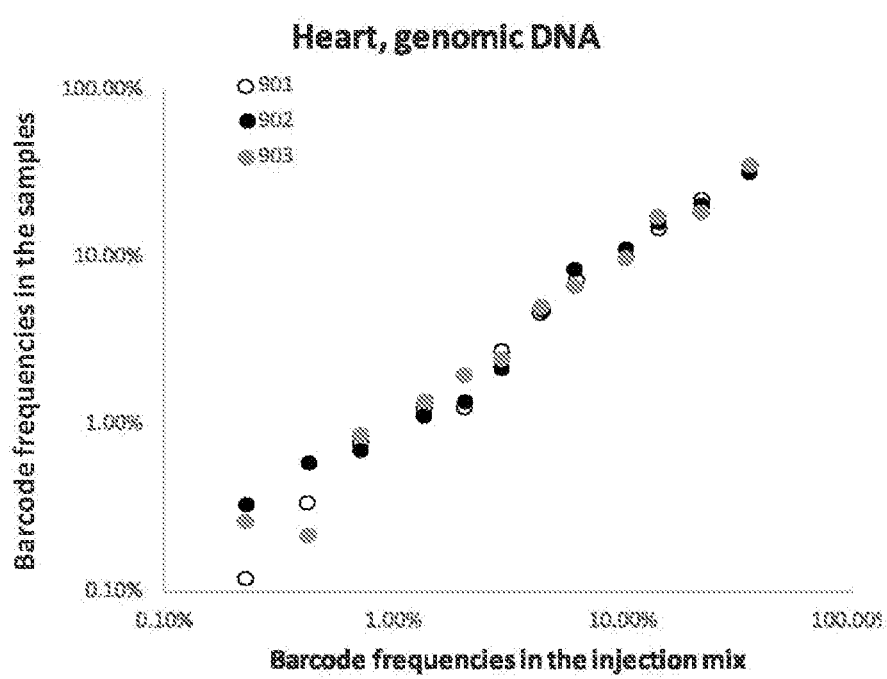
Figure 19D:
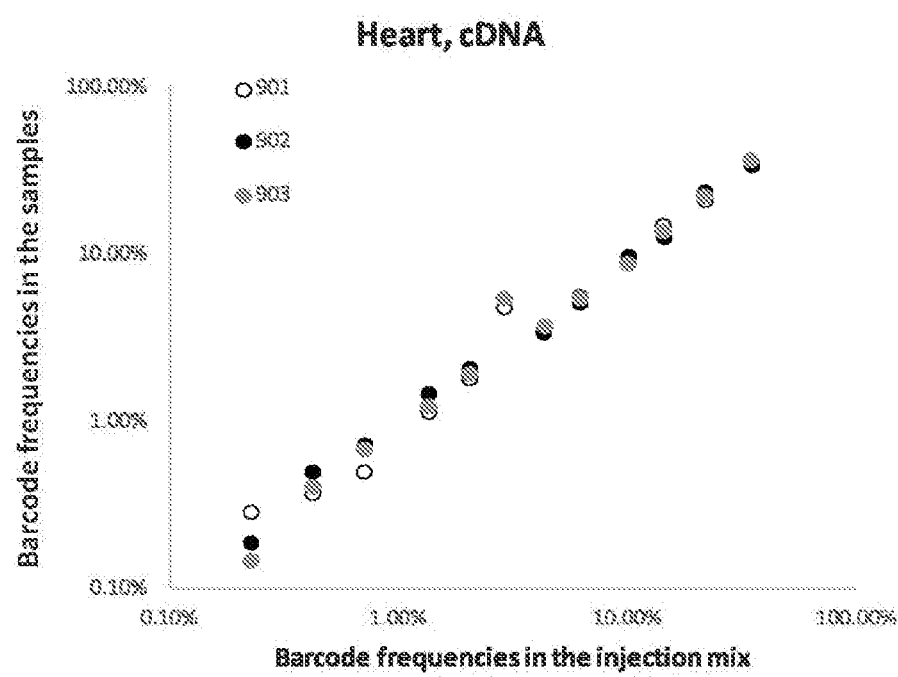
Figure 20C:
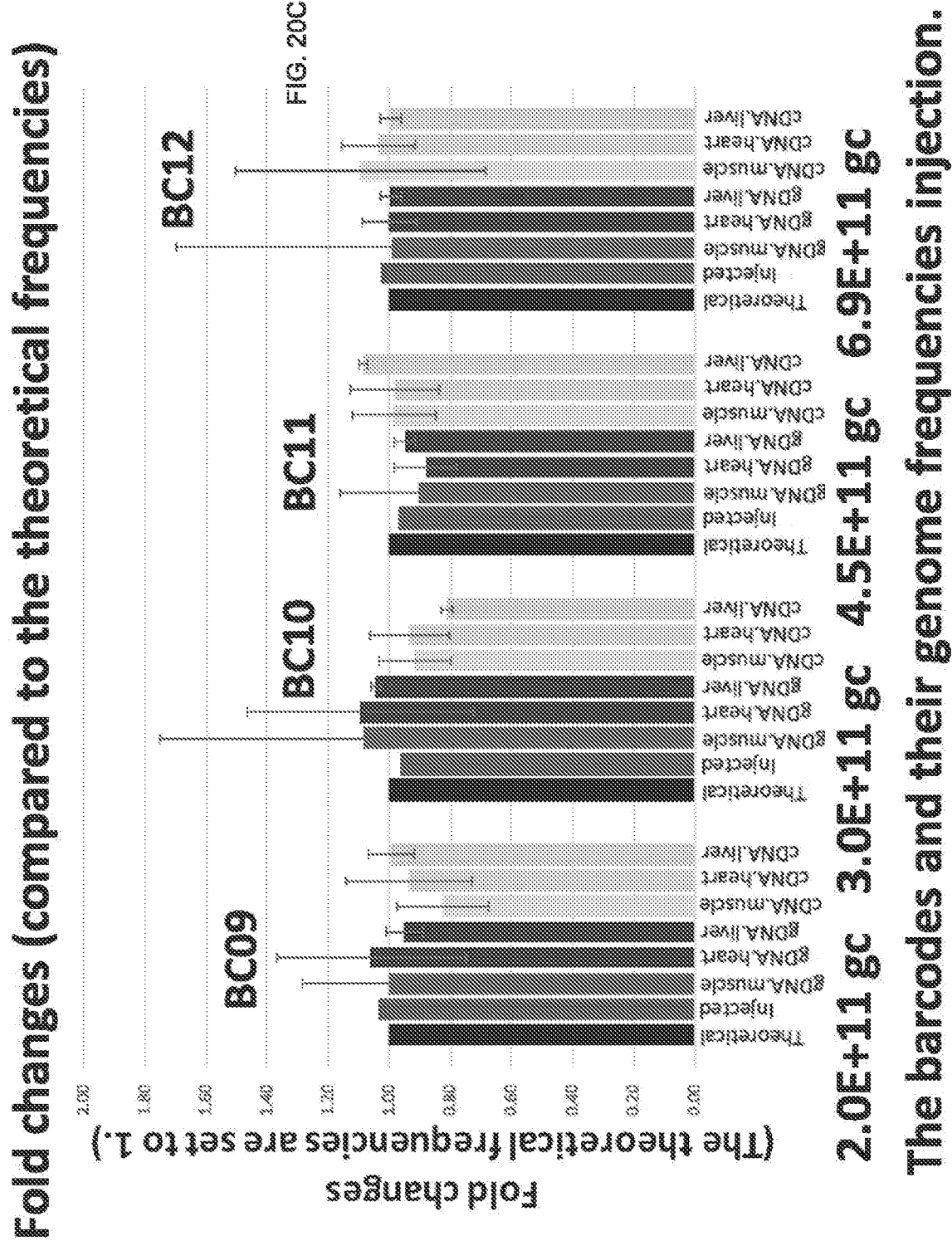
Figure 21:
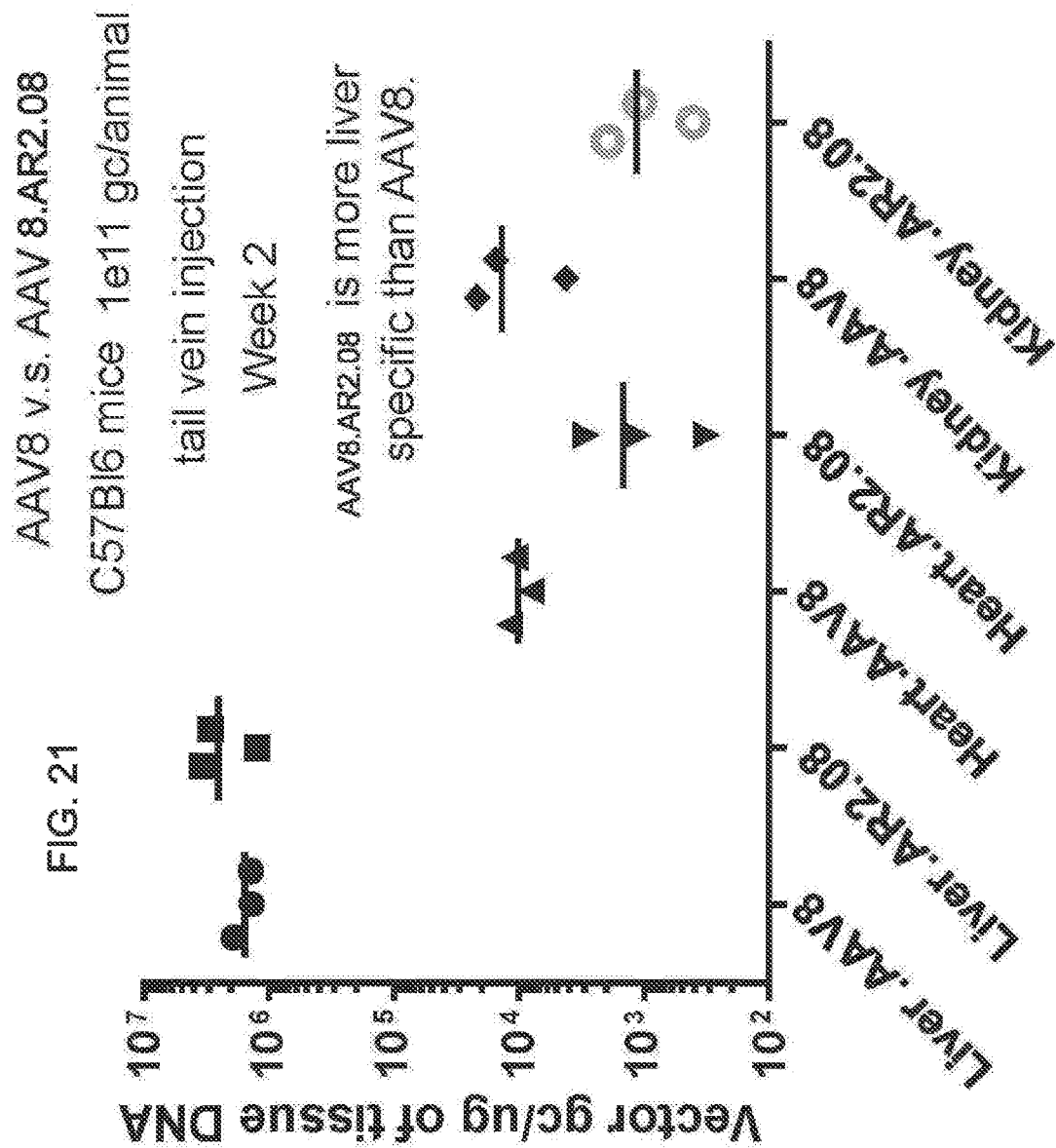
FIGS. 21 and 22 show AAV8.AR2.08 biodistribution in mice as compared to AAV8. The results show that AAV8.AR2.08 is more liver specific than AAV8.
Figure 22:
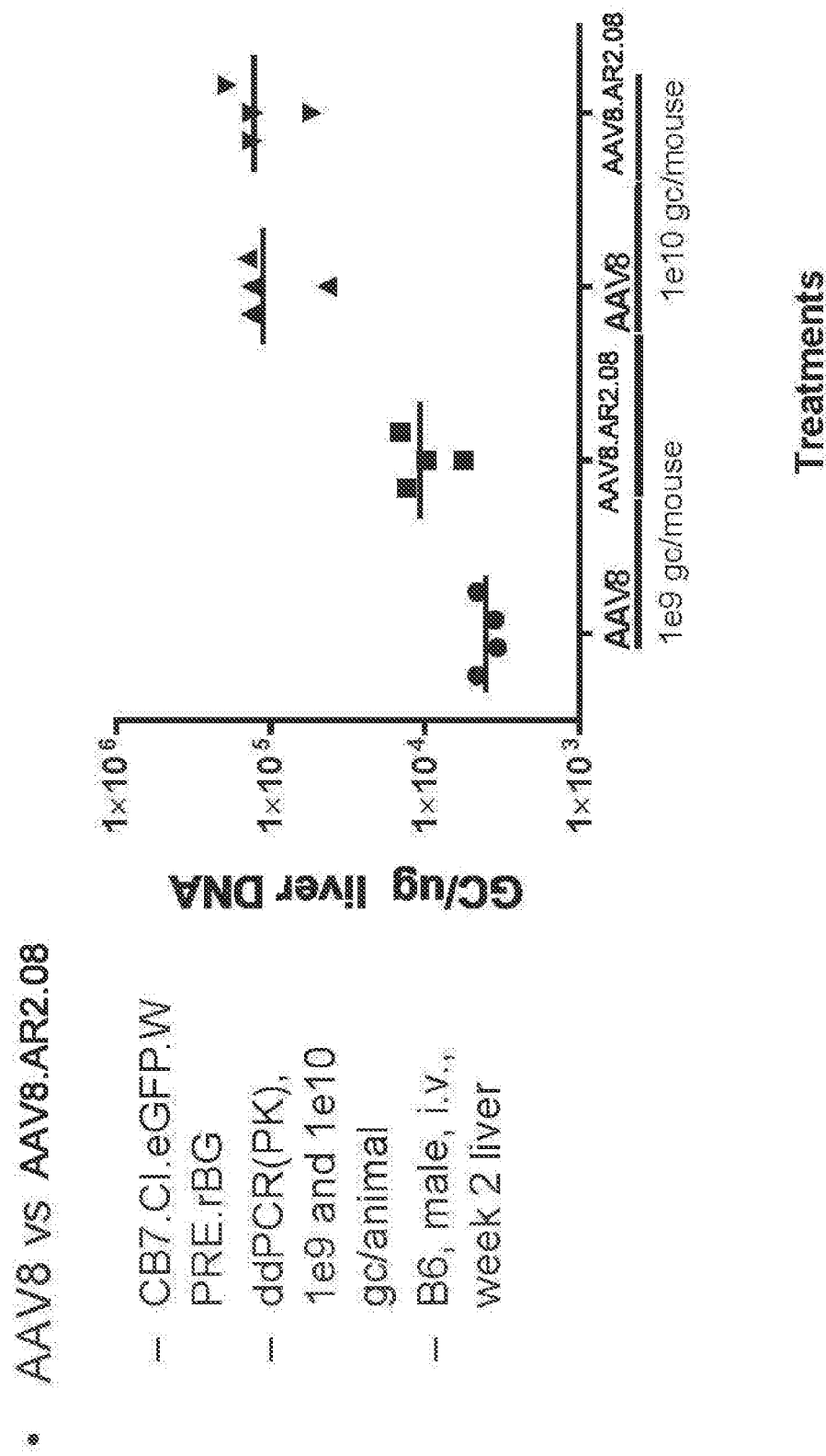

Black 6 mice were injected I.V. with $2\times10^{12}$ GC/mouse of a mixture of rAAVG3 derived from 12 preparations (FIG. 18B). Each preparation contains a separate barcode within the vector genome allowing identification of the specific preparation (FIG. 18A). After two weeks, animals were euthanized, and tissues harvested. As predicted, rAAVG3 expression was higher in liver than heart or muscle. FIG. 18C. Tissue distribution experiments show that actual frequencies match theoretical frequencies of barcodes in injected vector mix (FIG. 18D, total; FIG. 19A, 19B, muscle; FIG. 19C, 19D, heart; and FIG. 19E, 19F, liver), with slight anomalies in BC02 and BC06 (FIGS. 20A-20C).

All documents cited in this specification are incorporated herein by reference. U.S. Provisional Patent Application Nos. 62/722,388 and 62/722,382, both filed Aug. 24, 2018, U.S. Provisional Patent Application Nos. 62/703,670 and 62/703,673, both filed Jul. 26, 2018, U.S. Provisional Patent Application Nos. 62/677,471 and 62/677,474, both filed May 29, 2018, U.S. Provisional Patent Application No. 62/667,585, filed May 29, 2018, and U.S. Provisional Patent Application No. 62/635,964, filed Feb. 27, 2018 are incorporated herein by reference. U.S. Provisional Patent Application No. 62/667,881, filed May 7, 2018, U.S. Provisional Patent Application No. 62/667,888, filed May 7, 2018, U.S. Provisional Patent Application No. 62/667,587, filed May 6, 2018, U.S. Provisional Patent Application No. 62/663,797, filed Apr. 27, 2018, U.S. Provisional Patent Application No. 62/663,788, filed Apr. 27, 2018, U.S. Provisional Patent application No. 62/635,968, filed Feb. 27, 2018 are incorporated by reference. The SEQ ID NO which are referenced herein and which appear in the appended Sequence Listing are incorporated by reference. While the invention has been described with reference to particular embodiments, it will be appreciated that modifications can be made without departing from the spirit of the invention. Such modifications are intended to fall within the scope of the appended claims.

The invention claimed is:

1. A recombinant adeno-associated virus (rAAV) which comprises an AAVrh79 capsid comprising AAVrh79 vp1 proteins, AAVrh79 vp2 proteins, and AAVrh79 vp3 proteins comprising glutamic acid (E) at position 67 in the AAVrh79 vp1 proteins and arginine (R) at position 169 in the AAVrh79 vp1 and AAVrh79 vp2 proteins, wherein the AAVrh79 vp1 proteins contain amino acid modifications comprising at least 50% to 100% deamidated asparagines (N) in asparagine-glycine pairs in each of positions N57, N263, N385 and N514 relative to SEQ ID NO: 2, as determined by mass spectrometry, the AAVrh79 vp2 proteins contain amino acid modifications comprising at least 50% to 100% deamidated asparagines (N) in asparagine-glycine pairs in each of positions N263, N385 and N514 relative to SEQ ID NO: 2, as determined by mass spectrometry, and the AAVrh79 vp3 proteins contain amino acid modifications comprising at least 50% to 100% deamidated asparagines (N) in asparagine-glycine pairs in each of positions N57, N263, N385, and N514 relative to SEQ ID NO: 2, as determined by mass spectrometry, wherein the deamidated asparagines are deamidated to an aspartic acid, an isoaspartic acid, an interconverting aspartic acid/isoaspartic acid pair, or combinations thereof,
wherein the rAAV further comprises a vector genome in the AAVrh79 capsid, the vector genome comprising a nucleic acid molecule comprising AAV inverted terminal repeat (ITR) sequences and a non-AAV nucleic acid sequence encoding a product operably linked to sequences which direct expression of the product in a host cell.

2. The rAAV according to claim 1, wherein the capsid further comprises deamidated glutamine(s) which are deamidated to (α)-glutamic acid, γ-glutamic acid, an interconverting (α)-glutamic acid/γ-glutamic acid pair, or combinations thereof.

3. The rAAV according to claim 1, wherein the AAVrh79 capsid comprises subpopulations having one or more of:
  (a) at least 75% of asparagines (N) in asparagine-glycine pairs located at position 57 of the vp1 proteins are deamidated, based on the numbering of SEQ ID NO:2;
  (b) at least 75% of N in asparagine-glycine pairs in position 263 of the vp1, vp2 and vp3 proteins are deamidated, based on the residue numbering of the amino acid sequence of SEQ ID NO: 2,
  (c) at least 70% of N in asparagine-glycine pairs in position 385 of the vp1, vp2 and vp3 proteins are deamidated, based on the residue numbering of the amino acid sequence of SEQ ID NO: 2; and/or
  (d) at least 85% of N in asparagine-glycine pairs in position 514 of the vp1, vp2 and vp3 proteins are deamidated, based on the residue numbering of the amino acid sequence of SEQ ID NO: 2.

4. The rAAV according to claim 1, wherein the rAAVrh79 capsid comprises a subpopulation of vp1 in which 75% to 100% of the N at position 57 of the vp1 proteins are deamidated, as determined using mass spectrometry.

5. The rAAV according to claim 1, wherein the rAAVrh79 capsid comprises subpopulations of vp1 proteins, vp2 proteins, and/or vp3 proteins in which 75% to 100% of the N at position 263, based on the numbering of SEQ ID NO:2, are deamidated as determined using mass spectrometry.

6. The rAAV according to claim 1, wherein the rAAVrh79 capsid comprises subpopulations of vp1 proteins, vp2 proteins, and/or vp3 proteins in which 75% to 100% of the N at position 385, based on the numbering of SEQ ID NO:2, are deamidated as determined using mass spectrometry.

7. The rAAV according to claim 1, wherein the rAAVrh79 capsid comprises subpopulations of vp1 proteins, vp2 proteins, and/or vp3 proteins in which 75% to 100% of the N at position 514, based on the numbering of SEQ ID NO:2, are deamidated.

8. The rAAV according to claim 1, wherein the nucleic acid sequence encoding the vp1 proteins, vp2 proteins and/or vp3 proteins is SEQ ID NO: 1, or a nucleic acid sequence at least 80% to at least 99% identical to SEQ ID NO: 1 which encodes the amino acid sequence of SEQ ID NO:2.

9. The rAAV according to claim 8, wherein the nucleic acid sequence is at least 80% to 97% identical to SEQ ID NO: 1.

10. The rAAV according to claim 1, wherein the rAAVrh79 capsid comprises subpopulations of vp1 proteins, vp2 proteins and/or vp3 proteins which further comprise 1% to about 40% deamidation in at least one or more of positions N94, N254, N305, N410, N479, N653, or combinations thereof.

11. The rAAV according to claim 1, wherein the rAAVrh79 capsid comprises subpopulations of vp1 proteins, vp2 proteins and/or vp3 proteins which further comprise one or more modifications consisting of: acetylated lysine, phosphorylated serine and/or threonine, isomerized aspartic acid, oxidized tryptophan and/or methionine, or an amidated amino acid.

12. The rAAV according to claim 1, wherein the AAV ITR sequences are a 5' ITR and a 3' ITR from AAV2.

13. A composition comprising an AAV according to claim 1 and a pharmaceutical carrier, excipient and/or diluent.

14. A production cell in vitro comprising the rAAV according to claim 1.

15. An rAAV production system useful for producing an rAAV according to claim 1 in a production cell, wherein the production system comprises:
  (a) an AAV capsid nucleic acid sequence encoding the amino acid sequence of SEQ ID NO:2;
  (b) a nucleic acid molecule suitable for packaging into the AAV capsid, said nucleic acid molecule comprising at least one AAV inverted terminal repeat (ITR), a functional rep gene and a non-AAV nucleic acid sequence encoding a gene product operably linked to sequences which direct expression of the product in a host cell; and
  (c) sufficient AAV rep functions and helper functions to permit packaging of the nucleic acid molecule into the AAV capsid.

16. The system according to claim 15, wherein the nucleic acid sequence of (a) comprises at least SEQ ID NO: 1, or a nucleic acid sequence at least 70% to at least 99% identical to SEQ ID NO: 1 which encodes the amino acid sequence of SEQ ID NO:2.

17. The system according to claim 15, wherein the production cell culture comprises human embryonic kidney 293 cells.

18. The system according to claim 15, wherein the AAV rep is from AAV2.

19. The rAAV according to claim 1, wherein the AAVrh79 capsid comprises less than 1% deamidation at positions other than N57, N263, N365 and/or N514.

20. The rAAV according to claim 1, wherein the AAVrh79 vp1 proteins contain amino acid modification comprising at least 70% to 100% deamidated asparagines (N) in asparagine-glycine pairs in each of positions N57, N263, N385 and N514 relative to SEQ ID NO: 2, as determined by mass spectrometry, the AAVrh79 vp2 proteins contain amino acid modification comprising at least 70% to 100% deamidated asparagines (N) in asparagine-glycine pairs in each of positions N263, N385 and N514 relative to SEQ ID NO: 2, as determined by mass spectrometry, and the AAVrh79 vp3 proteins contain amino acid modifications comprising at least 70% to 100% deamidated asparagines (N) in asparagine-glycine pairs in each of positions N263, N385, and N514 relative to SEQ ID NO: 2, as determined by mass spectrometry.

21. A recombinant adeno-associated virus (rAAV) which comprises an AAVrh79 capsid comprising AAVrh79 vp1 proteins, AAVrh79 vp2 proteins, and AAVrh79 vp3 proteins produced by expression of a nucleic acid sequence which encodes the amino acid sequence of 1 to 738 of SEQ ID NO: 2,
wherein the rAAV further comprises a vector genome in the AAVrh79 capsid, the vector genome comprising a nucleic acid molecule comprising AAV inverted terminal repeat (ITR) sequences and a non-AAV nucleic acid sequence encoding a product operably linked to sequences which direct expression of the product in a host cell.

22. The rAAV according to claim 21, wherein the AAVrh79 capsid comprising AAVrh79 vp1 proteins, AAVrh79 vp2 proteins, and AAVrh79 vp3 proteins is produced by expression from SEQ ID NO: 1.

23. A composition comprising an AAV according to claim 21 and a pharmaceutical carrier, excipient and/or diluent.

24. A method of generating a recombinant AAV comprising an AAV capsid comprising the steps of culturing a host cell containing:
   (a) a nucleic acid sequence encoding an AAVrh79 vp1 capsid protein having amino acids 1 to 738 of SEQ ID NO: 2, wherein the AAVrh79 vp1 coding sequence is operably linked to regulatory sequences which permit expression of AAVrh79 vp1 proteins, AAVrh79 vp2 proteins and AAVrh79 vp3 proteins in the cultured host cell;
   (b) a functional rep gene;
   (c) a nucleic acid molecule which is a vector genome having a nucleic acid sequence comprising an AAV 5' inverted terminal repeats (ITRs), an expression cassette comprising a non-AAV nucleic acid sequence encoding a product, and an AAV 3' ITR sequence and a transgene; and
   (d) sufficient helper functions to permit packaging of the vector genome into the AAV capsid.

25. A cultured host cell comprising a recombinant nucleic acid molecule comprising:
   (a) a nucleic acid sequence encoding an AAVrh79 vp1 capsid protein having amino acids 1 to 738, of SEQ ID NO: 2, wherein the AAVrh79 vp1 coding sequence is operably linked to regulatory sequences which permit expression of AAVrh79 vp1 proteins, AAVrh79 vp2 proteins and AAVrh79 vp3 proteins in the cultured host cell;
   (b) a functional rep gene;
   (c) a nucleic acid molecule which is a vector genome having a nucleic acid sequence comprising an AAV 5' inverted terminal repeat (ITR), an expression cassette comprising a non-AAV nucleic acid sequence encoding a product, and an AAV 3' ITR sequence and a transgene; and
   (d) sufficient helper functions to permit packaging of the vector genome into an AAV capsid.

* * * * *

SEQUENCE LISTING

<160> NUMBER OF SEQ ID NOS: 128

<210> SEQ ID NO 1
<211> LENGTH: 2214
<212> TYPE: DNA
<213> ORGANISM: Artificial Sequence
<220> FEATURE:
<223> OTHER INFORMATION: AAVrh79
<220> FEATURE:
<221> NAME/KEY: CDS
<222> LOCATION: (1)..(2214)

<400> SEQUENCE: 1

| | | | | | | | | | | | | | | | | |
|---|---|---|---|---|---|---|---|---|---|---|---|---|---|---|---|---|
| atg | gct | gct | gac | ggt | tat | ctt | cca | gat | tgg | ctc | gag | gac | aac | ctc | tct | 48 |
| Met | Ala | Ala | Asp | Gly | Tyr | Leu | Pro | Asp | Trp | Leu | Glu | Asp | Asn | Leu | Ser | |
| 1 | | | | 5 | | | | | 10 | | | | | 15 | | |
| gag | ggc | att | cgc | gag | tgg | tgg | gac | ctg | aaa | cct | gga | gcc | ccc | aag | ccc | 96 |
| Glu | Gly | Ile | Arg | Glu | Trp | Trp | Asp | Leu | Lys | Pro | Gly | Ala | Pro | Lys | Pro | |
| | | | 20 | | | | | 25 | | | | | 30 | | | |
| aag | gcc | aac | cag | cag | aag | cag | gac | gac | ggc | cgg | ggt | ctg | gtg | ctt | cct | 144 |
| Lys | Ala | Asn | Gln | Gln | Lys | Gln | Asp | Asp | Gly | Arg | Gly | Leu | Val | Leu | Pro | |
| | | 35 | | | | | 40 | | | | | 45 | | | | |
| ggc | tac | aag | tac | ctc | gga | ccc | ttc | aac | gga | ctc | gac | aag | ggg | gag | ccc | 192 |
| Gly | Tyr | Lys | Tyr | Leu | Gly | Pro | Phe | Asn | Gly | Leu | Asp | Lys | Gly | Glu | Pro | |
| 50 | | | | | 55 | | | | | 60 | | | | | | |
| gtc | aac | gag | gcg | gac | gcc | gcg | gcc | ctc | gag | cac | gac | aag | gcc | tac | gac | 240 |
| Val | Asn | Glu | Ala | Asp | Ala | Ala | Ala | Leu | Glu | His | Asp | Lys | Ala | Tyr | Asp | |
| 65 | | | | | 70 | | | | | 75 | | | | | 80 | |
| cag | cag | ctc | aaa | gcg | ggt | gac | aat | ccg | tac | ctg | cgg | tat | aac | cac | gcc | 288 |
| Gln | Gln | Leu | Lys | Ala | Gly | Asp | Asn | Pro | Tyr | Leu | Arg | Tyr | Asn | His | Ala | |
| | | | | 85 | | | | | 90 | | | | | 95 | | |
| gac | gcc | gag | ttt | cag | gag | cgt | ctg | caa | gaa | gat | acg | tct | ttt | ggg | ggc | 336 |
| Asp | Ala | Glu | Phe | Gln | Glu | Arg | Leu | Gln | Glu | Asp | Thr | Ser | Phe | Gly | Gly | |
| | | | | 100 | | | | | 105 | | | | | 110 | | |
| aac | ctc | ggg | cga | gca | gtc | ttc | cag | gcc | aag | aag | cgg | gtt | ctc | gaa | cct | 384 |
| Asn | Leu | Gly | Arg | Ala | Val | Phe | Gln | Ala | Lys | Lys | Arg | Val | Leu | Glu | Pro | |
| | | | 115 | | | | | 120 | | | | | 125 | | | |
| ctc | ggt | ctg | gtt | gag | gaa | gct | gct | aag | acg | gct | cct | gga | aag | aag | aga | 432 |
| Leu | Gly | Leu | Val | Glu | Glu | Ala | Ala | Lys | Thr | Ala | Pro | Gly | Lys | Lys | Arg | |
| | | 130 | | | | | 135 | | | | | 140 | | | | |
| ccg | gta | gaa | ccg | tca | cct | cag | cga | tcc | ccc | gac | tcc | tcc | acg | ggc | atc | 480 |
| Pro | Val | Glu | Pro | Ser | Pro | Gln | Arg | Ser | Pro | Asp | Ser | Ser | Thr | Gly | Ile | |
| 145 | | | | | 150 | | | | | 155 | | | | | 160 | |
| ggc | aaa | aaa | ggc | cag | cag | ccc | gcg | aga | aag | aga | ctg | aac | ttt | ggg | cag | 528 |
| Gly | Lys | Lys | Gly | Gln | Gln | Pro | Ala | Arg | Lys | Arg | Leu | Asn | Phe | Gly | Gln | |
| | | | | 165 | | | | | 170 | | | | | 175 | | |
| act | ggc | gac | tca | gag | tca | gtc | ccc | gac | cct | caa | cca | atc | gga | gaa | cca | 576 |
| Thr | Gly | Asp | Ser | Glu | Ser | Val | Pro | Asp | Pro | Gln | Pro | Ile | Gly | Glu | Pro | |
| | | | 180 | | | | | 185 | | | | | 190 | | | |
| cca | gca | ggc | ccc | tct | ggt | ctg | gga | tct | ggt | aca | atg | gct | gca | ggc | ggt | 624 |
| Pro | Ala | Gly | Pro | Ser | Gly | Leu | Gly | Ser | Gly | Thr | Met | Ala | Ala | Gly | Gly | |
| | | 195 | | | | | 200 | | | | | 205 | | | | |
| ggc | gct | cca | atg | gca | gac | aat | aac | gaa | ggc | gcc | gac | gga | gtg | ggt | agt | 672 |
| Gly | Ala | Pro | Met | Ala | Asp | Asn | Asn | Glu | Gly | Ala | Asp | Gly | Val | Gly | Ser | |
| | 210 | | | | | 215 | | | | | 220 | | | | | |
| tcc | tca | gga | aat | tgg | cat | tgc | gat | tcc | aca | tgg | ctg | ggc | gac | aga | gtc | 720 |
| Ser | Ser | Gly | Asn | Trp | His | Cys | Asp | Ser | Thr | Trp | Leu | Gly | Asp | Arg | Val | |
| 225 | | | | | 230 | | | | | 235 | | | | | 240 | |
| atc | acc | acc | agc | acc | cga | acc | tgg | gcc | ctg | ccc | acc | tac | aac | aac | cac | 768 |
| Ile | Thr | Thr | Ser | Thr | Arg | Thr | Trp | Ala | Leu | Pro | Thr | Tyr | Asn | Asn | His | |
| | | | | 245 | | | | | 250 | | | | | 255 | | |
| ctc | tac | aag | caa | atc | tcc | aat | ggg | aca | tcg | gga | gga | agc | acc | aac | gac | 816 |
| Leu | Tyr | Lys | Gln | Ile | Ser | Asn | Gly | Thr | Ser | Gly | Gly | Ser | Thr | Asn | Asp | |
| | | | 260 | | | | | 265 | | | | | 270 | | | |
| aac | acc | tac | ttc | ggc | tac | agc | acc | ccc | tgg | ggg | tat | ttt | gac | ttc | aac | 864 |
| Asn | Thr | Tyr | Phe | Gly | Tyr | Ser | Thr | Pro | Trp | Gly | Tyr | Phe | Asp | Phe | Asn | |
| | | 275 | | | | | 280 | | | | | 285 | | | | |
| aga | ttc | cac | tgt | cac | ttc | tca | cca | cgt | gac | tgg | cag | aga | ctc | atc | aac | 912 |
| Arg | Phe | His | Cys | His | Phe | Ser | Pro | Arg | Asp | Trp | Gln | Arg | Leu | Ile | Asn | |
| | 290 | | | | | 295 | | | | | 300 | | | | | |

-continued

| | | |
|---|---|---|
| aac aac tgg gga ttc cgg ccc aag aga ctc agc ttc aag ctc ttc aac<br>Asn Asn Trp Gly Phe Arg Pro Lys Arg Leu Ser Phe Lys Leu Phe Asn<br>305                  310                       315                 320 | 960 |
| atc cag gtt aag gag gtc acg cag aat gaa ggc acc aag acc atc gcc<br>Ile Gln Val Lys Glu Val Thr Gln Asn Glu Gly Thr Lys Thr Ile Ala<br>325                     330                    335 | 1008 |
| aat aac ctt acc agc acg att cag gta ttt acg gac tcg gaa tac cag<br>Asn Asn Leu Thr Ser Thr Ile Gln Val Phe Thr Asp Ser Glu Tyr Gln<br>340                  345                    350 | 1056 |
| ctg ccg tac gtc ctc ggc tcc gcg cac cag ggc tgc ctg cct ccg ttc<br>Leu Pro Tyr Val Leu Gly Ser Ala His Gln Gly Cys Leu Pro Pro Phe<br>355                  360                  365 | 1104 |
| ccg gcg gat gtc ttc atg att ccc cag tac ggc tac ctg aca ctg aac<br>Pro Ala Asp Val Phe Met Ile Pro Gln Tyr Gly Tyr Leu Thr Leu Asn<br>370                  375                  380 | 1152 |
| aac gga agt caa gcc gta ggc cgt tcc tca ttc tac tgc ctg gaa tat<br>Asn Gly Ser Gln Ala Val Gly Arg Ser Ser Phe Tyr Cys Leu Glu Tyr<br>385                  390                    395                   400 | 1200 |
| ttt cca tct caa atg ctg cgg act gga aac aac ttt gaa ttt agc tac<br>Phe Pro Ser Gln Met Leu Arg Thr Gly Asn Asn Phe Glu Phe Ser Tyr<br>405                  410                  415 | 1248 |
| acc ttt gag gac gtg ccc ttc cac agc agc tac gca cac agc cag agc<br>Thr Phe Glu Asp Val Pro Phe His Ser Ser Tyr Ala His Ser Gln Ser<br>420                  425                  430 | 1296 |
| ctg gac cgg ctg atg aac cct ctc atc gac cag tac ctg tat tac cta<br>Leu Asp Arg Leu Met Asn Pro Leu Ile Asp Gln Tyr Leu Tyr Tyr Leu<br>435                  440                  445 | 1344 |
| tcc aga act cag tcc aca gga gga act caa ggt aca cag caa ttg tta<br>Ser Arg Thr Gln Ser Thr Gly Gly Thr Gln Gly Thr Gln Gln Leu Leu<br>450                  455                  460 | 1392 |
| ttt tct caa gcc ggg cct gca aat atg tcg gct cag gcc aag aac tgg<br>Phe Ser Gln Ala Gly Pro Ala Asn Met Ser Ala Gln Ala Lys Asn Trp<br>465                     470                    475                   480 | 1440 |
| cta cct gga cct tgc tac cgg cag cag cga gtc tcc acg aca ctg tcg<br>Leu Pro Gly Pro Cys Tyr Arg Gln Gln Arg Val Ser Thr Thr Leu Ser<br>485                  490                    495 | 1488 |
| caa aac aac aac agc aac ttt gct tgg act ggt gcc acg aaa tat cat<br>Gln Asn Asn Asn Ser Asn Phe Ala Trp Thr Gly Ala Thr Lys Tyr His<br>500                    505                   510 | 1536 |
| ctg aac gga aga gac tct ttg gtg aat ccc ggt gtt gct atg gca acg<br>Leu Asn Gly Arg Asp Ser Leu Val Asn Pro Gly Val Ala Met Ala Thr<br>515                  520                  525 | 1584 |
| cat aag gac gac gag gaa cgt ttc ttt cca tcg agc gga gtc ctg atg<br>His Lys Asp Asp Glu Glu Arg Phe Phe Pro Ser Ser Gly Val Leu Met<br>530                  535                  540 | 1632 |
| ttt gga aaa cag ggt gct gga aga gac aat gtg gac tat agc agc gtt<br>Phe Gly Lys Gln Gly Ala Gly Arg Asp Asn Val Asp Tyr Ser Ser Val<br>545                     550                    555                   560 | 1680 |
| atg cta acc agc gag gaa gaa atc aag acc act aac cct gta gcc act<br>Met Leu Thr Ser Glu Glu Glu Ile Lys Thr Thr Asn Pro Val Ala Thr<br>565                  570                  575 | 1728 |
| gaa caa tac ggc gtg gtg gct gat aac ttg cag caa acc aat aca gga<br>Glu Gln Tyr Gly Val Val Ala Asp Asn Leu Gln Gln Thr Asn Thr Gly<br>580                  585                  590 | 1776 |
| cct atc gtg gga aat gtc aac agc caa gga gcc tta cct ggc atg gtc<br>Pro Ile Val Gly Asn Val Asn Ser Gln Gly Ala Leu Pro Gly Met Val<br>595                  600                  605 | 1824 |
| tgg cag aac cga gac gtg tac ctg cag ggt ccc att tgg gcc aag att<br>Trp Gln Asn Arg Asp Val Tyr Leu Gln Gly Pro Ile Trp Ala Lys Ile<br>610                  615                  620 | 1872 |

```
cct cac acg gac ggc aac ttt cac ccg tct cct ctg atg ggc ggc ttt    1920
Pro His Thr Asp Gly Asn Phe His Pro Ser Pro Leu Met Gly Gly Phe
625             630             635             640 gga ctg aaa cac ccg cct cct caa atc ctg atc aag aac act ccc gtt    1968
Gly Leu Lys His Pro Pro Pro Gln Ile Leu Ile Lys Asn Thr Pro Val
            645             650             655 cct gcg gat cct cca acg acg ttc agc cag gcg aaa ttg gct tcc ttc    2016
Pro Ala Asp Pro Pro Thr Thr Phe Ser Gln Ala Lys Leu Ala Ser Phe
        660             665             670 atc acg cag tat agt acc ggc cag gtc agc gtg gag atc gag tgg gag    2064
Ile Thr Gln Tyr Ser Thr Gly Gln Val Ser Val Glu Ile Glu Trp Glu
    675             680             685 ctg cag aag gag aac agc aag cgc tgg aac cca gaa att cag tat act    2112
Leu Gln Lys Glu Asn Ser Lys Arg Trp Asn Pro Glu Ile Gln Tyr Thr
690             695             700 tcc aac tac tac aaa tct aca aat gtg gac ttt gct gtc aat acc gag    2160
Ser Asn Tyr Tyr Lys Ser Thr Asn Val Asp Phe Ala Val Asn Thr Glu
705             710             715             720 ggt aca tat tca gag cct cgc ccc att gga act cgt tac ctc acc cgt    2208
Gly Thr Tyr Ser Glu Pro Arg Pro Ile Gly Thr Arg Tyr Leu Thr Arg
            725             730             735 aat ctg                                                            2214
Asn Leu

<210> SEQ ID NO 2
<211> LENGTH: 738
<212> TYPE: PRT
<213> ORGANISM: Artificial Sequence
<220> FEATURE:
<223> OTHER INFORMATION: Synthetic Construct

<400> SEQUENCE: 2

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Glu Ala Asp Ala Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Ala Ala Lys Thr Ala Pro Gly Lys Lys Arg
    130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Arg Lys Arg Leu Asn Phe Gly Gln
                165                 170                 175

Thr Gly Asp Ser Glu Ser Val Pro Asp Pro Gln Pro Ile Gly Glu Pro
            180                 185                 190

Pro Ala Gly Pro Ser Gly Leu Gly Ser Gly Thr Met Ala Ala Gly Gly
```

-continued

```
            195                 200                 205
Gly Ala Pro Met Ala Asp Asn Asn Glu Gly Ala Asp Gly Val Gly Ser
210                 215                 220

Ser Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Asn Gly Thr Ser Gly Gly Ser Thr Asn Asp
                260                 265                 270

Asn Thr Tyr Phe Gly Tyr Ser Thr Pro Trp Gly Tyr Phe Asp Phe Asn
                275                 280                 285

Arg Phe His Cys His Phe Ser Pro Arg Asp Trp Gln Arg Leu Ile Asn
                290                 295                 300

Asn Asn Trp Gly Phe Arg Pro Lys Arg Leu Ser Phe Lys Leu Phe Asn
305                 310                 315                 320

Ile Gln Val Lys Glu Val Thr Gln Asn Glu Gly Thr Lys Thr Ile Ala
                325                 330                 335

Asn Asn Leu Thr Ser Thr Ile Gln Val Phe Thr Asp Ser Glu Tyr Gln
                340                 345                 350

Leu Pro Tyr Val Leu Gly Ser Ala His Gln Gly Cys Leu Pro Pro Phe
                355                 360                 365

Pro Ala Asp Val Phe Met Ile Pro Gln Tyr Gly Tyr Leu Thr Leu Asn
370                 375                 380

Asn Gly Ser Gln Ala Val Gly Arg Ser Ser Phe Tyr Cys Leu Glu Tyr
385                 390                 395                 400

Phe Pro Ser Gln Met Leu Arg Thr Gly Asn Asn Phe Glu Phe Ser Tyr
                405                 410                 415

Thr Phe Glu Asp Val Pro Phe His Ser Ser Tyr Ala His Ser Gln Ser
                420                 425                 430

Leu Asp Arg Leu Met Asn Pro Leu Ile Asp Gln Tyr Leu Tyr Tyr Leu
                435                 440                 445

Ser Arg Thr Gln Ser Thr Gly Gly Thr Gln Gly Thr Gln Gln Leu Leu
450                 455                 460

Phe Ser Gln Ala Gly Pro Ala Asn Met Ser Ala Gln Ala Lys Asn Trp
465                 470                 475                 480

Leu Pro Gly Pro Cys Tyr Arg Gln Gln Arg Val Ser Thr Thr Leu Ser
                485                 490                 495

Gln Asn Asn Asn Ser Asn Phe Ala Trp Thr Gly Ala Thr Lys Tyr His
                500                 505                 510

Leu Asn Gly Arg Asp Ser Leu Val Asn Pro Gly Val Ala Met Ala Thr
                515                 520                 525

His Lys Asp Asp Glu Glu Arg Phe Phe Pro Ser Ser Gly Val Leu Met
                530                 535                 540

Phe Gly Lys Gln Gly Ala Gly Arg Asp Asn Val Asp Tyr Ser Ser Val
545                 550                 555                 560

Met Leu Thr Ser Glu Glu Ile Lys Thr Thr Asn Pro Val Ala Thr
                565                 570                 575

Glu Gln Tyr Gly Val Val Ala Asp Asn Leu Gln Gln Thr Asn Thr Gly
                580                 585                 590

Pro Ile Val Gly Asn Val Asn Ser Gln Gly Ala Leu Pro Gly Met Val
                595                 600                 605

Trp Gln Asn Arg Asp Val Tyr Leu Gln Gly Pro Ile Trp Ala Lys Ile
610                 615                 620
```

```
Pro His Thr Asp Gly Asn Phe His Pro Ser Pro Leu Met Gly Gly Phe
625                 630                 635                 640

Gly Leu Lys His Pro Pro Gln Ile Leu Ile Lys Asn Thr Pro Val
            645                 650                 655

Pro Ala Asp Pro Pro Thr Thr Phe Ser Gln Ala Lys Leu Ala Ser Phe
            660                 665                 670

Ile Thr Gln Tyr Ser Thr Gly Gln Val Ser Val Glu Ile Glu Trp Glu
            675                 680                 685

Leu Gln Lys Glu Asn Ser Lys Arg Trp Asn Pro Glu Ile Gln Tyr Thr
            690                 695                 700

Ser Asn Tyr Tyr Lys Ser Thr Asn Val Asp Phe Ala Val Asn Thr Glu
705                 710                 715                 720

Gly Thr Tyr Ser Glu Pro Arg Pro Ile Gly Thr Arg Tyr Leu Thr Arg
                725                 730                 735

Asn Leu

<210> SEQ ID NO 3
<211> LENGTH: 2208
<212> TYPE: DNA
<213> ORGANISM: Artificial Sequence
<220> FEATURE:
<223> OTHER INFORMATION: AAV9
<220> FEATURE:
<221> NAME/KEY: CDS
<222> LOCATION: (1)..(2208)

<400> SEQUENCE: 3 atg gct gcc gat ggt tat ctt cca gat tgg ctc gag gac aac ctt agt      48
Met Ala Ala Asp Gly Tyr Leu Pro Asp Trp Leu Glu Asp Asn Leu Ser
1               5                   10                  15 gaa gga att cgc gag tgg tgg gct ttg aaa cct gga gcc cct caa ccc      96
Glu Gly Ile Arg Glu Trp Trp Ala Leu Lys Pro Gly Ala Pro Gln Pro
            20                  25                  30 aag gca aat caa caa cat caa gac aac gct cga ggt ctt gtg ctt ccg     144
Lys Ala Asn Gln Gln His Gln Asp Asn Ala Arg Gly Leu Val Leu Pro
        35                  40                  45 ggt tac aaa tac ctt gga ccc ggc aac gga ctc gac aag ggg gag ccg     192
Gly Tyr Lys Tyr Leu Gly Pro Gly Asn Gly Leu Asp Lys Gly Glu Pro
    50                  55                  60 gtc aac gca gca gac gcg gcg gcc ctc gag cac gac aag gcc tac gac     240
Val Asn Ala Ala Asp Ala Ala Ala Leu Glu His Asp Lys Ala Tyr Asp
65                  70                  75                  80 cag cag ctc aag gcc gga gac aac ccg tac ctc aag tac aac cac gcc     288
Gln Gln Leu Lys Ala Gly Asp Asn Pro Tyr Leu Lys Tyr Asn His Ala
                85                  90                  95 gac gcc gag ttc cag gag cgg ctc aaa gaa gat acg tct ttt ggg ggc     336
Asp Ala Glu Phe Gln Glu Arg Leu Lys Glu Asp Thr Ser Phe Gly Gly
            100                 105                 110 aac ctc ggg cga gca gtc ttc cag gcc aaa aag agg ctt ctt gaa cct     384
Asn Leu Gly Arg Ala Val Phe Gln Ala Lys Lys Arg Leu Leu Glu Pro
        115                 120                 125 ctt ggt ctg gtt gag gaa gcg gct aag acg gct cct gga aag aag agg     432
Leu Gly Leu Val Glu Glu Ala Ala Lys Thr Ala Pro Gly Lys Lys Arg
    130                 135                 140 cct gta gag cag tct cct cag gaa ccg gac tcc tcc gcg ggt att ggc     480
Pro Val Glu Gln Ser Pro Gln Glu Pro Asp Ser Ser Ala Gly Ile Gly
145                 150                 155                 160 aaa tcg ggt gca cag ccc gct aaa aag aga ctc aat ttc ggt cag act     528
Lys Ser Gly Ala Gln Pro Ala Lys Lys Arg Leu Asn Phe Gly Gln Thr
```

-continued

```
                    165                 170                 175
ggc gac aca gag tca gtc cca gac cct caa cca atc gga gaa cct ccc       576
Gly Asp Thr Glu Ser Val Pro Asp Pro Gln Pro Ile Gly Glu Pro Pro
        180                 185                 190 gca gcc ccc tca ggt gtg gga tct ctt aca atg gct tca ggt ggt ggc       624
Ala Ala Pro Ser Gly Val Gly Ser Leu Thr Met Ala Ser Gly Gly Gly
            195                 200                 205 gca cca gtg gca gac aat aac gaa ggt gcc gat gga gtg ggt agt tcc       672
Ala Pro Val Ala Asp Asn Asn Glu Gly Ala Asp Gly Val Gly Ser Ser
    210                 215                 220 tcg gga aat tgg cat tgc gat tcc caa tgg ctg ggg gac aga gtc atc       720
Ser Gly Asn Trp His Cys Asp Ser Gln Trp Leu Gly Asp Arg Val Ile
225                 230                 235                 240 acc acc agc acc cga acc tgg gcc ctg ccc acc tac aac aat cac ctc       768
Thr Thr Ser Thr Arg Thr Trp Ala Leu Pro Thr Tyr Asn Asn His Leu
                245                 250                 255 tac aag caa atc tcc aac agc aca tct gga gga tct tca aat gac aac       816
Tyr Lys Gln Ile Ser Asn Ser Thr Ser Gly Gly Ser Ser Asn Asp Asn
            260                 265                 270 gcc tac ttc ggc tac agc acc ccc tgg ggg tat ttt gac ttc aac aga       864
Ala Tyr Phe Gly Tyr Ser Thr Pro Trp Gly Tyr Phe Asp Phe Asn Arg
    275                 280                 285 ttc cac tgc cac ttc tca cca cgt gac tgg cag cga ctc atc aac aac       912
Phe His Cys His Phe Ser Pro Arg Asp Trp Gln Arg Leu Ile Asn Asn
290                 295                 300 aac tgg gga ttc cgg cct aag cga ctc aac ttc aag ctc ttc aac att       960
Asn Trp Gly Phe Arg Pro Lys Arg Leu Asn Phe Lys Leu Phe Asn Ile
305                 310                 315                 320 cag gtc aaa gag gtt acg gac aac aat gga gtc aag acc atc gcc aat      1008
Gln Val Lys Glu Val Thr Asp Asn Asn Gly Val Lys Thr Ile Ala Asn
                325                 330                 335 aac ctt acc agc acg gtc cag gtc ttc acg gac tca gac tat cag ctc      1056
Asn Leu Thr Ser Thr Val Gln Val Phe Thr Asp Ser Asp Tyr Gln Leu
            340                 345                 350 ccg tac gtg ctc ggg tcg gct cac gag ggc tgc ctc ccg ccg ttc cca      1104
Pro Tyr Val Leu Gly Ser Ala His Glu Gly Cys Leu Pro Pro Phe Pro
    355                 360                 365 gcg gac gtt ttc atg att cct cag tac ggg tat ctg acg ctt aat gat      1152
Ala Asp Val Phe Met Ile Pro Gln Tyr Gly Tyr Leu Thr Leu Asn Asp
370                 375                 380 gga agc cag gcc gtg ggt cgt tcg tcc ttt tac tgc ctg gaa tat ttc      1200
Gly Ser Gln Ala Val Gly Arg Ser Ser Phe Tyr Cys Leu Glu Tyr Phe
385                 390                 395                 400 ccg tcg caa atg cta aga acg ggt aac aac ttc cag ttc agc tac gag      1248
Pro Ser Gln Met Leu Arg Thr Gly Asn Asn Phe Gln Phe Ser Tyr Glu
                405                 410                 415 ttt gag aac gta cct ttc cat agc agc tac gct cac agc caa agc ctg      1296
Phe Glu Asn Val Pro Phe His Ser Ser Tyr Ala His Ser Gln Ser Leu
            420                 425                 430 gac cga cta atg aat cca ctc atc gac caa tac ttg tac tat ctc tca      1344
Asp Arg Leu Met Asn Pro Leu Ile Asp Gln Tyr Leu Tyr Tyr Leu Ser
    435                 440                 445 aag act att aac ggt tct gga cag aat caa caa acg cta aaa ttc agt      1392
Lys Thr Ile Asn Gly Ser Gly Gln Asn Gln Gln Thr Leu Lys Phe Ser
450                 455                 460 gtg gcc gga ccc agc aac atg gct gtc cag gga aga aac tac ata cct      1440
Val Ala Gly Pro Ser Asn Met Ala Val Gln Gly Arg Asn Tyr Ile Pro
465                 470                 475                 480 gga ccc agc tac cga caa caa cgt gtc tca acc act gtg act caa aac      1488
Gly Pro Ser Tyr Arg Gln Gln Arg Val Ser Thr Thr Val Thr Gln Asn
```

```
                Gly Pro Ser Tyr Arg Gln Gln Arg Val Ser Thr Thr Val Thr Gln Asn
                            485                 490                 495 aac aac agc gaa ttt gct tgg cct gga gct tct tct tgg gct ctc aat        1536
Asn Asn Ser Glu Phe Ala Trp Pro Gly Ala Ser Ser Trp Ala Leu Asn
            500                 505                 510 gga cgt aat agc ttg atg aat cct gga cct gct atg gcc agc cac aaa        1584
Gly Arg Asn Ser Leu Met Asn Pro Gly Pro Ala Met Ala Ser His Lys
        515                 520                 525 gaa gga gag gac cgt ttc ttt cct ttg tct gga tct tta att ttt ggc        1632
Glu Gly Glu Asp Arg Phe Phe Pro Leu Ser Gly Ser Leu Ile Phe Gly
    530                 535                 540 aaa caa gga act gga aga gac aac gtg gat gcg gac aaa gtc atg ata        1680
Lys Gln Gly Thr Gly Arg Asp Asn Val Asp Ala Asp Lys Val Met Ile
545                 550                 555                 560 acc aac gaa gaa gaa att aaa act act aac ccg gta gca acg gag tcc        1728
Thr Asn Glu Glu Glu Ile Lys Thr Thr Asn Pro Val Ala Thr Glu Ser
                565                 570                 575 tat gga caa gtg gcc aca aac cac cag agt gcc caa gca cag gcg cag        1776
Tyr Gly Gln Val Ala Thr Asn His Gln Ser Ala Gln Ala Gln Ala Gln
            580                 585                 590 acc ggc tgg gtt caa aac caa gga ata ctt ccg ggt atg gtt tgg cag        1824
Thr Gly Trp Val Gln Asn Gln Gly Ile Leu Pro Gly Met Val Trp Gln
        595                 600                 605 gac aga gat gtg tac ctg caa gga ccc att tgg gcc aaa att cct cac        1872
Asp Arg Asp Val Tyr Leu Gln Gly Pro Ile Trp Ala Lys Ile Pro His
    610                 615                 620 acg gac ggc aac ttt cac cct tct ccg ctg atg gga ggg ttt gga atg        1920
Thr Asp Gly Asn Phe His Pro Ser Pro Leu Met Gly Gly Phe Gly Met
625                 630                 635                 640 aag cac ccg cct cct cag atc ctc atc aaa aac aca cct gta cct gcg        1968
Lys His Pro Pro Pro Gln Ile Leu Ile Lys Asn Thr Pro Val Pro Ala
                645                 650                 655 gat cct cca acg gcc ttc aac aag gac aag ctg aac tct ttc atc acc        2016
Asp Pro Pro Thr Ala Phe Asn Lys Asp Lys Leu Asn Ser Phe Ile Thr
            660                 665                 670 cag tat tct act ggc caa gtc agc gtg gag atc gag tgg gag ctg cag        2064
Gln Tyr Ser Thr Gly Gln Val Ser Val Glu Ile Glu Trp Glu Leu Gln
        675                 680                 685 aag gaa aac agc aag cgc tgg aac ccg gag atc cag tac act tcc aac        2112
Lys Glu Asn Ser Lys Arg Trp Asn Pro Glu Ile Gln Tyr Thr Ser Asn
    690                 695                 700 tat tac aag tct aat aat gtt gaa ttt gct gtt aat act gaa ggt gta        2160
Tyr Tyr Lys Ser Asn Asn Val Glu Phe Ala Val Asn Thr Glu Gly Val
705                 710                 715                 720 tat agt gaa ccc cgc ccc att ggc acc aga tac ctg act cgt aat ctg        2208
Tyr Ser Glu Pro Arg Pro Ile Gly Thr Arg Tyr Leu Thr Arg Asn Leu
                725                 730                 735

<210> SEQ ID NO 4
<211> LENGTH: 736
<212> TYPE: PRT
<213> ORGANISM: Artificial Sequence
<220> FEATURE:
<223> OTHER INFORMATION: Synthetic Construct

<400> SEQUENCE: 4

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30
```

-continued

Lys Ala Asn Gln Gln His Gln Asp Asn Ala Arg Gly Leu Val Leu Pro
             35                  40                  45

Gly Tyr Lys Tyr Leu Gly Pro Gly Asn Gly Leu Asp Lys Gly Glu Pro
 50                  55                  60

Val Asn Ala Ala Asp Ala Ala Leu Glu His Asp Lys Ala Tyr Asp
 65                  70                  75                  80

Gln Gln Leu Lys Ala Gly Asp Asn Pro Tyr Leu Lys Tyr Asn His Ala
                 85                  90                  95

Asp Ala Glu Phe Gln Glu Arg Leu Lys Glu Asp Thr Ser Phe Gly Gly
                100                 105                 110

Asn Leu Gly Arg Ala Val Phe Gln Ala Lys Lys Arg Leu Leu Glu Pro
            115                 120                 125

Leu Gly Leu Val Glu Glu Ala Ala Lys Thr Ala Pro Gly Lys Lys Arg
130                 135                 140

Pro Val Glu Gln Ser Pro Gln Glu Pro Asp Ser Ser Ala Gly Ile Gly
145                 150                 155                 160

Lys Ser Gly Ala Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Gly Gly Gly
            195                 200                 205

Ala Pro Val Ala Asp Asn Asn Glu Gly Ala Asp Gly Val Gly Ser Ser
            210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Ser Thr Ser Gly Gly Ser Ser Asn Asp Asn
            260                 265                 270

Ala Tyr Phe Gly Tyr Ser Thr Pro Trp Gly Tyr Phe Asp Phe Asn Arg
            275                 280                 285

Phe His Cys His Phe Ser Pro Arg Asp Trp Gln Arg Leu Ile Asn Asn
            290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
                325                 330                 335

Asn Leu Thr Ser Thr Val Gln Val Phe Thr Asp Ser Asp Tyr Gln Leu
            340                 345                 350

Pro Tyr Val Leu Gly Ser Ala His Glu Gly Cys Leu Pro Pro Phe Pro
            355                 360                 365

Ala Asp Val Phe Met Ile Pro Gln Tyr Gly Tyr Leu Thr Leu Asn Asp
370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
                405                 410                 415

Phe Glu Asn Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Ser
            435                 440                 445

Lys Thr Ile Asn Gly Ser Gly Gln Asn Gln Gln Thr Leu Lys Phe Ser

```
                450             455             460
   Val Ala Gly Pro Ser Asn Met Ala Val Gln Gly Arg Asn Tyr Ile Pro
   465                 470                 475                 480

Gly Pro Ser Tyr Arg Gln Gln Arg Val Ser Thr Thr Val Thr Gln Asn
                   485                 490                 495

Asn Asn Ser Glu Phe Ala Trp Pro Gly Ala Ser Ser Trp Ala Leu Asn
               500                 505                 510

Gly Arg Asn Ser Leu Met Asn Pro Gly Pro Ala Met Ala Ser His Lys
                   515                 520                 525

Glu Gly Glu Asp Arg Phe Phe Pro Leu Ser Gly Ser Leu Ile Phe Gly
               530                 535                 540

Lys Gln Gly Thr Gly Arg Asp Asn Val Asp Ala Asp Lys Val Met Ile
   545                 550                 555                 560

Thr Asn Glu Glu Glu Ile Lys Thr Thr Asn Pro Val Ala Thr Glu Ser
                   565                 570                 575

Tyr Gly Gln Val Ala Thr Asn His Gln Ser Ala Gln Ala Gln Ala Gln
               580                 585                 590

Thr Gly Trp Val Gln Asn Gln Gly Ile Leu Pro Gly Met Val Trp Gln
               595                 600                 605

Asp Arg Asp Val Tyr Leu Gln Gly Pro Ile Trp Ala Lys Ile Pro His
   610                 615                 620

Thr Asp Gly Asn Phe His Pro Ser Pro Leu Met Gly Gly Phe Gly Met
   625                 630                 635                 640

Lys His Pro Pro Pro Gln Ile Leu Ile Lys Asn Thr Pro Val Pro Ala
                   645                 650                 655

Asp Pro Pro Thr Ala Phe Asn Lys Asp Lys Leu Asn Ser Phe Ile Thr
               660                 665                 670

Gln Tyr Ser Thr Gly Gln Val Ser Val Glu Ile Glu Trp Glu Leu Gln
                   675                 680                 685

Lys Glu Asn Ser Lys Arg Trp Asn Pro Glu Ile Gln Tyr Thr Ser Asn
               690                 695                 700

Tyr Tyr Lys Ser Asn Asn Val Glu Phe Ala Val Asn Thr Glu Gly Val
   705                 710                 715                 720

Tyr Ser Glu Pro Arg Pro Ile Gly Thr Arg Tyr Leu Thr Arg Asn Leu
                   725                 730                 735

<210> SEQ ID NO 5
<211> LENGTH: 2211
<212> TYPE: DNA
<213> ORGANISM: Artificial Sequence
<220> FEATURE:
<223> OTHER INFORMATION: AAVhu31
<220> FEATURE:
<221> NAME/KEY: CDS
<222> LOCATION: (1)..(2211)

<400> SEQUENCE: 5 atg gct gcc gat ggt tat ctt cca gat tgg ctc gag gac act ctc tct      48
Met Ala Ala Asp Gly Tyr Leu Pro Asp Trp Leu Glu Asp Thr Leu Ser
1               5                   10                  15 gaa gga ata aga cag tgg tgg aag ctc aaa cct ggc ccc cca cca cca      96
Glu Gly Ile Arg Gln Trp Trp Lys Leu Lys Pro Gly Pro Pro Pro Pro
                20                  25                  30 aag ccc gca gag cgg cat aag gac gac agc agg ggt ctt gtg ctt cct     144
Lys Pro Ala Glu Arg His Lys Asp Asp Ser Arg Gly Leu Val Leu Pro
            35                  40                  45 ggg tac aag tac ctc gga ccc ggc aac gga ctc gac aag ggg gag ccg     192
```

-continued

| | | | | | | | | | | | | | | |
|---|---|---|---|---|---|---|---|---|---|---|---|---|---|---|
| Gly | Tyr 50 | Lys | Tyr | Leu | Gly 55 | Pro | Gly | Asn | Gly | Leu 60 | Asp | Lys | Gly | Glu | Pro |

| gtc | aac | gca | gca | gac | gcg | gcg | gcc | ctc | gag | cac | gac | aag | gcc | tac | gac | 240 |
|---|---|---|---|---|---|---|---|---|---|---|---|---|---|---|---|---|
| Val 65 | Asn | Ala | Ala | Asp 70 | Ala | Ala | Leu | Glu | His 75 | Asp | Lys | Ala | Tyr | Asp 80 | | |

| cag | cag | ctc | aag | gcc | gga | gac | aac | ccg | tac | ctc | aag | tac | aac | cac | gcc | 288 |
|---|---|---|---|---|---|---|---|---|---|---|---|---|---|---|---|---|
| Gln | Gln | Leu | Lys | Ala 85 | Gly | Asp | Asn | Pro | Tyr 90 | Leu | Lys | Tyr | Asn | His 95 | Ala | |

| gac | gcc | gag | ttc | cag | gag | cgg | ctc | aaa | gaa | gat | acg | tct | ttt | ggg | ggc | 336 |
|---|---|---|---|---|---|---|---|---|---|---|---|---|---|---|---|---|
| Asp | Ala | Glu | Phe | Gln 100 | Glu | Arg | Leu | Lys | Glu 105 | Asp | Thr | Ser | Phe | Gly 110 | Gly | |

| aac | ctc | ggg | cga | gca | gtc | ttc | cag | gcc | aaa | aag | agg | ctt | ctt | gaa | cct | 384 |
|---|---|---|---|---|---|---|---|---|---|---|---|---|---|---|---|---|
| Asn | Leu | Gly 115 | Arg | Ala | Val | Phe | Gln 120 | Ala | Lys | Lys | Arg | Leu 125 | Leu | Glu | Pro | |

| ctt | ggt | ctg | gtt | gag | gaa | gcg | gct | aag | acg | gct | cct | gga | aag | aag | agg | 432 |
|---|---|---|---|---|---|---|---|---|---|---|---|---|---|---|---|---|
| Leu | Gly 130 | Leu | Val | Glu | Glu 135 | Ala | Ala | Lys | Thr | Ala 140 | Pro | Gly | Lys | Lys | Arg | |

| cct | gta | gag | cag | tct | cct | cag | gaa | ccg | gac | tcc | tcc | gcg | ggt | att | ggc | 480 |
|---|---|---|---|---|---|---|---|---|---|---|---|---|---|---|---|---|
| Pro 145 | Val | Glu | Gln | Ser | Pro 150 | Gln | Glu | Pro | Asp | Ser 155 | Ser | Ala | Gly | Ile | Gly 160 | |

| aaa | tcg | ggt | tca | cag | ccc | gct | aaa | aag | aaa | ctc | aat | ttc | ggt | cag | act | 528 |
|---|---|---|---|---|---|---|---|---|---|---|---|---|---|---|---|---|
| Lys | Ser | Gly | Ser | Gln 165 | Pro | Ala | Lys | Lys | Lys 170 | Leu | Asn | Phe | Gly | Gln 175 | Thr | |

| ggc | gac | aca | gag | tca | gtc | ccc | gac | cct | caa | cca | atc | gga | gaa | cct | ccc | 576 |
|---|---|---|---|---|---|---|---|---|---|---|---|---|---|---|---|---|
| Gly | Asp | Thr | Glu 180 | Ser | Val | Pro | Asp | Pro 185 | Gln | Pro | Ile | Gly | Glu 190 | Pro | Pro | |

| gca | gcc | ccc | tca | ggt | gtg | gga | tct | ctt | aca | atg | gct | tca | ggt | ggt | ggc | 624 |
|---|---|---|---|---|---|---|---|---|---|---|---|---|---|---|---|---|
| Ala | Ala | Pro 195 | Ser | Gly | Val | Gly | Ser 200 | Leu | Thr | Met | Ala | Ser 205 | Gly | Gly | Gly | |

| gca | cca | gtg | gca | gac | aat | aac | gaa | ggt | gcc | gat | gga | gtg | ggt | agt | tcc | 672 |
|---|---|---|---|---|---|---|---|---|---|---|---|---|---|---|---|---|
| Ala | Pro 210 | Val | Ala | Asp | Asn 215 | Asn | Glu | Gly | Ala | Asp 220 | Gly | Val | Gly | Ser | Ser | |

| tcg | gga | aat | tgg | cat | tgc | gat | tcc | caa | tgg | ctg | ggg | gac | aga | gtc | atc | 720 |
|---|---|---|---|---|---|---|---|---|---|---|---|---|---|---|---|---|
| Ser 225 | Gly | Asn | Trp | His | Cys 230 | Asp | Ser | Gln | Trp | Leu 235 | Gly | Asp | Arg | Val | Ile 240 | |

| acc | acc | agc | acc | cga | acc | tgg | gcc | ctg | ccc | acc | tac | aac | aat | cac | ctc | 768 |
|---|---|---|---|---|---|---|---|---|---|---|---|---|---|---|---|---|
| Thr | Thr | Ser | Thr | Arg 245 | Thr | Trp | Ala | Leu | Pro 250 | Thr | Tyr | Asn | Asn | His 255 | Leu | |

| tac | aag | caa | atc | tcc | aac | agc | aca | tct | gga | gga | tct | tca | aat | gac | aac | 816 |
|---|---|---|---|---|---|---|---|---|---|---|---|---|---|---|---|---|
| Tyr | Lys | Gln | Ile | Ser 260 | Asn | Ser | Thr | Ser | Gly 265 | Gly | Ser | Ser | Asn | Asp 270 | Asn | |

| gcc | tac | ttc | ggc | tac | agc | acc | ccc | tgg | ggg | tat | ttt | gac | ttc | aac | aga | 864 |
|---|---|---|---|---|---|---|---|---|---|---|---|---|---|---|---|---|
| Ala | Tyr | Phe 275 | Gly | Tyr | Ser | Thr | Pro 280 | Trp | Gly | Tyr | Phe | Asp 285 | Phe | Asn | Arg | |

| ttc | cac | tgc | cac | ttc | tca | cca | cgt | gac | tgg | cag | cga | ctc | atc | aac | aac | 912 |
|---|---|---|---|---|---|---|---|---|---|---|---|---|---|---|---|---|
| Phe | His 290 | Cys | His | Phe | Ser 295 | Pro | Arg | Asp | Trp | Gln 300 | Arg | Leu | Ile | Asn | Asn | |

| aac | tgg | gga | ttc | cgg | cct | aag | cga | ctc | aac | ttc | aag | ctc | ttc | aac | att | 960 |
|---|---|---|---|---|---|---|---|---|---|---|---|---|---|---|---|---|
| Asn 305 | Trp | Gly | Phe | Arg | Pro 310 | Lys | Arg | Leu | Asn | Phe 315 | Lys | Leu | Phe | Asn | Ile 320 | |

| cag | gtc | aaa | gag | gtt | acg | gac | aac | aat | gga | gtc | aag | acc | atc | gcc | aat | 1008 |
|---|---|---|---|---|---|---|---|---|---|---|---|---|---|---|---|---|
| Gln | Val | Lys | Glu | Val 325 | Thr | Asp | Asn | Asn | Gly 330 | Val | Lys | Thr | Ile | Ala 335 | Asn | |

| aac | ctt | acc | agc | acg | gtc | cag | gtc | ttc | acg | gac | tca | gac | tat | cag | ctc | 1056 |
|---|---|---|---|---|---|---|---|---|---|---|---|---|---|---|---|---|
| Asn | Leu | Thr | Ser | Thr 340 | Val | Gln | Val | Phe | Thr 345 | Asp | Ser | Asp | Tyr | Gln 350 | Leu | |

| ccg | tac | gtg | ctc | ggg | tcg | gct | cac | gag | ggc | tgc | ctc | ccg | ccg | ttc | cca | 1104 |
|---|---|---|---|---|---|---|---|---|---|---|---|---|---|---|---|---|
| Pro | Tyr | Val | Leu 355 | Gly | Ser | Ala | His | Glu 360 | Gly | Cys | Leu | Pro | Pro 365 | Phe | Pro | |

```
gcg gac gtt ttc atg att cct cag tac ggg tat ctg acg ctt aat gat    1152
Ala Asp Val Phe Met Ile Pro Gln Tyr Gly Tyr Leu Thr Leu Asn Asp
    370                 375                 380 gga ggc cag gcc gtg ggt cgt tcg tcc ttt tac tgc ctg gaa tat ttc    1200
Gly Gly Gln Ala Val Gly Arg Ser Ser Phe Tyr Cys Leu Glu Tyr Phe
385                 390                 395                 400 ccg tcg caa atg cta aga acg ggt aac aac ttc cag ttc agc tac gag    1248
Pro Ser Gln Met Leu Arg Thr Gly Asn Asn Phe Gln Phe Ser Tyr Glu
                405                 410                 415 ttt gag aac gta cct ttc cat agc agc tac gct cac agc caa agc ctg    1296
Phe Glu Asn Val Pro Phe His Ser Ser Tyr Ala His Ser Gln Ser Leu
            420                 425                 430 gac cga cta atg aat cca ctc atc gac caa tac ttg tac tat ctc tca    1344
Asp Arg Leu Met Asn Pro Leu Ile Asp Gln Tyr Leu Tyr Tyr Leu Ser
        435                 440                 445 aag act att aac ggt tct gga cag aat caa caa acg cta aaa ttc agt    1392
Lys Thr Ile Asn Gly Ser Gly Gln Asn Gln Gln Thr Leu Lys Phe Ser
    450                 455                 460 gtg gcc gga ccc agc aac atg gct gtc cag gga aga aac tac ata cct    1440
Val Ala Gly Pro Ser Asn Met Ala Val Gln Gly Arg Asn Tyr Ile Pro
465                 470                 475                 480 gga ccc agc tac cga caa caa cgt gtc tca acc act gtg act caa aac    1488
Gly Pro Ser Tyr Arg Gln Gln Arg Val Ser Thr Thr Val Thr Gln Asn
                485                 490                 495 aac aac agc gaa ttt gct tgg cct gga gct tct tct tgg gct ctc aat    1536
Asn Asn Ser Glu Phe Ala Trp Pro Gly Ala Ser Ser Trp Ala Leu Asn
            500                 505                 510 gga cgt aat agc ttg atg aat cct gga cct gct atg gcc agc cac aaa    1584
Gly Arg Asn Ser Leu Met Asn Pro Gly Pro Ala Met Ala Ser His Lys
        515                 520                 525 gaa gga gag gac cgt ttc ttt cct ttg tcc gga tct tta att ttt ggc    1632
Glu Gly Glu Asp Arg Phe Phe Pro Leu Ser Gly Ser Leu Ile Phe Gly
    530                 535                 540 aaa caa gga act gga aga gac aac gtg gat gcg gac aaa gtc atg ata    1680
Lys Gln Gly Thr Gly Arg Asp Asn Val Asp Ala Asp Lys Val Met Ile
545                 550                 555                 560 acc aac gaa gaa gaa att aaa act act aac ccg gta gca acg gag tcc    1728
Thr Asn Glu Glu Glu Ile Lys Thr Thr Asn Pro Val Ala Thr Glu Ser
                565                 570                 575 tat gga caa gtg gcc aca aac cac cag agt gcc caa gca cag gcg cag    1776
Tyr Gly Gln Val Ala Thr Asn His Gln Ser Ala Gln Ala Gln Ala Gln
            580                 585                 590 acc ggc tgg gtt caa aac caa gga ata ctt ccg ggt atg gtt tgg cag    1824
Thr Gly Trp Val Gln Asn Gln Gly Ile Leu Pro Gly Met Val Trp Gln
        595                 600                 605 gac aga gat gtg tac ctg caa gga ccc att tgg gcc aaa att cct cac    1872
Asp Arg Asp Val Tyr Leu Gln Gly Pro Ile Trp Ala Lys Ile Pro His
    610                 615                 620 acg gac ggc aac ttt cac cct tct ccg cta atg gga ggg ttt gga atg    1920
Thr Asp Gly Asn Phe His Pro Ser Pro Leu Met Gly Gly Phe Gly Met
625                 630                 635                 640 aag cac ccg cct cct cag atc ctc atc aaa aac aca cct gta cct gcg    1968
Lys His Pro Pro Pro Gln Ile Leu Ile Lys Asn Thr Pro Val Pro Ala
                645                 650                 655 gat cct cca acg gct ttc aat aag gac aag ctg aac tct ttc atc acc    2016
Asp Pro Pro Thr Ala Phe Asn Lys Asp Lys Leu Asn Ser Phe Ile Thr
            660                 665                 670 cag tat tct act ggc caa gtc agc gtg gag att gag tgg gag ctg cag    2064
Gln Tyr Ser Thr Gly Gln Val Ser Val Glu Ile Glu Trp Glu Leu Gln
        675                 680                 685
```

```
aag gaa aac agc aag cgc tgg aac ccg gag atc cag tac act tcc aac    2112
Lys Glu Asn Ser Lys Arg Trp Asn Pro Glu Ile Gln Tyr Thr Ser Asn
    690             695                 700 tat tac aag tct aat aat gtt gaa ttt gct gtt agt act gaa ggt gta    2160
Tyr Tyr Lys Ser Asn Asn Val Glu Phe Ala Val Ser Thr Glu Gly Val
705             710                 715                 720 tat agt gaa ccc cgc ccc att ggc acc aga tac ctg act cgt aat ctg    2208
Tyr Ser Glu Pro Arg Pro Ile Gly Thr Arg Tyr Leu Thr Arg Asn Leu
                725                 730                 735 taa                                                                2211
```

<210> SEQ ID NO 6
<211> LENGTH: 736
<212> TYPE: PRT
<213> ORGANISM: Artificial Sequence
<220> FEATURE:
<223> OTHER INFORMATION: Synthetic Construct

<400> SEQUENCE: 6

```
Met Ala Ala Asp Gly Tyr Leu Pro Asp Trp Leu Glu Asp Thr Leu Ser
1               5                   10                  15

Glu Gly Ile Arg Gln Trp Trp Lys Leu Lys Pro Gly Pro Pro Pro Pro
            20                  25                  30

Lys Pro Ala Glu Arg His Lys Asp Asp Ser Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
        115                 120                 125

Leu Gly Leu Val Glu Glu Ala Ala Lys Thr Ala Pro Gly Lys Lys Arg
    130                 135                 140

Pro Val Glu Gln Ser Pro Gln Glu Pro Asp Ser Ser Ala Gly Ile Gly
145                 150                 155                 160

Lys Ser Gly Ser Gln Pro Ala Lys Lys Lys Leu Asn Phe Gly Gln Thr
                165                 170                 175

Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Gly Gly Gly
        195                 200                 205

Ala Pro Val Ala Asp Asn Asn Glu Gly Ala Asp Gly Val Gly Ser Ser
    210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Ser Thr Ser Gly Gly Ser Ser Asn Asp Asn
            260                 265                 270

Ala Tyr Phe Gly Tyr Ser Thr Pro Trp Gly Tyr Phe Asp Phe Asn Arg
        275                 280                 285
```

```
Phe His Cys His Phe Ser Pro Arg Asp Trp Gln Arg Leu Ile Asn Asn
    290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
                325                 330                 335

Asn Leu Thr Ser Thr Val Gln Val Phe Thr Asp Ser Asp Tyr Gln Leu
            340                 345                 350

Pro Tyr Val Leu Gly Ser Ala His Glu Gly Cys Leu Pro Phe Pro
        355                 360                 365

Ala Asp Val Phe Met Ile Pro Gln Tyr Gly Tyr Leu Thr Leu Asn Asp
370                 375                 380

Gly Gly Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
                405                 410                 415

Phe Glu Asn Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Ser
        435                 440                 445

Lys Thr Ile Asn Gly Ser Gly Gln Asn Gln Gln Thr Leu Lys Phe Ser
450                 455                 460

Val Ala Gly Pro Ser Asn Met Ala Val Gln Gly Arg Asn Tyr Ile Pro
465                 470                 475                 480

Gly Pro Ser Tyr Arg Gln Gln Arg Val Ser Thr Thr Val Thr Gln Asn
                485                 490                 495

Asn Asn Ser Glu Phe Ala Trp Pro Gly Ala Ser Ser Trp Ala Leu Asn
            500                 505                 510

Gly Arg Asn Ser Leu Met Asn Pro Gly Pro Ala Met Ala Ser His Lys
        515                 520                 525

Glu Gly Glu Asp Arg Phe Phe Pro Leu Ser Gly Ser Leu Ile Phe Gly
530                 535                 540

Lys Gln Gly Thr Gly Arg Asp Asn Val Asp Ala Asp Lys Val Met Ile
545                 550                 555                 560

Thr Asn Glu Glu Glu Ile Lys Thr Thr Asn Pro Val Ala Thr Glu Ser
                565                 570                 575

Tyr Gly Gln Val Ala Thr Asn His Gln Ser Ala Gln Ala Gln Ala Gln
            580                 585                 590

Thr Gly Trp Val Gln Asn Gln Gly Ile Leu Pro Gly Met Val Trp Gln
        595                 600                 605

Asp Arg Asp Val Tyr Leu Gln Gly Pro Ile Trp Ala Lys Ile Pro His
610                 615                 620

Thr Asp Gly Asn Phe His Pro Ser Pro Leu Met Gly Gly Phe Gly Met
625                 630                 635                 640

Lys His Pro Pro Pro Gln Ile Leu Ile Lys Asn Thr Pro Val Pro Ala
                645                 650                 655

Asp Pro Pro Thr Ala Phe Asn Lys Asp Lys Leu Asn Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Ile Gln Tyr Thr Ser Asn
690                 695                 700

Tyr Tyr Lys Ser Asn Asn Val Glu Phe Ala Val Ser Thr Glu Gly Val
```

```
                705                 710                 715                 720
Tyr Ser Glu Pro Arg Pro Ile Gly Thr Arg Tyr Leu Thr Arg Asn Leu
                    725                 730                 735

<210> SEQ ID NO 7
<211> LENGTH: 2211
<212> TYPE: DNA
<213> ORGANISM: Artificial Sequence
<220> FEATURE:
<223> OTHER INFORMATION: AAVhu32
<220> FEATURE:
<221> NAME/KEY: CDS
<222> LOCATION: (1)..(2211)

<400> SEQUENCE: 7 atg gct gcc gat ggt tat ctt cca gat tgg ctc gag gac act ctc tct     48
Met Ala Ala Asp Gly Tyr Leu Pro Asp Trp Leu Glu Asp Thr Leu Ser
1               5                   10                  15 gaa gga ata aga cag tgg tgg aag ctc aaa cct ggc cca cca cca cca     96
Glu Gly Ile Arg Gln Trp Trp Lys Leu Lys Pro Gly Pro Pro Pro Pro
            20                  25                  30 aag ccc gca gag cgg cat aag gac gac agc agg ggt ctt gtg ctt cct    144
Lys Pro Ala Glu Arg His Lys Asp Asp Ser Arg Gly Leu Val Leu Pro
        35                  40                  45 ggg tac aag tac ctc gga ccc ggc aac gga ctc gac aag ggg gag ccg    192
Gly Tyr Lys Tyr Leu Gly Pro Gly Asn Gly Leu Asp Lys Gly Glu Pro
    50                  55                  60 gtc aac gca gca gac gcg gcg gcc ctc gag cac gac aag gcc tac gac    240
Val Asn Ala Ala Asp Ala Ala Ala Leu Glu His Asp Lys Ala Tyr Asp
65                  70                  75                  80 cag cag ctc aag gcc gga gac aac ccg tac ctc aag tac aac cac gcc    288
Gln Gln Leu Lys Ala Gly Asp Asn Pro Tyr Leu Lys Tyr Asn His Ala
                85                  90                  95 gac gcc gag ttc cag gag cgg ctc aaa gaa gat acg tct ttt ggg ggc    336
Asp Ala Glu Phe Gln Glu Arg Leu Lys Glu Asp Thr Ser Phe Gly Gly
            100                 105                 110 aac ctc ggg cga gca gtc ttc cag gcc aaa aag agg ctt ctt gaa cct    384
Asn Leu Gly Arg Ala Val Phe Gln Ala Lys Lys Arg Leu Leu Glu Pro
        115                 120                 125 ctt ggt ctg gtt gag gaa gcg gct aag acg gct cct gga aag aag agg    432
Leu Gly Leu Val Glu Glu Ala Ala Lys Thr Ala Pro Gly Lys Lys Arg
    130                 135                 140 cct gta gag cag tct cct cag gaa ccg gac tcc tcg gcg ggt att ggc    480
Pro Val Glu Gln Ser Pro Gln Glu Pro Asp Ser Ser Ala Gly Ile Gly
145                 150                 155                 160 aaa tcg ggt tca cag ccc gct aaa aag aaa ctc aat ttc ggt cag act    528
Lys Ser Gly Ser Gln Pro Ala Lys Lys Lys Leu Asn Phe Gly Gln Thr
                165                 170                 175 ggc gac aca gag tca gtc ccc gac cct caa cca atc gga gaa cct ccc    576
Gly Asp Thr Glu Ser Val Pro Asp Pro Gln Pro Ile Gly Glu Pro Pro
            180                 185                 190 gca gcc ccc tca ggt gtg gga tct ctt aca atg gct tca ggt ggt ggc    624
Ala Ala Pro Ser Gly Val Gly Ser Leu Thr Met Ala Ser Gly Gly Gly
        195                 200                 205 gca cca gtg gca gac aat aac gaa ggt gcc gat gga gtg ggt agt tcc    672
Ala Pro Val Ala Asp Asn Asn Glu Gly Ala Asp Gly Val Gly Ser Ser
    210                 215                 220 tcg gga aat tgg cat tgc gat tcc caa tgg ctg ggg aca aga gtc atc    720
Ser Gly Asn Trp His Cys Asp Ser Gln Trp Leu Gly Asp Arg Val Ile
225                 230                 235                 240 acc acc agc acc cga acc tgg gcc ctg ccc acc tac aac aat cac ctc    768
```

```
Thr Thr Ser Thr Arg Thr Trp Ala Leu Pro Thr Tyr Asn Asn His Leu
            245                 250                 255 tac aag caa atc tcc aac agc aca tct gga gga tct tca aat gac aac        816
Tyr Lys Gln Ile Ser Asn Ser Thr Ser Gly Gly Ser Ser Asn Asp Asn
        260                 265                 270 gcc tac ttc ggc tac agc acc ccc tgg ggg tat ttt gac ttc aac aga        864
Ala Tyr Phe Gly Tyr Ser Thr Pro Trp Gly Tyr Phe Asp Phe Asn Arg
            275                 280                 285 ttc cac tgc cac ttc tca cca cgt gac tgg cag cga ctc atc aac aac        912
Phe His Cys His Phe Ser Pro Arg Asp Trp Gln Arg Leu Ile Asn Asn
        290                 295                 300 aac tgg gga ttc cgg cct aag cga ctc aac ttc aag ctc ttc aac att        960
Asn Trp Gly Phe Arg Pro Lys Arg Leu Asn Phe Lys Leu Phe Asn Ile
305                 310                 315                 320 cag gtc aaa gag gtt acg gac aac aat gga gtc aag acc atc gcc aat       1008
Gln Val Lys Glu Val Thr Asp Asn Asn Gly Val Lys Thr Ile Ala Asn
            325                 330                 335 aac ctt acc agc acg gtc cag gtc ttc acg gac tca gac tat cag ctc       1056
Asn Leu Thr Ser Thr Val Gln Val Phe Thr Asp Ser Asp Tyr Gln Leu
        340                 345                 350 ccg tac gtg ctc ggg tcg gct cac gag ggc tgc ctc ccg ccg ttc cca       1104
Pro Tyr Val Leu Gly Ser Ala His Glu Gly Cys Leu Pro Pro Phe Pro
            355                 360                 365 gcg gac gtt ttc atg att cct cag tac ggg tat ctg acg ctt aat gat       1152
Ala Asp Val Phe Met Ile Pro Gln Tyr Gly Tyr Leu Thr Leu Asn Asp
370                 375                 380 ggg agc cag gcc gtg ggt cgt tcg tcc ttt tac tgc ctg gaa tat ttc       1200
Gly Ser Gln Ala Val Gly Arg Ser Ser Phe Tyr Cys Leu Glu Tyr Phe
385                 390                 395                 400 ccg tcg caa atg cta aga acg ggt aac aac ttc cag ttc agc tac gag       1248
Pro Ser Gln Met Leu Arg Thr Gly Asn Asn Phe Gln Phe Ser Tyr Glu
            405                 410                 415 ttt gag aac gta cct ttc cat agc agc tac gct cac agc caa agc ctg       1296
Phe Glu Asn Val Pro Phe His Ser Ser Tyr Ala His Ser Gln Ser Leu
        420                 425                 430 gac cga cta atg aat cca ctc atc gac caa tac ttg tac tat ctc tca       1344
Asp Arg Leu Met Asn Pro Leu Ile Asp Gln Tyr Leu Tyr Tyr Leu Ser
            435                 440                 445 aag act att aac ggt tct gga cag aat caa caa acg cta aaa ttc agc       1392
Lys Thr Ile Asn Gly Ser Gly Gln Asn Gln Gln Thr Leu Lys Phe Ser
450                 455                 460 gtg gcc gga ccc agc aac atg gct gtc cag gga aga aac tac ata cct       1440
Val Ala Gly Pro Ser Asn Met Ala Val Gln Gly Arg Asn Tyr Ile Pro
465                 470                 475                 480 gga ccc agc tac cga caa caa cgt gtc tca acc act gtg act caa aac       1488
Gly Pro Ser Tyr Arg Gln Gln Arg Val Ser Thr Thr Val Thr Gln Asn
            485                 490                 495 aac aac agc gaa ttt gct tgg cct gga gct tct tct tgg gct ctc aat       1536
Asn Asn Ser Glu Phe Ala Trp Pro Gly Ala Ser Ser Trp Ala Leu Asn
        500                 505                 510 gga cgt aat agc ttg atg aat cct gga cct gct atg gcc agc cac aaa       1584
Gly Arg Asn Ser Leu Met Asn Pro Gly Pro Ala Met Ala Ser His Lys
            515                 520                 525 gaa gga gag gac cgt ttc ttt cct ttg tct gga tct tta att ttt ggc       1632
Glu Gly Glu Asp Arg Phe Phe Pro Leu Ser Gly Ser Leu Ile Phe Gly
530                 535                 540 aaa caa gga act gga aga gac aac gtg gat gcg gac aaa gtc atg ata       1680
Lys Gln Gly Thr Gly Arg Asp Asn Val Asp Ala Asp Lys Val Met Ile
545                 550                 555                 560
```

| | | | | | | | | | | | | | | | |
|---|---|---|---|---|---|---|---|---|---|---|---|---|---|---|---|
| acc | aac | gaa | gaa | gaa | att | aaa | act | act | aac | ccg | gta | gca | acg | gag | tcc | 1728
| Thr | Asn | Glu | Glu | Glu | Ile | Lys | Thr | Thr | Asn | Pro | Val | Ala | Thr | Glu | Ser |
| | | | | 565 | | | | | 570 | | | | | 575 | |

```
acc aac gaa gaa gaa att aaa act act aac ccg gta gca acg gag tcc      1728
Thr Asn Glu Glu Glu Ile Lys Thr Thr Asn Pro Val Ala Thr Glu Ser
                565                 570                 575 tat gga caa gtg gcc aca aac cac cag agt gcc caa gca cag gcg cag      1776
Tyr Gly Gln Val Ala Thr Asn His Gln Ser Ala Gln Ala Gln Ala Gln
                580                 585                 590 acc ggc tgg gtt caa aac caa gga ata ctt ccg ggt atg gtt tgg cag      1824
Thr Gly Trp Val Gln Asn Gln Gly Ile Leu Pro Gly Met Val Trp Gln
                595                 600                 605 gac aga gat gtg tac ctg caa gga ccc att tgg gcc aaa att cct cac      1872
Asp Arg Asp Val Tyr Leu Gln Gly Pro Ile Trp Ala Lys Ile Pro His
            610                 615                 620 acg gac ggc aac ttt cac cct tct ccg cta atg gga ggg ttt gga atg      1920
Thr Asp Gly Asn Phe His Pro Ser Pro Leu Met Gly Gly Phe Gly Met
625                 630                 635                 640 aag cac ccg cct cct cag atc ctc atc aaa aac aca cct gta cct gcg      1968
Lys His Pro Pro Pro Gln Ile Leu Ile Lys Asn Thr Pro Val Pro Ala
                645                 650                 655 gat cct cca acg gct ttc aat aag gac aag ctg aac tct ttc atc acc      2016
Asp Pro Pro Thr Ala Phe Asn Lys Asp Lys Leu Asn Ser Phe Ile Thr
                660                 665                 670 cag tat tct act ggc caa gtc agc gtg gag att gag tgg gag ctg cag      2064
Gln Tyr Ser Thr Gly Gln Val Ser Val Glu Ile Glu Trp Glu Leu Gln
            675                 680                 685 aag gaa aac agc aag cgc tgg aac ccg gag atc cag tac act tcc aac      2112
Lys Glu Asn Ser Lys Arg Trp Asn Pro Glu Ile Gln Tyr Thr Ser Asn
            690                 695                 700 tat tac aag tct aat aat gtt gaa ttt gct gtt aat act gaa ggt gta      2160
Tyr Tyr Lys Ser Asn Asn Val Glu Phe Ala Val Asn Thr Glu Gly Val
705                 710                 715                 720 tat agt gaa ccc cgc ccc att ggc acc aga tac ctg act cgt aat ctg      2208
Tyr Ser Glu Pro Arg Pro Ile Gly Thr Arg Tyr Leu Thr Arg Asn Leu
                725                 730                 735 taa                                                                   2211

<210> SEQ ID NO 8
<211> LENGTH: 736
<212> TYPE: PRT
<213> ORGANISM: Artificial Sequence
<220> FEATURE:
<223> OTHER INFORMATION: Synthetic Construct

<400> SEQUENCE: 8

Met Ala Ala Asp Gly Tyr Leu Pro Asp Trp Leu Glu Asp Thr Leu Ser
1               5                   10                  15

Glu Gly Ile Arg Gln Trp Trp Lys Leu Lys Pro Gly Pro Pro Pro
            20                  25                  30

Lys Pro Ala Glu Arg His Lys Asp Asp Ser Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
        115                 120                 125
```

```
Leu Gly Leu Val Glu Ala Ala Lys Thr Ala Pro Gly Lys Lys Arg
    130                 135                 140
Pro Val Glu Gln Ser Pro Gln Glu Pro Asp Ser Ser Ala Gly Ile Gly
145                 150                 155                 160
Lys Ser Gly Ser Gln Pro Ala Lys Lys Lys Leu Asn Phe Gly Gln Thr
                165                 170                 175
Gly Asp Thr Glu Ser Val Pro Asp Pro Gln Pro Ile Gly Glu Pro Pro
            180                 185                 190
Ala Ala Pro Ser Gly Val Gly Ser Leu Thr Met Ala Ser Gly Gly Gly
        195                 200                 205
Ala Pro Val Ala Asp Asn Asn Glu Gly Ala Asp Gly Val Gly Ser Ser
210                 215                 220
Ser Gly Asn Trp His Cys Asp Ser Gln Trp Leu Gly Asp Arg Val Ile
225                 230                 235                 240
Thr Thr Ser Thr Arg Thr Trp Ala Leu Pro Thr Tyr Asn Asn His Leu
                245                 250                 255
Tyr Lys Gln Ile Ser Asn Ser Thr Ser Gly Gly Ser Ser Asn Asp Asn
            260                 265                 270
Ala Tyr Phe Gly Tyr Ser Thr Pro Trp Gly Tyr Phe Asp Phe Asn Arg
        275                 280                 285
Phe His Cys His Phe Ser Pro Arg Asp Trp Gln Arg Leu Ile Asn Asn
290                 295                 300
Asn Trp Gly Phe Arg Pro Lys Arg Leu Asn Phe Lys Leu Phe Asn Ile
305                 310                 315                 320
Gln Val Lys Glu Val Thr Asp Asn Asn Gly Val Lys Thr Ile Ala Asn
                325                 330                 335
Asn Leu Thr Ser Thr Val Gln Val Phe Thr Asp Ser Asp Tyr Gln Leu
            340                 345                 350
Pro Tyr Val Leu Gly Ser Ala His Glu Gly Cys Leu Pro Pro Phe Pro
        355                 360                 365
Ala Asp Val Phe Met Ile Pro Gln Tyr Gly Tyr Leu Thr Leu Asn Asp
370                 375                 380
Gly Ser Gln Ala Val Gly Arg Ser Ser Phe Tyr Cys Leu Glu Tyr Phe
385                 390                 395                 400
Pro Ser Gln Met Leu Arg Thr Gly Asn Asn Phe Gln Phe Ser Tyr Glu
                405                 410                 415
Phe Glu Asn Val Pro Phe His Ser Ser Tyr Ala His Ser Gln Ser Leu
            420                 425                 430
Asp Arg Leu Met Asn Pro Leu Ile Asp Gln Tyr Leu Tyr Tyr Leu Ser
        435                 440                 445
Lys Thr Ile Asn Gly Ser Gly Gln Asn Gln Gln Thr Leu Lys Phe Ser
450                 455                 460
Val Ala Gly Pro Ser Asn Met Ala Val Gln Gly Arg Asn Tyr Ile Pro
465                 470                 475                 480
Gly Pro Ser Tyr Arg Gln Gln Arg Val Ser Thr Thr Val Thr Gln Asn
                485                 490                 495
Asn Asn Ser Glu Phe Ala Trp Pro Gly Ala Ser Ser Trp Ala Leu Asn
            500                 505                 510
Gly Arg Asn Ser Leu Met Asn Pro Gly Pro Ala Met Ala Ser His Lys
        515                 520                 525
Glu Gly Glu Asp Arg Phe Phe Pro Leu Ser Gly Ser Leu Ile Phe Gly
530                 535                 540
```

```
Lys Gln Gly Thr Gly Arg Asp Asn Val Asp Ala Asp Lys Val Met Ile
545                 550                 555                 560

Thr Asn Glu Glu Glu Ile Lys Thr Thr Asn Pro Val Ala Thr Glu Ser
                565                 570                 575

Tyr Gly Gln Val Ala Thr Asn His Gln Ser Ala Gln Ala Gln Ala Gln
            580                 585                 590

Thr Gly Trp Val Gln Asn Gln Gly Ile Leu Pro Gly Met Val Trp Gln
        595                 600                 605

Asp Arg Asp Val Tyr Leu Gln Gly Pro Ile Trp Ala Lys Ile Pro His
    610                 615                 620

Thr Asp Gly Asn Phe His Pro Ser Pro Leu Met Gly Gly Phe Gly Met
625                 630                 635                 640

Lys His Pro Pro Gln Ile Leu Ile Lys Asn Thr Pro Val Pro Ala
                645                 650                 655

Asp Pro Pro Thr Ala Phe Asn Lys Asp Lys Leu Asn Ser Phe Ile Thr
                660                 665                 670

Gln Tyr Ser Thr Gly Gln Val Ser Val Glu Ile Glu Trp Glu Leu Gln
            675                 680                 685

Lys Glu Asn Ser Lys Arg Trp Asn Pro Glu Ile Gln Tyr Thr Ser Asn
        690                 695                 700

Tyr Tyr Lys Ser Asn Asn Val Glu Phe Ala Val Asn Thr Glu Gly Val
705                 710                 715                 720

Tyr Ser Glu Pro Arg Pro Ile Gly Thr Arg Tyr Leu Thr Arg Asn Leu
                725                 730                 735

<210> SEQ ID NO 9
<211> LENGTH: 2178
<212> TYPE: DNA
<213> ORGANISM: Artificial Sequence
<220> FEATURE:
<223> OTHER INFORMATION: AAV5.5.9
<220> FEATURE:
<221> NAME/KEY: CDS
<222> LOCATION: (1)..(2178)

<400> SEQUENCE: 9 atg tct ttt gtt gat cac cct cca gat tgg ttg gaa gaa gtt ggt gaa       48
Met Ser Phe Val Asp His Pro Pro Asp Trp Leu Glu Glu Val Gly Glu
1               5                   10                  15 ggt ctt cgc gag ttt ttg ggc ctt gaa gcg ggc cca ccg aaa cca aaa       96
Gly Leu Arg Glu Phe Leu Gly Leu Glu Ala Gly Pro Pro Lys Pro Lys
            20                  25                  30 ccc aat cag cag cat caa gat caa gcc cgt ggt ctt gtg ctg cct ggt      144
Pro Asn Gln Gln His Gln Asp Gln Ala Arg Gly Leu Val Leu Pro Gly
        35                  40                  45 tat aac tat ctc gga ccc gga aac ggt ctc gat cga gga gag cct gtc      192
Tyr Asn Tyr Leu Gly Pro Gly Asn Gly Leu Asp Arg Gly Glu Pro Val
    50                  55                  60 aac agg gca gac gag gtc gcg cga gag cac gac atc tcg tac aac gag      240
Asn Arg Ala Asp Glu Val Ala Arg Glu His Asp Ile Ser Tyr Asn Glu
65                  70                  75                  80 cag ctt gag gcg gga gac aac ccc tac ctc aag tac aac cac gcg gac      288
Gln Leu Glu Ala Gly Asp Asn Pro Tyr Leu Lys Tyr Asn His Ala Asp
                85                  90                  95 gcc gag ttt cag gag aag ctc gcc gac gac aca tcc ttc ggg gga aac      336
Ala Glu Phe Gln Glu Lys Leu Ala Asp Asp Thr Ser Phe Gly Gly Asn
            100                 105                 110 ctc gga aag gca gtc ttt cag gcc aag aaa agg gtt ctc gaa cct ttt      384
Leu Gly Lys Ala Val Phe Gln Ala Lys Lys Arg Val Leu Glu Pro Phe
```

-continued

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
|     | 115 |     |     |     |     | 120 |     |     |     |     | 125 |     |     |     |     |      |
| ggc | ctg | gtt | gaa | gag | ggt | gct | aag | acg | gcc | cct | acc | gga | aag | cgg | ata | 432  |
| Gly | Leu | Val | Glu | Glu | Gly | Ala | Lys | Thr | Ala | Pro | Thr | Gly | Lys | Arg | Ile |      |
|     | 130 |     |     |     | 135 |     |     |     |     | 140 |     |     |     |     |     |      |
| gac | gac | cac | ttt | cca | aaa | aga | aag | aag | gcc | cgg | acc | gaa | gag | gac | tcc | 480  |
| Asp | Asp | His | Phe | Pro | Lys | Arg | Lys | Lys | Ala | Arg | Thr | Glu | Glu | Asp | Ser |      |
| 145 |     |     |     |     | 150 |     |     |     |     | 155 |     |     |     |     | 160 |      |
| aag | cct | tcc | acc | tcg | tca | gac | gcc | gaa | gct | gga | ccc | agc | gga | tcc | cag | 528  |
| Lys | Pro | Ser | Thr | Ser | Ser | Asp | Ala | Glu | Ala | Gly | Pro | Ser | Gly | Ser | Gln |      |
|     |     |     |     | 165 |     |     |     |     | 170 |     |     |     |     | 175 |     |      |
| cag | ctg | caa | atc | cca | gcc | caa | cca | gcc | tca | agt | ttg | gga | gct | gat | aca | 576  |
| Gln | Leu | Gln | Ile | Pro | Ala | Gln | Pro | Ala | Ser | Ser | Leu | Gly | Ala | Asp | Thr |      |
|     |     |     | 180 |     |     |     |     | 185 |     |     |     |     | 190 |     |     |      |
| atg | gct | tca | ggt | ggt | ggc | gca | cca | gtg | gca | gac | aat | aac | gaa | ggt | gcc | 624  |
| Met | Ala | Ser | Gly | Gly | Gly | Ala | Pro | Val | Ala | Asp | Asn | Asn | Glu | Gly | Ala |      |
|     |     | 195 |     |     |     |     | 200 |     |     |     |     | 205 |     |     |     |      |
| gat | gga | gtg | ggt | agt | tcc | tcg | gga | aat | tgg | cat | tgc | gat | tcc | caa | tgg | 672  |
| Asp | Gly | Val | Gly | Ser | Ser | Ser | Gly | Asn | Trp | His | Cys | Asp | Ser | Gln | Trp |      |
|     | 210 |     |     |     |     | 215 |     |     |     |     | 220 |     |     |     |     |      |
| ctg | ggg | gac | aga | gtc | atc | acc | acc | agc | acc | cga | acc | tgg | gcc | ctg | ccc | 720  |
| Leu | Gly | Asp | Arg | Val | Ile | Thr | Thr | Ser | Thr | Arg | Thr | Trp | Ala | Leu | Pro |      |
| 225 |     |     |     |     | 230 |     |     |     |     | 235 |     |     |     |     | 240 |      |
| acc | tac | aac | aat | cac | ctc | tac | aag | caa | atc | tcc | aac | agc | aca | tct | gga | 768  |
| Thr | Tyr | Asn | Asn | His | Leu | Tyr | Lys | Gln | Ile | Ser | Asn | Ser | Thr | Ser | Gly |      |
|     |     |     |     | 245 |     |     |     |     | 250 |     |     |     |     | 255 |     |      |
| gga | tct | tca | aat | gac | aac | gcc | tac | ttc | ggc | tac | agc | acc | ccc | tgg | ggg | 816  |
| Gly | Ser | Ser | Asn | Asp | Asn | Ala | Tyr | Phe | Gly | Tyr | Ser | Thr | Pro | Trp | Gly |      |
|     |     |     | 260 |     |     |     |     | 265 |     |     |     |     | 270 |     |     |      |
| tat | ttt | gac | ttc | aac | aga | ttc | cac | tgc | cac | ttc | tca | cca | cgt | gac | tgg | 864  |
| Tyr | Phe | Asp | Phe | Asn | Arg | Phe | His | Cys | His | Phe | Ser | Pro | Arg | Asp | Trp |      |
|     |     | 275 |     |     |     |     | 280 |     |     |     |     | 285 |     |     |     |      |
| cag | cga | ctc | atc | aac | aac | aac | tgg | gga | ttc | cgg | cct | aag | cga | ctc | aac | 912  |
| Gln | Arg | Leu | Ile | Asn | Asn | Asn | Trp | Gly | Phe | Arg | Pro | Lys | Arg | Leu | Asn |      |
|     | 290 |     |     |     |     | 295 |     |     |     |     | 300 |     |     |     |     |      |
| ttc | aag | ctc | ttc | aac | att | cag | gtc | aaa | gag | gtt | acg | gac | aac | aat | gga | 960  |
| Phe | Lys | Leu | Phe | Asn | Ile | Gln | Val | Lys | Glu | Val | Thr | Asp | Asn | Asn | Gly |      |
| 305 |     |     |     |     | 310 |     |     |     |     | 315 |     |     |     |     | 320 |      |
| gtc | aag | acc | atc | gcc | aat | aac | ctt | acc | agc | acg | gtc | cag | gtc | ttc | acg | 1008 |
| Val | Lys | Thr | Ile | Ala | Asn | Asn | Leu | Thr | Ser | Thr | Val | Gln | Val | Phe | Thr |      |
|     |     |     |     | 325 |     |     |     |     | 330 |     |     |     |     | 335 |     |      |
| gac | tca | gac | tat | cag | ctc | ccg | tac | gtg | ctc | ggg | tcg | gct | cac | gag | ggc | 1056 |
| Asp | Ser | Asp | Tyr | Gln | Leu | Pro | Tyr | Val | Leu | Gly | Ser | Ala | His | Glu | Gly |      |
|     |     |     | 340 |     |     |     |     | 345 |     |     |     |     | 350 |     |     |      |
| tgc | ctc | ccg | ccg | ttc | cca | gcg | gac | gtt | ttc | atg | att | cct | cag | tac | ggg | 1104 |
| Cys | Leu | Pro | Pro | Phe | Pro | Ala | Asp | Val | Phe | Met | Ile | Pro | Gln | Tyr | Gly |      |
|     |     | 355 |     |     |     |     | 360 |     |     |     |     | 365 |     |     |     |      |
| tat | ctg | acg | ctt | aat | gat | gga | agc | cag | gcc | gtg | ggt | cgt | tcg | tcc | ttt | 1152 |
| Tyr | Leu | Thr | Leu | Asn | Asp | Gly | Ser | Gln | Ala | Val | Gly | Arg | Ser | Ser | Phe |      |
|     | 370 |     |     |     |     | 375 |     |     |     |     | 380 |     |     |     |     |      |
| tac | tgc | ctg | gaa | tat | ttc | ccg | tcg | caa | atg | cta | aga | acg | ggt | aac | aac | 1200 |
| Tyr | Cys | Leu | Glu | Tyr | Phe | Pro | Ser | Gln | Met | Leu | Arg | Thr | Gly | Asn | Asn |      |
| 385 |     |     |     |     | 390 |     |     |     |     | 395 |     |     |     |     | 400 |      |
| ttc | cag | ttc | agc | tac | gag | ttt | gag | aac | gta | cct | ttc | cat | agc | agc | tac | 1248 |
| Phe | Gln | Phe | Ser | Tyr | Glu | Phe | Glu | Asn | Val | Pro | Phe | His | Ser | Ser | Tyr |      |
|     |     |     |     | 405 |     |     |     |     | 410 |     |     |     |     | 415 |     |      |
| gct | cac | agc | caa | agc | ctg | gac | cga | cta | atg | aat | cca | ctc | atc | gac | caa | 1296 |
| Ala | His | Ser | Gln | Ser | Leu | Asp | Arg | Leu | Met | Asn | Pro | Leu | Ile | Asp | Gln |      |
|     |     |     | 420 |     |     |     |     | 425 |     |     |     |     | 430 |     |     |      |
| tac | ttg | tac | tat | ctc | tca | aag | act | att | aac | ggt | tct | gga | cag | aat | caa | 1344 |

```
                Tyr Leu Tyr Leu Ser Lys Thr Ile Asn Gly Ser Gly Gln Asn Gln
                        435                 440                 445 caa acg cta aaa ttc agt gtg gcc gga ccc agc aac atg gct gtc cag           1392
Gln Thr Leu Lys Phe Ser Val Ala Gly Pro Ser Asn Met Ala Val Gln
        450                 455                 460 gga aga aac tac ata cct gga ccc agc tac cga caa caa cgt gtc tca           1440
Gly Arg Asn Tyr Ile Pro Gly Pro Ser Tyr Arg Gln Gln Arg Val Ser
465                 470                 475                 480 acc act gtg act caa aac aac aac agc gaa ttt gct tgg cct gga gct           1488
Thr Thr Val Thr Gln Asn Asn Asn Ser Glu Phe Ala Trp Pro Gly Ala
                485                 490                 495 tct tct tgg gct ctc aat gga cgt aat agc ttg atg aat cct gga cct           1536
Ser Ser Trp Ala Leu Asn Gly Arg Asn Ser Leu Met Asn Pro Gly Pro
        500                 505                 510 gct atg gcc agc cac aaa gaa gga gag gac cgt ttc ttt cct ttg tct           1584
Ala Met Ala Ser His Lys Glu Gly Glu Asp Arg Phe Phe Pro Leu Ser
    515                 520                 525 gga tct tta att ttt ggc aaa caa gga act gga aga gac aac gtg gat           1632
Gly Ser Leu Ile Phe Gly Lys Gln Gly Thr Gly Arg Asp Asn Val Asp
530                 535                 540 gcg gac aaa gtc atg ata acc aac gaa gaa gaa att aaa act act aac           1680
Ala Asp Lys Val Met Ile Thr Asn Glu Glu Glu Ile Lys Thr Thr Asn
545                 550                 555                 560 ccg gta gca acg gag tcc tat gga caa gtg gcc aca aac cac cag agt           1728
Pro Val Ala Thr Glu Ser Tyr Gly Gln Val Ala Thr Asn His Gln Ser
                565                 570                 575 gcc caa gca cag gcg cag acc ggc tgg gtt caa aac caa gga ata ctt           1776
Ala Gln Ala Gln Ala Gln Thr Gly Trp Val Gln Asn Gln Gly Ile Leu
        580                 585                 590 ccg ggt atg gtt tgg cag gac aga gat gtg tac ctg caa gga ccc att           1824
Pro Gly Met Val Trp Gln Asp Arg Asp Val Tyr Leu Gln Gly Pro Ile
    595                 600                 605 tgg gcc aaa att cct cac acg gac ggc aac ttt cac cct tct ccg ctg           1872
Trp Ala Lys Ile Pro His Thr Asp Gly Asn Phe His Pro Ser Pro Leu
610                 615                 620 atg gga ggg ttt gga atg aag cac ccg cct cct cag atc ctc atc aaa           1920
Met Gly Gly Phe Gly Met Lys His Pro Pro Pro Gln Ile Leu Ile Lys
625                 630                 635                 640 aac aca cct gta cct gcg gat cct cca acg gcc ttc aac aag gac aag           1968
Asn Thr Pro Val Pro Ala Asp Pro Pro Thr Ala Phe Asn Lys Asp Lys
                645                 650                 655 ctg aac tct ttc atc acc cag tat tct act ggc caa gtc agc gtg gag           2016
Leu Asn Ser Phe Ile Thr Gln Tyr Ser Thr Gly Gln Val Ser Val Glu
        660                 665                 670 atc gag tgg gag ctg cag aag gaa aac agc aag cgc tgg aac ccg gag           2064
Ile Glu Trp Glu Leu Gln Lys Glu Asn Ser Lys Arg Trp Asn Pro Glu
    675                 680                 685 atc cag tac act tcc aac tat tac aag tct aat aat gtt gaa ttt gct           2112
Ile Gln Tyr Thr Ser Asn Tyr Tyr Lys Ser Asn Asn Val Glu Phe Ala
690                 695                 700 gtt aat act gaa ggt gta tat agt gaa ccc cgc ccc att ggc acc aga           2160
Val Asn Thr Glu Gly Val Tyr Ser Glu Pro Arg Pro Ile Gly Thr Arg
705                 710                 715                 720 tac ctg act cgt aat ctg                                                   2178
Tyr Leu Thr Arg Asn Leu
                725

<210> SEQ ID NO 10
<211> LENGTH: 726
<212> TYPE: PRT
```

<213> ORGANISM: Artificial Sequence
<220> FEATURE:
<223> OTHER INFORMATION: Synthetic Construct

<400> SEQUENCE: 10

```
Met Ser Phe Val Asp His Pro Pro Asp Trp Leu Glu Glu Val Gly Glu
1               5                   10                  15

Gly Leu Arg Glu Phe Leu Gly Leu Glu Ala Gly Pro Pro Lys Pro Lys
            20                  25                  30

Pro Asn Gln Gln His Gln Asp Gln Ala Arg Gly Leu Val Leu Pro Gly
        35                  40                  45

Tyr Asn Tyr Leu Gly Pro Gly Asn Gly Leu Asp Arg Gly Glu Pro Val
    50                  55                  60

Asn Arg Ala Asp Glu Val Ala Arg Glu His Asp Ile Ser Tyr Asn Glu
65                  70                  75                  80

Gln Leu Glu Ala Gly Asp Asn Pro Tyr Leu Lys Tyr Asn His Ala Asp
                85                  90                  95

Ala Glu Phe Gln Glu Lys Leu Ala Asp Asp Thr Ser Phe Gly Gly Asn
            100                 105                 110

Leu Gly Lys Ala Val Phe Gln Ala Lys Lys Arg Val Leu Glu Pro Phe
        115                 120                 125

Gly Leu Val Glu Glu Gly Ala Lys Thr Ala Pro Thr Gly Lys Arg Ile
    130                 135                 140

Asp Asp His Phe Pro Lys Arg Lys Lys Ala Arg Thr Glu Glu Asp Ser
145                 150                 155                 160

Lys Pro Ser Thr Ser Ser Asp Ala Glu Ala Gly Pro Ser Gly Ser Gln
                165                 170                 175

Gln Leu Gln Ile Pro Ala Gln Pro Ala Ser Ser Leu Gly Ala Asp Thr
            180                 185                 190

Met Ala Ser Gly Gly Gly Ala Pro Val Ala Asp Asn Asn Glu Gly Ala
        195                 200                 205

Asp Gly Val Gly Ser Ser Ser Gly Asn Trp His Cys Asp Ser Gln Trp
    210                 215                 220

Leu Gly Asp Arg Val Ile Thr Thr Ser Thr Arg Thr Trp Ala Leu Pro
225                 230                 235                 240

Thr Tyr Asn Asn His Leu Tyr Lys Gln Ile Ser Asn Ser Thr Ser Gly
                245                 250                 255

Gly Ser Ser Asn Asp Asn Ala Tyr Phe Gly Tyr Ser Thr Pro Trp Gly
            260                 265                 270

Tyr Phe Asp Phe Asn Arg Phe His Cys His Phe Ser Pro Arg Asp Trp
        275                 280                 285

Gln Arg Leu Ile Asn Asn Asn Trp Gly Phe Arg Pro Lys Arg Leu Asn
    290                 295                 300

Phe Lys Leu Phe Asn Ile Gln Val Lys Glu Val Thr Asp Asn Asn Gly
305                 310                 315                 320

Val Lys Thr Ile Ala Asn Asn Leu Thr Ser Thr Val Gln Val Phe Thr
                325                 330                 335

Asp Ser Asp Tyr Gln Leu Pro Tyr Val Leu Gly Ser Ala His Glu Gly
            340                 345                 350

Cys Leu Pro Pro Phe Pro Ala Asp Val Phe Met Ile Pro Gln Tyr Gly
        355                 360                 365

Tyr Leu Thr Leu Asn Asp Gly Ser Gln Ala Val Gly Arg Ser Ser Phe
    370                 375                 380

Tyr Cys Leu Glu Tyr Phe Pro Ser Gln Met Leu Arg Thr Gly Asn Asn
```

```
            385                 390                 395                 400
        Phe Gln Phe Ser Tyr Glu Phe Glu Asn Val Pro Phe His Ser Ser Tyr
                        405                 410                 415

Ala His Ser Gln Ser Leu Asp Arg Leu Met Asn Pro Leu Ile Asp Gln
                        420                 425                 430

Tyr Leu Tyr Tyr Leu Ser Lys Thr Ile Asn Gly Ser Gly Gln Asn Gln
                        435                 440                 445

Gln Thr Leu Lys Phe Ser Val Ala Gly Pro Ser Asn Met Ala Val Gln
        450                 455                 460

Gly Arg Asn Tyr Ile Pro Gly Pro Ser Tyr Arg Gln Gln Arg Val Ser
        465                 470                 475                 480

Thr Thr Val Thr Gln Asn Asn Asn Ser Glu Phe Ala Trp Pro Gly Ala
                        485                 490                 495

Ser Ser Trp Ala Leu Asn Gly Arg Asn Ser Leu Met Asn Pro Gly Pro
                        500                 505                 510

Ala Met Ala Ser His Lys Glu Gly Glu Asp Arg Phe Phe Pro Leu Ser
                        515                 520                 525

Gly Ser Leu Ile Phe Gly Lys Gln Gly Thr Gly Arg Asp Asn Val Asp
        530                 535                 540

Ala Asp Lys Val Met Ile Thr Asn Glu Glu Glu Ile Lys Thr Thr Asn
        545                 550                 555                 560

Pro Val Ala Thr Glu Ser Tyr Gly Gln Val Ala Thr Asn His Gln Ser
                        565                 570                 575

Ala Gln Ala Gln Ala Gln Thr Gly Trp Val Gln Asn Gln Gly Ile Leu
                        580                 585                 590

Pro Gly Met Val Trp Gln Asp Arg Asp Val Tyr Leu Gln Gly Pro Ile
                        595                 600                 605

Trp Ala Lys Ile Pro His Thr Asp Gly Asn Phe His Pro Ser Pro Leu
        610                 615                 620

Met Gly Gly Phe Gly Met Lys His Pro Pro Gln Ile Leu Ile Lys
        625                 630                 635                 640

Asn Thr Pro Val Pro Ala Asp Pro Pro Thr Ala Phe Asn Lys Asp Lys
                        645                 650                 655

Leu Asn Ser Phe Ile Thr Gln Tyr Ser Thr Gly Gln Val Ser Val Glu
                        660                 665                 670

Ile Glu Trp Glu Leu Gln Lys Glu Asn Ser Lys Arg Trp Asn Pro Glu
                        675                 680                 685

Ile Gln Tyr Thr Ser Asn Tyr Tyr Lys Ser Asn Asn Val Glu Phe Ala
                        690                 695                 700

Val Asn Thr Glu Gly Val Tyr Ser Glu Pro Arg Pro Ile Gly Thr Arg
        705                 710                 715                 720

Tyr Leu Thr Arg Asn Leu
                        725

<210> SEQ ID NO 11
<211> LENGTH: 2229
<212> TYPE: DNA
<213> ORGANISM: Artificial Sequence
<220> FEATURE:
<223> OTHER INFORMATION: AAVPHP.B
<220> FEATURE:
<221> NAME/KEY: CDS
<222> LOCATION: (1)..(2229)

<400> SEQUENCE: 11 atg gct gcc gat ggt tat ctt cca gat tgg ctc gag gac aac ctt agt        48
```

```
Met Ala Ala Asp Gly Tyr Leu Pro Asp Trp Leu Glu Asp Asn Leu Ser
1               5                   10                  15 gaa gga att cgc gag tgg tgg gct ttg aaa cct gga gcc cct caa ccc      96
Glu Gly Ile Arg Glu Trp Trp Ala Leu Lys Pro Gly Ala Pro Gln Pro
            20                  25                  30 aag gca aat caa caa cat caa gac aac gct cga ggt ctt gtg ctt ccg     144
Lys Ala Asn Gln Gln His Gln Asp Asn Ala Arg Gly Leu Val Leu Pro
                35                  40                  45 ggt tac aaa tac ctt gga ccc ggc aac gga ctc gac aag ggg gag ccg     192
Gly Tyr Lys Tyr Leu Gly Pro Gly Asn Gly Leu Asp Lys Gly Glu Pro
        50                  55                  60 gtc aac gca gca gac gcg gcg gcc ctc gag cac gac aag gcc tac gac     240
Val Asn Ala Ala Asp Ala Ala Ala Leu Glu His Asp Lys Ala Tyr Asp
65                  70                  75                  80 cag cag ctc aag gcc gga gac aac ccg tac ctc aag tac aac cac gcc     288
Gln Gln Leu Lys Ala Gly Asp Asn Pro Tyr Leu Lys Tyr Asn His Ala
                85                  90                  95 gac gcc gag ttc cag gag cgg ctc aaa gaa gat acg tct ttt ggg ggc     336
Asp Ala Glu Phe Gln Glu Arg Leu Lys Glu Asp Thr Ser Phe Gly Gly
            100                 105                 110 aac ctc ggg cga gca gtc ttc cag gcc aaa aag agg ctt ctt gaa cct     384
Asn Leu Gly Arg Ala Val Phe Gln Ala Lys Lys Arg Leu Leu Glu Pro
        115                 120                 125 ctt ggt ctg gtt gag gaa gcg gct aag acg gct cct gga aag aag agg     432
Leu Gly Leu Val Glu Glu Ala Ala Lys Thr Ala Pro Gly Lys Lys Arg
130                 135                 140 cct gta gag cag tct cct cag gaa ccg gac tcc tcc gcg ggt att ggc     480
Pro Val Glu Gln Ser Pro Gln Glu Pro Asp Ser Ser Ala Gly Ile Gly
145                 150                 155                 160 aaa tcg ggt gca cag ccc gct aaa aag aga ctc aat ttc ggt cag act     528
Lys Ser Gly Ala Gln Pro Ala Lys Lys Arg Leu Asn Phe Gly Gln Thr
                165                 170                 175 ggc gac aca gag tca gtc cca gac cct caa cca atc gga gaa cct ccc     576
Gly Asp Thr Glu Ser Val Pro Asp Pro Gln Pro Ile Gly Glu Pro Pro
            180                 185                 190 gca gcc ccc tca ggt gtg gga tct ctt aca atg gct tca ggt ggt ggc     624
Ala Ala Pro Ser Gly Val Gly Ser Leu Thr Met Ala Ser Gly Gly Gly
        195                 200                 205 gca cca gtg gca gac aat aac gaa ggt gcc gat gga gtg ggt agt tcc     672
Ala Pro Val Ala Asp Asn Asn Glu Gly Ala Asp Gly Val Gly Ser Ser
210                 215                 220 tcg gga aat tgg cat tgc gat tcc caa tgg ctg ggg gac aga gtc atc     720
Ser Gly Asn Trp His Cys Asp Ser Gln Trp Leu Gly Asp Arg Val Ile
225                 230                 235                 240 acc acc agc acc cga acc tgg gcc ctg ccc acc tac aac aat cac ctc     768
Thr Thr Ser Thr Arg Thr Trp Ala Leu Pro Thr Tyr Asn Asn His Leu
                245                 250                 255 tac aag caa atc tcc aac agc aca tct gga gga tca tca aat gac aac     816
Tyr Lys Gln Ile Ser Asn Ser Thr Ser Gly Gly Ser Ser Asn Asp Asn
            260                 265                 270 gcc tac ttc ggc tac agc acc ccc tgg ggg tat ttt gac ttc aac aga     864
Ala Tyr Phe Gly Tyr Ser Thr Pro Trp Gly Tyr Phe Asp Phe Asn Arg
        275                 280                 285 ttc cac tgc cac ttc tca cca cgt gac tgg cag cga ctc atc aac aac     912
Phe His Cys His Phe Ser Pro Arg Asp Trp Gln Arg Leu Ile Asn Asn
290                 295                 300 aac tgg gga ttc cgg cct aag cga ctc aac ttc aag ctc ttc aac att     960
Asn Trp Gly Phe Arg Pro Lys Arg Leu Asn Phe Lys Leu Phe Asn Ile
305                 310                 315                 320
```

-continued

| | |
|---|---|
| cag gtc aaa gag gtt acg gac aac aat gga gtc aag acc atc gcc aat<br>Gln Val Lys Glu Val Thr Asp Asn Asn Gly Val Lys Thr Ile Ala Asn<br>                    325                             330                          335 | 1008 |
| aac ctt acc agc acg gtc cag gtc ttc acg gac tca gac tat cag ctc<br>Asn Leu Thr Ser Thr Val Gln Val Phe Thr Asp Ser Asp Tyr Gln Leu<br>                  340                           345                           350 | 1056 |
| ccg tac gtg ctc ggg tcg gct cac gag ggc tgc ctc ccg ccg ttc cca<br>Pro Tyr Val Leu Gly Ser Ala His Glu Gly Cys Leu Pro Pro Phe Pro<br>               355                         360                       365 | 1104 |
| gcg gac gtt ttc atg att cct cag tac ggg tat ctg acg ctt aat gat<br>Ala Asp Val Phe Met Ile Pro Gln Tyr Gly Tyr Leu Thr Leu Asn Asp<br>          370                         375                        380 | 1152 |
| gga agc cag gcc gtg ggt cgt tcg tcc ttt tac tgc ctg gaa tat ttc<br>Gly Ser Gln Ala Val Gly Arg Ser Ser Phe Tyr Cys Leu Glu Tyr Phe<br>385                          390                        395                        400 | 1200 |
| ccg tcg caa atg cta aga acg ggt aac aac ttc cag ttc agc tac gag<br>Pro Ser Gln Met Leu Arg Thr Gly Asn Asn Phe Gln Phe Ser Tyr Glu<br>                  405                         410                       415 | 1248 |
| ttt gag aac gta cct ttc cat agc agc tac gct cac agc caa agc ctg<br>Phe Glu Asn Val Pro Phe His Ser Ser Tyr Ala His Ser Gln Ser Leu<br>              420                         425                        430 | 1296 |
| gac cga cta atg aat cca ctc atc gac caa tac ttg tac tat ctc tct<br>Asp Arg Leu Met Asn Pro Leu Ile Asp Gln Tyr Leu Tyr Tyr Leu Ser<br>                  435                         440                       445 | 1344 |
| aga act att aac ggt tct gga cag aat caa caa acg cta aaa ttc agt<br>Arg Thr Ile Asn Gly Ser Gly Gln Asn Gln Gln Thr Leu Lys Phe Ser<br>         450                          455                        460 | 1392 |
| gtg gcc gga ccc agc aac atg gct gtc cag gga aga aac tac ata cct<br>Val Ala Gly Pro Ser Asn Met Ala Val Gln Gly Arg Asn Tyr Ile Pro<br>465                          470                        475                        480 | 1440 |
| gga ccc agc tac cga caa caa cgt gtc tca acc act gtg act caa aac<br>Gly Pro Ser Tyr Arg Gln Gln Arg Val Ser Thr Thr Val Thr Gln Asn<br>                      485                         490                       495 | 1488 |
| aac aac agc gaa ttt gct tgg cct gga gct tct tct tgg gct ctc aat<br>Asn Asn Ser Glu Phe Ala Trp Pro Gly Ala Ser Ser Trp Ala Leu Asn<br>                  500                         505                       510 | 1536 |
| gga cgt aat agc ttg atg aat cct gga cct gct atg gcc agc cac aaa<br>Gly Arg Asn Ser Leu Met Asn Pro Gly Pro Ala Met Ala Ser His Lys<br>              515                         520                       525 | 1584 |
| gaa gga gag gac cgt ttc ttt cct ttg tct gga tct tta att ttt ggc<br>Glu Gly Glu Asp Arg Phe Phe Pro Leu Ser Gly Ser Leu Ile Phe Gly<br>         530                          535                        540 | 1632 |
| aaa caa ggt acc ggc aga gac aac gtg gat gcg gac aaa gtc atg ata<br>Lys Gln Gly Thr Gly Arg Asp Asn Val Asp Ala Asp Lys Val Met Ile<br>545                          550                        555                        560 | 1680 |
| acc aac gaa gaa gaa att aaa act act aac ccg gta gca acg gag tcc<br>Thr Asn Glu Glu Glu Ile Lys Thr Thr Asn Pro Val Ala Thr Glu Ser<br>                    565                         570                       575 | 1728 |
| tat gga caa gtg gcc aca aac cac cag agt gcc caa act ttg gcg gtg<br>Tyr Gly Gln Val Ala Thr Asn His Gln Ser Ala Gln Thr Leu Ala Val<br>              580                         585                       590 | 1776 |
| cct ttt aag gca cag gcg cag acc ggt tgg gtt caa aac caa gga ata<br>Pro Phe Lys Ala Gln Ala Gln Thr Gly Trp Val Gln Asn Gln Gly Ile<br>            595                         600                       605 | 1824 |
| ctt ccg ggt atg gtt tgg cag gac aga gat gtg tac ctg caa gga ccc<br>Leu Pro Gly Met Val Trp Gln Asp Arg Asp Val Tyr Leu Gln Gly Pro<br>         610                          615                        620 | 1872 |
| att tgg gcc aaa att cct cac acg gac ggc aac ttt cac cct tct ccg<br>Ile Trp Ala Lys Ile Pro His Thr Asp Gly Asn Phe His Pro Ser Pro<br>625                          630                        635                        640 | 1920 |

```
ctg atg gga ggg ttt gga atg aag cac ccg cct cct cag atc ctc atc     1968
Leu Met Gly Gly Phe Gly Met Lys His Pro Pro Pro Gln Ile Leu Ile
                645                 650                 655 aaa aac aca cct gta cct gcg gat cct cca acg gcc ttc aac aag gac     2016
Lys Asn Thr Pro Val Pro Ala Asp Pro Pro Thr Ala Phe Asn Lys Asp
            660                 665                 670 aag ctg aac tct ttc atc acc cag tat tct act ggc caa gtc agc gtg     2064
Lys Leu Asn Ser Phe Ile Thr Gln Tyr Ser Thr Gly Gln Val Ser Val
        675                 680                 685 gag atc gag tgg gag ctg cag aag gaa aac agc aag cgc tgg aac ccg     2112
Glu Ile Glu Trp Glu Leu Gln Lys Glu Asn Ser Lys Arg Trp Asn Pro
    690                 695                 700 gag atc cag tac act tcc aac tat tac aag tct aat aat gtt gaa ttt     2160
Glu Ile Gln Tyr Thr Ser Asn Tyr Tyr Lys Ser Asn Asn Val Glu Phe
705                 710                 715                 720 gct gtt aat act gaa ggt gta tat agt gaa ccc cgc ccc att ggc acc     2208
Ala Val Asn Thr Glu Gly Val Tyr Ser Glu Pro Arg Pro Ile Gly Thr
                725                 730                 735 aga tac ctg act cgt aat ctg                                          2229
Arg Tyr Leu Thr Arg Asn Leu
            740

<210> SEQ ID NO 12
<211> LENGTH: 743
<212> TYPE: PRT
<213> ORGANISM: Artificial Sequence
<220> FEATURE:
<223> OTHER INFORMATION: Synthetic Construct

<400> SEQUENCE: 12

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
        115                 120                 125

Leu Gly Leu Val Glu Glu Ala Lys Thr Ala Pro Gly Lys Lys Arg
    130                 135                 140

Pro Val Glu Gln Ser Pro Gln Pro Asp Ser Ser Ala Gly Ile Gly
145                 150                 155                 160

Lys Ser Gly Ala Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Gly Gly Gly
        195                 200                 205

Ala Pro Val Ala Asp Asn Asn Glu Gly Ala Asp Gly Val Gly Ser Ser
```

-continued

```
                210                 215                 220
Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Ser Thr Ser Gly Gly Ser Ser Asn Asp Asn
                260                 265                 270

Ala Tyr Phe Gly Tyr Ser Thr Pro Trp Gly Tyr Phe Asp Phe Asn Arg
                275                 280                 285

Phe His Cys His Phe Ser Pro Arg Asp Trp Gln Arg Leu Ile Asn Asn
                290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
                325                 330                 335

Asn Leu Thr Ser Thr Val Gln Val Phe Thr Asp Ser Asp Tyr Gln Leu
                340                 345                 350

Pro Tyr Val Leu Gly Ser Ala His Glu Gly Cys Leu Pro Pro Phe Pro
                355                 360                 365

Ala Asp Val Phe Met Ile Pro Gln Tyr Gly Tyr Leu Thr Leu Asn Asp
                370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
                405                 410                 415

Phe Glu Asn Val Pro Phe His Ser Ser Tyr Ala His Ser Gln Ser Leu
                420                 425                 430

Asp Arg Leu Met Asn Pro Leu Ile Asp Gln Tyr Leu Tyr Tyr Leu Ser
                435                 440                 445

Arg Thr Ile Asn Gly Ser Gly Gln Asn Gln Gln Thr Leu Lys Phe Ser
                450                 455                 460

Val Ala Gly Pro Ser Asn Met Ala Val Gln Gly Arg Asn Tyr Ile Pro
465                 470                 475                 480

Gly Pro Ser Tyr Arg Gln Gln Arg Val Ser Thr Thr Val Thr Gln Asn
                485                 490                 495

Asn Asn Ser Glu Phe Ala Trp Pro Gly Ala Ser Ser Trp Ala Leu Asn
                500                 505                 510

Gly Arg Asn Ser Leu Met Asn Pro Gly Pro Ala Met Ala Ser His Lys
                515                 520                 525

Glu Gly Glu Asp Arg Phe Phe Pro Leu Ser Gly Ser Leu Ile Phe Gly
                530                 535                 540

Lys Gln Gly Thr Gly Arg Asp Asn Val Asp Ala Asp Lys Val Met Ile
545                 550                 555                 560

Thr Asn Glu Glu Glu Ile Lys Thr Thr Asn Pro Val Ala Thr Glu Ser
                565                 570                 575

Tyr Gly Gln Val Ala Thr Asn His Gln Ser Ala Gln Thr Leu Ala Val
                580                 585                 590

Pro Phe Lys Ala Gln Ala Gln Thr Gly Trp Val Gln Asn Gln Gly Ile
                595                 600                 605

Leu Pro Gly Met Val Trp Gln Asp Arg Asp Val Tyr Leu Gln Gly Pro
                610                 615                 620

Ile Trp Ala Lys Ile Pro His Thr Asp Gly Asn Phe His Pro Ser Pro
625                 630                 635                 640
```

```
Leu Met Gly Gly Phe Gly Met Lys His Pro Pro Gln Ile Leu Ile
            645                 650                 655

Lys Asn Thr Pro Val Pro Ala Asp Pro Pro Thr Ala Phe Asn Lys Asp
                660                 665                 670

Lys Leu Asn Ser Phe Ile Thr Gln Tyr Ser Thr Gly Gln Val Ser Val
            675                 680                 685

Glu Ile Glu Trp Glu Leu Gln Lys Glu Asn Ser Lys Arg Trp Asn Pro
            690                 695                 700

Glu Ile Gln Tyr Thr Ser Asn Tyr Tyr Lys Ser Asn Asn Val Glu Phe
705                 710                 715                 720

Ala Val Asn Thr Glu Gly Val Tyr Ser Glu Pro Arg Pro Ile Gly Thr
                725                 730                 735

Arg Tyr Leu Thr Arg Asn Leu
            740

<210> SEQ ID NO 13
<211> LENGTH: 2208
<212> TYPE: DNA
<213> ORGANISM: Artificial Sequence
<220> FEATURE:
<223> OTHER INFORMATION: AAVhu68
<220> FEATURE:
<221> NAME/KEY: CDS
<222> LOCATION: (1)..(2208)

<400> SEQUENCE: 13 atg gct gcc gat ggt tat ctt cca gat tgg ctc gag gac aac ctc agt     48
Met Ala Ala Asp Gly Tyr Leu Pro Asp Trp Leu Glu Asp Asn Leu Ser
1               5                   10                  15 gaa ggc att cgc gag tgg tgg gct ttg aaa cct gga gcc cct caa ccc     96
Glu Gly Ile Arg Glu Trp Trp Ala Leu Lys Pro Gly Ala Pro Gln Pro
            20                  25                  30 aag gca aat caa caa cat caa gac aac gct cgg ggt ctt gtg ctt ccg    144
Lys Ala Asn Gln Gln His Gln Asp Asn Ala Arg Gly Leu Val Leu Pro
        35                  40                  45 ggt tac aaa tac ctt gga ccc ggc aac gga ctc gac aag ggg gag ccg    192
Gly Tyr Lys Tyr Leu Gly Pro Gly Asn Gly Leu Asp Lys Gly Glu Pro
    50                  55                  60 gtc aac gaa gca gac gcg gcg gcc ctc gag cac gac aag gcc tac gac    240
Val Asn Glu Ala Asp Ala Ala Ala Leu Glu His Asp Lys Ala Tyr Asp
65                  70                  75                  80 cag cag ctc aag gcc gga gac aac ccg tac ctc aag tac aac cac gcc    288
Gln Gln Leu Lys Ala Gly Asp Asn Pro Tyr Leu Lys Tyr Asn His Ala
                85                  90                  95 gac gcc gag ttc cag gag cgg ctc aaa gaa gat acg tct ttt ggg ggc    336
Asp Ala Glu Phe Gln Glu Arg Leu Lys Glu Asp Thr Ser Phe Gly Gly
            100                 105                 110 aac ctc ggg cga gca gtc ttc cag gcc aaa aag agg ctt ctt gaa cct    384
Asn Leu Gly Arg Ala Val Phe Gln Ala Lys Lys Arg Leu Leu Glu Pro
        115                 120                 125 ctt ggt ctg gtt gag gaa gcg gct aag acg gct cct gga aag aag agg    432
Leu Gly Leu Val Glu Glu Ala Ala Lys Thr Ala Pro Gly Lys Lys Arg
    130                 135                 140 cct gta gag cag tct cct cag gaa ccg gac tcc tcc gtg ggt att ggc    480
Pro Val Glu Gln Ser Pro Gln Glu Pro Asp Ser Ser Val Gly Ile Gly
145                 150                 155                 160 aaa tcg ggt gca cag ccc gct aaa aag aga ctc aat ttc ggt cag act    528
Lys Ser Gly Ala Gln Pro Ala Lys Lys Arg Leu Asn Phe Gly Gln Thr
                165                 170                 175
```

```
ggc gac aca gag tca gtc ccc gac cct caa cca atc gga gaa cct ccc    576
Gly Asp Thr Glu Ser Val Pro Asp Pro Gln Pro Ile Gly Glu Pro Pro
            180                 185                 190 gca gcc ccc tca ggt gtg gga tct ctt aca atg gct tca ggt ggt ggc    624
Ala Ala Pro Ser Gly Val Gly Ser Leu Thr Met Ala Ser Gly Gly Gly
        195                 200                 205 gca cca gtg gca gac aat aac gaa ggt gcc gat gga gtg ggt agt tcc    672
Ala Pro Val Ala Asp Asn Asn Glu Gly Ala Asp Gly Val Gly Ser Ser
    210                 215                 220 tcg gga aat tgg cat tgc gat tcc caa tgg ctg ggg gac aga gtc atc    720
Ser Gly Asn Trp His Cys Asp Ser Gln Trp Leu Gly Asp Arg Val Ile
225                 230                 235                 240 acc acc agc acc cga acc tgg gcc ctg ccc acc tac aac aat cac ctc    768
Thr Thr Ser Thr Arg Thr Trp Ala Leu Pro Thr Tyr Asn Asn His Leu
                245                 250                 255 tac aag caa atc tcc aac agc aca tct gga gga tct tca aat gac aac    816
Tyr Lys Gln Ile Ser Asn Ser Thr Ser Gly Gly Ser Ser Asn Asp Asn
            260                 265                 270 gcc tac ttc ggc tac agc acc ccc tgg ggg tat ttt gac ttc aac aga    864
Ala Tyr Phe Gly Tyr Ser Thr Pro Trp Gly Tyr Phe Asp Phe Asn Arg
        275                 280                 285 ttc cac tgc cac ttc tca cca cgt gac tgg caa aga ctc atc aac aac    912
Phe His Cys His Phe Ser Pro Arg Asp Trp Gln Arg Leu Ile Asn Asn
    290                 295                 300 aac tgg gga ttc cgg cct aag cga ctc aac ttc aag ctc ttc aac att    960
Asn Trp Gly Phe Arg Pro Lys Arg Leu Asn Phe Lys Leu Phe Asn Ile
305                 310                 315                 320 cag gtc aaa gag gtt acg gac aac aat gga gtc aag acc atc gct aat    1008
Gln Val Lys Glu Val Thr Asp Asn Asn Gly Val Lys Thr Ile Ala Asn
                325                 330                 335 aac ctt acc agc acg gtc cag gtc ttc acg gac tca gac tat cag ctc    1056
Asn Leu Thr Ser Thr Val Gln Val Phe Thr Asp Ser Asp Tyr Gln Leu
            340                 345                 350 ccg tac gtg ctc ggg tcg gct cac gag ggc tgc ctc ccg ccg ttc cca    1104
Pro Tyr Val Leu Gly Ser Ala His Glu Gly Cys Leu Pro Pro Phe Pro
        355                 360                 365 gcg gac gtt ttc atg att cct cag tac ggg tat cta acg ctt aat gat    1152
Ala Asp Val Phe Met Ile Pro Gln Tyr Gly Tyr Leu Thr Leu Asn Asp
    370                 375                 380 gga agc caa gcc gtg ggt cgt tcc tcc ttt tac tgc ctg gaa tat ttc    1200
Gly Ser Gln Ala Val Gly Arg Ser Ser Phe Tyr Cys Leu Glu Tyr Phe
385                 390                 395                 400 ccg tcg caa atg cta aga acg ggt aac aac ttc cag ttc agc tac gag    1248
Pro Ser Gln Met Leu Arg Thr Gly Asn Asn Phe Gln Phe Ser Tyr Glu
                405                 410                 415 ttt gag aac gta cct ttc cat agc agc tat gct cac agc caa agc ctg    1296
Phe Glu Asn Val Pro Phe His Ser Ser Tyr Ala His Ser Gln Ser Leu
            420                 425                 430 gac cga ctc atg aat cca ctc atc gac caa tac ttg tac tat ctc tca    1344
Asp Arg Leu Met Asn Pro Leu Ile Asp Gln Tyr Leu Tyr Tyr Leu Ser
        435                 440                 445 aag act att aac ggt tct gga cag aat caa caa acg cta aaa ttc agt    1392
Lys Thr Ile Asn Gly Ser Gly Gln Asn Gln Gln Thr Leu Lys Phe Ser
    450                 455                 460 gtg gcc gga ccc agc aac atg gct gtc cag gga aga aac tac ata cct    1440
Val Ala Gly Pro Ser Asn Met Ala Val Gln Gly Arg Asn Tyr Ile Pro
465                 470                 475                 480 gga ccc agc tac cga caa caa cgt gtc tca acc act gtg act caa aac    1488
Gly Pro Ser Tyr Arg Gln Gln Arg Val Ser Thr Thr Val Thr Gln Asn
                485                 490                 495
```

```
aac aac agc gaa ttt gct tgg cct gga gct tct tct tgg gct ctc aat    1536
Asn Asn Ser Glu Phe Ala Trp Pro Gly Ala Ser Ser Trp Ala Leu Asn
            500                 505                 510 gga cgt aat agc ttg atg aat cct gga cct gct atg gcc agc cac aaa    1584
Gly Arg Asn Ser Leu Met Asn Pro Gly Pro Ala Met Ala Ser His Lys
        515                 520                 525 gaa gga gag gac cgt ttc ttt cct ttg tct gga tct tta att ttt ggc    1632
Glu Gly Glu Asp Arg Phe Phe Pro Leu Ser Gly Ser Leu Ile Phe Gly
530                 535                 540 aaa caa gga act gga aga gac aac gtg gat gcg gac aaa gtc atg ata    1680
Lys Gln Gly Thr Gly Arg Asp Asn Val Asp Ala Asp Lys Val Met Ile
545                 550                 555                 560 acc aac gaa gaa gaa att aaa act acc aac cca gta gca acg gag tcc    1728
Thr Asn Glu Glu Glu Ile Lys Thr Thr Asn Pro Val Ala Thr Glu Ser
            565                 570                 575 tat gga caa gtg gcc aca aac cac cag agt gcc caa gca cag gcg cag    1776
Tyr Gly Gln Val Ala Thr Asn His Gln Ser Ala Gln Ala Gln Ala Gln
        580                 585                 590 acc ggc tgg gtt caa aac caa gga ata ctt ccg ggt atg gtt tgg cag    1824
Thr Gly Trp Val Gln Asn Gln Gly Ile Leu Pro Gly Met Val Trp Gln
    595                 600                 605 gac aga gat gtg tac ctg caa gga ccc att tgg gcc aaa att cct cac    1872
Asp Arg Asp Val Tyr Leu Gln Gly Pro Ile Trp Ala Lys Ile Pro His
610                 615                 620 acg gac ggc aac ttt cac cct tct ccg ctg atg gga ggg ttt gga atg    1920
Thr Asp Gly Asn Phe His Pro Ser Pro Leu Met Gly Gly Phe Gly Met
625                 630                 635                 640 aag cac ccg cct cct cag atc ctc atc aaa aac aca cct gta cct gcg    1968
Lys His Pro Pro Pro Gln Ile Leu Ile Lys Asn Thr Pro Val Pro Ala
            645                 650                 655 gat cct cca acg gct ttc aac aag gac aag ctg aac tct ttc atc acc    2016
Asp Pro Pro Thr Ala Phe Asn Lys Asp Lys Leu Asn Ser Phe Ile Thr
        660                 665                 670 cag tat tct act ggc caa gtc agc gtg gag att gag tgg gag ctg cag    2064
Gln Tyr Ser Thr Gly Gln Val Ser Val Glu Ile Glu Trp Glu Leu Gln
    675                 680                 685 aag gaa aac agc aag cgc tgg aac ccg gag atc cag tac act tcc aac    2112
Lys Glu Asn Ser Lys Arg Trp Asn Pro Glu Ile Gln Tyr Thr Ser Asn
690                 695                 700 tat tac aag tct aat aat gtt gaa ttt gct gtt aat act gaa ggt gtt    2160
Tyr Tyr Lys Ser Asn Asn Val Glu Phe Ala Val Asn Thr Glu Gly Val
705                 710                 715                 720 tat tct gaa ccc cgc ccc att ggc acc aga tac ctg act cgt aat ctg    2208
Tyr Ser Glu Pro Arg Pro Ile Gly Thr Arg Tyr Leu Thr Arg Asn Leu
            725                 730                 735

<210> SEQ ID NO 14
<211> LENGTH: 736
<212> TYPE: PRT
<213> ORGANISM: Artificial Sequence
<220> FEATURE:
<223> OTHER INFORMATION: Synthetic Construct

<400> SEQUENCE: 14

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30

Lys Ala Asn Gln Gln His Gln Asp Asn Ala Arg Gly Leu Val Leu Pro
        35                  40                  45
```

-continued

```
Gly Tyr Lys Tyr Leu Gly Pro Gly Asn Gly Leu Asp Lys Gly Glu Pro
             50                  55                  60

Val Asn Glu Ala Asp Ala Ala Leu Glu His Asp Lys Ala Tyr Asp
 65                  70                  75                  80

Gln Gln Leu Lys Ala Gly Asp Asn Pro Tyr Leu Lys Tyr Asn His Ala
                 85                  90                  95

Asp Ala Glu Phe Gln Glu Arg Leu Lys Glu Asp Thr Ser Phe Gly Gly
                100                 105                 110

Asn Leu Gly Arg Ala Val Phe Gln Ala Lys Lys Arg Leu Leu Glu Pro
                115                 120                 125

Leu Gly Leu Val Glu Glu Ala Ala Lys Thr Ala Pro Gly Lys Lys Arg
            130                 135                 140

Pro Val Glu Gln Ser Pro Gln Glu Pro Asp Ser Ser Val Gly Ile Gly
145                 150                 155                 160

Lys Ser Gly Ala Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
                180                 185                 190

Ala Ala Pro Ser Gly Val Gly Ser Leu Thr Met Ala Ser Gly Gly Gly
            195                 200                 205

Ala Pro Val Ala Asp Asn Asn Glu Gly Ala Asp Gly Val Gly Ser Ser
210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Ser Thr Ser Gly Gly Ser Ser Asn Asp Asn
                260                 265                 270

Ala Tyr Phe Gly Tyr Ser Thr Pro Trp Gly Tyr Phe Asp Phe Asn Arg
            275                 280                 285

Phe His Cys His Phe Ser Pro Arg Asp Trp Gln Arg Leu Ile Asn Asn
            290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
                325                 330                 335

Asn Leu Thr Ser Thr Val Gln Val Phe Thr Asp Ser Asp Tyr Gln Leu
                340                 345                 350

Pro Tyr Val Leu Gly Ser Ala His Glu Gly Cys Leu Pro Pro Phe Pro
            355                 360                 365

Ala Asp Val Phe Met Ile Pro Gln Tyr Gly Tyr Leu Thr Leu Asn Asp
370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
                405                 410                 415

Phe Glu Asn Val Pro Phe His Ser Ser Tyr Ala His Ser Gln Ser Leu
                420                 425                 430

Asp Arg Leu Met Asn Pro Leu Ile Asp Gln Tyr Leu Tyr Tyr Leu Ser
            435                 440                 445

Lys Thr Ile Asn Gly Ser Gly Gln Asn Gln Gln Thr Leu Lys Phe Ser
450                 455                 460
```

| | | | | | | | | | | | | | | |
|---|---|---|---|---|---|---|---|---|---|---|---|---|---|---|
|Val|Ala|Gly|Pro|Ser|Asn|Met|Ala|Val|Gln|Gly|Arg|Asn|Tyr|Ile|Pro|
|465| | | | |470| | | |475| | | | |480|

Gly Pro Ser Tyr Arg Gln Gln Arg Val Ser Thr Thr Val Thr Gln Asn
                485                 490                 495

Asn Asn Ser Glu Phe Ala Trp Pro Gly Ala Ser Ser Trp Ala Leu Asn
            500                 505                 510

Gly Arg Asn Ser Leu Met Asn Pro Gly Pro Ala Met Ala Ser His Lys
        515                 520                 525

Glu Gly Glu Asp Arg Phe Phe Pro Leu Ser Gly Ser Leu Ile Phe Gly
    530                 535                 540

Lys Gln Gly Thr Gly Arg Asp Asn Val Asp Ala Asp Lys Val Met Ile
545                 550                 555                 560

Thr Asn Glu Glu Glu Ile Lys Thr Thr Asn Pro Val Ala Thr Glu Ser
                565                 570                 575

Tyr Gly Gln Val Ala Thr Asn His Gln Ser Ala Gln Ala Gln Ala Gln
                580                 585                 590

Thr Gly Trp Val Gln Asn Gln Gly Ile Leu Pro Gly Met Val Trp Gln
            595                 600                 605

Asp Arg Asp Val Tyr Leu Gln Gly Pro Ile Trp Ala Lys Ile Pro His
        610                 615                 620

Thr Asp Gly Asn Phe His Pro Ser Pro Leu Met Gly Gly Phe Gly Met
625                 630                 635                 640

Lys His Pro Pro Pro Gln Ile Leu Ile Lys Asn Thr Pro Val Pro Ala
                645                 650                 655

Asp Pro Pro Thr Ala Phe Asn Lys Asp Lys Leu Asn Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Ile Gln Tyr Thr Ser Asn
690                 695                 700

Tyr Tyr Lys Ser Asn Asn Val Glu Phe Ala Val Asn Thr Glu Gly Val
705                 710                 715                 720

Tyr Ser Glu Pro Arg Pro Ile Gly Thr Arg Tyr Leu Thr Arg Asn Leu
                725                 730                 735

<210> SEQ ID NO 15
<211> LENGTH: 2211
<212> TYPE: DNA
<213> ORGANISM: Artificial Sequence
<220> FEATURE:
<223> OTHER INFORMATION: AAV8T
<220> FEATURE:
<221> NAME/KEY: CDS
<222> LOCATION: (1)..(2211)

<400> SEQUENCE: 15

```
atg gct gcc gat ggt tat ctt cca gat tgg ctc gag gac aac ctc tct     48
Met Ala Ala Asp Gly Tyr Leu Pro Asp Trp Leu Glu Asp Asn Leu Ser
1               5                   10                  15 gag ggc att cgc gag tgg tgg gcg ctg aaa cct gga gcc ccg aag ccc     96
Glu Gly Ile Arg Glu Trp Trp Ala Leu Lys Pro Gly Ala Pro Lys Pro
            20                  25                  30 aaa gcc aac cag caa aag cag gac gac ggc cgg ggt ctg gtg ctt cct    144
Lys Ala Asn Gln Gln Lys Gln Asp Asp Gly Arg Gly Leu Val Leu Pro
        35                  40                  45 ggc tac aag tac ctc gga ccc ttc aac gga ctc gac aag ggg gag ccc    192
Gly Tyr Lys Tyr Leu Gly Pro Phe Asn Gly Leu Asp Lys Gly Glu Pro
    50                  55                  60
```

```
gtc aac gcg gcg gac gca gcg gcc ctc gag cac gac aag gcc tac gac    240
Val Asn Ala Ala Asp Ala Ala Ala Leu Glu His Asp Lys Ala Tyr Asp
 65              70                  75                  80 cag cag ctg cag gcg ggt gac aat ccg tac ctg cgg tat aac cac gcc    288
Gln Gln Leu Gln Ala Gly Asp Asn Pro Tyr Leu Arg Tyr Asn His Ala
                 85                  90                  95 gac gcc gag ttt cag gag cgt ctg caa gaa gat acg tct ttt ggg ggc    336
Asp Ala Glu Phe Gln Glu Arg Leu Gln Glu Asp Thr Ser Phe Gly Gly
            100                 105                 110 aac ctc ggg cga gca gtc ttc cag gcc aag aag cgg gtt ctc gaa cct    384
Asn Leu Gly Arg Ala Val Phe Gln Ala Lys Lys Arg Val Leu Glu Pro
        115                 120                 125 ctc ggt ctg gtt gag gaa ggc gct aag acg gct cct gga aag aag aga    432
Leu Gly Leu Val Glu Glu Gly Ala Lys Thr Ala Pro Gly Lys Lys Arg
    130                 135                 140 ccg gta gag cca tca ccc cag cgt tct cca gac tcc tct acg ggc atc    480
Pro Val Glu Pro Ser Pro Gln Arg Ser Pro Asp Ser Ser Thr Gly Ile
145                 150                 155                 160 ggc aag aaa ggc caa cag ccc gcc aga aaa aga ctc aat ttt ggt cag    528
Gly Lys Lys Gly Gln Gln Pro Ala Arg Lys Arg Leu Asn Phe Gly Gln
                165                 170                 175 act ggc gac tca gag tca gtt cca gac cct caa cct ctc gga gaa cct    576
Thr Gly Asp Ser Glu Ser Val Pro Asp Pro Gln Pro Leu Gly Glu Pro
            180                 185                 190 cca gca gcg ccc tct ggt gtg gga cct aat aca atg gct gca ggc ggt    624
Pro Ala Ala Pro Ser Gly Val Gly Pro Asn Thr Met Ala Ala Gly Gly
        195                 200                 205 ggc gca cca atg gca gac aat aac gaa ggc gcc gac gga gtg ggt agt    672
Gly Ala Pro Met Ala Asp Asn Asn Glu Gly Ala Asp Gly Val Gly Ser
    210                 215                 220 tcc tcg gga aat tgg cat tgc gat tcc aca tgg ctg ggc gac aga gtc    720
Ser Ser Gly Asn Trp His Cys Asp Ser Thr Trp Leu Gly Asp Arg Val
225                 230                 235                 240 atc acc acc agc acc cga acc tgg gcc ctg ccc acc tac aac aac cac    768
Ile Thr Thr Ser Thr Arg Thr Trp Ala Leu Pro Thr Tyr Asn Asn His
                245                 250                 255 ctc tac aag caa atc tcc tct ggt act cat gga gcc acc aac gac aac    816
Leu Tyr Lys Gln Ile Ser Ser Gly Thr His Gly Ala Thr Asn Asp Asn
            260                 265                 270 acc tac ttc ggc tac agc acc ccc tgg ggg tat ttt gac ttt aac aga    864
Thr Tyr Phe Gly Tyr Ser Thr Pro Trp Gly Tyr Phe Asp Phe Asn Arg
        275                 280                 285 ttc cac tgc cac ttt tca cca cgt gac tgg cag cga ctc atc aac aac    912
Phe His Cys His Phe Ser Pro Arg Asp Trp Gln Arg Leu Ile Asn Asn
    290                 295                 300 aac tgg gga ttc cgg ccc aag aga ctc agc ttc aag ctc ttc aac atc    960
Asn Trp Gly Phe Arg Pro Lys Arg Leu Ser Phe Lys Leu Phe Asn Ile
305                 310                 315                 320 cag gtc aag gag gtc acg cag aat gaa ggc acc aag acc atc gcc aat   1008
Gln Val Lys Glu Val Thr Gln Asn Glu Gly Thr Lys Thr Ile Ala Asn
                325                 330                 335 aac ctc acc agc acc atc cag gtg ttt acg gac tcg gag tac cag ctg   1056
Asn Leu Thr Ser Thr Ile Gln Val Phe Thr Asp Ser Glu Tyr Gln Leu
            340                 345                 350 ccg tac gtt ctc ggc tct gcc cac cag ggc tgc ctg cct ccg ttc ccg   1104
Pro Tyr Val Leu Gly Ser Ala His Gln Gly Cys Leu Pro Pro Phe Pro
        355                 360                 365 gcg gac gtg ttc atg att ccc cag tac ggc tac cta aca ctc aac aac   1152
Ala Asp Val Phe Met Ile Pro Gln Tyr Gly Tyr Leu Thr Leu Asn Asn
```

-continued

|  |  |  |  |  |  |  |  |  |  |  |  |  |  |  |  |
|---|---|---|---|---|---|---|---|---|---|---|---|---|---|---|---|
| | | | 370 | | | | | 375 | | | | | 380 | | |
| ggt | agt | cag | gcc | gtg | gga | cgc | tcc | tcc | ttc | tac | tgc | ctg | gaa | tac | ttt |
| Gly | Ser | Gln | Ala | Val | Gly | Arg | Ser | Ser | Phe | Tyr | Cys | Leu | Glu | Tyr | Phe |
| 385 | | | | 390 | | | | | 395 | | | | | 400 | |

1200 cct tcg cag atg ctg aga acc ggc aac aac ttc cag ttt act tac acc    1248
Pro Ser Gln Met Leu Arg Thr Gly Asn Asn Phe Gln Phe Thr Tyr Thr
                    405                 410                 415 ttc gag gac gtg cct ttc cac agc agc tac gcc cac agc cag agc ttg    1296
Phe Glu Asp Val Pro Phe His Ser Ser Tyr Ala His Ser Gln Ser Leu
            420                 425                 430 gac cgg ctg atg aat cct ctg att gac cag tac ctg tac tac ttg tct    1344
Asp Arg Leu Met Asn Pro Leu Ile Asp Gln Tyr Leu Tyr Tyr Leu Ser
        435                 440                 445 cgg act caa aca aca ggt ggg agt agg cct acg cag act ctg ggc ttc    1392
Arg Thr Gln Thr Thr Gly Gly Ser Arg Pro Thr Gln Thr Leu Gly Phe
    450                 455                 460 agc caa ggt ggg cct aat aca atg gcc aat cag gca aag aac tgg ctg    1440
Ser Gln Gly Gly Pro Asn Thr Met Ala Asn Gln Ala Lys Asn Trp Leu
465                 470                 475                 480 cca gga ccc tgt tac cgc caa caa cgc gtc tca acg aca acc ggg caa    1488
Pro Gly Pro Cys Tyr Arg Gln Gln Arg Val Ser Thr Thr Thr Gly Gln
                485                 490                 495 aac aac aat agc aac ttt gcc tgg act gct ggg acc aaa tac cat ctg    1536
Asn Asn Asn Ser Asn Phe Ala Trp Thr Ala Gly Thr Lys Tyr His Leu
            500                 505                 510 aat gga aga aat tca ttg gct aat cct ggc atc gct atg gca aca cac    1584
Asn Gly Arg Asn Ser Leu Ala Asn Pro Gly Ile Ala Met Ala Thr His
        515                 520                 525 aaa gac gac gag gag cgt ttt ttt ccc agt aac ggg atc ctg att ttt    1632
Lys Asp Asp Glu Glu Arg Phe Phe Pro Ser Asn Gly Ile Leu Ile Phe
    530                 535                 540 ggc aaa caa aat gct gcc aga gac aat gcg gat tac agc gat gtc atg    1680
Gly Lys Gln Asn Ala Ala Arg Asp Asn Ala Asp Tyr Ser Asp Val Met
545                 550                 555                 560 ctc acc agc gag gaa gaa atc aaa acc act aac cct gtg gct aca gag    1728
Leu Thr Ser Glu Glu Glu Ile Lys Thr Thr Asn Pro Val Ala Thr Glu
                565                 570                 575 gaa tac ggt atc gtg ggt gat aac ttg cag ttg tat aac acg gct cct    1776
Glu Tyr Gly Ile Val Gly Asp Asn Leu Gln Leu Tyr Asn Thr Ala Pro
            580                 585                 590 ggt tcg gtg ttt gtc aac agc cag ggg gcc tta ccc ggt atg gtc tgg    1824
Gly Ser Val Phe Val Asn Ser Gln Gly Ala Leu Pro Gly Met Val Trp
        595                 600                 605 cag aac cgg gac gtg tac ctg cag ggt ccc atc tgg gcc aag att cct    1872
Gln Asn Arg Asp Val Tyr Leu Gln Gly Pro Ile Trp Ala Lys Ile Pro
    610                 615                 620 cac acg gac ggc aac ttc cac ccg tct ccg ctg atg ggc ggc ttt ggc    1920
His Thr Asp Gly Asn Phe His Pro Ser Pro Leu Met Gly Gly Phe Gly
625                 630                 635                 640 ctg aaa cat cct ccg cct cag atc ctg atc aag aac acg cct gta cct    1968
Leu Lys His Pro Pro Pro Gln Ile Leu Ile Lys Asn Thr Pro Val Pro
                645                 650                 655 gcg gat cct ccg acc acc ttc aac cag tca aag ctg aac tct ttc atc    2016
Ala Asp Pro Pro Thr Thr Phe Asn Gln Ser Lys Leu Asn Ser Phe Ile
            660                 665                 670 acg caa tac agc acc gga cag gtc agc gtg gaa att gaa tgg gag ctg    2064
Thr Gln Tyr Ser Thr Gly Gln Val Ser Val Glu Ile Glu Trp Glu Leu
        675                 680                 685 cag aag gaa aac agc aag cgc tgg aac ccc gag atc cag tac acc tcc    2112

```
                    Gln Lys Glu Asn Ser Lys Arg Trp Asn Pro Glu Ile Gln Tyr Thr Ser
                                    690                 695                 700 aac tac tac aaa tct aca agt gtg gac ttt gct gtt aat aca gaa ggc                          2160
Asn Tyr Tyr Lys Ser Thr Ser Val Asp Phe Ala Val Asn Thr Glu Gly
705                 710                 715                 720 gtg tac tct gaa ccc cgc ccc att ggc acc cgt tac ctc acc cgt aat                          2208
Val Tyr Ser Glu Pro Arg Pro Ile Gly Thr Arg Tyr Leu Thr Arg Asn
                725                 730                 735 ctg                                                                                       2211
Leu <210> SEQ ID NO 16
<211> LENGTH: 737
<212> TYPE: PRT
<213> ORGANISM: Artificial Sequence
<220> FEATURE:
<223> OTHER INFORMATION: Synthetic Construct

<400> SEQUENCE: 16

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Gln Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Arg Lys Arg Leu Asn Phe Gly Gln
                165                 170                 175

Thr Gly Asp Ser Glu Ser Val Pro Asp Pro Gln Pro Leu Gly Glu Pro
            180                 185                 190

Pro Ala Ala Pro Ser Gly Val Gly Pro Asn Thr Met Ala Ala Gly Gly
        195                 200                 205

Gly Ala Pro Met Ala Asp Asn Asn Glu Gly Ala Asp Gly Val Gly Ser
    210                 215                 220

Ser Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Ser Gly Thr His Gly Ala Thr Asn Asp Asn
            260                 265                 270

Thr Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn Asn
```

-continued

```
            290                 295                 300
Asn Trp Gly Phe Arg Pro Lys Arg Leu Ser Phe Lys Leu Phe Asn Ile
305                 310                 315                 320
Gln Val Lys Glu Val Thr Gln Asn Glu Gly Thr Lys Thr Ile Ala Asn
                325                 330                 335
Asn Leu Thr Ser Thr Ile Gln Val Phe Thr Asp Ser Glu Tyr Gln Leu
                340                 345                 350
Pro Tyr Val Leu Gly Ser Ala His Gln Gly Cys Leu Pro Pro Phe Pro
                355                 360                 365
Ala Asp Val Phe Met Ile Pro Gln Tyr Gly Tyr Leu Thr Leu Asn Asn
370                 375                 380
Gly Ser Gln Ala Val Gly Arg Ser Ser Phe Tyr Cys Leu Glu Tyr Phe
385                 390                 395                 400
Pro Ser Gln Met Leu Arg Thr Gly Asn Asn Phe Gln Phe Thr Tyr Thr
                405                 410                 415
Phe Glu Asp Val Pro Phe His Ser Ser Tyr Ala His Ser Gln Ser Leu
                420                 425                 430
Asp Arg Leu Met Asn Pro Leu Ile Asp Gln Tyr Leu Tyr Tyr Leu Ser
                435                 440                 445
Arg Thr Gln Thr Thr Gly Gly Ser Arg Pro Thr Gln Thr Leu Gly Phe
                450                 455                 460
Ser Gln Gly Gly Pro Asn Thr Met Ala Asn Gln Ala Lys Asn Trp Leu
465                 470                 475                 480
Pro Gly Pro Cys Tyr Arg Gln Gln Arg Val Ser Thr Thr Thr Gly Gln
                485                 490                 495
Asn Asn Asn Ser Asn Phe Ala Trp Thr Ala Gly Thr Lys Tyr His Leu
                500                 505                 510
Asn Gly Arg Asn Ser Leu Ala Asn Pro Gly Ile Ala Met Ala Thr His
                515                 520                 525
Lys Asp Asp Glu Glu Arg Phe Phe Pro Ser Asn Gly Ile Leu Ile Phe
530                 535                 540
Gly Lys Gln Asn Ala Ala Arg Asp Asn Ala Asp Tyr Ser Asp Val Met
545                 550                 555                 560
Leu Thr Ser Glu Glu Glu Ile Lys Thr Thr Asn Pro Val Ala Thr Glu
                565                 570                 575
Glu Tyr Gly Ile Val Gly Asp Asn Leu Gln Leu Tyr Asn Thr Ala Pro
                580                 585                 590
Gly Ser Val Phe Val Asn Ser Gln Gly Ala Leu Pro Gly Met Val Trp
                595                 600                 605
Gln Asn Arg Asp Val Tyr Leu Gln Gly Pro Ile Trp Ala Lys Ile Pro
610                 615                 620
His Thr Asp Gly Asn Phe His Pro Ser Pro Leu Met Gly Gly Phe Gly
625                 630                 635                 640
Leu Lys His Pro Pro Pro Gln Ile Leu Ile Lys Asn Thr Pro Val Pro
                645                 650                 655
Ala Asp Pro Pro Thr Thr Phe Asn Gln Ser Lys Leu Asn Ser Phe Ile
                660                 665                 670
Thr Gln Tyr Ser Thr Gly Gln Val Ser Val Glu Ile Glu Trp Glu Leu
                675                 680                 685
Gln Lys Glu Asn Ser Lys Arg Trp Asn Pro Glu Ile Gln Tyr Thr Ser
                690                 695                 700
Asn Tyr Tyr Lys Ser Thr Ser Val Asp Phe Ala Val Asn Thr Glu Gly
705                 710                 715                 720
```

```
Val Tyr Ser Glu Pro Arg Pro Ile Gly Thr Arg Tyr Leu Thr Arg Asn
                725                 730                 735

Leu

<210> SEQ ID NO 17
<211> LENGTH: 2214
<212> TYPE: DNA
<213> ORGANISM: Artificial Sequence
<220> FEATURE:
<223> OTHER INFORMATION: AAV8.AR2.08
<220> FEATURE:
<221> NAME/KEY: CDS
<222> LOCATION: (1)..(2214)

<400> SEQUENCE: 17 atg gct gcc gat ggt tat ctt cca gat tgg ctc gag gac aac ctc tct     48
Met Ala Ala Asp Gly Tyr Leu Pro Asp Trp Leu Glu Asp Asn Leu Ser
1               5                   10                  15 gag ggc att cgc gag tgg tgg gcg ctg aaa cct gga gcc ccg aag ccc     96
Glu Gly Ile Arg Glu Trp Trp Ala Leu Lys Pro Gly Ala Pro Lys Pro
            20                  25                  30 aaa gcc aac cag caa aag cag gac gac ggc cgg ggt ctg gtg ctt cct    144
Lys Ala Asn Gln Gln Lys Gln Asp Asp Gly Arg Gly Leu Val Leu Pro
        35                  40                  45 ggc tac aag tac ctc gga ccc ttc aac gga ctc gac aag ggg gag ccc    192
Gly Tyr Lys Tyr Leu Gly Pro Phe Asn Gly Leu Asp Lys Gly Glu Pro
    50                  55                  60 gtc aac gcg gcg gac gca gcg gcc ctc gag cac gac aag gcc tac gac    240
Val Asn Ala Ala Asp Ala Ala Ala Leu Glu His Asp Lys Ala Tyr Asp
65                  70                  75                  80 cag cag ctg cag gcg ggt gac aat ccg tac ctg cgg tat aac cac gcc    288
Gln Gln Leu Gln Ala Gly Asp Asn Pro Tyr Leu Arg Tyr Asn His Ala
                85                  90                  95 gac gcc gag ttt cag gag cgt ctg caa gaa gat acg tct ttt ggg ggc    336
Asp Ala Glu Phe Gln Glu Arg Leu Gln Glu Asp Thr Ser Phe Gly Gly
            100                 105                 110 aac ctc ggg cga gca gtc ttc cag gcc aag aag cgg gtt ctc gaa cct    384
Asn Leu Gly Arg Ala Val Phe Gln Ala Lys Lys Arg Val Leu Glu Pro
        115                 120                 125 ctc ggt ctg gtt gag gaa ggc gct aag acg gct cct gga aag aag aga    432
Leu Gly Leu Val Glu Glu Gly Ala Lys Thr Ala Pro Gly Lys Lys Arg
    130                 135                 140 ccg gta gag cca tca ccc cag cgt tct cca gac tcc tct acg ggc atc    480
Pro Val Glu Pro Ser Pro Gln Arg Ser Pro Asp Ser Ser Thr Gly Ile
145                 150                 155                 160 ggc aag aaa ggc caa cag ccc gcc aga aaa aga ctc aat ttt ggt cag    528
Gly Lys Lys Gly Gln Gln Pro Ala Arg Lys Arg Leu Asn Phe Gly Gln
                165                 170                 175 act ggc gac tca gag tca gtt cca gac cct caa cct ctc gga gaa cct    576
Thr Gly Asp Ser Glu Ser Val Pro Asp Pro Gln Pro Leu Gly Glu Pro
            180                 185                 190 cca gca gcg ccc tct ggt gtg gga cct aat aca atg gct gca ggc ggt    624
Pro Ala Ala Pro Ser Gly Val Gly Pro Asn Thr Met Ala Ala Gly Gly
        195                 200                 205 ggc gca cca atg gca gac aat aac gaa ggc gcc gac gga gtg ggt agt    672
Gly Ala Pro Met Ala Asp Asn Asn Glu Gly Ala Asp Gly Val Gly Ser
    210                 215                 220 tcc tcg gga aat tgg cat tgc gat tcc aca tgg ctg ggc gac aga gtc    720
Ser Ser Gly Asn Trp His Cys Asp Ser Thr Trp Leu Gly Asp Arg Val
225                 230                 235                 240
```

-continued

| | |
|---|---|
| atc acc acc agc acc cga acc tgg gcc ctg ccc acc tac aac aac cac<br>Ile Thr Thr Ser Thr Arg Thr Trp Ala Leu Pro Thr Tyr Asn Asn His<br>                                   245                          250                       255 | 768 |
| ctc tac aag caa atc tcc aac ggg aca tcg gga gga gcc acc aac gac<br>Leu Tyr Lys Gln Ile Ser Asn Gly Thr Ser Gly Gly Ala Thr Asn Asp<br>                     260                       265                   270 | 816 |
| aac acc tac ttc ggc tac agc acc ccc tgg ggg tat ttt gac ttt aac<br>Asn Thr Tyr Phe Gly Tyr Ser Thr Pro Trp Gly Tyr Phe Asp Phe Asn<br>              275                     280                   285 | 864 |
| aga ttc cac tgc cac ttt tca cca cgt gac tgg cag cga ctc atc aac<br>Arg Phe His Cys His Phe Ser Pro Arg Asp Trp Gln Arg Leu Ile Asn<br>            290                     295                   300 | 912 |
| aac aac tgg gga ttc cgg ccc aag aga ctc agc ttc aag ctc ttc aac<br>Asn Asn Trp Gly Phe Arg Pro Lys Arg Leu Ser Phe Lys Leu Phe Asn<br>305                   310                     315                   320 | 960 |
| atc cag gtc aag gag gtc acg cag aat gaa ggc acc aag acc atc gcc<br>Ile Gln Val Lys Glu Val Thr Gln Asn Glu Gly Thr Lys Thr Ile Ala<br>                     325                     330                   335 | 1008 |
| aat aac ctc acc agc acc atc cag gtg ttt acg gac tcg gag tac cag<br>Asn Asn Leu Thr Ser Thr Ile Gln Val Phe Thr Asp Ser Glu Tyr Gln<br>            340                     345                   350 | 1056 |
| ctg ccg tac gtt ctc ggc tct gcc cac cag ggc tgc ctg cct ccg ttc<br>Leu Pro Tyr Val Leu Gly Ser Ala His Gln Gly Cys Leu Pro Pro Phe<br>              355                     360                   365 | 1104 |
| ccg gcg gac gtg ttc atg att ccc cag tac ggc tac cta aca ctc aac<br>Pro Ala Asp Val Phe Met Ile Pro Gln Tyr Gly Tyr Leu Thr Leu Asn<br>         370                     375                   380 | 1152 |
| aac ggt agt cag gcc gtg gga cgc tcc tcc ttc tac tgc ctg gaa tac<br>Asn Gly Ser Gln Ala Val Gly Arg Ser Ser Phe Tyr Cys Leu Glu Tyr<br>385                   390                     395                   400 | 1200 |
| ttt cct tcg cag atg ctg aga acc ggc aac aac ttc cag ttt act tac<br>Phe Pro Ser Gln Met Leu Arg Thr Gly Asn Asn Phe Gln Phe Thr Tyr<br>                     405                     410                   415 | 1248 |
| acc ttc gag gac gtg cct ttc cac agc agc tac gcc cac agc cag agc<br>Thr Phe Glu Asp Val Pro Phe His Ser Ser Tyr Ala His Ser Gln Ser<br>              420                     425                   430 | 1296 |
| ttg gac cgg ctg atg aat cct ctg att gac cag tac ctg tac tac ttg<br>Leu Asp Arg Leu Met Asn Pro Leu Ile Asp Gln Tyr Leu Tyr Tyr Leu<br>         435                     440                   445 | 1344 |
| tct cgg act caa aca aca gga ggc acg gca aat acg cag act ctg ggc<br>Ser Arg Thr Gln Thr Thr Gly Gly Thr Ala Asn Thr Gln Thr Leu Gly<br>450                   455                     460 | 1392 |
| ttc agc caa ggt ggg cct aat aca atg gcc aat cag gca aag aac tgg<br>Phe Ser Gln Gly Gly Pro Asn Thr Met Ala Asn Gln Ala Lys Asn Trp<br>465                   470                     475                   480 | 1440 |
| ctg cca gga ccc tgt tac cgc caa caa cgc gtc tca acg aca acc ggg<br>Leu Pro Gly Pro Cys Tyr Arg Gln Gln Arg Val Ser Thr Thr Thr Gly<br>                     485                     490                   495 | 1488 |
| caa aac aac aat agc aac ttt gcc tgg act gct ggg acc aaa tac cat<br>Gln Asn Asn Asn Ser Asn Phe Ala Trp Thr Ala Gly Thr Lys Tyr His<br>            500                     505                   510 | 1536 |
| ctg aat gga aga aat tca ttg gct aat cct ggc atc gct atg gca aca<br>Leu Asn Gly Arg Asn Ser Leu Ala Asn Pro Gly Ile Ala Met Ala Thr<br>         515                     520                   525 | 1584 |
| cac aaa gac gac gag gag cgt ttt ttt ccc agt aac ggg atc ctg att<br>His Lys Asp Asp Glu Glu Arg Phe Phe Pro Ser Asn Gly Ile Leu Ile<br>            530                     535                   540 | 1632 |
| ttt ggc aaa caa aat gct gcc aga gac aat gcg gat tac agc gat gtc<br>Phe Gly Lys Gln Asn Ala Ala Arg Asp Asn Ala Asp Tyr Ser Asp Val<br>545                   550                     555                   560 | 1680 |

| | |
|---|---|
| atg ctc acc agc gag gaa gaa atc aaa acc act aac cct gtg gct aca<br>Met Leu Thr Ser Glu Glu Glu Ile Lys Thr Thr Asn Pro Val Ala Thr<br>565 570 575 | 1728 |
| gag gaa tac ggt atc gtg tgt gat aac ttg cag agt cgg aac acg gct<br>Glu Glu Tyr Gly Ile Val Cys Asp Asn Leu Gln Ser Arg Asn Thr Ala<br>580 585 590 | 1776 |
| cct cgt gag gag att gtc aac agc cag ggg gcc tta ccc ggt atg gtc<br>Pro Arg Glu Glu Ile Val Asn Ser Gln Gly Ala Leu Pro Gly Met Val<br>595 600 605 | 1824 |
| tgg cag aac cgg gac gtg tac ctg cag ggt ccc atc tgg gcc aag att<br>Trp Gln Asn Arg Asp Val Tyr Leu Gln Gly Pro Ile Trp Ala Lys Ile<br>610 615 620 | 1872 |
| cct cac acg gac ggc aac ttc cac ccg tct ccg ctg atg ggc ggc ttt<br>Pro His Thr Asp Gly Asn Phe His Pro Ser Pro Leu Met Gly Gly Phe<br>625 630 635 640 | 1920 |
| ggc ctg aaa cat cct ccg cct cag atc ctg atc aag aac acg cct gta<br>Gly Leu Lys His Pro Pro Pro Gln Ile Leu Ile Lys Asn Thr Pro Val<br>645 650 655 | 1968 |
| cct gcg gat cct ccg acc acc ttc aac cag tca aag ctg aac tct ttc<br>Pro Ala Asp Pro Pro Thr Thr Phe Asn Gln Ser Lys Leu Asn Ser Phe<br>660 665 670 | 2016 |
| atc acg caa tac agc acc gga cag gtc agc gtg gaa att gaa tgg gag<br>Ile Thr Gln Tyr Ser Thr Gly Gln Val Ser Val Glu Ile Glu Trp Glu<br>675 680 685 | 2064 |
| ctg cag aag gaa aac agc aag cgc tgg aac ccc gag atc cag tac acc<br>Leu Gln Lys Glu Asn Ser Lys Arg Trp Asn Pro Glu Ile Gln Tyr Thr<br>690 695 700 | 2112 |
| tcc aac tac tac aaa tct aca agt gtg gac ttt gct gtt aat aca gaa<br>Ser Asn Tyr Tyr Lys Ser Thr Ser Val Asp Phe Ala Val Asn Thr Glu<br>705 710 715 720 | 2160 |
| ggc gtg tac tct gaa ccc cgc ccc att ggc acc cgt tac ctc acc cgt<br>Gly Val Tyr Ser Glu Pro Arg Pro Ile Gly Thr Arg Tyr Leu Thr Arg<br>725 730 735 | 2208 |
| aat ctg<br>Asn Leu | 2214 |

<210> SEQ ID NO 18
<211> LENGTH: 738
<212> TYPE: PRT
<213> ORGANISM: Artificial Sequence
<220> FEATURE:
<223> OTHER INFORMATION: Synthetic Construct

<400> SEQUENCE: 18

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Gln Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

```
Asn Leu Gly Arg Ala Val Phe Gln Ala Lys Lys Arg Val Leu Glu Pro
            115                 120                 125
Leu Gly Leu Val Glu Glu Gly Ala Lys Thr Ala Pro Gly Lys Lys Arg
130                 135                 140
Pro Val Glu Pro Ser Pro Gln Arg Ser Pro Asp Ser Ser Thr Gly Ile
145                 150                 155                 160
Gly Lys Lys Gly Gln Gln Pro Ala Arg Lys Arg Leu Asn Phe Gly Gln
                165                 170                 175
Thr Gly Asp Ser Glu Ser Val Pro Asp Pro Gln Pro Leu Gly Glu Pro
            180                 185                 190
Pro Ala Ala Pro Ser Gly Val Gly Pro Asn Thr Met Ala Ala Gly Gly
                195                 200                 205
Gly Ala Pro Met Ala Asp Asn Asn Glu Gly Ala Asp Gly Val Gly Ser
            210                 215                 220
Ser Ser Gly Asn Trp His Cys Asp Ser Thr Trp Leu Gly Asp Arg Val
225                 230                 235                 240
Ile Thr Thr Ser Thr Arg Thr Trp Ala Leu Pro Thr Tyr Asn Asn His
                245                 250                 255
Leu Tyr Lys Gln Ile Ser Asn Gly Thr Ser Gly Gly Ala Thr Asn Asp
            260                 265                 270
Asn Thr Tyr Phe Gly Tyr Ser Thr Pro Trp Gly Tyr Phe Asp Phe Asn
        275                 280                 285
Arg Phe His Cys His Phe Ser Pro Arg Asp Trp Gln Arg Leu Ile Asn
    290                 295                 300
Asn Asn Trp Gly Phe Arg Pro Lys Arg Leu Ser Phe Lys Leu Phe Asn
305                 310                 315                 320
Ile Gln Val Lys Glu Val Thr Gln Asn Glu Gly Thr Lys Thr Ile Ala
                325                 330                 335
Asn Asn Leu Thr Ser Thr Ile Gln Val Phe Thr Asp Ser Glu Tyr Gln
            340                 345                 350
Leu Pro Tyr Val Leu Gly Ser Ala His Gln Gly Cys Leu Pro Pro Phe
        355                 360                 365
Pro Ala Asp Val Phe Met Ile Pro Gln Tyr Gly Tyr Leu Thr Leu Asn
370                 375                 380
Asn Gly Ser Gln Ala Val Gly Arg Ser Ser Phe Tyr Cys Leu Glu Tyr
385                 390                 395                 400
Phe Pro Ser Gln Met Leu Arg Thr Gly Asn Asn Phe Gln Phe Thr Tyr
                405                 410                 415
Thr Phe Glu Asp Val Pro Phe His Ser Ser Tyr Ala His Ser Gln Ser
            420                 425                 430
Leu Asp Arg Leu Met Asn Pro Leu Ile Asp Gln Tyr Leu Tyr Tyr Leu
        435                 440                 445
Ser Arg Thr Gln Thr Thr Gly Gly Thr Ala Asn Thr Gln Thr Leu Gly
    450                 455                 460
Phe Ser Gln Gly Gly Pro Asn Thr Met Ala Asn Gln Ala Lys Asn Trp
465                 470                 475                 480
Leu Pro Gly Pro Cys Tyr Arg Gln Gln Arg Val Ser Thr Thr Thr Gly
                485                 490                 495
Gln Asn Asn Asn Ser Asn Phe Ala Trp Thr Ala Gly Thr Lys Tyr His
            500                 505                 510
Leu Asn Gly Arg Asn Ser Leu Ala Asn Pro Gly Ile Ala Met Ala Thr
        515                 520                 525
His Lys Asp Asp Glu Glu Arg Phe Phe Pro Ser Asn Gly Ile Leu Ile
```

-continued

```
                530                 535                 540
Phe Gly Lys Gln Asn Ala Ala Arg Asp Asn Ala Asp Tyr Ser Asp Val
545                 550                 555                 560

Met Leu Thr Ser Glu Glu Ile Lys Thr Thr Asn Pro Val Ala Thr
                565                 570                 575

Glu Glu Tyr Gly Ile Val Cys Asp Asn Leu Gln Ser Arg Asn Thr Ala
                580                 585                 590

Pro Arg Glu Glu Ile Val Asn Ser Gln Gly Ala Leu Pro Gly Met Val
                595                 600                 605

Trp Gln Asn Arg Asp Val Tyr Leu Gln Gly Pro Ile Trp Ala Lys Ile
                610                 615                 620

Pro His Thr Asp Gly Asn Phe His Pro Ser Pro Leu Met Gly Gly Phe
625                 630                 635                 640

Gly Leu Lys His Pro Pro Gln Ile Leu Ile Lys Asn Thr Pro Val
                645                 650                 655

Pro Ala Asp Pro Pro Thr Thr Phe Asn Gln Ser Lys Leu Asn Ser Phe
                660                 665                 670

Ile Thr Gln Tyr Ser Thr Gly Gln Val Ser Val Glu Ile Glu Trp Glu
                675                 680                 685

Leu Gln Lys Glu Asn Ser Lys Arg Trp Asn Pro Glu Ile Gln Tyr Thr
                690                 695                 700

Ser Asn Tyr Tyr Lys Ser Thr Ser Val Asp Phe Ala Val Asn Thr Glu
705                 710                 715                 720

Gly Val Tyr Ser Glu Pro Arg Pro Ile Gly Thr Arg Tyr Leu Thr Arg
                725                 730                 735

Asn Leu
```

```
<210> SEQ ID NO 19
<211> LENGTH: 2214
<212> TYPE: DNA
<213> ORGANISM: Artificial Sequence
<220> FEATURE:
<223> OTHER INFORMATION: AAV8
<220> FEATURE:
<221> NAME/KEY: CDS
<222> LOCATION: (1)..(2214)

<400> SEQUENCE: 19
```

```
atg gct gcc gat ggt tat ctt cca gat tgg ctc gag gac aac ctc tct    48
Met Ala Ala Asp Gly Tyr Leu Pro Asp Trp Leu Glu Asp Asn Leu Ser
1               5                   10                  15 gag ggc att cgc gag tgg tgg gcg ctg aaa cct gga gcc ccg aag ccc    96
Glu Gly Ile Arg Glu Trp Trp Ala Leu Lys Pro Gly Ala Pro Lys Pro
            20                  25                  30 aaa gcc aac cag caa aag cag gac gac ggc cgg ggt ctg gtg ctt cct   144
Lys Ala Asn Gln Gln Lys Gln Asp Asp Gly Arg Gly Leu Val Leu Pro
        35                  40                  45 ggc tac aag tac ctc gga ccc ttc aac gga ctc gac aag ggg gag ccc   192
Gly Tyr Lys Tyr Leu Gly Pro Phe Asn Gly Leu Asp Lys Gly Glu Pro
    50                  55                  60 gtc aac gcg gcg gac gca gcg gcc ctc gag cac gac aag gcc tac gac   240
Val Asn Ala Ala Asp Ala Ala Ala Leu Glu His Asp Lys Ala Tyr Asp
65                  70                  75                  80 cag cag ctg cag gcg ggt gac aat ccg tac ctg cgg tat aac cac gcc   288
Gln Gln Leu Gln Ala Gly Asp Asn Pro Tyr Leu Arg Tyr Asn His Ala
                85                  90                  95 gac gcc gag ttt cag gag cgt ctg caa gaa gat acg tct ttt ggg ggc   336
Asp Ala Glu Phe Gln Glu Arg Leu Gln Glu Asp Thr Ser Phe Gly Gly
```

-continued

```
              100                 105                 110
aac ctc ggg cga gca gtc ttc cag gcc aag aag cgg gtt ctc gaa cct      384
Asn Leu Gly Arg Ala Val Phe Gln Ala Lys Lys Arg Val Leu Glu Pro
        115                 120                 125 ctc ggt ctg gtt gag gaa ggc gct aag acg gct cct gga aag aag aga      432
Leu Gly Leu Val Glu Glu Gly Ala Lys Thr Ala Pro Gly Lys Lys Arg
130                 135                 140 ccg gta gag cca tca ccc cag cgt tct cca gac tcc tct acg ggc atc      480
Pro Val Glu Pro Ser Pro Gln Arg Ser Pro Asp Ser Ser Thr Gly Ile
145                 150                 155                 160 ggc aag aaa ggc caa cag ccc gcc aga aaa aga ctc aat ttt ggt cag      528
Gly Lys Lys Gly Gln Gln Pro Ala Arg Lys Arg Leu Asn Phe Gly Gln
                165                 170                 175 act ggc gac tca gag tca gtt cca gac cct caa cct ctc gga gaa cct      576
Thr Gly Asp Ser Glu Ser Val Pro Asp Pro Gln Pro Leu Gly Glu Pro
            180                 185                 190 cca gca gcg ccc tct ggt gtg gga cct aat aca atg gct gca ggc ggt      624
Pro Ala Ala Pro Ser Gly Val Gly Pro Asn Thr Met Ala Ala Gly Gly
        195                 200                 205 ggc gca cca atg gca gac aat aac gaa ggc gcc gac gga gtg ggt agt      672
Gly Ala Pro Met Ala Asp Asn Asn Glu Gly Ala Asp Gly Val Gly Ser
210                 215                 220 tcc tcg gga aat tgg cat tgc gat tcc aca tgg ctg ggc gac aga gtc      720
Ser Ser Gly Asn Trp His Cys Asp Ser Thr Trp Leu Gly Asp Arg Val
225                 230                 235                 240 atc acc acc agc acc cga acc tgg gcc ctg ccc acc tac aac aac cac      768
Ile Thr Thr Ser Thr Arg Thr Trp Ala Leu Pro Thr Tyr Asn Asn His
                245                 250                 255 ctc tac aag caa atc tcc aac ggg aca tcg gga gga gcc acc aac gac      816
Leu Tyr Lys Gln Ile Ser Asn Gly Thr Ser Gly Gly Ala Thr Asn Asp
            260                 265                 270 aac acc tac ttc ggc tac agc acc ccc tgg ggg tat ttt gac ttt aac      864
Asn Thr Tyr Phe Gly Tyr Ser Thr Pro Trp Gly Tyr Phe Asp Phe Asn
        275                 280                 285 aga ttc cac tgc cac ttt tca cca cgt gac tgg cag cga ctc atc aac      912
Arg Phe His Cys His Phe Ser Pro Arg Asp Trp Gln Arg Leu Ile Asn
    290                 295                 300 aac aac tgg gga ttc cgg ccc aag aga ctc agc ttc aag ctc ttc aac      960
Asn Asn Trp Gly Phe Arg Pro Lys Arg Leu Ser Phe Lys Leu Phe Asn
305                 310                 315                 320 atc cag gtc aag gag gtc acg cag aat gaa ggc acc aag acc atc gcc     1008
Ile Gln Val Lys Glu Val Thr Gln Asn Glu Gly Thr Lys Thr Ile Ala
                325                 330                 335 aat aac ctc acc agc acc atc cag gtg ttt acg gac tcg gag tac cag     1056
Asn Asn Leu Thr Ser Thr Ile Gln Val Phe Thr Asp Ser Glu Tyr Gln
            340                 345                 350 ctg ccg tac gtt ctc ggc tct gcc cac cag ggc tgc ctg cct ccg ttc     1104
Leu Pro Tyr Val Leu Gly Ser Ala His Gln Gly Cys Leu Pro Pro Phe
        355                 360                 365 ccg gcg gac gtg ttc atg att ccc cag tac ggc tac cta aca ctc aac     1152
Pro Ala Asp Val Phe Met Ile Pro Gln Tyr Gly Tyr Leu Thr Leu Asn
    370                 375                 380 aac ggt agt cag gcc gtg gga cgc tcc tcc ttc tac tgc ctg gaa tac     1200
Asn Gly Ser Gln Ala Val Gly Arg Ser Ser Phe Tyr Cys Leu Glu Tyr
385                 390                 395                 400 ttt cct tcg cag atg ctg aga acc ggc aac aac ttc cag ttt act tac     1248
Phe Pro Ser Gln Met Leu Arg Thr Gly Asn Asn Phe Gln Phe Thr Tyr
                405                 410                 415 acc ttc gag gac gtg cct ttc cac agc agc tac gcc cac agc cag agc     1296
```

```
                Thr Phe Glu Asp Val Pro Phe His Ser Ser Tyr Ala His Ser Gln Ser
                                420                 425                 430 ttg gac cgg ctg atg aat cct ctg att gac cag tac ctg tac tac ttg             1344
Leu Asp Arg Leu Met Asn Pro Leu Ile Asp Gln Tyr Leu Tyr Tyr Leu
            435                 440                 445 tct cgg act caa aca aca gga ggc acg gca aat acg cag act ctg ggc             1392
Ser Arg Thr Gln Thr Thr Gly Gly Thr Ala Asn Thr Gln Thr Leu Gly
        450                 455                 460 ttc agc caa ggt ggg cct aat aca atg gcc aat cag gca aag aac tgg             1440
Phe Ser Gln Gly Gly Pro Asn Thr Met Ala Asn Gln Ala Lys Asn Trp
465                 470                 475                 480 ctg cca gga ccc tgt tac cgc caa caa cgc gtc tca acg aca acc ggg             1488
Leu Pro Gly Pro Cys Tyr Arg Gln Gln Arg Val Ser Thr Thr Thr Gly
                485                 490                 495 caa aac aac aat agc aac ttt gcc tgg act gct ggg acc aaa tac cat             1536
Gln Asn Asn Asn Ser Asn Phe Ala Trp Thr Ala Gly Thr Lys Tyr His
            500                 505                 510 ctg aat gga aga aat tca ttg gct aat cct ggc atc gct atg gca aca             1584
Leu Asn Gly Arg Asn Ser Leu Ala Asn Pro Gly Ile Ala Met Ala Thr
        515                 520                 525 cac aaa gac gac gag gag cgt ttt ttt ccc agt aac ggg atc ctg att             1632
His Lys Asp Asp Glu Glu Arg Phe Phe Pro Ser Asn Gly Ile Leu Ile
530                 535                 540 ttt ggc aaa caa aat gct gcc aga gac aat gcg gat tac agc gat gtc             1680
Phe Gly Lys Gln Asn Ala Ala Arg Asp Asn Ala Asp Tyr Ser Asp Val
            545                 550                 555                 560 atg ctc acc agc gag gaa gaa atc aaa acc act aac cct gtg gct aca             1728
Met Leu Thr Ser Glu Glu Glu Ile Lys Thr Thr Asn Pro Val Ala Thr
                565                 570                 575 gag gaa tac ggt atc gtg gca gat aac ttg cag cag caa aac acg gct             1776
Glu Glu Tyr Gly Ile Val Ala Asp Asn Leu Gln Gln Gln Asn Thr Ala
            580                 585                 590 cct caa att gga act gtc aac agc cag ggg gcc tta ccc ggt atg gtc             1824
Pro Gln Ile Gly Thr Val Asn Ser Gln Gly Ala Leu Pro Gly Met Val
        595                 600                 605 tgg cag aac cgg gac gtg tac ctg cag ggt ccc atc tgg gcc aag att             1872
Trp Gln Asn Arg Asp Val Tyr Leu Gln Gly Pro Ile Trp Ala Lys Ile
610                 615                 620 cct cac acg gac ggc aac ttc cac ccg tct ccg ctg atg ggc ggc ttt             1920
Pro His Thr Asp Gly Asn Phe His Pro Ser Pro Leu Met Gly Gly Phe
            625                 630                 635                 640 ggc ctg aaa cat cct ccg cct cag atc ctg atc aag aac acg cct gta             1968
Gly Leu Lys His Pro Pro Pro Gln Ile Leu Ile Lys Asn Thr Pro Val
                645                 650                 655 cct gcg gat cct ccg acc acc ttc aac cag tca aag ctg aac tct ttc             2016
Pro Ala Asp Pro Pro Thr Thr Phe Asn Gln Ser Lys Leu Asn Ser Phe
            660                 665                 670 atc acg caa tac agc acc gga cag gtc agc gtg gaa att gaa tgg gag             2064
Ile Thr Gln Tyr Ser Thr Gly Gln Val Ser Val Glu Ile Glu Trp Glu
        675                 680                 685 ctg cag aag gaa aac agc aag cgc tgg aac ccc gag atc cag tac acc             2112
Leu Gln Lys Glu Asn Ser Lys Arg Trp Asn Pro Glu Ile Gln Tyr Thr
690                 695                 700 tcc aac tac tac aaa tct aca agt gtg gac ttt gct gtt aat aca gaa             2160
Ser Asn Tyr Tyr Lys Ser Thr Ser Val Asp Phe Ala Val Asn Thr Glu
            705                 710                 715                 720 ggc gtg tac tct gaa ccc cgc ccc att ggc acc cgt tac ctc acc cgt             2208
Gly Val Tyr Ser Glu Pro Arg Pro Ile Gly Thr Arg Tyr Leu Thr Arg
                725                 730                 735
``` aat ctg 2214
Asn Leu

<210> SEQ ID NO 20
<211> LENGTH: 738
<212> TYPE: PRT
<213> ORGANISM: Artificial Sequence
<220> FEATURE:
<223> OTHER INFORMATION: Synthetic Construct

<400> SEQUENCE: 20

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Leu Glu His Asp Lys Ala Tyr Asp
65                  70                  75                  80

Gln Gln Leu Gln Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Arg Lys Arg Leu Asn Phe Gly Gln
                165                 170                 175

Thr Gly Asp Ser Glu Ser Val Pro Asp Pro Gln Pro Leu Gly Glu Pro
            180                 185                 190

Pro Ala Ala Pro Ser Gly Val Gly Pro Asn Thr Met Ala Ala Gly Gly
        195                 200                 205

Gly Ala Pro Met Ala Asp Asn Asn Glu Gly Ala Asp Gly Val Gly Ser
    210                 215                 220

Ser Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Asn Gly Thr Ser Gly Gly Ala Thr Asn Asp
            260                 265                 270

Asn Thr Tyr Phe Gly Tyr Ser Thr Pro Trp Gly Tyr Phe Asp Phe Asn
        275                 280                 285

Arg Phe His Cys His Phe Ser Pro Arg Asp Trp Gln Arg Leu Ile Asn
    290                 295                 300

Asn Asn Trp Gly Phe Arg Pro Lys Arg Leu Ser Phe Lys Leu Phe Asn
305                 310                 315                 320

Ile Gln Val Lys Glu Val Thr Gln Asn Glu Gly Thr Lys Thr Ile Ala
                325                 330                 335

Asn Asn Leu Thr Ser Thr Ile Gln Val Phe Thr Asp Ser Glu Tyr Gln
            340                 345                 350

Leu Pro Tyr Val Leu Gly Ser Ala His Gln Gly Cys Leu Pro Pro Phe
355                 360                 365

Pro Ala Asp Val Phe Met Ile Pro Gln Tyr Gly Tyr Leu Thr Leu Asn
370                 375                 380

Asn Gly Ser Gln Ala Val Gly Arg Ser Ser Phe Tyr Cys Leu Glu Tyr
385                 390                 395                 400

Phe Pro Ser Gln Met Leu Arg Thr Gly Asn Asn Phe Gln Phe Thr Tyr
            405                 410                 415

Thr Phe Glu Asp Val Pro Phe His Ser Ser Tyr Ala His Ser Gln Ser
            420                 425                 430

Leu Asp Arg Leu Met Asn Pro Leu Ile Asp Gln Tyr Leu Tyr Tyr Leu
            435                 440                 445

Ser Arg Thr Gln Thr Thr Gly Gly Thr Ala Asn Thr Gln Thr Leu Gly
450                 455                 460

Phe Ser Gln Gly Gly Pro Asn Thr Met Ala Asn Gln Ala Lys Asn Trp
465                 470                 475                 480

Leu Pro Gly Pro Cys Tyr Arg Gln Gln Arg Val Ser Thr Thr Thr Gly
            485                 490                 495

Gln Asn Asn Asn Ser Asn Phe Ala Trp Thr Ala Gly Thr Lys Tyr His
            500                 505                 510

Leu Asn Gly Arg Asn Ser Leu Ala Asn Pro Gly Ile Ala Met Ala Thr
515                 520                 525

His Lys Asp Asp Glu Glu Arg Phe Phe Pro Ser Asn Gly Ile Leu Ile
530                 535                 540

Phe Gly Lys Gln Asn Ala Ala Arg Asp Asn Ala Asp Tyr Ser Asp Val
545                 550                 555                 560

Met Leu Thr Ser Glu Glu Ile Lys Thr Thr Asn Pro Val Ala Thr
            565                 570                 575

Glu Glu Tyr Gly Ile Val Ala Asp Asn Leu Gln Gln Gln Asn Thr Ala
            580                 585                 590

Pro Gln Ile Gly Thr Val Asn Ser Gln Gly Ala Leu Pro Gly Met Val
            595                 600                 605

Trp Gln Asn Arg Asp Val Tyr Leu Gln Gly Pro Ile Trp Ala Lys Ile
610                 615                 620

Pro His Thr Asp Gly Asn Phe His Pro Ser Pro Leu Met Gly Gly Phe
625                 630                 635                 640

Gly Leu Lys His Pro Pro Pro Gln Ile Leu Ile Lys Asn Thr Pro Val
            645                 650                 655

Pro Ala Asp Pro Pro Thr Thr Phe Asn Gln Ser Lys Leu Asn Ser Phe
            660                 665                 670

Ile Thr Gln Tyr Ser Thr Gly Gln Val Ser Val Glu Ile Glu Trp Glu
            675                 680                 685

Leu Gln Lys Glu Asn Ser Lys Arg Trp Asn Pro Glu Ile Gln Tyr Thr
690                 695                 700

Ser Asn Tyr Tyr Lys Ser Thr Ser Val Asp Phe Ala Val Asn Thr Glu
705                 710                 715                 720

Gly Val Tyr Ser Glu Pro Arg Pro Ile Gly Thr Arg Tyr Leu Thr Arg
            725                 730                 735

Asn Leu

<210> SEQ ID NO 21
<211> LENGTH: 2214
<212> TYPE: DNA
<213> ORGANISM: Artificial Sequence
<220> FEATURE:
<223> OTHER INFORMATION: AAVhu37
<220> FEATURE:
<221> NAME/KEY: CDS
<222> LOCATION: (1)..(2214)

<400> SEQUENCE: 21

```
atg gct gct gac ggt tat ctt cca gat tgg ctc gag gac aac ctc tct      48
Met Ala Ala Asp Gly Tyr Leu Pro Asp Trp Leu Glu Asp Asn Leu Ser
 1               5                  10                  15 gag ggc att cgc gag tgg tgg gac ctg aaa cct gga gcc ccc aag ccc      96
Glu Gly Ile Arg Glu Trp Trp Asp Leu Lys Pro Gly Ala Pro Lys Pro
             20                  25                  30 aag gcc aac cag cag aag cag gac gac ggc cgg ggt ctg gtg ctt cct     144
Lys Ala Asn Gln Gln Lys Gln Asp Asp Gly Arg Gly Leu Val Leu Pro
         35                  40                  45 ggc tac aag tac ctc gga ccc ttc aac gga ctc gac aag ggg gag ccc     192
Gly Tyr Lys Tyr Leu Gly Pro Phe Asn Gly Leu Asp Lys Gly Glu Pro
     50                  55                  60 gtc aac gcg gcg gac gca gcg gcc ctc gag cac gac aag gcc tac gac     240
Val Asn Ala Ala Asp Ala Ala Ala Leu Glu His Asp Lys Ala Tyr Asp
 65                  70                  75                  80 cag cag ctc aaa gcg ggt gac aat ccg tac ctg cgg tat aac cac gcc     288
Gln Gln Leu Lys Ala Gly Asp Asn Pro Tyr Leu Arg Tyr Asn His Ala
                 85                  90                  95 gac gcc gag ttt cag gag cgt ctg caa gaa gat acg tct ttt ggg ggc     336
Asp Ala Glu Phe Gln Glu Arg Leu Gln Glu Asp Thr Ser Phe Gly Gly
            100                 105                 110 aac ctc ggg cga gca gtc ttc cag gcc aag aag cgg gtt ctc gaa cct     384
Asn Leu Gly Arg Ala Val Phe Gln Ala Lys Lys Arg Val Leu Glu Pro
        115                 120                 125 ctc ggt ctg gtt gag gaa gct gct aag acg gct cct gga aag aag aga     432
Leu Gly Leu Val Glu Glu Ala Ala Lys Thr Ala Pro Gly Lys Lys Arg
    130                 135                 140 ccg gta gaa ccg tca cct cag cgt tcc ccc gac tcc tcc acg ggc atc     480
Pro Val Glu Pro Ser Pro Gln Arg Ser Pro Asp Ser Ser Thr Gly Ile
145                 150                 155                 160 ggc aag aaa ggc cag cag ccc gct aaa aag aga ctg aac ttt ggt cag     528
Gly Lys Lys Gly Gln Gln Pro Ala Lys Lys Arg Leu Asn Phe Gly Gln
                165                 170                 175 act ggc gac tca gag tca gtc ccc gac cct caa cca atc gga gaa cca     576
Thr Gly Asp Ser Glu Ser Val Pro Asp Pro Gln Pro Ile Gly Glu Pro
            180                 185                 190 cca gca ggc ccc tct ggt ctg gga tct ggt aca atg gct gca ggc ggt     624
Pro Ala Gly Pro Ser Gly Leu Gly Ser Gly Thr Met Ala Ala Gly Gly
        195                 200                 205 ggc gct cca atg gca gac aat aac gaa ggc gcc gac gga gtg ggt agt     672
Gly Ala Pro Met Ala Asp Asn Asn Glu Gly Ala Asp Gly Val Gly Ser
    210                 215                 220 tcc tca gga aat tgg cat tgc gat tcc aca tgg ctg ggc gac aga gtc     720
Ser Ser Gly Asn Trp His Cys Asp Ser Thr Trp Leu Gly Asp Arg Val
225                 230                 235                 240 atc acc acc agc acc cga acc tgg gcc ctg ccc acc tac aac aac cac     768
Ile Thr Thr Ser Thr Arg Thr Trp Ala Leu Pro Thr Tyr Asn Asn His
                245                 250                 255 ctc tac aag caa ata tcc aat ggg aca tcg gga gga agc acc aac gac     816
Leu Tyr Lys Gln Ile Ser Asn Gly Thr Ser Gly Gly Ser Thr Asn Asp
            260                 265                 270 aac acc tac ttc ggc tac agc acc ccc tgg ggg tat ttt gac ttc aac     864
Asn Thr Tyr Phe Gly Tyr Ser Thr Pro Trp Gly Tyr Phe Asp Phe Asn
        275                 280                 285
```

| | | |
|---|---|---|
| aga ttc cac tgc cac ttc tca cca cgt gac tgg cag cga ctc atc aac<br>Arg Phe His Cys His Phe Ser Pro Arg Asp Trp Gln Arg Leu Ile Asn<br>290                              295                         300 | | 912 |
| aac aac tgg gga ttc cgg cca aaa aga ctc agc ttc aag ctc ttc aac<br>Asn Asn Trp Gly Phe Arg Pro Lys Arg Leu Ser Phe Lys Leu Phe Asn<br>305                        310                        315                    320 | | 960 |
| atc cag gtc aag gag gtc acg cag aat gaa ggc acc aag acc atc gcc<br>Ile Gln Val Lys Glu Val Thr Gln Asn Glu Gly Thr Lys Thr Ile Ala<br>                        325                        330                    335 | | 1008 |
| aat aac ctt acc agc acg att cag gta ttt acg gac tcg gaa tac cag<br>Asn Asn Leu Thr Ser Thr Ile Gln Val Phe Thr Asp Ser Glu Tyr Gln<br>                    340                        345                    350 | | 1056 |
| ctg ccg tac gtc ctc ggc tcc gcg cac cag ggc tgc ctg cct ccg ttc<br>Leu Pro Tyr Val Leu Gly Ser Ala His Gln Gly Cys Leu Pro Pro Phe<br>355                              360                        365 | | 1104 |
| ccg gcg gac gtc ttc atg att ccc cag tac ggc tac ctt aca ctg aac<br>Pro Ala Asp Val Phe Met Ile Pro Gln Tyr Gly Tyr Leu Thr Leu Asn<br>370                              375                        380 | | 1152 |
| aat gga agt caa gcc gta ggc cgt tcc tcc ttc tac tgc ctg gaa tat<br>Asn Gly Ser Gln Ala Val Gly Arg Ser Ser Phe Tyr Cys Leu Glu Tyr<br>385                              390                        395                    400 | | 1200 |
| ttt cca tct caa atg ctg cga act gga aac aat ttt gaa ttc agc tac<br>Phe Pro Ser Gln Met Leu Arg Thr Gly Asn Asn Phe Glu Phe Ser Tyr<br>                    405                        410                    415 | | 1248 |
| acc ttc gag gac gtg cct ttc cac agc agc tac gca cac agc cag agc<br>Thr Phe Glu Asp Val Pro Phe His Ser Ser Tyr Ala His Ser Gln Ser<br>                    420                        425                    430 | | 1296 |
| ttg gac cga ctg atg aat cct ctc atc gac cag tac ctg tac tac tta<br>Leu Asp Arg Leu Met Asn Pro Leu Ile Asp Gln Tyr Leu Tyr Tyr Leu<br>                435                        440                    445 | | 1344 |
| tcc aga act cag tcc aca gga gga act caa ggt acc cag caa ttg tta<br>Ser Arg Thr Gln Ser Thr Gly Gly Thr Gln Gly Thr Gln Gln Leu Leu<br>450                              455                        460 | | 1392 |
| ttt tct caa gct ggg cct gca aac atg tcg gct cag gct aag aac tgg<br>Phe Ser Gln Ala Gly Pro Ala Asn Met Ser Ala Gln Ala Lys Asn Trp<br>465                              470                        475                    480 | | 1440 |
| cta cct gga cct tgc tac cgg cag cag cga gtc tct acg aca ctg tcg<br>Leu Pro Gly Pro Cys Tyr Arg Gln Gln Arg Val Ser Thr Thr Leu Ser<br>                              485                        490                    495 | | 1488 |
| caa aac aac aac agc aac ttt gct tgg act ggt gcc acc aaa tat cac<br>Gln Asn Asn Asn Ser Asn Phe Ala Trp Thr Gly Ala Thr Lys Tyr His<br>                    500                        505                    510 | | 1536 |
| ctg aac gga aga gac tct ttg gta aat ccc ggt gtc gcc atg gca acc<br>Leu Asn Gly Arg Asp Ser Leu Val Asn Pro Gly Val Ala Met Ala Thr<br>515                              520                        525 | | 1584 |
| cac aag gac gac gag gaa cgc ttc ttc ccg tcg agt gga gtc ctg atg<br>His Lys Asp Asp Glu Glu Arg Phe Phe Pro Ser Ser Gly Val Leu Met<br>                530                        535                    540 | | 1632 |
| ttc gga aaa cag ggt gct gga aga gac aat gtg gac tac agc agc gtt<br>Phe Gly Lys Gln Gly Ala Gly Arg Asp Asn Val Asp Tyr Ser Ser Val<br>545                              550                        555                    560 | | 1680 |
| atg cta acc agc gaa gaa gaa att aaa acc act aac ccc gta gcc aca<br>Met Leu Thr Ser Glu Glu Glu Ile Lys Thr Thr Asn Pro Val Ala Thr<br>                    565                        570                    575 | | 1728 |
| gaa caa tac ggt gtg gtg gct gac aac ttg cag caa acc aat aca ggg<br>Glu Gln Tyr Gly Val Val Ala Asp Asn Leu Gln Gln Thr Asn Thr Gly<br>                    580                        585                    590 | | 1776 |
| cct att gtg gga aat gtc aac agc caa gga gcc tta cct ggc atg gtc<br>Pro Ile Val Gly Asn Val Asn Ser Gln Gly Ala Leu Pro Gly Met Val | | 1824 |

```
tgg cag aac cga gac gtg tac ctg cag ggt ccc atc tgg gcc aag att     1872
Trp Gln Asn Arg Asp Val Tyr Leu Gln Gly Pro Ile Trp Ala Lys Ile
610             615                 620 cct cac acg gac ggc aac ttc cac cct tca ccg cta atg gga gga ttt     1920
Pro His Thr Asp Gly Asn Phe His Pro Ser Pro Leu Met Gly Gly Phe
625             630                 635                 640 gga ctg aag cac cca cct cct cag atc ctg atc aag aac acg ccg gta     1968
Gly Leu Lys His Pro Pro Pro Gln Ile Leu Ile Lys Asn Thr Pro Val
                645                 650                 655 cct gcg gat cct cca aca acg ttc agc cag gcg aaa ttg gct tcc ttc     2016
Pro Ala Asp Pro Pro Thr Thr Phe Ser Gln Ala Lys Leu Ala Ser Phe
            660                 665                 670 att acg cag tac agc acc gga cag gtc agc gtg gaa atc gag tgg gag     2064
Ile Thr Gln Tyr Ser Thr Gly Gln Val Ser Val Glu Ile Glu Trp Glu
        675                 680                 685 ctg cag aag gag aac agc aaa cgc tgg aac cca gag att cag tac act     2112
Leu Gln Lys Glu Asn Ser Lys Arg Trp Asn Pro Glu Ile Gln Tyr Thr
690                 695                 700 tca aac tac tac aaa tct aca aat gtg gac ttt gct gtc aat aca gag     2160
Ser Asn Tyr Tyr Lys Ser Thr Asn Val Asp Phe Ala Val Asn Thr Glu
705                 710                 715                 720 gga act tat tct gag cct cgc ccc att ggt act cgt tac ctc acc cgt     2208
Gly Thr Tyr Ser Glu Pro Arg Pro Ile Gly Thr Arg Tyr Leu Thr Arg
            725                 730                 735 aat ctg                                                             2214
Asn Leu <210> SEQ ID NO 22
<211> LENGTH: 738
<212> TYPE: PRT
<213> ORGANISM: Artificial Sequence
<220> FEATURE:
<223> OTHER INFORMATION: Synthetic Construct

<400> SEQUENCE: 22

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Ala Ala Lys Thr Ala Pro Gly Lys Lys Arg
    130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Lys Lys Arg Leu Asn Phe Gly Gln
                165                 170                 175
```

-continued

```
Thr Gly Asp Ser Glu Ser Val Pro Asp Pro Gln Pro Ile Gly Glu Pro
            180                 185                 190

Pro Ala Gly Pro Ser Gly Leu Gly Ser Gly Thr Met Ala Ala Gly Gly
            195                 200                 205

Gly Ala Pro Met Ala Asp Asn Asn Glu Gly Ala Asp Gly Val Gly Ser
210                 215                 220

Ser Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Asn Gly Thr Ser Gly Gly Ser Thr Asn Asp
            260                 265                 270

Asn Thr Tyr Phe Gly Tyr Ser Thr Pro Trp Gly Tyr Phe Asp Phe Asn
            275                 280                 285

Arg Phe His Cys His Phe Ser Pro Arg Asp Trp Gln Arg Leu Ile Asn
            290                 295                 300

Asn Asn Trp Gly Phe Arg Pro Lys Arg Leu Ser Phe Lys Leu Phe Asn
305                 310                 315                 320

Ile Gln Val Lys Glu Val Thr Gln Asn Glu Gly Thr Lys Thr Ile Ala
                325                 330                 335

Asn Asn Leu Thr Ser Thr Ile Gln Val Phe Thr Asp Ser Glu Tyr Gln
            340                 345                 350

Leu Pro Tyr Val Leu Gly Ser Ala His Gln Gly Cys Leu Pro Pro Phe
            355                 360                 365

Pro Ala Asp Val Phe Met Ile Pro Gln Tyr Gly Tyr Leu Thr Leu Asn
            370                 375                 380

Asn Gly Ser Gln Ala Val Gly Arg Ser Ser Phe Tyr Cys Leu Glu Tyr
385                 390                 395                 400

Phe Pro Ser Gln Met Leu Arg Thr Gly Asn Asn Phe Glu Phe Ser Tyr
                405                 410                 415

Thr Phe Glu Asp Val Pro Phe His Ser Ser Tyr Ala His Ser Gln Ser
            420                 425                 430

Leu Asp Arg Leu Met Asn Pro Leu Ile Asp Gln Tyr Leu Tyr Tyr Leu
            435                 440                 445

Ser Arg Thr Gln Ser Thr Gly Gly Thr Gln Gly Thr Gln Gln Leu Leu
450                 455                 460

Phe Ser Gln Ala Gly Pro Ala Asn Met Ser Ala Gln Ala Lys Asn Trp
465                 470                 475                 480

Leu Pro Gly Pro Cys Tyr Arg Gln Gln Arg Val Ser Thr Thr Leu Ser
                485                 490                 495

Gln Asn Asn Asn Ser Asn Phe Ala Trp Thr Gly Ala Thr Lys Tyr His
            500                 505                 510

Leu Asn Gly Arg Asp Ser Leu Val Asn Pro Gly Val Ala Met Ala Thr
            515                 520                 525

His Lys Asp Asp Glu Glu Arg Phe Phe Pro Ser Ser Gly Val Leu Met
            530                 535                 540

Phe Gly Lys Gln Gly Ala Gly Arg Asp Asn Val Asp Tyr Ser Ser Val
545                 550                 555                 560

Met Leu Thr Ser Glu Glu Ile Lys Thr Thr Asn Pro Val Ala Thr
                565                 570                 575

Glu Gln Tyr Gly Val Val Ala Asp Asn Leu Gln Gln Thr Asn Thr Gly
            580                 585                 590
```

```
Pro Ile Val Gly Asn Val Asn Ser Gln Gly Ala Leu Pro Gly Met Val
        595                 600                 605

Trp Gln Asn Arg Asp Val Tyr Leu Gln Gly Pro Ile Trp Ala Lys Ile
610                 615                 620

Pro His Thr Asp Gly Asn Phe His Pro Ser Pro Leu Met Gly Gly Phe
625                 630                 635                 640

Gly Leu Lys His Pro Pro Gln Ile Leu Ile Lys Asn Thr Pro Val
                645                 650                 655

Pro Ala Asp Pro Pro Thr Thr Phe Ser Gln Ala Lys Leu Ala Ser Phe
                660                 665                 670

Ile Thr Gln Tyr Ser Thr Gly Gln Val Ser Val Glu Ile Glu Trp Glu
            675                 680                 685

Leu Gln Lys Glu Asn Ser Lys Arg Trp Asn Pro Glu Ile Gln Tyr Thr
        690                 695                 700

Ser Asn Tyr Tyr Lys Ser Thr Asn Val Asp Phe Ala Val Asn Thr Glu
705                 710                 715                 720

Gly Thr Tyr Ser Glu Pro Arg Pro Ile Gly Thr Arg Tyr Leu Thr Arg
                725                 730                 735

Asn Leu

<210> SEQ ID NO 23
<211> LENGTH: 2214
<212> TYPE: DNA
<213> ORGANISM: Artificial Sequence
<220> FEATURE:
<223> OTHER INFORMATION: AAVrh10
<220> FEATURE:
<221> NAME/KEY: CDS
<222> LOCATION: (1)..(2214)

<400> SEQUENCE: 23 atg gct gcc gat ggt tat ctt cca gat tgg ctc gag gac aac ctc tct      48
Met Ala Ala Asp Gly Tyr Leu Pro Asp Trp Leu Glu Asp Asn Leu Ser
1               5                   10                  15 gag ggc att cgc gag tgg tgg gac ttg aaa cct gga gcc ccg aaa ccc      96
Glu Gly Ile Arg Glu Trp Trp Asp Leu Lys Pro Gly Ala Pro Lys Pro
            20                  25                  30 aaa gcc aac cag caa aag cag gac gac ggc cgg ggt ctg gtg ctt cct     144
Lys Ala Asn Gln Gln Lys Gln Asp Asp Gly Arg Gly Leu Val Leu Pro
        35                  40                  45 ggc tac aag tac ctc gga ccc ttc aac gga ctc gac aag ggg gag ccc     192
Gly Tyr Lys Tyr Leu Gly Pro Phe Asn Gly Leu Asp Lys Gly Glu Pro
    50                  55                  60 gtc aac gcg gcg gac gca gcg gcc ctc gag cac gac aag gcc tac gac     240
Val Asn Ala Ala Asp Ala Ala Ala Leu Glu His Asp Lys Ala Tyr Asp
65                  70                  75                  80 cag cag ctc aaa gcg ggt gac aat ccg tac ctg cgg tat aac cac gcc     288
Gln Gln Leu Lys Ala Gly Asp Asn Pro Tyr Leu Arg Tyr Asn His Ala
                85                  90                  95 gac gcc gag ttt cag gag cgt ctg caa gaa gat acg tct ttt ggg ggc     336
Asp Ala Glu Phe Gln Glu Arg Leu Gln Glu Asp Thr Ser Phe Gly Gly
            100                 105                 110 aac ctc ggg cga gca gtc ttc cag gcc aag aag cgg gtt ctc gaa cct     384
Asn Leu Gly Arg Ala Val Phe Gln Ala Lys Lys Arg Val Leu Glu Pro
        115                 120                 125 ctc ggt ctg gtt gag gaa ggc gct aag acg gct cct gga aag aag aga     432
Leu Gly Leu Val Glu Glu Gly Ala Lys Thr Ala Pro Gly Lys Lys Arg
    130                 135                 140 ccg gta gag cca tca ccc cag cgt tct cca gac tcc tct acg ggc atc     480
```

```
Pro Val Glu Pro Ser Pro Gln Arg Ser Pro Asp Ser Ser Thr Gly Ile
145                 150                 155                 160 ggc aag aaa ggc cag cag ccc gcg aaa aag aga ctc aac ttt ggg cag        528
Gly Lys Lys Gly Gln Gln Pro Ala Lys Lys Arg Leu Asn Phe Gly Gln
                165                 170                 175 act ggc gac tca gag tca gtg ccc gac cct caa cca atc gga gaa ccc        576
Thr Gly Asp Ser Glu Ser Val Pro Asp Pro Gln Pro Ile Gly Glu Pro
                180                 185                 190 ccc gca ggc ccc tct ggt ctg gga tct ggt aca atg gct gca ggc ggt        624
Pro Ala Gly Pro Ser Gly Leu Gly Ser Gly Thr Met Ala Ala Gly Gly
                195                 200                 205 ggc gct cca atg gca gac aat aac gaa ggc gcc gac gga gtg ggt agt        672
Gly Ala Pro Met Ala Asp Asn Asn Glu Gly Ala Asp Gly Val Gly Ser
210                 215                 220 tcc tca gga aat tgg cat tgc gat tcc aca tgg ctg ggc gac aga gtc        720
Ser Ser Gly Asn Trp His Cys Asp Ser Thr Trp Leu Gly Asp Arg Val
225                 230                 235                 240 atc acc acc agc acc cga acc tgg gcc ctc ccc acc tac aac aac cac        768
Ile Thr Thr Ser Thr Arg Thr Trp Ala Leu Pro Thr Tyr Asn Asn His
                245                 250                 255 ctc tac aag caa atc tcc aac ggg act tcg gga gga agc acc aac gac        816
Leu Tyr Lys Gln Ile Ser Asn Gly Thr Ser Gly Gly Ser Thr Asn Asp
                260                 265                 270 aac acc tac ttc ggc tac agc acc ccc tgg ggg tat ttt gac ttt aac        864
Asn Thr Tyr Phe Gly Tyr Ser Thr Pro Trp Gly Tyr Phe Asp Phe Asn
                275                 280                 285 aga ttc cac tgc cac ttc tca cca cgt gac tgg cag cga ctc atc aac        912
Arg Phe His Cys His Phe Ser Pro Arg Asp Trp Gln Arg Leu Ile Asn
                290                 295                 300 aac aac tgg gga ttc cgg ccc aag aga ctc aac ttc aag ctc ttc aac        960
Asn Asn Trp Gly Phe Arg Pro Lys Arg Leu Asn Phe Lys Leu Phe Asn
305                 310                 315                 320 atc cag gtc aag gag gtc acg cag aat gaa ggc acc aag acc atc gcc       1008
Ile Gln Val Lys Glu Val Thr Gln Asn Glu Gly Thr Lys Thr Ile Ala
                325                 330                 335 aat aac ctt acc agc acg att cag gtc ttt acg gac tcg gaa tac cag       1056
Asn Asn Leu Thr Ser Thr Ile Gln Val Phe Thr Asp Ser Glu Tyr Gln
                340                 345                 350 ctc ccg tac gtc ctc ggc tct gcg cac cag ggc tgc ctg cct ccg ttc       1104
Leu Pro Tyr Val Leu Gly Ser Ala His Gln Gly Cys Leu Pro Pro Phe
                355                 360                 365 ccg gcg gac gtc ttc atg att cct cag tac ggg tac ctg act ctg aac       1152
Pro Ala Asp Val Phe Met Ile Pro Gln Tyr Gly Tyr Leu Thr Leu Asn
370                 375                 380 aat ggc agt cag gcc gtg ggc cgt tcc tcc ttc tac tgc ctg gag tac       1200
Asn Gly Ser Gln Ala Val Gly Arg Ser Ser Phe Tyr Cys Leu Glu Tyr
385                 390                 395                 400 ttt cct tct caa atg ctg aga acg ggc aac aac ttt gag ttc agc tac       1248
Phe Pro Ser Gln Met Leu Arg Thr Gly Asn Asn Phe Glu Phe Ser Tyr
                405                 410                 415 cag ttt gag gac gtg cct ttt cac agc agc tac gcg cac agc caa agc       1296
Gln Phe Glu Asp Val Pro Phe His Ser Ser Tyr Ala His Ser Gln Ser
                420                 425                 430 ctg gac cgg ctg atg aac ccc ctc atc gac cag tac ctg tac tac ctg       1344
Leu Asp Arg Leu Met Asn Pro Leu Ile Asp Gln Tyr Leu Tyr Tyr Leu
                435                 440                 445 tct cgg act cag tcc acg gga ggt acc gca gga act cag cag ttg cta       1392
Ser Arg Thr Gln Ser Thr Gly Gly Thr Ala Gly Thr Gln Gln Leu Leu
450                 455                 460
```

| | | |
|---|---|---|
| ttt tct cag gcc ggg cct aat aac atg tcg gct cag gcc aaa aac tgg<br>Phe Ser Gln Ala Gly Pro Asn Asn Met Ser Ala Gln Ala Lys Asn Trp<br>465                          470                          475                        480 | 1440 |
| cta ccc ggg ccc tgc tac cgg cag caa cgc gtc tcc acg aca ctg tcg<br>Leu Pro Gly Pro Cys Tyr Arg Gln Gln Arg Val Ser Thr Thr Leu Ser<br>                          485                          490                        495 | 1488 |
| caa aat aac aac agc aac ttt gcc tgg acc ggt gcc acc aag tat cat<br>Gln Asn Asn Asn Ser Asn Phe Ala Trp Thr Gly Ala Thr Lys Tyr His<br>                500                        505                        510 | 1536 |
| ctg aat ggc aga gac tct ctg gta aat ccc ggt gtc gct atg gca acc<br>Leu Asn Gly Arg Asp Ser Leu Val Asn Pro Gly Val Ala Met Ala Thr<br>                       515                        520                        525 | 1584 |
| cac aag gac gac gaa gag cga ttt ttt ccg tcc agc gga gtc tta atg<br>His Lys Asp Asp Glu Glu Arg Phe Phe Pro Ser Ser Gly Val Leu Met<br>            530                        535                        540 | 1632 |
| ttt ggg aaa cag gga gct gga aaa gac aac gtg gac tat agc agc gtt<br>Phe Gly Lys Gln Gly Ala Gly Lys Asp Asn Val Asp Tyr Ser Ser Val<br>545                          550                          555                        560 | 1680 |
| atg cta acc agt gag gaa gaa att aaa acc acc aac cca gtg gcc aca<br>Met Leu Thr Ser Glu Glu Glu Ile Lys Thr Thr Asn Pro Val Ala Thr<br>                       565                        570                        575 | 1728 |
| gaa cag tac ggc gtg gtg gcc gat aac ctg caa cag caa aac gcc gct<br>Glu Gln Tyr Gly Val Val Ala Asp Asn Leu Gln Gln Gln Asn Ala Ala<br>            580                        585                        590 | 1776 |
| cct att gta ggg gcc gtc aac agt caa gga gcc tta cct ggc atg gtc<br>Pro Ile Val Gly Ala Val Asn Ser Gln Gly Ala Leu Pro Gly Met Val<br>                       595                        600                        605 | 1824 |
| tgg cag aac cgg gac gtg tac ctg cag ggt cct atc tgg gcc aag att<br>Trp Gln Asn Arg Asp Val Tyr Leu Gln Gly Pro Ile Trp Ala Lys Ile<br>610                          615                          620 | 1872 |
| cct cac acg gac gga aac ttt cat ccc tcg ccg ctg atg gga ggc ttt<br>Pro His Thr Asp Gly Asn Phe His Pro Ser Pro Leu Met Gly Gly Phe<br>625                          630                          635                        640 | 1920 |
| gga ctg aaa cac ccg cct cct cag atc ctg att aag aat aca cct gtt<br>Gly Leu Lys His Pro Pro Pro Gln Ile Leu Ile Lys Asn Thr Pro Val<br>                       645                        650                        655 | 1968 |
| ccc gcg gat cct cca act acc ttc agt caa gct aag ctg gcg tcg ttc<br>Pro Ala Asp Pro Pro Thr Thr Phe Ser Gln Ala Lys Leu Ala Ser Phe<br>            660                        665                        670 | 2016 |
| atc acg cag tac agc acc gga cag gtc agc gtg gaa att gaa tgg gag<br>Ile Thr Gln Tyr Ser Thr Gly Gln Val Ser Val Glu Ile Glu Trp Glu<br>675                          680                          685 | 2064 |
| ctg cag aaa gaa aac agc aaa cgc tgg aac cca gag att caa tac act<br>Leu Gln Lys Glu Asn Ser Lys Arg Trp Asn Pro Glu Ile Gln Tyr Thr<br>690                          695                          700 | 2112 |
| tcc aac tac tac aaa tct aca aat gtg gac ttt gct gtt aac aca gat<br>Ser Asn Tyr Tyr Lys Ser Thr Asn Val Asp Phe Ala Val Asn Thr Asp<br>705                          710                          715                        720 | 2160 |
| ggc act tat tct gag cct cgc ccc atc ggc acc cgt tac ctc acc cgt<br>Gly Thr Tyr Ser Glu Pro Arg Pro Ile Gly Thr Arg Tyr Leu Thr Arg<br>                       725                        730                        735 | 2208 |
| aat ctg<br>Asn Leu | 2214 |

<210> SEQ ID NO 24
<211> LENGTH: 738
<212> TYPE: PRT
<213> ORGANISM: Artificial Sequence
<220> FEATURE:
<223> OTHER INFORMATION: Synthetic Construct

<400> SEQUENCE: 24

```
Met Ala Ala Asp Gly Tyr Leu Pro Asp Trp Leu Glu Asp Asn Leu Ser
1               5                   10                  15
Glu Gly Ile Arg Glu Trp Trp Asp Leu Lys Pro Gly Ala Pro Lys Pro
            20                  25                  30
Lys Ala Asn Gln Gln Lys Gln Asp Asp Gly Arg Gly Leu Val Leu Pro
        35                  40                  45
Gly Tyr Lys Tyr Leu Gly Pro Phe Asn Gly Leu Asp Lys Gly Glu Pro
    50                  55                  60
Val Asn Ala Ala Asp Ala Ala Leu Glu His Asp Lys Ala Tyr Asp
65                  70                  75                  80
Gln Gln Leu Lys Ala Gly Asp Asn Pro Tyr Leu Arg Tyr Asn His Ala
                85                  90                  95
Asp Ala Glu Phe Gln Glu Arg Leu Gln Glu Asp Thr Ser Phe Gly Gly
            100                 105                 110
Asn Leu Gly Arg Ala Val Phe Gln Ala Lys Lys Arg Val Leu Glu Pro
        115                 120                 125
Leu Gly Leu Val Glu Glu Gly Ala Lys Thr Ala Pro Gly Lys Lys Arg
    130                 135                 140
Pro Val Glu Pro Ser Pro Gln Arg Ser Pro Asp Ser Ser Thr Gly Ile
145                 150                 155                 160
Gly Lys Lys Gly Gln Gln Pro Ala Lys Lys Arg Leu Asn Phe Gly Gln
                165                 170                 175
Thr Gly Asp Ser Glu Ser Val Pro Asp Pro Gln Pro Ile Gly Glu Pro
            180                 185                 190
Pro Ala Gly Pro Ser Gly Leu Gly Ser Gly Thr Met Ala Ala Gly Gly
        195                 200                 205
Gly Ala Pro Met Ala Asp Asn Asn Glu Gly Ala Asp Gly Val Gly Ser
    210                 215                 220
Ser Ser Gly Asn Trp His Cys Asp Ser Thr Trp Leu Gly Asp Arg Val
225                 230                 235                 240
Ile Thr Thr Ser Thr Arg Thr Trp Ala Leu Pro Thr Tyr Asn Asn His
                245                 250                 255
Leu Tyr Lys Gln Ile Ser Asn Gly Thr Ser Gly Gly Ser Thr Asn Asp
            260                 265                 270
Asn Thr Tyr Phe Gly Tyr Ser Thr Pro Trp Gly Tyr Phe Asp Phe Asn
        275                 280                 285
Arg Phe His Cys His Phe Ser Pro Arg Asp Trp Gln Arg Leu Ile Asn
    290                 295                 300
Asn Asn Trp Gly Phe Arg Pro Lys Arg Leu Asn Phe Lys Leu Phe Asn
305                 310                 315                 320
Ile Gln Val Lys Glu Val Thr Gln Asn Glu Gly Thr Lys Thr Ile Ala
                325                 330                 335
Asn Asn Leu Thr Ser Thr Ile Gln Val Phe Thr Asp Ser Glu Tyr Gln
            340                 345                 350
Leu Pro Tyr Val Leu Gly Ser Ala His Gln Gly Cys Leu Pro Pro Phe
        355                 360                 365
Pro Ala Asp Val Phe Met Ile Pro Gln Tyr Gly Tyr Leu Thr Leu Asn
    370                 375                 380
Asn Gly Ser Gln Ala Val Gly Arg Ser Ser Phe Tyr Cys Leu Glu Tyr
385                 390                 395                 400
Phe Pro Ser Gln Met Leu Arg Thr Gly Asn Asn Phe Glu Phe Ser Tyr
                405                 410                 415
```

-continued

```
Gln Phe Glu Asp Val Pro Phe His Ser Ser Tyr Ala His Ser Gln Ser
            420                 425                 430

Leu Asp Arg Leu Met Asn Pro Leu Ile Asp Gln Tyr Leu Tyr Tyr Leu
            435                 440                 445

Ser Arg Thr Gln Ser Thr Gly Gly Thr Ala Gly Thr Gln Gln Leu Leu
        450                 455                 460

Phe Ser Gln Ala Gly Pro Asn Asn Met Ser Ala Gln Ala Lys Asn Trp
465                 470                 475                 480

Leu Pro Gly Pro Cys Tyr Arg Gln Gln Arg Val Ser Thr Thr Leu Ser
                485                 490                 495

Gln Asn Asn Asn Ser Asn Phe Ala Trp Thr Gly Ala Thr Lys Tyr His
            500                 505                 510

Leu Asn Gly Arg Asp Ser Leu Val Asn Pro Gly Val Ala Met Ala Thr
        515                 520                 525

His Lys Asp Asp Glu Glu Arg Phe Phe Pro Ser Ser Gly Val Leu Met
530                 535                 540

Phe Gly Lys Gln Gly Ala Gly Lys Asp Asn Val Asp Tyr Ser Ser Val
545                 550                 555                 560

Met Leu Thr Ser Glu Glu Glu Ile Lys Thr Thr Asn Pro Val Ala Thr
                565                 570                 575

Glu Gln Tyr Gly Val Val Ala Asp Asn Leu Gln Gln Gln Asn Ala Ala
            580                 585                 590

Pro Ile Val Gly Ala Val Asn Ser Gln Gly Ala Leu Pro Gly Met Val
        595                 600                 605

Trp Gln Asn Arg Asp Val Tyr Leu Gln Gly Pro Ile Trp Ala Lys Ile
610                 615                 620

Pro His Thr Asp Gly Asn Phe His Pro Ser Pro Leu Met Gly Gly Phe
625                 630                 635                 640

Gly Leu Lys His Pro Pro Pro Gln Ile Leu Ile Lys Asn Thr Pro Val
                645                 650                 655

Pro Ala Asp Pro Pro Thr Thr Phe Ser Gln Ala Lys Leu Ala Ser Phe
            660                 665                 670

Ile Thr Gln Tyr Ser Thr Gly Gln Val Ser Val Glu Ile Glu Trp Glu
        675                 680                 685

Leu Gln Lys Glu Asn Ser Lys Arg Trp Asn Pro Glu Ile Gln Tyr Thr
690                 695                 700

Ser Asn Tyr Tyr Lys Ser Thr Asn Val Asp Phe Ala Val Asn Thr Asp
705                 710                 715                 720

Gly Thr Tyr Ser Glu Pro Arg Pro Ile Gly Thr Arg Tyr Leu Thr Arg
                725                 730                 735

Asn Leu

<210> SEQ ID NO 25
<211> LENGTH: 33
<212> TYPE: PRT
<213> ORGANISM: Artificial Sequence
<220> FEATURE:
<223> OTHER INFORMATION: AAV9

<400> SEQUENCE: 25

Gln Arg Val Ser Thr Thr Val Thr Gln Asn Asn Asn Ser Glu Phe Ala
1               5                   10                  15

Trp Pro Gly Ala Ser Ser Trp Ala Leu Asn Gly Arg Asn Ser Leu Met
            20                  25                  30
```

Asn

<210> SEQ ID NO 26
<211> LENGTH: 33
<212> TYPE: PRT
<213> ORGANISM: Artificial Sequence
<220> FEATURE:
<223> OTHER INFORMATION: AAV8

<400> SEQUENCE: 26

```
Gln Arg Val Ser Thr Thr Thr Gly Gln Asn Asn Asn Ser Asn Phe Ala
1               5                   10                  15

Trp Thr Ala Gly Thr Lys Tyr His Leu Asn Gly Arg Asn Ser Leu Ala
            20                  25                  30

Asn
```

<210> SEQ ID NO 27
<211> LENGTH: 33
<212> TYPE: PRT
<213> ORGANISM: Artificial Sequence
<220> FEATURE:
<223> OTHER INFORMATION: AAVrh10

<400> SEQUENCE: 27

```
Gln Arg Val Ser Thr Thr Leu Ser Gln Asn Asn Asn Ser Asn Phe Ala
1               5                   10                  15

Trp Thr Gly Ala Thr Lys Tyr His Leu Asn Gly Arg Asp Ser Leu Val
            20                  25                  30

Asn
```

<210> SEQ ID NO 28
<211> LENGTH: 33
<212> TYPE: PRT
<213> ORGANISM: Artificial Sequence
<220> FEATURE:
<223> OTHER INFORMATION: AAV3B

<400> SEQUENCE: 28

```
Gln Arg Leu Ser Lys Thr Ala Asn Asp Asn Asn Asn Ser Asn Phe Pro
1               5                   10                  15

Trp Thr Ala Ala Ser Lys Tyr His Leu Asn Gly Arg Asp Ser Leu Val
            20                  25                  30

Asn
```

<210> SEQ ID NO 29
<211> LENGTH: 33
<212> TYPE: PRT
<213> ORGANISM: Artificial Sequence
<220> FEATURE:
<223> OTHER INFORMATION: AAV2

<400> SEQUENCE: 29

```
Gln Arg Val Ser Lys Thr Ser Ala Asp Asn Asn Asn Ser Glu Tyr Ser
1               5                   10                  15

Trp Thr Gly Ala Thr Lys Tyr His Leu Asn Gly Arg Asp Ser Leu Val
            20                  25                  30

Asn
```

<210> SEQ ID NO 30
<211> LENGTH: 33
<212> TYPE: PRT
<213> ORGANISM: Artificial Sequence

```
<220> FEATURE:
<223> OTHER INFORMATION: AAV9

<400> SEQUENCE: 30

Tyr Gly Gln Val Ala Thr Asn His Gln Ser Ala Gln Ala Gln Ala Gln
1               5                   10                  15

Thr Gly Trp Val Gln Asn Gln Gly Ile Leu Pro Gly Met Val Trp Gln
            20                  25                  30

Asp

<210> SEQ ID NO 31
<211> LENGTH: 33
<212> TYPE: PRT
<213> ORGANISM: Artificial Sequence
<220> FEATURE:
<223> OTHER INFORMATION: AAV8

<400> SEQUENCE: 31

Tyr Gly Ile Val Ala Asp Asn Leu Gln Gln Gln Asn Thr Ala Pro Gln
1               5                   10                  15

Ile Gly Thr Val Asn Ser Gln Gly Ala Leu Pro Gly Met Val Trp Gln
            20                  25                  30

Asn

<210> SEQ ID NO 32
<211> LENGTH: 33
<212> TYPE: PRT
<213> ORGANISM: Artificial Sequence
<220> FEATURE:
<223> OTHER INFORMATION: AAVrh10

<400> SEQUENCE: 32

Tyr Gly Val Val Ala Asp Asn Leu Gln Gln Gln Asn Ala Ala Pro Ile
1               5                   10                  15

Val Gly Ala Val Asn Ser Gln Gly Ala Leu Pro Gly Met Val Trp Gln
            20                  25                  30

Asn

<210> SEQ ID NO 33
<211> LENGTH: 33
<212> TYPE: PRT
<213> ORGANISM: Artificial Sequence
<220> FEATURE:
<223> OTHER INFORMATION: AAV3B

<400> SEQUENCE: 33

Tyr Gly Thr Val Ala Asn Asn Leu Gln Ser Ser Asn Thr Ala Pro Thr
1               5                   10                  15

Thr Arg Thr Val Asn Asp Gln Gly Ala Leu Pro Gly Met Val Trp Gln
            20                  25                  30

Asp

<210> SEQ ID NO 34
<211> LENGTH: 33
<212> TYPE: PRT
<213> ORGANISM: Artificial Sequence
<220> FEATURE:
<223> OTHER INFORMATION: AAV2

<400> SEQUENCE: 34

Tyr Gly Ser Val Ser Thr Asn Leu Gln Arg Gly Asn Arg Gln Ala Ala
1               5                   10                  15
```

```
Thr Ala Asp Val Asn Thr Gln Gly Val Leu Pro Gly Met Val Trp Gln
            20                  25                  30
Asp

<210> SEQ ID NO 35
<211> LENGTH: 736
<212> TYPE: PRT
<213> ORGANISM: Artificial Sequence
<220> FEATURE:
<223> OTHER INFORMATION: AAV1

<400> SEQUENCE: 35

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
130                 135                 140

Pro Val Glu Gln Ser Pro Gln Glu Pro Asp Ser Ser Ser Gly Ile Gly
145                 150                 155                 160

Lys Thr Gly Gln Gln Pro Ala Lys Lys Arg Leu Asn Phe Gly Gln Thr
                165                 170                 175

Gly Asp Ser Glu Ser Val Pro Asp Pro Gln Pro Leu Gly Glu Pro Pro
            180                 185                 190

Ala Thr Pro Ala Ala Val Gly Pro Thr Thr Met Ala Ser Gly Gly Gly
        195                 200                 205

Ala Pro Met Ala Asp Asn Asn Glu Gly Ala Asp Gly Val Gly Asn Ala
210                 215                 220

Ser Gly Asn Trp His Cys Asp Ser Thr Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Ala Ser Thr Gly Ala Ser Asn Asp Asn His
            260                 265                 270

Tyr Phe Gly Tyr Ser Thr Pro Trp Gly Tyr Phe Asp Phe Asn Arg Phe
        275                 280                 285

His Cys His Phe Ser Pro Arg Asp Trp Gln Arg Leu Ile Asn Asn Asn
290                 295                 300

Trp Gly Phe Arg Pro Lys Arg Leu Asn Phe Lys Leu Phe Asn Ile Gln
305                 310                 315                 320

Val Lys Glu Val Thr Thr Asn Asp Gly Val Thr Thr Ile Ala Asn Asn
                325                 330                 335
```

-continued

```
Leu Thr Ser Thr Val Gln Val Phe Ser Asp Ser Glu Tyr Gln Leu Pro
            340                 345                 350

Tyr Val Leu Gly Ser Ala His Gln Gly Cys Leu Pro Pro Phe Pro Ala
        355                 360                 365

Asp Val Phe Met Ile Pro Gln Tyr Gly Tyr Leu Thr Leu Asn Asn Gly
    370                 375                 380

Ser Gln Ala Val Gly Arg Ser Ser Phe Tyr Cys Leu Glu Tyr Phe Pro
385                 390                 395                 400

Ser Gln Met Leu Arg Thr Gly Asn Asn Phe Thr Phe Ser Tyr Thr Phe
                405                 410                 415

Glu Glu Val Pro Phe His Ser Ser Tyr Ala His Ser Gln Ser Leu Asp
            420                 425                 430

Arg Leu Met Asn Pro Leu Ile Asp Gln Tyr Leu Tyr Tyr Leu Asn Arg
        435                 440                 445

Thr Gln Asn Gln Ser Gly Ser Ala Gln Asn Lys Asp Leu Leu Phe Ser
    450                 455                 460

Arg Gly Ser Pro Ala Gly Met Ser Val Gln Pro Lys Asn Trp Leu Pro
465                 470                 475                 480

Gly Pro Cys Tyr Arg Gln Gln Arg Val Ser Lys Thr Lys Thr Asp Asn
                485                 490                 495

Asn Asn Ser Asn Phe Thr Trp Thr Gly Ala Ser Lys Tyr Asn Leu Asn
            500                 505                 510

Gly Arg Glu Ser Ile Ile Asn Pro Gly Thr Ala Met Ala Ser His Lys
        515                 520                 525

Asp Asp Glu Asp Lys Phe Phe Pro Met Ser Gly Val Met Ile Phe Gly
    530                 535                 540

Lys Glu Ser Ala Gly Ala Ser Asn Thr Ala Leu Asp Asn Val Met Ile
545                 550                 555                 560

Thr Asp Glu Glu Glu Ile Lys Ala Thr Asn Pro Val Ala Thr Glu Arg
                565                 570                 575

Phe Gly Thr Val Ala Val Asn Phe Gln Ser Ser Ser Thr Asp Pro Ala
            580                 585                 590

Thr Gly Asp Val His Ala Met Gly Ala Leu Pro Gly Met Val Trp Gln
        595                 600                 605

Asp Arg Asp Val Tyr Leu Gln Gly Pro Ile Trp Ala Lys Ile Pro His
    610                 615                 620

Thr Asp Gly His Phe His Pro Ser Pro Leu Met Gly Gly Phe Gly Leu
625                 630                 635                 640

Lys Asn Pro Pro Pro Gln Ile Leu Ile Lys Asn Thr Pro Val Pro Ala
                645                 650                 655

Asn Pro Pro Ala Glu Phe Ser Ala Thr Lys Phe Ala Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Val Gln Tyr Thr Ser Asn
    690                 695                 700

Tyr Ala Lys Ser Ala Asn Val Asp Phe Thr Val Asp Asn Asn Gly Leu
705                 710                 715                 720

Tyr Thr Glu Pro Arg Pro Ile Gly Thr Arg Tyr Leu Thr Arg Pro Leu
                725                 730                 735

<210> SEQ ID NO 36
<211> LENGTH: 736
<212> TYPE: PRT
```

<213> ORGANISM: Artificial Sequence
<220> FEATURE:
<223> OTHER INFORMATION: AAV3B

<400> SEQUENCE: 36

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Val Pro Gln Pro
            20                  25                  30

Lys Ala Asn Gln Gln His Gln Asp Asn Arg Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Glu Ala Asp Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Ile Leu Glu Pro
        115                 120                 125

Leu Gly Leu Val Glu Glu Ala Ala Lys Thr Ala Pro Gly Lys Lys Arg
    130                 135                 140

Pro Val Asp Gln Ser Pro Gln Glu Pro Asp Ser Ser Ser Gly Val Gly
145                 150                 155                 160

Lys Ser Gly Lys Gln Pro Ala Arg Lys Arg Leu Asn Phe Gly Gln Thr
                165                 170                 175

Gly Asp Ser Glu Ser Val Pro Asp Pro Gln Pro Leu Gly Glu Pro Pro
            180                 185                 190

Ala Ala Pro Thr Ser Leu Gly Ser Asn Thr Met Ala Ser Gly Gly Gly
        195                 200                 205

Ala Pro Met Ala Asp Asn Asn Glu Gly Ala Asp Gly Val Gly Asn Ser
    210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Gln Ser Gly Ala Ser Asn Asp Asn His Tyr
            260                 265                 270

Phe Gly Tyr Ser Thr Pro Trp Gly Tyr Phe Asp Phe Asn Arg Phe His
        275                 280                 285

Cys His Phe Ser Pro Arg Asp Trp Gln Arg Leu Ile Asn Asn Asn Trp
    290                 295                 300

Gly Phe Arg Pro Lys Lys Leu Ser Phe Lys Leu Phe Asn Ile Gln Val
305                 310                 315                 320

Lys Glu Val Thr Gln Asn Asp Gly Thr Thr Thr Ile Ala Asn Asn Leu
                325                 330                 335

Thr Ser Thr Val Gln Val Phe Thr Asp Ser Glu Tyr Gln Leu Pro Tyr
            340                 345                 350

Val Leu Gly Ser Ala His Gln Gly Cys Leu Pro Pro Phe Pro Ala Asp
        355                 360                 365

Val Phe Met Val Pro Gln Tyr Gly Tyr Leu Thr Leu Asn Asn Gly Ser
    370                 375                 380

Gln Ala Val Gly Arg Ser Ser Phe Tyr Cys Leu Glu Tyr Phe Pro Ser

```
                385                 390                 395                 400
        Gln Met Leu Arg Thr Gly Asn Asn Phe Gln Phe Ser Tyr Thr Phe Glu
                        405                 410                 415

Asp Val Pro Phe His Ser Ser Tyr Ala His Ser Gln Ser Leu Asp Arg
                        420                 425                 430

Leu Met Asn Pro Leu Ile Asp Gln Tyr Leu Tyr Tyr Leu Asn Arg Thr
                        435                 440                 445

Gln Gly Thr Thr Ser Gly Thr Thr Asn Gln Ser Arg Leu Leu Phe Ser
                450                 455                 460

Gln Ala Gly Pro Gln Ser Met Ser Leu Gln Ala Arg Asn Trp Leu Pro
        465                 470                 475                 480

Gly Pro Cys Tyr Arg Gln Gln Arg Leu Ser Lys Thr Ala Asn Asp Asn
                        485                 490                 495

Asn Asn Ser Asn Phe Pro Trp Thr Ala Ala Ser Lys Tyr His Leu Asn
                        500                 505                 510

Gly Arg Asp Ser Leu Val Asn Pro Gly Pro Ala Met Ala Ser His Lys
                        515                 520                 525

Asp Asp Glu Glu Lys Phe Phe Pro Met His Gly Asn Leu Ile Phe Gly
                530                 535                 540

Lys Glu Gly Thr Thr Ala Ser Asn Ala Glu Leu Asp Asn Val Met Ile
        545                 550                 555                 560

Thr Asp Glu Glu Glu Ile Arg Thr Thr Asn Pro Val Ala Thr Glu Gln
                        565                 570                 575

Tyr Gly Thr Val Ala Asn Asn Leu Gln Ser Ser Asn Thr Ala Pro Thr
                        580                 585                 590

Thr Arg Thr Val Asn Asp Gln Gly Ala Leu Pro Gly Met Val Trp Gln
                        595                 600                 605

Asp Arg Asp Val Tyr Leu Gln Gly Pro Ile Trp Ala Lys Ile Pro His
                610                 615                 620

Thr Asp Gly His Phe His Pro Ser Pro Leu Met Gly Gly Phe Gly Leu
        625                 630                 635                 640

Lys His Pro Pro Pro Gln Ile Met Ile Lys Asn Thr Pro Val Pro Ala
                        645                 650                 655

Asn Pro Pro Thr Thr Phe Ser Pro Ala Lys Phe Ala Ser Phe Ile Thr
                        660                 665                 670

Gln Tyr Ser Thr Gly Gln Val Ser Val Glu Ile Glu Trp Glu Leu Gln
                        675                 680                 685

Lys Glu Asn Ser Lys Arg Trp Asn Pro Glu Ile Gln Tyr Thr Ser Asn
                        690                 695                 700

Tyr Asn Lys Ser Val Asn Val Asp Phe Thr Val Asp Thr Asn Gly Val
        705                 710                 715                 720

Tyr Ser Glu Pro Arg Pro Ile Gly Thr Arg Tyr Leu Thr Arg Asn Leu
                        725                 730                 735

<210> SEQ ID NO 37
<211> LENGTH: 724
<212> TYPE: PRT
<213> ORGANISM: Artificial Sequence
<220> FEATURE:
<223> OTHER INFORMATION: AAV5

<400> SEQUENCE: 37

Met Ser Phe Val Asp His Pro Pro Asp Trp Leu Glu Glu Val Gly Glu
        1               5                   10                  15

Gly Leu Arg Glu Phe Leu Gly Leu Glu Ala Gly Pro Pro Lys Pro Lys
```

```
            20                  25                  30
Pro Asn Gln Gln His Gln Asp Gln Ala Arg Gly Leu Val Leu Pro Gly
            35                  40                  45
Tyr Asn Tyr Leu Gly Pro Gly Asn Gly Leu Asp Arg Gly Glu Pro Val
        50                  55                  60
Asn Arg Ala Asp Glu Val Ala Arg Glu His Asp Ile Ser Tyr Asn Glu
65                  70                  75                  80
Gln Leu Glu Ala Gly Asp Asn Pro Tyr Leu Lys Tyr Asn His Ala Asp
                85                  90                  95
Ala Glu Phe Gln Glu Lys Leu Ala Asp Asp Thr Ser Phe Gly Gly Asn
            100                 105                 110
Leu Gly Lys Ala Val Phe Gln Ala Lys Lys Arg Val Leu Glu Pro Phe
            115                 120                 125
Gly Leu Val Glu Glu Gly Ala Lys Thr Ala Pro Thr Gly Lys Arg Ile
        130                 135                 140
Asp Asp His Phe Pro Lys Arg Lys Lys Ala Arg Thr Glu Glu Asp Ser
145                 150                 155                 160
Lys Pro Ser Thr Ser Ser Asp Ala Glu Ala Gly Pro Ser Gly Ser Gln
                165                 170                 175
Gln Leu Gln Ile Pro Ala Gln Pro Ala Ser Ser Leu Gly Ala Asp Thr
            180                 185                 190
Met Ser Ala Gly Gly Gly Pro Leu Gly Asp Asn Asn Gln Gly Ala
            195                 200                 205
Asp Gly Val Gly Asn Ala Ser Gly Asp Trp His Cys Asp Ser Thr Trp
        210                 215                 220
Met Gly Asp Arg Val Val Thr Lys Ser Thr Arg Thr Trp Val Leu Pro
225                 230                 235                 240
Ser Tyr Asn Asn His Gln Tyr Arg Glu Ile Lys Ser Gly Ser Val Asp
                245                 250                 255
Gly Ser Asn Ala Asn Ala Tyr Phe Gly Tyr Ser Thr Pro Trp Gly Tyr
            260                 265                 270
Phe Asp Phe Asn Arg Phe His Ser His Trp Ser Pro Arg Asp Trp Gln
            275                 280                 285
Arg Leu Ile Asn Asn Tyr Trp Gly Phe Arg Pro Arg Ser Leu Arg Val
        290                 295                 300
Lys Ile Phe Asn Ile Gln Val Lys Glu Val Thr Val Gln Asp Ser Thr
305                 310                 315                 320
Thr Thr Ile Ala Asn Asn Leu Thr Ser Thr Val Gln Val Phe Thr Asp
                325                 330                 335
Asp Asp Tyr Gln Leu Pro Tyr Val Val Gly Asn Gly Thr Glu Gly Cys
            340                 345                 350
Leu Pro Ala Phe Pro Pro Gln Val Phe Thr Leu Pro Gln Tyr Gly Tyr
            355                 360                 365
Ala Thr Leu Asn Arg Asp Asn Thr Glu Asn Pro Thr Glu Arg Ser Ser
        370                 375                 380
Phe Phe Cys Leu Glu Tyr Phe Pro Ser Lys Met Leu Arg Thr Gly Asn
385                 390                 395                 400
Asn Phe Glu Phe Thr Tyr Asn Phe Glu Glu Val Pro Phe His Ser Ser
                405                 410                 415
Phe Ala Pro Ser Gln Asn Leu Phe Lys Leu Ala Asn Pro Leu Val Asp
            420                 425                 430
Gln Tyr Leu Tyr Arg Phe Val Ser Thr Asn Asn Thr Gly Gly Val Gln
            435                 440                 445
```

```
Phe Asn Lys Asn Leu Ala Gly Arg Tyr Ala Asn Thr Tyr Lys Asn Trp
    450                 455                 460

Phe Pro Gly Pro Met Gly Arg Thr Gln Gly Trp Asn Leu Gly Ser Gly
465                 470                 475                 480

Val Asn Arg Ala Ser Val Ser Ala Phe Ala Thr Thr Asn Arg Met Glu
                485                 490                 495

Leu Glu Gly Ala Ser Tyr Gln Val Pro Pro Gln Pro Asn Gly Met Thr
            500                 505                 510

Asn Asn Leu Gln Gly Ser Asn Thr Tyr Ala Leu Glu Asn Thr Met Ile
        515                 520                 525

Phe Asn Ser Gln Pro Ala Asn Pro Gly Thr Thr Ala Thr Tyr Leu Glu
    530                 535                 540

Gly Asn Met Leu Ile Thr Ser Glu Ser Glu Thr Gln Pro Val Asn Arg
545                 550                 555                 560

Val Ala Tyr Asn Val Gly Gly Gln Met Ala Thr Asn Asn Gln Ser Ser
                565                 570                 575

Thr Thr Ala Pro Ala Thr Gly Thr Tyr Asn Leu Gln Glu Ile Val Pro
            580                 585                 590

Gly Ser Val Trp Met Glu Arg Asp Val Tyr Leu Gln Gly Pro Ile Trp
        595                 600                 605

Ala Lys Ile Pro Glu Thr Gly Ala His Phe His Pro Ser Pro Ala Met
    610                 615                 620

Gly Gly Phe Gly Leu Lys His Pro Pro Met Met Leu Ile Lys Asn
625                 630                 635                 640

Thr Pro Val Pro Gly Asn Ile Thr Ser Phe Ser Asp Val Pro Val Ser
                645                 650                 655

Ser Phe Ile Thr Gln Tyr Ser Thr Gly Gln Val Thr Val Glu Met Glu
            660                 665                 670

Trp Glu Leu Lys Lys Glu Asn Ser Lys Arg Trp Asn Pro Glu Ile Gln
        675                 680                 685

Tyr Thr Asn Asn Tyr Asn Asp Pro Gln Phe Val Asp Phe Ala Pro Asp
    690                 695                 700

Ser Thr Gly Glu Tyr Arg Thr Thr Arg Pro Ile Gly Thr Arg Tyr Leu
705                 710                 715                 720

Thr Arg Pro Leu

<210> SEQ ID NO 38
<211> LENGTH: 737
<212> TYPE: PRT
<213> ORGANISM: Artificial Sequence
<220> FEATURE:
<223> OTHER INFORMATION: AAV7

<400> SEQUENCE: 38

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asn Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80
```

```
Gln Gln Leu Lys Ala Gly Asp Asn Pro Tyr Leu Arg Tyr Asn His Ala
             85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
            115                 120                 125

Leu Gly Leu Val Glu Glu Gly Ala Lys Thr Ala Pro Ala Lys Lys Arg
130                 135                 140

Pro Val Glu Pro Ser Pro Gln Arg Ser Pro Asp Ser Thr Gly Ile
145                 150                 155                 160

Gly Lys Lys Gly Gln Gln Pro Ala Arg Lys Arg Leu Asn Phe Gly Gln
                    165                 170                 175

Thr Gly Asp Ser Glu Ser Val Pro Asp Pro Gln Pro Leu Gly Glu Pro
            180                 185                 190

Pro Ala Ala Pro Ser Ser Val Gly Ser Gly Thr Val Ala Ala Gly Gly
            195                 200                 205

Gly Ala Pro Met Ala Asp Asn Asn Glu Gly Ala Asp Gly Val Gly Asn
            210                 215                 220

Ala Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Ser Glu Thr Ala Gly Ser Thr Asn Asp Asn
                260                 265                 270

Thr Tyr Phe Gly Tyr Ser Thr Pro Trp Gly Tyr Phe Asp Phe Asn Arg
                275                 280                 285

Phe His Cys His Phe Ser Pro Arg Asp Trp Gln Arg Leu Ile Asn Asn
            290                 295                 300

Asn Trp Gly Phe Arg Pro Lys Lys Leu Arg Phe Lys Leu Phe Asn Ile
305                 310                 315                 320

Gln Val Lys Glu Val Thr Thr Asn Asp Gly Val Thr Thr Ile Ala Asn
                325                 330                 335

Asn Leu Thr Ser Thr Ile Gln Val Phe Ser Asp Ser Glu Tyr Gln Leu
            340                 345                 350

Pro Tyr Val Leu Gly Ser Ala His Gln Gly Cys Leu Pro Pro Phe Pro
            355                 360                 365

Ala Asp Val Phe Met Ile Pro Gln Tyr Gly Tyr Leu Thr Leu Asn Asn
            370                 375                 380

Gly Ser Gln Ser Val Gly Arg Ser Ser Phe Tyr Cys Leu Glu Tyr Phe
385                 390                 395                 400

Pro Ser Gln Met Leu Arg Thr Gly Asn Asn Phe Glu Phe Ser Tyr Ser
            405                 410                 415

Phe Glu Asp Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Ala
            435                 440                 445

Arg Thr Gln Ser Asn Pro Gly Gly Thr Ala Gly Asn Arg Glu Leu Gln
            450                 455                 460

Phe Tyr Gln Gly Gly Pro Ser Thr Met Ala Glu Gln Ala Lys Asn Trp
465                 470                 475                 480

Leu Pro Gly Pro Cys Phe Arg Gln Gln Arg Val Ser Lys Thr Leu Asp
            485                 490                 495

Gln Asn Asn Asn Ser Asn Phe Ala Trp Thr Gly Ala Thr Lys Tyr His
```

```
                500             505                 510
Leu Asn Gly Arg Asn Ser Leu Val Asn Pro Gly Val Ala Met Ala Thr
            515                 520             525

His Lys Asp Asp Glu Asp Arg Phe Phe Pro Ser Ser Gly Val Leu Ile
530             535                 540

Phe Gly Lys Thr Gly Ala Thr Asn Lys Thr Thr Leu Glu Asn Val Leu
545             550                 555                 560

Met Thr Asn Glu Glu Glu Ile Arg Pro Thr Asn Pro Val Ala Thr Glu
            565                 570                 575

Glu Tyr Gly Ile Val Ser Ser Asn Leu Gln Ala Ala Asn Thr Ala Ala
            580                 585                 590

Gln Thr Gln Val Val Asn Asn Gln Gly Ala Leu Pro Gly Met Val Trp
            595                 600                 605

Gln Asn Arg Asp Val Tyr Leu Gln Gly Pro Ile Trp Ala Lys Ile Pro
            610                 615                 620

His Thr Asp Gly Asn Phe His Pro Ser Pro Leu Met Gly Gly Phe Gly
625                 630                 635                 640

Leu Lys His Pro Pro Pro Gln Ile Leu Ile Lys Asn Thr Pro Val Pro
                645                 650                 655

Ala Asn Pro Pro Glu Val Phe Thr Pro Ala Lys Phe Ala Ser Phe Ile
                660                 665                 670

Thr Gln Tyr Ser Thr Gly Gln Val Ser Val Glu Ile Glu Trp Glu Leu
            675                 680                 685

Gln Lys Glu Asn Ser Lys Arg Trp Asn Pro Glu Ile Gln Tyr Thr Ser
            690                 695                 700

Asn Phe Glu Lys Gln Thr Gly Val Asp Phe Ala Val Asp Ser Gln Gly
705                 710                 715                 720

Val Tyr Ser Glu Pro Arg Pro Ile Gly Thr Arg Tyr Leu Thr Arg Asn
                725                 730                 735

Leu

<210> SEQ ID NO 39
<211> LENGTH: 733
<212> TYPE: PRT
<213> ORGANISM: Artificial Sequence
<220> FEATURE:
<223> OTHER INFORMATION: AAVrh32.33

<400> SEQUENCE: 39

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
                20                  25                  30

Lys Ala Asn Gln Gln Lys Gln Asp Gly Arg Gly Leu Val Leu Pro
            35                  40                  45

Gly Tyr Lys Tyr Leu Gly Pro Phe Asn Gly Leu Asp Lys Gly Glu Pro
        50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125
```

```
Leu Gly Leu Val Glu Glu Gly Ala Lys Thr Ala Pro Gly Lys Lys Arg
    130                 135                 140
Pro Leu Glu Ser Pro Gln Glu Pro Asp Ser Ser Gly Ile Gly Lys
145                 150                 155                 160
Lys Gly Lys Gln Pro Ala Lys Lys Arg Leu Asn Phe Glu Glu Asp Thr
                165                 170                 175
Gly Ala Gly Asp Gly Pro Pro Glu Gly Ser Asp Thr Ser Ala Met Ser
                180                 185                 190
Ser Asp Ile Glu Met Arg Ala Ala Pro Gly Gly Asn Ala Val Asp Ala
            195                 200                 205
Gly Gln Gly Ser Asp Gly Val Gly Asn Ala Ser Gly Asp Trp His Cys
    210                 215                 220
Asp Ser Thr Trp Ser Glu Gly Lys Val Thr Thr Thr Ser Thr Arg Thr
225                 230                 235                 240
Trp Val Leu Pro Thr Tyr Asn Asn His Leu Tyr Leu Arg Leu Gly Thr
                245                 250                 255
Thr Ser Asn Ser Asn Thr Tyr Asn Gly Phe Ser Thr Pro Trp Gly Tyr
                260                 265                 270
Phe Asp Phe Asn Arg Phe His Cys His Phe Ser Pro Arg Asp Trp Gln
                275                 280                 285
Arg Leu Ile Asn Asn Asn Trp Gly Leu Arg Pro Lys Ala Met Arg Val
    290                 295                 300
Lys Ile Phe Asn Ile Gln Val Lys Glu Val Thr Thr Ser Asn Gly Glu
305                 310                 315                 320
Thr Thr Val Ala Asn Asn Leu Thr Ser Thr Val Gln Ile Phe Ala Asp
                325                 330                 335
Ser Ser Tyr Glu Leu Pro Tyr Val Met Asp Ala Gly Gln Glu Gly Ser
                340                 345                 350
Leu Pro Pro Phe Pro Asn Asp Val Phe Met Val Pro Gln Tyr Gly Tyr
                355                 360                 365
Cys Gly Ile Val Thr Gly Glu Asn Gln Asn Gln Thr Asp Arg Asn Ala
    370                 375                 380
Phe Tyr Cys Leu Glu Tyr Phe Pro Ser Gln Met Leu Arg Thr Gly Asn
385                 390                 395                 400
Asn Phe Glu Met Ala Tyr Asn Phe Glu Lys Val Pro Phe His Ser Met
                405                 410                 415
Tyr Ala His Ser Gln Ser Leu Asp Arg Leu Met Asn Pro Leu Leu Asp
                420                 425                 430
Gln Tyr Leu Trp His Leu Gln Ser Thr Thr Ser Gly Glu Thr Leu Asn
            435                 440                 445
Gln Gly Asn Ala Ala Thr Thr Phe Gly Lys Ile Arg Ser Gly Asp Phe
    450                 455                 460
Ala Phe Tyr Arg Lys Asn Trp Leu Pro Gly Pro Cys Val Lys Gln Gln
465                 470                 475                 480
Arg Phe Ser Lys Thr Ala Ser Gln Asn Tyr Lys Ile Pro Ala Ser Gly
                485                 490                 495
Gly Asn Ala Leu Leu Lys Tyr Asp Thr His Tyr Thr Leu Asn Asn Arg
                500                 505                 510
Trp Ser Asn Ile Ala Pro Gly Pro Pro Met Ala Thr Ala Gly Pro Ser
            515                 520                 525
Asp Gly Asp Phe Ser Asn Ala Gln Leu Ile Phe Pro Gly Pro Ser Val
    530                 535                 540
```

```
Thr Gly Asn Thr Thr Thr Ser Ala Asn Asn Leu Leu Phe Thr Ser Glu
545                 550                 555                 560

Glu Glu Ile Ala Ala Thr Asn Pro Arg Asp Thr Asp Met Phe Gly Gln
            565                 570                 575

Ile Ala Asp Asn Asn Gln Asn Ala Thr Thr Ala Pro Ile Thr Gly Asn
        580                 585                 590

Val Thr Ala Met Gly Val Leu Pro Gly Met Val Trp Gln Asn Arg Asp
    595                 600                 605

Ile Tyr Tyr Gln Gly Pro Ile Trp Ala Lys Ile Pro His Ala Asp Gly
610                 615                 620

His Phe His Pro Ser Pro Leu Ile Gly Gly Phe Gly Leu Lys His Pro
625                 630                 635                 640

Pro Pro Gln Ile Phe Ile Lys Asn Thr Pro Val Pro Ala Asn Pro Ala
            645                 650                 655

Thr Thr Phe Thr Ala Ala Arg Val Asp Ser Phe Ile Thr Gln Tyr Ser
        660                 665                 670

Thr Gly Gln Val Ala Val Gln Ile Glu Trp Glu Ile Glu Lys Glu Arg
    675                 680                 685

Ser Lys Arg Trp Asn Pro Glu Val Gln Phe Thr Ser Asn Tyr Gly Asn
690                 695                 700

Gln Ser Ser Met Leu Trp Ala Pro Asp Thr Thr Gly Lys Tyr Thr Glu
705                 710                 715                 720

Pro Arg Val Ile Gly Ser Arg Tyr Leu Thr Asn His Leu
            725                 730

<210> SEQ ID NO 40
<211> LENGTH: 2214
<212> TYPE: DNA
<213> ORGANISM: Artificial Sequence
<220> FEATURE:
<223> OTHER INFORMATION: AVV mutant 8G264AG515A
<220> FEATURE:
<221> NAME/KEY: CDS
<222> LOCATION: (1)..(2214)

<400> SEQUENCE: 40 atg gct gcc gat ggt tat ctt cca gat tgg ctc gag gac aac ctc tct      48
Met Ala Ala Asp Gly Tyr Leu Pro Asp Trp Leu Glu Asp Asn Leu Ser
1               5                   10                  15 gag ggc att cgc gag tgg tgg gcg ctg aaa cct gga gcc ccg aag ccc      96
Glu Gly Ile Arg Glu Trp Trp Ala Leu Lys Pro Gly Ala Pro Lys Pro
            20                  25                  30 aaa gcc aac cag caa aag cag gac gac ggc cgg ggt ctg gtg ctt cct     144
Lys Ala Asn Gln Gln Lys Gln Asp Asp Gly Arg Gly Leu Val Leu Pro
        35                  40                  45 ggc tac aag tac ctc gga ccc ttc aac gga ctc gac aag ggg gag ccc     192
Gly Tyr Lys Tyr Leu Gly Pro Phe Asn Gly Leu Asp Lys Gly Glu Pro
    50                  55                  60 gtc aac gcg gcg gac gca gcg gcc ctc gag cac gac aag gcc tac gac     240
Val Asn Ala Ala Asp Ala Ala Ala Leu Glu His Asp Lys Ala Tyr Asp
65                  70                  75                  80 cag cag ctg cag gcg ggt gac aat ccg tac ctg cgg tat aac cac gcc     288
Gln Gln Leu Gln Ala Gly Asp Asn Pro Tyr Leu Arg Tyr Asn His Ala
            85                  90                  95 gac gcc gag ttt cag gag cgt ctg caa gaa gat acg tct ttt ggg ggc     336
Asp Ala Glu Phe Gln Glu Arg Leu Gln Glu Asp Thr Ser Phe Gly Gly
        100                 105                 110 aac ctc ggg cga gca gtc ttc cag gcc aag aag cgg gtt ctc gaa cct     384
Asn Leu Gly Arg Ala Val Phe Gln Ala Lys Lys Arg Val Leu Glu Pro
```

-continued

```
              115                 120                 125
ctc ggt ctg gtt gag gaa ggc gct aag acg gct cct gga aag aag aga    432
Leu Gly Leu Val Glu Glu Gly Ala Lys Thr Ala Pro Gly Lys Lys Arg
    130                 135                 140 ccg gta gag cca tca ccc cag cgt tct cca gac tcc tct acg ggc atc    480
Pro Val Glu Pro Ser Pro Gln Arg Ser Pro Asp Ser Ser Thr Gly Ile
145                 150                 155                 160 ggc aag aaa ggc caa cag ccc gcc aga aaa aga ctc aat ttt ggt cag    528
Gly Lys Lys Gly Gln Gln Pro Ala Arg Lys Arg Leu Asn Phe Gly Gln
                165                 170                 175 act ggc gac tca gag tca gtt cca gac cct caa cct ctc gga gaa cct    576
Thr Gly Asp Ser Glu Ser Val Pro Asp Pro Gln Pro Leu Gly Glu Pro
            180                 185                 190 cca gca gcg ccc tct ggt gtg gga cct aat aca atg gct gca ggc ggt    624
Pro Ala Ala Pro Ser Gly Val Gly Pro Asn Thr Met Ala Ala Gly Gly
        195                 200                 205 ggc gca cca atg gca gac aat aac gaa ggc gcc gac gga gtg ggt agt    672
Gly Ala Pro Met Ala Asp Asn Asn Glu Gly Ala Asp Gly Val Gly Ser
    210                 215                 220 tcc tcg gga aat tgg cat tgc gat tcc aca tgg ctg ggc gac aga gtc    720
Ser Ser Gly Asn Trp His Cys Asp Ser Thr Trp Leu Gly Asp Arg Val
225                 230                 235                 240 atc acc acc agc acc cga acc tgg gcc ctg ccc acc tac aac aac cac    768
Ile Thr Thr Ser Thr Arg Thr Trp Ala Leu Pro Thr Tyr Asn Asn His
                245                 250                 255 ctc tac aag caa atc tcc aac gcg aca tcg gga gga gcc acc aac gac    816
Leu Tyr Lys Gln Ile Ser Asn Ala Thr Ser Gly Gly Ala Thr Asn Asp
            260                 265                 270 aac acc tac ttc ggc tac agc acc ccc tgg ggg tat ttt gac ttt aac    864
Asn Thr Tyr Phe Gly Tyr Ser Thr Pro Trp Gly Tyr Phe Asp Phe Asn
        275                 280                 285 aga ttc cac tgc cac ttt tca cca cgt gac tgg cag cga ctc atc aac    912
Arg Phe His Cys His Phe Ser Pro Arg Asp Trp Gln Arg Leu Ile Asn
    290                 295                 300 aac aac tgg gga ttc cgg ccc aag aga ctc agc ttc aag ctc ttc aac    960
Asn Asn Trp Gly Phe Arg Pro Lys Arg Leu Ser Phe Lys Leu Phe Asn
305                 310                 315                 320 atc cag gtc aag gag gtc acg cag aat gaa ggc acc aag acc atc gcc   1008
Ile Gln Val Lys Glu Val Thr Gln Asn Glu Gly Thr Lys Thr Ile Ala
                325                 330                 335 aat aac ctc acc agc acc atc cag gtg ttt acg gac tcg gag tac cag   1056
Asn Asn Leu Thr Ser Thr Ile Gln Val Phe Thr Asp Ser Glu Tyr Gln
            340                 345                 350 ctg ccg tac gtt ctc ggc tct gcc cac cag ggc tgc ctg cct ccg ttc   1104
Leu Pro Tyr Val Leu Gly Ser Ala His Gln Gly Cys Leu Pro Pro Phe
        355                 360                 365 ccg gcg gac gtg ttc atg att ccc cag tac ggc tac cta aca ctc aac   1152
Pro Ala Asp Val Phe Met Ile Pro Gln Tyr Gly Tyr Leu Thr Leu Asn
    370                 375                 380 aac gga agt cag gcc gtg gga cgc tcc tcc ttc tac tgc ctg gaa tac   1200
Asn Gly Ser Gln Ala Val Gly Arg Ser Ser Phe Tyr Cys Leu Glu Tyr
385                 390                 395                 400 ttt cct tcg cag atg ctg aga acc ggc aac aac ttc cag ttt act tac   1248
Phe Pro Ser Gln Met Leu Arg Thr Gly Asn Asn Phe Gln Phe Thr Tyr
                405                 410                 415 acc ttc gag gac gtg cct ttc cac agc agc tac gcc cac agc cag agc   1296
Thr Phe Glu Asp Val Pro Phe His Ser Ser Tyr Ala His Ser Gln Ser
            420                 425                 430 ttg gac cgg ctg atg aat cct ctg att gac cag tac ctg tac tac ttg   1344
```

```
                Leu Asp Arg Leu Met Asn Pro Leu Ile Asp Gln Tyr Leu Tyr Tyr Leu
                            435                 440                 445 tct cgg act caa aca aca gga ggc acg gca aat acg cag act ctg ggc          1392
Ser Arg Thr Gln Thr Thr Gly Gly Thr Ala Asn Thr Gln Thr Leu Gly
    450                 455                 460 ttc agc caa ggt ggg cct aat aca atg gcc aat cag gca aag aac tgg          1440
Phe Ser Gln Gly Gly Pro Asn Thr Met Ala Asn Gln Ala Lys Asn Trp
465                 470                 475                 480 ctg cca gga ccc tgt tac cgc caa caa cgc gtc tca acg aca acc ggg          1488
Leu Pro Gly Pro Cys Tyr Arg Gln Gln Arg Val Ser Thr Thr Thr Gly
                485                 490                 495 caa aac aac aat agc aac ttt gcc tgg act gct ggg acc aaa tac cat          1536
Gln Asn Asn Asn Ser Asn Phe Ala Trp Thr Ala Gly Thr Lys Tyr His
                    500                 505                 510 ctg aat gca aga aat tca ttg gct aat cct ggc atc gct atg gca aca          1584
Leu Asn Ala Arg Asn Ser Leu Ala Asn Pro Gly Ile Ala Met Ala Thr
                        515                 520                 525 cac aaa gac gac gag gag cgt ttt ttt ccc agt aac ggg atc ctg att          1632
His Lys Asp Asp Glu Glu Arg Phe Phe Pro Ser Asn Gly Ile Leu Ile
            530                 535                 540 ttt ggc aaa caa aat gct gcc aga gac aat gcg gat tac agc gat gtc          1680
Phe Gly Lys Gln Asn Ala Ala Arg Asp Asn Ala Asp Tyr Ser Asp Val
545                 550                 555                 560 atg ctc acc agc gag gaa gaa atc aaa acc act aac cct gtg gct aca          1728
Met Leu Thr Ser Glu Glu Glu Ile Lys Thr Thr Asn Pro Val Ala Thr
                565                 570                 575 gag gaa tac ggt atc gtg gca gat aac ttg cag cag caa aac acg gct          1776
Glu Glu Tyr Gly Ile Val Ala Asp Asn Leu Gln Gln Gln Asn Thr Ala
                    580                 585                 590 cct caa att gga act gtc aac agc cag ggg gcc tta ccc ggt atg gtc          1824
Pro Gln Ile Gly Thr Val Asn Ser Gln Gly Ala Leu Pro Gly Met Val
                        595                 600                 605 tgg cag aac cgg gac gtg tac ctg cag ggt ccc atc tgg gcc aag att          1872
Trp Gln Asn Arg Asp Val Tyr Leu Gln Gly Pro Ile Trp Ala Lys Ile
            610                 615                 620 cct cac acg gac ggc aac ttc cac ccg tct ccg ctg atg ggc ggc ttt          1920
Pro His Thr Asp Gly Asn Phe His Pro Ser Pro Leu Met Gly Gly Phe
625                 630                 635                 640 ggc ctg aaa cat cct ccg cct cag atc ctg atc aag aac acg cct gta          1968
Gly Leu Lys His Pro Pro Pro Gln Ile Leu Ile Lys Asn Thr Pro Val
                645                 650                 655 cct gcg gat cct ccg acc acc ttc aac cag tca aag ctg aac tct ttc          2016
Pro Ala Asp Pro Pro Thr Thr Phe Asn Gln Ser Lys Leu Asn Ser Phe
                    660                 665                 670 atc acg caa tac agc acc gga cag gtc agc gtg gaa att gaa tgg gag          2064
Ile Thr Gln Tyr Ser Thr Gly Gln Val Ser Val Glu Ile Glu Trp Glu
                        675                 680                 685 ctg cag aag gaa aac agc aag cgc tgg aac ccc gag atc cag tac acc          2112
Leu Gln Lys Glu Asn Ser Lys Arg Trp Asn Pro Glu Ile Gln Tyr Thr
            690                 695                 700 tcc aac tac tac aaa tct aca agt gtg gac ttt gct gtt aat aca gaa          2160
Ser Asn Tyr Tyr Lys Ser Thr Ser Val Asp Phe Ala Val Asn Thr Glu
705                 710                 715                 720 ggc gtg tac tct gaa ccc cgc ccc att ggc acc cgt tac ctc acc cgt          2208
Gly Val Tyr Ser Glu Pro Arg Pro Ile Gly Thr Arg Tyr Leu Thr Arg
                725                 730                 735 aat ctg                                                                  2214
Asn Leu
```

```
<210> SEQ ID NO 41
<211> LENGTH: 738
<212> TYPE: PRT
<213> ORGANISM: Artificial Sequence
<220> FEATURE:
<223> OTHER INFORMATION: Synthetic Construct

<400> SEQUENCE: 41
```

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Leu Glu His Asp Lys Ala Tyr Asp
65                  70                  75                  80

Gln Gln Leu Gln Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Arg Lys Arg Leu Asn Phe Gly Gln
                165                 170                 175

Thr Gly Asp Ser Glu Ser Val Pro Asp Pro Gln Pro Leu Gly Glu Pro
            180                 185                 190

Pro Ala Ala Pro Ser Gly Val Gly Pro Asn Thr Met Ala Ala Gly Gly
        195                 200                 205

Gly Ala Pro Met Ala Asp Asn Asn Glu Gly Ala Asp Gly Val Gly Ser
    210                 215                 220

Ser Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Asn Ala Thr Ser Gly Gly Ala Thr Asn Asp
            260                 265                 270

Asn Thr Tyr Phe Gly Tyr Ser Thr Pro Trp Gly Tyr Phe Asp Phe Asn
        275                 280                 285

Arg Phe His Cys His Phe Ser Pro Arg Asp Trp Gln Arg Leu Ile Asn
    290                 295                 300

Asn Asn Trp Gly Phe Arg Pro Lys Arg Leu Ser Phe Lys Leu Phe Asn
305                 310                 315                 320

Ile Gln Val Lys Glu Val Thr Gln Asn Glu Gly Thr Lys Thr Ile Ala
                325                 330                 335

Asn Asn Leu Thr Ser Thr Ile Gln Val Phe Thr Asp Ser Glu Tyr Gln
            340                 345                 350

Leu Pro Tyr Val Leu Gly Ser Ala His Gln Gly Cys Leu Pro Pro Phe
        355                 360                 365

Pro Ala Asp Val Phe Met Ile Pro Gln Tyr Gly Tyr Leu Thr Leu Asn

```
            370                 375                 380
Asn Gly Ser Gln Ala Val Gly Arg Ser Phe Tyr Cys Leu Glu Tyr
385                 390                 395                 400

Phe Pro Ser Gln Met Leu Arg Thr Gly Asn Asn Phe Gln Phe Thr Tyr
                405                 410                 415

Thr Phe Glu Asp Val Pro Phe His Ser Ser Tyr Ala His Ser Gln Ser
                420                 425                 430

Leu Asp Arg Leu Met Asn Pro Leu Ile Asp Gln Tyr Leu Tyr Tyr Leu
            435                 440                 445

Ser Arg Thr Gln Thr Thr Gly Gly Thr Ala Asn Thr Gln Thr Leu Gly
450                 455                 460

Phe Ser Gln Gly Gly Pro Asn Thr Met Ala Asn Gln Ala Lys Asn Trp
465                 470                 475                 480

Leu Pro Gly Pro Cys Tyr Arg Gln Gln Arg Val Ser Thr Thr Thr Gly
                485                 490                 495

Gln Asn Asn Asn Ser Asn Phe Ala Trp Thr Ala Gly Thr Lys Tyr His
            500                 505                 510

Leu Asn Ala Arg Asn Ser Leu Ala Asn Pro Gly Ile Ala Met Ala Thr
            515                 520                 525

His Lys Asp Asp Glu Glu Arg Phe Phe Pro Ser Asn Gly Ile Leu Ile
        530                 535                 540

Phe Gly Lys Gln Asn Ala Ala Arg Asp Asn Ala Asp Tyr Ser Asp Val
545                 550                 555                 560

Met Leu Thr Ser Glu Glu Glu Ile Lys Thr Thr Asn Pro Val Ala Thr
                565                 570                 575

Glu Glu Tyr Gly Ile Val Ala Asp Asn Leu Gln Gln Gln Asn Thr Ala
            580                 585                 590

Pro Gln Ile Gly Thr Val Asn Ser Gln Gly Ala Leu Pro Gly Met Val
        595                 600                 605

Trp Gln Asn Arg Asp Val Tyr Leu Gln Gly Pro Ile Trp Ala Lys Ile
610                 615                 620

Pro His Thr Asp Gly Asn Phe His Pro Ser Pro Leu Met Gly Gly Phe
625                 630                 635                 640

Gly Leu Lys His Pro Pro Pro Gln Ile Leu Ile Lys Asn Thr Pro Val
                645                 650                 655

Pro Ala Asp Pro Pro Thr Thr Phe Asn Gln Ser Lys Leu Asn Ser Phe
                660                 665                 670

Ile Thr Gln Tyr Ser Thr Gly Gln Val Ser Val Glu Ile Glu Trp Glu
            675                 680                 685

Leu Gln Lys Glu Asn Ser Lys Arg Trp Asn Pro Glu Ile Gln Tyr Thr
        690                 695                 700

Ser Asn Tyr Tyr Lys Ser Thr Ser Val Asp Phe Ala Val Asn Thr Glu
705                 710                 715                 720

Gly Val Tyr Ser Glu Pro Arg Pro Ile Gly Thr Arg Tyr Leu Thr Arg
                725                 730                 735

Asn Leu

<210> SEQ ID NO 42
<211> LENGTH: 2214
<212> TYPE: DNA
<213> ORGANISM: Artificial Sequence
<220> FEATURE:
<223> OTHER INFORMATION: AVV mutant 8G264AG541A
<220> FEATURE:
<221> NAME/KEY: CDS
```

<222> LOCATION: (1)..(2214)

<400> SEQUENCE: 42

| | | | | | | | | | | | | | | | | |
|---|---|---|---|---|---|---|---|---|---|---|---|---|---|---|---|---|
| atg | gct | gcc | gat | ggt | tat | ctt | cca | gat | tgg | ctc | gag | gac | aac | ctc | tct | 48 |
| Met | Ala | Ala | Asp | Gly | Tyr | Leu | Pro | Asp | Trp | Leu | Glu | Asp | Asn | Leu | Ser | |
| 1 | | | | 5 | | | | | 10 | | | | | 15 | | |
| gag | ggc | att | cgc | gag | tgg | tgg | gcg | ctg | aaa | cct | gga | gcc | ccg | aag | ccc | 96 |
| Glu | Gly | Ile | Arg | Glu | Trp | Trp | Ala | Leu | Lys | Pro | Gly | Ala | Pro | Lys | Pro | |
| | | | 20 | | | | | 25 | | | | | 30 | | | |
| aaa | gcc | aac | cag | caa | aag | cag | gac | gac | ggc | cgg | ggt | ctg | gtg | ctt | cct | 144 |
| Lys | Ala | Asn | Gln | Gln | Lys | Gln | Asp | Asp | Gly | Arg | Gly | Leu | Val | Leu | Pro | |
| | | 35 | | | | | 40 | | | | | 45 | | | | |
| ggc | tac | aag | tac | ctc | gga | ccc | ttc | aac | gga | ctc | gac | aag | ggg | gag | ccc | 192 |
| Gly | Tyr | Lys | Tyr | Leu | Gly | Pro | Phe | Asn | Gly | Leu | Asp | Lys | Gly | Glu | Pro | |
| | 50 | | | | | 55 | | | | | 60 | | | | | |
| gtc | aac | gcg | gcg | gac | gca | gcg | gcc | ctc | gag | cac | gac | aag | gcc | tac | gac | 240 |
| Val | Asn | Ala | Ala | Asp | Ala | Ala | Ala | Leu | Glu | His | Asp | Lys | Ala | Tyr | Asp | |
| 65 | | | | | 70 | | | | | 75 | | | | | 80 | |
| cag | cag | ctg | cag | gcg | ggt | gac | aat | ccg | tac | ctg | cgg | tat | aac | cac | gcc | 288 |
| Gln | Gln | Leu | Gln | Ala | Gly | Asp | Asn | Pro | Tyr | Leu | Arg | Tyr | Asn | His | Ala | |
| | | | | 85 | | | | | 90 | | | | | 95 | | |
| gac | gcc | gag | ttt | cag | gag | cgt | ctg | caa | gaa | gat | acg | tct | ttt | ggg | ggc | 336 |
| Asp | Ala | Glu | Phe | Gln | Glu | Arg | Leu | Gln | Glu | Asp | Thr | Ser | Phe | Gly | Gly | |
| | | | | 100 | | | | | 105 | | | | | 110 | | |
| aac | ctc | ggg | cga | gca | gtc | ttc | cag | gcc | aag | aag | cgg | gtt | ctc | gaa | cct | 384 |
| Asn | Leu | Gly | Arg | Ala | Val | Phe | Gln | Ala | Lys | Lys | Arg | Val | Leu | Glu | Pro | |
| | | | 115 | | | | | 120 | | | | | 125 | | | |
| ctc | ggt | ctg | gtt | gag | gaa | ggc | gct | aag | acg | gct | cct | gga | aag | aag | aga | 432 |
| Leu | Gly | Leu | Val | Glu | Glu | Gly | Ala | Lys | Thr | Ala | Pro | Gly | Lys | Lys | Arg | |
| | | 130 | | | | | 135 | | | | | 140 | | | | |
| ccg | gta | gag | cca | tca | ccc | cag | cgt | tct | cca | gac | tcc | tct | acg | ggc | atc | 480 |
| Pro | Val | Glu | Pro | Ser | Pro | Gln | Arg | Ser | Pro | Asp | Ser | Ser | Thr | Gly | Ile | |
| 145 | | | | | 150 | | | | | 155 | | | | | 160 | |
| ggc | aag | aaa | ggc | caa | cag | ccc | gcc | aga | aaa | aga | ctc | aat | ttt | ggt | cag | 528 |
| Gly | Lys | Lys | Gly | Gln | Gln | Pro | Ala | Arg | Lys | Arg | Leu | Asn | Phe | Gly | Gln | |
| | | | | 165 | | | | | 170 | | | | | 175 | | |
| act | ggc | gac | tca | gag | tca | gtt | cca | gac | cct | caa | cct | ctc | gga | gaa | cct | 576 |
| Thr | Gly | Asp | Ser | Glu | Ser | Val | Pro | Asp | Pro | Gln | Pro | Leu | Gly | Glu | Pro | |
| | | | 180 | | | | | 185 | | | | | 190 | | | |
| cca | gca | gcg | ccc | tct | ggt | gtg | gga | cct | aat | aca | atg | gct | gca | ggc | ggt | 624 |
| Pro | Ala | Ala | Pro | Ser | Gly | Val | Gly | Pro | Asn | Thr | Met | Ala | Ala | Gly | Gly | |
| | | 195 | | | | | 200 | | | | | 205 | | | | |
| ggc | gca | cca | atg | gca | gac | aat | aac | gaa | ggc | gcc | gac | gga | gtg | ggt | agt | 672 |
| Gly | Ala | Pro | Met | Ala | Asp | Asn | Asn | Glu | Gly | Ala | Asp | Gly | Val | Gly | Ser | |
| | 210 | | | | | 215 | | | | | 220 | | | | | |
| tcc | tcg | gga | aat | tgg | cat | tgc | gat | tcc | aca | tgg | ctg | ggc | gac | aga | gtc | 720 |
| Ser | Ser | Gly | Asn | Trp | His | Cys | Asp | Ser | Thr | Trp | Leu | Gly | Asp | Arg | Val | |
| 225 | | | | | 230 | | | | | 235 | | | | | 240 | |
| atc | acc | acc | agc | acc | cga | acc | tgg | gcc | ctg | ccc | acc | tac | aac | aac | cac | 768 |
| Ile | Thr | Thr | Ser | Thr | Arg | Thr | Trp | Ala | Leu | Pro | Thr | Tyr | Asn | Asn | His | |
| | | | | 245 | | | | | 250 | | | | | 255 | | |
| ctc | tac | aag | caa | atc | tcc | aac | gcg | aca | tcg | gga | gga | gcc | acc | aac | gac | 816 |
| Leu | Tyr | Lys | Gln | Ile | Ser | Asn | Ala | Thr | Ser | Gly | Gly | Ala | Thr | Asn | Asp | |
| | | | 260 | | | | | 265 | | | | | 270 | | | |
| aac | acc | tac | ttc | ggc | tac | agc | acc | ccc | tgg | ggg | tat | ttt | gac | ttt | aac | 864 |
| Asn | Thr | Tyr | Phe | Gly | Tyr | Ser | Thr | Pro | Trp | Gly | Tyr | Phe | Asp | Phe | Asn | |
| | | 275 | | | | | 280 | | | | | 285 | | | | |
| aga | ttc | cac | tgc | cac | ttt | tca | cca | cgt | gac | tgg | cag | cga | ctc | atc | aac | 912 |
| Arg | Phe | His | Cys | His | Phe | Ser | Pro | Arg | Asp | Trp | Gln | Arg | Leu | Ile | Asn | |
| | 290 | | | | | 295 | | | | | 300 | | | | | |

```
aac aac tgg gga ttc cgg ccc aag aga ctc agc ttc aag ctc ttc aac    960
Asn Asn Trp Gly Phe Arg Pro Lys Arg Leu Ser Phe Lys Leu Phe Asn
305             310                 315                 320 atc cag gtc aag gag gtc acg cag aat gaa ggc acc aag acc atc gcc   1008
Ile Gln Val Lys Glu Val Thr Gln Asn Glu Gly Thr Lys Thr Ile Ala
                325                 330                 335 aat aac ctc acc agc acc atc cag gtg ttt acg gac tcg gag tac cag   1056
Asn Asn Leu Thr Ser Thr Ile Gln Val Phe Thr Asp Ser Glu Tyr Gln
            340                 345                 350 ctg ccg tac gtt ctc ggc tct gcc cac cag ggc tgc ctg cct ccg ttc   1104
Leu Pro Tyr Val Leu Gly Ser Ala His Gln Gly Cys Leu Pro Pro Phe
        355                 360                 365 ccg gcg gac gtg ttc atg att ccc cag tac ggc tac cta aca ctc aac   1152
Pro Ala Asp Val Phe Met Ile Pro Gln Tyr Gly Tyr Leu Thr Leu Asn
370                 375                 380 aac ggt agt cag gcc gtg gga cgc tcc tcc ttc tac tgc ctg gaa tac   1200
Asn Gly Ser Gln Ala Val Gly Arg Ser Ser Phe Tyr Cys Leu Glu Tyr
385                 390                 395                 400 ttt cct tcg cag atg ctg aga acc ggc aac aac ttc cag ttt act tac   1248
Phe Pro Ser Gln Met Leu Arg Thr Gly Asn Asn Phe Gln Phe Thr Tyr
                405                 410                 415 acc ttc gag gac gtg cct ttc cac agc agc tac gcc cac agc cag agc   1296
Thr Phe Glu Asp Val Pro Phe His Ser Ser Tyr Ala His Ser Gln Ser
            420                 425                 430 ttg gac cgg ctg atg aat cct ctg att gac cag tac ctg tac tac ttg   1344
Leu Asp Arg Leu Met Asn Pro Leu Ile Asp Gln Tyr Leu Tyr Tyr Leu
        435                 440                 445 tct cgg act caa aca aca gga ggc acg gca aat acg cag act ctg ggc   1392
Ser Arg Thr Gln Thr Thr Gly Gly Thr Ala Asn Thr Gln Thr Leu Gly
    450                 455                 460 ttc agc caa ggt ggg cct aat aca atg gcc aat cag gca aag aac tgg   1440
Phe Ser Gln Gly Gly Pro Asn Thr Met Ala Asn Gln Ala Lys Asn Trp
465                 470                 475                 480 ctg cca gga ccc tgt tac cgc caa caa cgc gtc tca acg aca acc ggg   1488
Leu Pro Gly Pro Cys Tyr Arg Gln Gln Arg Val Ser Thr Thr Thr Gly
                485                 490                 495 caa aac aac aat agc aac ttt gcc tgg act gct ggg acc aaa tac cat   1536
Gln Asn Asn Asn Ser Asn Phe Ala Trp Thr Ala Gly Thr Lys Tyr His
            500                 505                 510 ctg aat gga aga aat tca ttg gct aat cct ggc atc gct atg gca aca   1584
Leu Asn Gly Arg Asn Ser Leu Ala Asn Pro Gly Ile Ala Met Ala Thr
        515                 520                 525 cac aaa gac gac gag gag cgt ttt ttt ccc agt aac gcg atc ctg att   1632
His Lys Asp Asp Glu Glu Arg Phe Phe Pro Ser Asn Ala Ile Leu Ile
    530                 535                 540 ttt ggc aaa caa aat gct gcc aga gac aat gcg gat tac agc gat gtc   1680
Phe Gly Lys Gln Asn Ala Ala Arg Asp Asn Ala Asp Tyr Ser Asp Val
545                 550                 555                 560 atg ctc acc agc gag gaa gaa atc aaa acc act aac cct gtg gct aca   1728
Met Leu Thr Ser Glu Glu Glu Ile Lys Thr Thr Asn Pro Val Ala Thr
                565                 570                 575 gag gaa tac ggt atc gtg gca gat aac ttg cag cag caa aac acg gct   1776
Glu Glu Tyr Gly Ile Val Ala Asp Asn Leu Gln Gln Gln Asn Thr Ala
            580                 585                 590 cct caa att gga act gtc aac agc cag ggg gcc tta ccc ggt atg gtc   1824
Pro Gln Ile Gly Thr Val Asn Ser Gln Gly Ala Leu Pro Gly Met Val
        595                 600                 605 tgg cag aac cgg gac gtg tac ctg cag ggt ccc atc tgg gcc aag att   1872
Trp Gln Asn Arg Asp Val Tyr Leu Gln Gly Pro Ile Trp Ala Lys Ile
```

```
                 610                 615                 620
cct cac acg gac ggc aac ttc cac ccg tct ccg ctg atg ggc ggc ttt    1920
Pro His Thr Asp Gly Asn Phe His Pro Ser Pro Leu Met Gly Gly Phe
625                 630                 635                 640 ggc ctg aaa cat cct ccg cct cag atc ctg atc aag aac acg cct gta    1968
Gly Leu Lys His Pro Pro Pro Gln Ile Leu Ile Lys Asn Thr Pro Val
                645                 650                 655 cct gcg gat cct ccg acc acc ttc aac cag tca aag ctg aac tct ttc    2016
Pro Ala Asp Pro Pro Thr Thr Phe Asn Gln Ser Lys Leu Asn Ser Phe
            660                 665                 670 atc acg caa tac agc acc gga cag gtc agc gtg gaa att gaa tgg gag    2064
Ile Thr Gln Tyr Ser Thr Gly Gln Val Ser Val Glu Ile Glu Trp Glu
        675                 680                 685 ctg cag aag gaa aac agc aag cgc tgg aac ccc gag atc cag tac acc    2112
Leu Gln Lys Glu Asn Ser Lys Arg Trp Asn Pro Glu Ile Gln Tyr Thr
    690                 695                 700 tcc aac tac tac aaa tct aca agt gtg gac ttt gct gtt aat aca gaa    2160
Ser Asn Tyr Tyr Lys Ser Thr Ser Val Asp Phe Ala Val Asn Thr Glu
705                 710                 715                 720 ggc gtg tac tct gaa ccc cgc ccc att ggc acc cgt tac ctc acc cgt    2208
Gly Val Tyr Ser Glu Pro Arg Pro Ile Gly Thr Arg Tyr Leu Thr Arg
                725                 730                 735 aat ctg                                                             2214
Asn Leu <210> SEQ ID NO 43
<211> LENGTH: 738
<212> TYPE: PRT
<213> ORGANISM: Artificial Sequence
<220> FEATURE:
<223> OTHER INFORMATION: Synthetic Construct

<400> SEQUENCE: 43

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Lys Pro
                20                  25                  30

Lys Ala Asn Gln Gln Lys Gln Asp Asp Gly Arg Gly Leu Val Leu Pro
            35                  40                  45

Gly Tyr Lys Tyr Leu Gly Pro Phe Asn Gly Leu Asp Lys Gly Glu Pro
        50                  55                  60

Val Asn Ala Ala Asp Ala Ala Leu Glu His Asp Lys Ala Tyr Asp
65                  70                  75                  80

Gln Gln Leu Gln Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Arg Lys Arg Leu Asn Phe Gly Gln
                165                 170                 175

Thr Gly Asp Ser Glu Ser Val Pro Asp Pro Gln Pro Leu Gly Glu Pro
            180                 185                 190
```

-continued

```
Pro Ala Ala Pro Ser Gly Val Gly Pro Asn Thr Met Ala Gly Gly
            195                 200                 205
Gly Ala Pro Met Ala Asp Asn Glu Gly Ala Asp Gly Val Gly Ser
    210                 215                 220
Ser Ser Gly Asn Trp His Cys Asp Ser Thr Trp Leu Gly Asp Arg Val
225                 230                 235                 240
Ile Thr Thr Ser Thr Arg Thr Trp Ala Leu Pro Thr Tyr Asn Asn His
                245                 250                 255
Leu Tyr Lys Gln Ile Ser Asn Ala Thr Ser Gly Gly Ala Thr Asn Asp
            260                 265                 270
Asn Thr Tyr Phe Gly Tyr Ser Thr Pro Trp Gly Tyr Phe Asp Phe Asn
        275                 280                 285
Arg Phe His Cys His Phe Ser Pro Arg Asp Trp Gln Arg Leu Ile Asn
    290                 295                 300
Asn Asn Trp Gly Phe Arg Pro Lys Arg Leu Ser Phe Lys Leu Phe Asn
305                 310                 315                 320
Ile Gln Val Lys Glu Val Thr Gln Asn Glu Gly Thr Lys Thr Ile Ala
                325                 330                 335
Asn Asn Leu Thr Ser Thr Ile Gln Val Phe Thr Asp Ser Glu Tyr Gln
            340                 345                 350
Leu Pro Tyr Val Leu Gly Ser Ala His Gln Gly Cys Leu Pro Pro Phe
        355                 360                 365
Pro Ala Asp Val Phe Met Ile Pro Gln Tyr Gly Tyr Leu Thr Leu Asn
    370                 375                 380
Asn Gly Ser Gln Ala Val Gly Arg Ser Ser Phe Tyr Cys Leu Glu Tyr
385                 390                 395                 400
Phe Pro Ser Gln Met Leu Arg Thr Gly Asn Asn Phe Gln Phe Thr Tyr
                405                 410                 415
Thr Phe Glu Asp Val Pro Phe His Ser Ser Tyr Ala His Ser Gln Ser
            420                 425                 430
Leu Asp Arg Leu Met Asn Pro Leu Ile Asp Gln Tyr Leu Tyr Tyr Leu
        435                 440                 445
Ser Arg Thr Gln Thr Thr Gly Gly Thr Ala Asn Thr Gln Thr Leu Gly
    450                 455                 460
Phe Ser Gln Gly Gly Pro Asn Thr Met Ala Asn Gln Ala Lys Asn Trp
465                 470                 475                 480
Leu Pro Gly Pro Cys Tyr Arg Gln Gln Arg Val Ser Thr Thr Thr Gly
                485                 490                 495
Gln Asn Asn Asn Ser Asn Phe Ala Trp Thr Ala Gly Thr Lys Tyr His
            500                 505                 510
Leu Asn Gly Arg Asn Ser Leu Ala Asn Pro Gly Ile Ala Met Ala Thr
        515                 520                 525
His Lys Asp Asp Glu Glu Arg Phe Phe Pro Ser Asn Ala Ile Leu Ile
    530                 535                 540
Phe Gly Lys Gln Asn Ala Ala Arg Asp Asn Ala Asp Tyr Ser Asp Val
545                 550                 555                 560
Met Leu Thr Ser Glu Glu Ile Lys Thr Thr Asn Pro Val Ala Thr
                565                 570                 575
Glu Glu Tyr Gly Ile Val Ala Asp Asn Leu Gln Gln Asn Thr Ala
            580                 585                 590
Pro Gln Ile Gly Thr Val Asn Ser Gln Gly Ala Leu Pro Gly Met Val
        595                 600                 605
Trp Gln Asn Arg Asp Val Tyr Leu Gln Gly Pro Ile Trp Ala Lys Ile
```

```
                    610                  615                  620

Pro His Thr Asp Gly Asn Phe His Pro Ser Pro Leu Met Gly Gly Phe
625                 630                 635                 640

Gly Leu Lys His Pro Pro Gln Ile Leu Ile Lys Asn Thr Pro Val
            645                 650                 655

Pro Ala Asp Pro Pro Thr Thr Phe Asn Gln Ser Lys Leu Asn Ser Phe
            660                 665                 670

Ile Thr Gln Tyr Ser Thr Gly Gln Val Ser Val Glu Ile Glu Trp Glu
                675                 680                 685

Leu Gln Lys Glu Asn Ser Lys Arg Trp Asn Pro Glu Ile Gln Tyr Thr
690                 695                 700

Ser Asn Tyr Tyr Lys Ser Thr Ser Val Asp Phe Ala Val Asn Thr Glu
705                 710                 715                 720

Gly Val Tyr Ser Glu Pro Arg Pro Ile Gly Thr Arg Tyr Leu Thr Arg
                725                 730                 735

Asn Leu

<210> SEQ ID NO 44
<211> LENGTH: 2214
<212> TYPE: DNA
<213> ORGANISM: Artificial Sequence
<220> FEATURE:
<223> OTHER INFORMATION: AVV mutant 8G515AG541A
<220> FEATURE:
<221> NAME/KEY: CDS
<222> LOCATION: (1)..(2214)

<400> SEQUENCE: 44 atg gct gcc gat ggt tat ctt cca gat tgg ctc gag gac aac ctc tct      48
Met Ala Ala Asp Gly Tyr Leu Pro Asp Trp Leu Glu Asp Asn Leu Ser
1               5                   10                  15 gag ggc att cgc gag tgg tgg gcg ctg aaa cct gga gcc ccg aag ccc      96
Glu Gly Ile Arg Glu Trp Trp Ala Leu Lys Pro Gly Ala Pro Lys Pro
            20                  25                  30 aaa gcc aac cag caa aag cag gac gac ggc cgg ggt ctg gtg ctt cct     144
Lys Ala Asn Gln Gln Lys Gln Asp Asp Gly Arg Gly Leu Val Leu Pro
        35                  40                  45 ggc tac aag tac ctc gga ccc ttc aac gga ctc gac aag ggg gag ccc     192
Gly Tyr Lys Tyr Leu Gly Pro Phe Asn Gly Leu Asp Lys Gly Glu Pro
    50                  55                  60 gtc aac gcg gcg gac gca gcg gcc ctc gag cac gac aag gcc tac gac     240
Val Asn Ala Ala Asp Ala Ala Ala Leu Glu His Asp Lys Ala Tyr Asp
65                  70                  75                  80 cag cag ctg cag gcg ggt gac aat ccg tac ctg cgg tat aac cac gcc     288
Gln Gln Leu Gln Ala Gly Asp Asn Pro Tyr Leu Arg Tyr Asn His Ala
                85                  90                  95 gac gcc gag ttt cag gag cgt ctg caa gaa gat acg tct ttt ggg ggc     336
Asp Ala Glu Phe Gln Glu Arg Leu Gln Glu Asp Thr Ser Phe Gly Gly
            100                 105                 110 aac ctc ggg cga gca gtc ttc cag gcc aag aag cgg gtt ctc gaa cct     384
Asn Leu Gly Arg Ala Val Phe Gln Ala Lys Lys Arg Val Leu Glu Pro
        115                 120                 125 ctc ggt ctg gtt gag gaa ggc gct aag acg gct cct gga aag aag aga     432
Leu Gly Leu Val Glu Glu Gly Ala Lys Thr Ala Pro Gly Lys Lys Arg
    130                 135                 140 ccg gta gag cca tca ccc cag cgt tct cca gac tcc tct acg ggc atc     480
Pro Val Glu Pro Ser Pro Gln Arg Ser Pro Asp Ser Ser Thr Gly Ile
145                 150                 155                 160 ggc aag aaa ggc caa cag ccc gcc aga aaa aga ctc aat ttt ggt cag     528
```

```
                Gly Lys Lys Gly Gln Gln Pro Ala Arg Lys Arg Leu Asn Phe Gly Gln
                            165                 170                 175 act ggc gac tca gag tca gtt cca gac cct caa cct ctc gga gaa cct        576
Thr Gly Asp Ser Glu Ser Val Pro Asp Pro Gln Pro Leu Gly Glu Pro
            180                 185                 190 cca gca gcg ccc tct ggt gtg gga cct aat aca atg gct gca ggc ggt        624
Pro Ala Ala Pro Ser Gly Val Gly Pro Asn Thr Met Ala Ala Gly Gly
            195                 200                 205 ggc gca cca atg gca gac aat aac gaa ggc gcc gac gga gtg ggt agt        672
Gly Ala Pro Met Ala Asp Asn Asn Glu Gly Ala Asp Gly Val Gly Ser
    210                 215                 220 tcc tcg gga aat tgg cat tgc gat tcc aca tgg ctg ggc gac aga gtc        720
Ser Ser Gly Asn Trp His Cys Asp Ser Thr Trp Leu Gly Asp Arg Val
225                 230                 235                 240 atc acc acc agc acc cga acc tgg gcc ctg ccc acc tac aac aac cac        768
Ile Thr Thr Ser Thr Arg Thr Trp Ala Leu Pro Thr Tyr Asn Asn His
                245                 250                 255 ctc tac aag caa atc tcc aac ggg aca tcg gga gga gcc acc aac gac        816
Leu Tyr Lys Gln Ile Ser Asn Gly Thr Ser Gly Gly Ala Thr Asn Asp
            260                 265                 270 aac acc tac ttc ggc tac agc acc ccc tgg ggg tat ttt gac ttt aac        864
Asn Thr Tyr Phe Gly Tyr Ser Thr Pro Trp Gly Tyr Phe Asp Phe Asn
            275                 280                 285 aga ttc cac tgc cac ttt tca cca cgt gac tgg cag cga ctc atc aac        912
Arg Phe His Cys His Phe Ser Pro Arg Asp Trp Gln Arg Leu Ile Asn
    290                 295                 300 aac aac tgg gga ttc cgg ccc aag aga ctc agc ttc aag ctc ttc aac        960
Asn Asn Trp Gly Phe Arg Pro Lys Arg Leu Ser Phe Lys Leu Phe Asn
305                 310                 315                 320 atc cag gtc aag gag gtc acg cag aat gaa ggc acc aag acc atc gcc       1008
Ile Gln Val Lys Glu Val Thr Gln Asn Glu Gly Thr Lys Thr Ile Ala
                325                 330                 335 aat aac ctc acc agc acc atc cag gtg ttt acg gac tcg gag tac cag       1056
Asn Asn Leu Thr Ser Thr Ile Gln Val Phe Thr Asp Ser Glu Tyr Gln
            340                 345                 350 ctg ccg tac gtt ctc ggc tct gcc cac cag ggc tgc ctg cct ccg ttc       1104
Leu Pro Tyr Val Leu Gly Ser Ala His Gln Gly Cys Leu Pro Pro Phe
            355                 360                 365 ccg gcg gac gtg ttc atg att ccc cag tac ggc tac cta aca ctc aac       1152
Pro Ala Asp Val Phe Met Ile Pro Gln Tyr Gly Tyr Leu Thr Leu Asn
    370                 375                 380 aac ggt agt cag gcc gtg gga cgc tcc tcc ttc tac tgc ctg gaa tac       1200
Asn Gly Ser Gln Ala Val Gly Arg Ser Ser Phe Tyr Cys Leu Glu Tyr
385                 390                 395                 400 ttt cct tcg cag atg ctg aga acc ggc aac aac ttc cag ttt act tac       1248
Phe Pro Ser Gln Met Leu Arg Thr Gly Asn Asn Phe Gln Phe Thr Tyr
                405                 410                 415 acc ttc gag gac gtg cct ttc cac agc agc tac gcc cac agc cag agc       1296
Thr Phe Glu Asp Val Pro Phe His Ser Ser Tyr Ala His Ser Gln Ser
            420                 425                 430 ttg gac cgg ctg atg aat cct ctg att gac cag tac ctg tac tac ttg       1344
Leu Asp Arg Leu Met Asn Pro Leu Ile Asp Gln Tyr Leu Tyr Tyr Leu
            435                 440                 445 tct cgg act caa aca aca gga ggc acg gca aat acg cag act ctg ggc       1392
Ser Arg Thr Gln Thr Thr Gly Gly Thr Ala Asn Thr Gln Thr Leu Gly
    450                 455                 460 ttc agc caa ggt ggg cct aat aca atg gcc aat cag gca aag aac tgg       1440
Phe Ser Gln Gly Gly Pro Asn Thr Met Ala Asn Gln Ala Lys Asn Trp
465                 470                 475                 480
```

| | | |
|---|---|---|
| ctg cca gga ccc tgt tac cgc caa caa cgc gtc tca acg aca acc ggg<br>Leu Pro Gly Pro Cys Tyr Arg Gln Gln Arg Val Ser Thr Thr Thr Gly<br>485 490 495 | | 1488 |
| caa aac aac aat agc aac ttt gcc tgg act gct ggg acc aaa tac cat<br>Gln Asn Asn Asn Ser Asn Phe Ala Trp Thr Ala Gly Thr Lys Tyr His<br>500 505 510 | | 1536 |
| ctg aat gca aga aat tca ttg gct aat cct ggc atc gct atg gca aca<br>Leu Asn Ala Arg Asn Ser Leu Ala Asn Pro Gly Ile Ala Met Ala Thr<br>515 520 525 | | 1584 |
| cac aaa gac gac gag gag cgt ttt ttt ccc agt aac gcg atc ctg att<br>His Lys Asp Asp Glu Glu Arg Phe Phe Pro Ser Asn Ala Ile Leu Ile<br>530 535 540 | | 1632 |
| ttt ggc aaa caa aat gct gcc aga gac aat gcg gat tac agc gat gtc<br>Phe Gly Lys Gln Asn Ala Ala Arg Asp Asn Ala Asp Tyr Ser Asp Val<br>545 550 555 560 | | 1680 |
| atg ctc acc agc gag gaa gaa atc aaa acc act aac cct gtg gct aca<br>Met Leu Thr Ser Glu Glu Glu Ile Lys Thr Thr Asn Pro Val Ala Thr<br>565 570 575 | | 1728 |
| gag gaa tac ggt atc gtg gca gat aac ttg cag cag caa aac acg gct<br>Glu Glu Tyr Gly Ile Val Ala Asp Asn Leu Gln Gln Gln Asn Thr Ala<br>580 585 590 | | 1776 |
| cct caa att gga act gtc aac agc cag ggg gcc tta ccc ggt atg gtc<br>Pro Gln Ile Gly Thr Val Asn Ser Gln Gly Ala Leu Pro Gly Met Val<br>595 600 605 | | 1824 |
| tgg cag aac cgg gac gtg tac ctg cag ggt ccc atc tgg gcc aag att<br>Trp Gln Asn Arg Asp Val Tyr Leu Gln Gly Pro Ile Trp Ala Lys Ile<br>610 615 620 | | 1872 |
| cct cac acg gac ggc aac ttc cac ccg tct ccg ctg atg ggc ggc ttt<br>Pro His Thr Asp Gly Asn Phe His Pro Ser Pro Leu Met Gly Gly Phe<br>625 630 635 640 | | 1920 |
| ggc ctg aaa cat cct ccg cct cag atc ctg atc aag aac acg cct gta<br>Gly Leu Lys His Pro Pro Pro Gln Ile Leu Ile Lys Asn Thr Pro Val<br>645 650 655 | | 1968 |
| cct gcg gat cct ccg acc acc ttc aac cag tca aag ctg aac tct ttc<br>Pro Ala Asp Pro Pro Thr Thr Phe Asn Gln Ser Lys Leu Asn Ser Phe<br>660 665 670 | | 2016 |
| atc acg caa tac agc acc gga cag gtc agc gtg gaa att gaa tgg gag<br>Ile Thr Gln Tyr Ser Thr Gly Gln Val Ser Val Glu Ile Glu Trp Glu<br>675 680 685 | | 2064 |
| ctg cag aag gaa aac agc aag cgc tgg aac ccc gag atc cag tac acc<br>Leu Gln Lys Glu Asn Ser Lys Arg Trp Asn Pro Glu Ile Gln Tyr Thr<br>690 695 700 | | 2112 |
| tcc aac tac tac aaa tct aca agt gtg gac ttt gct gtt aat aca gaa<br>Ser Asn Tyr Tyr Lys Ser Thr Ser Val Asp Phe Ala Val Asn Thr Glu<br>705 710 715 720 | | 2160 |
| ggc gtg tac tct gaa ccc cgc ccc att ggc acc cgt tac ctc acc cgt<br>Gly Val Tyr Ser Glu Pro Arg Pro Ile Gly Thr Arg Tyr Leu Thr Arg<br>725 730 735 | | 2208 |
| aat ctg<br>Asn Leu | | 2214 |

<210> SEQ ID NO 45
<211> LENGTH: 738
<212> TYPE: PRT
<213> ORGANISM: Artificial Sequence
<220> FEATURE:
<223> OTHER INFORMATION: Synthetic Construct

<400> SEQUENCE: 45

Met Ala Ala Asp Gly Tyr Leu Pro Asp Trp Leu Glu Asp Asn Leu Ser
1               5                   10                  15

-continued

Glu Gly Ile Arg Glu Trp Trp Ala Leu Lys Pro Gly Ala Pro Lys Pro
 20                  25                  30

Lys Ala Asn Gln Gln Lys Gln Asp Asp Gly Arg Gly Leu Val Leu Pro
         35                  40                  45

Gly Tyr Lys Tyr Leu Gly Pro Phe Asn Gly Leu Asp Lys Gly Glu Pro
 50                  55                  60

Val Asn Ala Ala Asp Ala Ala Leu Glu His Asp Lys Ala Tyr Asp
 65                  70                  75                  80

Gln Gln Leu Gln Ala Gly Asp Asn Pro Tyr Leu Arg Tyr Asn His Ala
                 85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
            115                 120                 125

Leu Gly Leu Val Glu Glu Gly Ala Lys Thr Ala Pro Gly Lys Lys Arg
130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Arg Lys Arg Leu Asn Phe Gly Gln
                165                 170                 175

Thr Gly Asp Ser Glu Ser Val Pro Asp Pro Gln Pro Leu Gly Glu Pro
            180                 185                 190

Pro Ala Ala Pro Ser Gly Val Gly Pro Asn Thr Met Ala Ala Gly Gly
            195                 200                 205

Gly Ala Pro Met Ala Asp Asn Asn Glu Gly Ala Asp Gly Val Gly Ser
            210                 215                 220

Ser Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Asn Gly Thr Ser Gly Gly Ala Thr Asn Asp
            260                 265                 270

Asn Thr Tyr Phe Gly Tyr Ser Thr Pro Trp Gly Tyr Phe Asp Phe Asn
            275                 280                 285

Arg Phe His Cys His Phe Ser Pro Arg Asp Trp Gln Arg Leu Ile Asn
            290                 295                 300

Asn Asn Trp Gly Phe Arg Pro Lys Arg Leu Ser Phe Lys Leu Phe Asn
305                 310                 315                 320

Ile Gln Val Lys Glu Val Thr Gln Asn Glu Gly Thr Lys Thr Ile Ala
                325                 330                 335

Asn Asn Leu Thr Ser Thr Ile Gln Val Phe Thr Asp Ser Glu Tyr Gln
            340                 345                 350

Leu Pro Tyr Val Leu Gly Ser Ala His Gln Gly Cys Leu Pro Pro Phe
            355                 360                 365

Pro Ala Asp Val Phe Met Ile Pro Gln Tyr Gly Tyr Leu Thr Leu Asn
            370                 375                 380

Asn Gly Ser Gln Ala Val Gly Arg Ser Ser Phe Tyr Cys Leu Glu Tyr
385                 390                 395                 400

Phe Pro Ser Gln Met Leu Arg Thr Gly Asn Asn Phe Gln Phe Thr Tyr
                405                 410                 415

Thr Phe Glu Asp Val Pro Phe His Ser Ser Tyr Ala His Ser Gln Ser
            420                 425                 430

```
Leu Asp Arg Leu Met Asn Pro Leu Ile Asp Gln Tyr Leu Tyr Tyr Leu
        435                 440                 445

Ser Arg Thr Gln Thr Thr Gly Gly Thr Ala Asn Thr Gln Thr Leu Gly
450                 455                 460

Phe Ser Gln Gly Gly Pro Asn Thr Met Ala Asn Gln Ala Lys Asn Trp
465                 470                 475                 480

Leu Pro Gly Pro Cys Tyr Arg Gln Gln Arg Val Ser Thr Thr Thr Gly
                485                 490                 495

Gln Asn Asn Asn Ser Asn Phe Ala Trp Thr Ala Gly Thr Lys Tyr His
                500                 505                 510

Leu Asn Ala Arg Asn Ser Leu Ala Asn Pro Gly Ile Ala Met Ala Thr
            515                 520                 525

His Lys Asp Asp Glu Glu Arg Phe Phe Pro Ser Asn Ala Ile Leu Ile
        530                 535                 540

Phe Gly Lys Gln Asn Ala Ala Arg Asp Asn Ala Asp Tyr Ser Asp Val
545                 550                 555                 560

Met Leu Thr Ser Glu Glu Ile Lys Thr Thr Asn Pro Val Ala Thr
                565                 570                 575

Glu Glu Tyr Gly Ile Val Ala Asp Asn Leu Gln Gln Gln Asn Thr Ala
                580                 585                 590

Pro Gln Ile Gly Thr Val Asn Ser Gln Gly Ala Leu Pro Gly Met Val
            595                 600                 605

Trp Gln Asn Arg Asp Val Tyr Leu Gln Gly Pro Ile Trp Ala Lys Ile
        610                 615                 620

Pro His Thr Asp Gly Asn Phe His Pro Ser Pro Leu Met Gly Gly Phe
625                 630                 635                 640

Gly Leu Lys His Pro Pro Pro Gln Ile Leu Ile Lys Asn Thr Pro Val
                645                 650                 655

Pro Ala Asp Pro Pro Thr Thr Phe Asn Gln Ser Lys Leu Asn Ser Phe
            660                 665                 670

Ile Thr Gln Tyr Ser Thr Gly Gln Val Ser Val Glu Ile Glu Trp Glu
        675                 680                 685

Leu Gln Lys Glu Asn Ser Lys Arg Trp Asn Pro Glu Ile Gln Tyr Thr
690                 695                 700

Ser Asn Tyr Tyr Lys Ser Thr Ser Val Asp Phe Ala Val Asn Thr Glu
705                 710                 715                 720

Gly Val Tyr Ser Glu Pro Arg Pro Ile Gly Thr Arg Tyr Leu Thr Arg
                725                 730                 735

Asn Leu

<210> SEQ ID NO 46
<211> LENGTH: 2214
<212> TYPE: DNA
<213> ORGANISM: Artificial Sequence
<220> FEATURE:
<223> OTHER INFORMATION: AVV mutant 8G264AG515AG541A
<220> FEATURE:
<221> NAME/KEY: CDS
<222> LOCATION: (1)..(2214)

<400> SEQUENCE: 46 atg gct gcc gat ggt tat ctt cca gat tgg ctc gag gac aac ctc tct    48
Met Ala Ala Asp Gly Tyr Leu Pro Asp Trp Leu Glu Asp Asn Leu Ser
1               5                   10                  15 gag ggc att cgc gag tgg tgg gcg ctg aaa cct gga gcc ccg aag ccc    96
Glu Gly Ile Arg Glu Trp Trp Ala Leu Lys Pro Gly Ala Pro Lys Pro
            20                  25                  30
```

| | | |
|---|---|---|
| aaa gcc aac cag caa aag cag gac gac ggc cgg ggt ctg gtg ctt cct<br>Lys Ala Asn Gln Gln Lys Gln Asp Asp Gly Arg Gly Leu Val Leu Pro<br>　　　　35　　　　　　　　40　　　　　　　　45 | | 144 |
| ggc tac aag tac ctc gga ccc ttc aac gga ctc gac aag ggg gag ccc<br>Gly Tyr Lys Tyr Leu Gly Pro Phe Asn Gly Leu Asp Lys Gly Glu Pro<br>　50　　　　　　　　55　　　　　　　　60 | | 192 |
| gtc aac gcg gcg gac gca gcg gcc ctc gag cac gac aag gcc tac gac<br>Val Asn Ala Ala Asp Ala Ala Ala Leu Glu His Asp Lys Ala Tyr Asp<br>65　　　　　　　　70　　　　　　　　75　　　　　　　　80 | | 240 |
| cag cag ctg cag gcg ggt gac aat ccg tac ctg cgg tat aac cac gcc<br>Gln Gln Leu Gln Ala Gly Asp Asn Pro Tyr Leu Arg Tyr Asn His Ala<br>　　　　　　　　85　　　　　　　　90　　　　　　　　95 | | 288 |
| gac gcc gag ttt cag gag cgt ctg caa gaa gat acg tct ttt ggg ggc<br>Asp Ala Glu Phe Gln Glu Arg Leu Gln Glu Asp Thr Ser Phe Gly Gly<br>　　　　　　　　100　　　　　　　　105　　　　　　　　110 | | 336 |
| aac ctc ggg cga gca gtc ttc cag gcc aag aag cgg gtt ctc gaa cct<br>Asn Leu Gly Arg Ala Val Phe Gln Ala Lys Lys Arg Val Leu Glu Pro<br>　　　　115　　　　　　　　120　　　　　　　　125 | | 384 |
| ctc ggt ctg gtt gag gaa ggc gct aag acg gct cct gga aag aag aga<br>Leu Gly Leu Val Glu Glu Gly Ala Lys Thr Ala Pro Gly Lys Lys Arg<br>　　　　130　　　　　　　　135　　　　　　　　140 | | 432 |
| ccg gta gag cca tca ccc cag cgt tct cca gac tcc tct acg ggc atc<br>Pro Val Glu Pro Ser Pro Gln Arg Ser Pro Asp Ser Ser Thr Gly Ile<br>145　　　　　　　　150　　　　　　　　155　　　　　　　　160 | | 480 |
| ggc aag aaa ggc caa cag ccc gcc aga aaa aga ctc aat ttt ggt cag<br>Gly Lys Lys Gly Gln Gln Pro Ala Arg Lys Arg Leu Asn Phe Gly Gln<br>　　　　　　　　165　　　　　　　　170　　　　　　　　175 | | 528 |
| act ggc gac tca gag tca gtt cca gac cct caa cct ctc gga gaa cct<br>Thr Gly Asp Ser Glu Ser Val Pro Asp Pro Gln Pro Leu Gly Glu Pro<br>　　　　　　　　180　　　　　　　　185　　　　　　　　190 | | 576 |
| cca gca gcg ccc tct ggt gtg gga cct aat aca atg gct gca ggc ggt<br>Pro Ala Ala Pro Ser Gly Val Gly Pro Asn Thr Met Ala Ala Gly Gly<br>　　　　195　　　　　　　　200　　　　　　　　205 | | 624 |
| ggc gca cca atg gca gac aat aac gaa ggc gcc gac gga gtg ggt agt<br>Gly Ala Pro Met Ala Asp Asn Asn Glu Gly Ala Asp Gly Val Gly Ser<br>　　　　210　　　　　　　　215　　　　　　　　220 | | 672 |
| tcc tcg gga aat tgg cat tgc gat tcc aca tgg ctg ggc gac aga gtc<br>Ser Ser Gly Asn Trp His Cys Asp Ser Thr Trp Leu Gly Asp Arg Val<br>225　　　　　　　　230　　　　　　　　235　　　　　　　　240 | | 720 |
| atc acc acc agc acc cga acc tgg gcc ctg ccc acc tac aac aac cac<br>Ile Thr Thr Ser Thr Arg Thr Trp Ala Leu Pro Thr Tyr Asn Asn His<br>　　　　　　　　245　　　　　　　　250　　　　　　　　255 | | 768 |
| ctc tac aag caa atc tcc aac gcg aca tcg gga gga gcc acc aac gac<br>Leu Tyr Lys Gln Ile Ser Asn Ala Thr Ser Gly Gly Ala Thr Asn Asp<br>　　　　260　　　　　　　　265　　　　　　　　270 | | 816 |
| aac acc tac ttc ggc tac agc acc ccc tgg ggg tat ttt gac ttt aac<br>Asn Thr Tyr Phe Gly Tyr Ser Thr Pro Trp Gly Tyr Phe Asp Phe Asn<br>　　　　　　　　275　　　　　　　　280　　　　　　　　285 | | 864 |
| aga ttc cac tgc cac ttt tca cca cgt gac tgg cag cga ctc atc aac<br>Arg Phe His Cys His Phe Ser Pro Arg Asp Trp Gln Arg Leu Ile Asn<br>　　　　290　　　　　　　　295　　　　　　　　300 | | 912 |
| aac aac tgg gga ttc cgg ccc aag aga ctc agc ttc aag ctc ttc aac<br>Asn Asn Trp Gly Phe Arg Pro Lys Arg Leu Ser Phe Lys Leu Phe Asn<br>305　　　　　　　　310　　　　　　　　315　　　　　　　　320 | | 960 |
| atc cag gtc aag gag gtc acg cag aat gaa ggc acc aag acc atc gcc<br>Ile Gln Val Lys Glu Val Thr Gln Asn Glu Gly Thr Lys Thr Ile Ala<br>　　　　　　　　325　　　　　　　　330　　　　　　　　335 | | 1008 |
| aat aac ctc acc agc acc atc cag gtg ttt acg gac tcg gag tac cag<br>Asn Asn Leu Thr Ser Thr Ile Gln Val Phe Thr Asp Ser Glu Tyr Gln | | 1056 |

```
                340               345               350
ctg ccg tac gtt ctc ggc tct gcc cac cag ggc tgc ctg cct ccg ttc    1104
Leu Pro Tyr Val Leu Gly Ser Ala His Gln Gly Cys Leu Pro Pro Phe
        355               360               365 ccg gcg gac gtg ttc atg att ccc cag tac ggc tac cta aca ctc aac    1152
Pro Ala Asp Val Phe Met Ile Pro Gln Tyr Gly Tyr Leu Thr Leu Asn
370               375               380 aac ggt agt cag gcc gtg gga cgc tcc tcc ttc tac tgc ctg gaa tac    1200
Asn Gly Ser Gln Ala Val Gly Arg Ser Ser Phe Tyr Cys Leu Glu Tyr
385               390               395               400 ttt cct tcg cag atg ctg aga acc ggc aac aac ttc cag ttt act tac    1248
Phe Pro Ser Gln Met Leu Arg Thr Gly Asn Asn Phe Gln Phe Thr Tyr
            405               410               415 acc ttc gag gac gtg cct ttc cac agc agc tac gcc cac agc cag agc    1296
Thr Phe Glu Asp Val Pro Phe His Ser Ser Tyr Ala His Ser Gln Ser
        420               425               430 ttg gac cgg ctg atg aat cct ctg att gac cag tac ctg tac tac ttg    1344
Leu Asp Arg Leu Met Asn Pro Leu Ile Asp Gln Tyr Leu Tyr Tyr Leu
    435               440               445 tct cgg act caa aca aca gga ggc acg gca aat acg cag act ctg ggc    1392
Ser Arg Thr Gln Thr Thr Gly Gly Thr Ala Asn Thr Gln Thr Leu Gly
450               455               460 ttc agc caa ggt ggg cct aat aca atg gcc aat cag gca aag aac tgg    1440
Phe Ser Gln Gly Gly Pro Asn Thr Met Ala Asn Gln Ala Lys Asn Trp
465               470               475               480 ctg cca gga ccc tgt tac cgc caa caa cgc gtc tca acg aca acc ggg    1488
Leu Pro Gly Pro Cys Tyr Arg Gln Gln Arg Val Ser Thr Thr Thr Gly
            485               490               495 caa aac aac aat agc aac ttt gcc tgg act gct ggg acc aaa tac cat    1536
Gln Asn Asn Asn Ser Asn Phe Ala Trp Thr Ala Gly Thr Lys Tyr His
        500               505               510 ctg aat gca aga aat tca ttg gct aat cct ggc atc gct atg gca aca    1584
Leu Asn Ala Arg Asn Ser Leu Ala Asn Pro Gly Ile Ala Met Ala Thr
    515               520               525 cac aaa gac gac gag gag cgt ttt ttt ccc agt aac gcg atc ctg att    1632
His Lys Asp Asp Glu Glu Arg Phe Phe Pro Ser Asn Ala Ile Leu Ile
530               535               540 ttt ggc aaa caa aat gct gcc aga gac aat gcg gat tac agc gat gtc    1680
Phe Gly Lys Gln Asn Ala Ala Arg Asp Asn Ala Asp Tyr Ser Asp Val
545               550               555               560 atg ctc acc agc gag gaa gaa atc aaa acc act aac cct gtg gct aca    1728
Met Leu Thr Ser Glu Glu Glu Ile Lys Thr Thr Asn Pro Val Ala Thr
            565               570               575 gag gaa tac ggt atc gtg gca gat aac ttg cag cag caa aac acg gct    1776
Glu Glu Tyr Gly Ile Val Ala Asp Asn Leu Gln Gln Gln Asn Thr Ala
        580               585               590 cct caa att gga act gtc aac agc cag ggg gcc tta ccc ggt atg gtc    1824
Pro Gln Ile Gly Thr Val Asn Ser Gln Gly Ala Leu Pro Gly Met Val
    595               600               605 tgg cag aac cgg gac gtg tac ctg cag ggt ccc atc tgg gcc aag att    1872
Trp Gln Asn Arg Asp Val Tyr Leu Gln Gly Pro Ile Trp Ala Lys Ile
610               615               620 cct cac acg gac ggc aac ttc cac ccg tct ccg ctg atg ggc ggc ttt    1920
Pro His Thr Asp Gly Asn Phe His Pro Ser Pro Leu Met Gly Gly Phe
625               630               635               640 ggc ctg aaa cat cct ccg cct cag atc ctg atc aag aac acg cct gta    1968
Gly Leu Lys His Pro Pro Pro Gln Ile Leu Ile Lys Asn Thr Pro Val
            645               650               655 cct gcg gat cct ccg acc acc ttc aac cag tca aag ctg aac tct ttc    2016
```

```
Pro Ala Asp Pro Pro Thr Thr Phe Asn Gln Ser Lys Leu Asn Ser Phe
                660                 665                 670 atc acg caa tac agc acc gga cag gtc agc gtg gaa att gaa tgg gag      2064
Ile Thr Gln Tyr Ser Thr Gly Gln Val Ser Val Glu Ile Glu Trp Glu
        675                 680                 685 ctg cag aag gaa aac agc aag cgc tgg aac ccc gag atc cag tac acc      2112
Leu Gln Lys Glu Asn Ser Lys Arg Trp Asn Pro Glu Ile Gln Tyr Thr
    690                 695                 700 tcc aac tac tac aaa tct aca agt gtg gac ttt gct gtt aat aca gaa      2160
Ser Asn Tyr Tyr Lys Ser Thr Ser Val Asp Phe Ala Val Asn Thr Glu
705                 710                 715                 720 ggc gtg tac tct gaa ccc cgc ccc att ggc acc cgt tac ctc acc cgt      2208
Gly Val Tyr Ser Glu Pro Arg Pro Ile Gly Thr Arg Tyr Leu Thr Arg
                725                 730                 735 aat ctg                                                              2214
Asn Leu
```

<210> SEQ ID NO 47
<211> LENGTH: 738
<212> TYPE: PRT
<213> ORGANISM: Artificial Sequence
<220> FEATURE:
<223> OTHER INFORMATION: Synthetic Construct

<400> SEQUENCE: 47

```
Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Lys Pro
                20                  25                  30

Lys Ala Asn Gln Gln Lys Gln Asp Asp Gly Arg Gly Leu Val Leu Pro
            35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Gln Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
    115                 120                 125

Leu Gly Leu Val Glu Glu Gly Ala Lys Thr Ala Pro Gly Lys Lys Arg
130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Arg Lys Arg Leu Asn Phe Gly Gln
                165                 170                 175

Thr Gly Asp Ser Glu Ser Val Pro Asp Pro Gln Pro Leu Gly Glu Pro
            180                 185                 190

Pro Ala Ala Pro Ser Gly Val Gly Pro Asn Thr Met Ala Ala Gly Gly
    195                 200                 205

Gly Ala Pro Met Ala Asp Asn Asn Glu Gly Ala Asp Gly Val Gly Ser
210                 215                 220

Ser Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255
```

-continued

```
Leu Tyr Lys Gln Ile Ser Asn Ala Thr Ser Gly Gly Ala Thr Asn Asp
            260                 265                 270

Asn Thr Tyr Phe Gly Tyr Ser Thr Pro Trp Gly Tyr Phe Asp Phe Asn
            275                 280                 285

Arg Phe His Cys His Phe Ser Pro Arg Asp Trp Gln Arg Leu Ile Asn
            290                 295                 300

Asn Asn Trp Gly Phe Arg Pro Lys Arg Leu Ser Phe Lys Leu Phe Asn
305                 310                 315                 320

Ile Gln Val Lys Glu Val Thr Gln Asn Glu Gly Thr Lys Thr Ile Ala
                325                 330                 335

Asn Asn Leu Thr Ser Thr Ile Gln Val Phe Thr Asp Ser Glu Tyr Gln
            340                 345                 350

Leu Pro Tyr Val Leu Gly Ser Ala His Gln Gly Cys Leu Pro Pro Phe
            355                 360                 365

Pro Ala Asp Val Phe Met Ile Pro Gln Tyr Gly Tyr Leu Thr Leu Asn
            370                 375                 380

Asn Gly Ser Gln Ala Val Gly Arg Ser Ser Phe Tyr Cys Leu Glu Tyr
385                 390                 395                 400

Phe Pro Ser Gln Met Leu Arg Thr Gly Asn Asn Phe Gln Phe Thr Tyr
                405                 410                 415

Thr Phe Glu Asp Val Pro Phe His Ser Ser Tyr Ala His Ser Gln Ser
            420                 425                 430

Leu Asp Arg Leu Met Asn Pro Leu Ile Asp Gln Tyr Leu Tyr Tyr Leu
            435                 440                 445

Ser Arg Thr Gln Thr Thr Gly Gly Thr Ala Asn Thr Gln Thr Leu Gly
            450                 455                 460

Phe Ser Gln Gly Gly Pro Asn Thr Met Ala Asn Gln Ala Lys Asn Trp
465                 470                 475                 480

Leu Pro Gly Pro Cys Tyr Arg Gln Gln Arg Val Ser Thr Thr Thr Gly
                485                 490                 495

Gln Asn Asn Asn Ser Asn Phe Ala Trp Thr Ala Gly Thr Lys Tyr His
            500                 505                 510

Leu Asn Ala Arg Asn Ser Leu Ala Asn Pro Gly Ile Ala Met Ala Thr
            515                 520                 525

His Lys Asp Asp Glu Glu Arg Phe Phe Pro Ser Asn Ala Ile Leu Ile
            530                 535                 540

Phe Gly Lys Gln Asn Ala Ala Arg Asp Asn Ala Asp Tyr Ser Asp Val
545                 550                 555                 560

Met Leu Thr Ser Glu Glu Ile Lys Thr Thr Asn Pro Val Ala Thr
                565                 570                 575

Glu Glu Tyr Gly Ile Val Ala Asp Asn Leu Gln Gln Asn Thr Ala
            580                 585                 590

Pro Gln Ile Gly Thr Val Asn Ser Gln Gly Ala Leu Pro Gly Met Val
            595                 600                 605

Trp Gln Asn Arg Asp Val Tyr Leu Gln Gly Pro Ile Trp Ala Lys Ile
            610                 615                 620

Pro His Thr Asp Gly Asn Phe His Pro Ser Pro Leu Met Gly Gly Phe
625                 630                 635                 640

Gly Leu Lys His Pro Pro Pro Gln Ile Leu Ile Lys Asn Thr Pro Val
                645                 650                 655

Pro Ala Asp Pro Pro Thr Thr Phe Asn Gln Ser Lys Leu Asn Ser Phe
            660                 665                 670
```

-continued

```
Ile Thr Gln Tyr Ser Thr Gly Gln Val Ser Val Glu Ile Glu Trp Glu
                675                 680                 685

Leu Gln Lys Glu Asn Ser Lys Arg Trp Asn Pro Glu Ile Gln Tyr Thr
    690                 695                 700

Ser Asn Tyr Tyr Lys Ser Thr Ser Val Asp Phe Ala Val Asn Thr Glu
705                 710                 715                 720

Gly Val Tyr Ser Glu Pro Arg Pro Ile Gly Thr Arg Tyr Leu Thr Arg
                725                 730                 735

Asn Leu

<210> SEQ ID NO 48
<211> LENGTH: 2211
<212> TYPE: DNA
<213> ORGANISM: Artificial Sequence
<220> FEATURE:
<223> OTHER INFORMATION: AVV mutant 9G330AG453A
<220> FEATURE:
<221> NAME/KEY: CDS
<222> LOCATION: (1)..(2211)

<400> SEQUENCE: 48
```

| | | | | | | | | | | | | | | | | |
|---|---|---|---|---|---|---|---|---|---|---|---|---|---|---|---|---|
| atg | gct | gcc | gat | ggt | tat | ctt | cca | gat | tgg | ctc | gag | gac | aac | ctt | agt | 48 |
| Met | Ala | Ala | Asp | Gly | Tyr | Leu | Pro | Asp | Trp | Leu | Glu | Asp | Asn | Leu | Ser | |
| 1 | | | | 5 | | | | | 10 | | | | | 15 | | |
| gaa | gga | att | cgc | gag | tgg | tgg | gct | ttg | aaa | cct | gga | gcc | cct | caa | ccc | 96 |
| Glu | Gly | Ile | Arg | Glu | Trp | Trp | Ala | Leu | Lys | Pro | Gly | Ala | Pro | Gln | Pro | |
| | | | 20 | | | | | 25 | | | | | 30 | | | |
| aag | gca | aat | caa | caa | cat | caa | gac | aac | gct | cga | ggt | ctt | gtg | ctt | ccg | 144 |
| Lys | Ala | Asn | Gln | Gln | His | Gln | Asp | Asn | Ala | Arg | Gly | Leu | Val | Leu | Pro | |
| | | 35 | | | | | 40 | | | | | 45 | | | | |
| ggt | tac | aaa | tac | ctt | gga | ccc | ggc | aac | gga | ctc | gac | aag | ggg | gag | ccg | 192 |
| Gly | Tyr | Lys | Tyr | Leu | Gly | Pro | Gly | Asn | Gly | Leu | Asp | Lys | Gly | Glu | Pro | |
| | 50 | | | | | 55 | | | | | 60 | | | | | |
| gtc | aac | gca | gca | gac | gcg | gcg | gcc | ctc | gag | cac | gac | aag | gcc | tac | gac | 240 |
| Val | Asn | Ala | Ala | Asp | Ala | Ala | Ala | Leu | Glu | His | Asp | Lys | Ala | Tyr | Asp | |
| 65 | | | | | 70 | | | | | 75 | | | | | 80 | |
| cag | cag | ctc | aag | gcc | gga | gac | aac | ccg | tac | ctc | aag | tac | aac | cac | gcc | 288 |
| Gln | Gln | Leu | Lys | Ala | Gly | Asp | Asn | Pro | Tyr | Leu | Lys | Tyr | Asn | His | Ala | |
| | | | | 85 | | | | | 90 | | | | | 95 | | |
| gac | gcc | gag | ttc | cag | gag | cgg | ctc | aaa | gaa | gat | acg | tct | ttt | ggg | ggc | 336 |
| Asp | Ala | Glu | Phe | Gln | Glu | Arg | Leu | Lys | Glu | Asp | Thr | Ser | Phe | Gly | Gly | |
| | | | 100 | | | | | 105 | | | | | 110 | | | |
| aac | ctc | ggg | cga | gca | gtc | ttc | cag | gcc | aaa | aag | agg | ctt | ctt | gaa | cct | 384 |
| Asn | Leu | Gly | Arg | Ala | Val | Phe | Gln | Ala | Lys | Lys | Arg | Leu | Leu | Glu | Pro | |
| | | 115 | | | | | 120 | | | | | 125 | | | | |
| ctt | ggt | ctg | gtt | gag | gaa | gcg | gct | aag | acg | gct | cct | gga | aag | aag | agg | 432 |
| Leu | Gly | Leu | Val | Glu | Glu | Ala | Ala | Lys | Thr | Ala | Pro | Gly | Lys | Lys | Arg | |
| | 130 | | | | | 135 | | | | | 140 | | | | | |
| cct | gta | gag | cag | tct | cct | cag | gaa | ccg | gac | tcc | tcc | gcg | ggt | att | ggc | 480 |
| Pro | Val | Glu | Gln | Ser | Pro | Gln | Glu | Pro | Asp | Ser | Ser | Ala | Gly | Ile | Gly | |
| 145 | | | | | 150 | | | | | 155 | | | | | 160 | |
| aaa | tcg | ggt | gca | cag | ccc | gct | aaa | aag | aga | ctc | aat | ttc | ggt | cag | act | 528 |
| Lys | Ser | Gly | Ala | Gln | Pro | Ala | Lys | Lys | Arg | Leu | Asn | Phe | Gly | Gln | Thr | |
| | | | | 165 | | | | | 170 | | | | | 175 | | |
| ggc | gac | aca | gag | tca | gtc | cca | gac | cct | caa | cca | atc | gga | gaa | cct | ccc | 576 |
| Gly | Asp | Thr | Glu | Ser | Val | Pro | Asp | Pro | Gln | Pro | Ile | Gly | Glu | Pro | Pro | |
| | | | 180 | | | | | 185 | | | | | 190 | | | |
| gca | gcc | ccc | tca | ggt | gtg | gga | tct | ctt | aca | atg | gct | tca | ggt | ggt | ggc | 624 |
| Ala | Ala | Pro | Ser | Gly | Val | Gly | Ser | Leu | Thr | Met | Ala | Ser | Gly | Gly | Gly | |
| | | 195 | | | | | 200 | | | | | 205 | | | | |

```
gca cca gtg gca gac aat aac gaa ggt gcc gat gga gtg ggt agt tcc    672
Ala Pro Val Ala Asp Asn Asn Glu Gly Ala Asp Gly Val Gly Ser Ser
210             215                 220 tcg gga aat tgg cat tgc gat tcc caa tgg ctg ggg gac aga gtc atc    720
Ser Gly Asn Trp His Cys Asp Ser Gln Trp Leu Gly Asp Arg Val Ile
225             230                 235                 240 acc acc agc acc cga acc tgg gcc ctg ccc acc tac aac aat cac ctc    768
Thr Thr Ser Thr Arg Thr Trp Ala Leu Pro Thr Tyr Asn Asn His Leu
                245                 250                 255 tac aag caa atc tcc aac agc aca tct gga gga tct tca aat gac aac    816
Tyr Lys Gln Ile Ser Asn Ser Thr Ser Gly Gly Ser Ser Asn Asp Asn
            260                 265                 270 gcc tac ttc ggc tac agc acc ccc tgg ggg tat ttt gac ttc aac aga    864
Ala Tyr Phe Gly Tyr Ser Thr Pro Trp Gly Tyr Phe Asp Phe Asn Arg
        275                 280                 285 ttc cac tgc cac ttc tca cca cgt gac tgg cag cga ctc atc aac aac    912
Phe His Cys His Phe Ser Pro Arg Asp Trp Gln Arg Leu Ile Asn Asn
    290                 295                 300 aac tgg gga ttc cgg cct aag cga ctc aac ttc aag ctc ttc aac att    960
Asn Trp Gly Phe Arg Pro Lys Arg Leu Asn Phe Lys Leu Phe Asn Ile
305                 310                 315                 320 cag gtc aaa gag gtt acg gac aac aat gca gtc aag acc atc gcc aat   1008
Gln Val Lys Glu Val Thr Asp Asn Asn Ala Val Lys Thr Ile Ala Asn
                325                 330                 335 aac ctt acc agc acg gtc cag gtc ttc acg gac tca gac tat cag ctc   1056
Asn Leu Thr Ser Thr Val Gln Val Phe Thr Asp Ser Asp Tyr Gln Leu
            340                 345                 350 ccg tac gtg ctc ggg tcg gct cac gag ggc tgc ctc ccg ccg ttc cca   1104
Pro Tyr Val Leu Gly Ser Ala His Glu Gly Cys Leu Pro Pro Phe Pro
        355                 360                 365 gcg gac gtt ttc atg att cct cag tac ggg tat ctg acg ctt aat gat   1152
Ala Asp Val Phe Met Ile Pro Gln Tyr Gly Tyr Leu Thr Leu Asn Asp
370                 375                 380 gga agc cag gcc gtg ggt cgt tcg tcc ttt tac tgc ctg gaa tat ttc   1200
Gly Ser Gln Ala Val Gly Arg Ser Ser Phe Tyr Cys Leu Glu Tyr Phe
385                 390                 395                 400 ccg tcg caa atg cta aga acg ggt aac aac ttc cag ttc agc tac gag   1248
Pro Ser Gln Met Leu Arg Thr Gly Asn Asn Phe Gln Phe Ser Tyr Glu
                405                 410                 415 ttt gag aac gta cct ttc cat agc agc tac gct cac agc caa agc ctg   1296
Phe Glu Asn Val Pro Phe His Ser Ser Tyr Ala His Ser Gln Ser Leu
            420                 425                 430 gac cga cta atg aat cca ctc atc gac caa tac ttg tac tat ctc tca   1344
Asp Arg Leu Met Asn Pro Leu Ile Asp Gln Tyr Leu Tyr Tyr Leu Ser
        435                 440                 445 aag act att aac gct tct gga cag aat caa caa acg cta aaa ttc agt   1392
Lys Thr Ile Asn Ala Ser Gly Gln Asn Gln Gln Thr Leu Lys Phe Ser
450                 455                 460 gtg gcc gga ccc agc aac atg gct gtc cag gga aga aac tac ata cct   1440
Val Ala Gly Pro Ser Asn Met Ala Val Gln Gly Arg Asn Tyr Ile Pro
465                 470                 475                 480 gga ccc agc tac cga caa caa cgt gtc tca acc act gtg act caa aac   1488
Gly Pro Ser Tyr Arg Gln Gln Arg Val Ser Thr Thr Val Thr Gln Asn
                485                 490                 495 aac aac agc gaa ttt gct tgg cct gga gct tct tct tgg gct ctc aat   1536
Asn Asn Ser Glu Phe Ala Trp Pro Gly Ala Ser Ser Trp Ala Leu Asn
            500                 505                 510 gga cgt aat agc ttg atg aat cct gga cct gct atg gcc agc cac aaa   1584
Gly Arg Asn Ser Leu Met Asn Pro Gly Pro Ala Met Ala Ser His Lys
        515                 520                 525
```

```
gaa gga gag gac cgt ttc ttt cct ttg tct gga tct tta att ttt ggc    1632
Glu Gly Glu Asp Arg Phe Phe Pro Leu Ser Gly Ser Leu Ile Phe Gly
530                 535                 540 aaa caa gga act gga aga gac aac gtg gat gcg gac aaa gtc atg ata    1680
Lys Gln Gly Thr Gly Arg Asp Asn Val Asp Ala Asp Lys Val Met Ile
545                 550                 555                 560 acc aac gaa gaa gaa att aaa act act aac ccg gta gca acg gag tcc    1728
Thr Asn Glu Glu Glu Ile Lys Thr Thr Asn Pro Val Ala Thr Glu Ser
                565                 570                 575 tat gga caa gtg gcc aca aac cac cag agt gcc caa gca cag gcg cag    1776
Tyr Gly Gln Val Ala Thr Asn His Gln Ser Ala Gln Ala Gln Ala Gln
            580                 585                 590 acc ggc tgg gtt caa aac caa gga ata ctt ccg ggt atg gtt tgg cag    1824
Thr Gly Trp Val Gln Asn Gln Gly Ile Leu Pro Gly Met Val Trp Gln
        595                 600                 605 gac aga gat gtg tac ctg caa gga ccc att tgg gcc aaa att cct cac    1872
Asp Arg Asp Val Tyr Leu Gln Gly Pro Ile Trp Ala Lys Ile Pro His
610                 615                 620 acg gac ggc aac ttt cac cct tct ccg ctg atg gga ggg ttt gga atg    1920
Thr Asp Gly Asn Phe His Pro Ser Pro Leu Met Gly Gly Phe Gly Met
625                 630                 635                 640 aag cac ccg cct cct cag atc ctc atc aaa aac aca cct gta cct gcg    1968
Lys His Pro Pro Pro Gln Ile Leu Ile Lys Asn Thr Pro Val Pro Ala
                645                 650                 655 gat cct cca acg gcc ttc aac aag gac aag ctg aac tct ttc atc acc    2016
Asp Pro Pro Thr Ala Phe Asn Lys Asp Lys Leu Asn Ser Phe Ile Thr
            660                 665                 670 cag tat tct act ggc caa gtc agc gtg gag atc gag tgg gag ctg cag    2064
Gln Tyr Ser Thr Gly Gln Val Ser Val Glu Ile Glu Trp Glu Leu Gln
        675                 680                 685 aag gaa aac agc aag cgc tgg aac ccg gag atc cag tac act tcc aac    2112
Lys Glu Asn Ser Lys Arg Trp Asn Pro Glu Ile Gln Tyr Thr Ser Asn
690                 695                 700 tat tac aag tct aat aat gtt gaa ttt gct gtt aat act gaa ggt gta    2160
Tyr Tyr Lys Ser Asn Asn Val Glu Phe Ala Val Asn Thr Glu Gly Val
705                 710                 715                 720 tat agt gaa ccc cgc ccc att ggc acc aga tac ctg act cgt aat ctg    2208
Tyr Ser Glu Pro Arg Pro Ile Gly Thr Arg Tyr Leu Thr Arg Asn Leu
                725                 730                 735 taa                                                                2211
```

<210> SEQ ID NO 49
<211> LENGTH: 736
<212> TYPE: PRT
<213> ORGANISM: Artificial Sequence
<220> FEATURE:
<223> OTHER INFORMATION: Synthetic Construct

<400> SEQUENCE: 49

```
Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80
```

-continued

```
Gln Gln Leu Lys Ala Gly Asp Asn Pro Tyr Leu Lys Tyr Asn His Ala
            85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
            115                 120                 125

Leu Gly Leu Val Glu Glu Ala Ala Lys Thr Ala Pro Gly Lys Lys Arg
130                 135                 140

Pro Val Glu Gln Ser Pro Gln Glu Pro Asp Ser Ser Ala Gly Ile Gly
145                 150                 155                 160

Lys Ser Gly Ala Gln Pro Ala Lys Lys Arg Leu Asn Phe Gly Gln Thr
            165                 170                 175

Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Gly Gly Gly
            195                 200                 205

Ala Pro Val Ala Asp Asn Asn Glu Gly Ala Asp Gly Val Gly Ser Ser
210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
            245                 250                 255

Tyr Lys Gln Ile Ser Asn Ser Thr Ser Gly Gly Ser Ser Asn Asp Asn
            260                 265                 270

Ala Tyr Phe Gly Tyr Ser Thr Pro Trp Gly Tyr Phe Asp Phe Asn Arg
            275                 280                 285

Phe His Cys His Phe Ser Pro Arg Asp Trp Gln Arg Leu Ile Asn Asn
            290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Ala Val Lys Thr Ile Ala Asn
            325                 330                 335

Asn Leu Thr Ser Thr Val Gln Val Phe Thr Asp Ser Asp Tyr Gln Leu
            340                 345                 350

Pro Tyr Val Leu Gly Ser Ala His Glu Gly Cys Leu Pro Pro Phe Pro
            355                 360                 365

Ala Asp Val Phe Met Ile Pro Gln Tyr Gly Tyr Leu Thr Leu Asn Asp
            370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
            405                 410                 415

Phe Glu Asn Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Ser
            435                 440                 445

Lys Thr Ile Asn Ala Ser Gly Gln Asn Gln Gln Thr Leu Lys Phe Ser
450                 455                 460

Val Ala Gly Pro Ser Asn Met Ala Val Gln Gly Arg Asn Tyr Ile Pro
465                 470                 475                 480

Gly Pro Ser Tyr Arg Gln Gln Arg Val Ser Thr Thr Val Thr Gln Asn
            485                 490                 495
```

```
Asn Asn Ser Glu Phe Ala Trp Pro Gly Ala Ser Ser Trp Ala Leu Asn
            500                 505                 510

Gly Arg Asn Ser Leu Met Asn Pro Gly Pro Ala Met Ala Ser His Lys
        515                 520                 525

Glu Gly Glu Asp Arg Phe Phe Pro Leu Ser Gly Ser Leu Ile Phe Gly
    530                 535                 540

Lys Gln Gly Thr Gly Arg Asp Asn Val Asp Ala Asp Lys Val Met Ile
545                 550                 555                 560

Thr Asn Glu Glu Glu Ile Lys Thr Thr Asn Pro Val Ala Thr Glu Ser
                565                 570                 575

Tyr Gly Gln Val Ala Thr Asn His Gln Ser Ala Gln Ala Gln Ala Gln
            580                 585                 590

Thr Gly Trp Val Gln Asn Gln Gly Ile Leu Pro Gly Met Val Trp Gln
        595                 600                 605

Asp Arg Asp Val Tyr Leu Gln Gly Pro Ile Trp Ala Lys Ile Pro His
    610                 615                 620

Thr Asp Gly Asn Phe His Pro Ser Pro Leu Met Gly Gly Phe Gly Met
625                 630                 635                 640

Lys His Pro Pro Gln Ile Leu Ile Lys Asn Thr Pro Val Pro Ala
                645                 650                 655

Asp Pro Pro Thr Ala Phe Asn Lys Asp Lys Leu Asn Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Ile Gln Tyr Thr Ser Asn
    690                 695                 700

Tyr Tyr Lys Ser Asn Asn Val Glu Phe Ala Val Asn Thr Glu Gly Val
705                 710                 715                 720

Tyr Ser Glu Pro Arg Pro Ile Gly Thr Arg Tyr Leu Thr Arg Asn Leu
                725                 730                 735
```

<210> SEQ ID NO 50
<211> LENGTH: 2211
<212> TYPE: DNA
<213> ORGANISM: Artificial Sequence
<220> FEATURE:
<223> OTHER INFORMATION: AVV mutant 9G330AG513A
<220> FEATURE:
<221> NAME/KEY: CDS
<222> LOCATION: (1)..(2211)

<400> SEQUENCE: 50

```
atg gct gcc gat ggt tat ctt cca gat tgg ctc gag gac aac ctt agt      48
Met Ala Ala Asp Gly Tyr Leu Pro Asp Trp Leu Glu Asp Asn Leu Ser
1               5                   10                  15 gaa gga att cgc gag tgg tgg gct ttg aaa cct gga gcc cct caa ccc      96
Glu Gly Ile Arg Glu Trp Trp Ala Leu Lys Pro Gly Ala Pro Gln Pro
            20                  25                  30 aag gca aat caa caa cat caa gac aac gct cga ggt ctt gtg ctt ccg     144
Lys Ala Asn Gln Gln His Gln Asp Asn Ala Arg Gly Leu Val Leu Pro
        35                  40                  45 ggt tac aaa tac ctt gga ccc ggc aac gga ctc gac aag ggg gag ccg     192
Gly Tyr Lys Tyr Leu Gly Pro Gly Asn Gly Leu Asp Lys Gly Glu Pro
    50                  55                  60 gtc aac gca gca gac gcg gcg gcc ctc gag cac gac aag gcc tac gac     240
Val Asn Ala Ala Asp Ala Ala Ala Leu Glu His Asp Lys Ala Tyr Asp
65                  70                  75                  80 cag cag ctc aag gcc gga gac aac ccg tac ctc aag tac aac cac gcc     288
```

```
                Gln Gln Leu Lys Ala Gly Asp Asn Pro Tyr Leu Lys Tyr Asn His Ala
                                85              90              95 gac gcc gag ttc cag gag cgg ctc aaa gaa gat acg tct ttt ggg ggc         336
Asp Ala Glu Phe Gln Glu Arg Leu Lys Glu Asp Thr Ser Phe Gly Gly
        100             105             110 aac ctc ggg cga gca gtc ttc cag gcc aaa aag agg ctt ctt gaa cct         384
Asn Leu Gly Arg Ala Val Phe Gln Ala Lys Lys Arg Leu Leu Glu Pro
            115             120             125 ctt ggt ctg gtt gag gaa gcg gct aag acg gct cct gga aag aag agg         432
Leu Gly Leu Val Glu Glu Ala Ala Lys Thr Ala Pro Gly Lys Lys Arg
        130             135             140 cct gta gag cag tct cct cag gaa ccg gac tcc tcc gcg ggt att ggc         480
Pro Val Glu Gln Ser Pro Gln Glu Pro Asp Ser Ser Ala Gly Ile Gly
145             150             155             160 aaa tcg ggt gca cag ccc gct aaa aag aga ctc aat ttc ggt cag act         528
Lys Ser Gly Ala Gln Pro Ala Lys Lys Arg Leu Asn Phe Gly Gln Thr
            165             170             175 ggc gac aca gag tca gtc cca gac cct caa cca atc gga gaa cct ccc         576
Gly Asp Thr Glu Ser Val Pro Asp Pro Gln Pro Ile Gly Glu Pro Pro
        180             185             190 gca gcc ccc tca ggt gtg gga tct ctt aca atg gct tca ggt ggt ggc         624
Ala Ala Pro Ser Gly Val Gly Ser Leu Thr Met Ala Ser Gly Gly Gly
            195             200             205 gca cca gtg gca gac aat aac gaa ggt gcc gat gga gtg ggt agt tcc         672
Ala Pro Val Ala Asp Asn Asn Glu Gly Ala Asp Gly Val Gly Ser Ser
210             215             220 tcg gga aat tgg cat tgc gat tcc caa tgg ctg ggg gac aga gtc atc         720
Ser Gly Asn Trp His Cys Asp Ser Gln Trp Leu Gly Asp Arg Val Ile
225             230             235             240 acc acc agc acc cga acc tgg gcc ctg ccc acc tac aac aat cac ctc         768
Thr Thr Ser Thr Arg Thr Trp Ala Leu Pro Thr Tyr Asn Asn His Leu
            245             250             255 tac aag caa atc tcc aac agc aca tct gga gga tct tca aat gac aac         816
Tyr Lys Gln Ile Ser Asn Ser Thr Ser Gly Gly Ser Ser Asn Asp Asn
        260             265             270 gcc tac ttc ggc tac agc acc ccc tgg ggg tat ttt gac ttc aac aga         864
Ala Tyr Phe Gly Tyr Ser Thr Pro Trp Gly Tyr Phe Asp Phe Asn Arg
            275             280             285 ttc cac tgc cac ttc tca cca cgt gac tgg cag cga ctc atc aac aac         912
Phe His Cys His Phe Ser Pro Arg Asp Trp Gln Arg Leu Ile Asn Asn
        290             295             300 aac tgg gga ttc cgg cct aag cga ctc aac ttc aag ctc ttc aac att         960
Asn Trp Gly Phe Arg Pro Lys Arg Leu Asn Phe Lys Leu Phe Asn Ile
305             310             315             320 cag gtc aaa gag gtt acg gac aac aat gca gtc aag acc atc gcc aat        1008
Gln Val Lys Glu Val Thr Asp Asn Asn Ala Val Lys Thr Ile Ala Asn
            325             330             335 aac ctt acc agc acg gtc cag gtc ttc acg gac tca gac tat cag ctc        1056
Asn Leu Thr Ser Thr Val Gln Val Phe Thr Asp Ser Asp Tyr Gln Leu
        340             345             350 ccg tac gtg ctc ggg tcg gct cac gag ggc tgc ctc ccg ccg ttc cca        1104
Pro Tyr Val Leu Gly Ser Ala His Glu Gly Cys Leu Pro Pro Phe Pro
            355             360             365 gcg gac gtt ttc atg att cct cag tac ggg tat ctg acg ctt aat gat        1152
Ala Asp Val Phe Met Ile Pro Gln Tyr Gly Tyr Leu Thr Leu Asn Asp
        370             375             380 gga agc cag gcc gtg ggt cgt tcg tcc ttt tac tgc ctg gaa tat ttc        1200
Gly Ser Gln Ala Val Gly Arg Ser Ser Phe Tyr Cys Leu Glu Tyr Phe
385             390             395             400
```

| | | |
|---|---|---|
| ccg tcg caa atg cta aga acg ggt aac aac ttc cag ttc agc tac gag<br>Pro Ser Gln Met Leu Arg Thr Gly Asn Asn Phe Gln Phe Ser Tyr Glu<br>405 410 415 | | 1248 |
| ttt gag aac gta cct ttc cat agc agc tac gct cac agc caa agc ctg<br>Phe Glu Asn Val Pro Phe His Ser Ser Tyr Ala His Ser Gln Ser Leu<br>420 425 430 | | 1296 |
| gac cga cta atg aat cca ctc atc gac caa tac ttg tac tat ctc tca<br>Asp Arg Leu Met Asn Pro Leu Ile Asp Gln Tyr Leu Tyr Tyr Leu Ser<br>435 440 445 | | 1344 |
| aag act att aac ggt tct gga cag aat caa caa acg cta aaa ttc agt<br>Lys Thr Ile Asn Gly Ser Gly Gln Asn Gln Gln Thr Leu Lys Phe Ser<br>450 455 460 | | 1392 |
| gtg gcc gga ccc agc aac atg gct gtc cag gga aga aac tac ata cct<br>Val Ala Gly Pro Ser Asn Met Ala Val Gln Gly Arg Asn Tyr Ile Pro<br>465 470 475 480 | | 1440 |
| gga ccc agc tac cga caa caa cgt gtc tca acc act gtg act caa aac<br>Gly Pro Ser Tyr Arg Gln Gln Arg Val Ser Thr Thr Val Thr Gln Asn<br>485 490 495 | | 1488 |
| aac aac agc gaa ttt gct tgg cct gga gct tct tct tgg gct ctc aat<br>Asn Asn Ser Glu Phe Ala Trp Pro Gly Ala Ser Ser Trp Ala Leu Asn<br>500 505 510 | | 1536 |
| gca cgt aat agc ttg atg aat cct gga cct gct atg gcc agc cac aaa<br>Ala Arg Asn Ser Leu Met Asn Pro Gly Pro Ala Met Ala Ser His Lys<br>515 520 525 | | 1584 |
| gaa gga gag gac cgt ttc ttt cct ttg tct gga tct tta att ttt ggc<br>Glu Gly Glu Asp Arg Phe Phe Pro Leu Ser Gly Ser Leu Ile Phe Gly<br>530 535 540 | | 1632 |
| aaa caa gga act gga aga gac aac gtg gat gcg gac aaa gtc atg ata<br>Lys Gln Gly Thr Gly Arg Asp Asn Val Asp Ala Asp Lys Val Met Ile<br>545 550 555 560 | | 1680 |
| acc aac gaa gaa gaa att aaa act act aac ccg gta gca acg gag tcc<br>Thr Asn Glu Glu Glu Ile Lys Thr Thr Asn Pro Val Ala Thr Glu Ser<br>565 570 575 | | 1728 |
| tat gga caa gtg gcc aca aac cac cag agt gcc caa gca cag gcg cag<br>Tyr Gly Gln Val Ala Thr Asn His Gln Ser Ala Gln Ala Gln Ala Gln<br>580 585 590 | | 1776 |
| acc ggc tgg gtt caa aac caa gga ata ctt ccg ggt atg gtt tgg cag<br>Thr Gly Trp Val Gln Asn Gln Gly Ile Leu Pro Gly Met Val Trp Gln<br>595 600 605 | | 1824 |
| gac aga gat gtg tac ctg caa gga ccc att tgg gcc aaa att cct cac<br>Asp Arg Asp Val Tyr Leu Gln Gly Pro Ile Trp Ala Lys Ile Pro His<br>610 615 620 | | 1872 |
| acg gac ggc aac ttt cac cct tct ccg ctg atg gga ggg ttt gga atg<br>Thr Asp Gly Asn Phe His Pro Ser Pro Leu Met Gly Gly Phe Gly Met<br>625 630 635 640 | | 1920 |
| aag cac ccg cct cct cag atc ctc atc aaa aac aca cct gta cct gcg<br>Lys His Pro Pro Pro Gln Ile Leu Ile Lys Asn Thr Pro Val Pro Ala<br>645 650 655 | | 1968 |
| gat cct cca acg gcc ttc aac aag gac aag ctg aac tct ttc atc acc<br>Asp Pro Pro Thr Ala Phe Asn Lys Asp Lys Leu Asn Ser Phe Ile Thr<br>660 665 670 | | 2016 |
| cag tat tct act ggc caa gtc agc gtg gag atc gag tgg gag ctg cag<br>Gln Tyr Ser Thr Gly Gln Val Ser Val Glu Ile Glu Trp Glu Leu Gln<br>675 680 685 | | 2064 |
| aag gaa aac agc aag cgc tgg aac ccg gag atc cag tac act tcc aac<br>Lys Glu Asn Ser Lys Arg Trp Asn Pro Glu Ile Gln Tyr Thr Ser Asn<br>690 695 700 | | 2112 |
| tat tac aag tct aat aat gtt gaa ttt gct gtt aat act gaa ggt gta<br>Tyr Tyr Lys Ser Asn Asn Val Glu Phe Ala Val Asn Thr Glu Gly Val<br>705 710 715 720 | | 2160 |

```
tat agt gaa ccc cgc ccc att ggc acc aga tac ctg act cgt aat ctg    2208
Tyr Ser Glu Pro Arg Pro Ile Gly Thr Arg Tyr Leu Thr Arg Asn Leu
            725                 730                 735 taa                                                                 2211
```

<210> SEQ ID NO 51
<211> LENGTH: 736
<212> TYPE: PRT
<213> ORGANISM: Artificial Sequence
<220> FEATURE:
<223> OTHER INFORMATION: Synthetic Construct

<400> SEQUENCE: 51

```
Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
        115                 120                 125

Leu Gly Leu Val Glu Glu Ala Ala Lys Thr Ala Pro Gly Lys Lys Arg
    130                 135                 140

Pro Val Glu Gln Ser Pro Gln Glu Pro Asp Ser Ser Ala Gly Ile Gly
145                 150                 155                 160

Lys Ser Gly Ala Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Gly Gly Gly
        195                 200                 205

Ala Pro Val Ala Asp Asn Asn Glu Gly Ala Asp Gly Val Gly Ser Ser
    210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Ser Thr Ser Gly Gly Ser Ser Asn Asp Asn
            260                 265                 270

Ala Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn Asn
    290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Ala Val Lys Thr Ile Ala Asn
                325                 330                 335
```

Asn Leu Thr Ser Thr Val Gln Val Phe Thr Asp Ser Asp Tyr Gln Leu
            340                 345                 350

Pro Tyr Val Leu Gly Ser Ala His Glu Gly Cys Leu Pro Pro Phe Pro
            355                 360                 365

Ala Asp Val Phe Met Ile Pro Gln Tyr Gly Tyr Leu Thr Leu Asn Asp
370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
            405                 410                 415

Phe Glu Asn Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Ser
            435                 440                 445

Lys Thr Ile Asn Gly Ser Gly Gln Asn Gln Gln Thr Leu Lys Phe Ser
450                 455                 460

Val Ala Gly Pro Ser Asn Met Ala Val Gln Gly Arg Asn Tyr Ile Pro
465                 470                 475                 480

Gly Pro Ser Tyr Arg Gln Gln Arg Val Ser Thr Thr Val Thr Gln Asn
            485                 490                 495

Asn Asn Ser Glu Phe Ala Trp Pro Gly Ala Ser Ser Trp Ala Leu Asn
            500                 505                 510

Ala Arg Asn Ser Leu Met Asn Pro Gly Pro Ala Met Ala Ser His Lys
            515                 520                 525

Glu Gly Glu Asp Arg Phe Phe Pro Leu Ser Gly Ser Leu Ile Phe Gly
530                 535                 540

Lys Gln Gly Thr Gly Arg Asp Asn Val Asp Ala Asp Lys Val Met Ile
545                 550                 555                 560

Thr Asn Glu Glu Glu Ile Lys Thr Thr Asn Pro Val Ala Thr Glu Ser
            565                 570                 575

Tyr Gly Gln Val Ala Thr Asn His Gln Ser Ala Gln Ala Gln Ala Gln
            580                 585                 590

Thr Gly Trp Val Gln Asn Gln Gly Ile Leu Pro Gly Met Val Trp Gln
            595                 600                 605

Asp Arg Asp Val Tyr Leu Gln Gly Pro Ile Trp Ala Lys Ile Pro His
610                 615                 620

Thr Asp Gly Asn Phe His Pro Ser Pro Leu Met Gly Gly Phe Gly Met
625                 630                 635                 640

Lys His Pro Pro Pro Gln Ile Leu Ile Lys Asn Thr Pro Val Pro Ala
            645                 650                 655

Asp Pro Pro Thr Ala Phe Asn Lys Asp Lys Leu Asn Ser Phe Ile Thr
            660                 665                 670

Gln Tyr Ser Thr Gly Gln Val Ser Val Glu Ile Glu Trp Glu Leu Gln
            675                 680                 685

Lys Glu Asn Ser Lys Arg Trp Asn Pro Glu Ile Gln Tyr Thr Ser Asn
690                 695                 700

Tyr Tyr Lys Ser Asn Asn Val Glu Phe Ala Val Asn Thr Glu Gly Val
705                 710                 715                 720

Tyr Ser Glu Pro Arg Pro Ile Gly Thr Arg Tyr Leu Thr Arg Asn Leu
            725                 730                 735

<210> SEQ ID NO 52
<211> LENGTH: 2211

-continued

```
<212> TYPE: DNA
<213> ORGANISM: Artificial Sequence
<220> FEATURE:
<223> OTHER INFORMATION: AVV mutant 9G453AG513A
<220> FEATURE:
<221> NAME/KEY: CDS
<222> LOCATION: (1)..(2211)

<400> SEQUENCE: 52
```

| | | | | | | | | | | | | | | | | |
|---|---|---|---|---|---|---|---|---|---|---|---|---|---|---|---|---|
| atg | gct | gcc | gat | ggt | tat | ctt | cca | gat | tgg | ctc | gag | gac | aac | ctt | agt | 48 |
| Met | Ala | Ala | Asp | Gly | Tyr | Leu | Pro | Asp | Trp | Leu | Glu | Asp | Asn | Leu | Ser | |
| 1 | | | | 5 | | | | | 10 | | | | | 15 | | |
| gaa | gga | att | cgc | gag | tgg | tgg | gct | ttg | aaa | cct | gga | gcc | cct | caa | ccc | 96 |
| Glu | Gly | Ile | Arg | Glu | Trp | Trp | Ala | Leu | Lys | Pro | Gly | Ala | Pro | Gln | Pro | |
| | | | 20 | | | | | 25 | | | | | 30 | | | |
| aag | gca | aat | caa | caa | cat | caa | gac | aac | gct | cga | ggt | ctt | gtg | ctt | ccg | 144 |
| Lys | Ala | Asn | Gln | Gln | His | Gln | Asp | Asn | Ala | Arg | Gly | Leu | Val | Leu | Pro | |
| | 35 | | | | | 40 | | | | | 45 | | | | | |
| ggt | tac | aaa | tac | ctt | gga | ccc | ggc | aac | gga | ctc | gac | aag | ggg | gag | ccg | 192 |
| Gly | Tyr | Lys | Tyr | Leu | Gly | Pro | Gly | Asn | Gly | Leu | Asp | Lys | Gly | Glu | Pro | |
| 50 | | | | | 55 | | | | | 60 | | | | | | |
| gtc | aac | gca | gca | gac | gcg | gcg | gcc | ctc | gag | cac | gac | aag | gcc | tac | gac | 240 |
| Val | Asn | Ala | Ala | Asp | Ala | Ala | Ala | Leu | Glu | His | Asp | Lys | Ala | Tyr | Asp | |
| 65 | | | | | 70 | | | | | 75 | | | | | 80 | |
| cag | cag | ctc | aag | gcc | gga | gac | aac | ccg | tac | ctc | aag | tac | aac | cac | gcc | 288 |
| Gln | Gln | Leu | Lys | Ala | Gly | Asp | Asn | Pro | Tyr | Leu | Lys | Tyr | Asn | His | Ala | |
| | | | | 85 | | | | | 90 | | | | | 95 | | |
| gac | gcc | gag | ttc | cag | gag | cgg | ctc | aaa | gaa | gat | acg | tct | ttt | ggg | ggc | 336 |
| Asp | Ala | Glu | Phe | Gln | Glu | Arg | Leu | Lys | Glu | Asp | Thr | Ser | Phe | Gly | Gly | |
| | | | 100 | | | | | 105 | | | | | 110 | | | |
| aac | ctc | ggg | cga | gca | gtc | ttc | cag | gcc | aaa | aag | agg | ctt | ctt | gaa | cct | 384 |
| Asn | Leu | Gly | Arg | Ala | Val | Phe | Gln | Ala | Lys | Lys | Arg | Leu | Leu | Glu | Pro | |
| | 115 | | | | | 120 | | | | | 125 | | | | | |
| ctt | ggt | ctg | gtt | gag | gaa | gcg | gct | aag | acg | gct | cct | gga | aag | aag | agg | 432 |
| Leu | Gly | Leu | Val | Glu | Glu | Ala | Ala | Lys | Thr | Ala | Pro | Gly | Lys | Lys | Arg | |
| | 130 | | | | | 135 | | | | | 140 | | | | | |
| cct | gta | gag | cag | tct | cct | cag | gaa | ccg | gac | tcc | tcc | gcg | ggt | att | ggc | 480 |
| Pro | Val | Glu | Gln | Ser | Pro | Gln | Glu | Pro | Asp | Ser | Ser | Ala | Gly | Ile | Gly | |
| 145 | | | | | 150 | | | | | 155 | | | | | 160 | |
| aaa | tcg | ggt | gca | cag | ccc | gct | aaa | aag | aga | ctc | aat | ttc | ggt | cag | act | 528 |
| Lys | Ser | Gly | Ala | Gln | Pro | Ala | Lys | Lys | Arg | Leu | Asn | Phe | Gly | Gln | Thr | |
| | | | 165 | | | | | 170 | | | | | 175 | | | |
| ggc | gac | aca | gag | tca | gtc | cca | gac | cct | caa | cca | atc | gga | gaa | cct | ccc | 576 |
| Gly | Asp | Thr | Glu | Ser | Val | Pro | Asp | Pro | Gln | Pro | Ile | Gly | Glu | Pro | Pro | |
| | | | | 180 | | | | | 185 | | | | | 190 | | |
| gca | gcc | ccc | tca | ggt | gtg | gga | tct | ctt | aca | atg | gct | tca | ggt | ggt | ggc | 624 |
| Ala | Ala | Pro | Ser | Gly | Val | Gly | Ser | Leu | Thr | Met | Ala | Ser | Gly | Gly | Gly | |
| | | 195 | | | | | 200 | | | | | 205 | | | | |
| gca | cca | gtg | gca | gac | aat | aac | gaa | ggt | gcc | gat | gga | gtg | ggt | agt | tcc | 672 |
| Ala | Pro | Val | Ala | Asp | Asn | Asn | Glu | Gly | Ala | Asp | Gly | Val | Gly | Ser | Ser | |
| 210 | | | | | 215 | | | | | 220 | | | | | | |
| tcg | gga | aat | tgg | cat | tgc | gat | tcc | caa | tgg | ctg | ggg | gac | aga | gtc | atc | 720 |
| Ser | Gly | Asn | Trp | His | Cys | Asp | Ser | Gln | Trp | Leu | Gly | Asp | Arg | Val | Ile | |
| 225 | | | | | 230 | | | | | 235 | | | | | 240 | |
| acc | acc | agc | acc | cga | acc | tgg | gcc | ctg | ccc | acc | tac | aat | aat | cac | ctc | 768 |
| Thr | Thr | Ser | Thr | Arg | Thr | Trp | Ala | Leu | Pro | Thr | Tyr | Asn | Asn | His | Leu | |
| | | | | 245 | | | | | 250 | | | | | 255 | | |
| tac | aag | caa | atc | tcc | aac | agc | aca | tct | gga | gga | tct | tca | aat | gac | aac | 816 |
| Tyr | Lys | Gln | Ile | Ser | Asn | Ser | Thr | Ser | Gly | Gly | Ser | Ser | Asn | Asp | Asn | |
| | | | 260 | | | | | 265 | | | | | 270 | | | |
| gcc | tac | ttc | ggc | tac | agc | acc | ccc | tgg | ggg | tat | ttt | gac | ttc | aac | aga | 864 |

```
                Ala Tyr Phe Gly Tyr Ser Thr Pro Trp Gly Tyr Phe Asp Phe Asn Arg
                        275                 280                 285 ttc cac tgc cac ttc tca cca cgt gac tgg cag cga ctc atc aac aac                  912
Phe His Cys His Phe Ser Pro Arg Asp Trp Gln Arg Leu Ile Asn Asn
        290                 295                 300 aac tgg gga ttc cgg cct aag cga ctc aac ttc aag ctc ttc aac att                  960
Asn Trp Gly Phe Arg Pro Lys Arg Leu Asn Phe Lys Leu Phe Asn Ile
305                 310                 315                 320 cag gtc aaa gag gtt acg gac aac aat gga gtc aag acc atc gcc aat                 1008
Gln Val Lys Glu Val Thr Asp Asn Asn Gly Val Lys Thr Ile Ala Asn
                325                 330                 335 aac ctt acc agc acg gtc cag gtc ttc acg gac tca gac tat cag ctc                 1056
Asn Leu Thr Ser Thr Val Gln Val Phe Thr Asp Ser Asp Tyr Gln Leu
        340                 345                 350 ccg tac gtg ctc ggg tcg gct cac gag ggc tgc ctc ccg ccg ttc cca                 1104
Pro Tyr Val Leu Gly Ser Ala His Glu Gly Cys Leu Pro Pro Phe Pro
                355                 360                 365 gcg gac gtt ttc atg att cct cag tac ggg tat ctg acg ctt aat gat                 1152
Ala Asp Val Phe Met Ile Pro Gln Tyr Gly Tyr Leu Thr Leu Asn Asp
370                 375                 380 gga agc cag gcc gtg ggt cgt tcg tcc ttt tac tgc ctg gaa tat ttc                 1200
Gly Ser Gln Ala Val Gly Arg Ser Ser Phe Tyr Cys Leu Glu Tyr Phe
385                 390                 395                 400 ccg tcg caa atg cta aga acg ggt aac aac ttc cag ttc agc tac gag                 1248
Pro Ser Gln Met Leu Arg Thr Gly Asn Asn Phe Gln Phe Ser Tyr Glu
                405                 410                 415 ttt gag aac gta cct ttc cat agc agc tac gct cac agc caa agc ctg                 1296
Phe Glu Asn Val Pro Phe His Ser Ser Tyr Ala His Ser Gln Ser Leu
        420                 425                 430 gac cga cta atg aat cca ctc atc gac caa tac ttg tac tat ctc tca                 1344
Asp Arg Leu Met Asn Pro Leu Ile Asp Gln Tyr Leu Tyr Tyr Leu Ser
                435                 440                 445 aag act att aac gct tct gga cag aat caa caa acg cta aaa ttc agt                 1392
Lys Thr Ile Asn Ala Ser Gly Gln Asn Gln Gln Thr Leu Lys Phe Ser
450                 455                 460 gtg gcc gga ccc agc aac atg gct gtc cag gga aga aac tac ata cct                 1440
Val Ala Gly Pro Ser Asn Met Ala Val Gln Gly Arg Asn Tyr Ile Pro
465                 470                 475                 480 gga ccc agc tac cga caa caa cgt gtc tca acc act gtg act caa aac                 1488
Gly Pro Ser Tyr Arg Gln Gln Arg Val Ser Thr Thr Val Thr Gln Asn
                485                 490                 495 aac aac agc gaa ttt gct tgg cct gga gct tct tct tgg gct ctc aat                 1536
Asn Asn Ser Glu Phe Ala Trp Pro Gly Ala Ser Ser Trp Ala Leu Asn
                500                 505                 510 gca cgt aat agc ttg atg aat cct gga cct gct atg gcc agc cac aaa                 1584
Ala Arg Asn Ser Leu Met Asn Pro Gly Pro Ala Met Ala Ser His Lys
        515                 520                 525 gaa gga gag gac cgt ttc ttt cct ttg tct gga tct tta att ttt ggc                 1632
Glu Gly Glu Asp Arg Phe Phe Pro Leu Ser Gly Ser Leu Ile Phe Gly
530                 535                 540 aaa caa gga act gga aga gac aac gtg gat gcg gac aaa gtc atg ata                 1680
Lys Gln Gly Thr Gly Arg Asp Asn Val Asp Ala Asp Lys Val Met Ile
545                 550                 555                 560 acc aac gaa gaa gaa att aaa act act aac ccg gta gca acg gag tcc                 1728
Thr Asn Glu Glu Glu Ile Lys Thr Thr Asn Pro Val Ala Thr Glu Ser
                565                 570                 575 tat gga caa gtg gcc aca aac cac cag agt gcc caa gca cag gcg cag                 1776
Tyr Gly Gln Val Ala Thr Asn His Gln Ser Ala Gln Ala Gln Ala Gln
        580                 585                 590
```

-continued

| | | |
|---|---|---|
| acc ggc tgg gtt caa aac caa gga ata ctt ccg ggt atg gtt tgg cag<br>Thr Gly Trp Val Gln Asn Gln Gly Ile Leu Pro Gly Met Val Trp Gln<br>595 600 605 | | 1824 |
| gac aga gat gtg tac ctg caa gga ccc att tgg gcc aaa att cct cac<br>Asp Arg Asp Val Tyr Leu Gln Gly Pro Ile Trp Ala Lys Ile Pro His<br>610 615 620 | | 1872 |
| acg gac ggc aac ttt cac cct tct ccg ctg atg gga ggg ttt gga atg<br>Thr Asp Gly Asn Phe His Pro Ser Pro Leu Met Gly Gly Phe Gly Met<br>625 630 635 640 | | 1920 |
| aag cac ccg cct cct cag atc ctc atc aaa aac aca cct gta cct gcg<br>Lys His Pro Pro Pro Gln Ile Leu Ile Lys Asn Thr Pro Val Pro Ala<br>645 650 655 | | 1968 |
| gat cct cca acg gcc ttc aac aag gac aag ctg aac tct ttc atc acc<br>Asp Pro Pro Thr Ala Phe Asn Lys Asp Lys Leu Asn Ser Phe Ile Thr<br>660 665 670 | | 2016 |
| cag tat tct act ggc caa gtc agc gtg gag atc gag tgg gag ctg cag<br>Gln Tyr Ser Thr Gly Gln Val Ser Val Glu Ile Glu Trp Glu Leu Gln<br>675 680 685 | | 2064 |
| aag gaa aac agc aag cgc tgg aac ccg gag atc cag tac act tcc aac<br>Lys Glu Asn Ser Lys Arg Trp Asn Pro Glu Ile Gln Tyr Thr Ser Asn<br>690 695 700 | | 2112 |
| tat tac aag tct aat aat gtt gaa ttt gct gtt aat act gaa ggt gta<br>Tyr Tyr Lys Ser Asn Asn Val Glu Phe Ala Val Asn Thr Glu Gly Val<br>705 710 715 720 | | 2160 |
| tat agt gaa ccc cgc ccc att ggc acc aga tac ctg act cgt aat ctg<br>Tyr Ser Glu Pro Arg Pro Ile Gly Thr Arg Tyr Leu Thr Arg Asn Leu<br>725 730 735 | | 2208 |
| taa | | 2211 |

<210> SEQ ID NO 53
<211> LENGTH: 736
<212> TYPE: PRT
<213> ORGANISM: Artificial Sequence
<220> FEATURE:
<223> OTHER INFORMATION: Synthetic Construct

<400> SEQUENCE: 53

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
        115                 120                 125

Leu Gly Leu Val Glu Glu Ala Lys Thr Ala Pro Gly Lys Lys Arg
    130                 135                 140

Pro Val Glu Gln Ser Pro Gln Glu Pro Asp Ser Ser Ala Gly Ile Gly
145                 150                 155                 160

Lys Ser Gly Ala Gln Pro Ala Lys Lys Arg Leu Asn Phe Gly Gln Thr

```
                165                 170                 175
Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Gly Gly Gly
            195                 200                 205

Ala Pro Val Ala Asp Asn Asn Glu Gly Ala Asp Gly Val Gly Ser Ser
            210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Ser Thr Ser Gly Gly Ser Ser Asn Asp Asn
            260                 265                 270

Ala Tyr Phe Gly Tyr Ser Thr Pro Trp Gly Tyr Phe Asp Phe Asn Arg
            275                 280                 285

Phe His Cys His Phe Ser Pro Arg Asp Trp Gln Arg Leu Ile Asn Asn
            290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
                325                 330                 335

Asn Leu Thr Ser Thr Val Gln Val Phe Thr Asp Ser Asp Tyr Gln Leu
            340                 345                 350

Pro Tyr Val Leu Gly Ser Ala His Glu Gly Cys Leu Pro Pro Phe Pro
            355                 360                 365

Ala Asp Val Phe Met Ile Pro Gln Tyr Gly Tyr Leu Thr Leu Asn Asp
            370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
                405                 410                 415

Phe Glu Asn Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Ser
            435                 440                 445

Lys Thr Ile Asn Ala Ser Gly Gln Asn Gln Gln Thr Leu Lys Phe Ser
450                 455                 460

Val Ala Gly Pro Ser Asn Met Ala Val Gln Gly Arg Asn Tyr Ile Pro
465                 470                 475                 480

Gly Pro Ser Tyr Arg Gln Gln Arg Val Ser Thr Thr Val Thr Gln Asn
                485                 490                 495

Asn Asn Ser Glu Phe Ala Trp Pro Gly Ala Ser Ser Trp Ala Leu Asn
            500                 505                 510

Ala Arg Asn Ser Leu Met Asn Pro Gly Pro Ala Met Ala Ser His Lys
            515                 520                 525

Glu Gly Glu Asp Arg Phe Phe Pro Leu Ser Gly Ser Leu Ile Phe Gly
            530                 535                 540

Lys Gln Gly Thr Gly Arg Asp Asn Val Asp Ala Asp Lys Val Met Ile
545                 550                 555                 560

Thr Asn Glu Glu Glu Ile Lys Thr Thr Asn Pro Val Ala Thr Glu Ser
                565                 570                 575

Tyr Gly Gln Val Ala Thr Asn His Gln Ser Ala Gln Ala Gln Ala Gln
            580                 585                 590
```

```
                Thr Gly Trp Val Gln Asn Gln Gly Ile Leu Pro Gly Met Val Trp Gln
                            595                 600                 605

Asp Arg Asp Val Tyr Leu Gln Gly Pro Ile Trp Ala Lys Ile Pro His
                        610                 615                 620

Thr Asp Gly Asn Phe His Pro Ser Pro Leu Met Gly Gly Phe Gly Met
                625                 630                 635                 640

Lys His Pro Pro Gln Ile Leu Ile Lys Asn Thr Pro Val Pro Ala
                            645                 650                 655

Asp Pro Pro Thr Ala Phe Asn Lys Asp Lys Leu Asn Ser Phe Ile Thr
                        660                 665                 670

Gln Tyr Ser Thr Gly Gln Val Ser Val Glu Ile Glu Trp Glu Leu Gln
                            675                 680                 685

Lys Glu Asn Ser Lys Arg Trp Asn Pro Glu Ile Gln Tyr Thr Ser Asn
                        690                 695                 700

Tyr Tyr Lys Ser Asn Asn Val Glu Phe Ala Val Asn Thr Glu Gly Val
                705                 710                 715                 720

Tyr Ser Glu Pro Arg Pro Ile Gly Thr Arg Tyr Leu Thr Arg Asn Leu
                            725                 730                 735

<210> SEQ ID NO 54
<211> LENGTH: 2211
<212> TYPE: DNA
<213> ORGANISM: Artificial Sequence
<220> FEATURE:
<223> OTHER INFORMATION: AVV mutant 9G330AG453AG513A
<220> FEATURE:
<221> NAME/KEY: CDS
<222> LOCATION: (1)..(2211)

<400> SEQUENCE: 54 atg gct gcc gat ggt tat ctt cca gat tgg ctc gag gac aac ctt agt        48
Met Ala Ala Asp Gly Tyr Leu Pro Asp Trp Leu Glu Asp Asn Leu Ser
1               5                   10                  15 gaa gga att cgc gag tgg tgg gct ttg aaa cct gga gcc cct caa ccc        96
Glu Gly Ile Arg Glu Trp Trp Ala Leu Lys Pro Gly Ala Pro Gln Pro
            20                  25                  30 aag gca aat caa caa cat caa gac aac gct cga ggt ctt gtg ctt ccg       144
Lys Ala Asn Gln Gln His Gln Asp Asn Ala Arg Gly Leu Val Leu Pro
        35                  40                  45 ggt tac aaa tac ctt gga ccc ggc aac gga ctc gac aag ggg gag ccg       192
Gly Tyr Lys Tyr Leu Gly Pro Gly Asn Gly Leu Asp Lys Gly Glu Pro
    50                  55                  60 gtc aac gca gca gac gcg gcg gcc ctc gag cac gac aag gcc tac gac       240
Val Asn Ala Ala Asp Ala Ala Ala Leu Glu His Asp Lys Ala Tyr Asp
65                  70                  75                  80 cag cag ctc aag gcc gga gac aac ccg tac ctc aag tac aac cac gcc       288
Gln Gln Leu Lys Ala Gly Asp Asn Pro Tyr Leu Lys Tyr Asn His Ala
                85                  90                  95 gac gcc gag ttc cag gag cgg ctc aaa gaa gat acg tct ttt ggg ggc       336
Asp Ala Glu Phe Gln Glu Arg Leu Lys Glu Asp Thr Ser Phe Gly Gly
            100                 105                 110 aac ctc ggg cga gca gtc ttc cag gcc aaa aag agg ctt ctt gaa cct       384
Asn Leu Gly Arg Ala Val Phe Gln Ala Lys Lys Arg Leu Leu Glu Pro
        115                 120                 125 ctt ggt ctg gtt gag gaa gcg gct aag acg gct cct gga aag aag agg       432
Leu Gly Leu Val Glu Glu Ala Ala Lys Thr Ala Pro Gly Lys Lys Arg
    130                 135                 140 cct gta gag cag tct cct cag gaa ccg gac tcc tcc gcg ggt att ggc       480
Pro Val Glu Gln Ser Pro Gln Glu Pro Asp Ser Ser Ala Gly Ile Gly
145                 150                 155                 160
```

```
              145                 150                 155                 160
aaa tcg ggt gca cag ccc gct aaa aag aga ctc aat ttc ggt cag act           528
Lys Ser Gly Ala Gln Pro Ala Lys Lys Arg Leu Asn Phe Gly Gln Thr
                    165                 170                 175 ggc gac aca gag tca gtc cca gac cct caa cca atc gga gaa cct ccc           576
Gly Asp Thr Glu Ser Val Pro Asp Pro Gln Pro Ile Gly Glu Pro Pro
            180                 185                 190 gca gcc ccc tca ggt gtg gga tct ctt aca atg gct tca ggt ggt ggc           624
Ala Ala Pro Ser Gly Val Gly Ser Leu Thr Met Ala Ser Gly Gly Gly
        195                 200                 205 gca cca gtg gca gac aat aac gaa ggt gcc gat gga gtg ggt agt tcc           672
Ala Pro Val Ala Asp Asn Asn Glu Gly Ala Asp Gly Val Gly Ser Ser
    210                 215                 220 tcg gga aat tgg cat tgc gat tcc caa tgg ctg ggg gac aga gtc atc           720
Ser Gly Asn Trp His Cys Asp Ser Gln Trp Leu Gly Asp Arg Val Ile
225                 230                 235                 240 acc acc agc acc cga acc tgg gcc ctg ccc acc tac aac aat cac ctc           768
Thr Thr Ser Thr Arg Thr Trp Ala Leu Pro Thr Tyr Asn Asn His Leu
                245                 250                 255 tac aag caa atc tcc aac agc aca tct gga gga tct tca aat gac aac           816
Tyr Lys Gln Ile Ser Asn Ser Thr Ser Gly Gly Ser Ser Asn Asp Asn
            260                 265                 270 gcc tac ttc ggc tac agc acc ccc tgg ggg tat ttt gac ttc aac aga           864
Ala Tyr Phe Gly Tyr Ser Thr Pro Trp Gly Tyr Phe Asp Phe Asn Arg
        275                 280                 285 ttc cac tgc cac ttc tca cca cgt gac tgg cag cga ctc atc aac aac           912
Phe His Cys His Phe Ser Pro Arg Asp Trp Gln Arg Leu Ile Asn Asn
    290                 295                 300 aac tgg gga ttc cgg cct aag cga ctc aac ttc aag ctc ttc aac att           960
Asn Trp Gly Phe Arg Pro Lys Arg Leu Asn Phe Lys Leu Phe Asn Ile
305                 310                 315                 320 cag gtc aaa gag gtt acg gac aac aat gca gtc aag acc atc gcc aat          1008
Gln Val Lys Glu Val Thr Asp Asn Asn Ala Val Lys Thr Ile Ala Asn
                325                 330                 335 aac ctt acc agc acg gtc cag gtc ttc acg gac tca gac tat cag ctc          1056
Asn Leu Thr Ser Thr Val Gln Val Phe Thr Asp Ser Asp Tyr Gln Leu
            340                 345                 350 ccg tac gtg ctc ggg tcg gct cac gag ggc tgc ctc ccg ccg ttc cca          1104
Pro Tyr Val Leu Gly Ser Ala His Glu Gly Cys Leu Pro Pro Phe Pro
        355                 360                 365 gcg gac gtt ttc atg att cct cag tac ggg tat ctg acg ctt aat gat          1152
Ala Asp Val Phe Met Ile Pro Gln Tyr Gly Tyr Leu Thr Leu Asn Asp
    370                 375                 380 gga agc cag gcc gtg ggt cgt tcc tcc ttt tac tgc ctg gaa tat ttc          1200
Gly Ser Gln Ala Val Gly Arg Ser Ser Phe Tyr Cys Leu Glu Tyr Phe
385                 390                 395                 400 ccg tcg caa atg cta aga acg ggt aac aac ttc cag ttc agc tac gag          1248
Pro Ser Gln Met Leu Arg Thr Gly Asn Asn Phe Gln Phe Ser Tyr Glu
                405                 410                 415 ttt gag aac gta cct ttc cat agc agc tac gct cac agc caa agc ctg          1296
Phe Glu Asn Val Pro Phe His Ser Ser Tyr Ala His Ser Gln Ser Leu
            420                 425                 430 gac cga cta atg aat cca ctc atc gac caa tac ttg tac tat ctc tca          1344
Asp Arg Leu Met Asn Pro Leu Ile Asp Gln Tyr Leu Tyr Tyr Leu Ser
        435                 440                 445 aag act att aac gct tct gga cag aat caa caa acg cta aaa ttc agt          1392
Lys Thr Ile Asn Ala Ser Gly Gln Asn Gln Gln Thr Leu Lys Phe Ser
    450                 455                 460 gtg gcc gga ccc agc aac atg gct gtc cag gga aga aac tac ata cct          1440
```

```
                Val Ala Gly Pro Ser Asn Met Ala Val Gln Gly Arg Asn Tyr Ile Pro
                465                 470                 475                 480 gga ccc agc tac cga caa caa cgt gtc tca acc act gtg act caa aac          1488
Gly Pro Ser Tyr Arg Gln Gln Arg Val Ser Thr Thr Val Thr Gln Asn
                485                 490                 495 aac aac agc gaa ttt gct tgg cct gga gct tct tct tgg gct ctc aat          1536
Asn Asn Ser Glu Phe Ala Trp Pro Gly Ala Ser Ser Trp Ala Leu Asn
                500                 505                 510 gca cgt aat agc ttg atg aat cct gga cct gct atg gcc agc cac aaa          1584
Ala Arg Asn Ser Leu Met Asn Pro Gly Pro Ala Met Ala Ser His Lys
            515                 520                 525 gaa gga gag gac cgt ttc ttt cct ttg tct gga tct tta att ttt ggc          1632
Glu Gly Glu Asp Arg Phe Phe Pro Leu Ser Gly Ser Leu Ile Phe Gly
530                 535                 540 aaa caa gga act gga aga gac aac gtg gat gcg gac aaa gtc atg ata          1680
Lys Gln Gly Thr Gly Arg Asp Asn Val Asp Ala Asp Lys Val Met Ile
545                 550                 555                 560 acc aac gaa gaa gaa att aaa act act aac ccg gta gca acg gag tcc          1728
Thr Asn Glu Glu Glu Ile Lys Thr Thr Asn Pro Val Ala Thr Glu Ser
                565                 570                 575 tat gga caa gtg gcc aca aac cac cag agt gcc caa gca cag gcg cag          1776
Tyr Gly Gln Val Ala Thr Asn His Gln Ser Ala Gln Ala Gln Ala Gln
                580                 585                 590 acc ggc tgg gtt caa aac caa gga ata ctt ccg ggt atg gtt tgg cag          1824
Thr Gly Trp Val Gln Asn Gln Gly Ile Leu Pro Gly Met Val Trp Gln
                595                 600                 605 gac aga gat gtg tac ctg caa gga ccc att tgg gcc aaa att cct cac          1872
Asp Arg Asp Val Tyr Leu Gln Gly Pro Ile Trp Ala Lys Ile Pro His
610                 615                 620 acg gac ggc aac ttt cac cct tct ccg ctg atg gga ggg ttt gga atg          1920
Thr Asp Gly Asn Phe His Pro Ser Pro Leu Met Gly Gly Phe Gly Met
625                 630                 635                 640 aag cac ccg cct cct cag atc ctc atc aaa aac aca cct gta cct gcg          1968
Lys His Pro Pro Pro Gln Ile Leu Ile Lys Asn Thr Pro Val Pro Ala
                645                 650                 655 gat cct cca acg gcc ttc aac aag gac aag ctg aac tct ttc atc acc          2016
Asp Pro Pro Thr Ala Phe Asn Lys Asp Lys Leu Asn Ser Phe Ile Thr
                660                 665                 670 cag tat tct act ggc caa gtc agc gtg gag atc gag tgg gag ctg cag          2064
Gln Tyr Ser Thr Gly Gln Val Ser Val Glu Ile Glu Trp Glu Leu Gln
                675                 680                 685 aag gaa aac agc aag cgc tgg aac ccg gag atc cag tac act tcc aac          2112
Lys Glu Asn Ser Lys Arg Trp Asn Pro Glu Ile Gln Tyr Thr Ser Asn
690                 695                 700 tat tac aag tct aat aat gtt gaa ttt gct gtt aat act gaa ggt gta          2160
Tyr Tyr Lys Ser Asn Asn Val Glu Phe Ala Val Asn Thr Glu Gly Val
705                 710                 715                 720 tat agt gaa ccc cgc ccc att ggc acc aga tac ctg act cgt aat ctg          2208
Tyr Ser Glu Pro Arg Pro Ile Gly Thr Arg Tyr Leu Thr Arg Asn Leu
                725                 730                 735 taa                                                                       2211

<210> SEQ ID NO 55
<211> LENGTH: 736
<212> TYPE: PRT
<213> ORGANISM: Artificial Sequence
<220> FEATURE:
<223> OTHER INFORMATION: Synthetic Construct

<400> SEQUENCE: 55
```

```
Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30

Lys Ala Asn Gln Gln His Gln Asp Asn Ala Arg Gly Leu Val Leu Pro
                35                  40                  45

Gly Tyr Lys Tyr Leu Gly Pro Gly Asn Gly Leu Asp Lys Gly Glu Pro
    50                  55                  60

Val Asn Ala Ala Asp Ala Ala Leu Glu His Asp Lys Ala Tyr Asp
65              70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
                100                 105                 110

Asn Leu Gly Arg Ala Val Phe Gln Ala Lys Lys Arg Leu Leu Glu Pro
            115                 120                 125

Leu Gly Leu Val Glu Glu Ala Ala Lys Thr Ala Pro Gly Lys Lys Arg
    130                 135                 140

Pro Val Glu Gln Ser Pro Gln Glu Pro Asp Ser Ser Ala Gly Ile Gly
145                 150                 155                 160

Lys Ser Gly Ala Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
                180                 185                 190

Ala Ala Pro Ser Gly Val Gly Ser Leu Thr Met Ala Ser Gly Gly Gly
                195                 200                 205

Ala Pro Val Ala Asp Asn Asn Glu Gly Ala Asp Gly Val Gly Ser Ser
210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Ser Thr Ser Gly Gly Ser Ser Asn Asp Asn
                260                 265                 270

Ala Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn Asn
        290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Ala Val Lys Thr Ile Ala Asn
                325                 330                 335

Asn Leu Thr Ser Thr Val Gln Val Phe Thr Asp Ser Asp Tyr Gln Leu
                340                 345                 350

Pro Tyr Val Leu Gly Ser Ala His Glu Gly Cys Leu Pro Pro Phe Pro
        355                 360                 365

Ala Asp Val Phe Met Ile Pro Gln Tyr Gly Tyr Leu Thr Leu Asn Asp
370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
                405                 410                 415

Phe Glu Asn Val Pro Phe His Ser Ser Tyr Ala His Ser Gln Ser Leu
```

420                 425                 430
Asp Arg Leu Met Asn Pro Leu Ile Asp Gln Tyr Leu Tyr Tyr Leu Ser
                435                 440                 445

Lys Thr Ile Asn Ala Ser Gly Gln Asn Gln Gln Thr Leu Lys Phe Ser
        450                 455                 460

Val Ala Gly Pro Ser Asn Met Ala Val Gln Gly Arg Asn Tyr Ile Pro
465                 470                 475                 480

Gly Pro Ser Tyr Arg Gln Gln Arg Val Ser Thr Thr Val Thr Gln Asn
                485                 490                 495

Asn Asn Ser Glu Phe Ala Trp Pro Gly Ala Ser Ser Trp Ala Leu Asn
            500                 505                 510

Ala Arg Asn Ser Leu Met Asn Pro Gly Pro Ala Met Ala Ser His Lys
        515                 520                 525

Glu Gly Glu Asp Arg Phe Phe Pro Leu Ser Gly Ser Leu Ile Phe Gly
    530                 535                 540

Lys Gln Gly Thr Gly Arg Asp Asn Val Asp Ala Asp Lys Val Met Ile
545                 550                 555                 560

Thr Asn Glu Glu Glu Ile Lys Thr Thr Asn Pro Val Ala Thr Glu Ser
                565                 570                 575

Tyr Gly Gln Val Ala Thr Asn His Gln Ser Ala Gln Ala Gln Ala Gln
            580                 585                 590

Thr Gly Trp Val Gln Asn Gln Gly Ile Leu Pro Gly Met Val Trp Gln
        595                 600                 605

Asp Arg Asp Val Tyr Leu Gln Gly Pro Ile Trp Ala Lys Ile Pro His
    610                 615                 620

Thr Asp Gly Asn Phe His Pro Ser Pro Leu Met Gly Gly Phe Gly Met
625                 630                 635                 640

Lys His Pro Pro Pro Gln Ile Leu Ile Lys Asn Thr Pro Val Pro Ala
                645                 650                 655

Asp Pro Pro Thr Ala Phe Asn Lys Asp Lys Leu Asn Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Ile Gln Tyr Thr Ser Asn
    690                 695                 700

Tyr Tyr Lys Ser Asn Asn Val Glu Phe Ala Val Asn Thr Glu Gly Val
705                 710                 715                 720

Tyr Ser Glu Pro Arg Pro Ile Gly Thr Arg Tyr Leu Thr Arg Asn Leu
                725                 730                 735

<210> SEQ ID NO 56
<211> LENGTH: 38
<212> TYPE: DNA
<213> ORGANISM: Artificial Sequence
<220> FEATURE:
<223> OTHER INFORMATION: primer sequence

<400> SEQUENCE: 56
cgacaaccgg gcaaaaccag aatagcaact ttgcctgg                              38

<210> SEQ ID NO 57
<211> LENGTH: 38
<212> TYPE: DNA
<213> ORGANISM: Artificial Sequence
<220> FEATURE:
<223> OTHER INFORMATION: primer sequence

```
<400> SEQUENCE: 57
ccaggcaaag ttgctattct ggttttgccc ggttgtcg                              38

<210> SEQ ID NO 58
<211> LENGTH: 36
<212> TYPE: DNA
<213> ORGANISM: Artificial Sequence
<220> FEATURE:
<223> OTHER INFORMATION: primer sequence

<400> SEQUENCE: 58
gacaaccggg caaaacgaca atagcaactt tgcctg                                36

<210> SEQ ID NO 59
<211> LENGTH: 36
<212> TYPE: DNA
<213> ORGANISM: Artificial Sequence
<220> FEATURE:
<223> OTHER INFORMATION: primer sequence

<400> SEQUENCE: 59
caggcaaagt tgctattgtc gttttgcccg gttgtc                                36

<210> SEQ ID NO 60
<211> LENGTH: 29
<212> TYPE: DNA
<213> ORGANISM: Artificial Sequence
<220> FEATURE:
<223> OTHER INFORMATION: primer sequence

<400> SEQUENCE: 60
ggaggcacgg cacagacgca gactctggg                                        29

<210> SEQ ID NO 61
<211> LENGTH: 29
<212> TYPE: DNA
<213> ORGANISM: Artificial Sequence
<220> FEATURE:
<223> OTHER INFORMATION: primer sequence

<400> SEQUENCE: 61
cccagagtct gcgtctgtgc cgtgcctcc                                        29

<210> SEQ ID NO 62
<211> LENGTH: 30
<212> TYPE: DNA
<213> ORGANISM: Artificial Sequence
<220> FEATURE:
<223> OTHER INFORMATION: primer sequence

<400> SEQUENCE: 62
caggaggcac ggcagatacg cagactctgg                                       30

<210> SEQ ID NO 63
<211> LENGTH: 30
<212> TYPE: DNA
<213> ORGANISM: Artificial Sequence
<220> FEATURE:
<223> OTHER INFORMATION: primer sequence

<400> SEQUENCE: 63
ccagagtctg cgtatctgcc gtgcctcctg                                       30

<210> SEQ ID NO 64
<211> LENGTH: 29
```

```
<212> TYPE: DNA
<213> ORGANISM: Artificial Sequence
<220> FEATURE:
<223> OTHER INFORMATION: primer sequence

<400> SEQUENCE: 64
ctcctcccga tgtcgcgttg gagatttgc                                    29

<210> SEQ ID NO 65
<211> LENGTH: 29
<212> TYPE: DNA
<213> ORGANISM: Artificial Sequence
<220> FEATURE:
<223> OTHER INFORMATION: primer sequence

<400> SEQUENCE: 65
gcaaatctcc aacgcgacat cgggaggag                                    29

<210> SEQ ID NO 66
<211> LENGTH: 31
<212> TYPE: DNA
<213> ORGANISM: Artificial Sequence
<220> FEATURE:
<223> OTHER INFORMATION: primer sequence

<400> SEQUENCE: 66
cccacggcct gactagcgtt gttgagtgtt a                                 31

<210> SEQ ID NO 67
<211> LENGTH: 31
<212> TYPE: DNA
<213> ORGANISM: Artificial Sequence
<220> FEATURE:
<223> OTHER INFORMATION: primer sequence

<400> SEQUENCE: 67
taacactcaa caacgctagt caggccgtgg g                                 31

<210> SEQ ID NO 68
<211> LENGTH: 43
<212> TYPE: DNA
<213> ORGANISM: Artificial Sequence
<220> FEATURE:
<223> OTHER INFORMATION: primer sequence

<400> SEQUENCE: 68
ggattagcca atgaatttct tgcattcaga tggtatttgg tcc                    43

<210> SEQ ID NO 69
<211> LENGTH: 43
<212> TYPE: DNA
<213> ORGANISM: Artificial Sequence
<220> FEATURE:
<223> OTHER INFORMATION: primer sequence

<400> SEQUENCE: 69
ggaccaaata ccatctgaat gcaagaaatt cattggctaa tcc                    43

<210> SEQ ID NO 70
<211> LENGTH: 39
<212> TYPE: DNA
<213> ORGANISM: Artificial Sequence
<220> FEATURE:
<223> OTHER INFORMATION: primer sequence

<400> SEQUENCE: 70
```
tttgccaaaa atcaggatcg cgttactggg aaaaaaacg          39

<210> SEQ ID NO 71
<211> LENGTH: 39
<212> TYPE: DNA
<213> ORGANISM: Artificial Sequence
<220> FEATURE:
<223> OTHER INFORMATION: primer sequence

<400> SEQUENCE: 71 cgttttttc ccagtaacgc gatcctgatt tttggcaaa           39

<210> SEQ ID NO 72
<211> LENGTH: 27
<212> TYPE: DNA
<213> ORGANISM: Artificial Sequence
<220> FEATURE:
<223> OTHER INFORMATION: primer sequence

<400> SEQUENCE: 72
ggacccttca acgcactcga caagggg                       27

<210> SEQ ID NO 73
<211> LENGTH: 27
<212> TYPE: DNA
<213> ORGANISM: Artificial Sequence
<220> FEATURE:
<223> OTHER INFORMATION: primer sequence

<400> SEQUENCE: 73 cccttgtcg agtgcgttga agggtcc                        27

<210> SEQ ID NO 74
<211> LENGTH: 35
<212> TYPE: DNA
<213> ORGANISM: Artificial Sequence
<220> FEATURE:
<223> OTHER INFORMATION: primer sequence

<400> SEQUENCE: 74
tggctcctcc cgatgtgctg ttggagattt gcttg              35

<210> SEQ ID NO 75
<211> LENGTH: 35
<212> TYPE: DNA
<213> ORGANISM: Artificial Sequence
<220> FEATURE:
<223> OTHER INFORMATION: primer sequence

<400> SEQUENCE: 75
caagcaaatc tccaacagca catcgggagg agcca              35

<210> SEQ ID NO 76
<211> LENGTH: 33
<212> TYPE: DNA
<213> ORGANISM: Artificial Sequence
<220> FEATURE:
<223> OTHER INFORMATION: primer sequence

<400> SEQUENCE: 76
cccacggcct gactactgtt gttgagtgtt agg                33

<210> SEQ ID NO 77
<211> LENGTH: 33
<212> TYPE: DNA
<213> ORGANISM: Artificial Sequence

```
<220> FEATURE:
<223> OTHER INFORMATION: primer sequence

<400> SEQUENCE: 77
cctaacactc aacaacagta gtcaggccgt ggg                              33

<210> SEQ ID NO 78
<211> LENGTH: 46
<212> TYPE: DNA
<213> ORGANISM: Artificial Sequence
<220> FEATURE:
<223> OTHER INFORMATION: primer sequence

<400> SEQUENCE: 78
ttagccaatg aatttctgct attcagatgg tatttggtcc cagcag               46

<210> SEQ ID NO 79
<211> LENGTH: 46
<212> TYPE: DNA
<213> ORGANISM: Artificial Sequence
<220> FEATURE:
<223> OTHER INFORMATION: primer sequence

<400> SEQUENCE: 79
ctgctgggac caaataccat ctgaatagca gaaattcatt ggctaa               46

<210> SEQ ID NO 80
<211> LENGTH: 45
<212> TYPE: DNA
<213> ORGANISM: Artificial Sequence
<220> FEATURE:
<223> OTHER INFORMATION: primer sequence

<400> SEQUENCE: 80
ttgtttgcca aaaatcagga tgctgttact gggaaaaaaa cgctc                45

<210> SEQ ID NO 81
<211> LENGTH: 45
<212> TYPE: DNA
<213> ORGANISM: Artificial Sequence
<220> FEATURE:
<223> OTHER INFORMATION: primer sequence

<400> SEQUENCE: 81
gagcgttttt ttcccagtaa cagcatcctg attttggca aacaa                 45

<210> SEQ ID NO 82
<211> LENGTH: 33
<212> TYPE: DNA
<213> ORGANISM: Artificial Sequence
<220> FEATURE:
<223> OTHER INFORMATION: primer sequence

<400> SEQUENCE: 82
ctcccccttg tcgaggctgt tgaagggtcc gag                              33

<210> SEQ ID NO 83
<211> LENGTH: 33
<212> TYPE: DNA
<213> ORGANISM: Artificial Sequence
<220> FEATURE:
<223> OTHER INFORMATION: primer sequence

<400> SEQUENCE: 83
ctcggaccct tcaacagcct cgacaagggg gag                              33
```

<210> SEQ ID NO 84
<211> LENGTH: 32
<212> TYPE: DNA
<213> ORGANISM: Artificial Sequence
<220> FEATURE:
<223> OTHER INFORMATION: primer sequence

<400> SEQUENCE: 84
cagcgactca tcaacgacaa ctggggattc cg                                32

<210> SEQ ID NO 85
<211> LENGTH: 28
<212> TYPE: DNA
<213> ORGANISM: Artificial Sequence
<220> FEATURE:
<223> OTHER INFORMATION: primer sequence

<400> SEQUENCE: 85
ggaggcacgg cagatacgca gactctgg                                    28

<210> SEQ ID NO 86
<211> LENGTH: 36
<212> TYPE: DNA
<213> ORGANISM: Artificial Sequence
<220> FEATURE:
<223> OTHER INFORMATION: primer sequence

<400> SEQUENCE: 86
gacaaccggg caaaacgaca atagcaactt tgcctg                           36

<210> SEQ ID NO 87
<211> LENGTH: 40
<212> TYPE: DNA
<213> ORGANISM: Artificial Sequence
<220> FEATURE:
<223> OTHER INFORMATION: primer sequence

<400> SEQUENCE: 87
ccatctgaat ggaagagatt cattggctaa tcctggcatc                       40

<210> SEQ ID NO 88
<211> LENGTH: 30
<212> TYPE: DNA
<213> ORGANISM: Artificial Sequence
<220> FEATURE:
<223> OTHER INFORMATION: primer sequence

<400> SEQUENCE: 88
cgaagcccaa agccgaccag caaaagcagg                                  30

<210> SEQ ID NO 89
<211> LENGTH: 28
<212> TYPE: DNA
<213> ORGANISM: Artificial Sequence
<220> FEATURE:
<223> OTHER INFORMATION: primer sequence

<400> SEQUENCE: 89
gtacctgcgg tatgaccacg ccgacgcc                                    28

<210> SEQ ID NO 90
<211> LENGTH: 37
<212> TYPE: DNA
<213> ORGANISM: Artificial Sequence
<220> FEATURE:
<223> OTHER INFORMATION: primer sequence

<400> SEQUENCE: 90
gatgctgaga accggcgaca acttccagtt tacttac                        37

<210> SEQ ID NO 91
<211> LENGTH: 39
<212> TYPE: DNA
<213> ORGANISM: Artificial Sequence
<220> FEATURE:
<223> OTHER INFORMATION: primer sequence

<400> SEQUENCE: 91
cagactctgg gcttcagcga tggtgggcct aatacaatg                      39

<210> SEQ ID NO 92
<211> LENGTH: 30
<212> TYPE: DNA
<213> ORGANISM: Artificial Sequence
<220> FEATURE:
<223> OTHER INFORMATION: primer sequence

<400> SEQUENCE: 92
ccaatcaggc aaaggactgg ctgccaggac                                30

<210> SEQ ID NO 93
<211> LENGTH: 26
<212> TYPE: DNA
<213> ORGANISM: Artificial Sequence
<220> FEATURE:
<223> OTHER INFORMATION: primer sequence

<400> SEQUENCE: 93
cacggacggc gacttccacc cgtctc                                    26

<210> SEQ ID NO 94
<211> LENGTH: 31
<212> TYPE: DNA
<213> ORGANISM: Artificial Sequence
<220> FEATURE:
<223> OTHER INFORMATION: primer sequence

<400> SEQUENCE: 94
gatcctgatc aaggacacgc ctgtacctgc g                              31

<210> SEQ ID NO 95
<211> LENGTH: 33
<212> TYPE: DNA
<213> ORGANISM: Artificial Sequence
<220> FEATURE:
<223> OTHER INFORMATION: primer sequence

<400> SEQUENCE: 95
gtacctcgga cccttccagg gactcgacaa ggg                            33

<210> SEQ ID NO 96
<211> LENGTH: 36
<212> TYPE: DNA
<213> ORGANISM: Artificial Sequence
<220> FEATURE:
<223> OTHER INFORMATION: primer sequence

<400> SEQUENCE: 96
ctacaagcaa atctcccagg ggacatcggg aggagc                         36

<210> SEQ ID NO 97

```
<211> LENGTH: 36
<212> TYPE: DNA
<213> ORGANISM: Artificial Sequence
<220> FEATURE:
<223> OTHER INFORMATION: primer sequence

<400> SEQUENCE: 97
gctacctaac actcaaccag ggtagtcagg ccgtgg                              36

<210> SEQ ID NO 98
<211> LENGTH: 41
<212> TYPE: DNA
<213> ORGANISM: Artificial Sequence
<220> FEATURE:
<223> OTHER INFORMATION: primer sequence

<400> SEQUENCE: 98
gctgggacca aataccatct gcagggaaga aattcattgg c                        41

<210> SEQ ID NO 99
<211> LENGTH: 40
<212> TYPE: DNA
<213> ORGANISM: Artificial Sequence
<220> FEATURE:
<223> OTHER INFORMATION: primer sequence

<400> SEQUENCE: 99
ggagcgtttt tttcccagtc aggggatcct gatttttggc                          40

<210> SEQ ID NO 100
<211> LENGTH: 32
<212> TYPE: DNA
<213> ORGANISM: Artificial Sequence
<220> FEATURE:
<223> OTHER INFORMATION: primer sequence

<400> SEQUENCE: 100
cggaatcccc agttgtcgtt gatgagtcgc tg                                  32

<210> SEQ ID NO 101
<211> LENGTH: 28
<212> TYPE: DNA
<213> ORGANISM: Artificial Sequence
<220> FEATURE:
<223> OTHER INFORMATION: primer sequence

<400> SEQUENCE: 101
ccagagtctg cgtatctgcc gtgcctcc                                       28

<210> SEQ ID NO 102
<211> LENGTH: 36
<212> TYPE: DNA
<213> ORGANISM: Artificial Sequence
<220> FEATURE:
<223> OTHER INFORMATION: primer sequence

<400> SEQUENCE: 102
caggcaaagt tgctattgtc gttttgcccg gttgtc                              36

<210> SEQ ID NO 103
<211> LENGTH: 40
<212> TYPE: DNA
<213> ORGANISM: Artificial Sequence
<220> FEATURE:
<223> OTHER INFORMATION: primer sequence

<400> SEQUENCE: 103
```
gatgccagga ttagccaatg aatctcttcc attcagatgg        40

<210> SEQ ID NO 104
<211> LENGTH: 30
<212> TYPE: DNA
<213> ORGANISM: Artificial Sequence
<220> FEATURE:
<223> OTHER INFORMATION: primer sequence

<400> SEQUENCE: 104
cctgcttttg ctggtcggct ttgggcttcg        30

<210> SEQ ID NO 105
<211> LENGTH: 28
<212> TYPE: DNA
<213> ORGANISM: Artificial Sequence
<220> FEATURE:
<223> OTHER INFORMATION: primer sequence

<400> SEQUENCE: 105
ggcgtcggcg tggtcatacc gcaggtac        28

<210> SEQ ID NO 106
<211> LENGTH: 37
<212> TYPE: DNA
<213> ORGANISM: Artificial Sequence
<220> FEATURE:
<223> OTHER INFORMATION: primer sequence

<400> SEQUENCE: 106
gtaagtaaac tggaagttgt cgccggttct cagcatc        37

<210> SEQ ID NO 107
<211> LENGTH: 39
<212> TYPE: DNA
<213> ORGANISM: Artificial Sequence
<220> FEATURE:
<223> OTHER INFORMATION: primer sequence

<400> SEQUENCE: 107
cattgtatta ggcccaccat cgctgaagcc cagagtctg        39

<210> SEQ ID NO 108
<211> LENGTH: 30
<212> TYPE: DNA
<213> ORGANISM: Artificial Sequence
<220> FEATURE:
<223> OTHER INFORMATION: primer sequence

<400> SEQUENCE: 108
gtcctggcag ccagtccttt gcctgattgg        30

<210> SEQ ID NO 109
<211> LENGTH: 26
<212> TYPE: DNA
<213> ORGANISM: Artificial Sequence
<220> FEATURE:
<223> OTHER INFORMATION: primer sequence

<400> SEQUENCE: 109
gagacgggtg gaagtcgccg tccgtg        26

<210> SEQ ID NO 110
<211> LENGTH: 31
<212> TYPE: DNA

```
<213> ORGANISM: Artificial Sequence
<220> FEATURE:
<223> OTHER INFORMATION: primer sequence

<400> SEQUENCE: 110
cgcaggtaca ggcgtgtcct tgatcaggat c                              31

<210> SEQ ID NO 111
<211> LENGTH: 35
<212> TYPE: DNA
<213> ORGANISM: Artificial Sequence
<220> FEATURE:
<223> OTHER INFORMATION: primer sequence

<400> SEQUENCE: 111
gcagcgactc atcaacgaca actggggatt ccggc                          35

<210> SEQ ID NO 112
<211> LENGTH: 35
<212> TYPE: DNA
<213> ORGANISM: Artificial Sequence
<220> FEATURE:
<223> OTHER INFORMATION: primer sequence

<400> SEQUENCE: 112
gccggaatcc ccagttgtcg ttgatgagtc gctgc                          35

<210> SEQ ID NO 113
<211> LENGTH: 34
<212> TYPE: DNA
<213> ORGANISM: Artificial Sequence
<220> FEATURE:
<223> OTHER INFORMATION: primer sequence

<400> SEQUENCE: 113
cagcgactca tcaacgacaa ctggggattc cggc                           34

<210> SEQ ID NO 114
<211> LENGTH: 34
<212> TYPE: DNA
<213> ORGANISM: Artificial Sequence
<220> FEATURE:
<223> OTHER INFORMATION: primer sequence

<400> SEQUENCE: 114
gccggaatcc ccagttgtcg ttgatgagtc gctg                           34

<210> SEQ ID NO 115
<211> LENGTH: 30
<212> TYPE: DNA
<213> ORGANISM: Artificial Sequence
<220> FEATURE:
<223> OTHER INFORMATION: primer sequence

<400> SEQUENCE: 115
gcgactcatc aacgacaact ggggattccg                                30

<210> SEQ ID NO 116
<211> LENGTH: 30
<212> TYPE: DNA
<213> ORGANISM: Artificial Sequence
<220> FEATURE:
<223> OTHER INFORMATION: primer sequence

<400> SEQUENCE: 116
cggaatcccc agttgtcgtt gatgagtcgc                                30
```

<210> SEQ ID NO 117
<211> LENGTH: 31
<212> TYPE: DNA
<213> ORGANISM: Artificial Sequence
<220> FEATURE:
<223> OTHER INFORMATION: primer sequence

<400> SEQUENCE: 117
ctctgggctt cagcgaaggt gggcctaata c                         31

<210> SEQ ID NO 118
<211> LENGTH: 31
<212> TYPE: DNA
<213> ORGANISM: Artificial Sequence
<220> FEATURE:
<223> OTHER INFORMATION: primer sequence

<400> SEQUENCE: 118
gtattaggcc caccttcgct gaagcccaga g                         31

<210> SEQ ID NO 119
<211> LENGTH: 29
<212> TYPE: DNA
<213> ORGANISM: Artificial Sequence
<220> FEATURE:
<223> OTHER INFORMATION: primer sequence

<400> SEQUENCE: 119
cctcggaccc ttcgacggac tcgacaagg                            29

<210> SEQ ID NO 120
<211> LENGTH: 34
<212> TYPE: DNA
<213> ORGANISM: Artificial Sequence
<220> FEATURE:
<223> OTHER INFORMATION: primer sequence

<400> SEQUENCE: 120
tacaagcaaa tctccgacgg gacatcggga ggag                      34

<210> SEQ ID NO 121
<211> LENGTH: 34
<212> TYPE: DNA
<213> ORGANISM: Artificial Sequence
<220> FEATURE:
<223> OTHER INFORMATION: primer sequence

<400> SEQUENCE: 121
ctacctaaca ctcaacgacg gtagtcaggc cgtg                      34

<210> SEQ ID NO 122
<211> LENGTH: 45
<212> TYPE: DNA
<213> ORGANISM: Artificial Sequence
<220> FEATURE:
<223> OTHER INFORMATION: primer sequence

<400> SEQUENCE: 122
ctgggaccaa ataccatctg gatggaagaa attcattggc taatc          45

<210> SEQ ID NO 123
<211> LENGTH: 39
<212> TYPE: DNA
<213> ORGANISM: Artificial Sequence
<220> FEATURE:

```
<223> OTHER INFORMATION: primer sequence

<400> SEQUENCE: 123
gagcgttttt ttcccagtga cgggatcctg atttttggc                              39

<210> SEQ ID NO 124
<211> LENGTH: 29
<212> TYPE: DNA
<213> ORGANISM: Artificial Sequence
<220> FEATURE:
<223> OTHER INFORMATION: primer sequence

<400> SEQUENCE: 124
ccttgtcgag tccgtcgaag ggtccgagg                                         29

<210> SEQ ID NO 125
<211> LENGTH: 34
<212> TYPE: DNA
<213> ORGANISM: Artificial Sequence
<220> FEATURE:
<223> OTHER INFORMATION: primer sequence

<400> SEQUENCE: 125
ctcctcccga tgtcccgtcg gagatttgct tgta                                   34

<210> SEQ ID NO 126
<211> LENGTH: 34
<212> TYPE: DNA
<213> ORGANISM: Artificial Sequence
<220> FEATURE:
<223> OTHER INFORMATION: primer sequence

<400> SEQUENCE: 126
cacggcctga ctaccgtcgt tgagtgttag gtag                                   34

<210> SEQ ID NO 127
<211> LENGTH: 45
<212> TYPE: DNA
<213> ORGANISM: Artificial Sequence
<220> FEATURE:
<223> OTHER INFORMATION: primer sequence

<400> SEQUENCE: 127
gattagccaa tgaatttctt ccatccagat ggtatttggt cccag                       45

<210> SEQ ID NO 128
<211> LENGTH: 39
<212> TYPE: DNA
<213> ORGANISM: Artificial Sequence
<220> FEATURE:
<223> OTHER INFORMATION: primer sequence

<400> SEQUENCE: 128
gccaaaaatc aggatcccgt cactgggaaa aaaacgctc                              39
```